(12) United States Patent
Moore et al.

(10) Patent No.: US 11,299,554 B2
(45) Date of Patent: *Apr. 12, 2022

(54) HETERODIMERIC PROTEINS

(71) Applicant: Xencor, Inc., Monrovia, CA (US)

(72) Inventors: Gregory Moore, Azuza, CA (US); Rumana Rashid, Temple City, CA (US); John Desjarlais, Pasadena, CA (US)

(73) Assignee: Xencor, Inc., Monrovia, CA (US)

( * ) Notice: Subject to any disclaimer, the term of this patent is extended or adjusted under 35 U.S.C. 154(b) by 118 days.

This patent is subject to a terminal disclaimer.

(21) Appl. No.: 16/364,093

(22) Filed: Mar. 25, 2019

(65) Prior Publication Data

US 2020/0048370 A1 Feb. 13, 2020

Related U.S. Application Data

(63) Continuation of application No. 15/444,026, filed on Feb. 27, 2017, now Pat. No. 10,287,364, which is a continuation of application No. 14/200,821, filed on Mar. 7, 2014, now Pat. No. 9,605,084.

(60) Provisional application No. 61/794,695, filed on Mar. 15, 2013.

(51) Int. Cl.
*C07K 16/46* (2006.01)
*C07K 16/22* (2006.01)
*A61K 39/00* (2006.01)

(52) U.S. Cl.
CPC ............ *C07K 16/468* (2013.01); *C07K 16/22* (2013.01); *A61K 2039/505* (2013.01); *C07K 2317/52* (2013.01); *C07K 2317/72* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,169,888 A | 10/1979 | Hanka et al. |
| 4,179,337 A | 12/1979 | Davis et al. |
| 4,256,746 A | 3/1981 | Miyashita et al. |
| 4,294,757 A | 10/1981 | Asai |
| 4,301,144 A | 11/1981 | Iwashita et al. |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 5/1982 | Asai et al. |
| 4,362,663 A | 12/1982 | Kida et al. |
| 4,364,866 A | 12/1982 | Asai et al. |
| 4,364,935 A | 12/1982 | Kung et al. |
| 4,371,533 A | 2/1983 | Akimoto et al. |
| 4,424,219 A | 1/1984 | Hashimoto et al. |
| 4,450,254 A | 5/1984 | Isley et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,880,935 A | 11/1989 | Thorpe |
| 4,923,990 A | 5/1990 | Nakano et al. |
| 4,943,533 A | 7/1990 | Mendelsohn et al. |
| 4,970,198 A | 11/1990 | Lee et al. |
| 5,053,394 A | 10/1991 | Ellestad et al. |
| 5,070,092 A | 12/1991 | Kanda et al. |
| 5,084,468 A | 1/1992 | Saito et al. |
| 5,101,038 A | 3/1992 | Nakano et al. |
| 5,122,368 A | 6/1992 | Greenfield et al. |
| 5,187,186 A | 2/1993 | Kanda et al. |
| 5,208,020 A | 5/1993 | Chari et al. |
| 5,264,586 A | 11/1993 | Nicolaou et al. |
| 5,384,412 A | 1/1995 | Nicolaou et al. |
| 5,416,064 A | 5/1995 | Chari et al. |
| 5,475,092 A | 12/1995 | Chari et al. |
| 5,500,362 A | 3/1996 | Robinson et al. |
| 5,530,101 A | 6/1996 | Queen et al. |
| 5,541,087 A | 7/1996 | Lo et al. |
| 5,550,246 A | 8/1996 | Nicolaou et al. |
| 5,558,864 A | 9/1996 | Bendig et al. |
| 5,585,089 A | 12/1996 | Queen et al. |
| 5,585,097 A | 12/1996 | Bolt et al. |

(Continued)

FOREIGN PATENT DOCUMENTS

EP 0425235 B1 9/1996
EP 1752471 2/2007

(Continued)

OTHER PUBLICATIONS

U.S. Appl. No. 12/875,015, 2011-0054151, U.S. Pat. No. 9,493,578, filed Sep. 2, 2010, Mar. 3, 2011, Nov. 15, 2016.

(Continued)

*Primary Examiner* — Daniel C Gamett
(74) *Attorney, Agent, or Firm* — Louis-Vu T. Nguyen; Christopher J. Betti; Morgan, Lewis & Bockius, LLP

(57) ABSTRACT

The present invention describes novel immunoglobulin compositions that co-engage at least two antigens, e.g. a first and second antigen, or, as outlined herein, three or four antigens can be bound, in some of the scaffold formats described herein. First and second antigens of the invention are herein referred to as antigen-1 and antigen-2 respectively (or antigen-3 and antigen-4, if applicable. As outlined herein, a number of different formats can be used, with some scaffolds relying combinations of monovalent and bivalent bindings.

10 Claims, 160 Drawing Sheets

Specification includes a Sequence Listing.

(56) References Cited

U.S. PATENT DOCUMENTS

| | | |
|---|---|---|
| 5,585,499 A | 12/1996 | Chari et al. |
| 5,622,929 A | 4/1997 | Willner et al. |
| 5,635,483 A | 6/1997 | Pettit et al. |
| 5,641,780 A | 6/1997 | Amishiro et al. |
| 5,663,149 A | 9/1997 | Pettit et al. |
| 5,677,171 A | 10/1997 | Hudziak et al. |
| 5,693,761 A | 12/1997 | Queen et al. |
| 5,693,762 A | 12/1997 | Queen et al. |
| 5,703,080 A | 12/1997 | Nakakura et al. |
| 5,712,374 A | 1/1998 | Kuntsmann et al. |
| 5,714,586 A | 2/1998 | Kuntsmann et al. |
| 5,726,044 A | 3/1998 | Lo et al. |
| 5,731,168 A | 3/1998 | Carter et al. |
| 5,736,137 A | 4/1998 | Anderson et al. |
| 5,739,116 A | 4/1998 | Hamann et al. |
| 5,767,237 A | 6/1998 | Sakakibara et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,807,706 A | 9/1998 | Carter et al. |
| 5,821,333 A | 10/1998 | Carter et al. |
| 5,821,337 A | 10/1998 | Carter et al. |
| 5,824,805 A | 10/1998 | King et al. |
| 5,846,545 A | 12/1998 | Chari et al. |
| 5,859,205 A | 1/1999 | Adair et al. |
| 5,877,291 A | 3/1999 | Mezes et al. |
| 5,877,296 A | 3/1999 | Hamann et al. |
| 5,891,996 A | 4/1999 | Mateo de Acosta del Rio et al. |
| 5,892,020 A | 4/1999 | Mezes et al. |
| 5,945,311 A | 8/1999 | Lindhofer et al. |
| 5,968,509 A | 10/1999 | Gorman et al. |
| 6,054,297 A | 4/2000 | Carter et al. |
| 6,071,515 A | 6/2000 | Mezes et al. |
| 6,124,431 A | 9/2000 | Sakakibara et al. |
| 6,177,078 B1 | 1/2001 | Lopez |
| 6,180,370 B1 | 1/2001 | Queen et al. |
| 6,214,345 B1 | 4/2001 | Firestone et al. |
| 6,235,883 B1 | 5/2001 | Jakobovits et al. |
| 6,329,507 B1 | 12/2001 | Mezes et al. |
| 6,407,213 B1 | 6/2002 | Carter et al. |
| 6,441,163 B1 | 8/2002 | Chari et al. |
| 6,455,677 B1 | 9/2002 | Park et al. |
| 6,506,883 B2 | 1/2003 | Meteo de Acosta del Rio et al. |
| 6,602,684 B1 | 8/2003 | Umana et al. |
| 6,632,927 B2 | 10/2003 | Adair et al. |
| 6,706,265 B1 | 3/2004 | Bolt et al. |
| 6,716,410 B1 | 4/2004 | Witztum |
| 6,723,538 B2 | 4/2004 | Mack et al. |
| 6,884,869 B2 | 4/2005 | Senter et al. |
| 6,989,452 B2 | 1/2006 | Ng et al. |
| 7,087,600 B2 | 8/2006 | Ng et al. |
| 7,112,324 B1 | 9/2006 | Dorken et al. |
| 7,129,261 B2 | 10/2006 | Ng et al. |
| 7,276,497 B2 | 10/2007 | Chari et al. |
| 7,303,749 B1 | 12/2007 | Chari |
| 7,368,565 B2 | 5/2008 | Chari et al. |
| 7,498,302 B2 | 3/2009 | Ng et al. |
| 7,507,420 B2 | 3/2009 | Ng et al. |
| 7,517,903 B2 | 4/2009 | Chen et al. |
| 7,601,354 B2 | 10/2009 | Chari |
| 7,642,228 B2 | 1/2010 | Carter et al. |
| 7,691,962 B2 | 4/2010 | Boyd et al. |
| 7,695,936 B2 | 4/2010 | Carter et al. |
| 7,696,338 B2 | 4/2010 | Neville, Jr. et al. |
| 7,728,114 B2 | 6/2010 | Mach et al. |
| 8,063,187 B2 | 11/2011 | Chu et al. |
| 8,114,967 B2 | 2/2012 | Bhatt et al. |
| 8,216,805 B2 | 7/2012 | Carter et al. |
| 8,236,308 B2 | 8/2012 | Kischel et al. |
| 8,309,690 B2 | 11/2012 | Allan et al. |
| 8,367,805 B2 | 2/2013 | Chamberlain et al. |
| 8,409,568 B2 | 4/2013 | Gao et al. |
| 8,592,562 B2 | 11/2013 | Kannan et al. |
| 8,637,641 B2 | 1/2014 | Dahiyat et al. |
| 8,946,387 B2 | 2/2015 | Koenig et al. |
| 9,181,334 B2 | 11/2015 | Kobayashi et al. |
| 9,822,181 B2 | 11/2017 | Bonvini et al. |
| 9,856,327 B2 | 1/2018 | Bernett et al. |
| 2001/0035606 A1 | 11/2001 | Schoen |
| 2002/0076406 A1 | 6/2002 | Leung |
| 2002/0103345 A1 | 8/2002 | Zhu |
| 2002/0131968 A1 | 9/2002 | Waldmann et al. |
| 2003/0003097 A1 | 1/2003 | Reff et al. |
| 2003/0017979 A1 | 1/2003 | Mack et al. |
| 2003/0091561 A1 | 5/2003 | Van de Winkel |
| 2003/0157108 A1 | 8/2003 | Presta |
| 2003/0223999 A1 | 12/2003 | Lindhofer |
| 2004/0018191 A1 | 1/2004 | Wang |
| 2004/0071696 A1 | 4/2004 | Adams et al. |
| 2004/0162411 A1 | 8/2004 | Lanzavecchia |
| 2004/0170626 A1 | 9/2004 | Schuurman |
| 2004/0242851 A1 | 12/2004 | Zhu |
| 2005/0114037 A1 | 5/2005 | Desjarlais et al. |
| 2005/0136050 A1 | 6/2005 | Kufer et al. |
| 2005/0142133 A1 | 6/2005 | Lazar et al. |
| 2005/0176028 A1 | 8/2005 | Hofmeiser et al. |
| 2005/0191702 A1 | 9/2005 | Mack et al. |
| 2005/0238648 A1 | 10/2005 | Jacobs |
| 2005/0238649 A1 | 10/2005 | Doronina |
| 2006/0008883 A1 | 1/2006 | Lazar |
| 2006/0018897 A1 | 1/2006 | Lee et al. |
| 2006/0024298 A1 | 2/2006 | Lazar et al. |
| 2006/0024317 A1 | 2/2006 | Boyd |
| 2006/0073142 A1 | 4/2006 | Chan et al. |
| 2006/0074008 A1 | 4/2006 | Senter |
| 2006/0115481 A1 | 6/2006 | Lindhofer et al. |
| 2006/0121032 A1 | 6/2006 | Dahiyat et al. |
| 2006/0134105 A1 | 6/2006 | Lazar et al. |
| 2006/0235208 A1 | 10/2006 | Lazar |
| 2007/0071675 A1 | 3/2007 | Wu et al. |
| 2007/0105199 A1 | 5/2007 | Yan et al. |
| 2007/0123479 A1 | 5/2007 | Kufer et al. |
| 2007/0148170 A1 | 6/2007 | Desjarlais |
| 2007/0287170 A1 | 12/2007 | Davis et al. |
| 2008/0044413 A1 | 2/2008 | Hammond et al. |
| 2008/0050370 A1 | 2/2008 | Glaser et al. |
| 2008/0138335 A1 | 6/2008 | Takahashi et al. |
| 2008/0213273 A1 | 9/2008 | Burge |
| 2008/0219974 A1 | 9/2008 | Bernett et al. |
| 2008/0242845 A1 | 10/2008 | Lazar et al. |
| 2009/0082213 A1 | 3/2009 | Horowitz et al. |
| 2009/0163699 A1 | 6/2009 | Desjarlais |
| 2009/0214539 A1 | 8/2009 | Grosmaire et al. |
| 2009/0252683 A1 | 10/2009 | Kischel et al. |
| 2009/0252729 A1 | 10/2009 | Farrington et al. |
| 2009/0274692 A1 | 11/2009 | Tan et al. |
| 2009/0311253 A1 | 12/2009 | Ghayur et al. |
| 2009/0317869 A1 | 12/2009 | Alley et al. |
| 2010/0004431 A1 | 1/2010 | Bernett et al. |
| 2010/0015133 A1 | 1/2010 | Igawa et al. |
| 2010/0080814 A1 | 4/2010 | Desjarlais et al. |
| 2010/0150918 A1 | 6/2010 | Kufer et al. |
| 2010/0174053 A1 | 7/2010 | Johnson et al. |
| 2010/0178298 A1 | 7/2010 | Lindhofer |
| 2010/0183554 A1 | 7/2010 | Mach et al. |
| 2010/0226925 A1 | 9/2010 | Dillon et al. |
| 2010/0239567 A1 | 9/2010 | Esue |
| 2010/0239582 A1 | 9/2010 | Humphreys et al. |
| 2010/0256339 A1 | 10/2010 | Bossenmaier et al. |
| 2010/0256340 A1 | 10/2010 | Brinkmann et al. |
| 2010/0298542 A1 | 11/2010 | Igawa et al. |
| 2010/0322933 A1 | 12/2010 | Lindhofer et al. |
| 2010/0330089 A1 | 12/2010 | Damle et al. |
| 2010/0331527 A1 | 12/2010 | Davis et al. |
| 2011/0054151 A1 | 3/2011 | Lazar et al. |
| 2011/0076275 A1 | 3/2011 | Igawa et al. |
| 2011/0177500 A1 | 7/2011 | Winther et al. |
| 2011/0189178 A1 | 8/2011 | Desjarlais et al. |
| 2011/0189209 A1 | 8/2011 | Neville, Jr. et al. |
| 2011/0201032 A1 | 8/2011 | Zeng et al. |
| 2011/0217302 A1 | 9/2011 | Odegard et al. |
| 2011/0262439 A1 | 10/2011 | Kufer et al. |

(56) References Cited

U.S. PATENT DOCUMENTS

| | | |
|---|---|---|
| 2011/0275787 A1 | 11/2011 | Kufer et al. |
| 2011/0293619 A1 | 12/2011 | Kufer et al. |
| 2012/0028304 A1 | 2/2012 | Dahiyat et al. |
| 2012/0034228 A1 | 2/2012 | Kufer et al. |
| 2012/0121597 A1 | 5/2012 | Ho et al. |
| 2012/0149876 A1 | 6/2012 | Von Kreudenstein et al. |
| 2012/0156207 A1 | 6/2012 | Chu et al. |
| 2012/0251531 A1 | 10/2012 | Baehner et al. |
| 2012/0251541 A1 | 10/2012 | Baurin et al. |
| 2013/0089541 A1 | 4/2013 | D'Angelo et al. |
| 2013/0095097 A1 | 4/2013 | Blakenship et al. |
| 2013/0101586 A1 | 4/2013 | Riegler et al. |
| 2013/0115208 A1 | 5/2013 | Ho et al. |
| 2013/0129723 A1 | 5/2013 | Blakenship et al. |
| 2013/0142793 A1 | 6/2013 | Ledbetter et al. |
| 2013/0171095 A1 | 7/2013 | Bernett et al. |
| 2013/0195849 A1 | 8/2013 | Von Kreudenstein et al. |
| 2013/0209355 A1 | 8/2013 | De Weers et al. |
| 2013/0267686 A1 | 10/2013 | Brinkmann |
| 2013/0336981 A1 | 12/2013 | de Kruif et al. |
| 2014/0024111 A1 | 1/2014 | Kannan et al. |
| 2014/0056879 A1 | 2/2014 | Lazar |
| 2014/0072581 A1 | 3/2014 | Dixit et al. |
| 2014/0086916 A1 | 3/2014 | Zha |
| 2014/0212435 A1 | 7/2014 | Moore et al. |
| 2014/0212436 A1 | 7/2014 | Moore et al. |
| 2014/0249297 A1 | 9/2014 | Lazar et al. |
| 2014/0288275 A1 | 9/2014 | Moore et al. |
| 2014/0294759 A1 | 10/2014 | Chu et al. |
| 2014/0294823 A1 | 10/2014 | Moore et al. |
| 2014/0294833 A1 | 10/2014 | Desjarlais et al. |
| 2014/0294835 A1 | 10/2014 | Moore et al. |
| 2014/0294836 A1 | 10/2014 | Chu et al. |
| 2014/0302064 A1 | 10/2014 | Moore |
| 2014/0322217 A1 | 10/2014 | Moore et al. |
| 2014/0356381 A1 | 12/2014 | Moore et al. |
| 2014/0363426 A1 | 12/2014 | Moore et al. |
| 2014/0370013 A1 | 12/2014 | Desjarlais et al. |
| 2014/0370020 A1 | 12/2014 | Kuramochi et al. |
| 2014/0377269 A1 | 12/2014 | Mabry et al. |
| 2014/0377270 A1 | 12/2014 | Moore et al. |
| 2015/0071948 A1 | 3/2015 | Lazar et al. |
| 2015/0307628 A1 | 10/2015 | Kim et al. |
| 2015/0307629 A1 | 10/2015 | Bernett et al. |
| 2016/0060360 A1 | 3/2016 | Moore et al. |
| 2016/0068588 A1 | 3/2016 | Bernett et al. |
| 2016/0176969 A1 | 6/2016 | Bernett et al. |
| 2016/0215063 A1 | 7/2016 | Bernett et al. |
| 2016/0229924 A1 | 8/2016 | Bernett et al. |
| 2017/0020963 A1 | 1/2017 | Qu et al. |
| 2017/0320947 A1 | 11/2017 | Moore et al. |
| 2018/0118828 A1 | 5/2018 | Bernett et al. |
| 2018/0118836 A1 | 5/2018 | Bernett et al. |
| 2018/0127501 A1 | 5/2018 | Bernett et al. |
| 2019/0263909 A1 | 8/2019 | Bernett et al. |
| 2019/0270816 A1 | 9/2019 | Bernett et al. |
| 2019/0382495 A1 | 12/2019 | Bernett et al. |
| 2019/0389954 A1 | 12/2019 | Bernett et al. |

FOREIGN PATENT DOCUMENTS

| | | |
|---|---|---|
| EP | 1829895 | 5/2007 |
| EP | 2006381 | 12/2008 |
| EP | 2009101 A1 | 12/2008 |
| EP | 2194066 | 6/2010 |
| EP | 2202245 A1 | 6/2010 |
| EP | 2522724 | 6/2011 |
| EP | 2155788 | 2/2014 |
| EP | 3252078 | 12/2017 |
| WO | WO8705330 | 9/1987 |
| WO | WO9211018 | 7/1992 |
| WO | WO9321232 | 10/1993 |
| WO | WO9413804 | 5/1994 |
| WO | WO9520045 | 1/1995 |
| WO | WO9640210 | 6/1996 |
| WO | WO96027011 | 9/1996 |
| WO | WO1997024373 | 7/1997 |
| WO | WO98050431 | 11/1998 |
| WO | WO199937791 | 7/1999 |
| WO | WO99054440 | 10/1999 |
| WO | WO99066951 | 12/1999 |
| WO | WO200061739 A1 | 10/2000 |
| WO | WO200124763 A2 | 4/2001 |
| WO | WO200129246 A1 | 4/2001 |
| WO | WO200162931 A1 | 8/2001 |
| WO | WO200188138 | 11/2001 |
| WO | WO2001083525 | 11/2001 |
| WO | WO2001090192 | 11/2001 |
| WO | WO200216368 | 2/2002 |
| WO | WO200230954 A1 | 4/2002 |
| WO | WO200231140 A1 | 4/2002 |
| WO | WO2002088172 A2 | 7/2002 |
| WO | WO2002062850 | 8/2002 |
| WO | WO2002083180 | 10/2002 |
| WO | WO2002098883 | 12/2002 |
| WO | WO2004010957 | 2/2004 |
| WO | WO2004043493 | 5/2004 |
| WO | WO2004103272 | 12/2004 |
| WO | WO2004106383 | 12/2004 |
| WO | WO2005063816 | 7/2005 |
| WO | WO2005112919 A2 | 12/2005 |
| WO | WO2005118635 | 12/2005 |
| WO | WO2006020258 | 2/2006 |
| WO | WO2006034488 | 3/2006 |
| WO | WO2006036834 | 4/2006 |
| WO | WO2006072620 | 7/2006 |
| WO | WO2006110476 A2 | 10/2006 |
| WO | WO2006106905 | 12/2006 |
| WO | WO2006131013 | 12/2006 |
| WO | WO2007005612 | 1/2007 |
| WO | WO2007018431 A2 | 2/2007 |
| WO | WO2007033230 | 3/2007 |
| WO | WO2007042261 | 4/2007 |
| WO | WO2007046006 | 4/2007 |
| WO | WO2007047829 | 4/2007 |
| WO | WO2007059404 A2 | 5/2007 |
| WO | WO2007062037 | 5/2007 |
| WO | WO2007084342 | 7/2007 |
| WO | WO2007089149 A2 | 8/2007 |
| WO | WO2007093630 | 8/2007 |
| WO | WO2007098934 | 9/2007 |
| WO | WO2007110205 | 10/2007 |
| WO | WO2007113648 | 10/2007 |
| WO | WO20070147901 | 12/2007 |
| WO | WO2008003103 | 1/2008 |
| WO | WO2008003115 | 1/2008 |
| WO | WO2008003116 | 1/2008 |
| WO | WO2008119096 | 10/2008 |
| WO | WO2008119566 | 10/2008 |
| WO | WO2008124858 | 10/2008 |
| WO | WO2008145142 | 12/2008 |
| WO | WO2008150494 | 12/2008 |
| WO | WO2009000006 | 12/2008 |
| WO | WO2009017394 A1 | 2/2009 |
| WO | WO2009017823 | 2/2009 |
| WO | WO2009030734 | 3/2009 |
| WO | WO2009032782 | 3/2009 |
| WO | WO2009086320 | 7/2009 |
| WO | WO2009089004 | 7/2009 |
| WO | WO2009106096 | 9/2009 |
| WO | WO2009106321 | 9/2009 |
| WO | WO2010028796 | 3/2010 |
| WO | WO2010033736 | 3/2010 |
| WO | WO2010034441 | 4/2010 |
| WO | WO2010037835 | 4/2010 |
| WO | WO2010042904 | 4/2010 |
| WO | WO2010062171 A2 | 6/2010 |
| WO | WO2010085682 | 7/2010 |
| WO | WO2010106180 | 9/2010 |
| WO | WO2010115551 | 10/2010 |
| WO | WO2010115552 | 10/2010 |
| WO | WO2010115553 | 10/2010 |
| WO | WO2010115589 | 10/2010 |
| WO | WO2010119119 | 10/2010 |

(56) References Cited

FOREIGN PATENT DOCUMENTS

| | | |
|---|---|---|
| WO | WO20100112193 | 10/2010 |
| WO | WO2010136172 | 12/2010 |
| WO | WO2010151792 | 12/2010 |
| WO | WO2010151808 | 12/2010 |
| WO | WO2011005621 | 1/2011 |
| WO | WO2011028952 | 3/2011 |
| WO | WO2011036183 | 3/2011 |
| WO | WO2011066342 | 3/2011 |
| WO | WO2011051307 | 5/2011 |
| WO | WO2011063348 | 5/2011 |
| WO | WO2011066501 | 6/2011 |
| WO | WO2011121110 | 10/2011 |
| WO | WO2011131746 | 10/2011 |
| WO | WO2011133886 | 10/2011 |
| WO | WO2011143545 | 11/2011 |
| WO | WO2011159877 | 12/2011 |
| WO | WO2012016227 | 2/2012 |
| WO | WO2012018687 | 2/2012 |
| WO | WO2012032080 | 3/2012 |
| WO | WO2012058768 | 5/2012 |
| WO | WO2012062596 | 5/2012 |
| WO | WO2012107417 | 8/2012 |
| WO | WO2012116453 | 9/2012 |
| WO | WO2012125495 | 9/2012 |
| WO | WO2012125850 | 9/2012 |
| WO | WO2012131555 | 10/2012 |
| WO | WO2012146394 | 11/2012 |
| WO | WO2012146628 | 11/2012 |
| WO | WO2012162067 | 11/2012 |
| WO | WO2013006544 | 1/2013 |
| WO | WO2013016714 | 1/2013 |
| WO | WO2013022855 | 2/2013 |
| WO | WO2013023251 | 2/2013 |
| WO | WO2013026833 | 2/2013 |
| WO | WO2013033008 | 3/2013 |
| WO | WO2013047748 | 4/2013 |
| WO | WO2013055809 | 4/2013 |
| WO | WO2013063702 | 5/2013 |
| WO | WO2013070565 | 5/2013 |
| WO | WO2013096828 | 6/2013 |
| WO | WO2013125667 | 8/2013 |
| WO | WO2013164694 | 11/2013 |
| WO | WO2013180201 | 12/2013 |
| WO | WO2014004586 | 1/2014 |
| WO | WO2014012085 | 1/2014 |
| WO | WO2014047231 | 3/2014 |
| WO | WO2014056783 | 4/2014 |
| WO | WO2014079000 | 5/2014 |
| WO | WO2014110601 | 7/2014 |
| WO | WO2014113510 | 7/2014 |
| WO | WO2014145806 | 9/2014 |
| WO | WO2014145907 | 9/2014 |
| WO | WO2014164553 | 10/2014 |
| WO | WO2014207064 | 12/2014 |
| WO | WO2014209804 | 12/2014 |
| WO | WO2015018528 | 2/2015 |
| WO | WO2015026892 | 2/2015 |
| WO | WO2015063339 | 5/2015 |
| WO | WO2015095392 | 6/2015 |
| WO | WO2015095410 | 6/2015 |
| WO | WO2015095423 | 6/2015 |
| WO | WO2015103072 | 7/2015 |
| WO | WO2015143079 | 9/2015 |
| WO | WO2015149077 | 10/2015 |
| WO | WO2015168379 | 11/2015 |
| WO | WO2015184207 | 12/2015 |
| WO | WO2016014984 | 1/2016 |
| WO | WO2016028672 | 2/2016 |
| WO | WO2016028896 | 2/2016 |
| WO | WO2016079050 | 5/2016 |
| WO | WO2016086186 | 6/2016 |
| WO | WO2016086189 | 6/2016 |
| WO | WO2016086196 | 6/2016 |
| WO | WO2016105450 | 6/2016 |
| WO | WO2016110584 | 7/2016 |
| WO | WO2016115274 | 7/2016 |
| WO | WO2016120789 | 8/2016 |
| WO | WO2016141387 | 9/2016 |
| WO | WO2016182751 | 11/2016 |
| WO | WO2017019846 | 2/2017 |
| WO | WO2017112775 | 6/2017 |
| WO | WO2017210443 | 12/2017 |
| WO | WO2017210485 | 12/2017 |
| WO | WO2017214092 | 12/2017 |
| WO | WO2018041838 | 3/2018 |
| WO | WO2019050521 | 3/2019 |

OTHER PUBLICATIONS

U.S. Appl. No. 15/279,266, 2017-0058053, filed Sep. 28, 2016, Mar. 2, 2017.
U.S. Appl. No. 16/539,986, 2020-0123274, filed Aug. 13, 2019, Apr. 23, 2020.
U.S. Appl. No. 14/084,515, 2014-0161790, filed Nov. 19, 2013, Jun. 12, 2014.
U.S. Appl. No. 13/009,820, 2011-0236375, U.S. Pat. No. 8,362,210, filed Jan. 19, 2011, Sep. 29, 2011, Jan. 29, 2013.
U.S. Appl. No. 13/747,317, 2013-0122001, U.S. Pat. No. 9,475,881, filed Jan. 22, 2013, May 16, 2013, Oct. 25, 2016.
U.S. Appl. No. 15/264,495, filed Sep. 13, 2016.
U.S. Appl. No. 13/648,951, 2013-0171095, filed Oct. 10, 2012, Jul. 4, 2013.
U.S. Appl. No. 13/032,491, 2011-0287032, U.S. Pat. No. 8,329,867, filed Feb. 22, 2011, Nov. 24, 2011, Dec. 11, 2012.
U.S. Appl. No. 13/710,305, 2013-0089550, U.S. Pat. No. 8,629,113, filed Dec. 10, 2012, Apr. 11, 2013, Jan. 14, 2014.
U.S. Appl. No. 14/142,705, 2014-0112924, U.S. Pat. No. 9,371,397, filed Dec. 27, 2013, Apr. 24, 2014, Jun. 21, 2016.
U.S. Appl. No. 15/159,667, 2016-0264643, U.S. Pat. No. 10,155,800, filed May 19, 2016, Sep. 15, 2016, Dec. 18, 2018.
U.S. Appl. No. 16/189,917, 2019-0127437, filed Nov. 13, 2018, May 2, 2019.
U.S. Appl. No. 13/194,904, 2012-0028304, U.S. Pat. No. 8,637,641, filed Jul. 29, 2011, Feb. 2, 2012, Jan. 28, 2014.
U.S. Appl. No. 14/165,487, 2014-0249297, U.S. Pat. No. 9,605,061, filed Jan. 27, 2014, Sep. 4, 2014, Mar. 28, 2017.
U.S. Appl. No. 15/444,087, 2017-0174757, filed Feb. 27, 2017, Jun. 22, 2017.
U.S. Appl. No. 13/568,028, filed Aug. 6, 2012.
U.S. Appl. No. 14/853,622, 2016-0068588, filed Sep. 14, 2015, Mar. 10, 2016.
U.S. Appl. No. 13/887,234, filed May 3, 2013.
U.S. Appl. No. 14/156,431, 2014-0212435, filed Jan. 15, 2014, Jul. 31, 2014.
U.S. Appl. No. 14/156,432, 2014-0212436, U.S. Pat. No. 9,738,722, filed Jan. 15, 2014, Jul. 31, 2014, Aug. 22, 2017.
U.S. Appl. No. 14/808,826, 2016-0060360, filed Jul. 24, 2015, Mar. 3, 2016.
U.S. Appl. No. 15/682,380, 2018-0201686, filed Aug. 21, 2017, Jul. 19, 2018.
U.S. Appl. No. 14/155,248, 2014-0322217, U.S. Pat. No. 10,487,155, filed Jan. 14, 2014, Oct. 30, 2014, Nov. 26, 2019.
U.S. Appl. No. 14/155,334, 2014-0370013, filed Jan. 14, 2014, Dec. 18, 2014.
U.S. Appl. No. 14/155,344, 2014-0294833, U.S. Pat. No. 9,701,759, filed Jan. 14, 2014, Oct. 2, 2014, Jul. 11, 2017.
U.S. Appl. No. 14/205,227, 2014-0294835, filed Mar. 11, 2014, Oct. 2, 2014.
U.S. Appl. No. 14/205,248, 2014-0288275, U.S. Pat. No. 9,650,446, filed Mar. 11, 2014, Sep. 25, 2014, May 16, 2017.
U.S. Appl. No. 15/589,908, 2018-0142040, filed May 8, 2017, May 24, 2018.
U.S. Appl. No. 15/633,629, 2018-0215834, U.S. Pat. No. 10,472,427, filed Jun. 26, 2017, Aug. 2, 2018, Nov. 12, 2019.
U.S. Appl. No. 16/584,317, filed Sep. 26, 2019.
U.S. Appl. No. 16/918,922, filed Jul. 1, 2020.
U.S. Appl. No. 14/214,418, 2014-0356381, U.S. Pat. No. 10,106,624, filed Mar. 14, 2014, Dec. 4, 2014, Oct. 23, 2018.

(56) References Cited

OTHER PUBLICATIONS

U.S. Appl. No. 16/137,389, filed Sep. 20, 2018.
U.S. Appl. No. 14/214,475, 2014-0294836, U.S. Pat. No. 10,519,242, filed Mar. 14, 2014, Oct. 2, 2014, Dec. 31, 2019.
U.S. Appl. No. 14/217,166, 2014-0294759, U.S. Pat. No. 10,544,187, filed Mar. 17, 2014, Oct. 2, 2014, Jan. 28, 2020.
U.S. Appl. No. 16/721,356, filed Dec. 19, 2019.
U.S. Appl. No. 14/200,652, 2014-0302064, filed Mar. 7, 2014, Oct. 9, 2014.
U.S. Appl. No. 14/207,489, 2014-0377270, U.S. Pat. No. 10,131,710, filed Mar. 12, 2014, Dec. 25, 2014, Nov. 20, 2018.
U.S. Appl. No. 16/162,172, 2019-0270810, filed Oct. 16, 2018, Sep. 5, 2019.
U.S. Appl. No. 14/210,236, 2015-0071948, filed Mar. 13, 2014, Mar. 12, 2015.
U.S. Appl. No. 15/406,588, 2017-0166655, filed Jan. 13, 2017, Jun. 15, 2017.
U.S. Appl. No. 15/624,531, filed Jun. 15, 2017.
U.S. Appl. No. 15/883,006, 2018-0360981, filed Jan. 29, 2018, Dec. 20, 2018.
U.S. Appl. No. 14/200,821, 2014-0294823, U.S. Pat. No. 9,605,084, filed Mar. 7, 2014, Oct. 2, 2014, Mar. 28, 2017.
U.S. Appl. No. 14/216,705, 2014-0363426, filed Mar. 17, 2014, Dec. 11, 2014.
U.S. Appl. No. 15/444,026, 2018-0037668, U.S. Pat. No. 10,287,364, filed Feb. 27, 2017, Feb. 8, 2018, May 14, 2019.
U.S. Appl. No. 16/364,093, 2020-0048370, filed Mar. 25, 2019, Feb. 13, 2020.
U.S. Appl. No. 14/673,695, 2015-0307629, filed Mar. 30, 2015, Oct. 29, 2015.
U.S. Appl. No. 15/786,252, 2018-0094079, filed Oct. 17, 2017, Apr. 5, 2018.
U.S. Appl. No. 14/952,705, 2016-0176969, filed Nov. 25, 2015, Jun. 23, 2016.
U.S. Appl. No. 14/952,714, 2016-0229924, filed Nov. 25, 2015, Aug. 11, 2016.
U.S. Appl. No. 15/141,350, 2016-0355608, U.S. Pat. No. 10,259,887, filed Apr. 28, 2016, Dec. 8, 2016, Apr. 16, 2019.
U.S. Appl. No. 15/945,679, 2018-0282432, filed Apr. 4, 2018, Oct. 4, 2018.
U.S. Appl. No. 15/945,681, 2018-0223000, filed Apr. 4, 2018, Aug. 9, 2018.
U.S. Appl. No. 16/354,058, 2019-0202938, filed Mar. 14, 2019, Jul. 4, 2019.
U.S. Appl. No. 14/952,786, 2016-0215063, filed Nov. 25, 2015, Jul. 28, 2016.
U.S. Appl. No. 15/779,325, filed May 25, 2018.
U.S. Appl. No. 14/757,809, 2016-0355600, U.S. Pat. No. 10,428,155, filed Dec. 22, 2015, Dec. 8, 2016, Oct. 1, 2019.
U.S. Appl. No. 16/530,946, 2019-0352416, filed Aug. 2, 2019, Nov. 21, 2019.
U.S. Appl. No. 15/063,441, 2017-0037131, U.S. Pat. No. 10,227,411, filed Mar. 7, 2016, Feb. 9, 2017, Mar. 12, 2019.
U.S. Appl. No. 16/297,255, 2019-0194325, filed Mar. 8, 2019, Jun. 27, 2019.
U.S. Appl. No. 15/372,360, 2017-0320947, U.S. Pat. No. 10,227,410, filed Dec. 7, 2016, Nov. 9, 2017, Mar. 12, 2019.
U.S. Appl. No. 16/489,539, filed Aug. 28, 2019.
U.S. Appl. No. 15/623,314, 2018-0118836, filed Jun. 14, 2017, May 3, 2018.
U.S. Appl. No. 16/435,373, 2019-0382495, filed Jun. 7, 2019, Dec. 19, 2019.
U.S. Appl. No. 16/435,375, 2019-0389954, filed Jun. 7, 2019, Dec. 26, 2019.
U.S. Appl. No. 15/611,361, 2017-0349660, filed Jun. 1, 2017, Dec. 7, 2017.
U.S. Appl. No. 15/611,683, 2017-0349657, filed Jun. 1, 2017, Dec. 7, 2017.
U.S. Appl. No. 15/636,590, 2018-0118827, U.S. Pat. No. 10,316,088, filed Jun. 28, 2017, May 3, 2018, Jun. 11, 2019.
U.S. Appl. No. 16/393,900, 2019-0248898, filed Apr. 24, 2019, Aug. 15, 2019.
U.S. Appl. No. 15/185,958, 2017-0081420, U.S. Pat. No. 9,850,320, filed Jun. 17, 2016, Mar. 23, 2017, Dec. 26, 2017.
U.S. Appl. No. 15/186,167, 2017-0081424, U.S. Pat. No. 9,856,327, filed Jun. 17, 2016, Mar. 23, 2017, Jan. 2, 2018.
U.S. Appl. No. 15/691,665, 2018-0127501, filed Aug. 30, 2017, May 10, 2018.
U.S. Appl. No. 16/820,375, filed Mar. 16, 2020.
U.S. Appl. No. 15/785,401, 2018-0118805, U.S. Pat. No. 10,501,543, filed Oct. 16, 2017, May 3, 2018, Dec. 10, 2019.
U.S. Appl. No. 16/660,028, 2020-0040083, filed Oct. 22, 2019, Feb. 6, 2020.
U.S. Appl. No. 15/785,393, 2018-0118828, U.S. Pat. No. 10,550,185, filed Oct. 16, 2017, May 3, 2018, Feb. 4, 2020.
U.S. Appl. No. 16/718,072, 2020-0123259, filed Dec. 17, 2019, Apr. 23, 2020.
U.S. Appl. No. 16/388,174, 2019-0365861, filed Apr. 18, 2019, Dec. 5, 2019.
U.S. Appl. No. 16/388,811, 2019-0389933, filed Apr. 18, 2019, Dec. 26, 2019.
U.S. Appl. No. 16/600,236, 2020-0140512, filed Oct. 11, 2019, May 7, 2020.
U.S. Appl. No. 15/525,007, 2017-0335007, U.S. Pat. No. 10,556,959, filed May 5, 2017, Nov. 23, 2017, Feb. 11, 2020.
U.S. Appl. No. 16/607,241, filed Oct. 22, 2019.
U.S. Appl. No. 16/025,963, 2019-0016778, filed Jul. 2, 2018, Jan. 17, 2019.
U.S. Appl. No. 16/184,895, 2019-0263909, filed Nov. 8, 2018, Aug. 29, 2019.
U.S. Appl. No. 16/184,929, 2019-0270816, filed Nov. 8, 2018, Sep. 5, 2019.
U.S. Appl. No. 16/206,849, 2019-0241638, filed Nov. 30, 2018, Aug. 8, 2019.
U.S. Appl. No. 16/375,777, 2020-0165356, filed Apr. 4, 2019, May 28, 2020.
U.S. Appl. No. 16/388,646, 2019-0352362, filed Apr. 18, 2019, Nov. 21, 2019.
U.S. Appl. No. 16/388,729, 2019-0359684, filed Apr. 18, 2019, Nov. 28, 2019.
U.S. Appl. No. 16/592,656, filed Oct. 3, 2019.
U.S. Appl. No. 16/798,247, filed Feb. 21, 2020.
U.S. Appl. No. 16/832,440, filed Mar. 27, 2020.
U.S. Appl. No. 16/724,118, filed Dec. 20, 2019.
U.S. Appl. No. 16/875,878, filed May 15, 2020.
U.S. Appl. No. 16/805,453, filed Feb. 28, 2020.
U.S. Appl. No. 14/210,363, 2014-0294812, filed Mar. 13, 2014, Oct. 2, 2014.
U.S. Appl. No. 15/811,315, 2018-0222965, filed Nov. 13, 2017, Aug. 9, 2018.
Julg, B. et al "Enhanced Anti-HIV Functional Activity Associated with Gag-Specific CD8 T-Cell Responses." Journal of Virology 84.11 (2010): 5540-5549. Web. Jul. 13, 2020.
Tutt et al., Trispecific F(ab')3 derivatives that use cooperative signaling via the TCR/CD3 complex and CD2 to activate and redirect resting cytotoxic T cells., The Journal of Immunology Jul. 1, 1991, 147 (1) 60-69.
Armour et al., Recombinant human IgG molecules lacking Fcγ receptor I binding and monocyte triggering activities., Eur. J. Immunol. 1999. 29: 2613-2624.
Bogolyubova et al., Cancer immunotherapy based on the blockade of immune checkpoints, Oct. 2015, Medical Immunology (Russia) 17(5):395.
U.S. Appl. No. 12/631,508, filed Dec. 4, 2009, Chari et al.
(No Author Name) "A method for making multispecific antibodies having heteromultimeric and common components", Expert Opinion on Therapeutic Patents, Genentech, Inc. (1999) 9(6): 785-790, pp. 785-790.
"Polythene Glycol and Derivatives for Advanced PEGylation", Catalog 2005-2006, Nektar Therapeutics.
"Xencor Provides Data Updates on XmaB Bispecific Antibody Program and Announces Presentations at Upcoming American Society of Hematology 2014 Annual Meeting", Nov. 6, 2014,

(56) References Cited

OTHER PUBLICATIONS

XP055255549, retrieved from the internet: http://files.shareholder.com/downloads/AMDA-2B2V8N/0xOx792404/77590b72-837a-4085-bc55-78fa500638dc/XNCR_News_2014_11_6_General_Releases.pdf.

Abbott Laboratories, Strategies and Current Approaches for Improving Drug-Like-Properties During Biologies Drug Candidate Selection, AAPS Webinar—Nov. 10, 2011.

Adams, et al., Avidity-Mediated Enhancement of In vivo Tumor Targeting by Single-Chain Fv Dimers, Clin Cancer Res, 2006, vol. 12(5), pp. 1599-1605, doi:10.1158/1078-0432.CCR-05-2217.

Alberola-Ila et al., Stimulation Through the TCR/CD3 Complex Up-Regulates the CD2 Srface Expression on Human T Lymphocytes, Feb. 15, 1991.

Alibaud et al., A New Monoclonal Anti-CD3? Antibody Reactive on Paraffin Sections, Journal of Histochemistry & Cytochemistry, 2000, vol. 48, p. 1609.

An, et al., IgG2m4, an engineered antibody isotype with reduced Fc function, mAbs, 2009, vol. 1, Issue 6, pp. 572-579, www.landesbioscience.com/journals/mabs/article/10185.

Aplin et al., , Preparation, properties, and applications of carbohydrate conjugates of proteins and lipids, 1981, CRC Crit. Rev. Biochem., pp. 259-306.

Arnett, et al., Crystal structure of a human CD3-ε/δ dimer in complex with a UCHT1 single-chain antibody fragment, PNAS, 2004, vol. 101, No. 46, pp. 16268-16273.

Asano, et al., Cytotoxic enhancement of a bispecific diabody (Db) by format conversion to tandem single-chain variable fragment (taFv): The Case of the hEx3 Diabody, JBC Papers in Press, 2010, http://www.jbc.org/cgi/doi/10.1074/jbc.M110.172957.

Asano, et al., Highly Effective Recombinant Format of a Humanized IgG-like Bispecific Antibody for Cancer Immunotherapy with Retargeting of Lymphocytes to Tumor Cells, The Journal of Biological Chemistry, 2007, vol. 282, No. 38, pp. 27659-27665.

Atwell, et al., Stable Heterodimers from Remodeling the Domain Interface of a Homodimer using a Phage Display Library, J. Mol. Biol., 1997, vol. 270, pp. 26-35.

Baca et al., Antibody humanization using monovalent phage display, 1997, J. Biol. Chem. 272(16):10678-10684.

Baeuerle, et al., Response to Letter, "Correct TandAb protein," Molecular Immunology, 2007, vol. 44, p. 3084.

Baeuerle, et al., Review—Bispecific T-Cell Engaging Antibodies for Cancer Therapy, Cancer Res, 2009, vol. 69: (12), pp. 4941-4944.

Barbas, et al. In vitro evolution of a neutralizing human antibody to human immunodeficiency virus type 1 to enhance affinity and broaden strain cross-reactivity, 1994, Proc. Nat. Acad. Sci, USA 91:3809-3813.

Bargou et al., Tumor Regression in Cancer Patients by Very Low Doses of a T Cell-Engaging Antibody, Science, 2008, vol. 321, pp. 974-977.

Bernett et al., Multiple Bispecific Checkpoint Combinations Promote T cell activation., Nov. 11, 2016, retrieved from the internet: http://files.shareholder.com/downloads/AMDA-2B2V8N/0x0x916283/67AE1A8B-40E8-4316-9F79-384D06B2C395/XNCR_SITC_2016_PD1xCTLA4_Poster126_12Nov2016.pdf.

Bhatt, Sea Lane—DDD presentation, "Surrobodies™—A Novel Approach to Bispecifics . . . ," Aug. 8, 2012.

Bibollet-Ruche et al., The Quality of Chimpanzee T-Cell Activation and Simian Immunodeficiency Virus/Human Immunodeficiency Virus Susceptibility Achieved via Antibody-Mediated T-Cell Receptor/CD3 Stimulation Is a Function of the Anti-CD3 Antibody Isotype, Jul. 30, 2008.

Biochemica, Your apoptosis specialist, 1999, No. 2, pp. 34-37 (Roche Molecular Biochemicals).

Bird et al., Single-chain antigen-binding proteins, 1988, Science 242:423-426.

Bluemel, et al., Epitope distance to the target cell membrane and antigen size determine the potency of T cell-mediated lysis by BiTE antibodies specific for a large melanoma surface antigen, Cancer Immunol Immunother, 2010, vol. 59(8), pp. 1197-1209.

Borras, et al., Generic Approach for the Generation of Stable Humanized Single-chain Fv Fragments from Rabbit Monoclonal Antibodies, The Journal of Biological Chemistry, 2010, vol. 285, No. 12, pp. 9054-9066.

Bortoletto, Nicola et al., "Optimizing anti-CD3 affinity for effective T cell targeting against tumor cells.", Eur J Immunol. Nov. 2002;32(11):3102-7.

Boswell et al., Effects of Charge on Antibody Tissue Distribution and Pharmacokinetics, 2010, Bioconjugate Chem, 21(21):2153-2163.

Brandl, et al., Bispecific antibody fragments with CD20 3 CD28 specificity allow effective autologous and allogeneic T-cell activation against malignant cells in peripheral blood and bone marrow cultures from patients with B-cell lineage leukemia and lymphoma, Experimental Hematology, 1999, vol. 27, pp. 1264-1270.

Brinkmann , et al., presentation slideshow—"Roche Penzberg & Roche Glycart, Schlieren: Centers of Excellence for Recombinant Proteins".

Brinkmann, et al., A recombinant immunotoxin containing a disulfide-stabilized Fv fragment, Proc. Natl. Acad. Sci. USA, 1993, vol. 90, pp. 7538-7542.

Cao, et al., Oligomerization is required for the activity of recombinant soluble LOX-1., FEBS J. Sep. 2009;276(17):4909-20. doi: 10.1111/j.1742-4658.2009.07190.x. Epub Jul. 31, 2009.

Carpenter, et al., Non-Fc Receptor-Binding Humanized Anti-CD3 Antibodies Induce Apoptosis of Activated Human T Cells, J. Immunol., 2000, vol. 165, No. 11, pp. 6205-6213.

Carter et al., Antibody-drug conjugates for cancer therapy, 2008, Cancer J. 14(3):154-169.

Carter et al., Humanization of an anti-p185HER2 antibody for human cancer therapy, 1992, Proc Natl Acad Sci USA 89:4285-9.

Castoldi, et al., Molecular characterization of novel trispecific ErbB-cMet-IGF1R antibodies and their antigen-binding properties, Protein Engineering, Design & Selection, 2012, vol. 25, No. 10, pp. 551-559.

Cemerski, et al., Suppression of mast cell degranulation through a dual-targeting tandem IgE-IgGFc domain biologic engineered to bind with high affinity to FcγRIIb., Immunol Lett. Mar. 30, 2012;143(1):34-43. doi: 10.1016/j.imlet.2012.01.008. Epub Jan. 25, 2012.

Chames et al., Bispecific antibodies for cancer therapy—The light at the end of the tunnel?, mAbs, 2009, vol. 1, Issue 6, pp. 1-9.

Chang, et al., Monoclonal antibodies against oxidized low-density lipoprotein bind to apoptotic cells and inhibit their phagocytosis by elicited macrophages: evidence that oxidation-specific epitopes mediate macrophage recognition., Proc Natl Acad Sci U S A. May 25, 1999;96(11):6353-8.

Chari et al., Immunoconjugates containing novel maytansinoids: promising anticancer drugs, 1992, Cancer Research 52: 127-131.

Chatal, 1989, Monoclonal Antibodies in Immunoscintigraphy, CRC Press (Book Abstract).

Chelius, et al., Structural and functional characterization of the trifunctional antibody catumaxomab, mAbs, 2010, vol. 2, Issue 3, pp. 309-319.

Chichili et al., A CD3xCD123 bispecific DART for redirecting host T cells to myelogenous leukemia: preclinical activity and safety in nonhuman primates., Sci Transl Med. May 27, 2015;7(289):289ra82. doi: 10.1126/scitranslmed.aaa5693.

Chichili et al., Co-targeting of PD-1 and CTLA-4 Inhibitory Pathways with Bispecific DART® and TRIDENT™ Molecules., Apr. 4, 2017, retrieved from the internet: http://files.shareholder.com/downloads/AMDA-278VRP/0x0x935572/8CC86417-40BA-41C0-935D-EF1B7DBOB5BB/AACR_2017_-_Co-targeting_PD-1_and_CTLA-4_Inhibitory_Pathways_with_DART_and_TRIDENT_Molecules.pdf.

Chothia et al., Canonical structures for the hypervariable regions of immunoglobulins, 1987, J. Mol. Biol. 196:901-917.

Chothia, et al., Structural Determinants in the Sequences of Immunoglobulin Variable Domain, J. Mol. Biol., 1998, vol. 278, pp. 457-479.

Chu et al., Immunotherapy with Long-Lived Anti-CD123 x Anti-CD3 Bispecific Antibodies Stimulates Potent T Cell Mediated

(56) References Cited

OTHER PUBLICATIONS

Killing of Human AML Cell Lines and of CD123+ Cells in Monkeys: A Potential Therapy for Acute Myelogenous Leukemia, Blood 2014, 124:2316.

Chu et al., Immunotherapy with Long-Lived Anti-CD123 x Anti-CD3 Bispecific Antibodies Stimulates Potent T Cell-Mediated Killing of Human B Cell Lines and of Circulating and Lymphoid B Cells in Monkeys: A Potential Therapy for B Cell Lymphomas and Leukemias, Blood 2014, 124:3111.

Chu et al., Inhibition of B cell receptor-mediated activation of primary human B cells by coengagement of CD19 and FcgammaRIIb with Fc-engineered antibodies., Mol Immunol. Sep. 2008;45(15):3926-33. doi: 10.1016/j.molimm.2008.06.027. Epub Aug. 8, 2008.

Chu et al., Reduction of total IgE by targeted coengagement of IgE B-cell receptor and FcγRIIb with Fc-engineered antibody., J Allergy Clin Immunol. Apr. 2012;129(4):1102-15. doi: 10.1016/j.jaci.2011. 11.029. Epub Jan. 16, 2012.

Conrad, et al., TCR and CD3 Antibody Cross-Reactivity in 44 Species, Cytometry Part A, 2007, vol. 71 A, pp. 925-933.

Conrath, et al., Antigen Binding and Solubility Effects upon the Veneering of a Camel VHH in Framework-2 to Mimic a VH, J. Mol. Biol. , 2005, vol. 350, pp. 112-125.

Counterman et al., "Volumns of Individual Amino Acid Residues in Gas-Phase Peptide Ions.", J. Am. Chem. Soc., 1999, 121 (16), pp. 4031-4039.

Cuesta, et al., Multivalent antibodies: when design surpasses evolution, Trends in Biotechnology, 2010, vol. 28, No. 7, pp. 355-362, doi:10.1016/j.tibtech.2010.03.007.

D'Argouges, et al., Combination of rituximab with blinatumomab (MT103/MEDI-538), a T cell-engaging CD19-/CD3-bispecific antibody, for highly efficient lysis of human B lymphoma cells, Leukemia Research, 2009, vol. 33, pp. 465-473.

Davies et al., Expression of GnTIII in recombinant anti-CD20 CHO production cell line: expression of antibodies with altered glycoforms leads to an increase in ADCC through higher affinity for FCγRIII, 2001, Biotechnol Bioeng 74:288-294.

Davila, et al., Efficacy and Toxicity Management of 19-28z CAR T Cell Therapy in B Cell Acute Lymphoblastic Leukemia, Sci. Transl. Med., 2014, vol. 6, Issue 224, pp. 1-10, 224ra25.

Davis, et al., SEEDbodies: fusion proteins based on strand-exchange engineered domain (SEED) $C_H3$ heterodimers in an Fc analogue platform for asymmetric binders or immunofusions and bispecific antibodies, Protein Engineering, Design & Selection, 2010, vol. 23, No. 4 pp. 195-202.

De Groot et al., De-Immunization of Therapeutic Proteins by T-Cell Epitope Modification, 2005, Dev. in Biologicals, 2005, 122:171-194.

De Pascalis et al., Grafting of "abbreviated" complementarity-determining regions containing specificity-determining residues essential for ligand contact to engineer a less immunogenic humanized monoclonal antibody, 2002, J. Immunol. 169:3076-3084.

Del Nagro et al., A critical role for complement C3d and the B cell coreceptor (CD19/CD21) complex in the initiation of inflammatory arthritis., J Immunol. Oct. 15, 2005:175(8):5379-89.

Demarest et al., Antibody therapeutics, antibody engineering, and the merits of protein stability, Current Opinin in Drug Discovery & Development, 2008 11(5): 675-587, Sep. 11, 2008.

Deyev, et al., Multivalency: the hallmark of antibodies used for optimization of tumor targeting by design, BioEssays, 2008, vol. 30, pp. 904-918.

DiGiammarino et al., Ligand association rates to the inner-variable-domain of a dual-variable-domain immunoglobulin are significantly impacted by linker design, mAbs3:5, 1-8; Sep.-Oct.; 3(5):487-94, Landes Bioscience, Sep. 1, 2011.

DiGiandomenico et al., A multifunctional bispecific antibody protects against Pseudomonas aerucinosa., Sci Transl Med. Nov. 12, 2014;6(262):262ra155. doi: 10.1126/scitranslmed.3009655.

Dixon, et al., Activation of Human T Lymphocytes by Crosslinking of Anti-CD3 Monoclonal Antibodies, Journal of Leukocyte Biology, 1989, vol. 46, pp. 214-220.

Dong et al., A stable IgG-like bispecific antibody targeting the epidermal growth factor receptor and the type I insulin-like growth factor receptor demonstrates superior anti-tumor activity, mAbs 3:3, May-Jun. 2011: 273-288, May 1, 2011.

Doronina , Development of potent monoclonal antibody auristatin conjugates for cancer therapy, 2003, Nat Biotechnol 21(7):778-784.

Dreier, et al., Extremely Potent, Rapid and Costimulation-lndependent Cytotoxic T-cell Response Against Lymphoma Cells Catalyzed by a Single-Chain Bispecific Antibody, Int. J. Cancer, 2002, vol. 100, pp. 690-697.

Dreier, et al., T Cell Costimulus-lndependent and Very Efficacious Inhibition of Tumor Growth in Mice Bearing Subcutaneous or Leukemic Human B Cell Lymphoma Xenografts by a CD19-/CD3-Bispecific Single-Chain Antibody Construct, The Journal of Immunology, 2003, vol. 170, pp. 4397-4402.

Dubowchik et al., Receptor-mediated and enzyme-dependent targeting of cytotoxic anticancer drugs, 1999, Pharm. Therapeutics 83:67-123.

Ducry et al., Antibody-drug conjugates: linking cytotoxic payloads to monoclonal antibodies, 2010, Bioconjugate Chem. 21:5-13.

Dudgeon, et al., General strategy for the generation of human antibody variable domains with increased aggregation resistance, PNAS Early Edition, 2012, pp. 10879-10884, www.pnas.org/cgi/doi/10.1073/pnas.1202866109 & Supporting Information.

Duke, et al., Measurement of apoptosis and other forms of cell death, 2004, Curr protocols immunol. 3.17.1-3.17.16.

Duksin et al., Relationship of the structure and biological activity of the natural homologues of tunicamycin, 1982, J. Biol. Chem. 257:3105.

Duval, et al., A Bispecific Antibody Composed of a Nonneutralizing Antibody to the gp41 Immunodominant Region and an Anti-CD89 Antibody Directs Broad Human Immunodeficiency Virus Destruction by Neutrophils, Journal of Virology, 2008, pp. 4671-4674, doi:10.1128/JVI.02499-07.

Edge et al., Deglycosylation of glycoproteins by trifluoromethanesulfonic acid, 1981, Anal. Biochem. 118:131.

Elliott, et al., Antiparallel Conformation of Knob and Hole Aglycosylated Half-Antibody Homodimers Is Mediated by a CH2—CH3 Hydrophobic Interaction, Journal of Molecular Biology, 2014, vol. 426, Issue 9, pp. 1947-1957.

Feldmann et al., Novel Humanized and Highly Efficient Bispecific Antibodies Mediate Killing of Prostate Stem Cell Antigen-Expressing Tumor Cells by CD8+ and CD4+ T cells, Aug. 8, 2012.

Feldmann et al., Retargeting of T Cells to Prostate Stem Cell Antigen Expressing Tumor Cells: Comparison of Different Antibody Formats, Dec. 28, 2010.

Fernandes, et al., T Cell Receptors are Structures Capable of Initiating Signaling in the Absence of Large Conformational Rearrangements, The Journal of Biological Chemistry, 2012, vol. 287, No. 16, pp. 13324-13335.

Fischer, Nicolas et al., "Bispecifc antibodies: molecules that enable novel therapeutic strategies", 2007, vol. 74, pp. 3-14.

Foreman, et al., ErbB3 Inhibitory Surrobodies Inhibit Tumor Cell Proliferation In Vitro and In Vivo, Mol Cancer Ther, 2012, vol. 11(7) , pp. 1411-1420.

Foreman, et al., PEGS poster, "ErbB3 Inhibitory Surrobodies Inhibit Tumor Cell Proliferation In Vitro and In Vivo," 2012.

Fraker et al., Crystal structure of peptide cyclo-(D-VAL-L-PRO-L-VAL-D-PRO)$_3$,1978, Biochem. Biophys. Res. Commun. 80(4):849-57.

Francois, et al., Construction of a Bispecific Antibody Reacting with the α- and β-Chains of the Human IL-2 Receptor, The Journal of Immunology, May 15, 1993, vol. 150, No. 10, pp. 4610-4619.

F-star Modular Antibodies Fact Sheet, Apr. 2008, "Modular Antibody Technology" (w/ reference to Ruker WO 2006/072620 A1).

F-star Modular Antibodies Press Release, Mar. 28, 2008, "Antibody Engineering Company F-Star Buys Back Royalty Obligations. TVM Capital Joins Investor Syndicate.".

(56) References Cited

OTHER PUBLICATIONS

Fudenberg, et al., Serologic Demonstration of Dual Specificity of Rabbit Bivalent Hybrid Antibody, The Journal of Experimental Medicine, 1964, vol. 119(1), pp. 151-166.
Ganesan, et al., FγγRIIb on Liver Sinusoidal Endothelium Clears Small Immune Complexes, The Journal of Immunology, Nov. 15, 2012, vol. 189 No. 10, pp. 4981-4988.
GenBankAAA38124.1, immunoglobulin heavy-chain VJ region [Mus musculus] Protein/NCBI.
GenBank AAA39180.1, immunoglobulin light-chain VJ region [Mus musculus] Protein/NCBI.
Ghendler et al., One of the CD3ε Subunits within a T Cell Receptor Complex Lies in Close Proximity to the Cβ FG Loop, J. Exp. Med., 1998, vol. 187, No. 9. pp. 1529-1536.
Ghetie et al., Multiple roles for the major histocompatibility complex Class I-related receptor FcRn, 2000, Annu Rev Immunol 18:739-766.
Gilliland, et al., Universal bispecific antibody for targeting tumor cells for destruction by cytotoxic T cells, Proc. Natl. Acad. Sci. USA, 1988, vol. 85, pp. 7719-7723.
Gorman et al., Reshaping a therapeutic CD4 antibody, Proc. Natl. Acad. Sci. USA 88:4181-4185.
Grodzki & Bernstein, "Antibody Purification: Ion-Exchange Chromatography.", Methods Mol Biol 2010 ;588:27-32.
Gunasekaran et al., Enhancing Antibody Fc Heterodimer Formation through Electrostatic Steering Effects, Journal of Biological Cheminstry, vol. 285, No. 25, pp. 19637-10946, Apr. 16, 2010 & Supplementary Tables.
Haagen, et al., The Efficacy of CD3 x CD19 Bispecific Monoclonal Antibody (BsAb) in a Clonogenic Assay: The Effect of Repeated Addition of BsAb, and Interleukin-2, Blood, 1995, vol. 85, No. 11, pp. 3208-3212.
Hakimuddin et al., A chemical method for the deglycosylation of proteins, 1987, Arch. Biochem. Biophys. 259:52.
Hamel, et al., The Role of the $V_L$- and $V_H$-Segments in the Preferential Reassociation of Immunoglobulin Subunits, Molecular Immunology, 1986, vol. 23, No. 5, pp. 503-510.
HAwkins et al., Selection of phage antibodies by binding affinity mimicking affinity maturation, 1992, J. Mol. Biol. 226:889-896.
Hayden-Ledbetter, et al., CD20-Directed Small Modular Immunopharmaceutical, TRU-015, Depletes Normal and Malignant B Cells, Clin Cancer Res, 2009, vol. 15(8), pp. 2739-2746.
He et al., Humanization and pharmacokinetics of a monoclonal antibody with specificity for both E- and P-selectin, 1998, J. Immunol. 160:1029-1035.
Hedvat et al., Dual Blockade of PD-1 and CTLA-4 with Bispecific Antibodies Promotes Human T cell Activation and Proliferation., Nov. 11, 2016, retrieved from the internet: http://files.shareholder.com/downloads/AMDA-2B2V8N/0x0x916284/D8084990-61EC-4DFE-8B76-60CF58B8C06F/CPI_bispecifics.pdf.
Hennecke et al., "Non-repetitive single-chain Fv linkers selected by selectively infective phage (SIP) technology.", Protein Eng. May 1998;11(5):405-10.
Hernandez-Caselles, et al., A study of CD33 (SIGLEC-3) antigen expression and function on activated human T and NK cells: two isoforms of CD33 are generated by alternative splicing, J. Leukoc. Biol., 2006, vol. 79, pp. 46-58.
Hexham, et al., Influence of relative binding affinity on efficacy in a panel of anti-CD3 scFv immunotoxins, Molecular Immunology, 2001, vol. 38, pp. 397-408.
Hinman et al., Preparation and characterization of monoclonal antibody conjugates of the calicheamicins: a novel and potent family of antitumor antibodies, 1993 Cancer Res. 53:3336-3342.
Hoffmann, et al., Serial killing of tumor cells by cytotoxic T cells redirected with a CD19-/CD3-bispecific single-chain antibody construct, Int. J. Cancer, 2005, vol. 115, pp. 98-104.
Holliger et al., "Diabodies": Small Bivalent and bispecific antibody fragments, 1993, Proc. Natl. Acad. Sci. U.S.A. 90:6444-6448.
Holliger et al., Engineering bispecific antibodies, 1993, Current Opinion Biotechnol. 4:446-449.
Houtenbos, et al., The novel bispecific diabody αCD40/αCD28 strengthens leukaemic dendritic cell-induced T-cell reactivity, British Journal of Haematology, 2008, vol. 142, pp. 273-283.
Hu et al., Minibody: A novel engineered anti-carcinoembryonic antigen antibody fragment (single-chain Fv-$C_H3$) which exhibits rapid, high-level targeting of xenografts, 1996, Cancer Res. 56:3055-3061.
Huston et al., Protein engineering antibody binding sites: recovery of specific activity in an anti-digoxin single-chain Fv analogue produced in *Escherichia coli*, 1988, Proc. Natl. Acad. Sci. U.S.A. 85:5879-5883.
Igawa et al., Reduced elimination of IgG antibodies by engineering the variable region, 2010, PEDS. 23(5): 385-392.
Igawa, $V_H/L$ interface engineering to promote selective expression and inhibit conformational isomerization of thrombopoietin receptor agonist single-chain diabody, Protein Engineering, Design & Selection, 2010, vol. 23, No. 8, pp. 667-677.
Ishigaki et al., Impact of Plasma Oxidized Low-Density Lipoprotein Removal on Atherosclerosis., Circulation 118: 75-83, 2008.
Jackson et al., In vitro antibody maturation, 1995, J. Immunol. 154(7):3310-9.
Jäger, et al., The Trifunctional Antibody Ertumaxomab Destroys Tumor Cells That Express Low Levels of Human Epidermal Growth Factor Receptor 2, Cancer Res, 2009, vol. 69(10), pp. 4270-4276.
Jefferis et al., Interaction sites on human IgG-Fc for FcγR: current models, 2002, Immunol Lett 82:57-65.
Jespers, et al., Crystal Structure of HEL4, a Soluble, Refoldable Human $V_H$ Single Domain with a Germ-line Scaffold, J. Mol. Biol., 2004, vol. 337, pp. 893-903.
Jimenez, et al., A recombinant, fully human, bispecific antibody neutralizes the biological activities mediated by both vascular endothelial growth factor receptors 2 and 3, Mol Cancer Ther, 2005, vol. 4(3), pp. 427-434.
Jin et al. The Design and Engineering of IgG-Like Bispecific Antibodies., Chapter 9, Bispecific Antibodies, pp. 151-169.
Jin, et al., MetMAb, the One-Armed 5D5 Anti-c-Met Antibody, Inhibits Orthotopic Pancreatic Tumor Growth and Improves Survival, Cancer Res 2008, vol. 68, pp. 4360-4368.
Johnson et al., Anti-tumor activity of CC49-doxorubicin immunoconjugates, 1995, Anticancer Res. 15:1387-93.
Johnson, et al., Effector Cell Recruitment with Novel Fv-based Dual-affinity Re-targeting Protein Leads to Potent Tumor Cytolysis and in Vivo B-cell Depletion, J. Mol. Biol., 2010, vol. 399, pp. 436-449.
Jones et al., Replacing the complementarity-determining regions in a human antibody with those from a mouse, 1986, Nature 321:522-525.
Jordan et al., Structural understanding of stabilization patterns in engineered bispecific Ig-like antibody molecules, Proteins 2009; 77:832-841, Jun. 19, 2009.
Jung, et al., Design of interchain disulfide bonds in the framework region of the Fv fragment of the monoclonal antibody B3, Proteins, 1994, vol. 19(1), pp. 35-47.
Jung, et al., Target Cell-restricted Triggering of the CD95 (APO-1/Fas) Death Receptor with Bispecific Antibody Fragments, Cancer Research, 2001, vol. 61, pp. 1846-1848.
Jungbluth et al., A monoclonal antibody recognizing human cancers with amplification/overexpression of the human epidermal growth factor receptor, 2003, Proc Natl Acad Sci USA. 100(2):639-44.
Kabat et al., 1991, Sequences of proteins of immunological interest, Department of Health and Human Services, Bethesda, vol. 1, $5^{th}$ Ed.
Kakutani et al., Accumulation of LOX-1 ligand in plasma and atherosclerotic lesions of Watanabe heritable hyperlipidemic rabbits: identification by a novel enzyme immunoassay.,Biochem Biophys Res Commun. Mar. 23, 2001;282(1):180-5.
Kanakaraj, et al., Simultaneous targeting of TNF and Ang2 with a novel bispecific antibody enhances efficacy in an in vivo model of arthritis, mAbs, 2012, vol. 4, Issue 5, pp. 600-613, http://dx.doi.org/10.4161/mabs.21227 & Supplemental Data.
Kettleborough et al., Humanization of a mouse monoclonal antibody by CDR-grafting: the importance of framework residues on loop conformation, 1991, Protein Eng. 4(7):773-83.

(56) References Cited

OTHER PUBLICATIONS

Keyna, et al., Surrogate Light Chain-Dependent Selection of Ig Heavy Chain V Regions, J. Immunol., 1995, vol. 155, pp. 5536-5542.

Kharmate et al., Inhibition of tumor promoting signals by activation of SSTR2 and opioid receptors in human breast cancer cells., Cancer Cell Int. Sep. 23, 2013;13(1):93. doi: 10.1186/1475-2867-13-93.

Kiewe, et al., Phase I Trial of the Trifunctional Anti-HER2 x Anti-CD3 Antibody Ertumaxomab in Metastatic Breast Cancer, Clin Cancer Res., 2006, vol. 12(10), pp. 3085-3091.

Kim et al., "Localization of the site of murine IgG1 molecule that is involved in binding the murine intestinal Fc receptor," Eur. J. Immunol., 24:2429-2434, 1994.

Kim et al., Mutational approaches to improve the biophysical properties of human single-domain antibodies., Biochim Biophys Acta. Nov. 2014;1844(11):1983-2001. doi: 10.1016/j.bbapap.2014.07.008. Epub Jul. 24, 2014.

Kipriyanov, et al., Bispecific CD3 x CD19 Diabody forT Cell-Mediated Lysis of Malignant Human B Cells, Int. J. Cancer, 1998. vol. 77, pp. 763-772.

Kipriyanov, et al., Bispecific Tandem Diabody for Tumor Therapy with Improved Antigen Binding and Pharmacokinetics, J. Mol. Biol., 1999, vol. 293, pp. 41-56.

Kipriyanov, et al., Effect of Domain Order on the Activity of Bacterially Produced Bispecific Single-chain Fv Antibodies, J. Mol. Biol., 2003, vol. 330, pp. 99-111.

Kipriyanov, et al., Two amino acid mutations in an anti-human CD3 single chain Fv antibody fragment that affect the yield on bacterial secretion but not the affinity, Protein Engineering, 1997, vol. 10, No. 4, pp. 445-453.

Klein et al., Progression of metastatic human prostate cancer to androgen independence in immunodeficient SDIC mice, 1997, Nature Medicine 3: 402-408.

Klein et al., Progress in overcoming the chain association issue in bispecific heterodimeric IgG antibodies, mAbs, Nov.-Dec. 2012, vol. 4, issue 6, pp. 653-663, doi: 10.4161/mabs.21379, Epub Aug. 27, 2012.

Klinger, et al., Immunopharmacologic response of patients with B-lineage acute lymphoblastic leukemia to continuous infusion of T cell-engaging CD19/CD3-bispecific BiTE antibody blinatumomab, Blood, 2012, vol. 119, No. 26, pp. 6226-6233.

Koristka, et al., Retargeting of Human Regulatory T Cells by Single-Chain Bispecific Antibodies, The Journal of Immunology, 2012, vol. 188, pp. 1551-1558, www.jimmunol.org/cgi/doi/10.4049/jimmunol.1101760.

Kostelny, et al., Formation of a Bispecific Antibody by the Use of Leucine Zippers, The Journal of Immunology 1992, vol. 148, pp. 1547-1553.

Krah et al., "Single-domain antibodies for biomedical applications.", Immunopharmacol Immunotoxicol.2016;38(1):21-8. doi: 10.3109/08923973.2015.1102934. Epub Nov. 9, 2015.

Krauss et al., Specificity grafting of human antibody frameworks selected from a phage display library: generation of a highly stable humanized anti-CD22 single-chain Fv fragment, 2003, Protein Engineering 16(10):753-759.

Krupka, et al., CD33 target validation and sustained depletion of AML blasts in long-term cultures by the bispecific T-cell-engaging antibody AMG 330, Blood, 2014, vol. 123, No. 3, pp. 356-365, Prepublished online Dec. 3, 2013; doi:10.1182/blood-2013-08-523548 & Data Supplement.

Kung, et al., Monoclonal Antibodies Defining Distinctive Human T Cell Surface Antigens, Science, 1979, vol. 206, pp. 347-349.

Kuppen, peter et al., The development and purification of a bispecific antibody for lymphokine-activated killer cell targeting against the rat colon carcinoma CC531., Cancer Immunol Immunother. Jun. 1993;36(6):403-8.

Labrijn, et al., Efficient generation of stable bispecific IgG1 by controlled Fab-arm exchange, www.pnas.org/cgi/doi/10.1073/pnas.1220145110 & Supporting Information.

Laszlo et al., Cellular determinants for preclinical activity of a novel CD33/CD3 bispecific T-cell engager (BiTE) antibody, AMG 330, against human AML, blood 2014 123: 554-561, Dec. 5, 2013.

Lau et al., Conjugation of Doxorubicin to monoclonal anti-carcinoembryonic antigen antibody via novel thiol-directed cross-linking regents, 1995, Bioorg-Med-Chem. 3(10):1299-1304.

Lau et al., Novel doxorubicin-monoclonal anti-carcinoembryonic antigen antibody immunoconjugate activity in vitro, 1995, Bioorg-Med-Chem. 3(10):1305-12.

Lazar Declaration, Dec. 27, 2010, pp. 1-4.

Lewis, et al., Generation of bispecific IgG antibodies by structure-based design of an orthogonal Fab interface, Nature Biotechnology, 2014, doi:10.1038/nbt.2797 & Supplemental Information.

Li, et al., Construction and characterization of a humanized anti-human CD3 monoclonal antibody 12F6 with effective immunoregulation functions, Immunology, 2005, vol. 116, pp. 487-498.

Lindhofer, et al., Preferential Species-Restricted Heavy/Light Chain Pairing in Rat/Mouse Quadromas: Implications for a Single-Step Purification of Bispecific Antibodies, The Journal of Immunology, 1995, vol. 155, pp. 219-225.

Ling, et al., Interspecies Scaling of Therapeutic Monoclonal Antibodies: Initial Look, J Clin Pharmacol, 2009, vol. 49, pp. 1382-1402, doi: 10.1177/0091270009337134.

Link, et al., Production and Characterization of a Bispecific IgG Capable of Inducing T-Cell-Mediated Lysis of Malignant B Cells, Blood, 1993, vol. 81, No. 12, pp. 3343-3349.

Linke, et al., Catumaxomab, Clinical development and future directions, mAbs, 2010, vol. 2, Issue 2, pp. 129-136.

Little, et al., Letter to the Editor, "Flawed TandAb production," Molecular Immunology, 2007, vol. 44, p. 3083.

Liu et al, Asymmetrical Fc Engineering Greatly Enhances Antibody-dependent Cellular Cytotoxicity (ADCC) Effector Function and Stability of the Modified Antibodies, J. Biol. Chem. 2014, 289: 3571-3590, Dec. 5, 2013.

Liu et al., Eradication of large colon tumor xenografts by targeted delivery of maytansinoids, 1996 Proc. Natl. Acad. Sci. USA 93:8618-8623.

Liu, et al., Crystallization of a Deglycosylated T Cell Receptor (TCR) Complexed with an Anti-TCR Fab Fragment, The Journal of Biological Chemistry, 1996, vol. 271, No. 52, pp. 33639-33646.

Lode et al., Targeted therapy with a novel enediyene antibiotic calicheamicins $o^I_1$ effectively suppress growth and dissemination of liver metastases in a syngeneic model of murine neuroblastoma, 1998, Cancer Res. 58:2928.

Löffler, et al., A recombinant bispecific single-chain antibody, CD19 x CD3, induces rapid, and high lymphoma-directed cytotoxicity by unstimulated T lymphocytes, Blood, 2000, vol. 95, No. 6, pp. 2098-2103.

Lu, et al., A Fully Human Recombinant IgG-like Bispecific Antibody to Both the Epidermal Growth Factor Receptor and the Insulin-like Growth Factor Receptor for Enhanced Antitumor Activity, The Journal of Biological Chemistry, 2005, vol. 280, No. 20, pp. 19665-19672.

Lu, et al., Di-diabody: a novel tetravalent bispecific antibody molecule by design, Journal of Immunological Methods, 2003, vol. 279, pp. 219-232.

Lu, et al., Fab-scFv fusion protein: an efficient approach to production of bispecific antibody fragments, Journal of Immunological Methods, 2002, vol. 267, pp. 213-226.

Lu, et al., The effect of variable domain orientation and arrangement on the antigen-binding activity of a recombinant human bispecific diabody, Biochemical and Biophysical Research Communications, 2004, vol. 318, pp. 507-513.

Lum, et al., The new face of bispecific antibodies: targeting cancer and much more, Experimental Hematology, 2006, vol. 34, pp. 1-6.

Lutterbuese, et al., AACR Poster, "Conversion of Cetuximab, Panitumumab, Trastuzumab and Omalizumab into T Cell-engaging BiTE Antibodies Creates Novel Drug Candidates of High Potency," 2008.

Lutterbuese, et al., T cell-engaging BiTE antibodies specific for EGFR potently eliminate KRAS-and BRAF-mutated colorectal cancer cells, PNAS Early Edition, 2010, www.pnas.org/cgi/doi/10.1073/pnas.1000976107 & Supporting Information.

(56) References Cited

OTHER PUBLICATIONS

Ma, et al., Expression and Characterization of a Divalent Chimeric Anti-Human CD3 Single Chain Antibody, Scand.J.Immunol, 1996, vol. 43, pp. 134-139.
Mabry, et al., A dual-targeting PDGFRβ/VEGF-A molecule assembled from stable antibody fragments demonstrates anti-angiogenic activity in vitro and in vivo, mAbs, 2010, vol. 2, Issue 1, pp. 20-34; www.landesbioscience.com/journals/mabs/article/10498 & Supplemental Information.
Mabry, et al., Engineering of stable bispecific antibodies targeting IL-17A and IL-23, Protein Engineering, Design & Selection, 2009, vol. 23, No. 3, pp. 115-127; doi:10.1093/protein/gzp073 & Supplementary Figures 1-8.
Mack, et al., A small bispecific antibody construct expressed as a functional single-chain molecule with high tumor cell cytotoxicity, Proc. Natl. Acad. Sci. USA, 1995, vol. 92, pp. 7021-7025.
Mack, et al., Biologic Properties of a Bispecific Single-Chain Antibody Directed Against 17-1A (EpCAM) and CD3—Tumor Cell-Dependent T Cell Stimulation and Cytotoxic Activity, The Journal of Immunology, 1997, vol. 158, pp. 3965-3970.
MacroGenics Factsheet, Dual Affinity Re-Targeting ("DART") Platform, 2010.
Mandler et al., Immunoconjugates of geldanamycin and anti-HER2 Monoclonal antibodies: antiproliferative activity on human breast carcinoma cell lines, 2000, J. Nat. Cancer Inst. 92(19):1573-1581.
Mandler et al., Modifications in synthesis strategy improve the yield and efficacy of geldanamycin-herceptin immunoconjugates, 2002, Bioconjugate Chem. 13:786-791).
Mandler et al., Synthesis and evaluation of antiproliferative activity of a geldanaymcin-herceptin™ immunoconjugates, 2000, Bioorganic & Med. Chem. Letters 10:1025-1028.
Mandy, et al., Effect of Reduction of Several Disulfide Bonds on the Properties and Recombination of Univalent Fragments of Rabbit Antibody, The Journal of Biological Chemistry, 1963, vol. 238, No. 1, pp. 206-213.
Mandy, et al., Recombination of Univalent Subunits Derived from Rabbit Antibody, The Journal of Biological Chemistry, 1961, vol. 236, No. 12, pp. 3221-3226.
Marks et al., By-passing immunization: building high affinity human antibodies by chain shuffling, 1992, Biotechnology 10:779-783.
Martin, et al., Generation of the Germline Peripheral B Cell Repertoire: VH81X-λ B Cells Are Unable to Complete All Developmental Programs, J. Immunol., 1998, vol. 160, pp. 3748-3758.
Martinez, et al., Characterization of a novel modification on IgG2 light chain: Evidence for the presence of O-linked mannosylation, J. Chromatogr. A, 2007, vol. 1156 pp. 183-187.
Marvin, Bispecific antibodies for dual-modality cancer therapy: killing two signaling cascades with one stone, Curr Opin Drug Discov Devel, 2006, vol. 9(2), pp. 184-193.
Marvin, et al., Recombinant approaches to IgG-like bispecific antibodies, Acta Pharmacologica Sinica, 2005, vol. 26 (6), pp. 649-658.
Mateo et al, Humanization of a mouse nonoclonal antibody that blocks the epidermal growth factor receptor: recovery of antagonistic activity, 1997, Immunotechnology, 3(1):71-81.
McPhee, Engineering human immunodeficiency virus 1 protease heterodimers as macromolecular inhibitors of viral maturation, Proc. Natl. Acad. Sci. USA, 1996, vol. 93, pp. 11477-11481.
Meijer, et al., Isolation of Human Antibody Repertoires with Preservation of the Natural Heavy and Light Chain Pairing, J. Mol. Biol., 2006, vol. 358, pp. 764-772.
Merchant, et al., An efficient route to human bispecific IgG, Nature Biotechnology, 1998, vol. 16, pp. 677-681.
Mertens, Nico, "Tribodies: Fab-scFv fusion proteins as a platform to create multi-functional pharmaceuticals.", SpringerLink 2011, 135-149.
Metz, et al., Bispecific antibody derivatives with restricted binding functionalities that are activated by proteolytic processing, Protein Engineering, Design & Selection, 2012, vol. 25, No. 10, pp. 571-580.

Metz, et al., Bispecific digoxigenin-binding antibodies for targeted payload delivery, PNAS, 2011, vol. 108, No. 20, pp. 8194-8199.
Michaelson et al., Anti-tumor activity of stability-engineered IgG-like bispecific antibodies targeting TRAIL-R2 and LTbetaR, [mAbs 1:2, 128-141; Mar./Apr. 2009]; Mar. 11, 2009.
Michalk et al., Characterization of a novel single-chain bispecific antibody for retargeting of T cells to tumor cells via the TCR co-receptor CD8., PLoS One. Apr. 21, 2014;9(4):e95517. doi: 10.1371/journal.pone.0095517.
Miller et al., Stability engineering of scFvs for the development of bispecific and multivalent antibodies, PEDS, 2010, vol. 23, No. 7, pp. 549-557 & Supplementary Data.
Miller, biogen idec Stability Engineering and Production of IgG-like Bispecifc Antibodies, AAPS National Biotechnology Conference, Jun. 24 to Jun. 27, 2007.
Milutinovic, et al., Sanford Burnham Medical Research Institute / AACR Poster, #4318, "Development of a novel dual agonist Surrobody™ that simultaneously activates both death receptors DR4 and DR5 and induces cancer cell death with high potency".
Mimoto et al., Engineered antibody Fc variant with selectively enhanced FcγRIIb binding over both FcγRIIa(R131) and FcγRIIa(H131)., Protein Eng Des Sel. Oct. 2013;26(10):589-98. doi: 10.1093/protein/gzt022. Epub Jun. 5, 2013.
Mimoto, et al., Novel asymmetrically engineered antibody Fc variant with superior FcγR binding affinity and specificity compared with afucosylated Fc variant, mAbs, 2013, vol. 5, Issue 2, pp. 229-236.
Modjtahedi et al., Phase I trial and tumour localization of the anti-EGFR monoclonal antibody ICR62 in head and neck or lung cancer, 1996, Br J Cancer, 73(2):228-35.
Modjtahedi et al., Targeting of cells expressing wild-type EGFR and type-III mutant EGFR (EGFRVIII) by anti-EGFR MaB ICR62: a two-pronged attack for tumor therapy, 2003, Int J Cancer, 105(2):273-80.
Modjtahedi et al., Antitumor activity of combinations of antibodies directed against different epitopes on the extracellular domain of the human EGF receptor, 1993, J. Cell Biophys. 1993, 22(1-3):129-46.
Modjtahedi et al., The human EGF receptor as a target for cancer therapy: six new rat mAbs against the receptor on the breast carcinoma MDA-MB 468, 1993, Br J Cancer. 1993, 67(2):247-53.
Mølhøj, et al., CD19-/CD3-bispecific antibody of the BiTE class is far superior to tandem diabody with respect to redirected tumor cell lysis, Molecular Immunology 2007, vol. 44 , pp. 1935-1943.
Moore et al., Tuning T Cell Affinity Improves Efficacy and Safety of Anti-CD38 x Anti-CD3 Bispecific Antibodies in Monkeys—a Potential Therapy for Multiple Myeloma., 57th ASH Annual Meeting and Exposition (Dec. 5-8, 2015), American Society of Hematology, Orlando, Florida.
Moore, et al., A novel bispecific antibody format enables simultaneous bivalent and monovalent co-engagement of distinct target antigens., MAbs. Nov.-Dec. 2011; 3(6): 546-557; Published online Nov. 1, 2011. doi: 10.4161/mabs.3.6.18123.
Moore, et al., Application of dual affinity retargeting molecules to achieve optimal redirected T-cell killing of B-cell lymphoma, Blood, 2011, vol. 117, No. 17, pp. 4542-4551.
Moretti et al., BEAT® the bispecific challenge: a novel and efficient platform for the expression of bispecific IgGs. BMC Proceedings 2013 7(Suppl 6):O9.
Morrison, et al., News and Views: Two heads are better than one, Nature Biotechnology, 2007, vol. 25, No. 11, pp. 1233-1234.
Mosmann, 1983, Rapid colorimetric assay for cellular growth and survival: application to proliferation and cytotoxicity assays, J. Immunol. Methods 65:55-63.
Muda, et al., Therapeutic assessment of SEED: a new engineered antibody platform designed to generate mono and bispecific antibodies, Protein Engineering, Design & Selection, 2011, vol. 24, No. 5, pp. 447-454.
Muramatsu et al., Production and characterization of an active single-chain variable fragment antibody recognizing CD25., Cancer Lett. Jul. 28, 2005;225(2):225-36. Epub Jan. 23, 2005.
Murthy et al., Binding of an antagonistic monoclonal antibody to an intact and fragmented EGF-receptor polypeptide, 1987, Arch Biochem Biophys. 252(2):549-60.

(56) References Cited

OTHER PUBLICATIONS

Nagorsen, et al., Blinatumomab: A historical perspective, Pharmacology & Therapeutics, 2012, vol. 136, pp. 334-342, http://dx.doi.org/10.1016/j.pharmthera.2012.07.013.

Nelson, et al., Point of View: Antibody fragments—Hope and hype, mAbs, 2010, vol. 2, Issue 1, pp. 77-83.

Neville et al., Enhancement of immunotoxin efficacy by acid-cleavable cross-ling agents utilizing diphtheria toxin and toxin mutants, 1989, Biol. Chem. 264:14653-14661.

Nielsen, et al., Human T cells resistant to complement lysis by bivalent antibody can be efficiently lysed by dimers of monovalent antibody, Blood, 2002, vol. 100, No. 12, pp. 4067-4073.

Nisonoff, et al., Letters to the Editors: Recombination of a Mixture of Univalent Antibody Fragments of Different Specificity, Arch. Biochem. Biophys., 1961, pp. 460-462.

Nisonoff, et al., Quantitative Estimation of the Hybridization of Rabbit Antibodies, Nature, 1962, vol. 194, No. 4826, pp. 355-359.

North, et al., A New Clustering of Antibody CDR Loop Conformations, J. Mol. Biol., 2011, vol. 406, pp. 228-256, doi:10.1016/j.jmb.2010.10.030.

O'Connor et al., Humanization of an antibody against human protein C and calcium-dependence involving framework residues, 1998, Protein Eng 11:321-8.

Olafsen, et al., Covalent disulfide-linked anti-CEA diabody allows site-specific conjugation and radiolabeling for tumor targeting applications, Protein Engineering, Design & Selection, 2004, vol. 17, No. 1, pp. 21-27.

Ott et al., CTLA-4 and PD-1/PD-L1 blockade: new immunotherapeutic modalities with durable clinical benefit in melanoma patients., Clin Cancer Res. Oct. 1, 2013;19(19):5300-9. doi: 10.1158/1078-0432.CCR-13-0143.

Page et al., 1993, Intermantional. Journal of Oncology 3:473-476.

Panke, et al., Quantification of cell surface proteins with bispecific antibodies, Protein Engineering, Design & Selection, 2013, vol. 26, No. 10, pp. 645-654.

Pessano, et al., The T3/T cell receptor complex: antigenic distinction between the two 20-kd T3 (T3-σ and T3-ε) subunits, The EMBO Journal, 1985, vol. 4, No. 2, pp. 337-344.

Pettit et al., Antineoplastic agents 365. Dolastatin 10 SAR probes, 1998, Anti-Cancer Drug Design 13:243-277.

Pettit et al., Dolastatins 24. Synthesis of (-)-dolastatin 10.1 X-ray molecular structure of N,N-dimethylvalyl-valyl-dolaisoleuine tert-butyl ester, 1996, J. Chem. Soc. Perkin Trans. 1 5:859-863.

Pettit et al., Specific activities of dolastatin 10 and peptide derivatives against Cryptococcus neoformans, 1998, Antimicrob. Agents Chemother. 42(11):2961-2965.

Pettit et al., Structure-activity studies with chiral isomers and with segments of the antimitotic marine peptide dolastation 10, 1989, J. Am. Chem. Soc. 111:5463-5465.

Pettit, et al., The dolastatins; 18: Sterospecific synthesis of dolaproine1, 1996, Synthesis 719-725.

Pichler et al., Differences of T-Cell Activation by the Anti-CD3 Antibodies Leu4 and BMA030, Mar. 30, 1987.

Potapov et al., Protein-Protein Recognition: Juxtaposition of Domain and Interface Cores in Immunoglobulins and Other Sandwich-like Proteins, J. Mol. Biol., 2004, vol. 342, pp. 665-679.

Presta et al., Humanization of an anti-vascular endothelial growth factor monoclonal antibody for the therapy of solid tumors and other disorders, 1997, Cancer Res.57(20):4593-9.

Queen et al., A humanized antibody that binds to the interleukin 2 receptor, 1989, Proc Natl Acad Sci, USA 86:10029-33.

Rader et al., A phage display approach for rapid antibody humanization: designed combinatorial V gene libraries, 1998, Proc. Natl. Acad. Sci. USA 95: 8910-8915.

Raghavan et al., Fc receptors and their interactios with immunoglobulins, 1996, Annu Rev Cell Dev Biol 12:181-220.

Rattel, et al., AACR Poster, "Validation of Cynomolgus Monkeys as Relevant Species for Safety Assessment of a Novel Human BiTE Antibody Platform for Cancer Therapy," 2010.

Reddy et al., Elimination of Fc receptor-dependent effector functions of a modified IgG4 monoclonal antibody to human CD4., J Immunol. Feb. 15, 2000;164(4):1925-33.

Reiter et al., Disulfide stabilization of antibody Fv: computer predictions and experimental evaluation, Protein Eng., 1995, vol. 8(12), pp. 1323-1331.

Reiter et al., Engineering interchain disulfide bonds into conserved framework regions of Fv fragments: improved biochemical characteristics of recombinant immunotoxins containing disulfide-stabilized Fv, Protein Eng., 1994, vol. 7(5), pp. 697-704.

Remington's Pharmaceutical Sciences 16th edition, Osol, A. Ed. (1980) (Book Abstract).

Repp, et al., Combined Fc-protein- and Fc-glyco-engineering of scFv-Fc fusion proteins synergistically enhances CD16a binding but does not further enhance NK-cell mediated ADCC, Journal of Immunological Methods, 2011, vol. 373, Issues 1-2, pp. 67-78.

Ridgway, et al., 'Knobs-into-holes' engineering of antibody CH3 domains for heavy chain heterodimerization, Protein Engineering, 1996, vol. 9, No. 7, pp. 617-621.

Riechmann et al., Reshaping human antibodies for therapy, 1988, Nature 332:323-329.

Riethmüller, Symmetry breaking: bispecific antibodies, the beginnings, and 50 years on, Cancer Immunity, 2012, vol. 12, p. 12, pp. 1-7.

Rodeck et al., Interactions between growth factor receptors and corresponding monoclonal antibodies in human tumors, 1987, J Cell Biochem. 35(4):315-20.

Roguska et al., Humanization of murine monoclonal antibodies through variable domain resurfacing, 1994, Proc. Natl. Acad. Sci. USA 91:969-973.

Roosnek, et al., Triggering T Cells by Otherwise Inert Hybrid Anti-CD3/Antitumor Antibodies Requires Encounter with the Specific Target Cell, J . Exp. Med., 1989, vol. 170, pp. 297-302.

Roque et al., Antibodies and genetically engineered related molecules: production and purification, 2004, Biotechnol. Prog. 20:639-654.

Rose, et al., Mutation of Y407 in the CH3 domain dramatically alters glycosylation and structure of human IgG, mAbs, 2013, vol. 5, Issue 2, pp. 219-228.

Rose, et al., Quantitative Analysis of the Interaction Strength and Dynamics of Human IgG4 Half Molecules by Native Mass Spectrometry, Structure , 2011, vol. 19, pp. 1274-1282.

Rosok et al., A combinatorial library strategy for the rapid humanization of anticarcinoma BR 96 Fab, 1996, J. Biol. Chem. 271(37): 22611-22618.

Rossi, et al., A new class of bispecific antibodies to redirect T cells for cancer immunotherapy, mAbs 2014, vol. 6, Issue 2, pp. 381-391.

Roux, et al., Structural analysis of the nurse shark (new) antigen receptor (NAR): Molecular convergence of NAR and unusual mammalian immunoglobulins, Proc. Natl. Acad. Sci. USA, 1998, vol. 95, pp. 11804-11809.

Rudnick, et al., Affinity and Avidity in Antibody-Based Tumor Targeting, Cancer Biotherapy and Radiopharmaceuticals, 2009, vol. 24, No. 2, pp. 155-161, doi: 10.1089/cbr.2009.0627.

Röthlisberger, et al., Domain Interactions in the Fab Fragment: A Comparative Evaluation of the Single-chain Fv and Fab Format Engineered with Variable Domains of Different Stability, J. Mol. Biol. , 2005, vol. 347, pp. 773-789.

Salmeron et al., A conformational epitope expressed upon association of CD3-epsilon with either CD3-delta or CD3-gamma is the main target for recognition by anti-CD3 monoclonal antibodies, Nov. 1, 1991.

Sancho et al., CD3-Surface Expression Is Required for CD4-p56ick-mediated Up-regulation of T Cell Antigen Receptor-CD3 Signaling in T Cells, Apr. 16, 1992.

Schaefer, et al., A Two-in-One Antibody against HER3 and EGFR Has Superior Inhibitory Activity Compared with Monospecific Antibodies, Cancer Cell, 2011, vol. 20, pp. 472-486 & Supplemental Information, pp. 1-21.

Schaefer, et al., Immunoglobulin domain crossover as a generic approach for the production of bispecific IgG antibodies, PNAS, 2011, vol. 108, No. 27, pp. 11187-11192.

(56) References Cited

OTHER PUBLICATIONS

Schlapschy, et al., Functional humanization of an anti-CD16 Fab fragment: obstacles of switching from murine λ to human λ or κ light chains, Protein Engineering, Design & Selection, 2009, vol. 22, No. 3, pp. 175-188, doi:10.1093/protein/gzn066.
Schlereth, et al., Eradication of Tumors from a Human Colon Cancer Cell Line and from Ovarian Cancer Metastases in Immunodeficient Mice by a Single-Chain Ep-CAM-/CD3-Bispecific Antibody Construct, Cancer Res 2005, vol. 65(7), pp. 2882-2889.
Schlereth, et al., T-cell activation and B-cell depletion in chimpanzees treated with a bispecific anti-CD19/anti-CD3 single-chain antibody construct, Cancer Immunol Immunother, 2006, vol. 55, pp. 503-514, doi:10.1007/s00262-005-0001-1.
Schoonjans, et al., Fab Chains As an Efficient Heterodimerization Scaffold for the Production of Recombinant Bispecific and Trispecific Antibody Derivatives, The Journal of Immunology, 2000, vol. 165, pp. 7050-7057.
Schroder et al., The Peptides, vol. pp 76-136, 1965, Academic Press.
Senter et al., Proceedings of the American Association for Cancer Research, 2004, vol. 45, Abstract No. 623.
Senter, Potent antibody drug conjugates for cancer therapy, 2009, Current Opin. Chem. Biol. 13:235.
Sforzini et al., Targeting of saporin to Hodgkin's lymphoma cells by anti-CD30 and anti-CD25 bispecific antibodies., Br J Haematol. Sep. 1998;102(4):1061-8.
Shalaby, et al., Development of Humanized Bispecific Antibodies Reactive with Cytotoxic Lymphocytes and Tumor Cells Overexpressing the HER2 Protooncogene, J.Exp.Med., 1992, vol. 175, pp. 217-225.
Shan, et al., Characterization of scFv-Ig Constructs Generated from the Anti-CD20 mAb 1F5 Using Linker Peptides of Varying Lengths, J Immunol, 1999, vol. 162, pp. 6589-6595.
Shearman, et al., Construction, Expression and Characterization of Humanized Antibodies Directed Against the Human α/β T Cell Receptor, The Journal of Immunology, 1991, vol. 147, No. 12, pp. 4366-4373.
Shen, et al., Catumaxomab, a rat/murine hybrid trifunctional bispecific monoclonal antibody for the treatment of cancer, Curr Opin Mol Ther, 2008, vol. 10(3), pp. 273-284.
Shen, et al., Single Variable Domain-IgG Fusion: A Novel Recombinant Approach to Fc Domain-Containing Bispecific Antibodies, The Journal of Biological Chemistry, 2006, vol. 281, No. 16, pp. 10706-10714.
Shields et al., Lack of fucose on human IgG1 N-linked oligosaccharide improves binding to human FcγRIII and antibody-dependent cellular toxicity, 2002, J Biol Chem 277:26733-26740.
Shier et al., Identification of functional and structural amino-acid residues by parsimonious mutagenesis, 1995, Gene 169:147-155.
Shinkawa et al., The absence of fucose but not the presence of galactose or bisecting N-acetylglucosamine of human IgG1 complex-type oligosaccharides shows the critical role of enhancing antibody-dependent cellular cytotoxicity, 2003, J Biol Chem 278:3466-3473.
Skehan et al., Identification of functional and structural amino-acid residues by parsimonious mutagenesis, 1990, J. Natl. Cancer Inst. 82(13):1107-12.
Smith et al., Mouse model recapitulating human Fcγ receptor structural and functional diversity., Proc Natl Acad Sci U S A. Apr. 17, 2012;109(16):6181-6. doi: 10.1073/pnas.1203954109. Epub Apr. 2, 2012.
Soumyarani et al, Oxidatively modified high density lipoprotein promotes inflammatory response in human monocytes-macrophages by enhanced production of ROS, TNF-α, MMP-9, and MMP-2., Mol Cell Biochem. Jul. 2012;366(1-2):277-85. doi: 10.1007/s11010-012-1306-y. Epub Apr. 17, 2012.
Spies et al., Alternative molecular formats and therapeutic applications for bispecific antibodies., Mol Immunol. Jan. 27, 2015. pii: S0161-5890(15)00005-X. doi: 10.1016/j.molimm.2015.01.003.
Spiess, et al., Bispecific antibodies with natural architecture produced by co-culture of bacteria expressing two distinct half-antibodies, Nature Biotechnology, 2013, doi:10.1038/nbt.2621 & Supplemental Information.
Spranger et al., Mechanism of tumor rejection with doublets of CTLA-4, PD-1/PD-L1, or IDO blockade involves restored IL-2 production and proliferation of CD8(+) T cells directly within the tumor microenvironment., J Immunother Cancer. Feb. 18, 2014;2:3. doi: 10.1186/2051-1426-2-3. eCollection 2014.
Stamova, Unexpected recombinations in single chain bispecific anti-CD3-anti-CD33 antibodies can be avoided by a novel linker module, Oct. 29, 2011.
Stanfield, et al., Maturation of Shark Single-domain (IgNAR) Antibodies: Evidence for Induced-fit Binding, J. Mol. Biol., 2007, vol. 367, pp. 358-372.
Stewart, et al., Recombinant CD36 inhibits oxLDL-induced ICAM-1-dependent monocyte adhesion., Mol Immunol. Feb. 2006;43(3):255-67.
Strop, P. et al., Generating Bispecific Human IgG1 and IgG2 Antibodies from Any Antibody Pair, J. Mol. Biol., 2012, doi:10.1016/j.jmb.2012.04.020.
Szymkowski et al., Creating the next generation of protein therapeutics through rational drug design, Current opinion in drug discovery & development, Sep. 1, 2005, p. 590, XP055354917, England.
Tabrizi et al., Biodistribution mechanisms of therapeutic monoclonal antibodies in health and disease., AAPS J. Mar. 2010;12(1):33-43. doi: 10.1208/s12248-009-9157-5. Epub Nov. 19, 2009.
Tan et al., "Superhumanized" antibodies: reduction of immunogenic potential by complementarity-determining region grafting with human germline sequences: application to an anti-CD28, 2002, J. Immunol. 169:1119-1125.
Tan, Philip, Presentation at PepTalk, Jan. 25, 2013, "Bi-specific ADAPTIR Molecule Targeting CD86 and Delivering Monomeric IL10 to Inhibit Antigen Presenting Cells".
Tang et al., Selection of linkers for a catalytic single-chain antibody using phage display technology., Journal of Biological Chemistry, American Society for Biochemistry and Molecular Biology, US, vol. 271, No. 26, Jan. 1, 1996, pp. 15682-9258.
Tarcsa et al, Chapter 10 Dual-Variable Domain Immunoglobulin (DVD-Ig™) Technology: A Versatile, Novel Format for the Next Generation of Dual-Targeting Biologies, Bispecific Antibodies 2011, pp. 171-185, 2011.
Teachey, et al., Cytokine release syndrome after blinatumomab treatment related to abnormal macrophage activation and ameliorated with cytokine-directed therapy, Blood, 2013, vol. 121, No. 26, pp. 5154-5157.
Tedgui, et al., Cytokines in atherosclerosis: pathogenic and regulatory pathways., Physiol Rev. Apr. 2006;86(2):515-81.
Terry M., "FDA Places Clinical Hold on AML Drug Co-Developed by Johnson & Johnson (JNJ) and Genmab A/S (Gen Co.)", Biospace 2016, Retrieved from the internet: https://www.biospace.com/article/fda-places-clinical-hold-on-aml-drug-co-developed-by-johnson-and-johnson-and-genmab-a-s-/.
Thompson, et al., An Anti-CD3 Single-chain Immunotoxin with a Truncated Diphtheria Toxin Avoids Inhibition by Pre-existing Antibodies in Human Blood, J.Biol.Chem., 1995, vol. 270, No. 47, pp. 28037-28041.
Thompson, et al., Improved binding of a bivalent single-chain immunotoxin results in increased efficacy for in vivo T-cell depletion, Protein Engineering, 2001, vol. 14, No. 12, pp. 1035-1041.
Thorne, et al., CD36 is a receptor for oxidized high density lipoprotein: implications for the development of atherosclerosis., FEBS Lett. Mar. 20, 2007;581(6):1227-32. Epub Feb. 28, 2007.
Thorpe et al., New coupling agents for the synthesis of immunotoxins containing a hindered disulfide bond with improved stability in Vivo, 1987, Cancer Res. 47:5924-5931.
Thotakura et al., Enzymatic deglycosylating of glycoproteins, 1987, Meth. Enzymol. 138:350.
Thurman et al., Detection of complement activation using monoclonal antibodies against C3d., J Clin Invest. May 2013;123(5):2218-30. doi: 10.1172/JCI65861. Epub Apr. 24, 2013.

(56) References Cited

OTHER PUBLICATIONS

Tomlinson et. al., Methods for generating multivalent and bispecific antibody fragments, 2000, Methods Enzymol. 326:461-479.

Topp, et al., Targeted Therapy With the T-Cell-Engaging Antibody Blinatumomab of Chemotherapy-Refractory Minimal Residual Disease in B-Lineage Acute Lymphoblastic Leukemia Patients Results in High Response Rate and Prolonged Leukemia-Free Survival, J Clin Oncol vol. 29, No. 18, pp. 2493-2498.

Traunecker, et al., Bispecific single chain molecules (Janusins) target cytotoxic lymphocytes on HIV infected cells, The EMBO Journal, 1991, vol. 1, No. 12, pp. 3655-3659.

Tsurushita et al., Humanization of monoclonal antibodies, 2004, Molecular Biology of B Cells 533-545.

Umaña et al., Engineered glycoforms of an antineuro-blastoma IgG1 with optimized antibody-dependent cellular cytotoxic activity, 1999, Nat Biotechnol 17:176-180.

Valliere-Douglass, et al., O-Fucosylation of an antibody light chain: Characterization of a modification occurring on an IgG1 molecule, Glycobiology, 2009, vol. 19, No. 2, pp. 144-152, doi: 10.1093/glycob/cwn116.

Van Boxel, et al., Some lessons from the systematic production and structural analysis of soluble $\alpha\beta$ T-cell receptors, Journal of Immunological Methods, 2009, vol. 350, pp. 14-21.

Van Wauwe, et al., OKT3: A Monoclonal Anti-Human T Lymphoctye Antibody with Potent Mitogenic Properties, The Journal of Immunology, 1980, vol. 124, No. 6, pp. 2708-2713.

Verdier, et al., Determination of lymphocyte subsets and cytokine levels in Cynomolgus monkeys, Toxicology, 1995, vol. 105, pp. 81-90.

Verhoeyen et al., Reshaping human antibodies: grafting an antilysozyme activity, 1988, Science, 239:1534-1536.

Veri, et al., Therapeutic Control of B Cell Activation via Recruitment of Fc$\gamma$ Receptor IIb (CD32B) Inhibitory Function With a Novel Bispecific Antibody Scaffold, Arthritis & Rheumatism, 2010, vol. 62, No. 7, pp. 1933-1943.

Vettermann, et al., Powered by pairing: The surrogate light chain amplifies immunoglobulin heavy chain signaling and pre-selects the antibody repertoire, Seminars in Immunology 18, 2006, pp. 44-55.

Von Kreudenstein, et al., Improving biophysical properties of a bispecific antibody scaffold to aid developability: Quality by molecular design, mAbs, 2013, vol. 5, Issue 5, pp. 1-9, http://dx.doi.org/10.4161/mabs.25632 & Supplemental Material.

Wang et al., Conserved amino acid networks involved in antibody variable domain interactions, Proteins, 2009, vol. 76, pp. 99-114.

Wang et al., Expression and characterization of recombinant soluble monkey CD3 molecules: mapping the FN18 polymorphic epitope, Molecular Immunology, 2004, vol. 40, pp. 1179-1188.

Wang, et al., A block in both early T lymphocyte and natural killer cell development in transgenic mice with high-copy numbers of the human CD3E gene, Proc. Natl. Acad. Sci. USA, 1994, vol. 91, pp. 9402-9406.

Ward, et al., Protein Engineering of Homodimeric Tyrosyl-tRNA Synthetase to Produce Active Heterodimers, The Journal of Biological Chemistry, 1986, vol. 261, No. 21, pp. 9576-9578.

Wawrzynczak et al., Methods for preparing immunotoxins: Effect of the linkage on activity and stability. In Immunoconjugates. Antibody Conjugates in Radio imaging and Therapy of Cancer. (C.-W. Vogel, editor). New York, Oxford University Press, pp. 28-55.

Weatherill, et al., Towards a universal disulphide stabilised single chain Fv format: importance of interchain disulphide bond location and vL-vH orientation, Protein Engineering, Design & Selection, 2012, vol. 25, No. 7, pp. 321-329.

Weiner, et al., The Role of T Cell Activation Bispecific Antibody Therapy in Anti-CD3 X Antitumor, Journal of Immunology, 1994, vol. 152, pp. 2385-2392.

Wesolowski, et al., Single domain antibodies: promising experimental and therapeutic tools in infection and immunity, Med Microbiol Immunol, 2009, vol. 198, pp. 157-174.

Whitlow, et al., An improved linker for single-chain Fv with reduced aggregation and enhanced proteolytic stability, Protein Engineering, 1993, vol. 6 , No. 8, pp. 989-995.

Wigginton et al., An immunoglobulin E-reactive chimeric human immunoglobulin G1 anti-idiotype inhibits basophil degranulation through cross-linking of Fc$\epsilon$RI with Fc$\gamma$RIIb., Clinical & Experimental Allergy, 38: 313-319.

Wong, et al., The Mechanism of Anti-CD3 Monoclonal Antibodies, Transplantation, 1990, vol. 50, No. 4, pp. 683-689.

Woods, et al., LC-MS characterization and purity assessment of a prototype bispecific antibody, mAbs, 2013, vol. 5, Issue 5, pp. 711-722, http://dx.doi.org/10.4161/mabs.25488.

Woyke et al., In vitro activities and postantifungal effects of the potent dolastation 10 derivative auristatin PHE, 2001, Antimicrob. Agents and Chemother. 45(12):3580-3584.

Wu et al, Molecular construction and optimization of anti-human IL-11$\alpha$/$\beta$ dual variable domain immunoglobulin (DVD-Ig™) molecules, [mAbs 1:4, 339-347; Jul./Aug. 2009]; Landes Bioscience, Apr. 10, 2009.

Wu et al., Simultaneous targeting of multiple disease mediators by a dual-variable-domain immunoglobulin, (DVD-Ig™) molecules, Jul.-Aug. 2009; 339-347, Oct. 14, 2007.

Wu et al., Humanization of a murine monoclonal antibody by simultaneous optimization of framework and CDR residues, 1999, J. Mol. Biol. 294:151-162.

Wu, et al., Multimerization of a chimeric anti-CD20 single-chain Fv-Fc fusion protein is mediated through variable domain exchange, Protein Engineering, 2001, vol. 14, No. 12, pp. 1025-1033.

Wucherpfennig, et al., Structural Biology of the T-cell Receptor: Insights into Receptor Assembly, Ligand Recognition, and Initiation of Signaling, Cold Spring Harb Perspect Biol 2010;2:a005140.

Xie, et al., A new format of bispecific antibody: highly efficient heterodimerization, expression and tumor cell lysis, Journal of Immunological Methods, 2005, vol. 296 , pp. 95-101, doi:10.1016/j.jim.2004.11.005.

Xu, et al., Combinatorial surrobody libraries, PNAS, 2008, vol. 105, No. 31, pp. 10756-10761.

Xu, et al., Rapid optimization and prototyping for therapeutic antibody-like molecules, mAbs, 2013, vol. 5, Issue 2, pp. 237-254.

Xu, et al., Surrobodies with Functional Tails, J. Mol. Biol., 2010, vol. 397, pp. 352-360.

Yang et al., Differential in vitro activation of CD8-CD4+ and CD4-CD8+ T lymphocytes by combinations of anti-CD2 and anti-CD3 antibodies, Apr. 1, 1988.

Yelton et al., Affinity maturation of the BR96 anti-carcinoma antibody by codon-based mutagenesis, 1995, J. Immunol. 155:1994-2004.

Yeung, et al., Engineering human IgG1 affinity to human neonatal Fc receptor: impact of affinity improvement on pharmacokinetics in primates, J Immunol. Jun. 15, 2009;182(12):7663-71. doi: 10.4049/jimmunol.0804182.

Yoshino et al., Upgrading of flow cytometric analysis for absolute counts, cytokines and other antigenic molecules of cynomolgus monkeys (*Macaca fascicularis*) by using anti-human cross-reactive antibodies, Exp. Anim., 2000, vol. 49(2), pp. 97-100.

Yu et al., The biosynthetic gene cluster of the maytansinoids antitumor agent ansamitocin from actinosynnema pretiosum, 2002, PNAS 99:7968-7973.

Zalevsky et al. "Enhanced antibody half-life improves in vivo activity." Nature Biotechnology, vol. 28, No. 2, Feb. 1, 2010, pp. 157-159.

Zamyatnin AA., Amino acid, peptide, and protein volume in solution., Annu Rev Biophys Bioeng. 1984;13:145-65.

Zeidler, et al., The Fc-region of a new class of intact bispecific antibody mediates activation of accessory cells and NK cells and induces direct phagocytosis of tumour cells, Br J Cancer, 2000, vol. 83(2), pp. 261-266.

Zhu, et al., Identification of Heavy Chain Residues in a Humanized Anti-CD3 Antibody Important for Efficient Antigen Binding and T Cell Activation, The Journal of Immunology, 1995, vol. 155, pp. 1903-1910.

Zhu, et al., Remodeling domain interfaces to enhance heterodimer formation, Protein Science, 1997, vol. 6, pp. 781-788.

(56) References Cited

OTHER PUBLICATIONS

Zeibig et al., Effect of the oxLDL Binding Protein Fc-CD68 on Plaque Extension and Vulnerability in Atherosclerosis., Circulation Research 108: 695-703, 2011.
Zuo, et al., An efficient route to the production of an IgG-like bispecific antibody, Protein Engineering, 2000, vol. 13, No. 5, pp. 361-367.
Sun et al., Anti-CD20/CD3 T cell-dependent bispecific antibody for the treatment of B cell malignancies., Science Translational Medicine May 13, 2015: vol. 7, Issue 287, pp. 287ra70 DOI: 10.1126/scitranslmed.aaa480.
Capizzi et al., Curative chemotherapy for acute myeloid leukemia: the development of high-dose ara-C from the laboratory to bedside., Invest New Drugs. 1996;14(3):249-56.
Giles et al., Intravenous corticosteroids to reduce gemtuzumab ozogamicin infusion reactions. Ann Pharmacother. Sep. 2003;37(9):1182-5.
Duong et al., Targeted treatment of acute myeloid leukemia in older adults: role of gemtuzumab ozogamicin., Clin Interv Aging. 2009;4:197-205. Epub May 14, 2009.
Sun et al. , Preclinical Characterization of Combinability and Potential Synergy of Anti-CD20/CD3 T-Cell Dependent Bispecific Antibody with Chemotherapy and PD-1/PD-L1 Blockade., Blood 2016 128:4168.
Gantke et al., Trispecific antibodies for CD16A-directed NK cell engagement and dual-targeting of tumor cells., Protein Eng Des Sel. Sep. 1, 2017;30(9):673-684. doi: 10.1093/protein/gzx043.
Zhang et al., The development of bispecific antibodies and their applications in tumor immune escape., Experimental Hematology & Qncology20176:12.
Krupka et al.,Blockade of the PD-1/PD-L1 axis augments lysis of AML cells by the CD33/CD3 BiTE antibody construct AMG 330: reversing a T-cell-induced immune escape mechanism., Leukemia. Feb. 2016;30(2):484-91. doi: 10.1038/leu.2015.214. Epub Aug. 4, 2015.
Osada et al., CEA/CD3-bispecific T cell-engaging (BiTE) antibody-mediated T lymphocyte cytotoxicity maximized by inhibition of both PD1 and PD-L1., Cancer Immunol Immunother. Jun. 2015;64(6):677-88. doi: 10.1007/s00262-015-1671-y. Epub Mar. 6, 2015.
Masarova et al., Immune Checkpoint Approaches in AML and MDS: A Next Frontier?, The Journal of Targeted Therapies in Cancer, Mar. 6, 2017 (Mar. 6, 2017), XP002784099.
Scott et al., Antibody therapy of cancer., Nat Rev Cancer. Mar. 22, 2012;12(4):278-87. doi: 10.1038/nrc3236.
Clynes et al., Redirected T Cell Cytotoxicity in Cancer Therapy., Annu Rev Med. Jan. 27, 2019;70:437-450. doi: 10.1146/annurev-med-062617-035821. Epub Oct. 31, 2018.
Merchant et al., Monovalent antibody design and mechanism of action of onartuzumab, a MET antagonist with anti-tumor activity as a therapeutic agent., Proc Natl Acad Sci U S A. Aug. 6, 2013; 110(32):E2987-96. doi: 10.1073/pnas.1302725110. Epub Jul. 23, 2013.
Fos et al., ICOS ligation recruits the p50alpha PI3K regulatory subunit to the immunological synapse., J Immunol. Aug. 1, 2008;181 (3):1969-77.
Sanmamed et al., Agonists of Co-stimulation in Cancer Immunotherapy Directed Against CD137, OX40, GITR, CD27, CD28, and ICOS., Semin Oncol. Aug. 2015;42(4):640-55. doi: 10.1053/j.seminoncol. 2015.05.014. Epub Jun. 11, 2015.
Vieira et al., ICOS-mediated signaling regulates cytokine production by human T cells and provides a unique signal to selectively control the clonal expansion of Th2 helper cells., Eur J Immunol. May 2004;34(5):1282-90.
Madrenas et al., Conversion of CTLA-4 from inhibitor to activator of T cells with a bispecific tandem single-chain Fv ligand., J Immunol. May 15, 2004;172(10):5948-56.
Yokosuka et al., Spatiotemporal basis of CTLA-4 costimulatory molecule-mediated negative regulation of T cell activation., Immunity. Sep. 24, 2010;33(3):326-39. doi: 10.1016/j.immuni.2010.09. 006.
Carpenter et al., Activation of human B cells by the agonist CD40 antibody CP-870,893 and augmentation with simultaneous toll-like receptor 9 stimulation., J Transl Med. Nov. 11, 2009 ;7:93. doi: 10.1186/1479-5876-7-93.
Fan et al., Engagement of the ICOS pathway markedly enhances efficacy of CTLA-4 blockade in cancer immunotherapy., J Exp Med. Apr. 7, 2014;211(4):715-25. doi: 10.1084/jem.20130590. Epub Mar. 31, 2014.
Gilboa et al., Use of oligonucleotide aptamer ligands to modulate the function of immune receptors., Clin Cancer Res. Mar. 1, 2013;19(5):1054-62. doi: 10.1158/1078-0432.CCR-12-2067.
Uy et al., Preliminary Results of a Phase 1 Study of Flotetuzumab, a CD123 x CD3 Bispecific Dart® Protein, in Patients with Relapsed/Refractory Acute Myeloid Leukemia and Myelodysplastic Syndrome., Blood 2017 130:637.
Vey et al., Interim Results from a Phase 1 First-in-Human study of flotetuzumab, a CD123 x CD3 bispecific DART molecule, in AML/MDS., Annals of Oncology (2017) 28 (suppl_5): v355-v371. 10.1093/annonc/mdx373.
Ravandi et al., Complete Responses in Relapsed/Refractory Acute Myeloid Leukemia (AML) Patients on a Weekly Dosing Schedule of XmAb14045, a CD123 x CD3 T Cell-Engaging Bispecific Antibody: Initial Results of a Phase 1 Study., Blood 2018 132:763; doi: https://doi.org/10.1182/blood-2018-99-119786.
Bacac et al., A Novel Carcinoembryonic Antigen T-Cell Bispecific Antibody (CEA TCB) for the Treatment of Solid Tumors., Clin Cancer Res. Jul. 1, 2016;22(13):3286-97.
Schuster et al., Immunotherapy with the trifunctional anti-CD20 x anti-CD3 antibody FBTA05 (Lymphomun) in paediatric high-risk patients with recurrent CD20-positive B cell malignancies., Br J Haematol. Apr. 2015;169(1):90-102. doi: 10.1111/bjh.13242. Epub Dec. 11, 2014.
Shields et al; "High Resolution Mapping of the Binding Site on Human IgG 1 for FcyRI, FcyRII, FcyRIII, and FcRn and Design of IgG1 Variants with Improved Binding to the FcyR*", The Journal of Biological Chemistry, 2001, 276(2):6591-6604.
Szymkowski et al;"Anti-CD38—anti-CD3 bispecific antibody in multiple myeloma", Xencor, pp. 1-15.

Figure 1

Kappa constant light chain (CK) (SEQ ID NO: 1)

RTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

IgG1 constant heavy chain (CH1-hinge-CH2-CH3) (SEQ ID NO: 2)

ASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPGK

IgG2 constant heavy chain (CH1-hinge-CH2-CH3) (SEQ ID NO: 3)

ASTKGPSVFPLAPCSRSTSESTAALGCLVKDYFPEPVTVSWNSGALTSGVHTFPAVLQS
SGLYSLSSVVTVPSSNFGTQTYTCNVDHKPSNTKVDKTVERKCCVECPPCPAPPVAGPS
VFLFPPKPKDTLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQVYTLPPSREE
MTKNQVSLTCLVKGFYPSDIAVEWESNGQPENNYKTTPPMLDSDGSFFLYSKLTVDKSR
WQQGNVFSCSVMHEALHNHYTQKSLSLSPGK

IgG3 constant heavy chain (CH1-hinge-CH2-CH3) (SEQ ID NO: 4)

ASTKGPSVFPLAPCSRSTSGGTAALGCLVKDYFPEPVTVSWNSGALTSGVHTFPAVLQS
SGLYSLSSVVTVPSSSLGTQTYTCNVNHKPSNTKVDKRVELKTPLGDTTHTCPRCPEPK
SCDTPPPCPRCPEPKSCDTPPPCPRCPEPKSCDTPPPCPRCPAPELLGGPSVFLFPPKP
KDTLMISRTPEVTCVVVDVSHEDPEVQFKWYVDGVEVHNAKTKPREEQYNSTFRVVSVL
TVLHQDWLNGKEYKCKVSNKALPAPIEKTISKTKGQPREPQVYTLPPSREEMTKNQVSL
TCLVKGFYPSDIAVEWESSGQPENNYNTTPPMLDSDGSFFLYSKLTVDKSRWQQGNIFS
CSVMHEALHNRFTQKSLSLSPGK

IgG4 constant heavy chain (CH1-hinge-CH2-CH3) (SEQ ID NO: 5)

ASTKGPSVFPLAPCSRSTSESTAALGCLVKDYFPEPVTVSWNSGALTSGVHTFPAVLQS
SGLYSLSSVVTVPSSSLGTKTYTCNVDHKPSNTKVDKRVESKYGPPCPSCPAPEFLGGP
SVFLFPPKPKDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLYSRLTVDKS
RWQEGNVFSCSVMHEALHNHYTQKSLSLSLGK

IgG1/2 constant heavy chain (CH1-hinge-CH2-CH3) (SEQ ID NO: 6)

ASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPPVA
GPSVFLFPPKPKDTLMISRTPEVTCVVVDVSHEDPEVQFNWYVDGVEVHNAKTKPREEQ
FNSTFRVVSVLTVVHQDWLNGKEYKCKVSNKGLPAPIEKTISKTKGQPREPQVYTLPPSR
EEMTKNQVSLTCLVKGFYPSDIAVEWESNGQPENNYKTTPPMLDSDGSFFLYSKLTVDK
SRWQQGNVFSCSVMHEALHNHYTQKSLSLSPGK

Figure 2A

SEQ ID NOS. 126-129

| EU | Domain | 126<br>IgG1 | 127<br>IgG2 | 128<br>IgG3 | 129<br>IgG4 | Fraction<br>Exposed | Notes | Subs |
|---|---|---|---|---|---|---|---|---|
| 118 | CH1 | A | A | A | A | 0.44 | | |
| 119 | CH1 | S | S | S | S | 0.69 | | DE |
| 120 | CH1 | T | T | T | T | 0.40 | | |
| 121 | CH1 | K | K | K | K | 0.37 | | DE |
| 122 | CH1 | G | G | G | G | 0.27 | | |
| 123 | CH1 | P | P | P | P | 0.10 | | |
| 124 | CH1 | S | S | S | S | 0.38 | | DE |
| 125 | CH1 | V | V | V | V | 0.05 | | |
| 126 | CH1 | F | F | F | F | 0.07 | | |
| 127 | CH1 | P | P | P | P | 0.21 | | |
| 128 | CH1 | L | L | L | L | 0.02 | | |
| 129 | CH1 | A | A | A | A | 0.22 | | DE |
| 130 | CH1 | P | P | P | P | 0.05 | | |
| 131 | CH1 | S | C | C | C | 1.00 | | DE |
| 132 | CH1 | S | S | S | S | 1.00 | | DE |
| 133 | CH1 | K | R | R | R | 1.00 | Isotypic | DE |
| 134 | CH1 | S | S | S | S | 1.00 | | DE |
| 135 | CH1 | T | T | T | T | 1.00 | | DE |
| 136 | CH1 | S | S | S | S | 1.00 | | DE |
| 137 | CH1 | G | E | G | E | 1.00 | Isotypic | DE |
| 138 | CH1 | G | S | G | S | 1.00 | | DE |
| 139 | CH1 | T | T | T | T | 0.55 | | |
| 140 | CH1 | A | A | A | A | 0.08 | | |
| 141 | CH1 | A | A | A | A | 0.02 | | |
| 142 | CH1 | L | L | L | L | 0.00 | | |
| 143 | CH1 | G | G | G | G | 0.00 | | |
| 144 | CH1 | C | C | C | C | 0.00 | | |
| 145 | CH1 | L | L | L | L | 0.02 | | |
| 146 | CH1 | V | V | V | V | 0.00 | | |
| 147 | CH1 | K | K | K | K | 0.06 | Interface<br>w/ CL | |
| 148 | CH1 | D | D | D | D | 0.26 | | |
| 149 | CH1 | Y | Y | Y | Y | 0.00 | | |
| 150 | CH1 | F | F | F | F | 0.10 | | |
| 151 | CH1 | P | P | P | P | 0.01 | | |
| 152 | CH1 | E | E | E | E | 0.27 | | DE |
| 153 | CH1 | P | P | P | P | 0.47 | | |
| 154 | CH1 | V | V | V | V | 0.12 | | |
| 155 | CH1 | T | T | T | T | 0.44 | | DE |
| 156 | CH1 | V | V | V | V | 0.14 | | |
| 157 | CH1 | S | S | S | S | 0.32 | | DE |
| 158 | CH1 | W | W | W | W | 0.01 | | |
| 159 | CH1 | N | N | N | N | 0.20 | | DE |
| 160 | CH1 | S | S | S | S | 0.82 | | DE |
| 161 | CH1 | G | G | G | G | 0.47 | | DE |
| 162 | CH1 | A | A | A | A | 0.79 | | DE |
| 163 | CH1 | L | L | L | L | 0.18 | | |
| 164 | CH1 | T | T | T | T | 0.71 | | DE |
| 165 | CH1 | S | S | S | S | 0.66 | | DE |
| 166 | CH1 | G | G | G | G | 0.38 | | |

Figure 2B

| EU | Domain | 126 IgG1 | 127 IgG2 | 128 IgG3 | 129 IgG4 | Fraction Exposed | Notes | Subs |
|---|---|---|---|---|---|---|---|---|
| 167 | CH1 | V | V | V | V | 0.24 | | |
| 168 | CH1 | H | H | H | H | 0.12 | | |
| 169 | CH1 | T | T | T | T | 0.37 | | |
| 170 | CH1 | F | F | F | F | 0.02 | | |
| 171 | CH1 | P | P | P | P | 0.42 | | |
| 172 | CH1 | A | A | A | A | 0.24 | | |
| 173 | CH1 | V | V | V | V | 0.23 | | |
| 174 | CH1 | L | L | L | L | 0.47 | | |
| 175 | CH1 | Q | Q | Q | Q | 0.13 | | |
| 176 | CH1 | S | S | S | S | 1.00 | | DE |
| 177 | CH1 | S | S | S | S | 0.61 | | DE |
| 178 | CH1 | G | G | G | G | 0.35 | | DE |
| 179 | CH1 | L | L | L | L | 0.19 | | |
| 180 | CH1 | Y | Y | Y | Y | 0.19 | | |
| 181 | CH1 | S | S | S | S | 0.06 | | |
| 182 | CH1 | L | L | L | L | 0.08 | | |
| 183 | CH1 | S | S | S | S | 0.02 | | |
| 184 | CH1 | S | S | S | S | 0.00 | | |
| 185 | CH1 | V | V | V | V | 0.01 | | |
| 186 | CH1 | V | V | V | V | 0.00 | | |
| 187 | CH1 | T | T | T | T | 0.21 | | |
| 188 | CH1 | V | V | V | V | 0.04 | | |
| 189 | CH1 | P | P | P | P | 0.54 | | |
| 190 | CH1 | S | S | S | S | 0.42 | | DE |
| 191 | CH1 | S | S | S | S | 0.81 | | DE |
| 192 | CH1 | S | N | S | S | 0.16 | | |
| 193 | CH1 | L | F | L | L | 0.16 | | |
| 194 | CH1 | G | G | G | G | 0.91 | | DE |
| 195 | CH1 | T | T | T | T | 0.82 | | DE |
| 196 | CH1 | Q | Q | Q | K | 0.44 | | DE |
| 197 | CH1 | T | T | T | T | 0.39 | | DE |
| 198 | CH1 | Y | Y | Y | Y | 0.04 | | |
| 199 | CH1 | I | T | T | T | 0.26 | | DE |
| 200 | CH1 | C | C | C | C | 0.00 | | |
| 201 | CH1 | N | N | N | N | 0.15 | | |
| 202 | CH1 | V | V | V | V | 0.02 | | |
| 203 | CH1 | N | D | N | D | 0.18 | Isotypic | DE |
| 204 | CH1 | H | H | H | H | 0.00 | | |
| 205 | CH1 | K | K | K | K | 0.62 | | DE |
| 206 | CH1 | P | P | P | P | 0.30 | | |
| 207 | CH1 | S | S | S | S | 0.26 | | |
| 208 | CH1 | N | N | N | N | 0.80 | | DE |
| 209 | CH1 | T | T | T | T | 0.21 | | |
| 210 | CH1 | K | K | K | K | 0.73 | | DE |
| 211 | CH1 | V | V | V | V | 0.28 | | |
| 212 | CH1 | D | D | D | D | 0.66 | | DE |
| 213 | CH1 | K | K | K | K | 0.20 | Interface w/ CL | |
| 214 | CH1 | K/R | T | R | R | 0.43 | Isotypic | DE |
| 215 | CH1 | V | V | V | V | 0.03 | | |
| 216 | CH1 | E | E | E | E | 0.50 | | DE |
| 217 | CH1 | P | R | L | S | 0.41 | | |
| 218 | CH1 | K | K | K | K | 0.86 | | DE |

Figure 2C

| EU | Domain | 126 IgG1 | 127 IgG2 | 128 IgG3 | 129 IgG4 | Fraction Exposed | Notes | Subs |
|---|---|---|---|---|---|---|---|---|
| 219 | CH1 | S | C | T | Y | | | DE |
| 220 | CH1 | C | C | P | G | | | |

Figure 3A

SEQ ID NO: 130

| EU | Ckappa | Fraction Exposed | Notes | Subs |
|---|---|---|---|---|
| 108 | R | 0.33 | | DE |
| 109 | T | 0.68 | | DE |
| 110 | V | 0.42 | | DE |
| 111 | A | 0.20 | | |
| 112 | A | 0.38 | | DE |
| 113 | P | 0.09 | | |
| 114 | S | 0.46 | | DE |
| 115 | V | 0.08 | | |
| 116 | F | 0.20 | | |
| 117 | I | 0.11 | | |
| 118 | F | 0.02 | | |
| 119 | P | 0.40 | | |
| 120 | P | 0.08 | | |
| 121 | S | 0.11 | | |
| 122 | D | 0.54 | | DE |
| 123 | E | 0.46 | | DE |
| 124 | Q | 0.01 | | |
| 125 | L | 0.07 | | |
| 126 | K | 0.76 | | DE |
| 127 | S | 0.65 | | DE |
| 128 | G | 0.37 | | DE |
| 129 | T | 0.34 | | DE |
| 130 | A | 0.00 | | |
| 131 | S | 0.02 | | |
| 132 | V | 0.00 | | |
| 133 | V | 0.00 | | |
| 134 | C | 0.00 | | |
| 135 | L | 0.00 | | |
| 136 | L | 0.00 | | |
| 137 | N | 0.04 | | |
| 138 | N | 0.31 | | |
| 139 | F | 0.00 | | |
| 140 | Y | 0.12 | | |
| 141 | P | 0.16 | | |
| 142 | R | 0.37 | Interface w/ VL | |
| 143 | E | 0.67 | | DE |
| 144 | A | 0.25 | | |
| 145 | K | 0.48 | | DE |
| 146 | V | 0.15 | | |
| 147 | Q | 0.17 | | DE |
| 148 | W | 0.01 | | |
| 149 | K | 0.27 | | DE |
| 150 | V | 0.04 | | |
| 151 | D | 0.43 | | DE |
| 152 | N | 0.72 | | DE |
| 153 | A | 0.47 | | DE |
| 154 | L | 0.56 | exposed hydrophobic | DE |
| 155 | Q | 0.22 | | |
| 156 | S | 0.80 | | DE |
| 157 | G | 0.97 | | DE |

Figure 3B

SEQ ID NO: 130

| EU | Ckappa | Fraction Exposed | Notes | Subs |
|---|---|---|---|---|
| 158 | N | 0.35 | | |
| 159 | S | 0.36 | | |
| 160 | Q | 0.34 | | |
| 161 | E | 0.46 | | |
| 162 | S | 0.11 | | |
| 163 | V | 0.28 | | |
| 164 | T | 0.11 | | |
| 165 | E | 0.42 | | |
| 166 | Q | 0.04 | | |
| 167 | D | 0.27 | | DE |
| 168 | S | 0.36 | | DE |
| 169 | K | 0.79 | Interface w/ VL | DE |
| 170 | D | 0.38 | | DE |
| 171 | S | 0.03 | | |
| 172 | T | 0.04 | | |
| 173 | Y | 0.04 | | |
| 174 | S | 0.00 | | |
| 175 | L | 0.02 | | |
| 176 | S | 0.05 | | |
| 177 | S | 0.01 | | |
| 178 | T | 0.17 | | |
| 179 | L | 0.00 | | |
| 180 | T | 0.42 | | DE |
| 181 | L | 0.12 | | |
| 182 | S | 0.37 | | DE |
| 183 | K | 0.33 | | DE |
| 184 | A | 0.53 | | DE |
| 185 | D | 0.45 | | DE |
| 186 | Y | 0.05 | | |
| 187 | E | 0.46 | | DE |
| 188 | K | 0.65 | | DE |
| 189 | H | 0.30 | | |
| 190 | K | 0.44 | | DE |
| 191 | V | 0.35 | | DE |
| 192 | Y | 0.00 | | |
| 193 | A | 0.11 | | DE |
| 194 | C | 0.00 | | |
| 195 | E | 0.24 | | DE |
| 196 | V | 0.00 | | |
| 197 | T | 0.34 | | DE |
| 198 | H | 0.05 | | |
| 199 | Q | 0.66 | | DE |
| 200 | G | 0.37 | | DE |
| 201 | L | 0.16 | | |
| 202 | S | 0.98 | | DE |
| 203 | S | 0.55 | | DE |
| 204 | P | 0.51 | | |
| 205 | V | 0.26 | | |
| 206 | T | 0.50 | | DE |
| 207 | K | 0.36 | | DE |
| 208 | S | 0.50 | | DE |
| 209 | F | 0.14 | | |
| 210 | N | 0.30 | | DE |
| 211 | R | 0.26 | | DE |

Figure 3C

|  | EU | Ckappa | Fraction Exposed | Notes | Subs |
|---|---|---|---|---|---|
| SEQ ID NO: 130 | 212 | G | 0.97 |  | DE |
|  | 213 | E | 0.91 |  | DE |
|  | 214 | C |  |  |  |

Figure 4

IgG1-CH1-pI(6) (SEQ ID NO: 7)

AETKGPSVFPLAPSSESTSGGTAALGCLVKDYFPEPVTVSWNSGALESGVHTFPAVLQS
SGLYSLSSVVTVPSSSLGTQTYICNVNHEPSDTEVDKKVEPKSCDKTHTCPPCPAPELLG
GPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPGK

CK-pI(6) (SEQ ID NO: 8)

RTVAAPSVFIFPPSDEQLESGTASVVCLLNNFYPREAEVQWKVDDALQEGNSQESVTEQ
DSEDSTYSLSSTLTLSKADYEKHKVYACEVTHQGLESPVTKSFNRGEC

IgG1-CH1-pI(6)-434S (SEQ ID NO: 52)

AETKGPSVFPLAPSSESTSGGTAALGCLVKDYFPEPVTVSWNSGALESGVHTFPAVLQS
SGLYSLSSVVTVPSSSLGTQTYICNVNHEPSDTEVDKKVEPKSCDKTHTCPPCPAPELLG
GPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHSHYTQKSLSLSPGK

IgG1-CH1-pI(6)-428L/434S (SEQ ID NO: 53)

AETKGPSVFPLAPSSESTSGGTAALGCLVKDYFPEPVTVSWNSGALESGVHTFPAVLQS
SGLYSLSSVVTVPSSSLGTQTYICNVNHEPSDTEVDKKVEPKSCDKTHTCPPCPAPELLG
GPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVLHEALHSHYTQKSLSLSPGK

Figure 5

Anti-VEGF VH (SEQ ID NO: 9)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSS

Anti-VEGF VL (SEQ ID NO: 10)

DIQMTQSPSSLSASVGDRVTITCSASQDISNYLNWYQQKPGKAPKVLIYFTSSLHSGVPS
RFSGSGSGTDFTLTISSLQPEDFATYYCQQYSTVPWTFGQGTKVEIK

Figure 6

Heavy chain of XENP9493_Bevacizumab-IgG1-CH1-pI(6)-CK-pI(6) (SEQ ID NO: 11)
EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSAETKGPSVFPLAPSSESTSGGTAALGCLVKDYFPEPVTVSWNSGALESGVH
TFPAVLQSSGLYSLSSVVTVPSSSLGTQTYICNVNHEPSDTEVDKKVEPKSCDKTHTCPP
CPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK Light chain of XENP9493_Bevacizumab-IgG1-CH1-pI(6)-CK-pI(6) (SEQ ID NO: 12)
DIQMTQSPSSLSASVGDRVTITCSASQDISNYLNWYQQKPGKAPKVLIYFTSSLHSGVPS
RFSGSGSGTDFTLTISSLQPEDFATYYCQQYSTVPWTFGQGTKVEIKRTVAAPSVFIFPP
SDEQLESGTASVVCLLNNFYPREAEVQWKVDDALQEGNSQESVTEQDSEDSTYSLSST
LTLSKADYEKHKVYACEVTHQGLESPVTKSFNRGEC Anti-VEGF IgG1-CH1-pI(6) + Cκ-pI(6) (XENP9493)

Figure 17A

SEQ ID NOS: 2 - 5

| EU Index | 118 | 119 | 120 | 121 | 122 | 123 | 124 | 125 | 126 | 127 | 128 | 129 | 130 | 131 | 132 | 133 | 134 | 135 | 136 | 137 | 138 |
|---|---|---|---|---|---|---|---|---|---|---|---|---|---|---|---|---|---|---|---|---|---|
| IgG1 | A | S | T | K | G | P | S | V | F | P | L | A | P | S | S | K | S | T | S | G | G |
| IgG2 | A | S | T | K | G | P | S | V | F | P | L | A | P | C | S | R | S | T | S | G | E |
| IgG3 | A | S | T | K | G | P | S | V | F | P | L | A | P | C | S | R | S | T | S | G | G |
| IgG4 | A | S | T | K | G | P | S | V | F | P | L | A | P | C | S | R | S | T | S | G | E |

| EU Index | 139 | 140 | 141 | 142 | 143 | 144 | 145 | 146 | 147 | 148 | 149 | 150 | 151 | 152 | 153 | 154 | 155 | 156 | 157 | 158 | 159 |
|---|---|---|---|---|---|---|---|---|---|---|---|---|---|---|---|---|---|---|---|---|---|
| IgG1 | T | A | A | L | G | C | L | V | K | D | Y | F | P | E | P | V | T | V | S | W | N |
| IgG2 | T | A | A | L | G | C | L | V | K | D | Y | F | P | E | P | V | T | V | S | W | N |
| IgG3 | T | A | A | L | G | C | L | V | K | D | Y | F | P | E | P | V | T | V | S | W | N |
| IgG4 | T | A | A | L | G | C | L | V | K | D | Y | F | P | E | P | V | T | V | S | W | N |

| EU Index | 160 | 161 | 162 | 163 | 164 | 165 | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|---|---|---|---|---|---|
| IgG1 | S | G | A | L | T | S | G | V | H | T | F | P | A | V | L | Q | S | S | G | L | Y |
| IgG2 | S | G | A | L | T | S | G | V | H | T | F | P | A | V | L | Q | S | S | G | L | Y |
| IgG3 | S | G | A | L | T | S | G | V | H | T | F | P | A | V | L | Q | S | S | G | L | Y |
| IgG4 | S | G | A | L | T | S | G | V | H | T | F | P | A | V | L | Q | S | S | G | L | Y |

| EU Index | 181 | 182 | 183 | 184 | 185 | 186 | 187 | 188 | 189 | 190 | 191 | 192 | 193 | 194 | 195 | 196 | 197 | 198 | 199 | 200 | 201 |
|---|---|---|---|---|---|---|---|---|---|---|---|---|---|---|---|---|---|---|---|---|---|
| IgG1 | S | L | S | S | V | V | T | V | P | S | S | S | L | G | T | Q | T | Y | I | C | N |
| IgG2 | S | L | S | S | V | V | T | V | P | S | S | N | F | G | T | Q | T | Y | T | C | N |
| IgG3 | S | L | S | S | V | V | T | V | P | S | S | S | L | G | T | Q | T | Y | T | C | N |
| IgG4 | S | L | S | S | V | V | T | V | P | S | S | L | L | G | T | K | T | Y | T | C | N |

| EU Index | 202 | 203 | 204 | 205 | 206 | 207 | 208 | 209 | 210 | 211 | 212 | 213 | 214 | 215 | 216 | 217 | 218 | 219 | 220 |
|---|---|---|---|---|---|---|---|---|---|---|---|---|---|---|---|---|---|---|---|
| IgG1 | V | N | H | K | P | S | N | T | K | V | D | K | K/R | V | E | P | K | S | C |
| IgG2 | V | D | H | K | P | S | N | T | K | V | D | K | T | V | E | R | K | C | C |
| IgG3 | V | N | H | K | P | S | N | T | K | V | D | K | R | V | E | L | K | C | T |
| IgG4 | V | D | H | K | P | S | N | T | K | V | D | K | R | V | E | S | K | Y | G |

Figure 17B

SEQ ID NOS: 2 - 5

| EU Index | 221 | 222 | 223 | 224 | 225 | 226 | 227 | 228 |
|---|---|---|---|---|---|---|---|---|
| IgG1 | D | K | T | H | T | C | P | P |
| IgG2 |   | V |   | E |   | C | P | P |
| IgG3 |   |   |   |   |   | C | P | R |
| IgG4 | L | G |   |   | P | C | P | S |

| EU Index |   |   |   |   |   |   |   |   |
|---|---|---|---|---|---|---|---|---|
| IgG1 | P | C | P | E | P | K | S | C | D | T |
| IgG2 | P | C | P |   |   |   |   |   |   |   |
| IgG3 | P | R | C |   |   |   |   |   |   |   |
| IgG4 |   |   |   |   |   |   |   |   |   |   |

| EU Index | 229 | 230 | 231 | 232 | 233 | 234 | 235 | 236 |
|---|---|---|---|---|---|---|---|---|
| IgG1 | C | P | A | P | E | L | L | G |
| IgG2 | C | P | A | P | P | V | A | G |
| IgG3 | C | P | A | P | E | L | L | G |
| IgG4 | C | P | A | P | E | F | L | G |

| EU Index | 237 | 238 | 239 | 240 | 241 | 242 | 243 | 244 | 245 | 246 | 247 | 248 | 249 | 250 | 251 | 252 | 253 | 254 | 255 | 256 | 257 |
|---|---|---|---|---|---|---|---|---|---|---|---|---|---|---|---|---|---|---|---|---|---|
| IgG1 | G | P | S | V | F | L | F | P | P | K | P | K | D | T | L | M | — | S | R | T | P |
| IgG2 | G | P | S | V | F | L | F | P | P | K | P | K | D | T | L | M | — | S | R | T | P |
| IgG3 | G | P | S | V | F | L | F | P | P | K | P | K | D | T | L | M | — | S | R | T | P |
| IgG4 | G | P | S | V | F | L | F | P | P | K | P | K | D | T | L | M | — | S | R | T | P |

Figure 17C

SEQ ID NOS: 2 - 5

| EU Index | 258 | 259 | 260 | 261 | 262 | 263 | 264 | 265 | 266 | 267 | 268 | 269 | 270 | 271 | 272 | 273 | 274 | 275 | 276 | 277 | 278 |
|---|---|---|---|---|---|---|---|---|---|---|---|---|---|---|---|---|---|---|---|---|---|
| IgG1 | E | V | T | C | V | V | V | D | V | S | H | E | D | P | E | V | K | F | N | W | Y |
| IgG2 | E | V | T | C | V | V | V | D | V | S | H | E | D | P | E | V | Q | F | N | W | Y |
| IgG3 | E | V | T | C | V | V | V | D | V | S | H | E | D | P | E | V | Q | F | K | W | Y |
| IgG4 | E | V | T | C | V | V | V | D | V | S | Q | E | D | P | E | V | Q | F | N | W | Y |

| EU Index | 279 | 280 | 281 | 282 | 283 | 284 | 285 | 286 | 287 | 288 | 289 | 290 | 291 | 292 | 293 | 294 | 295 | 296 | 297 | 298 | 299 |
|---|---|---|---|---|---|---|---|---|---|---|---|---|---|---|---|---|---|---|---|---|---|
| IgG1 | V | D | G | V | E | V | H | N | A | K | T | K | P | R | E | E | Q | Y | N | S | T |
| IgG2 | V | D | G | V/M | E | V | H | N | A | K | T | K | P | R | E | E | Q | F | N | S | T |
| IgG3 | V | D | G | V | E | V | H | N | A | K | T | K | P | R | E | E | Q | Y | N | S | T |
| IgG4 | V | D | G | V | E | V | H | N | A | K | T | K | P | R | E | E | Q | F | N | S | T |

| EU Index | 300 | 301 | 302 | 303 | 304 | 305 | 306 | 307 | 308 | 309 | 310 | 311 | 312 | 313 | 314 | 315 | 316 | 317 | 318 | 319 | 320 |
|---|---|---|---|---|---|---|---|---|---|---|---|---|---|---|---|---|---|---|---|---|---|
| IgG1 | Y | R | V | V | S | V | L | T | V | L | H | Q | D | W | L | N | G | K | E | Y | K |
| IgG2 | F | R | V | V | S | V | L | T | V | V | H | Q | D | W | L | N | G | K | E | Y | K |
| IgG3 | F | R | V | V | S | V | L | T | V | L | H | Q | D | W | L | N | G | K | E | Y | K |
| IgG4 | Y | R | V | V | S | V | L | T | V | L | H | Q | D | W | L | N | G | K | E | Y | K |

| EU Index | 321 | 322 | 323 | 324 | 325 | 326 | 327 | 328 | 329 | 330 | 331 | 332 | 333 | 334 | 335 | 336 | 337 | 338 | 339 | 340 |
|---|---|---|---|---|---|---|---|---|---|---|---|---|---|---|---|---|---|---|---|---|
| IgG1 | C | K | V | S | N | K | A | L | P | A | P | I | E | K | T | I | S | K | A | K |
| IgG2 | C | K | V | S | N | K | G | L | P | A | P | — | E | K | T | — | S | K | T | K |
| IgG3 | C | K | V | S | N | K | A | L | P | A | P | I | E | K | T | I | S | K | T | K |
| IgG4 | C | K | V | S | N | K | G | L | P | S | S | — | E | K | T | — | S | K | A | K |

| EU Index | 341 | 342 | 343 | 344 | 345 | 346 | 347 | 348 | 349 | 350 | 351 | 352 | 353 | 354 | 355 | 356 | 357 | 358 | 359 | 360 | 361 |
|---|---|---|---|---|---|---|---|---|---|---|---|---|---|---|---|---|---|---|---|---|---|
| IgG1 | G | Q | P | R | E | P | Q | V | Y | T | L | P | P | S | R | D/E | E | L/M | T | K | N |
| IgG2 | G | Q | P | R | E | P | Q | V | Y | T | L | P | P | S | R | E | E | M | T | K | N |
| IgG3 | G | Q | P | R | E | P | Q | V | Y | T | L | P | P | S | R | E | E | M | T | K | N |
| IgG4 | G | Q | P | R | E | P | Q | V | Y | T | L | P | P | S | Q | E | E | M | T | K | N |

Figure 17D

SEQ ID NOS: 2 - 5

| EU Index | 362 | 363 | 364 | 365 | 366 | 367 | 368 | 369 | 370 | 371 | 372 | 373 | 374 | 375 | 376 | 377 | 378 | 379 | 380 | 381 | 382 |
|---|---|---|---|---|---|---|---|---|---|---|---|---|---|---|---|---|---|---|---|---|---|
| IgG1 | Q | V | S | L | T | C | L | V | K | G | F | Y | P | S | D | I | A | V | E | W | E |
| IgG2 | Q | V | S | L | T | C | L | V | K | G | F | Y | P | S | D | I | A | V | E | W | E |
| IgG3 | Q | V | S | L | T | C | L | V | K | G | F | Y | P | S | D | I | A | V | E | W | E |
| IgG4 | Q | V | S | L | T | C | L | V | K | G | F | Y | P | S | D | I | A | V | E | W | E |

| EU Index | 383 | 384 | 385 | 386 | 387 | 388 | 389 | 390 | 391 | 392 | 393 | 394 | 395 | 396 | 397 | 398 | 399 | 400 | 401 | 402 | 403 |
|---|---|---|---|---|---|---|---|---|---|---|---|---|---|---|---|---|---|---|---|---|---|
| IgG1 | S | N | G | Q | P | E | N | N | Y | K | T | T | P | P | V | L | D | S | D | G | S |
| IgG2 | S | N | G | Q | P | E | N | N | Y | K | T | T | P | P | M | L | D | S | D | G | S |
| IgG3 | S | S | G | Q | P | E | N | N | Y | N | T | T | P | P | M | L | D | S | D | G | S |
| IgG4 | S | N | G | Q | P | E | N | N | Y | K | T | T | P | P | V | L | D | S | D | G | S |

| EU Index | 404 | 405 | 406 | 407 | 408 | 409 | 410 | 411 | 412 | 413 | 414 | 415 | 416 | 417 | 418 | 419 | 420 | 421 | 422 | 423 | 424 |
|---|---|---|---|---|---|---|---|---|---|---|---|---|---|---|---|---|---|---|---|---|---|
| IgG1 | F | F | L | Y | S | K | L | T | V | D | K | S | R | W | Q | Q | G | N | V | F | S |
| IgG2 | F | F | L | Y | S | K | L | T | V | D | K | S | R | W | Q | Q | G | N | V | F | S |
| IgG3 | F | F | L | Y | S | K | L | T | V | D | K | S | R | W | Q | Q | G | N | I | F | S |
| IgG4 | F | F | L | Y | S | R | L | T | V | D | K | S | R | W | Q | E | G | N | V | F | S |

| EU Index | 425 | 426 | 427 | 428 | 429 | 430 | 431 | 432 | 433 | 434 | 435 | 436 | 437 | 438 | 439 | 440 | 441 | 442 | 443 | 444 | 445 |
|---|---|---|---|---|---|---|---|---|---|---|---|---|---|---|---|---|---|---|---|---|---|
| IgG1 | C | S | V | M | H | E | A/G | L | H | N | H | Y | T | Q | K | S | L | S | L | S | P |
| IgG2 | C | S | V | M | H | E | A | L | H | N | H | Y | T | Q | K | S | L | S | L | S | P |
| IgG3 | C | S | V | M | H | E | A | L | H | N | R | F | T | Q | K | S | L | S | L | S | P |
| IgG4 | C | S | V | M | H | E | A | L | H | N | H | Y | T | Q | K | S | L | S | L | S | L |

| EU Index | 446 | 447 | | | | | | |
|---|---|---|---|---|---|---|---|---|
| IgG1 | G | K | | | | | | D |
| IgG2 | G | K | | | | | | E |
| IgG3 | G | K | | | | | | D |
| IgG4 | G | K | | | | | | E |

Figure 18

SEQ ID NO: 131
SEQ ID NO: 132

| EU Index | 108 | 109 | 110 | 111 | 112 | 113 | 114 | 115 | 116 | 117 | 118 | 119 | 120 | 121 | 122 | 123 | 124 | 125 |
|---|---|---|---|---|---|---|---|---|---|---|---|---|---|---|---|---|---|---|
| Cκ | R | T | V | A | A | P | S | V | F | I | F | P | P | S | D | E | Q | L |
| Cλ | Q | P | K | A | A | P | S | V | T | L | F | P | P | S | S | E | E | L |

| EU Index | 126 | 127 | 128 | 129 | 130 | 131 | 132 | 133 | 134 | 135 | 136 | 137 | 138 | 139 | 140 | 141 | 142 | 143 |
|---|---|---|---|---|---|---|---|---|---|---|---|---|---|---|---|---|---|---|
| Cκ | K | S | G | T | A | S | V | V | C | L | L | N | N | F | Y | P | R | E |
| Cλ | Q | A | N | K | A | T | L | V | C | L | I | S | D | F | Y | P | G | A |

| EU Index | 144 | 145 | 146 | 147 | 148 | 149 | 150 | 151 | 152 | 153 | | 154 | 155 | 156 | 157 | 158 | 159 | 160 |
|---|---|---|---|---|---|---|---|---|---|---|---|---|---|---|---|---|---|---|
| Cκ | A | K | V | Q | W | K | V | D | N | A | | L | Q | S | G | N | S | Q |
| Cλ | V | T | V | A | W | K | A | D | S | S | P | V | K | A | G | | | V |

| EU Index | 161 | 162 | 163 | 164 | 165 | 166 | 167 | 168 | 169 | 170 | 171 | 172 | 173 | 174 | 175 | 176 | 177 | 178 |
|---|---|---|---|---|---|---|---|---|---|---|---|---|---|---|---|---|---|---|
| Cκ | E | S | V | T | E | Q | D | S | K | D | S | T | Y | S | L | S | S | T |
| Cλ | E | T | T | T | P | S | K | Q | S | N | N | K | Y | A | A | S | S | Y |

| EU Index | 179 | 180 | 181 | 182 | 183 | 184 | 185 | 186 | 187 | 188 | 189 | 190 | 191 | 192 | 193 | 194 | 195 | 196 |
|---|---|---|---|---|---|---|---|---|---|---|---|---|---|---|---|---|---|---|
| Cκ | L | T | L | S | K | A | D | Y | E | K | H | K | V | Y | A | C | E | V |
| Cλ | L | S | L | T | P | E | Q | W | K | S | H | R | S | Y | S | C | Q | V |

| EU Index | 197 | 198 | 199 | 200 | 201 | 202 | 203 | 204 | 205 | 206 | 207 | 208 | 209 | 210 | 211 | 212 | 213 | 214 |
|---|---|---|---|---|---|---|---|---|---|---|---|---|---|---|---|---|---|---|
| Cκ | T | H | Q | G | L | S | S | P | V | T | K | S | F | N | R | G | E | C |
| Cλ | T | H | E | G | | | S | T | V | E | K | T | V | A | P | T | E | C |

Figure 19A

IgG1-WT (SEQ ID NO: 138)
ASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPGK

IgG2-WT (SEQ ID NO: 139)
ASTKGPSVFPLAPCSRSTSESTAALGCLVKDYFPEPVTVSWNSGALTSGVHTFPAVLQS
SGLYSLSSVVTVPSSNFGTQTYTCNVDHKPSNTKVDKTVERKCCVECPPCPAPPVAGPS
VFLFPPKPKDTLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQVYTLPPSREE
MTKNQVSLTCLVKGFYPSDIAVEWESNGQPENNYKTTPPMLDSDGSFFLYSKLTVDKSR
WQQGNVFSCSVMHEALHNHYTQKSLSLSPGK pI-iso1 (SEQ ID NO: 13)
ASTKGPSVFPLAPSSKSTSESTAALGCLVKDYFPEPVTVSWNSGALTSGVHTFPAVLQS
SGLYSLSSVVTVPSSSLGTQTYTCNVDHKPSNTKVDKTVEPKSCDTTHTCPPCPAPELL
GGPSVFLFPPKPKDTLMISRTPEVTCVVVDVSQEDPEVQFNWYVDGVEVHNAKTKPRE
EQYNSTYRVVSVLTVLHQDWLNGKEYKCKVSNKALPAPIEKTISKAKGQPREPQVYTLPP
SQEEMTKNQVSLTCLVKGFYPSDIAVEWESSGQPENNYNTTPPMLDSDGSFFLYSKLTV
DKSRWQEGNVFSCSVMHEALHNHYTQKSLSLSPG pI-iso1(NF) (SEQ ID NO: 14)
ASTKGPSVFPLAPSSKSTSESTAALGCLVKDYFPEPVTVSWNSGALTSGVHTFPAVLQS
SGLYSLSSVVTVPSSNFGTQTYTCNVDHKPSNTKVDKTVEPKSCDTTHTCPPCPAPELL
GGPSVFLFPPKPKDTLMISRTPEVTCVVVDVSQEDPEVQFNWYVDGVEVHNAKTKPRE
EQYNSTYRVVSVLTVLHQDWLNGKEYKCKVSNKALPAPIEKTISKAKGQPREPQVYTLPP
SQEEMTKNQVSLTCLVKGFYPSDIAVEWESSGQPENNYNTTPPMLDSDGSFFLYSKLTV
DKSRWQEGNVFSCSVMHEALHNHYTQKSLSLSPG pI-iso1(NF-VE) (SEQ ID NO: 15)
ASTKGPSVFPLAPSSKSTSESTAALGCLVKDYFPEPVTVSWNSGALTSGVHTFPAVLQS
SGLYSLSSVVTVPSSNFGTQTYTCNVDHKPSNTKVDKTVEPKSCVECPPCPAPELLGGP
SVFLFPPKPKDTLMISRTPEVTCVVVDVSQEDPEVQFNWYVDGVEVHNAKTKPREEQYN
STYRVVSVLTVLHQDWLNGKEYKCKVSNKALPAPIEKTISKAKGQPREPQVYTLPPSQEE
MTKNQVSLTCLVKGFYPSDIAVEWESSGQPENNYNTTPPMLDSDGSFFLYSKLTVDKSR
WQEGNVFSCSVMHEALHNHYTQKSLSLSPG pI-iso1(NF-VE-DEDE) (SEQ ID NO:16)
ASTKGPSVFPLAPSSKSTSESTAALGCLVKDYFPEPVTVSWNSGALTSGVHTFPAVLQS
SGLYSLSSVVTVPSSNFGTQTYTCNVDHKPSNTKVDKTVEPKSCVECPPCPAPELLGGP
SVFLFPPKPKDTLMISRTPEVTCVVVDVSQEDPEVQFNWYVDGVEVHNAKTKPREEQYN
STYRVVSVLTVLHQDWLNGKEYKCKVSNKALPAPIEKTISKAKGQPREPQVYTLPPSQEE
MTKNQVSLTCLVKGFYPSDIAVEWESSGQPENNYNTTPPMLDSDGSFFLYSKLTVDKSR
WQEGNVFSCSVMHEALHNHYTQKSLSLSPGDEDE

Figure 19B

Bevacizumab VH (SEQ ID NO:140)
EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSS

IgG1-434S (SEQ ID NO: 50)
ASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHSHYTQKSLSLSPGK

IgG2-434S (SEQ ID NO: 51)
ASTKGPSVFPLAPCSRSTSESTAALGCLVKDYFPEPVTVSWNSGALTSGVHTFPAVLQS
SGLYSLSSVVTVPSSNFGTQTYTCNVDHKPSNTKVDKTVERKCC_V_E_CPPCPAPPV_
AGPSVFLFPPKPKDTLMISRTPEVTCVVVDVSHEDPEVQFNWYVDGVEVHNAKTKPREE
QFNSTFRVVSVLTVVHQDWLNGKEYKCKVSNKGLPAPIEKTISKTKGQPREPQVYTLPP
SREEMTKNQVSLTCLVKGFYPSDIAVEWESNGQPENNYKTTPPMLDSDGSFFLYSKLTV
DKSRWQQGNVFSCSVMHEALHSHYTQKSLSLSPGK

IgG1-pI(6)-Neutral-to-DE (SEQ ID NO: 55)
AETKGPSVFPLAPSSKSTSGGTAALGCLVKDYFPEPVTVSWNSGALESGVHTFPAVLQS
SGLYSLSSVVTVPSSSLGTQTYICNVNHKPSDTKVDKKVEPKSCDKTHTCPPCPAPELLG
GPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPGK

IgG1-pI(6)-KR-to-Neutral (SEQ ID NO: 56)
ASTKGPSVFPLAPSSQSTSGGTAALGCLVKDYFPEPVTVSWNSGALTSGVHTFPAVLQS
SGLYSLSSVVTVPSSSLGTQTYICNVNHQPSNTQVDKKVEPKSCDKTHTCPPCPAPELL
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVD
KSRWQQGNVFSCSVMHEALHNHYTQKSLSLSPGK

IgG1-pI(6)-KR-to-DE (SEQ ID NO: 57)
ASTKGPSVFPLAPSSESTSGGTAALGCLVKDYFPEPVTVSWNSGALTSGVHTFPAVLQS
SGLYSLSSVVTVPSSSLGTQTYICNVNHEPSNTEVDKKVEPKSCDKTHTCPPCPAPELLG
GPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPGK

Figure 20

CK-WT (SEQ ID NO: 141)
RTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

CK-pI(3) (SEQ ID NO: 17)
RTVAAPSVFIFPPSDEQLESGTASVVCLLNNFYPREAEVQWKVDNALQSGNSQESVTEQ
DSEDSTYSLSSTLTLSKADYEKHKVYACEVTHQGLSSPVTKSFNRGEC

CK-pI(6) (SEQ ID NO:142)
RTVAAPSVFIFPPSDEQLESGTASVVCLLNNFYPREAEVQWKVDDALQEGNSQESVTEQ
DSEDSTYSLSSTLTLSKADYEKHKVYACEVTHQGLESPVTKSFNRGEC

CK-pI(6-DEDE) (SEQ ID NO: 18)
RTVAAPSVFIFPPSDEQLESGTASVVCLLNNFYPREAEVQWKVDDALQEGNSQESVTEQ
DSEDSTYSLSSTLTLSKADYEKHKVYACEVTHQGLESPVTKSFNRGECDEDE

Bevacizumab VL (SEQ ID NO:143)
DIQMTQSPSSLSASVGDRVTITCSASQDISNYLNWYQQKPGKAPKVLIYFTSSLHSGVPS
RFSGSGSGTDFTLTISSLQPEDFATYYCQQYSTVPWTFGQGTKVEIK

CK-Pi(3) (SEQ ID NO: 54)
RTVAAPSVFIFPPSDEQLESGTASVVCLLNNFYPREAEVQWKVDNALQSGNSQESVTEQ
DSEDSTYSLSSTLTLSKADYEKHKVYACEVTHQGLSSPVTKSFNRGEC

CK-N152D S156E S202E (SEQ ID NO: 58)
RTVAAPSVFIFPPSDEQLKSGTASVVCLLNNFYPREAKVQWKVDDALQEGNSQESVTEQ
DSKDSTYSLSSTLTLSKADYEKHKVYACEVTHQGLESPVTKSFNRGEC

CK-K126Q K145Q K169Q (SEQ ID NO: 59)
RTVAAPSVFIFPPSDEQLQSGTASVVCLLNNFYPREAQVQWKVDNALQSGNSQESVTE
QDSQDSTYSLSSTLTLSKADYEKHKVYACEVTHQGLSSPVTKSFNRGEC

CK-K126E K145E K169E (SEQ ID NO: 60)
RTVAAPSVFIFPPSDEQLESGTASVVCLLNNFYPREAEVQWKVDNALQSGNSQESVTEQ
DSEDSTYSLSSTLTLSKADYEKHKVYACEVTHQGLSSPVTKSFNRGEC

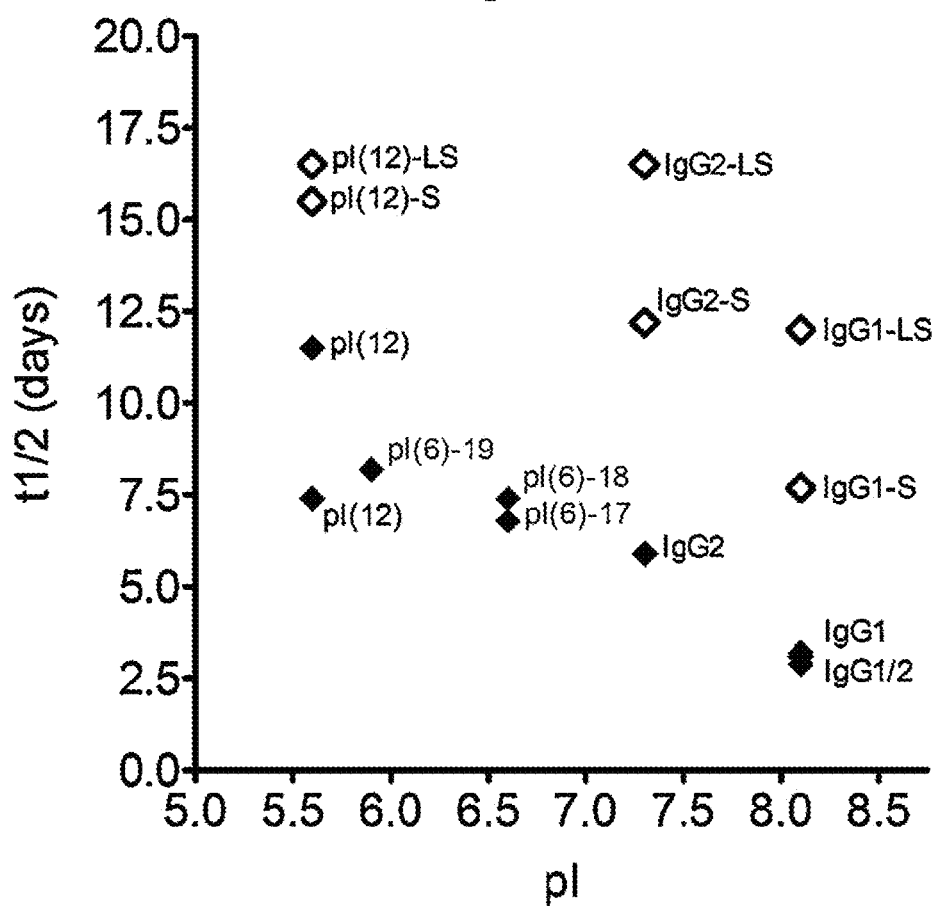

| EU | 118 | 119 | 120 | 121 | 122 | 123 | 124 | 125 | 126 | 127 | 128 | 129 | 130 | 131 | 132 | 133 | 134 | 135 | 136 | 137 | 138 | 139 |
|---|---|---|---|---|---|---|---|---|---|---|---|---|---|---|---|---|---|---|---|---|---|---|
| pI-iso3 | A | S | T | K | G | P | S | V | F | P | L | A | P | S | S | K | S | T | S | E | S | T |
| IgG1 | A | S | T | K | G | P | S | V | F | P | L | A | P | S | S | K | S | T | S | G | G | T |
| IgG2 | A | S | T | K | G | P | S | V | F | P | L | A | P | C | S | R | S | T | S | E | S | T |
| IgG3 | A | S | T | K | G | P | S | V | F | P | L | A | P | C | S | R | S | T | S | G | G | T |
| IgG4 | A | S | T | K | G | P | S | V | F | P | L | A | P | C | S | R | S | T | S | E | S | T |

| EU | 140 | 141 | 142 | 143 | 144 | 145 | 146 | 147 | 148 | 149 | 150 | 151 | 152 | 153 | 154 | 155 | 156 | 157 | 158 | 159 | 160 | 161 |
|---|---|---|---|---|---|---|---|---|---|---|---|---|---|---|---|---|---|---|---|---|---|---|
| pI-iso3 | A | A | L | G | C | L | V | K | D | Y | F | P | E | P | V | T | V | S | W | N | S | G |
| IgG1 | A | A | L | G | C | L | V | K | D | Y | F | P | E | P | V | T | V | S | W | N | S | G |
| IgG2 | A | A | L | G | C | L | V | K | D | Y | F | P | E | P | V | T | V | S | W | N | S | G |
| IgG3 | A | A | L | G | C | L | V | K | D | Y | F | P | E | P | V | T | V | S | W | N | S | G |
| IgG4 | A | A | L | G | C | L | V | K | D | Y | F | P | E | P | V | T | V | S | W | N | S | G |

| EU | 162 | 163 | 164 | 165 | 166 | 167 | 168 | 169 | 170 | 171 | 172 | 173 | 174 | 175 | 176 | 177 | 178 | 179 | 180 | 181 | 182 | 183 |
|---|---|---|---|---|---|---|---|---|---|---|---|---|---|---|---|---|---|---|---|---|---|---|
| pI-iso3 | A | L | T | S | G | V | H | T | F | P | A | V | L | Q | S | S | G | L | Y | S | L | S |
| IgG1 | A | L | T | S | G | V | H | T | F | P | A | V | L | Q | S | S | G | L | Y | S | L | S |
| IgG2 | A | L | T | S | G | V | H | T | F | P | A | V | L | Q | S | S | G | L | Y | S | L | S |
| IgG3 | A | L | T | S | G | V | H | T | F | P | A | V | L | Q | S | S | G | L | Y | S | L | S |
| IgG4 | A | L | T | S | G | V | H | T | F | P | A | V | L | Q | S | S | G | L | Y | S | L | S |

| EU | 184 | 185 | 186 | 187 | 188 | 189 | 190 | 191 | 192 | 193 | 194 | 195 | 196 | 197 | 198 | 199 | 200 | 201 | 202 | 203 | 204 | 205 |
|---|---|---|---|---|---|---|---|---|---|---|---|---|---|---|---|---|---|---|---|---|---|---|
| pI-iso3 | S | V | V | T | V | P | S | S | N | F | G | T | Q | T | Y | T | C | N | V | D | H | K |
| IgG1 | S | V | V | T | V | P | S | S | L | G | T | Q | T | Y | I | C | N | V | N | H | K | |
| IgG2 | S | V | V | T | V | P | S | S | N | F | G | T | Q | T | Y | T | C | N | V | D | H | K |
| IgG3 | S | V | V | T | V | P | S | S | L | G | T | Q | T | Y | T | C | N | V | N | H | K | |
| IgG4 | S | V | V | T | V | P | S | S | L | G | T | K | T | Y | T | C | N | V | D | H | K | |

| EU | 206 | 207 | 208 | 209 | 210 | 211 | 212 | 213 | 214 | 215 | 216 | 217 | 218 | 219 | 220 |
|---|---|---|---|---|---|---|---|---|---|---|---|---|---|---|---|
| pI-iso3 | P | S | N | T | K | V | D | K | T | V | E | P | K | S | C |
| IgG1 | P | S | N | T | K | V | D | K | K/R | V | E | P | K | S | C |
| IgG2 | P | S | N | T | K | V | D | K | T | V | E | R | K | C | C |
| IgG3 | P | S | N | T | K | V | D | K | R | V | E | L | K | T | P |
| IgG4 | P | S | N | T | K | V | D | K | R | V | E | S | K | Y | G |

Hinge

| EU | | 221 | 222 | 223 | 224 | 225 | | | | | | | | | | | | | |
|---|---|---|---|---|---|---|---|---|---|---|---|---|---|---|---|---|---|---|---|
| pI-iso3 | | D | T | T | H | T | | | | | | | | | | | | | |
| IgG1 | | D | K | T | H | T | | | | | | | | | | | | | |
| IgG2 | | | V | | E | | | | | | | | | | | | | | |
| IgG3 | L | G | D | T | T | H | T | C | P | R | C | P | E | P | K | S | C | D | T | P | P | P |
| IgG4 | | | | | P | P | | | | | | | | | | | | | |

| EU | | | | | | | | | | | | | | | | | | | |
|---|---|---|---|---|---|---|---|---|---|---|---|---|---|---|---|---|---|---|---|
| pI-iso3 | | | | | | | | | | | | | | | | | | | |
| IgG1 | | | | | | | | | | | | | | | | | | | |
| IgG2 | | | | | | | | | | | | | | | | | | | |
| IgG3 | C | P | R | C | P | E | P | K | S | C | D | T | P | P | P | C | P | R | C | P | E | P |
| IgG4 | | | | | | | | | | | | | | | | | | | |

| EU | | | | | | | 226 | 227 | 228 | 229 | 230 | 231 | 232 | 233 | 234 | 235 | 236 |
|---|---|---|---|---|---|---|---|---|---|---|---|---|---|---|---|---|---|
| pI-iso3 | | | | | | | C | P | P | C | P | A | P | E | L | L | G |
| IgG1 | | | | | | | C | P | P | C | P | A | P | E | L | L | G |
| IgG2 | | | | | | | C | P | P | C | P | A | P | P | V | A | |
| IgG3 | K | S | C | D | T | P | P | P | C | P | R | C | P | E | L | L | G |
| IgG4 | | | | | | | C | P | S | C | P | A | P | E | F | L | G |

| EU | 237 | 238 | 239 | 240 | 241 | 242 | 243 | 244 | 245 | 246 | 247 | 248 | 249 | 250 | 251 | 252 | 253 | 254 | 255 | 256 | 257 | 258 |
|---|---|---|---|---|---|---|---|---|---|---|---|---|---|---|---|---|---|---|---|---|---|---|
| pl-iso3 | G | P | S | V | F | L | F | P | P | K | P | K | D | T | L | M | I | S | R | T | P | E |
| IgG1 | G | P | S | V | F | L | F | P | P | K | P | K | D | T | L | M | I | S | R | T | P | E |
| IgG2 | G | P | S | V | F | L | F | P | P | K | P | K | D | T | L | M | I | S | R | T | P | E |
| IgG3 | G | P | S | V | F | L | F | P | P | K | P | K | D | T | L | M | I | S | R | T | P | E |
| IgG4 | G | P | S | V | F | L | F | P | P | K | P | K | D | T | L | M | I | S | R | T | P | E |

| EU | 259 | 260 | 261 | 262 | 263 | 264 | 265 | 266 | 267 | 268 | 269 | 270 | 271 | 272 | 273 | 274 | 275 | 276 | 277 | 278 | 279 | 280 |
|---|---|---|---|---|---|---|---|---|---|---|---|---|---|---|---|---|---|---|---|---|---|---|
| pl-iso3 | V | T | C | V | V | V | D | V | S | H | E | D | P | E | V | Q | F | N | W | Y | V | D |
| IgG1 | V | T | C | V | V | V | D | V | S | H | E | D | P | E | V | K | F | N | W | Y | V | D |
| IgG2 | V | T | C | V | V | V | D | V | S | H | E | D | P | E | V | Q | F | N | W | Y | V | D |
| IgG3 | V | T | C | V | V | V | D | V | S | H | E | D | P | E | V | Q | F | K | W | Y | V | D |
| IgG4 | V | T | C | V | V | V | D | V | S | Q | E | D | P | E | V | Q | F | N | W | Y | V | D |

| EU | 281 | 282 | 283 | 284 | 285 | 286 | 287 | 288 | 289 | 290 | 291 | 292 | 293 | 294 | 295 | 296 | 297 | 298 | 299 | 300 | 301 | 302 |
|---|---|---|---|---|---|---|---|---|---|---|---|---|---|---|---|---|---|---|---|---|---|---|
| pl-iso3 | G | V | E | V | H | N | A | K | T | K | P | R | E | E | Q | F | N | S | T | F | R | V |
| IgG1 | G | V | E | V | H | N | A | K | T | K | P | R | E | E | Q | Y | N | S | T | Y | R | V |
| IgG2 | G | V/M | E | V | H | N | A | K | T | K | P | R | E | E | Q | F | N | S | T | F | R | V |
| IgG3 | G | V | E | V | H | N | A | K | T | K | P | R | E | E | Q | Y | N | S | T | F | R | V |
| IgG4 | G | V | E | V | H | N | A | K | T | K | P | R | E | E | Q | F | N | S | T | Y | R | V |

| EU | 303 | 304 | 305 | 306 | 307 | 308 | 309 | 310 | 311 | 312 | 313 | 314 | 315 | 316 | 317 | 318 | 319 | 320 | 321 | 322 | 323 | 324 |
|---|---|---|---|---|---|---|---|---|---|---|---|---|---|---|---|---|---|---|---|---|---|---|
| pl-iso3 | V | S | V | L | T | V | V | H | Q | D | W | L | N | G | K | E | Y | K | C | K | V | S |
| IgG1 | V | S | V | L | T | V | L | H | Q | D | W | L | N | G | K | E | Y | K | C | K | V | S |
| IgG2 | V | S | V | L | T | V | V | H | Q | D | W | L | N | G | K | E | Y | K | C | K | V | S |
| IgG3 | V | S | V | L | T | V | L | H | Q | D | W | L | N | G | K | E | Y | K | C | K | V | S |
| IgG4 | V | S | V | L | T | V | L | H | Q | D | W | L | N | G | K | E | Y | K | C | K | V | S |

| EU | 325 | 326 | 327 | 328 | 329 | 330 | 331 | 332 | 333 | 334 | 335 | 336 | 337 | 338 | 339 | 340 |
|---|---|---|---|---|---|---|---|---|---|---|---|---|---|---|---|---|
| pl-iso3 | N | K | A | L | P | A | P | I | E | K | T | I | S | K | T | K |
| IgG1 | N | K | A | L | P | A | P | I | E | K | T | I | S | K | A | K |
| IgG2 | N | K | G | L | P | A | P | I | E | K | T | I | S | K | T | K |
| IgG3 | N | K | A | L | P | A | P | I | E | K | T | I | S | K | T | K |
| IgG4 | N | K | G | L | P | S | S | I | E | K | T | I | S | K | A | K |

| EU | 341 | 342 | 343 | 344 | 345 | 346 | 347 | 348 | 349 | 350 | 351 | 352 | 353 | 354 | 355 | 356 | 357 | 358 | 359 | 360 | 361 | 362 |
|---|---|---|---|---|---|---|---|---|---|---|---|---|---|---|---|---|---|---|---|---|---|---|
| pI-iso3 | G | Q | P | R | E | P | Q | V | Y | T | L | P | P | S | Q | E | E | M | T | K | N | Q |
| IgG1 | G | Q | P | R | E | P | Q | V | Y | T | L | P | P | S | R | D/E | E | L/M | T | K | N | Q |
| IgG2 | G | Q | P | R | E | P | Q | V | Y | T | L | P | P | S | R | E | E | M | T | K | N | Q |
| IgG3 | G | Q | P | R | E | P | Q | V | Y | T | L | P | P | S | R | E | E | M | T | K | N | Q |
| IgG4 | G | Q | P | R | E | P | Q | V | Y | T | L | P | P | S | Q | E | E | M | T | K | N | Q |

| EU | 363 | 364 | 365 | 366 | 367 | 368 | 369 | 370 | 371 | 372 | 373 | 374 | 375 | 376 | 377 | 378 | 379 | 380 | 381 | 382 | 383 | 384 |
|---|---|---|---|---|---|---|---|---|---|---|---|---|---|---|---|---|---|---|---|---|---|---|
| pI-iso3 | V | S | L | T | C | L | V | K | G | F | Y | P | S | D | I | A | V | E | W | E | S | S |
| IgG1 | V | S | L | T | C | L | V | K | G | F | Y | P | S | D | I | A | V | E | W | E | S | N |
| IgG2 | V | S | L | T | C | L | V | K | G | F | Y | P | S | D | I | A | V | E | W | E | S | N |
| IgG3 | V | S | L | T | C | L | V | K | G | F | Y | P | S | D | I | A | V | E | W | E | S | S |
| IgG4 | V | S | L | T | C | L | V | K | G | F | Y | P | S | D | I | A | V | E | W | E | S | N |

| EU | 385 | 386 | 387 | 388 | 389 | 390 | 391 | 392 | 393 | 394 | 395 | 396 | 397 | 398 | 399 | 400 | 401 | 402 | 403 | 404 | 405 | 406 |
|---|---|---|---|---|---|---|---|---|---|---|---|---|---|---|---|---|---|---|---|---|---|---|
| pI-iso3 | G | Q | P | E | N | N | Y | N | T | T | P | P | M | L | D | S | D | G | S | F | F | L |
| IgG1 | G | Q | P | E | N | N | Y | K | T | T | P | P | V | L | D | S | D | G | S | F | F | L |
| IgG2 | G | Q | P | E | N | N | Y | K | T | T | P | P | M | L | D | S | D | G | S | F | F | L |
| IgG3 | G | Q | P | E | N | N | Y | N | T | T | P | P | M | L | D | S | D | G | S | F | F | L |
| IgG4 | G | Q | P | E | N | N | Y | K | T | T | P | P | V | L | D | S | D | G | S | F | F | L |

| EU | 407 | 408 | 409 | 410 | 411 | 412 | 413 | 414 | 415 | 416 | 417 | 418 | 419 | 420 | 421 | 422 | 423 | 424 | 425 | 426 | 427 | 428 |
|---|---|---|---|---|---|---|---|---|---|---|---|---|---|---|---|---|---|---|---|---|---|---|
| pI-iso3 | Y | S | K | L | T | V | D | K | S | R | W | Q | E | G | N | V | F | S | C | S | V | M |
| IgG1 | Y | S | K | L | T | V | D | K | S | R | W | Q | Q | G | N | V | F | S | C | S | V | M |
| IgG2 | Y | S | K | L | T | V | D | K | S | R | W | Q | Q | G | N | V | F | S | C | S | V | M |
| IgG3 | Y | S | K | L | T | V | D | K | S | R | W | Q | Q | G | N | I | F | S | C | S | V | M |
| IgG4 | Y | S | R | L | T | V | D | K | S | R | W | Q | E | G | N | V | F | S | C | S | V | M |

| EU | 429 | 430 | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|---|
| pI-iso3 | H | E | A | L | H | N | H | Y | T | Q | K | S | L | S | L | S | P | G | |
| IgG1 | H | E | A/G | L | H | N | H | Y | T | Q | K | S | L | S | L | S | P | G | K |
| IgG2 | H | E | A | L | H | N | H | Y | T | Q | K | S | L | S | L | S | P | G | K |
| IgG3 | H | E | A | L | H | N | R | F | T | Q | K | S | L | S | L | S | P | G | K |
| IgG4 | H | E | A | L | H | N | H | Y | T | Q | K | S | L | S | L | G | | | K | pI-is o3 = SEQ ID NO: 22
IgG1 = SEQ ID NO: 2
IgG2 = SEQ ID NO: 3
IgG3 = SEQ ID NO: 4
IgG4 = SEQ ID NO: 5

```
IgG1      DKTHTCPPCPAPELLG  SEQ ID NO: 133
pI_Iso3   DTTHTCPPCPAPELLG  SEQ ID NO: 134
```

DTTHT present in IgG3

*pI iso3-SL has 192S/193L

†pI-iso3-charges-only contains all pI lowering substitutions (e.g. N203D), but does not contain neighboring isotypic mutations (e.g. I199T) that do not affect charge.

Figure 27

SEQ ID NO: 135

| EU | 108 | 109 | 110 | 111 | 112 | 113 | 114 | 115 | 116 | 117 | 118 | 119 | 120 | 121 | 122 | 123 | 124 | 125 |
|---|---|---|---|---|---|---|---|---|---|---|---|---|---|---|---|---|---|---|
| $C_K$ | R | T | V | A | A | P | S | V | F | I | F | P | P | S | D | E | Q | L |

| EU | 126 | 127 | 128 | 129 | 130 | 131 | 132 | 133 | 134 | 135 | 136 | 137 | 138 | 139 | 140 | 141 | 142 | 143 |
|---|---|---|---|---|---|---|---|---|---|---|---|---|---|---|---|---|---|---|
| $C_K$ | *E* | S | G | T | A | S | V | V | C | L | L | N | N | F | Y | P | R | E |

| EU | 144 | 145 | 146 | 147 | 148 | 149 | 150 | 151 | 152 | 153 | 154 | 155 | 156 | 157 | 158 | 159 | 160 | |
|---|---|---|---|---|---|---|---|---|---|---|---|---|---|---|---|---|---|---|
| $C_K$ | A | *E* | V | Q | W | K | V | D | N | A | L | Q | S | G | N | S | Q | |

| EU | 161 | 162 | 163 | 164 | 165 | 166 | 167 | 168 | 169 | 170 | 171 | 172 | 173 | 174 | 175 | 176 | 177 | 178 |
|---|---|---|---|---|---|---|---|---|---|---|---|---|---|---|---|---|---|---|
| $C_K$ | E | S | V | T | E | Q | D | S | *E* | D | S | T | Y | S | L | S | S | T |

| EU | 179 | 180 | 181 | 182 | 183 | 184 | 185 | 186 | 187 | 188 | 189 | 190 | 191 | 192 | 193 | 194 | 195 | 196 |
|---|---|---|---|---|---|---|---|---|---|---|---|---|---|---|---|---|---|---|
| $C_K$ | L | T | L | S | K | A | D | Y | E | K | H | K | V | Y | A | C | E | V |

| EU | 197 | 198 | 199 | 200 | 201 | 202 | 203 | 204 | 205 | 206 | 207 | 208 | 209 | 210 | 211 | 212 | 213 | 214 |
|---|---|---|---|---|---|---|---|---|---|---|---|---|---|---|---|---|---|---|
| $C_K$ | T | H | Q | G | L | S | S | P | V | T | *E* | S | F | N | R | G | E | C |

Figure 28A

IgG-pI-Iso2 (SEQ ID NO: 19)
ASTKGPSVFPLAPSSKSTSESTAALGCLVKDYFPEPVTVSWNSGALTSGVHTFPAVLQS
SGLYSLSSVVTVPSSNFGTQTYTCNVDHKPSNTKVDKTVEPKSCVECPPCPAPPVAGPS
VFLFPPKPKDTLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQVYTLPPSQEE
MTKNQVSLTCLVKGFYPSDIAVEWESSGQPENNYNTTPPMLDSDGSFFLYSKLTVDKSR
WQEGNVFSCSVMHEALHNHYTQKSLSLSPG

IgG-pI-Iso2-434S (SEQ ID NO: 61)
ASTKGPSVFPLAPSSKSTSESTAALGCLVKDYFPEPVTVSWNSGALTSGVHTFPAVLQS
SGLYSLSSVVTVPSSNFGTQTYTCNVDHKPSNTKVDKTVEPKSCVECPPCPAPPVAGPS
VFLFPPKPKDTLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQVYTLPPSQEE
MTKNQVSLTCLVKGFYPSDIAVEWESSGQPENNYNTTPPMLDSDGSFFLYSKLTVDKSR
WQEGNVFSCSVMHEALHSHYTQKSLSLSPG

IgG-pI-Iso2-SL-434S (SEQ ID NO: 65)
ASTKGPSVFPLAPSSKSTSESTAALGCLVKDYFPEPVTVSWNSGALTSGVHTFPAVLQS
SGLYSLSSVVTVPSSSLGTQTYTCNVDHKPSNTKVDKTVEPKSCVECPPCPAPPVAGPS
VFLFPPKPKDTLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQVYTLPPSQEE
MTKNQVSLTCLVKGFYPSDIAVEWESSGQPENNYNTTPPMLDSDGSFFLYSKLTVDKSR
WQEGNVFSCSVMHEALHSHYTQKSLSLSPG

IgG-pI-Iso2-SL (SEQ ID NO: 20)
ASTKGPSVFPLAPSSKSTSESTAALGCLVKDYFPEPVTVSWNSGALTSGVHTFPAVLQS
SGLYSLSSVVTVPSSSLGTQTYTCNVDHKPSNTKVDKTVEPKSCVECPPCPAPPVAGPS
VFLFPPKPKDTLMISRTPEVTCVVVDVSHEDPEVQFNWYVDGVEVHNAKTKPREEQFNS
TFRVVSVLTVVHQDWLNGKEYKCKVSNKGLPAPIEKTISKTKGQPREPQVYTLPPSQEE
MTKNQVSLTCLVKGFYPSDIAVEWESSGQPENNYNTTPPMLDSDGSFFLYSKLTVDKSR
WQEGNVFSCSVMHEALHNHYTQKSLSLSPG

IgG-pI-Iso2-charges-only (SEQ ID NO: 21)
ASTKGPSVFPLAPSSKSTSEGTAALGCLVKDYFPEPVTVSWNSGALTSGVHTFPAVLQS
SGLYSLSSVVTVPSSSLGTQTYICNVDHKPSNTKVDKTVEPKSCVECPPCPAPPVAGPS
VFLFPPKPKDTLMISRTPEVTCVVVDVSHEDPEVQFNWYVDGVEVHNAKTKPREEQYNS
TYRVVSVLTVLHQDWLNGKEYKCKVSNKGLPAPIEKTISKAKGQPREPQVYTLPPSQEE
MTKNQVSLTCLVKGFYPSDIAVEWESNGQPENNYNTTPPVLDSDGSFFLYSKLTVDKSR
WQEGNVFSCSVMHEALHNHYTQKSLSLSPG

IgG-pI-Iso2-charges-only-434S (SEQ ID NO: 67)
ASTKGPSVFPLAPSSKSTSEGTAALGCLVKDYFPEPVTVSWNSGALTSGVHTFPAVLQS
SGLYSLSSVVTVPSSSLGTQTYICNVDHKPSNTKVDKTVEPKSCVECPPCPAPPVAGPS
VFLFPPKPKDTLMISRTPEVTCVVVDVSHEDPEVQFNWYVDGVEVHNAKTKPREEQYNS
TYRVVSVLTVLHQDWLNGKEYKCKVSNKGLPAPIEKTISKAKGQPREPQVYTLPPSQEE
MTKNQVSLTCLVKGFYPSDIAVEWESNGQPENNYNTTPPVLDSDGSFFLYSKLTVDKSR
WQEGNVFSCSVMHEALHSHYTQKSLSLSPG

Figure 28B

IgG-pI-Iso3 (SEQ ID NO: 22)
ASTKGPSVFPLAPSSKSTSESTAALGCLVKDYFPEPVTVSWNSGALTSGVHTFPAVLQS
SGLYSLSSVVTVPSSNFGTQTYTCNVDHKPSNTKVDKTVEPKSCDTTHTCPPCPAPELL
GGPSVFLFPPKPKDTLMISRTPEVTCVVVDVSHEDPEVQFNWYVDGVEVHNAKTKPREE
QFNSTFRVVSVLTVVHQDWLNGKEYKCKVSNKALPAPIEKTISKTKGQPREPQVYTLPPS
QEEMTKNQVSLTCLVKGFYPSDIAVEWESSGQPENNYNTTPPMLDSDGSFFLYSKLTVD
KSRWQEGNVFSCSVMHEALHNHYTQKSLSLSPG

IgG-pI-Iso3-434S (SEQ ID NO: 62)
ASTKGPSVFPLAPSSKSTSESTAALGCLVKDYFPEPVTVSWNSGALTSGVHTFPAVLQS
SGLYSLSSVVTVPSSNFGTQTYTCNVDHKPSNTKVDKTVEPKSCDTTHTCPPCPAPELL
GGPSVFLFPPKPKDTLMISRTPEVTCVVVDVSHEDPEVQFNWYVDGVEVHNAKTKPREE
QFNSTFRVVSVLTVVHQDWLNGKEYKCKVSNKALPAPIEKTISKTKGQPREPQVYTLPPS
QEEMTKNQVSLTCLVKGFYPSDIAVEWESSGQPENNYNTTPPMLDSDGSFFLYSKLTVD
KSRWQEGNVFSCSVMHEALHSHYTQKSLSLSPG

IgG-pI-Iso3-SL-434S (SEQ ID NO: 63)
ASTKGPSVFPLAPSSKSTSESTAALGCLVKDYFPEPVTVSWNSGALTSGVHTFPAVLQS
SGLYSLSSVVTVPSSSLGTQTYTCNVDHKPSNTKVDKTVEPKSCDTTHTCPPCPAPELL
GGPSVFLFPPKPKDTLMISRTPEVTCVVVDVSHEDPEVQFNWYVDGVEVHNAKTKPREE
QFNSTFRVVSVLTVVHQDWLNGKEYKCKVSNKALPAPIEKTISKTKGQPREPQVYTLPPS
QEEMTKNQVSLTCLVKGFYPSDIAVEWESSGQPENNYNTTPPMLDSDGSFFLYSKLTVD
KSRWQEGNVFSCSVMHEALHSHYTQKSLSLSPG

IgG-pI-Iso3-SL-428L/434S (SEQ ID NO: 64)
ASTKGPSVFPLAPSSKSTSESTAALGCLVKDYFPEPVTVSWNSGALTSGVHTFPAVLQS
SGLYSLSSVVTVPSSSLGTQTYTCNVDHKPSNTKVDKTVEPKSCDTTHTCPPCPAPELL
GGPSVFLFPPKPKDTLMISRTPEVTCVVVDVSHEDPEVQFNWYVDGVEVHNAKTKPREE
QFNSTFRVVSVLTVVHQDWLNGKEYKCKVSNKALPAPIEKTISKTKGQPREPQVYTLPPS
QEEMTKNQVSLTCLVKGFYPSDIAVEWESSGQPENNYNTTPPMLDSDGSFFLYSKLTVD
KSRWQEGNVFSCSVLHEALHSHYTQKSLSLSPG

IgG-pI-Iso3-SL (SEQ ID NO: 23)
ASTKGPSVFPLAPSSKSTSESTAALGCLVKDYFPEPVTVSWNSGALTSGVHTFPAVLQS
SGLYSLSSVVTVPSSSLGTQTYTCNVDHKPSNTKVDKTVEPKSCDTTHTCPPCPAPELL
GGPSVFLFPPKPKDTLMISRTPEVTCVVVDVSHEDPEVQFNWYVDGVEVHNAKTKPREE
QFNSTFRVVSVLTVVHQDWLNGKEYKCKVSNKALPAPIEKTISKTKGQPREPQVYTLPPS
QEEMTKNQVSLTCLVKGFYPSDIAVEWESSGQPENNYNTTPPMLDSDGSFFLYSKLTVD
KSRWQEGNVFSCSVMHEALHNHYTQKSLSLSPG

IgG-pI-Iso3-charges-only (SEQ ID NO: 24)
ASTKGPSVFPLAPSSKSTSEGTAALGCLVKDYFPEPVTVSWNSGALTSGVHTFPAVLQS
SGLYSLSSVVTVPSSSLGTQTYICNVDHKPSNTKVDKTVEPKSCDTTHTCPPCPAPELLG
GPSVFLFPPKPKDTLMISRTPEVTCVVVDVSHEDPEVQFNWYVDGVEVHNAKTKPREEQ
YNSTYRVVSVLTVLHQDWLNGKEYKCKVSNKALPAPIEKTISKAKGQPREPQVYTLPPSQ
EEMTKNQVSLTCLVKGFYPSDIAVEWESNGQPENNYNTTPPVLDSDGSFFLYSKLTVDK
SRWQEGNVFSCSVMHEALHNHYTQKSLSLSPG

Figure 28C

IgG-pI-Iso3-charges-only-434S (SEQ ID NO: 66)
ASTKGPSVFPLAPSSKSTSEGTAALGCLVKDYFPEPVTVSWNSGALTSGVHTFPAVLQS
SGLYSLSSVVTVPSSSLGTQTYICNVDHKPSNTKVDKTVEPKSCDTTHTCPPCPAPELLG
GPSVFLFPPKPKDTLMISRTPEVTCVVVDVSHEDPEVQFNWYVDGVEVHNAKTKPREEQ
YNSTYRVVSVLTVLHQDWLNGKEYKCKVSNKALPAPIEKTISKAKGQPREPQVYTLPPSQ
EEMTKNQVSLTCLVKGFYPSDIAVEWESNGQPENNYNTTPPVLDSDGSFFLYSKLTVDK
SRWQEGNVFSCSVMHEALHSHYTQKSLSLSPG

IgG1-pI(7) (SEQ ID NO: 25)
ASTKGPSVFPLAPSSESTSGGTAALGCLVKDYFPEPVTVSWNSGALTSGVHTFPAVLQS
SGLYSLSSVVTVPSSSLGTQTYICNVNHEPSNTEVDKKVEPKSCDKTHTCPPCPAPELLG
GPSVFLFPPKPKDTLMISRTPEVTCVVVDVSHEDPEVEFNWYVDGVEVHNAKTKPREEQ
YNSTYRVVSVLTVLHQDWLNGKEYKCKVSNKALPAPIEKTISKAKGQPREPQVYTLPPSE
EEMTKNQVSLTCLVKGFYPSDIAVEWESNGQPENNYETTPPVLDSDGSFFLYSKLTVDK
SRWQQGNVFSCSVMHEALHNHYTQKSLSLSPG

IgG1-pI(7)-434S (SEQ ID NO: 68)
ASTKGPSVFPLAPSSESTSGGTAALGCLVKDYFPEPVTVSWNSGALTSGVHTFPAVLQS
SGLYSLSSVVTVPSSSLGTQTYICNVNHEPSNTEVDKKVEPKSCDKTHTCPPCPAPELLG
GPSVFLFPPKPKDTLMISRTPEVTCVVVDVSHEDPEVEFNWYVDGVEVHNAKTKPREEQ
YNSTYRVVSVLTVLHQDWLNGKEYKCKVSNKALPAPIEKTISKAKGQPREPQVYTLPPSE
EEMTKNQVSLTCLVKGFYPSDIAVEWESNGQPENNYETTPPVLDSDGSFFLYSKLTVDK
SRWQQGNVFSCSVMHEALHSHYTQKSLSLSPG

IgG1-pI(11) (SEQ ID NO: 26)
ASTKGPSVFPLAPSSESTSGGTAALGCLVKDYFPEPVTVSWNSGALTSGVHTFPAVLQS
SGLYSLSSVVTVPSSSLGTQTYICNVNHEPSNTEVDKKVEPKSCDKTHTCPPCPAPELLG
GPSVFLFPPKPKDTLMISRTPEVTCVVVDVSHEDPEVEFNWYVDGVEVHNAKTKPREEQ
YNSTYRVVSVLTVLHQDWLNGKEYECEVSNEALPAPIEETISKAKGQPREPQVYTLPPSE
EEMTKNQVSLTCLVKGFYPSDIAVEWESNGQPENNYETTPPVLDSDGSFFLYSKLTVDK
SRWQQGNVFSCSVMHEALHNHYTQKSLSLSPG

IgG1/2-pI(7) (SEQ ID NO: 27)
ASTKGPSVFPLAPSSESTSGGTAALGCLVKDYFPEPVTVSWNSGALTSGVHTFPAVLQS
SGLYSLSSVVTVPSSSLGTQTYICNVNHEPSNTEVDKKVEPKSCDKTHTCPPCPAPPVA
GPSVFLFPPKPKDTLMISRTPEVTCVVVDVSHEDPEVEFNWYVDGVEVHNAKTKPREEQ
FNSTFRVVSVLTVVHQDWLNGKEYKCKVSNKGLPAPIEKTISKTKGQPREPQVYTLPPSE
EEMTKNQVSLTCLVKGFYPSDIAVEWESNGQPENNYETTPPMLDSDGSFFLYSKLTVDK
SRWQQGNVFSCSVMHEALHNHYTQKSLSLSPG

IgG1/2_pI(7)-434S (SEQ ID NO: 69)
ASTKGPSVFPLAPSSESTSGGTAALGCLVKDYFPEPVTVSWNSGALTSGVHTFPAVLQS
SGLYSLSSVVTVPSSSLGTQTYICNVNHEPSNTEVDKKVEPKSCDKTHTCPPCPAPPVA
GPSVFLFPPKPKDTLMISRTPEVTCVVVDVSHEDPEVEFNWYVDGVEVHNAKTKPREEQ
FNSTFRVVSVLTVVHQDWLNGKEYKCKVSNKGLPAPIEKTISKTKGQPREPQVYTLPPSE
EEMTKNQVSLTCLVKGFYPSDIAVEWESNGQPENNYETTPPMLDSDGSFFLYSKLTVDK
SRWQQGNVFSCSVMHEALHSHYTQKSLSLSPG

Figure 28D

IgG1/2-pI(11) (SEQ ID NO: 28)
ASTKGPSVFPLAPSSESTSGGTAALGCLVKDYFPEPVTVSWNSGALTSGVHTFPAVLQS
SGLYSLSSVVTVPSSSLGTQTYICNVNHEPSNTEVDKKVEPKSCDKTHTCPPCPAPPVA
GPSVFLFPPKPKDTLMISRTPEVTCVVVDVSHEDPEVEFNWYVDGVEVHNAKTKPREEQ
FNSTFRVVSVLTVVHQDWLNGKEYECEVSNEGLPAPIEETISKTKGQPREPQVYTLPPSE
EEMTKNQVSLTCLVKGFYPSDIAVEWESNGQPENNYETTPPMLDSDGSFFLYSKLTVDK
SRWQQGNVFSCSVMHEALHNHYTQKSLSLSPG

CK-pI(4) (SEQ ID NO: 29)
RTVAAPSVFIFPPSDEQLESGTASVVCLLNNFYPREAEVQWKVDNALQSGNSQESVTEQ
DSEDSTYSLSSTLTLSKADYEKHKVYACEVTHQGLSSPVTESFNRGEC

CK-Iso(3) (SEQ ID NO: 30)
QTVAAPSVFIFPPSDEQLQSGTASVVCLLNNFYPREAKVQWKVDNALQSGNSQESVTE
QDSKDSTYSLSSTLTLSKADYEKHKVYACEVTHEGLSSPVTKSFNRGEC

CK-Iso(4) (SEQ ID NO: 31)
QTVAAPSVFIFPPSDEQLQSGTASVVCLLNNFYPREATVQWKVDNALQSGNSQESVTEQ
DSKDSTYSLSSTLTLSKADYEKHKVYACEVTHEGLSSPVTKSFNRGEC

CK-Iso(5) (SEQ ID NO: 32)
QTVAAPSVFIFPPSDEELQSGTASVVCLLNNFYPREATVQWKVDNALQSGNSQESVTEQ
DSKDSTYSLSSTLTLSKADYEKHKVYACEVTHEGLSSPVTKSFNRGEC

CK-Iso(6) (SEQ ID NO: 33)
QTVAAPSVFIFPPSDEELQSGTASVVCLLNDFYPREATVQWKVDNALQSGNSQESVTEQ
DSKDSTYSLSSTLTLSKADYEKHKVYACEVTHEGLSSPVTKSFNRGEC

Figure 29

| Position | WT | fraction exposed (avg) | Delta E Glu (Avg) |
|---|---|---|---|
| 246 | K | 0.60 | -0.65 |
| 248 | K | 0.21 | -0.16 |
| 255 | R | 0.37 | 1.36 |
| 274 | K | 0.57 | -0.95 |
| 288 | K | 0.58 | -0.81 |
| 290 | K | 0.42 | -0.23 |
| 292 | R | 0.51 | 0.64 |
| 301 | R | 0.29 | 0.17 |
| 317 | K | 0.28 | 1.75 |
| 320 | K | 0.26 | -0.22 |
| 322 | K | 0.21 | -0.43 |
| 326 | K | 0.71 | -0.58 |
| 334 | K | 0.35 | -0.20 |
| 338 | K | 0.08 | 1.21 |
| 340 | K | 0.72 | -0.57 |
| 344 | R | 0.45 | 0.28 |
| 355 | R | 0.78 | -0.28 |
| 360 | K | 0.32 | -1.26 |
| 370 | K | 0.13 | -0.45 |
| 392 | K | 0.31 | 0.08 |
| 409 | K | 0.01 | 1.19 |
| 414 | K | 0.22 | 0.19 |
| 416 | R | 0.28 | 0.07 |
| 439 | K | 0.30 | -0.15 |

| | |
|---|---|
| ■ Bevacizumab (IgG1-WT) | $t_{1/2}$ = 3.7 ± 1.1 |
| ◈ IgG2-434S | $t_{1/2}$ = 14.4 ± 1.3 |
| ▲ IgG1-CH1-pI(6)-434S-CK-pI(6) | $t_{1/2}$ = 15.8 ± 2.8 |
| ▼ IgG-pI-Iso3-SL-434S-CK-WT | $t_{1/2}$ = 11.5 ± 1.3 |
| ◆ IgG-pI-Iso2-SL-434S-CK-WT | $t_{1/2}$ = 10.7 ± 1.7 |
| ◈ IgG-pI-Iso3-charges-only-434S-CK-WT | $t_{1/2}$ = 12.0 ± 2.1 |
| □ IgG-pI-Iso3-SL-434S-CK-Iso(5) | $t_{1/2}$ = 13.2 ± 1.2 |

Structural alignment of CKappa and C-lambda domains

Figure 36

| AMINO ACID | pI |
|---|---|
| Alanine Ala A | 6.00 |
| Arginine Arg R | 11.15 |
| Asparagine Asn N | 5.41 |
| Aspartic acid Asp D | 2.77 |
| Cysteine Cys C | 5.02 |
| Glutamic acid Glu E | 3.22 |
| Glutamine Gln Q | 5.65 |
| Glycine Gly G | 5.97 |
| Histidine His H | 7.47 |
| Isoleucine Ile I | 5.94 |
| Leucine Leu L | 5.98 |
| Lysine Lys K | 9.59 |
| Methionine Met M | 5.74 |
| Phenylalanine Phe F | 5.48 |
| Proline Pro P | 6.30 |
| Serine Ser S | 5.68 |
| Threonine Thr T | 5.64 |
| Tryptophan Trp W | 5.89 |
| Tyrosine Tyr Y | 5.66 |
| Valine Val V | 5.96 |

Heavy Chain 1 of XENP10653 (SEQ ID NO: 34)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK

Heavy Chain 2 of XENP10653 (SEQ ID NO: 35)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALESGVH
TFPAVLQSSGLYSLSSVVTVPSSSLGTQTYICNVNHKPSDTEVDKKVEPKSCDKTHTCPP
CPAPELLGGPSVFLFPPKPKDTLMISRTPEVTCVVVDVSHEDPEVQFNWYVDGVEVHNA
KTKPREEQYNSTYRVVSVLTVLHQDWLNGKEYKCKVSNKALPAPIEKTISKAKGQPREP
QVYTLPPSQEEMTKNQVSLTCLVKGFYPSDIAVEWESSGQPENNYNTTPPMLDSDGSF
FLYSKLTVDKSRWQEGNVFSCSVMHEALHNHYTQKSLSLSPG

Light Chain of XENP10653 (SEQ ID NO: 36)

DIQMTQSPSSLSASVGDRVTITCSASQDISNYLNWYQQKPGKAPKVLIYFTSSLHSGVPS
RFSGSGSGTDFTLTISSLQPEDFATYYCQQYSTVPWTFGQGTKVEIKRTVAAPSVFIFPP
SDEQLKSGTASVVCLLNNFYPREAKVQWKVDNALQSGNSQESVTEQDSKDSTYSLSST
LTLSKADYEKHKVYACEVTHQGLSSPVTKSFNRGEC

Heavy Chain 1 of anti-HER2 x anti-CD16 mAb-Fv (SEQ ID NO: 37)

EVQLVESGGGLVQPGGSLRLSCAASGFNIKDTYIHWVRQAPGKGLEWVARIYPTNGYTR
YADSVKGRFTISADTSKNTAYLQMNSLRAEDTAVYYCSRWGGDGFYAMDYWGQGTLV
TVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVC
TLPPSREEMTKNQVHLTCLVKGFYPSDIAVEWESNGQPENNYKTTPPVLDSDGSFALYS
KLTVDKSRWQQGNVFSCSVMHEALHNHYTQKSLSLSPGKSSDKTHTSPPSPGGGGSG
GGGSGGGGSGGGGQVTLKESGPGILQPSQTLSLTCSFSGFSLRTSGMGVGWIRQPSG
KGLEWLAHIWWDDDKRYNPALKSRLTISKDTSSNQVFLKIASVDTADTATYYCAQINPAW
FAYWGQGTLVTVSA

Heavy Chain 2 of anti-HER2 x anti-CD16 mAb-Fv (SEQ ID NO: 38)

EVQLVESGGGLVQPGGSLRLSCAASGFNIKDTYIHWVRQAPGKGLEWVARIYPTNGYTR
YADSVKGRFTISADTSKNTAYLQMNSLRAEDTAVYYCSRWGGDGFYAMDYWGQGTLV
TVSSASTKGPSVFPLAPSSKSTSGGTAALGCLVKDYFPEPVTVSWNSGALESGVHTFPA
VLQSSGLYSLSSVVTVPSSSLGTQTYICNVNHKPSDTEVDKKVEPKSCDKTHTCPPCPA

Figure 39B

PELLGGPSVFLFPPKPKDTLMISRTPEVTCVVVDVSHEDPEVQFNWYVDGVEVHNAKTK
PREEQYNSTYRVVSVLTVLHQDWLNGKEYKCKVSNKALPAPIEKTISKAKGQPREPQVT
TLPPCQEEMTKNQVSLTCLVKGFYPSDIAVEWESSGQPENNYNTFPPMLDSDGSFFLYS
KLTVDKSRWQEGNVFSCSVMHEALHNHYTQKSLSLSPGKSSDKTHTSPPSPGGGGSG
GGGSGGGGSGGGGDIVLTQSPASLAVSLGQRATISCKASQSVDFDGDSFMNWYQQKP
GQPPKLLIYTTSNLESGIPARFSASGSGTDFTLNIHPVEEEDTATYYCQQSNEDPYTFGG
GTKLELK

Light Chain of anti-HER2 x anti-CD16 mAb-Fv (SEQ ID NO: 39)

DIQMTQSPSSLSASVGDRVTITCRASQDVNTAVAWYQQKPGKAPKLLIYSASFLYSGVPS
RFSGSRSGTDFTLTISSLQPEDFATYYCQQHYTTPPTFGQGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC

Heavy Chain 1 of anti-CD19 x anti-CD16 mAb-Fv (SEQ ID NO: 40)

EVQLVESGGGLVKPGGSLKLSCAASGYTFTSYVMHWVRQAPGKGLEWIGYINPYNDGT
KYNEKFQGRVTISSDKSISTAYMELSSLRSEDTAMYYCARGTYYYGTRVFDYWGQGTLV
TVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVC
TLPPSREEMTKNQVHLTCLVKGFYPSDIAVEWESNGQPENNYKTTPPVLDSDGSFALYS
KLTVDKSRWQQGNVFSCSVMHEALHNHYTQKSLSLSPGKSSDKTHTSPPSPGGGGSG
GGGSGGGGSGGGGQVTLKESGPGILQPSQTLSLTCSFSGFSLRTSGMGVGWIRQPSG
KGLEWLAHIWWDDDKRYNPALKSRLTISKDTSSNQVFLKIASVDTADTATYYCAQINPAW
FAYWGQGTLVTVSA

Heavy Chain 2 of anti-CD19 x anti-CD16 mAb-Fv (SEQ ID NO: 41)

EVQLVESGGGLVKPGGSLKLSCAASGYTFTSYVMHWVRQAPGKGLEWIGYINPYNDGT
KYNEKFQGRVTISSDKSISTAYMELSSLRSEDTAMYYCARGTYYYGTRVFDYWGQGTLV
TVSSASTKGPSVFPLAPSSKSTSGGTAALGCLVKDYFPEPVTVSWNSGALESGVHTFPA
VLQSSGLYSLSSVVTVPSSSLGTQTYICNVNHKPSDTEVDKKVEPKSCDKTHTCPPCPA
PELLGGPSVFLFPPKPKDTLMISRTPEVTCVVVDVSHEDPEVQFNWYVDGVEVHNAKTK
PREEQYNSTYRVVSVLTVLHQDWLNGKEYKCKVSNKALPAPIEKTISKAKGQPREPQVT
TLPPCQEEMTKNQVSLTCLVKGFYPSDIAVEWESSGQPENNYNTFPPMLDSDGSFFLYS
KLTVDKSRWQEGNVFSCSVMHEALHNHYTQKSLSLSPGKSSDKTHTSPPSPGGGGSG
GGGSGGGGSGGGGDIVLTQSPASLAVSLGQRATISCKASQSVDFDGDSFMNWYQQKP
GQPPKLLIYTTSNLESGIPARFSASGSGTDFTLNIHPVEEEDTATYYCQQSNEDPYTFGG
GTKLELK

Light Chain of anti-CD19 x anti-CD16 mAb-Fv (SEQ ID NO:42)

DIVMTQSPATLSLSPGERATLSCRSSKSLQNVNGNTYLYWFQQKPGQSPQLLIYRMSNL
NSGVPDRFSGSGSGTEFTLTISSLEPEDFAVYYCMQHLEYPITFGAGTKLEIKRTVAAPSV
FIFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC

Figure 39C

Heavy Chain 1 of anti-CD19 x anti-CD32b mAb-Fv (SEQ ID NO: 43)

EVQLVESGGGLVKPGGSLKLSCAASGYTFTSYVMHWVRQAPGKGLEWIGYINPYNDGT
KYNEKFQGRVTISSDKSISTAYMELSSLRSEDTAMYYCARGTYYYGTRVFDYWGQTLV
TVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVC
TLPPSREEMTKNQVHLTCLVKGFYPSDIAVEWESNGQPENNYKTTPPVLDSDGSFALYS
KLTVDKSRWQQGNVFSCSVMHEALHNHYTQKSLSLSPGKSSDKTHTSPPSPGGGGSG
GGGSGGGGSGGGGEVQLVESGGGLVSPGGSLKLSCVASGFAFSSYDMSWVRQTPEK
RLEWVAKINSAGGRTNYPDTVKGRFTISRDNAENTLYLQMSSLKSEDTAMYYCAGHSYD
YPFTYWGQGTLVTVSA

Heavy Chain 2 of anti-CD19 x anti-CD32b mAb-Fv (SEQ ID NO: (44)

EVQLVESGGGLVKPGGSLKLSCAASGYTFTSYVMHWVRQAPGKGLEWIGYINPYNDGT
KYNEKFQGRVTISSDKSISTAYMELSSLRSEDTAMYYCARGTYYYGTRVFDYWGQTLV
TVSSASTKGPSVFPLAPSSKSTSGGTAALGCLVKDYFPEPVTVSWNSGALESGVHTFPA
VLQSSGLYSLSSVVTVPSSSLGTQTYICNVNHKPSDTEVDKKVEPKSCDKTHTCPPCPA
PELLGGPSVFLFPPKPKDTLMISRTPEVTCVVVDVSHEDPEVQFNWYVDGVEVHNAKTK
PREEQYNSTYRVVSVLTVLHQDWLNGKEYKCKVSNKALPAPIEKTISKAKGQPREPQVT
TLPPCQEEMTKNQVSLTCLVKGFYPSDIAVEWESSGQPENNYNTFPPMLDSDGSFFLYS
KLTVDKSRWQEGNVFSCSVMHEALHNHYTQKSLSLSPGKSSDKTHTSPPSPGGGGSG
GGGSGGGGSGGGGDVVLTQSPATLSVTPGDSVSLCRASQGISNNLHWYQQKSHESP
RLLIKYASQSISGIPSRFSGSGSGTDFTLSINSVETEDFGMYFCQQSDSWPHTFGGGTKL
EIK

Light Chain of anti-CD19 x anti-CD32b mAb-Fv (SEQ ID NO: 45)

DIVMTQSPATLSLSPGERATLSCRSSKSLQNVNGNTYLYWFQQKPGQSPQLLIYRMSNL
NSGVPDRFSGSGSGTEFTLTISSLEPEDFAVYYCMQHLEYPITFGAGTKLEIKRTVAAPSV
FIFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC

Heavy Chain 1 of anti-CD40 x anti-CD32b mAb-Fv (SEQ ID NO: 46)

QVKLEESGPGLVAPSQSLSITCTVSGFSLSRYSVYWVRQPPGKGLEWLGMMWGGGST
DYNSALKSRLSISKDTSKSQVFLKMNSLQTDDTAMYYCVRTGDYWGQGTSVTVSSAS
TKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVCTLPPSREE
MTKNQVHLTCLVKGFYPSDIAVEWESNGQPENNYKTTPPVLDSDGSFALYSKLTVDKSR
WQQGNVFSCSVMHEALHNHYTQKSLSLSPGKSSDKTHTSPPSPGGGGSGGGGSGGG
GSGGGGEVQLVESGGGLVSPGGSLKLSCVASGFAFSSYDMSWVRQTPEKRLEWVAKI
NSAGGRTNYPDTVKGRFTISRDNAENTLYLQMSSLKSEDTAMYYCAGHSYDYPFTYWG
QGTLVTVSA

Figure 39D

Heavy Chain 2 of anti-CD40 x anti-CD32b mAb-Fv (SEQ ID NO: 47)

QVKLEESGPGLVAPSQSLSITCTVSGFSLSRYSVYWVRQPPGKGLEWLGMMWGGGST
DYNSALKSRLSISKDTSKSQVFLKMNSLQTDDTAMYYCVRTDGDYWGQGTSVTVSSAS
TKGPSVFPLAPSSKSTSGGTAALGCLVKDYFPEPVTVSWNSGALESGVHTFPAVLQSSG
LYSLSSVVTVPSSSLGTQTYICNVNHKPSDTEVDKKVEPKSCDKTHTCPPCPAPELLGGP
SVFLFPPKPKDTLMISRTPEVTCVVVDVSHEDPEVQFNWYVDGVEVHNAKTKPREEQYN
STYRVVSVLTVLHQDWLNGKEYKCKVSNKALPAPIEKTISKAKGQPREPQVTTLPPCQEE
MTKNQVSLTCLVKGFYPSDIAVEWESSGQPENNYNTFPPMLDSDGSFFLYSKLTVDKSR
WQEGNVFSCSVMHEALHNHYTQKSLSLSPGKSSDKTHTSPPSPGGGGSGGGGSGGG
GSGGGGDVVLTQSPATLSVTPGDSVSLSCRASQGISNNLHWYQQKSHESPRLLIKYASQ
SISGIPSRFSGSGSGTDFTLSINSVETEDFGMYFCQQSDSWPHTFGGGTKLEIK

Light Chain of anti-CD40 x anti-CD32b mAb-Fv (SEQ ID NO: 48)

ELQLTQSPLSLPVSLGDQASISCRSSQSLVNSNGNTYLHWYLQKPGQSPKLLIYKVSNRF
SGVPDRFSGSGSGTDFTLKISRVEAEDLGVYFCSQSTHVPWTFGGGTKLEIKRTVAAPS
VFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC

Heavy Chain 1 of anti-HER2 x anti-CD3 mAb-Fv (SEQ ID NO: 49)

EVQLVESGGGLVQPGGSLRLSCAASGFNIKDTYIHWVRQAPGKGLEWVARIYPTNGYTR
YADSVKGRFTISADTSKNTAYLQMNSLRAEDTAVYYCSRWGGDGFYAMDYWGQGTLV
TVSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVC
TLPPSREEMTKNQVHLTCLVKGFYPSDIAVEWESNGQPENNYKTTPPVLDSDGSFALYS
KLTVDKSRWQQGNVFSCSVMHEALHNHYTQKSLSLSPGKSSDKTHTSPPSPGGGGSG
GGGSGGGGSGGGGQVQLVQSGAEVKKPGASVKVSCKASGYTFTRYTMHWVRQAPG
QGLEWMGYINPSRGYTNYNQKFQGRVTMTTDKSTSTAYMELSSLRSEDTAVYYCARYY
DDHYSLDYWGQGTTVTVSS

Heavy Chain 2 of anti-HER2 x anti-CD3 mAb-Fv (SEQ ID NO: 70)

EVQLVESGGGLVQPGGSLRLSCAASGFNIKDTYIHWVRQAPGKGLEWVARIYPTNGYTR
YADSVKGRFTISADTSKNTAYLQMNSLRAEDTAVYYCSRWGGDGFYAMDYWGQGTLV
TVSSASTKGPSVFPLAPSSKSTSGGTAALGCLVKDYFPEPVTVSWNSGALESGVHTFPA
VLQSSGLYSLSSVVTVPSSSLGTQTYICNVNHKPSDTEVDKKVEPKSCDKTHTCPPCPA
PELLGGPSVFLFPPKPKDTLMISRTPEVTCVVVDVSHEDPEVQFNWYVDGVEVHNAKTK
PREEQYNSTYRVVSVLTVLHQDWLNGKEYKCKVSNKALPAPIEKTISKAKGQPREPQVT
TLPPCQEEMTKNQVSLTCLVKGFYPSDIAVEWESSGQPENNYNTFPPMLDSDGSFFLYS
KLTVDKSRWQEGNVFSCSVMHEALHNHYTQKSLSLSPGKSSDKTHTSPPSPGGGGSG
GGGSGGGGSGGGGQIVLTQSPATLSLSPGERATLSCRASSSVSYMNWYQQKPGQSPR
RLIYDTSKLASGVPARFRGSGSGTDYTLTISSLEPEDFAVYYCQQWSSNPFTFGSGTKLE
IK

Figure 39E

Light Chain of anti-HER2 x anti-CD3 mAb-Fv (SEQ ID NO: 71)

DIQMTQSPSSLSASVGDRVTITCRASQDVNTAVAWYQQKPGKAPKLLIYSASFLYSGVPS
RFSGSRSGTDFTLTISSLQPEDFATYYCQQHYTTPPTFGQGTKVEIKRTVAAPSVFIFPPS

DEQLKSGTASVVCLLNNFYPREAKVQWKVDNALQSGNSQESVTEQDSKDSTYSLSSTL
TLSKADYEKHKVYACEVTHQGLSSPVTKSFNRGEC

Heavy Chain 1 of anti-HER2 x anti-CD3 scFv-Fc (SEQ ID NO: 72)

QVQLVQSGAEVKKPGASVKVSCKASGYTFTRYTMHWVRQAPGQGLEWMGYINPSRGY
TNYNQKFQGRVTMTTDKSTSTAYMELSSLRSEDTAVYYCARYYDDHYSLDYWGQGTTV
TVSSGGGGSGGGGSGGGGSQIVLTQSPATLSLSPGERATLSCRASSSVSYMNWYQQK
PGQSPRRLIYDTSKLASGVPARFRGSGSGTDYTLTISSLEPEDFAVYYCQQWSSNPFTF
GSGTKLEIKRTEPKSSDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKC
KVSNKALPAPIEKTISKAKGQPREPQVCTLPPSREEMTKNQVHLTCLVKGFYPSDIAVEW
ESNGQPENNYKTTPPVLDSDGSFALYSKLTVDKSRWQQGNVFSCSVMHEALHNHYTQK
SLSLSPGK

Heavy Chain 2 of anti-HER2 x anti-CD3 scFv-Fc (SEQ ID NO: 73)

EVQLVESGGGLVQPGGSLRLSCAASGFNIKDTYIHWVRQAPGKGLEWVARIYPTNGYTR
YADSVKGRFTISADTSKNTAYLQMNSLRAEDTAVYYCSRWGGDGFYAMDYWGQGTLV
TVSSGGGGSGGGGSGGGGSDIQMTQSPSSLSASVGDRVTITCRASQDVNTAVAWYQQ
KPGKAPKLLIYSASFLYSGVPSRFSGSRSGTDFTLTISSLQPEDFATYYCQQHYTTPPTF
GQGTKVEIKRTEPKSSDKTHTCPPCPAPELLGGPSVFLFPPKPKDTLMISRTPEVTCVVV
DVSHEDPEVQFNWYVDGVEVHNAKTKPREEQYNSTYRVVSVLTVLHQDWLNGKEYKC
KVSNKALPAPIEKTISKAKGQPREPQVTTLPPCQEEMTKNQVSLTCLVKGFYPSDIAVEW
ESSGQPENNYNTFPPMLDSDGSFFLYSKLTVDKSRWQEGNVFSCSVMHEALHNHYTQK
SLSLSPGK

Figure 40
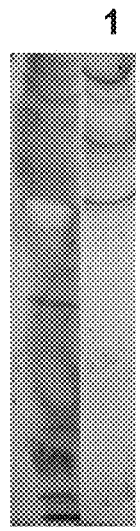
1 – XENP10653 Protein A purified (pre-anion exchange)
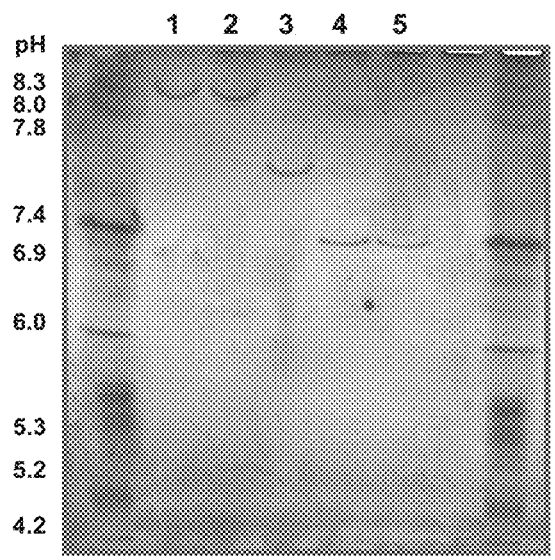
|   | XENP# |
|---|---|
|   | Marker |
| 1 | XENP10653_FT_20111004 |
| 2 | XENP10653_wash_20111004 |
| 3 | XENP10653_Elution1_20111004<br>Elution1 [20mM Tris (7.6), 50mM NaCl] |
| 4 | XENP10653_Elution2_20111004<br>Elution2 [20mM Tris (7.6), 100mM NaCl] |
| 5 | XENP10653_Elution3_20111004<br>Elution3 [20mM Tris (7.6), 200mM NaCl] |
|   | Marker |

Figure 43A

SEQ ID NOS: 136 and 137
Chain H = SEQ ID NO: 136
Chain L = SEQ ID NO: 137

| Chain | Position | Amino acid | % exposed | Chain | Position | Amino acid | % exposed |
|---|---|---|---|---|---|---|---|
| H | 118 | A | 18% | H | 338 | K | 10% |
| H | 119 | S | 60% | H | 339 | A | 44% |
| H | 120 | T | 51% | H | 340 | K | 60% |
| H | 121 | K | 38% | H | 341 | G | 47% |
| H | 122 | G | 25% | H | 342 | Q | 72% |
| H | 123 | P | 9% | H | 343 | P | 48% |
| H | 124 | S | 20% | H | 344 | R | 39% |
| H | 125 | V | 8% | H | 345 | E | 63% |
| H | 126 | F | 14% | H | 346 | P | 4% |
| H | 127 | P | 18% | H | 347 | Q | 24% |
| H | 128 | L | 2% | H | 348 | V | 4% |
| H | 129 | A | 17% | H | 349 | Y | 5% |
| H | 130 | P | 4% | H | 350 | T | 9% |
| H | 131 | S | 79% | H | 351 | L | 2% |
| H | 132 | S | 83% | H | 352 | P | 39% |
| H | 133 | K | 40% | H | 353 | P | 9% |
| H | 134 | S | 77% | H | 354 | S | 10% |
| H | 135 | T | 55% | H | 355 | R | 71% |
| H | 136 | S | 94% | H | 356 | D | 46% |
| H | 137 | G | 91% | H | 357 | E | 1% |
| H | 138 | G | 49% | H | 358 | L | 30% |
| H | 139 | T | 61% | H | 359 | T | 70% |
| H | 140 | A | 12% | H | 360 | K | 39% |
| H | 141 | A | 2% | H | 361 | N | 75% |
| H | 142 | L | 0% | H | 362 | Q | 46% |
| H | 143 | G | 0% | H | 363 | V | 0% |
| H | 144 | C | 0% | H | 364 | S | 2% |
| H | 145 | L | 1% | H | 365 | L | 0% |
| H | 146 | V | 0% | H | 366 | T | 0% |
| H | 147 | K | 3% | H | 367 | C | 0% |
| H | 148 | D | 22% | H | 368 | L | 1% |
| H | 149 | Y | 0% | H | 369 | V | 0% |
| H | 150 | F | 3% | H | 370 | K | 15% |
| H | 151 | P | 6% | H | 371 | G | 15% |
| H | 152 | E | 38% | H | 372 | F | 0% |
| H | 153 | P | 64% | H | 373 | Y | 23% |
| H | 154 | V | 12% | H | 374 | P | 2% |
| H | 155 | T | 54% | H | 375 | S | 29% |
| H | 156 | V | 13% | H | 376 | D | 31% |
| H | 157 | S | 27% | H | 377 | I | 11% |
| H | 158 | W | 0% | H | 378 | A | 12% |
| H | 159 | N | 20% | H | 379 | V | 11% |
| H | 160 | S | 77% | H | 380 | E | 24% |
| H | 161 | G | 54% | H | 381 | W | 0% |
| H | 162 | A | 68% | H | 382 | E | 25% |

Figure 43B

| Chain | Position | Amino acid | % exposed | Chain | Position | Amino acid | % exposed |
|---|---|---|---|---|---|---|---|
| H | 163 | L | 18% | H | 383 | S | 5% |
| H | 164 | T | 62% | H | 384 | N | 76% |
| H | 165 | S | 70% | H | 385 | G | 72% |
| H | 166 | G | 38% | H | 386 | Q | 61% |
| H | 167 | V | 19% | H | 387 | P | 60% |
| H | 168 | H | 14% | H | 388 | E | 13% |
| H | 169 | T | 38% | H | 389 | N | 86% |
| H | 170 | F | 1% | H | 390 | N | 35% |
| H | 171 | P | 45% | H | 391 | Y | 25% |
| H | 172 | A | 26% | H | 392 | K | 34% |
| H | 173 | V | 16% | H | 393 | T | 26% |
| H | 174 | L | 51% | H | 394 | T | 2% |
| H | 175 | Q | 11% | H | 395 | P | 47% |
| H | 176 | S | 102% | H | 396 | P | 37% |
| H | 177 | S | 59% | H | 397 | V | 10% |
| H | 178 | G | 19% | H | 398 | L | 48% |
| H | 179 | L | 12% | H | 399 | D | 14% |
| H | 180 | Y | 10% | H | 400 | S | 65% |
| H | 181 | S | 7% | H | 401 | D | 67% |
| H | 182 | L | 6% | H | 402 | G | 37% |
| H | 183 | S | 4% | H | 403 | S | 2% |
| H | 184 | S | 0% | H | 404 | F | 17% |
| H | 185 | V | 0% | H | 405 | F | 0% |
| H | 186 | V | 0% | H | 406 | L | 2% |
| H | 187 | T | 21% | H | 407 | Y | 0% |
| H | 188 | V | 7% | H | 408 | S | 0% |
| H | 189 | P | 52% | H | 409 | K | 1% |
| H | 190 | S | 34% | H | 410 | L | 0% |
| H | 191 | S | 75% | H | 411 | T | 15% |
| H | 192 | S | 15% | H | 412 | V | 3% |
| H | 193 | L | 24% | H | 413 | D | 45% |
| H | 194 | G | 81% | H | 414 | K | 23% |
| H | 195 | T | 72% | H | 415 | S | 48% |
| H | 196 | Q | 52% | H | 416 | R | 30% |
| H | 197 | T | 47% | H | 417 | W | 2% |
| H | 198 | Y | 5% | H | 418 | Q | 42% |
| H | 199 | I | 24% | H | 419 | Q | 67% |
| H | 200 | C | 0% | H | 420 | G | 35% |
| H | 201 | N | 13% | H | 421 | N | 24% |
| H | 202 | V | 1% | H | 422 | V | 43% |
| H | 203 | N | 20% | H | 423 | F | 0% |
| H | 204 | H | 0% | H | 424 | S | 10% |
| H | 205 | K | 72% | H | 425 | C | 0% |
| H | 206 | P | 38% | H | 426 | S | 1% |
| H | 207 | S | 24% | H | 427 | V | 0% |
| H | 208 | N | 82% | H | 428 | M | 2% |
| H | 209 | T | 21% | H | 429 | H | 0% |
| H | 210 | K | 67% | H | 430 | E | 20% |
| H | 211 | V | 29% | H | 431 | A | 22% |

Figure 43C

| Chain | Position | Amino acid | % exposed | Chain | Position | Amino acid | % exposed |
|---|---|---|---|---|---|---|---|
| H | 212 | D | 53% | H | 432 | L | 7% |
| H | 213 | K | 26% | H | 433 | H | 80% |
| H | 214 | K | 45% | H | 434 | N | 69% |
| H | 215 | A | 2% | H | 435 | H | 38% |
| H | 216 | E | 59% | H | 436 | Y | 40% |
| H | 217 | P | 34% | H | 437 | T | 23% |
| H | 218 | K | 37% | H | 438 | Q | 42% |
| H | 219 | S | 76% | H | 439 | K | 27% |
| H | 220 | C | 43% | H | 440 | S | 53% |
| H | 221 | D | 45% | H | 441 | L | 7% |
| H | 222 | K | 83% | H | 442 | S | 35% |
| H | 223 | T | 62% | H | 443 | L | 32% |
| H | 224 | H | 64% | H | 444 | S | 78% |
| H | 225 | T | 41% | H | 445 | P | 91% |
| H | 226 | C | 54% | H | 446 | G | 97% |
| H | 227 | P | 78% | H | 447 | K | 86% |
| H | 228 | P | 79% | L | 108 | R | 15% |
| H | 229 | C | 80% | L | 109 | T | 51% |
| H | 230 | P | 79% | L | 110 | V | 43% |
| H | 231 | A | 46% | L | 111 | A | 9% |
| H | 232 | P | 74% | L | 112 | A | 30% |
| H | 233 | E | 65% | L | 113 | P | 7% |
| H | 234 | L | 52% | L | 114 | S | 40% |
| H | 235 | L | 40% | L | 115 | V | 3% |
| H | 236 | G | 63% | L | 116 | F | 13% |
| H | 237 | G | 19% | L | 117 | I | 12% |
| H | 238 | P | 4% | L | 118 | F | 2% |
| H | 239 | S | 30% | L | 119 | P | 24% |
| H | 240 | V | 3% | L | 120 | P | 6% |
| H | 241 | F | 48% | L | 121 | S | 8% |
| H | 242 | L | 12% | L | 122 | D | 62% |
| H | 243 | F | 46% | L | 123 | E | 39% |
| H | 244 | P | 43% | L | 124 | Q | 1% |
| H | 245 | P | 5% | L | 125 | L | 18% |
| H | 246 | K | 56% | L | 126 | K | 74% |
| H | 247 | P | 27% | L | 127 | S | 66% |
| H | 248 | K | 18% | L | 128 | G | 31% |
| H | 249 | D | 13% | L | 129 | T | 36% |
| H | 250 | T | 5% | L | 130 | A | 1% |
| H | 251 | L | 14% | L | 131 | S | 2% |
| H | 252 | M | 21% | L | 132 | V | 2% |
| H | 253 | I | 90% | L | 133 | V | 0% |
| H | 254 | S | 73% | L | 134 | C | 0% |
| H | 255 | R | 37% | L | 135 | L | 0% |
| H | 256 | T | 54% | L | 136 | L | 0% |
| H | 257 | P | 0% | L | 137 | N | 7% |
| H | 258 | E | 39% | L | 138 | N | 26% |
| H | 259 | V | 0% | L | 139 | F | 0% |
| H | 260 | T | 19% | L | 140 | Y | 2% |

Figure 43D

| Chain | Position | Amino acid | % exposed | Chain | Position | Amino acid | % exposed |
|---|---|---|---|---|---|---|---|
| H | 261 | C | 0% | L | 141 | P | 15% |
| H | 262 | V | 6% | L | 142 | R | 33% |
| H | 263 | V | 0% | L | 143 | E | 62% |
| H | 264 | V | 22% | L | 144 | A | 18% |
| H | 265 | D | 36% | L | 145 | K | 55% |
| H | 266 | V | 0% | L | 146 | V | 14% |
| H | 267 | S | 13% | L | 147 | Q | 32% |
| H | 268 | H | 37% | L | 148 | W | 2% |
| H | 269 | E | 39% | L | 149 | K | 24% |
| H | 270 | D | 12% | L | 150 | V | 6% |
| H | 271 | P | 22% | L | 151 | D | 32% |
| H | 272 | E | 69% | L | 152 | N | 81% |
| H | 273 | V | 16% | L | 153 | A | 39% |
| H | 274 | K | 60% | L | 154 | L | 62% |
| H | 275 | F | 13% | L | 155 | Q | 17% |
| H | 276 | N | 15% | L | 156 | S | 70% |
| H | 277 | W | 2% | L | 157 | G | 99% |
| H | 278 | Y | 21% | L | 158 | N | 22% |
| H | 279 | V | 15% | L | 159 | S | 33% |
| H | 280 | D | 52% | L | 160 | Q | 34% |
| H | 281 | G | 56% | L | 161 | E | 44% |
| H | 282 | V | 65% | L | 162 | S | 12% |
| H | 283 | E | 38% | L | 163 | V | 19% |
| H | 284 | V | 23% | L | 164 | T | 13% |
| H | 285 | H | 76% | L | 165 | E | 62% |
| H | 286 | N | 57% | L | 166 | Q | 19% |
| H | 287 | A | 27% | L | 167 | D | 26% |
| H | 288 | K | 60% | L | 168 | S | 88% |
| H | 289 | T | 45% | L | 169 | K | 76% |
| H | 290 | K | 40% | L | 170 | D | 28% |
| H | 291 | P | 76% | L | 171 | S | 6% |
| H | 292 | R | 46% | L | 172 | T | 2% |
| H | 293 | E | 51% | L | 173 | Y | 0% |
| H | 294 | E | 55% | L | 174 | S | 0% |
| H | 295 | Q | 31% | L | 175 | L | 1% |
| H | 296 | Y | 101% | L | 176 | S | 2% |
| H | 297 | N | 58% | L | 177 | S | 1% |
| H | 298 | S | 40% | L | 178 | T | 11% |
| H | 299 | T | 16% | L | 179 | L | 1% |
| H | 300 | Y | 14% | L | 180 | T | 29% |
| H | 301 | R | 38% | L | 181 | L | 23% |
| H | 302 | V | 4% | L | 182 | S | 32% |
| H | 303 | V | 8% | L | 183 | K | 35% |
| H | 304 | S | 0% | L | 184 | A | 52% |
| H | 305 | V | 9% | L | 185 | D | 35% |
| H | 306 | L | 2% | L | 186 | Y | 6% |
| H | 307 | T | 40% | L | 187 | E | 48% |
| H | 308 | V | 5% | L | 188 | K | 63% |
| H | 309 | L | 55% | L | 189 | H | 26% |

Figure 43E

| Chain | Position | Amino acid | % exposed | Chain | Position | Amino acid | % exposed |
|---|---|---|---|---|---|---|---|
| H | 310 | H | 24% | L | 190 | K | 64% |
| H | 311 | Q | 62% | L | 191 | V | 33% |
| H | 312 | D | 19% | L | 192 | Y | 2% |
| H | 313 | W | 4% | L | 193 | A | 8% |
| H | 314 | L | 25% | L | 194 | C | 0% |
| H | 315 | N | 72% | L | 195 | E | 18% |
| H | 316 | G | 28% | L | 196 | V | 0% |
| H | 317 | K | 33% | L | 197 | T | 32% |
| H | 318 | E | 44% | L | 198 | H | 6% |
| H | 319 | Y | 2% | L | 199 | Q | 60% |
| H | 320 | K | 27% | L | 200 | G | 35% |
| H | 321 | C | 0% | L | 201 | L | 14% |
| H | 322 | K | 25% | L | 202 | R | 80% |
| H | 323 | V | 0% | L | 203 | S | 49% |
| H | 324 | S | 30% | L | 204 | P | 45% |
| H | 325 | N | 8% | L | 205 | V | 21% |
| H | 326 | K | 61% | L | 206 | T | 42% |
| H | 327 | A | 16% | L | 207 | K | 37% |
| H | 328 | L | 9% | L | 208 | S | 45% |
| H | 329 | P | 46% | L | 209 | F | 14% |
| H | 330 | A | 40% | L | 210 | N | 47% |
| H | 331 | P | 43% | L | 211 | R | 35% |
| H | 332 | I | 34% | L | 212 | G | 61% |
| H | 333 | E | 51% | L | 213 | E | 69% |
| H | 334 | K | 35% | L | 214 | C | 68% |
| H | 335 | T | 47% | | | | |
| H | 336 | I | 19% | | | | |
| H | 337 | S | 28% | | | | |

SEQ ID NOS:   and
Chain H = SEQ ID NO:
Chain L = SEQ ID NO:

Figure 44A

| Variant | Neutral or Basic to Acidic | | | |
|---|---|---|---|---|
| | IgG1 / IgG1 | pI / IgG1 | pI / pI | delta pI |
| HC S119D | 8.02 | 7.94 | 7.85 | -0.09 |
| HC S119E | 8.02 | 7.94 | 7.85 | -0.09 |
| HC T120D | 8.02 | 7.94 | 7.85 | -0.09 |
| HC T120E | 8.02 | 7.94 | 7.85 | -0.09 |
| HC K121D | 8.02 | 7.85 | 7.61 | -0.21 |
| HC K121E | 8.02 | 7.85 | 7.61 | -0.21 |
| HC G122D | 8.02 | 7.94 | 7.85 | -0.09 |
| HC G122E | 8.02 | 7.94 | 7.85 | -0.09 |
| HC S131D | 8.02 | 7.94 | 7.85 | -0.09 |
| HC S131E | 8.02 | 7.94 | 7.85 | -0.09 |
| HC S132D | 8.02 | 7.94 | 7.85 | -0.09 |
| HC S132E | 8.02 | 7.94 | 7.85 | -0.09 |
| HC K133D | 8.02 | 7.85 | 7.61 | -0.21 |
| HC K133E | 8.02 | 7.85 | 7.61 | -0.21 |
| HC S134D | 8.02 | 7.94 | 7.85 | -0.09 |
| HC S134E | 8.02 | 7.94 | 7.85 | -0.09 |
| HC T135D | 8.02 | 7.94 | 7.85 | -0.09 |
| HC T135E | 8.02 | 7.94 | 7.85 | -0.09 |
| HC S136D | 8.02 | 7.94 | 7.85 | -0.09 |
| HC S136E | 8.02 | 7.94 | 7.85 | -0.09 |
| HC G137D | 8.02 | 7.94 | 7.85 | -0.09 |
| HC G137E | 8.02 | 7.94 | 7.85 | -0.09 |
| HC G138D | 8.02 | 7.94 | 7.85 | -0.09 |
| HC G138E | 8.02 | 7.94 | 7.85 | -0.09 |
| HC T139D | 8.02 | 7.94 | 7.85 | -0.09 |
| HC T139E | 8.02 | 7.94 | 7.85 | -0.09 |
| HC P153D | 8.02 | 7.94 | 7.85 | -0.09 |
| HC P153E | 8.02 | 7.94 | 7.85 | -0.09 |
| HC T155D | 8.02 | 7.94 | 7.85 | -0.09 |
| HC T155E | 8.02 | 7.94 | 7.85 | -0.09 |
| HC S157D | 8.02 | 7.94 | 7.85 | -0.09 |
| HC S157E | 8.02 | 7.94 | 7.85 | -0.09 |
| HC N159D | 8.02 | 7.94 | 7.85 | -0.09 |
| HC N159E | 8.02 | 7.94 | 7.85 | -0.09 |
| HC S160D | 8.02 | 7.94 | 7.85 | -0.09 |
| HC S160E | 8.02 | 7.94 | 7.85 | -0.09 |
| HC G161D | 8.02 | 7.94 | 7.85 | -0.09 |
| HC G161E | 8.02 | 7.94 | 7.85 | -0.09 |
| HC A162D | 8.02 | 7.94 | 7.85 | -0.09 |
| HC A162E | 8.02 | 7.94 | 7.85 | -0.09 |
| HC T164D | 8.02 | 7.94 | 7.85 | -0.09 |
| HC T164E | 8.02 | 7.94 | 7.85 | -0.09 |
| HC S165D | 8.02 | 7.94 | 7.85 | -0.09 |
| HC S165E | 8.02 | 7.94 | 7.85 | -0.09 |
| HC G166D | 8.02 | 7.94 | 7.85 | -0.09 |
| HC G166E | 8.02 | 7.94 | 7.85 | -0.09 |
| HC T169D | 8.02 | 7.94 | 7.85 | -0.09 |
| HC T169E | 8.02 | 7.94 | 7.85 | -0.09 |

Figure 44B

| Variant | Neutral or Basic to Acidic | | | |
|---|---|---|---|---|
| | IgG1 / IgG1 | pI / IgG1 | pI / pI | delta pI |
| HC P171D | 8.02 | 7.94 | 7.85 | -0.09 |
| HC P171E | 8.02 | 7.94 | 7.85 | -0.09 |
| HC A172D | 8.02 | 7.94 | 7.85 | -0.09 |
| HC A172E | 8.02 | 7.94 | 7.85 | -0.09 |
| HC L174D | 8.02 | 7.94 | 7.85 | -0.09 |
| HC L174E | 8.02 | 7.94 | 7.85 | -0.09 |
| HC S176D | 8.02 | 7.94 | 7.85 | -0.09 |
| HC S176E | 8.02 | 7.94 | 7.85 | -0.09 |
| HC S177D | 8.02 | 7.94 | 7.85 | -0.09 |
| HC S177E | 8.02 | 7.94 | 7.85 | -0.09 |
| HC T187D | 8.02 | 7.94 | 7.85 | -0.09 |
| HC T187E | 8.02 | 7.94 | 7.85 | -0.09 |
| HC P189D | 8.02 | 7.94 | 7.85 | -0.09 |
| HC P189E | 8.02 | 7.94 | 7.85 | -0.09 |
| HC S190D | 8.02 | 7.94 | 7.85 | -0.09 |
| HC S190E | 8.02 | 7.94 | 7.85 | -0.09 |
| HC S191D | 8.02 | 7.94 | 7.85 | -0.09 |
| HC S191E | 8.02 | 7.94 | 7.85 | -0.09 |
| HC L193D | 8.02 | 7.94 | 7.85 | -0.09 |
| HC L193E | 8.02 | 7.94 | 7.85 | -0.09 |
| HC G194D | 8.02 | 7.94 | 7.85 | -0.09 |
| HC G194E | 8.02 | 7.94 | 7.85 | -0.09 |
| HC T195D | 8.02 | 7.94 | 7.85 | -0.09 |
| HC T195E | 8.02 | 7.94 | 7.85 | -0.09 |
| HC Q196D | 8.02 | 7.94 | 7.85 | -0.09 |
| HC Q196E | 8.02 | 7.94 | 7.85 | -0.09 |
| HC T197D | 8.02 | 7.94 | 7.85 | -0.09 |
| HC T197E | 8.02 | 7.94 | 7.85 | -0.09 |
| HC I199D | 8.02 | 7.94 | 7.85 | -0.09 |
| HC I199E | 8.02 | 7.94 | 7.85 | -0.09 |
| HC N203D | 8.02 | 7.94 | 7.85 | -0.09 |
| HC N203E | 8.02 | 7.94 | 7.85 | -0.09 |
| HC K205D | 8.02 | 7.85 | 7.61 | -0.21 |
| HC K205E | 8.02 | 7.85 | 7.61 | -0.21 |
| HC P206D | 8.02 | 7.94 | 7.85 | -0.09 |
| HC P206E | 8.02 | 7.94 | 7.85 | -0.09 |
| HC S207D | 8.02 | 7.94 | 7.85 | -0.09 |
| HC S207E | 8.02 | 7.94 | 7.85 | -0.09 |
| HC N208D | 8.02 | 7.94 | 7.85 | -0.09 |
| HC N208E | 8.02 | 7.94 | 7.85 | -0.09 |
| HC T209D | 8.02 | 7.94 | 7.85 | -0.09 |
| HC T209E | 8.02 | 7.94 | 7.85 | -0.09 |
| HC K210D | 8.02 | 7.85 | 7.61 | -0.21 |
| HC K210E | 8.02 | 7.85 | 7.61 | -0.21 |
| HC V211D | 8.02 | 7.94 | 7.85 | -0.09 |
| HC V211E | 8.02 | 7.94 | 7.85 | -0.09 |
| HC K213D | 8.02 | 7.85 | 7.61 | -0.21 |
| HC K213E | 8.02 | 7.85 | 7.61 | -0.21 |
| HC K214D | 8.02 | 7.85 | 7.61 | -0.21 |
| HC K214E | 8.02 | 7.85 | 7.61 | -0.21 |

Figure 44C

| Variant | Neutral or Basic to Acidic | | | |
|---|---|---|---|---|
| | IgG1 / IgG1 | pI / IgG1 | pI / pI | delta pI |
| HC P217D | 8.02 | 7.94 | 7.85 | -0.09 |
| HC P217E | 8.02 | 7.94 | 7.85 | -0.09 |
| HC K218D | 8.02 | 7.85 | 7.61 | -0.21 |
| HC K218E | 8.02 | 7.85 | 7.61 | -0.21 |
| HC S219D | 8.02 | 7.94 | 7.85 | -0.09 |
| HC S219E | 8.02 | 7.94 | 7.85 | -0.09 |
| HC C220D | 8.02 | 7.95 | 7.86 | -0.08 |
| HC C220E | 8.02 | 7.95 | 7.86 | -0.08 |
| HC K222D | 8.02 | 7.85 | 7.61 | -0.21 |
| HC K222E | 8.02 | 7.85 | 7.61 | -0.21 |
| HC T223D | 8.02 | 7.94 | 7.85 | -0.09 |
| HC T223E | 8.02 | 7.94 | 7.85 | -0.09 |
| HC H224D | 8.02 | 7.94 | 7.84 | -0.09 |
| HC H224E | 8.02 | 7.94 | 7.84 | -0.09 |
| HC T225D | 8.02 | 7.94 | 7.85 | -0.09 |
| HC T225E | 8.02 | 7.94 | 7.85 | -0.09 |
| HC C226D | 8.02 | 7.95 | 7.86 | -0.08 |
| HC C226E | 8.02 | 7.95 | 7.86 | -0.08 |
| HC P227D | 8.02 | 7.94 | 7.85 | -0.09 |
| HC P227E | 8.02 | 7.94 | 7.85 | -0.09 |
| HC P228D | 8.02 | 7.94 | 7.85 | -0.09 |
| HC P228E | 8.02 | 7.94 | 7.85 | -0.09 |
| HC C229D | 8.02 | 7.95 | 7.86 | -0.08 |
| HC C229E | 8.02 | 7.95 | 7.86 | -0.08 |
| HC P230D | 8.02 | 7.94 | 7.85 | -0.09 |
| HC P230E | 8.02 | 7.94 | 7.85 | -0.09 |
| HC A231D | 8.02 | 7.94 | 7.85 | -0.09 |
| HC A231E | 8.02 | 7.94 | 7.85 | -0.09 |
| HC P232D | 8.02 | 7.94 | 7.85 | -0.09 |
| HC P232E | 8.02 | 7.94 | 7.85 | -0.09 |
| HC L234D | 8.02 | 7.94 | 7.85 | -0.09 |
| HC L234E | 8.02 | 7.94 | 7.85 | -0.09 |
| HC L235D | 8.02 | 7.94 | 7.85 | -0.09 |
| HC L235E | 8.02 | 7.94 | 7.85 | -0.09 |
| HC G236D | 8.02 | 7.94 | 7.85 | -0.09 |
| HC G236E | 8.02 | 7.94 | 7.85 | -0.09 |
| HC S239D | 8.02 | 7.94 | 7.85 | -0.09 |
| HC S239E | 8.02 | 7.94 | 7.85 | -0.09 |
| HC F241D | 8.02 | 7.94 | 7.85 | -0.09 |
| HC F241E | 8.02 | 7.94 | 7.85 | -0.09 |
| HC F243D | 8.02 | 7.94 | 7.85 | -0.09 |
| HC F243E | 8.02 | 7.94 | 7.85 | -0.09 |
| HC P244D | 8.02 | 7.94 | 7.85 | -0.09 |
| HC P244E | 8.02 | 7.94 | 7.85 | -0.09 |
| HC K246D | 8.02 | 7.85 | 7.61 | -0.21 |
| HC K246E | 8.02 | 7.85 | 7.61 | -0.21 |
| HC P247D | 8.02 | 7.94 | 7.85 | -0.09 |
| HC P247E | 8.02 | 7.94 | 7.85 | -0.09 |
| HC M252D | 8.02 | 7.94 | 7.85 | -0.09 |
| HC M252E | 8.02 | 7.94 | 7.85 | -0.09 |

Figure 44D

| Variant | Neutral or Basic to Acidic | | | |
|---|---|---|---|---|
| | IgG1 / IgG1 | pI / IgG1 | pI / pI | delta pI |
| HC I253D | 8.02 | 7.94 | 7.85 | -0.09 |
| HC I253E | 8.02 | 7.94 | 7.85 | -0.09 |
| HC S254D | 8.02 | 7.94 | 7.85 | -0.09 |
| HC S254E | 8.02 | 7.94 | 7.85 | -0.09 |
| HC R255D | 8.02 | 7.85 | 7.61 | -0.21 |
| HC R255E | 8.02 | 7.85 | 7.61 | -0.21 |
| HC T256D | 8.02 | 7.94 | 7.85 | -0.09 |
| HC T256E | 8.02 | 7.94 | 7.85 | -0.09 |
| HC V264D | 8.02 | 7.94 | 7.85 | -0.09 |
| HC V264E | 8.02 | 7.94 | 7.85 | -0.09 |
| HC H268D | 8.02 | 7.94 | 7.84 | -0.09 |
| HC H268E | 8.02 | 7.94 | 7.84 | -0.09 |
| HC P271D | 8.02 | 7.94 | 7.85 | -0.09 |
| HC P271E | 8.02 | 7.94 | 7.85 | -0.09 |
| HC K274D | 8.02 | 7.85 | 7.61 | -0.21 |
| HC K274E | 8.02 | 7.85 | 7.61 | -0.21 |
| HC Y278D | 8.02 | 7.94 | 7.85 | -0.09 |
| HC Y278E | 8.02 | 7.94 | 7.85 | -0.09 |
| HC G281D | 8.02 | 7.94 | 7.85 | -0.09 |
| HC G281E | 8.02 | 7.94 | 7.85 | -0.09 |
| HC V282D | 8.02 | 7.94 | 7.85 | -0.09 |
| HC V282E | 8.02 | 7.94 | 7.85 | -0.09 |
| HC V284D | 8.02 | 7.94 | 7.85 | -0.09 |
| HC V284E | 8.02 | 7.94 | 7.85 | -0.09 |
| HC H285D | 8.02 | 7.94 | 7.84 | -0.09 |
| HC H285E | 8.02 | 7.94 | 7.84 | -0.09 |
| HC N286D | 8.02 | 7.94 | 7.85 | -0.09 |
| HC N286E | 8.02 | 7.94 | 7.85 | -0.09 |
| HC A287D | 8.02 | 7.94 | 7.85 | -0.09 |
| HC A287E | 8.02 | 7.94 | 7.85 | -0.09 |
| HC K288D | 8.02 | 7.85 | 7.61 | -0.21 |
| HC K288E | 8.02 | 7.85 | 7.61 | -0.21 |
| HC T289D | 8.02 | 7.94 | 7.85 | -0.09 |
| HC T289E | 8.02 | 7.94 | 7.85 | -0.09 |
| HC K290D | 8.02 | 7.85 | 7.61 | -0.21 |
| HC K290E | 8.02 | 7.85 | 7.61 | -0.21 |
| HC P291D | 8.02 | 7.94 | 7.85 | -0.09 |
| HC P291E | 8.02 | 7.94 | 7.85 | -0.09 |
| HC R292D | 8.02 | 7.85 | 7.61 | -0.21 |
| HC R292E | 8.02 | 7.85 | 7.61 | -0.21 |
| HC Q295D | 8.02 | 7.94 | 7.85 | -0.09 |
| HC Q295E | 8.02 | 7.94 | 7.85 | -0.09 |
| HC Y296D | 8.02 | 7.94 | 7.85 | -0.09 |
| HC Y296E | 8.02 | 7.94 | 7.85 | -0.09 |
| HC N297D | 8.02 | 7.94 | 7.85 | -0.09 |
| HC N297E | 8.02 | 7.94 | 7.85 | -0.09 |
| HC S298D | 8.02 | 7.94 | 7.85 | -0.09 |
| HC S298E | 8.02 | 7.94 | 7.85 | -0.09 |
| HC R301D | 8.02 | 7.85 | 7.61 | -0.21 |
| HC R301E | 8.02 | 7.85 | 7.61 | -0.21 |

Figure 44E

| Variant | Neutral or Basic to Acidic | | | |
|---|---|---|---|---|
| | IgG1 / IgG1 | pI / IgG1 | pI / pI | delta pI |
| HC T307D | 8.02 | 7.94 | 7.85 | -0.09 |
| HC T307E | 8.02 | 7.94 | 7.85 | -0.09 |
| HC L309D | 8.02 | 7.94 | 7.85 | -0.09 |
| HC L309E | 8.02 | 7.94 | 7.85 | -0.09 |
| HC H310D | 8.02 | 7.94 | 7.84 | -0.09 |
| HC H310E | 8.02 | 7.94 | 7.84 | -0.09 |
| HC Q311D | 8.02 | 7.94 | 7.85 | -0.09 |
| HC Q311E | 8.02 | 7.94 | 7.85 | -0.09 |
| HC L314D | 8.02 | 7.94 | 7.85 | -0.09 |
| HC L314E | 8.02 | 7.94 | 7.85 | -0.09 |
| HC N315D | 8.02 | 7.94 | 7.85 | -0.09 |
| HC N315E | 8.02 | 7.94 | 7.85 | -0.09 |
| HC G316D | 8.02 | 7.94 | 7.85 | -0.09 |
| HC G316E | 8.02 | 7.94 | 7.85 | -0.09 |
| HC K317D | 8.02 | 7.85 | 7.61 | -0.21 |
| HC K317E | 8.02 | 7.85 | 7.61 | -0.21 |
| HC K320D | 8.02 | 7.85 | 7.61 | -0.21 |
| HC K320E | 8.02 | 7.85 | 7.61 | -0.21 |
| HC K322D | 8.02 | 7.85 | 7.61 | -0.21 |
| HC K322E | 8.02 | 7.85 | 7.61 | -0.21 |
| HC S324D | 8.02 | 7.94 | 7.85 | -0.09 |
| HC S324E | 8.02 | 7.94 | 7.85 | -0.09 |
| HC K326D | 8.02 | 7.85 | 7.61 | -0.21 |
| HC K326E | 8.02 | 7.85 | 7.61 | -0.21 |
| HC P329D | 8.02 | 7.94 | 7.85 | -0.09 |
| HC P329E | 8.02 | 7.94 | 7.85 | -0.09 |
| HC A330D | 8.02 | 7.94 | 7.85 | -0.09 |
| HC A330E | 8.02 | 7.94 | 7.85 | -0.09 |
| HC P331D | 8.02 | 7.94 | 7.85 | -0.09 |
| HC P331E | 8.02 | 7.94 | 7.85 | -0.09 |
| HC I332D | 8.02 | 7.94 | 7.85 | -0.09 |
| HC I332E | 8.02 | 7.94 | 7.85 | -0.09 |
| HC K334D | 8.02 | 7.85 | 7.61 | -0.21 |
| HC K334E | 8.02 | 7.85 | 7.61 | -0.21 |
| HC T335D | 8.02 | 7.94 | 7.85 | -0.09 |
| HC T335E | 8.02 | 7.94 | 7.85 | -0.09 |
| HC S337D | 8.02 | 7.94 | 7.85 | -0.09 |
| HC S337E | 8.02 | 7.94 | 7.85 | -0.09 |
| HC A339D | 8.02 | 7.94 | 7.85 | -0.09 |
| HC A339E | 8.02 | 7.94 | 7.85 | -0.09 |
| HC K340D | 8.02 | 7.85 | 7.61 | -0.21 |
| HC K340E | 8.02 | 7.85 | 7.61 | -0.21 |
| HC G341D | 8.02 | 7.94 | 7.85 | -0.09 |
| HC G341E | 8.02 | 7.94 | 7.85 | -0.09 |
| HC Q342D | 8.02 | 7.94 | 7.85 | -0.09 |
| HC Q342E | 8.02 | 7.94 | 7.85 | -0.09 |
| HC P343D | 8.02 | 7.94 | 7.85 | -0.09 |
| HC P343E | 8.02 | 7.94 | 7.85 | -0.09 |
| HC R344D | 8.02 | 7.85 | 7.61 | -0.21 |
| HC R344E | 8.02 | 7.85 | 7.61 | -0.21 |

Figure 44F

| Variant | Neutral or Basic to Acidic | | | |
|---|---|---|---|---|
| | IgG1 / IgG1 | pI / IgG1 | pI / pI | delta pI |
| HC Q347D | 8.02 | 7.94 | 7.85 | -0.09 |
| HC Q347E | 8.02 | 7.94 | 7.85 | -0.09 |
| HC P352D | 8.02 | 7.94 | 7.85 | -0.09 |
| HC P352E | 8.02 | 7.94 | 7.85 | -0.09 |
| HC R355D | 8.02 | 7.85 | 7.61 | -0.21 |
| HC R355E | 8.02 | 7.85 | 7.61 | -0.21 |
| HC M358D | 8.02 | 7.94 | 7.85 | -0.09 |
| HC M358E | 8.02 | 7.94 | 7.85 | -0.09 |
| HC T359D | 8.02 | 7.94 | 7.85 | -0.09 |
| HC T359E | 8.02 | 7.94 | 7.85 | -0.09 |
| HC K360D | 8.02 | 7.85 | 7.61 | -0.21 |
| HC K360E | 8.02 | 7.85 | 7.61 | -0.21 |
| HC N361D | 8.02 | 7.94 | 7.85 | -0.09 |
| HC N361E | 8.02 | 7.94 | 7.85 | -0.09 |
| HC Q362D | 8.02 | 7.94 | 7.85 | -0.09 |
| HC Q362E | 8.02 | 7.94 | 7.85 | -0.09 |
| HC Y373D | 8.02 | 7.94 | 7.85 | -0.09 |
| HC Y373E | 8.02 | 7.94 | 7.85 | -0.09 |
| HC S375D | 8.02 | 7.94 | 7.85 | -0.09 |
| HC S375E | 8.02 | 7.94 | 7.85 | -0.09 |
| HC N384D | 8.02 | 7.94 | 7.85 | -0.09 |
| HC N384E | 8.02 | 7.94 | 7.85 | -0.09 |
| HC G385D | 8.02 | 7.94 | 7.85 | -0.09 |
| HC G385E | 8.02 | 7.94 | 7.85 | -0.09 |
| HC Q386D | 8.02 | 7.94 | 7.85 | -0.09 |
| HC Q386E | 8.02 | 7.94 | 7.85 | -0.09 |
| HC P387D | 8.02 | 7.94 | 7.85 | -0.09 |
| HC P387E | 8.02 | 7.94 | 7.85 | -0.09 |
| HC N389D | 8.02 | 7.94 | 7.85 | -0.09 |
| HC N389E | 8.02 | 7.94 | 7.85 | -0.09 |
| HC N390D | 8.02 | 7.94 | 7.85 | -0.09 |
| HC N390E | 8.02 | 7.94 | 7.85 | -0.09 |
| HC Y391D | 8.02 | 7.94 | 7.85 | -0.09 |
| HC Y391E | 8.02 | 7.94 | 7.85 | -0.09 |
| HC K392D | 8.02 | 7.85 | 7.61 | -0.21 |
| HC K392E | 8.02 | 7.85 | 7.61 | -0.21 |
| HC T393D | 8.02 | 7.94 | 7.85 | -0.09 |
| HC T393E | 8.02 | 7.94 | 7.85 | -0.09 |
| HC P395D | 8.02 | 7.94 | 7.85 | -0.09 |
| HC P395E | 8.02 | 7.94 | 7.85 | -0.09 |
| HC P396D | 8.02 | 7.94 | 7.85 | -0.09 |
| HC P396E | 8.02 | 7.94 | 7.85 | -0.09 |
| HC L398D | 8.02 | 7.94 | 7.85 | -0.09 |
| HC L398E | 8.02 | 7.94 | 7.85 | -0.09 |
| HC S400D | 8.02 | 7.94 | 7.85 | -0.09 |
| HC S400E | 8.02 | 7.94 | 7.85 | -0.09 |
| HC G402D | 8.02 | 7.94 | 7.85 | -0.09 |
| HC G402E | 8.02 | 7.94 | 7.85 | -0.09 |
| HC K414D | 8.02 | 7.85 | 7.61 | -0.21 |
| HC K414E | 8.02 | 7.85 | 7.61 | -0.21 |

Figure 44G

| Variant | Neutral or Basic to Acidic | | | |
|---|---|---|---|---|
| | IgG1 / IgG1 | pI / IgG1 | pI / pI | delta pI |
| HC S415D | 8.02 | 7.94 | 7.85 | -0.09 |
| HC S415E | 8.02 | 7.94 | 7.85 | -0.09 |
| HC R416D | 8.02 | 7.85 | 7.61 | -0.21 |
| HC R416E | 8.02 | 7.85 | 7.61 | -0.21 |
| HC Q418D | 8.02 | 7.94 | 7.85 | -0.09 |
| HC Q418E | 8.02 | 7.94 | 7.85 | -0.09 |
| HC Q419D | 8.02 | 7.94 | 7.85 | -0.09 |
| HC Q419E | 8.02 | 7.94 | 7.85 | -0.09 |
| HC G420D | 8.02 | 7.94 | 7.85 | -0.09 |
| HC G420E | 8.02 | 7.94 | 7.85 | -0.09 |
| HC N421D | 8.02 | 7.94 | 7.85 | -0.09 |
| HC N421E | 8.02 | 7.94 | 7.85 | -0.09 |
| HC V422D | 8.02 | 7.94 | 7.85 | -0.09 |
| HC V422E | 8.02 | 7.94 | 7.85 | -0.09 |
| HC A431D | 8.02 | 7.94 | 7.85 | -0.09 |
| HC A431E | 8.02 | 7.94 | 7.85 | -0.09 |
| HC H433D | 8.02 | 7.94 | 7.84 | -0.09 |
| HC H433E | 8.02 | 7.94 | 7.84 | -0.09 |
| HC N434D | 8.02 | 7.94 | 7.85 | -0.09 |
| HC N434E | 8.02 | 7.94 | 7.85 | -0.09 |
| HC H435D | 8.02 | 7.94 | 7.84 | -0.09 |
| HC H435E | 8.02 | 7.94 | 7.84 | -0.09 |
| HC Y436D | 8.02 | 7.94 | 7.85 | -0.09 |
| HC Y436E | 8.02 | 7.94 | 7.85 | -0.09 |
| HC T437D | 8.02 | 7.94 | 7.85 | -0.09 |
| HC T437E | 8.02 | 7.94 | 7.85 | -0.09 |
| HC Q438D | 8.02 | 7.94 | 7.85 | -0.09 |
| HC Q438E | 8.02 | 7.94 | 7.85 | -0.09 |
| HC K439D | 8.02 | 7.85 | 7.61 | -0.21 |
| HC K439E | 8.02 | 7.85 | 7.61 | -0.21 |
| HC S440D | 8.02 | 7.94 | 7.85 | -0.09 |
| HC S440E | 8.02 | 7.94 | 7.85 | -0.09 |
| HC S442D | 8.02 | 7.94 | 7.85 | -0.09 |
| HC S442E | 8.02 | 7.94 | 7.85 | -0.09 |
| HC L443D | 8.02 | 7.94 | 7.85 | -0.09 |
| HC L443E | 8.02 | 7.94 | 7.85 | -0.09 |
| HC S444D | 8.02 | 7.94 | 7.85 | -0.09 |
| HC S444E | 8.02 | 7.94 | 7.85 | -0.09 |
| HC P445D | 8.02 | 7.94 | 7.85 | -0.09 |
| HC P445E | 8.02 | 7.94 | 7.85 | -0.09 |
| HC G446D | 8.02 | 7.94 | 7.85 | -0.09 |
| HC G446E | 8.02 | 7.94 | 7.85 | -0.09 |
| HC K447D | 8.02 | 7.85 | 7.61 | -0.21 |
| HC K447E | 8.02 | 7.85 | 7.61 | -0.21 |

Figure 45A

| Variant | IgG1 / IgG1 | Basic to Neutral pI / IgG1 | pI / pI | delta pI |
|---|---|---|---|---|
| HC K121A | 8.38 | 8.32 | 8.24 | -0.07 |
| HC K121F | 8.38 | 8.32 | 8.24 | -0.07 |
| HC K121G | 8.38 | 8.32 | 8.24 | -0.07 |
| HC K121H | 8.38 | 8.32 | 8.24 | -0.07 |
| HC K121I | 8.38 | 8.32 | 8.24 | -0.07 |
| HC K121L | 8.38 | 8.32 | 8.24 | -0.07 |
| HC K121M | 8.38 | 8.32 | 8.24 | -0.07 |
| HC K121N | 8.38 | 8.32 | 8.24 | -0.07 |
| HC K121P | 8.38 | 8.32 | 8.24 | -0.07 |
| HC K121Q | 8.38 | 8.32 | 8.24 | -0.07 |
| HC K121S | 8.38 | 8.32 | 8.24 | -0.07 |
| HC K121T | 8.38 | 8.32 | 8.24 | -0.07 |
| HC K121V | 8.38 | 8.32 | 8.24 | -0.07 |
| HC K121W | 8.38 | 8.32 | 8.24 | -0.07 |
| HC K121Y | 8.38 | 8.31 | 8.24 | -0.07 |
| HC K133A | 8.38 | 8.32 | 8.24 | -0.07 |
| HC K133F | 8.38 | 8.32 | 8.24 | -0.07 |
| HC K133G | 8.38 | 8.32 | 8.24 | -0.07 |
| HC K133H | 8.38 | 8.32 | 8.24 | -0.07 |
| HC K133I | 8.38 | 8.32 | 8.24 | -0.07 |
| HC K133L | 8.38 | 8.32 | 8.24 | -0.07 |
| HC K133M | 8.38 | 8.32 | 8.24 | -0.07 |
| HC K133N | 8.38 | 8.32 | 8.24 | -0.07 |
| HC K133P | 8.38 | 8.32 | 8.24 | -0.07 |
| HC K133Q | 8.38 | 8.32 | 8.24 | -0.07 |
| HC K133S | 8.38 | 8.32 | 8.24 | -0.07 |
| HC K133T | 8.38 | 8.32 | 8.24 | -0.07 |
| HC K133V | 8.38 | 8.32 | 8.24 | -0.07 |
| HC K133W | 8.38 | 8.32 | 8.24 | -0.07 |
| HC K133Y | 8.38 | 8.31 | 8.24 | -0.07 |
| HC K205A | 8.38 | 8.32 | 8.24 | -0.07 |
| HC K205F | 8.38 | 8.32 | 8.24 | -0.07 |
| HC K205G | 8.38 | 8.32 | 8.24 | -0.07 |
| HC K205H | 8.38 | 8.32 | 8.24 | -0.07 |
| HC K205I | 8.38 | 8.32 | 8.24 | -0.07 |
| HC K205L | 8.38 | 8.32 | 8.24 | -0.07 |
| HC K205M | 8.38 | 8.32 | 8.24 | -0.07 |
| HC K205N | 8.38 | 8.32 | 8.24 | -0.07 |
| HC K205P | 8.38 | 8.32 | 8.24 | -0.07 |
| HC K205Q | 8.38 | 8.32 | 8.24 | -0.07 |
| HC K205S | 8.38 | 8.32 | 8.24 | -0.07 |
| HC K205T | 8.38 | 8.32 | 8.24 | -0.07 |
| HC K205V | 8.38 | 8.32 | 8.24 | -0.07 |
| HC K205W | 8.38 | 8.32 | 8.24 | -0.07 |
| HC K205Y | 8.38 | 8.31 | 8.24 | -0.07 |
| HC K210A | 8.38 | 8.32 | 8.24 | -0.07 |
| HC K210F | 8.38 | 8.32 | 8.24 | -0.07 |
| HC K210G | 8.38 | 8.32 | 8.24 | -0.07 |

Figure 45B

| Variant | Basic to Neutral | | | |
|---|---|---|---|---|
| | IgG1 / IgG1 | pI / IgG1 | pI / pI | delta pI |
| HC K210H | 8.38 | 8.32 | 8.24 | -0.07 |
| HC K210I | 8.38 | 8.32 | 8.24 | -0.07 |
| HC K210L | 8.38 | 8.32 | 8.24 | -0.07 |
| HC K210M | 8.38 | 8.32 | 8.24 | -0.07 |
| HC K210N | 8.38 | 8.32 | 8.24 | -0.07 |
| HC K210P | 8.38 | 8.32 | 8.24 | -0.07 |
| HC K210Q | 8.38 | 8.32 | 8.24 | -0.07 |
| HC K210S | 8.38 | 8.32 | 8.24 | -0.07 |
| HC K210T | 8.38 | 8.32 | 8.24 | -0.07 |
| HC K210V | 8.38 | 8.32 | 8.24 | -0.07 |
| HC K210W | 8.38 | 8.32 | 8.24 | -0.07 |
| HC K210Y | 8.38 | 8.31 | 8.24 | -0.07 |
| HC K213A | 8.38 | 8.32 | 8.24 | -0.07 |
| HC K213F | 8.38 | 8.32 | 8.24 | -0.07 |
| HC K213G | 8.38 | 8.32 | 8.24 | -0.07 |
| HC K213H | 8.38 | 8.32 | 8.24 | -0.07 |
| HC K213I | 8.38 | 8.32 | 8.24 | -0.07 |
| HC K213L | 8.38 | 8.32 | 8.24 | -0.07 |
| HC K213M | 8.38 | 8.32 | 8.24 | -0.07 |
| HC K213N | 8.38 | 8.32 | 8.24 | -0.07 |
| HC K213P | 8.38 | 8.32 | 8.24 | -0.07 |
| HC K213Q | 8.38 | 8.32 | 8.24 | -0.07 |
| HC K213S | 8.38 | 8.32 | 8.24 | -0.07 |
| HC K213T | 8.38 | 8.32 | 8.24 | -0.07 |
| HC K213V | 8.38 | 8.32 | 8.24 | -0.07 |
| HC K213W | 8.38 | 8.32 | 8.24 | -0.07 |
| HC K213Y | 8.38 | 8.31 | 8.24 | -0.07 |
| HC K214A | 8.38 | 8.32 | 8.24 | -0.07 |
| HC K214F | 8.38 | 8.32 | 8.24 | -0.07 |
| HC K214G | 8.38 | 8.32 | 8.24 | -0.07 |
| HC K214H | 8.38 | 8.32 | 8.24 | -0.07 |
| HC K214I | 8.38 | 8.32 | 8.24 | -0.07 |
| HC K214L | 8.38 | 8.32 | 8.24 | -0.07 |
| HC K214M | 8.38 | 8.32 | 8.24 | -0.07 |
| HC K214N | 8.38 | 8.32 | 8.24 | -0.07 |
| HC K214P | 8.38 | 8.32 | 8.24 | -0.07 |
| HC K214Q | 8.38 | 8.32 | 8.24 | -0.07 |
| HC K214S | 8.38 | 8.32 | 8.24 | -0.07 |
| HC K214T | 8.38 | 8.32 | 8.24 | -0.07 |
| HC K214V | 8.38 | 8.32 | 8.24 | -0.07 |
| HC K214W | 8.38 | 8.32 | 8.24 | -0.07 |
| HC K214Y | 8.38 | 8.31 | 8.24 | -0.07 |
| HC K218A | 8.38 | 8.32 | 8.24 | -0.07 |
| HC K218F | 8.38 | 8.32 | 8.24 | -0.07 |
| HC K218G | 8.38 | 8.32 | 8.24 | -0.07 |
| HC K218H | 8.38 | 8.32 | 8.24 | -0.07 |
| HC K218I | 8.38 | 8.32 | 8.24 | -0.07 |
| HC K218L | 8.38 | 8.32 | 8.24 | -0.07 |
| HC K218M | 8.38 | 8.32 | 8.24 | -0.07 |
| HC K218N | 8.38 | 8.32 | 8.24 | -0.07 |

Figure 45C

| Variant | Basic to Neutral | | | |
|---|---|---|---|---|
| | IgG1 / IgG1 | pI / IgG1 | pI / pI | delta pI |
| HC K218P | 8.38 | 8.32 | 8.24 | -0.07 |
| HC K218Q | 8.38 | 8.32 | 8.24 | -0.07 |
| HC K218S | 8.38 | 8.32 | 8.24 | -0.07 |
| HC K218T | 8.38 | 8.32 | 8.24 | -0.07 |
| HC K218V | 8.38 | 8.32 | 8.24 | -0.07 |
| HC K218W | 8.38 | 8.32 | 8.24 | -0.07 |
| HC K218Y | 8.38 | 8.31 | 8.24 | -0.07 |
| HC K222A | 8.38 | 8.32 | 8.24 | -0.07 |
| HC K222F | 8.38 | 8.32 | 8.24 | -0.07 |
| HC K222G | 8.38 | 8.32 | 8.24 | -0.07 |
| HC K222H | 8.38 | 8.32 | 8.24 | -0.07 |
| HC K222I | 8.38 | 8.32 | 8.24 | -0.07 |
| HC K222L | 8.38 | 8.32 | 8.24 | -0.07 |
| HC K222M | 8.38 | 8.32 | 8.24 | -0.07 |
| HC K222N | 8.38 | 8.32 | 8.24 | -0.07 |
| HC K222P | 8.38 | 8.32 | 8.24 | -0.07 |
| HC K222Q | 8.38 | 8.32 | 8.24 | -0.07 |
| HC K222S | 8.38 | 8.32 | 8.24 | -0.07 |
| HC K222T | 8.38 | 8.32 | 8.24 | -0.07 |
| HC K222V | 8.38 | 8.32 | 8.24 | -0.07 |
| HC K222W | 8.38 | 8.32 | 8.24 | -0.07 |
| HC K222Y | 8.38 | 8.31 | 8.24 | -0.07 |
| HC K246A | 8.38 | 8.32 | 8.24 | -0.07 |
| HC K246F | 8.38 | 8.32 | 8.24 | -0.07 |
| HC K246G | 8.38 | 8.32 | 8.24 | -0.07 |
| HC K246H | 8.38 | 8.32 | 8.24 | -0.07 |
| HC K246I | 8.38 | 8.32 | 8.24 | -0.07 |
| HC K246L | 8.38 | 8.32 | 8.24 | -0.07 |
| HC K246M | 8.38 | 8.32 | 8.24 | -0.07 |
| HC K246N | 8.38 | 8.32 | 8.24 | -0.07 |
| HC K246P | 8.38 | 8.32 | 8.24 | -0.07 |
| HC K246Q | 8.38 | 8.32 | 8.24 | -0.07 |
| HC K246S | 8.38 | 8.32 | 8.24 | -0.07 |
| HC K246T | 8.38 | 8.32 | 8.24 | -0.07 |
| HC K246V | 8.38 | 8.32 | 8.24 | -0.07 |
| HC K246W | 8.38 | 8.32 | 8.24 | -0.07 |
| HC K246Y | 8.38 | 8.31 | 8.24 | -0.07 |
| HC R255A | 8.38 | 8.31 | 8.24 | -0.07 |
| HC R255F | 8.38 | 8.31 | 8.24 | -0.07 |
| HC R255G | 8.38 | 8.31 | 8.24 | -0.07 |
| HC R255H | 8.38 | 8.31 | 8.24 | -0.07 |
| HC R255I | 8.38 | 8.31 | 8.24 | -0.07 |
| HC R255L | 8.38 | 8.31 | 8.24 | -0.07 |
| HC R255M | 8.38 | 8.31 | 8.24 | -0.07 |
| HC R255N | 8.38 | 8.31 | 8.24 | -0.07 |
| HC R255P | 8.38 | 8.31 | 8.24 | -0.07 |
| HC R255Q | 8.38 | 8.31 | 8.24 | -0.07 |
| HC R255S | 8.38 | 8.31 | 8.24 | -0.07 |
| HC R255T | 8.38 | 8.31 | 8.24 | -0.07 |
| HC R255V | 8.38 | 8.31 | 8.24 | -0.07 |

Figure 45D

| Variant | Basic to Neutral IgG1 / IgG1 | pI / IgG1 | pI / pI | delta pI |
|---|---|---|---|---|
| HC R255W | 8.38 | 8.31 | 8.24 | -0.07 |
| HC R255Y | 8.38 | 8.31 | 8.23 | -0.08 |
| HC K274A | 8.38 | 8.32 | 8.24 | -0.07 |
| HC K274F | 8.38 | 8.32 | 8.24 | -0.07 |
| HC K274G | 8.38 | 8.32 | 8.24 | -0.07 |
| HC K274H | 8.38 | 8.32 | 8.24 | -0.07 |
| HC K274I | 8.38 | 8.32 | 8.24 | -0.07 |
| HC K274L | 8.38 | 8.32 | 8.24 | -0.07 |
| HC K274M | 8.38 | 8.32 | 8.24 | -0.07 |
| HC K274N | 8.38 | 8.32 | 8.24 | -0.07 |
| HC K274P | 8.38 | 8.32 | 8.24 | -0.07 |
| HC K274Q | 8.38 | 8.32 | 8.24 | -0.07 |
| HC K274S | 8.38 | 8.32 | 8.24 | -0.07 |
| HC K274T | 8.38 | 8.32 | 8.24 | -0.07 |
| HC K274V | 8.38 | 8.32 | 8.24 | -0.07 |
| HC K274W | 8.38 | 8.32 | 8.24 | -0.07 |
| HC K274Y | 8.38 | 8.31 | 8.24 | -0.07 |
| HC K288A | 8.38 | 8.32 | 8.24 | -0.07 |
| HC K288F | 8.38 | 8.32 | 8.24 | -0.07 |
| HC K288G | 8.38 | 8.32 | 8.24 | -0.07 |
| HC K288H | 8.38 | 8.32 | 8.24 | -0.07 |
| HC K288I | 8.38 | 8.32 | 8.24 | -0.07 |
| HC K288L | 8.38 | 8.32 | 8.24 | -0.07 |
| HC K288M | 8.38 | 8.32 | 8.24 | -0.07 |
| HC K288N | 8.38 | 8.32 | 8.24 | -0.07 |
| HC K288P | 8.38 | 8.32 | 8.24 | -0.07 |
| HC K288Q | 8.38 | 8.32 | 8.24 | -0.07 |
| HC K288S | 8.38 | 8.32 | 8.24 | -0.07 |
| HC K288T | 8.38 | 8.32 | 8.24 | -0.07 |
| HC K288V | 8.38 | 8.32 | 8.24 | -0.07 |
| HC K288W | 8.38 | 8.32 | 8.24 | -0.07 |
| HC K288Y | 8.38 | 8.31 | 8.24 | -0.07 |
| HC K290A | 8.38 | 8.32 | 8.24 | -0.07 |
| HC K290F | 8.38 | 8.32 | 8.24 | -0.07 |
| HC K290G | 8.38 | 8.32 | 8.24 | -0.07 |
| HC K290H | 8.38 | 8.32 | 8.24 | -0.07 |
| HC K290I | 8.38 | 8.32 | 8.24 | -0.07 |
| HC K290L | 8.38 | 8.32 | 8.24 | -0.07 |
| HC K290M | 8.38 | 8.32 | 8.24 | -0.07 |
| HC K290N | 8.38 | 8.32 | 8.24 | -0.07 |
| HC K290P | 8.38 | 8.32 | 8.24 | -0.07 |
| HC K290Q | 8.38 | 8.32 | 8.24 | -0.07 |
| HC K290S | 8.38 | 8.32 | 8.24 | -0.07 |
| HC K290T | 8.38 | 8.32 | 8.24 | -0.07 |
| HC K290V | 8.38 | 8.32 | 8.24 | -0.07 |
| HC K290W | 8.38 | 8.32 | 8.24 | -0.07 |
| HC K290Y | 8.38 | 8.31 | 8.24 | -0.07 |
| HC R292A | 8.38 | 8.31 | 8.24 | -0.07 |
| HC R292F | 8.38 | 8.31 | 8.24 | -0.07 |
| HC R292G | 8.38 | 8.31 | 8.24 | -0.07 |

Figure 45E

| Variant | Basic to Neutral IgG1 / IgG1 | pI / IgG1 | pI / pI | delta pI |
|---|---|---|---|---|
| HC R292H | 8.38 | 8.31 | 8.24 | -0.07 |
| HC R292I | 8.38 | 8.31 | 8.24 | -0.07 |
| HC R292L | 8.38 | 8.31 | 8.24 | -0.07 |
| HC R292M | 8.38 | 8.31 | 8.24 | -0.07 |
| HC R292N | 8.38 | 8.31 | 8.24 | -0.07 |
| HC R292P | 8.38 | 8.31 | 8.24 | -0.07 |
| HC R292Q | 8.38 | 8.31 | 8.24 | -0.07 |
| HC R292S | 8.38 | 8.31 | 8.24 | -0.07 |
| HC R292T | 8.38 | 8.31 | 8.24 | -0.07 |
| HC R292V | 8.38 | 8.31 | 8.24 | -0.07 |
| HC R292W | 8.38 | 8.31 | 8.24 | -0.07 |
| HC R292Y | 8.38 | 8.31 | 8.23 | -0.08 |
| HC R301A | 8.38 | 8.31 | 8.24 | -0.07 |
| HC R301F | 8.38 | 8.31 | 8.24 | -0.07 |
| HC R301G | 8.38 | 8.31 | 8.24 | -0.07 |
| HC R301H | 8.38 | 8.31 | 8.24 | -0.07 |
| HC R301I | 8.38 | 8.31 | 8.24 | -0.07 |
| HC R301L | 8.38 | 8.31 | 8.24 | -0.07 |
| HC R301M | 8.38 | 8.31 | 8.24 | -0.07 |
| HC R301N | 8.38 | 8.31 | 8.24 | -0.07 |
| HC R301P | 8.38 | 8.31 | 8.24 | -0.07 |
| HC R301Q | 8.38 | 8.31 | 8.24 | -0.07 |
| HC R301S | 8.38 | 8.31 | 8.24 | -0.07 |
| HC R301T | 8.38 | 8.31 | 8.24 | -0.07 |
| HC R301V | 8.38 | 8.31 | 8.24 | -0.07 |
| HC R301W | 8.38 | 8.31 | 8.24 | -0.07 |
| HC R301Y | 8.38 | 8.31 | 8.23 | -0.08 |
| HC K317A | 8.38 | 8.32 | 8.24 | -0.07 |
| HC K317F | 8.38 | 8.32 | 8.24 | -0.07 |
| HC K317G | 8.38 | 8.32 | 8.24 | -0.07 |
| HC K317H | 8.38 | 8.32 | 8.24 | -0.07 |
| HC K317I | 8.38 | 8.32 | 8.24 | -0.07 |
| HC K317L | 8.38 | 8.32 | 8.24 | -0.07 |
| HC K317M | 8.38 | 8.32 | 8.24 | -0.07 |
| HC K317N | 8.38 | 8.32 | 8.24 | -0.07 |
| HC K317P | 8.38 | 8.32 | 8.24 | -0.07 |
| HC K317Q | 8.38 | 8.32 | 8.24 | -0.07 |
| HC K317S | 8.38 | 8.32 | 8.24 | -0.07 |
| HC K317T | 8.38 | 8.32 | 8.24 | -0.07 |
| HC K317V | 8.38 | 8.32 | 8.24 | -0.07 |
| HC K317W | 8.38 | 8.32 | 8.24 | -0.07 |
| HC K317Y | 8.38 | 8.31 | 8.24 | -0.07 |
| HC K320A | 8.38 | 8.32 | 8.24 | -0.07 |
| HC K320F | 8.38 | 8.32 | 8.24 | -0.07 |
| HC K320G | 8.38 | 8.32 | 8.24 | -0.07 |
| HC K320H | 8.38 | 8.32 | 8.24 | -0.07 |
| HC K320I | 8.38 | 8.32 | 8.24 | -0.07 |
| HC K320L | 8.38 | 8.32 | 8.24 | -0.07 |
| HC K320M | 8.38 | 8.32 | 8.24 | -0.07 |
| HC K320N | 8.38 | 8.32 | 8.24 | -0.07 |

Figure 45F

| Variant | IgG1 / IgG1 | Basic to Neutral pI / IgG1 | pI / pI | delta pI |
|---|---|---|---|---|
| HC K320P | 8.38 | 8.32 | 8.24 | -0.07 |
| HC K320Q | 8.38 | 8.32 | 8.24 | -0.07 |
| HC K320S | 8.38 | 8.32 | 8.24 | -0.07 |
| HC K320T | 8.38 | 8.32 | 8.24 | -0.07 |
| HC K320V | 8.38 | 8.32 | 8.24 | -0.07 |
| HC K320W | 8.38 | 8.32 | 8.24 | -0.07 |
| HC K320Y | 8.38 | 8.31 | 8.24 | -0.07 |
| HC K322A | 8.38 | 8.32 | 8.24 | -0.07 |
| HC K322F | 8.38 | 8.32 | 8.24 | -0.07 |
| HC K322G | 8.38 | 8.32 | 8.24 | -0.07 |
| HC K322H | 8.38 | 8.32 | 8.24 | -0.07 |
| HC K322I | 8.38 | 8.32 | 8.24 | -0.07 |
| HC K322L | 8.38 | 8.32 | 8.24 | -0.07 |
| HC K322M | 8.38 | 8.32 | 8.24 | -0.07 |
| HC K322N | 8.38 | 8.32 | 8.24 | -0.07 |
| HC K322P | 8.38 | 8.32 | 8.24 | -0.07 |
| HC K322Q | 8.38 | 8.32 | 8.24 | -0.07 |
| HC K322S | 8.38 | 8.32 | 8.24 | -0.07 |
| HC K322T | 8.38 | 8.32 | 8.24 | -0.07 |
| HC K322V | 8.38 | 8.32 | 8.24 | -0.07 |
| HC K322W | 8.38 | 8.32 | 8.24 | -0.07 |
| HC K322Y | 8.38 | 8.31 | 8.24 | -0.07 |
| HC K326A | 8.38 | 8.32 | 8.24 | -0.07 |
| HC K326F | 8.38 | 8.32 | 8.24 | -0.07 |
| HC K326G | 8.38 | 8.32 | 8.24 | -0.07 |
| HC K326H | 8.38 | 8.32 | 8.24 | -0.07 |
| HC K326I | 8.38 | 8.32 | 8.24 | -0.07 |
| HC K326L | 8.38 | 8.32 | 8.24 | -0.07 |
| HC K326M | 8.38 | 8.32 | 8.24 | -0.07 |
| HC K326N | 8.38 | 8.32 | 8.24 | -0.07 |
| HC K326P | 8.38 | 8.32 | 8.24 | -0.07 |
| HC K326Q | 8.38 | 8.32 | 8.24 | -0.07 |
| HC K326S | 8.38 | 8.32 | 8.24 | -0.07 |
| HC K326T | 8.38 | 8.32 | 8.24 | -0.07 |
| HC K326V | 8.38 | 8.32 | 8.24 | -0.07 |
| HC K326W | 8.38 | 8.32 | 8.24 | -0.07 |
| HC K326Y | 8.38 | 8.31 | 8.24 | -0.07 |
| HC K334A | 8.38 | 8.32 | 8.24 | -0.07 |
| HC K334F | 8.38 | 8.32 | 8.24 | -0.07 |
| HC K334G | 8.38 | 8.32 | 8.24 | -0.07 |
| HC K334H | 8.38 | 8.32 | 8.24 | -0.07 |
| HC K334I | 8.38 | 8.32 | 8.24 | -0.07 |
| HC K334L | 8.38 | 8.32 | 8.24 | -0.07 |
| HC K334M | 8.38 | 8.32 | 8.24 | -0.07 |
| HC K334N | 8.38 | 8.32 | 8.24 | -0.07 |
| HC K334P | 8.38 | 8.32 | 8.24 | -0.07 |
| HC K334Q | 8.38 | 8.32 | 8.24 | -0.07 |
| HC K334S | 8.38 | 8.32 | 8.24 | -0.07 |
| HC K334T | 8.38 | 8.32 | 8.24 | -0.07 |
| HC K334V | 8.38 | 8.32 | 8.24 | -0.07 |

Figure 45G

| Variant | Basic to Neutral IgG1 / IgG1 | pI / IgG1 | pI / pI | delta pI |
|---|---|---|---|---|
| HC K334W | 8.38 | 8.32 | 8.24 | -0.07 |
| HC K334Y | 8.38 | 8.31 | 8.24 | -0.07 |
| HC K340A | 8.38 | 8.32 | 8.24 | -0.07 |
| HC K340F | 8.38 | 8.32 | 8.24 | -0.07 |
| HC K340G | 8.38 | 8.32 | 8.24 | -0.07 |
| HC K340H | 8.38 | 8.32 | 8.24 | -0.07 |
| HC K340I | 8.38 | 8.32 | 8.24 | -0.07 |
| HC K340L | 8.38 | 8.32 | 8.24 | -0.07 |
| HC K340M | 8.38 | 8.32 | 8.24 | -0.07 |
| HC K340N | 8.38 | 8.32 | 8.24 | -0.07 |
| HC K340P | 8.38 | 8.32 | 8.24 | -0.07 |
| HC K340Q | 8.38 | 8.32 | 8.24 | -0.07 |
| HC K340S | 8.38 | 8.32 | 8.24 | -0.07 |
| HC K340T | 8.38 | 8.32 | 8.24 | -0.07 |
| HC K340V | 8.38 | 8.32 | 8.24 | -0.07 |
| HC K340W | 8.38 | 8.32 | 8.24 | -0.07 |
| HC K340Y | 8.38 | 8.31 | 8.24 | -0.07 |
| HC R344A | 8.38 | 8.31 | 8.24 | -0.07 |
| HC R344F | 8.38 | 8.31 | 8.24 | -0.07 |
| HC R344G | 8.38 | 8.31 | 8.24 | -0.07 |
| HC R344H | 8.38 | 8.31 | 8.24 | -0.07 |
| HC R344I | 8.38 | 8.31 | 8.24 | -0.07 |
| HC R344L | 8.38 | 8.31 | 8.24 | -0.07 |
| HC R344M | 8.38 | 8.31 | 8.24 | -0.07 |
| HC R344N | 8.38 | 8.31 | 8.24 | -0.07 |
| HC R344P | 8.38 | 8.31 | 8.24 | -0.07 |
| HC R344Q | 8.38 | 8.31 | 8.24 | -0.07 |
| HC R344S | 8.38 | 8.31 | 8.24 | -0.07 |
| HC R344T | 8.38 | 8.31 | 8.24 | -0.07 |
| HC R344V | 8.38 | 8.31 | 8.24 | -0.07 |
| HC R344W | 8.38 | 8.31 | 8.24 | -0.07 |
| HC R344Y | 8.38 | 8.31 | 8.23 | -0.08 |
| HC R355A | 8.38 | 8.31 | 8.24 | -0.07 |
| HC R355F | 8.38 | 8.31 | 8.24 | -0.07 |
| HC R355G | 8.38 | 8.31 | 8.24 | -0.07 |
| HC R355H | 8.38 | 8.31 | 8.24 | -0.07 |
| HC R355I | 8.38 | 8.31 | 8.24 | -0.07 |
| HC R355L | 8.38 | 8.31 | 8.24 | -0.07 |
| HC R355M | 8.38 | 8.31 | 8.24 | -0.07 |
| HC R355N | 8.38 | 8.31 | 8.24 | -0.07 |
| HC R355P | 8.38 | 8.31 | 8.24 | -0.07 |
| HC R355Q | 8.38 | 8.31 | 8.24 | -0.07 |
| HC R355S | 8.38 | 8.31 | 8.24 | -0.07 |
| HC R355T | 8.38 | 8.31 | 8.24 | -0.07 |
| HC R355V | 8.38 | 8.31 | 8.24 | -0.07 |
| HC R355W | 8.38 | 8.31 | 8.24 | -0.07 |
| HC R355Y | 8.38 | 8.31 | 8.23 | -0.08 |
| HC K360A | 8.38 | 8.32 | 8.24 | -0.07 |
| HC K360F | 8.38 | 8.32 | 8.24 | -0.07 |
| HC K360G | 8.38 | 8.32 | 8.24 | -0.07 |

Figure 45H

| Variant | Basic to Neutral IgG1 / IgG1 | pI / IgG1 | pI / pI | delta pI |
|---|---|---|---|---|
| HC K360H | 8.38 | 8.32 | 8.24 | -0.07 |
| HC K360I | 8.38 | 8.32 | 8.24 | -0.07 |
| HC K360L | 8.38 | 8.32 | 8.24 | -0.07 |
| HC K360M | 8.38 | 8.32 | 8.24 | -0.07 |
| HC K360N | 8.38 | 8.32 | 8.24 | -0.07 |
| HC K360P | 8.38 | 8.32 | 8.24 | -0.07 |
| HC K360Q | 8.38 | 8.32 | 8.24 | -0.07 |
| HC K360S | 8.38 | 8.32 | 8.24 | -0.07 |
| HC K360T | 8.38 | 8.32 | 8.24 | -0.07 |
| HC K360V | 8.38 | 8.32 | 8.24 | -0.07 |
| HC K360W | 8.38 | 8.32 | 8.24 | -0.07 |
| HC K360Y | 8.38 | 8.31 | 8.24 | -0.07 |
| HC K392A | 8.38 | 8.32 | 8.24 | -0.07 |
| HC K392F | 8.38 | 8.32 | 8.24 | -0.07 |
| HC K392G | 8.38 | 8.32 | 8.24 | -0.07 |
| HC K392H | 8.38 | 8.32 | 8.24 | -0.07 |
| HC K392I | 8.38 | 8.32 | 8.24 | -0.07 |
| HC K392L | 8.38 | 8.32 | 8.24 | -0.07 |
| HC K392M | 8.38 | 8.32 | 8.24 | -0.07 |
| HC K392N | 8.38 | 8.32 | 8.24 | -0.07 |
| HC K392P | 8.38 | 8.32 | 8.24 | -0.07 |
| HC K392Q | 8.38 | 8.32 | 8.24 | -0.07 |
| HC K392S | 8.38 | 8.32 | 8.24 | -0.07 |
| HC K392T | 8.38 | 8.32 | 8.24 | -0.07 |
| HC K392V | 8.38 | 8.32 | 8.24 | -0.07 |
| HC K392W | 8.38 | 8.32 | 8.24 | -0.07 |
| HC K392Y | 8.38 | 8.31 | 8.24 | -0.07 |
| HC K414A | 8.38 | 8.32 | 8.24 | -0.07 |
| HC K414F | 8.38 | 8.32 | 8.24 | -0.07 |
| HC K414G | 8.38 | 8.32 | 8.24 | -0.07 |
| HC K414H | 8.38 | 8.32 | 8.24 | -0.07 |
| HC K414I | 8.38 | 8.32 | 8.24 | -0.07 |
| HC K414L | 8.38 | 8.32 | 8.24 | -0.07 |
| HC K414M | 8.38 | 8.32 | 8.24 | -0.07 |
| HC K414N | 8.38 | 8.32 | 8.24 | -0.07 |
| HC K414P | 8.38 | 8.32 | 8.24 | -0.07 |
| HC K414Q | 8.38 | 8.32 | 8.24 | -0.07 |
| HC K414S | 8.38 | 8.32 | 8.24 | -0.07 |
| HC K414T | 8.38 | 8.32 | 8.24 | -0.07 |
| HC K414V | 8.38 | 8.32 | 8.24 | -0.07 |
| HC K414W | 8.38 | 8.32 | 8.24 | -0.07 |
| HC K414Y | 8.38 | 8.31 | 8.24 | -0.07 |
| HC R416A | 8.38 | 8.31 | 8.24 | -0.07 |
| HC R416F | 8.38 | 8.31 | 8.24 | -0.07 |
| HC R416G | 8.38 | 8.31 | 8.24 | -0.07 |
| HC R416H | 8.38 | 8.31 | 8.24 | -0.07 |
| HC R416I | 8.38 | 8.31 | 8.24 | -0.07 |
| HC R416L | 8.38 | 8.31 | 8.24 | -0.07 |
| HC R416M | 8.38 | 8.31 | 8.24 | -0.07 |
| HC R416N | 8.38 | 8.31 | 8.24 | -0.07 |

Figure 45I

| Variant | Basic to Neutral | | | |
|---|---|---|---|---|
| | IgG1 / IgG1 | pI / IgG1 | pI / pI | delta pI |
| HC R416P | 8.38 | 8.31 | 8.24 | -0.07 |
| HC R416Q | 8.38 | 8.31 | 8.24 | -0.07 |
| HC R416S | 8.38 | 8.31 | 8.24 | -0.07 |
| HC R416T | 8.38 | 8.31 | 8.24 | -0.07 |
| HC R416V | 8.38 | 8.31 | 8.24 | -0.07 |
| HC R416W | 8.38 | 8.31 | 8.24 | -0.07 |
| HC R416Y | 8.38 | 8.31 | 8.23 | -0.08 |
| HC K439A | 8.38 | 8.32 | 8.24 | -0.07 |
| HC K439F | 8.38 | 8.32 | 8.24 | -0.07 |
| HC K439G | 8.38 | 8.32 | 8.24 | -0.07 |
| HC K439H | 8.38 | 8.32 | 8.24 | -0.07 |
| HC K439I | 8.38 | 8.32 | 8.24 | -0.07 |
| HC K439L | 8.38 | 8.32 | 8.24 | -0.07 |
| HC K439M | 8.38 | 8.32 | 8.24 | -0.07 |
| HC K439N | 8.38 | 8.32 | 8.24 | -0.07 |
| HC K439P | 8.38 | 8.32 | 8.24 | -0.07 |
| HC K439Q | 8.38 | 8.32 | 8.24 | -0.07 |
| HC K439S | 8.38 | 8.32 | 8.24 | -0.07 |
| HC K439T | 8.38 | 8.32 | 8.24 | -0.07 |
| HC K439V | 8.38 | 8.32 | 8.24 | -0.07 |
| HC K439W | 8.38 | 8.32 | 8.24 | -0.07 |
| HC K439Y | 8.38 | 8.31 | 8.24 | -0.07 |
| HC K447A | 8.38 | 8.32 | 8.24 | -0.07 |
| HC K447F | 8.38 | 8.32 | 8.24 | -0.07 |
| HC K447G | 8.38 | 8.32 | 8.24 | -0.07 |
| HC K447H | 8.38 | 8.32 | 8.24 | -0.07 |
| HC K447I | 8.38 | 8.32 | 8.24 | -0.07 |
| HC K447L | 8.38 | 8.32 | 8.24 | -0.07 |
| HC K447M | 8.38 | 8.32 | 8.24 | -0.07 |
| HC K447N | 8.38 | 8.32 | 8.24 | -0.07 |
| HC K447P | 8.38 | 8.32 | 8.24 | -0.07 |
| HC K447Q | 8.38 | 8.32 | 8.24 | -0.07 |
| HC K447S | 8.38 | 8.32 | 8.24 | -0.07 |
| HC K447T | 8.38 | 8.32 | 8.24 | -0.07 |
| HC K447V | 8.38 | 8.32 | 8.24 | -0.07 |
| HC K447W | 8.38 | 8.32 | 8.24 | -0.07 |
| HC K447Y | 8.38 | 8.31 | 8.24 | -0.07 |

Figure 46A

| Variant | IgG1 / IgG1 | Neutral or Acidic to Basic pI / IgG1 | pI / pI | delta pI |
|---|---|---|---|---|
| HC S119K | 8.38 | 8.45 | 8.50 | 0.06 |
| HC S119R | 8.38 | 8.45 | 8.50 | 0.06 |
| HC T120K | 8.38 | 8.45 | 8.50 | 0.06 |
| HC T120R | 8.38 | 8.45 | 8.50 | 0.06 |
| HC G122K | 8.38 | 8.45 | 8.50 | 0.06 |
| HC G122R | 8.38 | 8.45 | 8.50 | 0.06 |
| HC S131K | 8.38 | 8.45 | 8.50 | 0.06 |
| HC S131R | 8.38 | 8.45 | 8.50 | 0.06 |
| HC S132K | 8.38 | 8.45 | 8.50 | 0.06 |
| HC S132R | 8.38 | 8.45 | 8.50 | 0.06 |
| HC S134K | 8.38 | 8.45 | 8.50 | 0.06 |
| HC S134R | 8.38 | 8.45 | 8.50 | 0.06 |
| HC T135K | 8.38 | 8.45 | 8.50 | 0.06 |
| HC T135R | 8.38 | 8.45 | 8.50 | 0.06 |
| HC S136K | 8.38 | 8.45 | 8.50 | 0.06 |
| HC S136R | 8.38 | 8.45 | 8.50 | 0.06 |
| HC G137K | 8.38 | 8.45 | 8.50 | 0.06 |
| HC G137R | 8.38 | 8.45 | 8.50 | 0.06 |
| HC G138K | 8.38 | 8.45 | 8.50 | 0.06 |
| HC G138R | 8.38 | 8.45 | 8.50 | 0.06 |
| HC T139K | 8.38 | 8.45 | 8.50 | 0.06 |
| HC T139R | 8.38 | 8.45 | 8.50 | 0.06 |
| HC D148K | 8.38 | 8.50 | 8.60 | 0.11 |
| HC D148R | 8.38 | 8.50 | 8.61 | 0.11 |
| HC E152K | 8.38 | 8.50 | 8.60 | 0.11 |
| HC E152R | 8.38 | 8.50 | 8.61 | 0.11 |
| HC P153K | 8.38 | 8.45 | 8.50 | 0.06 |
| HC P153R | 8.38 | 8.45 | 8.50 | 0.06 |
| HC T155K | 8.38 | 8.45 | 8.50 | 0.06 |
| HC T155R | 8.38 | 8.45 | 8.50 | 0.06 |
| HC S157K | 8.38 | 8.45 | 8.50 | 0.06 |
| HC S157R | 8.38 | 8.45 | 8.50 | 0.06 |
| HC N159K | 8.38 | 8.45 | 8.50 | 0.06 |
| HC N159R | 8.38 | 8.45 | 8.50 | 0.06 |
| HC S160K | 8.38 | 8.45 | 8.50 | 0.06 |
| HC S160R | 8.38 | 8.45 | 8.50 | 0.06 |
| HC G161K | 8.38 | 8.45 | 8.50 | 0.06 |
| HC G161R | 8.38 | 8.45 | 8.50 | 0.06 |
| HC A162K | 8.38 | 8.45 | 8.50 | 0.06 |
| HC A162R | 8.38 | 8.45 | 8.50 | 0.06 |
| HC T164K | 8.38 | 8.45 | 8.50 | 0.06 |
| HC T164R | 8.38 | 8.45 | 8.50 | 0.06 |
| HC S165K | 8.38 | 8.45 | 8.50 | 0.06 |
| HC S165R | 8.38 | 8.45 | 8.50 | 0.06 |
| HC G166K | 8.38 | 8.45 | 8.50 | 0.06 |
| HC G166R | 8.38 | 8.45 | 8.50 | 0.06 |
| HC T169K | 8.38 | 8.45 | 8.50 | 0.06 |
| HC T169R | 8.38 | 8.45 | 8.50 | 0.06 |

Figure 46B

| Variant | Neutral or Acidic to Basic | | | |
|---|---|---|---|---|
| | IgG1 / IgG1 | pI / IgG1 | pI / pI | delta pI |
| HC P171K | 8.38 | 8.45 | 8.50 | 0.06 |
| HC P171R | 8.38 | 8.45 | 8.50 | 0.06 |
| HC A172K | 8.38 | 8.45 | 8.50 | 0.06 |
| HC A172R | 8.38 | 8.45 | 8.50 | 0.06 |
| HC L174K | 8.38 | 8.45 | 8.50 | 0.06 |
| HC L174R | 8.38 | 8.45 | 8.50 | 0.06 |
| HC S176K | 8.38 | 8.45 | 8.50 | 0.06 |
| HC S176R | 8.38 | 8.45 | 8.50 | 0.06 |
| HC S177K | 8.38 | 8.45 | 8.50 | 0.06 |
| HC S177R | 8.38 | 8.45 | 8.50 | 0.06 |
| HC T187K | 8.38 | 8.45 | 8.50 | 0.06 |
| HC T187R | 8.38 | 8.45 | 8.50 | 0.06 |
| HC P189K | 8.38 | 8.45 | 8.50 | 0.06 |
| HC P189R | 8.38 | 8.45 | 8.50 | 0.06 |
| HC S190K | 8.38 | 8.45 | 8.50 | 0.06 |
| HC S190R | 8.38 | 8.45 | 8.50 | 0.06 |
| HC S191K | 8.38 | 8.45 | 8.50 | 0.06 |
| HC S191R | 8.38 | 8.45 | 8.50 | 0.06 |
| HC L193K | 8.38 | 8.45 | 8.50 | 0.06 |
| HC L193R | 8.38 | 8.45 | 8.50 | 0.06 |
| HC G194K | 8.38 | 8.45 | 8.50 | 0.06 |
| HC G194R | 8.38 | 8.45 | 8.50 | 0.06 |
| HC T195K | 8.38 | 8.45 | 8.50 | 0.06 |
| HC T195R | 8.38 | 8.45 | 8.50 | 0.06 |
| HC Q196K | 8.38 | 8.45 | 8.50 | 0.06 |
| HC Q196R | 8.38 | 8.45 | 8.50 | 0.06 |
| HC T197K | 8.38 | 8.45 | 8.50 | 0.06 |
| HC T197R | 8.38 | 8.45 | 8.50 | 0.06 |
| HC I199K | 8.38 | 8.45 | 8.50 | 0.06 |
| HC I199R | 8.38 | 8.45 | 8.50 | 0.06 |
| HC N203K | 8.38 | 8.45 | 8.50 | 0.06 |
| HC N203R | 8.38 | 8.45 | 8.50 | 0.06 |
| HC P206K | 8.38 | 8.45 | 8.50 | 0.06 |
| HC P206R | 8.38 | 8.45 | 8.50 | 0.06 |
| HC S207K | 8.38 | 8.45 | 8.50 | 0.06 |
| HC S207R | 8.38 | 8.45 | 8.50 | 0.06 |
| HC N208K | 8.38 | 8.45 | 8.50 | 0.06 |
| HC N208R | 8.38 | 8.45 | 8.50 | 0.06 |
| HC T209K | 8.38 | 8.45 | 8.50 | 0.06 |
| HC T209R | 8.38 | 8.45 | 8.50 | 0.06 |
| HC V211K | 8.38 | 8.45 | 8.50 | 0.06 |
| HC V211R | 8.38 | 8.45 | 8.50 | 0.06 |
| HC D212K | 8.38 | 8.50 | 8.60 | 0.11 |
| HC D212R | 8.38 | 8.50 | 8.61 | 0.11 |
| HC E216K | 8.38 | 8.50 | 8.60 | 0.11 |
| HC E216R | 8.38 | 8.50 | 8.61 | 0.11 |
| HC P217K | 8.38 | 8.45 | 8.50 | 0.06 |
| HC P217R | 8.38 | 8.45 | 8.50 | 0.06 |
| HC S219K | 8.38 | 8.45 | 8.50 | 0.06 |
| HC S219R | 8.38 | 8.45 | 8.50 | 0.06 |

Figure 46C

| Variant | Neutral or Acidic to Basic | | | |
| --- | --- | --- | --- | --- |
| | IgG1 / IgG1 | pI / IgG1 | pI / pI | delta pI |
| HC C220K | 8.38 | 8.46 | 8.53 | 0.07 |
| HC C220R | 8.38 | 8.46 | 8.53 | 0.07 |
| HC D221K | 8.38 | 8.50 | 8.60 | 0.11 |
| HC D221R | 8.38 | 8.50 | 8.61 | 0.11 |
| HC T223K | 8.38 | 8.45 | 8.50 | 0.06 |
| HC T223R | 8.38 | 8.45 | 8.50 | 0.06 |
| HC H224K | 8.38 | 8.44 | 8.50 | 0.06 |
| HC H224R | 8.38 | 8.45 | 8.50 | 0.06 |
| HC T225K | 8.38 | 8.45 | 8.50 | 0.06 |
| HC T225R | 8.38 | 8.45 | 8.50 | 0.06 |
| HC C226K | 8.38 | 8.46 | 8.53 | 0.07 |
| HC C226R | 8.38 | 8.46 | 8.53 | 0.07 |
| HC P227K | 8.38 | 8.45 | 8.50 | 0.06 |
| HC P227R | 8.38 | 8.45 | 8.50 | 0.06 |
| HC P228K | 8.38 | 8.45 | 8.50 | 0.06 |
| HC P228R | 8.38 | 8.45 | 8.50 | 0.06 |
| HC C229K | 8.38 | 8.46 | 8.53 | 0.07 |
| HC C229R | 8.38 | 8.46 | 8.53 | 0.07 |
| HC P230K | 8.38 | 8.45 | 8.50 | 0.06 |
| HC P230R | 8.38 | 8.45 | 8.50 | 0.06 |
| HC A231K | 8.38 | 8.45 | 8.50 | 0.06 |
| HC A231R | 8.38 | 8.45 | 8.50 | 0.06 |
| HC P232K | 8.38 | 8.45 | 8.50 | 0.06 |
| HC P232R | 8.38 | 8.45 | 8.50 | 0.06 |
| HC E233K | 8.38 | 8.50 | 8.60 | 0.11 |
| HC E233R | 8.38 | 8.50 | 8.61 | 0.11 |
| HC L234K | 8.38 | 8.45 | 8.50 | 0.06 |
| HC L234R | 8.38 | 8.45 | 8.50 | 0.06 |
| HC L235K | 8.38 | 8.45 | 8.50 | 0.06 |
| HC L235R | 8.38 | 8.45 | 8.50 | 0.06 |
| HC G236K | 8.38 | 8.45 | 8.50 | 0.06 |
| HC G236R | 8.38 | 8.45 | 8.50 | 0.06 |
| HC S239K | 8.38 | 8.45 | 8.50 | 0.06 |
| HC S239R | 8.38 | 8.45 | 8.50 | 0.06 |
| HC F241K | 8.38 | 8.45 | 8.50 | 0.06 |
| HC F241R | 8.38 | 8.45 | 8.50 | 0.06 |
| HC F243K | 8.38 | 8.45 | 8.50 | 0.06 |
| HC F243R | 8.38 | 8.45 | 8.50 | 0.06 |
| HC P244K | 8.38 | 8.45 | 8.50 | 0.06 |
| HC P244R | 8.38 | 8.45 | 8.50 | 0.06 |
| HC P247K | 8.38 | 8.45 | 8.50 | 0.06 |
| HC P247R | 8.38 | 8.45 | 8.50 | 0.06 |
| HC M252K | 8.38 | 8.45 | 8.50 | 0.06 |
| HC M252R | 8.38 | 8.45 | 8.50 | 0.06 |
| HC I253K | 8.38 | 8.45 | 8.50 | 0.06 |
| HC I253R | 8.38 | 8.45 | 8.50 | 0.06 |
| HC S254K | 8.38 | 8.45 | 8.50 | 0.06 |
| HC S254R | 8.38 | 8.45 | 8.50 | 0.06 |
| HC T256K | 8.38 | 8.45 | 8.50 | 0.06 |
| HC T256R | 8.38 | 8.45 | 8.50 | 0.06 |

Figure 46D

| Variant | Neutral or Acidic to Basic | | | |
|---|---|---|---|---|
| | IgG1 / IgG1 | pI / IgG1 | pI / pI | delta pI |
| HC E258K | 8.38 | 8.50 | 8.60 | 0.11 |
| HC E258R | 8.38 | 8.50 | 8.61 | 0.11 |
| HC V264K | 8.38 | 8.45 | 8.50 | 0.06 |
| HC V264R | 8.38 | 8.45 | 8.50 | 0.06 |
| HC D265K | 8.38 | 8.50 | 8.60 | 0.11 |
| HC D265R | 8.38 | 8.50 | 8.61 | 0.11 |
| HC H268K | 8.38 | 8.44 | 8.50 | 0.06 |
| HC H268R | 8.38 | 8.45 | 8.50 | 0.06 |
| HC E269K | 8.38 | 8.50 | 8.60 | 0.11 |
| HC E269R | 8.38 | 8.50 | 8.61 | 0.11 |
| HC P271K | 8.38 | 8.45 | 8.50 | 0.06 |
| HC P271R | 8.38 | 8.45 | 8.50 | 0.06 |
| HC E272K | 8.38 | 8.50 | 8.60 | 0.11 |
| HC E272R | 8.38 | 8.50 | 8.61 | 0.11 |
| HC Y278K | 8.38 | 8.45 | 8.50 | 0.06 |
| HC Y278R | 8.38 | 8.45 | 8.51 | 0.06 |
| HC D280K | 8.38 | 8.50 | 8.60 | 0.11 |
| HC D280R | 8.38 | 8.50 | 8.61 | 0.11 |
| HC G281K | 8.38 | 8.45 | 8.50 | 0.06 |
| HC G281R | 8.38 | 8.45 | 8.50 | 0.06 |
| HC V282K | 8.38 | 8.45 | 8.50 | 0.06 |
| HC V282R | 8.38 | 8.45 | 8.50 | 0.06 |
| HC E283K | 8.38 | 8.50 | 8.60 | 0.11 |
| HC E283R | 8.38 | 8.50 | 8.61 | 0.11 |
| HC V284K | 8.38 | 8.45 | 8.50 | 0.06 |
| HC V284R | 8.38 | 8.45 | 8.50 | 0.06 |
| HC H285K | 8.38 | 8.44 | 8.50 | 0.06 |
| HC H285R | 8.38 | 8.45 | 8.50 | 0.06 |
| HC N286K | 8.38 | 8.45 | 8.50 | 0.06 |
| HC N286R | 8.38 | 8.45 | 8.50 | 0.06 |
| HC A287K | 8.38 | 8.45 | 8.50 | 0.06 |
| HC A287R | 8.38 | 8.45 | 8.50 | 0.06 |
| HC T289K | 8.38 | 8.45 | 8.50 | 0.06 |
| HC T289R | 8.38 | 8.45 | 8.50 | 0.06 |
| HC P291K | 8.38 | 8.45 | 8.50 | 0.06 |
| HC P291R | 8.38 | 8.45 | 8.50 | 0.06 |
| HC E293K | 8.38 | 8.50 | 8.60 | 0.11 |
| HC E293R | 8.38 | 8.50 | 8.61 | 0.11 |
| HC E294K | 8.38 | 8.50 | 8.60 | 0.11 |
| HC E294R | 8.38 | 8.50 | 8.61 | 0.11 |
| HC Q295K | 8.38 | 8.45 | 8.50 | 0.06 |
| HC Q295R | 8.38 | 8.45 | 8.50 | 0.06 |
| HC Y296K | 8.38 | 8.45 | 8.50 | 0.06 |
| HC Y296R | 8.38 | 8.45 | 8.51 | 0.06 |
| HC N297K | 8.38 | 8.45 | 8.50 | 0.06 |
| HC N297R | 8.38 | 8.45 | 8.50 | 0.06 |
| HC S298K | 8.38 | 8.45 | 8.50 | 0.06 |
| HC S298R | 8.38 | 8.45 | 8.50 | 0.06 |
| HC T307K | 8.38 | 8.45 | 8.50 | 0.06 |
| HC T307R | 8.38 | 8.45 | 8.50 | 0.06 |

Figure 46E

| Variant | Neutral or Acidic to Basic | | | |
| --- | --- | --- | --- | --- |
| | IgG1 / IgG1 | pI / IgG1 | pI / pI | delta pI |
| HC L309K | 8.38 | 8.45 | 8.50 | 0.06 |
| HC L309R | 8.38 | 8.45 | 8.50 | 0.06 |
| HC H310K | 8.38 | 8.44 | 8.50 | 0.06 |
| HC H310R | 8.38 | 8.45 | 8.50 | 0.06 |
| HC Q311K | 8.38 | 8.45 | 8.50 | 0.06 |
| HC Q311R | 8.38 | 8.45 | 8.50 | 0.06 |
| HC L314K | 8.38 | 8.45 | 8.50 | 0.06 |
| HC L314R | 8.38 | 8.45 | 8.50 | 0.06 |
| HC N315K | 8.38 | 8.45 | 8.50 | 0.06 |
| HC N315R | 8.38 | 8.45 | 8.50 | 0.06 |
| HC G316K | 8.38 | 8.45 | 8.50 | 0.06 |
| HC G316R | 8.38 | 8.45 | 8.50 | 0.06 |
| HC E318K | 8.38 | 8.50 | 8.60 | 0.11 |
| HC E318R | 8.38 | 8.50 | 8.61 | 0.11 |
| HC S324K | 8.38 | 8.45 | 8.50 | 0.06 |
| HC S324R | 8.38 | 8.45 | 8.50 | 0.06 |
| HC P329K | 8.38 | 8.45 | 8.50 | 0.06 |
| HC P329R | 8.38 | 8.45 | 8.50 | 0.06 |
| HC A330K | 8.38 | 8.45 | 8.50 | 0.06 |
| HC A330R | 8.38 | 8.45 | 8.50 | 0.06 |
| HC P331K | 8.38 | 8.45 | 8.50 | 0.06 |
| HC P331R | 8.38 | 8.45 | 8.50 | 0.06 |
| HC I332K | 8.38 | 8.45 | 8.50 | 0.06 |
| HC I332R | 8.38 | 8.45 | 8.50 | 0.06 |
| HC E333K | 8.38 | 8.50 | 8.60 | 0.11 |
| HC E333R | 8.38 | 8.50 | 8.61 | 0.11 |
| HC T335K | 8.38 | 8.45 | 8.50 | 0.06 |
| HC T335R | 8.38 | 8.45 | 8.50 | 0.06 |
| HC S337K | 8.38 | 8.45 | 8.50 | 0.06 |
| HC S337R | 8.38 | 8.45 | 8.50 | 0.06 |
| HC A339K | 8.38 | 8.45 | 8.50 | 0.06 |
| HC A339R | 8.38 | 8.45 | 8.50 | 0.06 |
| HC G341K | 8.38 | 8.45 | 8.50 | 0.06 |
| HC G341R | 8.38 | 8.45 | 8.50 | 0.06 |
| HC Q342K | 8.38 | 8.45 | 8.50 | 0.06 |
| HC Q342R | 8.38 | 8.45 | 8.50 | 0.06 |
| HC P343K | 8.38 | 8.45 | 8.50 | 0.06 |
| HC P343R | 8.38 | 8.45 | 8.50 | 0.06 |
| HC E345K | 8.38 | 8.50 | 8.60 | 0.11 |
| HC E345R | 8.38 | 8.50 | 8.61 | 0.11 |
| HC Q347K | 8.38 | 8.45 | 8.50 | 0.06 |
| HC Q347R | 8.38 | 8.45 | 8.50 | 0.06 |
| HC P352K | 8.38 | 8.45 | 8.50 | 0.06 |
| HC P352R | 8.38 | 8.45 | 8.50 | 0.06 |
| HC D356K | 8.38 | 8.50 | 8.60 | 0.11 |
| HC D356R | 8.38 | 8.50 | 8.61 | 0.11 |
| HC L358K | 8.38 | 8.45 | 8.50 | 0.06 |
| HC L358R | 8.38 | 8.45 | 8.50 | 0.06 |
| HC T359K | 8.38 | 8.45 | 8.50 | 0.06 |
| HC T359R | 8.38 | 8.45 | 8.50 | 0.06 |

Figure 46F

| Variant | Neutral or Acidic to Basic | | | |
|---|---|---|---|---|
| | IgG1 / IgG1 | pI / IgG1 | pI / pI | delta pI |
| HC N361K | 8.38 | 8.45 | 8.50 | 0.06 |
| HC N361R | 8.38 | 8.45 | 8.50 | 0.06 |
| HC Q362K | 8.38 | 8.45 | 8.50 | 0.06 |
| HC Q362R | 8.38 | 8.45 | 8.50 | 0.06 |
| HC Y373K | 8.38 | 8.45 | 8.50 | 0.06 |
| HC Y373R | 8.38 | 8.45 | 8.51 | 0.06 |
| HC S375K | 8.38 | 8.45 | 8.50 | 0.06 |
| HC S375R | 8.38 | 8.45 | 8.50 | 0.06 |
| HC D376K | 8.38 | 8.50 | 8.60 | 0.11 |
| HC D376R | 8.38 | 8.50 | 8.61 | 0.11 |
| HC E380K | 8.38 | 8.50 | 8.60 | 0.11 |
| HC E380R | 8.38 | 8.50 | 8.61 | 0.11 |
| HC E382K | 8.38 | 8.50 | 8.60 | 0.11 |
| HC E382R | 8.38 | 8.50 | 8.61 | 0.11 |
| HC N384K | 8.38 | 8.45 | 8.50 | 0.06 |
| HC N384R | 8.38 | 8.45 | 8.50 | 0.06 |
| HC G385K | 8.38 | 8.45 | 8.50 | 0.06 |
| HC G385R | 8.38 | 8.45 | 8.50 | 0.06 |
| HC Q386K | 8.38 | 8.45 | 8.50 | 0.06 |
| HC Q386R | 8.38 | 8.45 | 8.50 | 0.06 |
| HC P387K | 8.38 | 8.45 | 8.50 | 0.06 |
| HC P387R | 8.38 | 8.45 | 8.50 | 0.06 |
| HC N389K | 8.38 | 8.45 | 8.50 | 0.06 |
| HC N389R | 8.38 | 8.45 | 8.50 | 0.06 |
| HC N390K | 8.38 | 8.45 | 8.50 | 0.06 |
| HC N390R | 8.38 | 8.45 | 8.50 | 0.06 |
| HC Y391K | 8.38 | 8.45 | 8.50 | 0.06 |
| HC Y391R | 8.38 | 8.45 | 8.51 | 0.06 |
| HC T393K | 8.38 | 8.45 | 8.50 | 0.06 |
| HC T393R | 8.38 | 8.45 | 8.50 | 0.06 |
| HC P395K | 8.38 | 8.45 | 8.50 | 0.06 |
| HC P395R | 8.38 | 8.45 | 8.50 | 0.06 |
| HC P396K | 8.38 | 8.45 | 8.50 | 0.06 |
| HC P396R | 8.38 | 8.45 | 8.50 | 0.06 |
| HC L398K | 8.38 | 8.45 | 8.50 | 0.06 |
| HC L398R | 8.38 | 8.45 | 8.50 | 0.06 |
| HC S400K | 8.38 | 8.45 | 8.50 | 0.06 |
| HC S400R | 8.38 | 8.45 | 8.50 | 0.06 |
| HC D401K | 8.38 | 8.50 | 8.60 | 0.11 |
| HC D401R | 8.38 | 8.50 | 8.61 | 0.11 |
| HC G402K | 8.38 | 8.45 | 8.50 | 0.06 |
| HC G402R | 8.38 | 8.45 | 8.50 | 0.06 |
| HC D413K | 8.38 | 8.50 | 8.60 | 0.11 |
| HC D413R | 8.38 | 8.50 | 8.61 | 0.11 |
| HC S415K | 8.38 | 8.45 | 8.50 | 0.06 |
| HC S415R | 8.38 | 8.45 | 8.50 | 0.06 |
| HC Q418K | 8.38 | 8.45 | 8.50 | 0.06 |
| HC Q418R | 8.38 | 8.45 | 8.50 | 0.06 |
| HC Q419K | 8.38 | 8.45 | 8.50 | 0.06 |
| HC Q419R | 8.38 | 8.45 | 8.50 | 0.06 |

Figure 46G

| Variant | Neutral or Acidic to Basic | | | |
|---|---|---|---|---|
| | IgG1 / IgG1 | pI / IgG1 | pI / pI | delta pI |
| HC G420K | 8.38 | 8.45 | 8.50 | 0.06 |
| HC G420R | 8.38 | 8.45 | 8.50 | 0.06 |
| HC N421K | 8.38 | 8.45 | 8.50 | 0.06 |
| HC N421R | 8.38 | 8.45 | 8.50 | 0.06 |
| HC V422K | 8.38 | 8.45 | 8.50 | 0.06 |
| HC V422R | 8.38 | 8.45 | 8.50 | 0.06 |
| HC E430K | 8.38 | 8.50 | 8.60 | 0.11 |
| HC E430R | 8.38 | 8.50 | 8.61 | 0.11 |
| HC A431K | 8.38 | 8.45 | 8.50 | 0.06 |
| HC A431R | 8.38 | 8.45 | 8.50 | 0.06 |
| HC H433K | 8.38 | 8.44 | 8.50 | 0.06 |
| HC H433R | 8.38 | 8.45 | 8.50 | 0.06 |
| HC N434K | 8.38 | 8.45 | 8.50 | 0.06 |
| HC N434R | 8.38 | 8.45 | 8.50 | 0.06 |
| HC H435K | 8.38 | 8.44 | 8.50 | 0.06 |
| HC H435R | 8.38 | 8.45 | 8.50 | 0.06 |
| HC Y436K | 8.38 | 8.45 | 8.50 | 0.06 |
| HC Y436R | 8.38 | 8.45 | 8.51 | 0.06 |
| HC T437K | 8.38 | 8.45 | 8.50 | 0.06 |
| HC T437R | 8.38 | 8.45 | 8.50 | 0.06 |
| HC Q438K | 8.38 | 8.45 | 8.50 | 0.06 |
| HC Q438R | 8.38 | 8.45 | 8.50 | 0.06 |
| HC S440K | 8.38 | 8.45 | 8.50 | 0.06 |
| HC S440R | 8.38 | 8.45 | 8.50 | 0.06 |
| HC S442K | 8.38 | 8.45 | 8.50 | 0.06 |
| HC S442R | 8.38 | 8.45 | 8.50 | 0.06 |
| HC L443K | 8.38 | 8.45 | 8.50 | 0.06 |
| HC L443R | 8.38 | 8.45 | 8.50 | 0.06 |
| HC S444K | 8.38 | 8.45 | 8.50 | 0.06 |
| HC S444R | 8.38 | 8.45 | 8.50 | 0.06 |
| HC P445K | 8.38 | 8.45 | 8.50 | 0.06 |
| HC P445R | 8.38 | 8.45 | 8.50 | 0.06 |
| HC G446K | 8.38 | 8.45 | 8.50 | 0.06 |
| HC G446R | 8.38 | 8.45 | 8.50 | 0.06 |

Figure 47A

| Variant | Acidic to Neutral | | | |
|---|---|---|---|---|
| | IgG1 / IgG1 | pI / IgG1 | pI / pI | delta pI |
| HC D148A | 8.38 | 8.45 | 8.50 | 0.06 |
| HC D148F | 8.38 | 8.45 | 8.50 | 0.06 |
| HC D148G | 8.38 | 8.45 | 8.50 | 0.06 |
| HC D148H | 8.38 | 8.45 | 8.50 | 0.06 |
| HC D148I | 8.38 | 8.45 | 8.50 | 0.06 |
| HC D148L | 8.38 | 8.45 | 8.50 | 0.06 |
| HC D148M | 8.38 | 8.45 | 8.50 | 0.06 |
| HC D148N | 8.38 | 8.45 | 8.50 | 0.06 |
| HC D148P | 8.38 | 8.45 | 8.50 | 0.06 |
| HC D148Q | 8.38 | 8.45 | 8.50 | 0.06 |
| HC D148S | 8.38 | 8.45 | 8.50 | 0.06 |
| HC D148T | 8.38 | 8.45 | 8.50 | 0.06 |
| HC D148V | 8.38 | 8.45 | 8.50 | 0.06 |
| HC D148W | 8.38 | 8.45 | 8.50 | 0.06 |
| HC D148Y | 8.38 | 8.45 | 8.50 | 0.06 |
| HC E152A | 8.38 | 8.45 | 8.50 | 0.06 |
| HC E152F | 8.38 | 8.45 | 8.50 | 0.06 |
| HC E152G | 8.38 | 8.45 | 8.50 | 0.06 |
| HC E152H | 8.38 | 8.45 | 8.50 | 0.06 |
| HC E152I | 8.38 | 8.45 | 8.50 | 0.06 |
| HC E152L | 8.38 | 8.45 | 8.50 | 0.06 |
| HC E152M | 8.38 | 8.45 | 8.50 | 0.06 |
| HC E152N | 8.38 | 8.45 | 8.50 | 0.06 |
| HC E152P | 8.38 | 8.45 | 8.50 | 0.06 |
| HC E152Q | 8.38 | 8.45 | 8.50 | 0.06 |
| HC E152S | 8.38 | 8.45 | 8.50 | 0.06 |
| HC E152T | 8.38 | 8.45 | 8.50 | 0.06 |
| HC E152V | 8.38 | 8.45 | 8.50 | 0.06 |
| HC E152W | 8.38 | 8.45 | 8.50 | 0.06 |
| HC E152Y | 8.38 | 8.45 | 8.50 | 0.06 |
| HC D212A | 8.38 | 8.45 | 8.50 | 0.06 |
| HC D212F | 8.38 | 8.45 | 8.50 | 0.06 |
| HC D212G | 8.38 | 8.45 | 8.50 | 0.06 |
| HC D212H | 8.38 | 8.45 | 8.50 | 0.06 |
| HC D212I | 8.38 | 8.45 | 8.50 | 0.06 |
| HC D212L | 8.38 | 8.45 | 8.50 | 0.06 |
| HC D212M | 8.38 | 8.45 | 8.50 | 0.06 |
| HC D212N | 8.38 | 8.45 | 8.50 | 0.06 |
| HC D212P | 8.38 | 8.45 | 8.50 | 0.06 |
| HC D212Q | 8.38 | 8.45 | 8.50 | 0.06 |
| HC D212S | 8.38 | 8.45 | 8.50 | 0.06 |
| HC D212T | 8.38 | 8.45 | 8.50 | 0.06 |
| HC D212V | 8.38 | 8.45 | 8.50 | 0.06 |
| HC D212W | 8.38 | 8.45 | 8.50 | 0.06 |
| HC D212Y | 8.38 | 8.45 | 8.50 | 0.06 |
| HC E216A | 8.38 | 8.45 | 8.50 | 0.06 |
| HC E216F | 8.38 | 8.45 | 8.50 | 0.06 |
| HC E216G | 8.38 | 8.45 | 8.50 | 0.06 |

Figure 47B

| Variant | Acidic to Neutral | | | |
|---|---|---|---|---|
| | IgG1 / IgG1 | pI / IgG1 | pI / pI | delta pI |
| HC E216H | 8.38 | 8.45 | 8.50 | 0.06 |
| HC E216I | 8.38 | 8.45 | 8.50 | 0.06 |
| HC E216L | 8.38 | 8.45 | 8.50 | 0.06 |
| HC E216M | 8.38 | 8.45 | 8.50 | 0.06 |
| HC E216N | 8.38 | 8.45 | 8.50 | 0.06 |
| HC E216P | 8.38 | 8.45 | 8.50 | 0.06 |
| HC E216Q | 8.38 | 8.45 | 8.50 | 0.06 |
| HC E216S | 8.38 | 8.45 | 8.50 | 0.06 |
| HC E216T | 8.38 | 8.45 | 8.50 | 0.06 |
| HC E216V | 8.38 | 8.45 | 8.50 | 0.06 |
| HC E216W | 8.38 | 8.45 | 8.50 | 0.06 |
| HC E216Y | 8.38 | 8.45 | 8.50 | 0.06 |
| HC D221A | 8.38 | 8.45 | 8.50 | 0.06 |
| HC D221F | 8.38 | 8.45 | 8.50 | 0.06 |
| HC D221G | 8.38 | 8.45 | 8.50 | 0.06 |
| HC D221H | 8.38 | 8.45 | 8.50 | 0.06 |
| HC D221I | 8.38 | 8.45 | 8.50 | 0.06 |
| HC D221L | 8.38 | 8.45 | 8.50 | 0.06 |
| HC D221M | 8.38 | 8.45 | 8.50 | 0.06 |
| HC D221N | 8.38 | 8.45 | 8.50 | 0.06 |
| HC D221P | 8.38 | 8.45 | 8.50 | 0.06 |
| HC D221Q | 8.38 | 8.45 | 8.50 | 0.06 |
| HC D221S | 8.38 | 8.45 | 8.50 | 0.06 |
| HC D221T | 8.38 | 8.45 | 8.50 | 0.06 |
| HC D221V | 8.38 | 8.45 | 8.50 | 0.06 |
| HC D221W | 8.38 | 8.45 | 8.50 | 0.06 |
| HC D221Y | 8.38 | 8.45 | 8.50 | 0.06 |
| HC E233A | 8.38 | 8.45 | 8.50 | 0.06 |
| HC E233F | 8.38 | 8.45 | 8.50 | 0.06 |
| HC E233G | 8.38 | 8.45 | 8.50 | 0.06 |
| HC E233H | 8.38 | 8.45 | 8.50 | 0.06 |
| HC E233I | 8.38 | 8.45 | 8.50 | 0.06 |
| HC E233L | 8.38 | 8.45 | 8.50 | 0.06 |
| HC E233M | 8.38 | 8.45 | 8.50 | 0.06 |
| HC E233N | 8.38 | 8.45 | 8.50 | 0.06 |
| HC E233P | 8.38 | 8.45 | 8.50 | 0.06 |
| HC E233Q | 8.38 | 8.45 | 8.50 | 0.06 |
| HC E233S | 8.38 | 8.45 | 8.50 | 0.06 |
| HC E233T | 8.38 | 8.45 | 8.50 | 0.06 |
| HC E233V | 8.38 | 8.45 | 8.50 | 0.06 |
| HC E233W | 8.38 | 8.45 | 8.50 | 0.06 |
| HC E233Y | 8.38 | 8.45 | 8.50 | 0.06 |
| HC E258A | 8.38 | 8.45 | 8.50 | 0.06 |
| HC E258F | 8.38 | 8.45 | 8.50 | 0.06 |
| HC E258G | 8.38 | 8.45 | 8.50 | 0.06 |
| HC E258H | 8.38 | 8.45 | 8.50 | 0.06 |
| HC E258I | 8.38 | 8.45 | 8.50 | 0.06 |
| HC E258L | 8.38 | 8.45 | 8.50 | 0.06 |
| HC E258M | 8.38 | 8.45 | 8.50 | 0.06 |
| HC E258N | 8.38 | 8.45 | 8.50 | 0.06 |

Figure 47C

| Variant | Acidic to Neutral | | | |
|---|---|---|---|---|
| | IgG1 / IgG1 | pI / IgG1 | pI / pI | delta pI |
| HC E258P | 8.38 | 8.45 | 8.50 | 0.06 |
| HC E258Q | 8.38 | 8.45 | 8.50 | 0.06 |
| HC E258S | 8.38 | 8.45 | 8.50 | 0.06 |
| HC E258T | 8.38 | 8.45 | 8.50 | 0.06 |
| HC E258V | 8.38 | 8.45 | 8.50 | 0.06 |
| HC E258W | 8.38 | 8.45 | 8.50 | 0.06 |
| HC E258Y | 8.38 | 8.45 | 8.50 | 0.06 |
| HC D265A | 8.38 | 8.45 | 8.50 | 0.06 |
| HC D265F | 8.38 | 8.45 | 8.50 | 0.06 |
| HC D265G | 8.38 | 8.45 | 8.50 | 0.06 |
| HC D265H | 8.38 | 8.45 | 8.50 | 0.06 |
| HC D265I | 8.38 | 8.45 | 8.50 | 0.06 |
| HC D265L | 8.38 | 8.45 | 8.50 | 0.06 |
| HC D265M | 8.38 | 8.45 | 8.50 | 0.06 |
| HC D265N | 8.38 | 8.45 | 8.50 | 0.06 |
| HC D265P | 8.38 | 8.45 | 8.50 | 0.06 |
| HC D265Q | 8.38 | 8.45 | 8.50 | 0.06 |
| HC D265S | 8.38 | 8.45 | 8.50 | 0.06 |
| HC D265T | 8.38 | 8.45 | 8.50 | 0.06 |
| HC D265V | 8.38 | 8.45 | 8.50 | 0.06 |
| HC D265W | 8.38 | 8.45 | 8.50 | 0.06 |
| HC D265Y | 8.38 | 8.45 | 8.50 | 0.06 |
| HC E269A | 8.38 | 8.45 | 8.50 | 0.06 |
| HC E269F | 8.38 | 8.45 | 8.50 | 0.06 |
| HC E269G | 8.38 | 8.45 | 8.50 | 0.06 |
| HC E269H | 8.38 | 8.45 | 8.50 | 0.06 |
| HC E269I | 8.38 | 8.45 | 8.50 | 0.06 |
| HC E269L | 8.38 | 8.45 | 8.50 | 0.06 |
| HC E269M | 8.38 | 8.45 | 8.50 | 0.06 |
| HC E269N | 8.38 | 8.45 | 8.50 | 0.06 |
| HC E269P | 8.38 | 8.45 | 8.50 | 0.06 |
| HC E269Q | 8.38 | 8.45 | 8.50 | 0.06 |
| HC E269S | 8.38 | 8.45 | 8.50 | 0.06 |
| HC E269T | 8.38 | 8.45 | 8.50 | 0.06 |
| HC E269V | 8.38 | 8.45 | 8.50 | 0.06 |
| HC E269W | 8.38 | 8.45 | 8.50 | 0.06 |
| HC E269Y | 8.38 | 8.45 | 8.50 | 0.06 |
| HC E272A | 8.38 | 8.45 | 8.50 | 0.06 |
| HC E272F | 8.38 | 8.45 | 8.50 | 0.06 |
| HC E272G | 8.38 | 8.45 | 8.50 | 0.06 |
| HC E272H | 8.38 | 8.45 | 8.50 | 0.06 |
| HC E272I | 8.38 | 8.45 | 8.50 | 0.06 |
| HC E272L | 8.38 | 8.45 | 8.50 | 0.06 |
| HC E272M | 8.38 | 8.45 | 8.50 | 0.06 |
| HC E272N | 8.38 | 8.45 | 8.50 | 0.06 |
| HC E272P | 8.38 | 8.45 | 8.50 | 0.06 |
| HC E272Q | 8.38 | 8.45 | 8.50 | 0.06 |
| HC E272S | 8.38 | 8.45 | 8.50 | 0.06 |
| HC E272T | 8.38 | 8.45 | 8.50 | 0.06 |
| HC E272V | 8.38 | 8.45 | 8.50 | 0.06 |

Figure 47D

| Variant | Acidic to Neutral | | | |
|---|---|---|---|---|
| | IgG1 / IgG1 | pI / IgG1 | pI / pI | delta pI |
| HC E272W | 8.38 | 8.45 | 8.50 | 0.06 |
| HC E272Y | 8.38 | 8.45 | 8.50 | 0.06 |
| HC D280A | 8.38 | 8.45 | 8.50 | 0.06 |
| HC D280F | 8.38 | 8.45 | 8.50 | 0.06 |
| HC D280G | 8.38 | 8.45 | 8.50 | 0.06 |
| HC D280H | 8.38 | 8.45 | 8.50 | 0.06 |
| HC D280I | 8.38 | 8.45 | 8.50 | 0.06 |
| HC D280L | 8.38 | 8.45 | 8.50 | 0.06 |
| HC D280M | 8.38 | 8.45 | 8.50 | 0.06 |
| HC D280N | 8.38 | 8.45 | 8.50 | 0.06 |
| HC D280P | 8.38 | 8.45 | 8.50 | 0.06 |
| HC D280Q | 8.38 | 8.45 | 8.50 | 0.06 |
| HC D280S | 8.38 | 8.45 | 8.50 | 0.06 |
| HC D280T | 8.38 | 8.45 | 8.50 | 0.06 |
| HC D280V | 8.38 | 8.45 | 8.50 | 0.06 |
| HC D280W | 8.38 | 8.45 | 8.50 | 0.06 |
| HC D280Y | 8.38 | 8.45 | 8.50 | 0.06 |
| HC E283A | 8.38 | 8.45 | 8.50 | 0.06 |
| HC E283F | 8.38 | 8.45 | 8.50 | 0.06 |
| HC E283G | 8.38 | 8.45 | 8.50 | 0.06 |
| HC E283H | 8.38 | 8.45 | 8.50 | 0.06 |
| HC E283I | 8.38 | 8.45 | 8.50 | 0.06 |
| HC E283L | 8.38 | 8.45 | 8.50 | 0.06 |
| HC E283M | 8.38 | 8.45 | 8.50 | 0.06 |
| HC E283N | 8.38 | 8.45 | 8.50 | 0.06 |
| HC E283P | 8.38 | 8.45 | 8.50 | 0.06 |
| HC E283Q | 8.38 | 8.45 | 8.50 | 0.06 |
| HC E283S | 8.38 | 8.45 | 8.50 | 0.06 |
| HC E283T | 8.38 | 8.45 | 8.50 | 0.06 |
| HC E283V | 8.38 | 8.45 | 8.50 | 0.06 |
| HC E283W | 8.38 | 8.45 | 8.50 | 0.06 |
| HC E283Y | 8.38 | 8.45 | 8.50 | 0.06 |
| HC E293A | 8.38 | 8.45 | 8.50 | 0.06 |
| HC E293F | 8.38 | 8.45 | 8.50 | 0.06 |
| HC E293G | 8.38 | 8.45 | 8.50 | 0.06 |
| HC E293H | 8.38 | 8.45 | 8.50 | 0.06 |
| HC E293I | 8.38 | 8.45 | 8.50 | 0.06 |
| HC E293L | 8.38 | 8.45 | 8.50 | 0.06 |
| HC E293M | 8.38 | 8.45 | 8.50 | 0.06 |
| HC E293N | 8.38 | 8.45 | 8.50 | 0.06 |
| HC E293P | 8.38 | 8.45 | 8.50 | 0.06 |
| HC E293Q | 8.38 | 8.45 | 8.50 | 0.06 |
| HC E293S | 8.38 | 8.45 | 8.50 | 0.06 |
| HC E293T | 8.38 | 8.45 | 8.50 | 0.06 |
| HC E293V | 8.38 | 8.45 | 8.50 | 0.06 |
| HC E293W | 8.38 | 8.45 | 8.50 | 0.06 |
| HC E293Y | 8.38 | 8.45 | 8.50 | 0.06 |
| HC E294A | 8.38 | 8.45 | 8.50 | 0.06 |
| HC E294F | 8.38 | 8.45 | 8.50 | 0.06 |
| HC E294G | 8.38 | 8.45 | 8.50 | 0.06 |

Figure 47E

| | Acidic to Neutral | | | |
|---|---|---|---|---|
| Variant | IgG1 / IgG1 | pI / IgG1 | pI / pI | delta pI |
| HC E294H | 8.38 | 8.45 | 8.50 | 0.06 |
| HC E294I | 8.38 | 8.45 | 8.50 | 0.06 |
| HC E294L | 8.38 | 8.45 | 8.50 | 0.06 |
| HC E294M | 8.38 | 8.45 | 8.50 | 0.06 |
| HC E294N | 8.38 | 8.45 | 8.50 | 0.06 |
| HC E294P | 8.38 | 8.45 | 8.50 | 0.06 |
| HC E294Q | 8.38 | 8.45 | 8.50 | 0.06 |
| HC E294S | 8.38 | 8.45 | 8.50 | 0.06 |
| HC E294T | 8.38 | 8.45 | 8.50 | 0.06 |
| HC E294V | 8.38 | 8.45 | 8.50 | 0.06 |
| HC E294W | 8.38 | 8.45 | 8.50 | 0.06 |
| HC E294Y | 8.38 | 8.45 | 8.50 | 0.06 |
| HC E318A | 8.38 | 8.45 | 8.50 | 0.06 |
| HC E318F | 8.38 | 8.45 | 8.50 | 0.06 |
| HC E318G | 8.38 | 8.45 | 8.50 | 0.06 |
| HC E318H | 8.38 | 8.45 | 8.50 | 0.06 |
| HC E318I | 8.38 | 8.45 | 8.50 | 0.06 |
| HC E318L | 8.38 | 8.45 | 8.50 | 0.06 |
| HC E318M | 8.38 | 8.45 | 8.50 | 0.06 |
| HC E318N | 8.38 | 8.45 | 8.50 | 0.06 |
| HC E318P | 8.38 | 8.45 | 8.50 | 0.06 |
| HC E318Q | 8.38 | 8.45 | 8.50 | 0.06 |
| HC E318S | 8.38 | 8.45 | 8.50 | 0.06 |
| HC E318T | 8.38 | 8.45 | 8.50 | 0.06 |
| HC E318V | 8.38 | 8.45 | 8.50 | 0.06 |
| HC E318W | 8.38 | 8.45 | 8.50 | 0.06 |
| HC E318Y | 8.38 | 8.45 | 8.50 | 0.06 |
| HC E333A | 8.38 | 8.45 | 8.50 | 0.06 |
| HC E333F | 8.38 | 8.45 | 8.50 | 0.06 |
| HC E333G | 8.38 | 8.45 | 8.50 | 0.06 |
| HC E333H | 8.38 | 8.45 | 8.50 | 0.06 |
| HC E333I | 8.38 | 8.45 | 8.50 | 0.06 |
| HC E333L | 8.38 | 8.45 | 8.50 | 0.06 |
| HC E333M | 8.38 | 8.45 | 8.50 | 0.06 |
| HC E333N | 8.38 | 8.45 | 8.50 | 0.06 |
| HC E333P | 8.38 | 8.45 | 8.50 | 0.06 |
| HC E333Q | 8.38 | 8.45 | 8.50 | 0.06 |
| HC E333S | 8.38 | 8.45 | 8.50 | 0.06 |
| HC E333T | 8.38 | 8.45 | 8.50 | 0.06 |
| HC E333V | 8.38 | 8.45 | 8.50 | 0.06 |
| HC E333W | 8.38 | 8.45 | 8.50 | 0.06 |
| HC E333Y | 8.38 | 8.45 | 8.50 | 0.06 |
| HC E345A | 8.38 | 8.45 | 8.50 | 0.06 |
| HC E345F | 8.38 | 8.45 | 8.50 | 0.06 |
| HC E345G | 8.38 | 8.45 | 8.50 | 0.06 |
| HC E345H | 8.38 | 8.45 | 8.50 | 0.06 |
| HC E345I | 8.38 | 8.45 | 8.50 | 0.06 |
| HC E345L | 8.38 | 8.45 | 8.50 | 0.06 |
| HC E345M | 8.38 | 8.45 | 8.50 | 0.06 |
| HC E345N | 8.38 | 8.45 | 8.50 | 0.06 |

Figure 47F

| Variant | Acidic to Neutral | | | |
|---|---|---|---|---|
| | IgG1 / IgG1 | pI / IgG1 | pI / pI | delta pI |
| HC E345P | 8.38 | 8.45 | 8.50 | 0.06 |
| HC E345Q | 8.38 | 8.45 | 8.50 | 0.06 |
| HC E345S | 8.38 | 8.45 | 8.50 | 0.06 |
| HC E345T | 8.38 | 8.45 | 8.50 | 0.06 |
| HC E345V | 8.38 | 8.45 | 8.50 | 0.06 |
| HC E345W | 8.38 | 8.45 | 8.50 | 0.06 |
| HC E345Y | 8.38 | 8.45 | 8.50 | 0.06 |
| HC D356A | 8.38 | 8.45 | 8.50 | 0.06 |
| HC D356F | 8.38 | 8.45 | 8.50 | 0.06 |
| HC D356G | 8.38 | 8.45 | 8.50 | 0.06 |
| HC D356H | 8.38 | 8.45 | 8.50 | 0.06 |
| HC D356I | 8.38 | 8.45 | 8.50 | 0.06 |
| HC D356L | 8.38 | 8.45 | 8.50 | 0.06 |
| HC D356M | 8.38 | 8.45 | 8.50 | 0.06 |
| HC D356N | 8.38 | 8.45 | 8.50 | 0.06 |
| HC D356P | 8.38 | 8.45 | 8.50 | 0.06 |
| HC D356Q | 8.38 | 8.45 | 8.50 | 0.06 |
| HC D356S | 8.38 | 8.45 | 8.50 | 0.06 |
| HC D356T | 8.38 | 8.45 | 8.50 | 0.06 |
| HC D356V | 8.38 | 8.45 | 8.50 | 0.06 |
| HC D356W | 8.38 | 8.45 | 8.50 | 0.06 |
| HC D356Y | 8.38 | 8.45 | 8.50 | 0.06 |
| HC D376A | 8.38 | 8.45 | 8.50 | 0.06 |
| HC D376F | 8.38 | 8.45 | 8.50 | 0.06 |
| HC D376G | 8.38 | 8.45 | 8.50 | 0.06 |
| HC D376H | 8.38 | 8.45 | 8.50 | 0.06 |
| HC D376I | 8.38 | 8.45 | 8.50 | 0.06 |
| HC D376L | 8.38 | 8.45 | 8.50 | 0.06 |
| HC D376M | 8.38 | 8.45 | 8.50 | 0.06 |
| HC D376N | 8.38 | 8.45 | 8.50 | 0.06 |
| HC D376P | 8.38 | 8.45 | 8.50 | 0.06 |
| HC D376Q | 8.38 | 8.45 | 8.50 | 0.06 |
| HC D376S | 8.38 | 8.45 | 8.50 | 0.06 |
| HC D376T | 8.38 | 8.45 | 8.50 | 0.06 |
| HC D376V | 8.38 | 8.45 | 8.50 | 0.06 |
| HC D376W | 8.38 | 8.45 | 8.50 | 0.06 |
| HC D376Y | 8.38 | 8.45 | 8.50 | 0.06 |
| HC E380A | 8.38 | 8.45 | 8.50 | 0.06 |
| HC E380F | 8.38 | 8.45 | 8.50 | 0.06 |
| HC E380G | 8.38 | 8.45 | 8.50 | 0.06 |
| HC E380H | 8.38 | 8.45 | 8.50 | 0.06 |
| HC E380I | 8.38 | 8.45 | 8.50 | 0.06 |
| HC E380L | 8.38 | 8.45 | 8.50 | 0.06 |
| HC E380M | 8.38 | 8.45 | 8.50 | 0.06 |
| HC E380N | 8.38 | 8.45 | 8.50 | 0.06 |
| HC E380P | 8.38 | 8.45 | 8.50 | 0.06 |
| HC E380Q | 8.38 | 8.45 | 8.50 | 0.06 |
| HC E380S | 8.38 | 8.45 | 8.50 | 0.06 |
| HC E380T | 8.38 | 8.45 | 8.50 | 0.06 |
| HC E380V | 8.38 | 8.45 | 8.50 | 0.06 |

Figure 47G

| Variant | Acidic to Neutral | | | |
|---|---|---|---|---|
| | IgG1 / IgG1 | pI / IgG1 | pI / pI | delta pI |
| HC E380W | 8.38 | 8.45 | 8.50 | 0.06 |
| HC E380Y | 8.38 | 8.45 | 8.50 | 0.06 |
| HC E382A | 8.38 | 8.45 | 8.50 | 0.06 |
| HC E382F | 8.38 | 8.45 | 8.50 | 0.06 |
| HC E382G | 8.38 | 8.45 | 8.50 | 0.06 |
| HC E382H | 8.38 | 8.45 | 8.50 | 0.06 |
| HC E382I | 8.38 | 8.45 | 8.50 | 0.06 |
| HC E382L | 8.38 | 8.45 | 8.50 | 0.06 |
| HC E382M | 8.38 | 8.45 | 8.50 | 0.06 |
| HC E382N | 8.38 | 8.45 | 8.50 | 0.06 |
| HC E382P | 8.38 | 8.45 | 8.50 | 0.06 |
| HC E382Q | 8.38 | 8.45 | 8.50 | 0.06 |
| HC E382S | 8.38 | 8.45 | 8.50 | 0.06 |
| HC E382T | 8.38 | 8.45 | 8.50 | 0.06 |
| HC E382V | 8.38 | 8.45 | 8.50 | 0.06 |
| HC E382W | 8.38 | 8.45 | 8.50 | 0.06 |
| HC E382Y | 8.38 | 8.45 | 8.50 | 0.06 |
| HC D401A | 8.38 | 8.45 | 8.50 | 0.06 |
| HC D401F | 8.38 | 8.45 | 8.50 | 0.06 |
| HC D401G | 8.38 | 8.45 | 8.50 | 0.06 |
| HC D401H | 8.38 | 8.45 | 8.50 | 0.06 |
| HC D401I | 8.38 | 8.45 | 8.50 | 0.06 |
| HC D401L | 8.38 | 8.45 | 8.50 | 0.06 |
| HC D401M | 8.38 | 8.45 | 8.50 | 0.06 |
| HC D401N | 8.38 | 8.45 | 8.50 | 0.06 |
| HC D401P | 8.38 | 8.45 | 8.50 | 0.06 |
| HC D401Q | 8.38 | 8.45 | 8.50 | 0.06 |
| HC D401S | 8.38 | 8.45 | 8.50 | 0.06 |
| HC D401T | 8.38 | 8.45 | 8.50 | 0.06 |
| HC D401V | 8.38 | 8.45 | 8.50 | 0.06 |
| HC D401W | 8.38 | 8.45 | 8.50 | 0.06 |
| HC D401Y | 8.38 | 8.45 | 8.50 | 0.06 |
| HC D413A | 8.38 | 8.45 | 8.50 | 0.06 |
| HC D413F | 8.38 | 8.45 | 8.50 | 0.06 |
| HC D413G | 8.38 | 8.45 | 8.50 | 0.06 |
| HC D413H | 8.38 | 8.45 | 8.50 | 0.06 |
| HC D413I | 8.38 | 8.45 | 8.50 | 0.06 |
| HC D413L | 8.38 | 8.45 | 8.50 | 0.06 |
| HC D413M | 8.38 | 8.45 | 8.50 | 0.06 |
| HC D413N | 8.38 | 8.45 | 8.50 | 0.06 |
| HC D413P | 8.38 | 8.45 | 8.50 | 0.06 |
| HC D413Q | 8.38 | 8.45 | 8.50 | 0.06 |
| HC D413S | 8.38 | 8.45 | 8.50 | 0.06 |
| HC D413T | 8.38 | 8.45 | 8.50 | 0.06 |
| HC D413V | 8.38 | 8.45 | 8.50 | 0.06 |
| HC D413W | 8.38 | 8.45 | 8.50 | 0.06 |
| HC D413Y | 8.38 | 8.45 | 8.50 | 0.06 |
| HC E430A | 8.38 | 8.45 | 8.50 | 0.06 |
| HC E430F | 8.38 | 8.45 | 8.50 | 0.06 |
| HC E430G | 8.38 | 8.45 | 8.50 | 0.06 |

Figure 47H

| Variant | Acidic to Neutral | | | |
| --- | --- | --- | --- | --- |
| | IgG1 / IgG1 | pI / IgG1 | pI / pI | delta pI |
| HC E430H | 8.38 | 8.45 | 8.50 | 0.06 |
| HC E430I | 8.38 | 8.45 | 8.50 | 0.06 |
| HC E430L | 8.38 | 8.45 | 8.50 | 0.06 |
| HC E430M | 8.38 | 8.45 | 8.50 | 0.06 |
| HC E430N | 8.38 | 8.45 | 8.50 | 0.06 |
| HC E430P | 8.38 | 8.45 | 8.50 | 0.06 |
| HC E430Q | 8.38 | 8.45 | 8.50 | 0.06 |
| HC E430S | 8.38 | 8.45 | 8.50 | 0.06 |
| HC E430T | 8.38 | 8.45 | 8.50 | 0.06 |
| HC E430V | 8.38 | 8.45 | 8.50 | 0.06 |
| HC E430W | 8.38 | 8.45 | 8.50 | 0.06 |
| HC E430Y | 8.38 | 8.45 | 8.50 | 0.06 |

Figure 48A

| Variant | Neutral or Basic to Acidic | | | |
| --- | --- | --- | --- | --- |
| | IgG1 / IgG1 | pI / IgG1 | pI / pI | delta pI |
| LC T109D | 8.02 | 7.94 | 7.85 | -0.09 |
| LC T109E | 8.02 | 7.94 | 7.85 | -0.09 |
| LC V110D | 8.02 | 7.94 | 7.85 | -0.09 |
| LC V110E | 8.02 | 7.94 | 7.85 | -0.09 |
| LC A112D | 8.02 | 7.94 | 7.85 | -0.09 |
| LC A112E | 8.02 | 7.94 | 7.85 | -0.09 |
| LC S114D | 8.02 | 7.94 | 7.85 | -0.09 |
| LC S114E | 8.02 | 7.94 | 7.85 | -0.09 |
| LC P119D | 8.02 | 7.94 | 7.85 | -0.09 |
| LC P119E | 8.02 | 7.94 | 7.85 | -0.09 |
| LC K126D | 8.02 | 7.85 | 7.61 | -0.21 |
| LC K126E | 8.02 | 7.85 | 7.61 | -0.21 |
| LC S127D | 8.02 | 7.94 | 7.85 | -0.09 |
| LC S127E | 8.02 | 7.94 | 7.85 | -0.09 |
| LC G128D | 8.02 | 7.94 | 7.85 | -0.09 |
| LC G128E | 8.02 | 7.94 | 7.85 | -0.09 |
| LC T129D | 8.02 | 7.94 | 7.85 | -0.09 |
| LC T129E | 8.02 | 7.94 | 7.85 | -0.09 |
| LC N138D | 8.02 | 7.94 | 7.85 | -0.09 |
| LC N138E | 8.02 | 7.94 | 7.85 | -0.09 |
| LC R142D | 8.02 | 7.85 | 7.61 | -0.21 |
| LC R142E | 8.02 | 7.85 | 7.61 | -0.21 |
| LC K145D | 8.02 | 7.85 | 7.61 | -0.21 |
| LC K145E | 8.02 | 7.85 | 7.61 | -0.21 |
| LC Q147D | 8.02 | 7.94 | 7.85 | -0.09 |
| LC Q147E | 8.02 | 7.94 | 7.85 | -0.09 |
| LC K149D | 8.02 | 7.85 | 7.61 | -0.21 |
| LC K149E | 8.02 | 7.85 | 7.61 | -0.21 |
| LC N152D | 8.02 | 7.94 | 7.85 | -0.09 |
| LC N152E | 8.02 | 7.94 | 7.85 | -0.09 |
| LC A153D | 8.02 | 7.94 | 7.85 | -0.09 |
| LC A153E | 8.02 | 7.94 | 7.85 | -0.09 |
| LC L154D | 8.02 | 7.94 | 7.85 | -0.09 |
| LC L154E | 8.02 | 7.94 | 7.85 | -0.09 |
| LC S156D | 8.02 | 7.94 | 7.85 | -0.09 |
| LC S156E | 8.02 | 7.94 | 7.85 | -0.09 |
| LC G157D | 8.02 | 7.94 | 7.85 | -0.09 |
| LC G157E | 8.02 | 7.94 | 7.85 | -0.09 |
| LC N158D | 8.02 | 7.94 | 7.85 | -0.09 |
| LC N158E | 8.02 | 7.94 | 7.85 | -0.09 |
| LC S159D | 8.02 | 7.94 | 7.85 | -0.09 |
| LC S159E | 8.02 | 7.94 | 7.85 | -0.09 |
| LC Q160D | 8.02 | 7.94 | 7.85 | -0.09 |
| LC Q160E | 8.02 | 7.94 | 7.85 | -0.09 |
| LC S168D | 8.02 | 7.94 | 7.85 | -0.09 |
| LC S168E | 8.02 | 7.94 | 7.85 | -0.09 |
| LC K169D | 8.02 | 7.85 | 7.61 | -0.21 |
| LC K169E | 8.02 | 7.85 | 7.61 | -0.21 |

Figure 48B

| Variant | Neutral or Basic to Acidic | | | |
| --- | --- | --- | --- | --- |
| | IgG1 / IgG1 | pI / IgG1 | pI / pI | delta pI |
| LC T180D | 8.02 | 7.94 | 7.85 | -0.09 |
| LC T180E | 8.02 | 7.94 | 7.85 | -0.09 |
| LC L181D | 8.02 | 7.94 | 7.85 | -0.09 |
| LC L181E | 8.02 | 7.94 | 7.85 | -0.09 |
| LC S182D | 8.02 | 7.94 | 7.85 | -0.09 |
| LC S182E | 8.02 | 7.94 | 7.85 | -0.09 |
| LC K183D | 8.02 | 7.85 | 7.61 | -0.21 |
| LC K183E | 8.02 | 7.85 | 7.61 | -0.21 |
| LC A184D | 8.02 | 7.94 | 7.85 | -0.09 |
| LC A184E | 8.02 | 7.94 | 7.85 | -0.09 |
| LC K188D | 8.02 | 7.85 | 7.61 | -0.21 |
| LC K188E | 8.02 | 7.85 | 7.61 | -0.21 |
| LC H189D | 8.02 | 7.94 | 7.84 | -0.09 |
| LC H189E | 8.02 | 7.94 | 7.84 | -0.09 |
| LC K190D | 8.02 | 7.85 | 7.61 | -0.21 |
| LC K190E | 8.02 | 7.85 | 7.61 | -0.21 |
| LC V191D | 8.02 | 7.94 | 7.85 | -0.09 |
| LC V191E | 8.02 | 7.94 | 7.85 | -0.09 |
| LC T197D | 8.02 | 7.94 | 7.85 | -0.09 |
| LC T197E | 8.02 | 7.94 | 7.85 | -0.09 |
| LC Q199D | 8.02 | 7.94 | 7.85 | -0.09 |
| LC Q199E | 8.02 | 7.94 | 7.85 | -0.09 |
| LC G200D | 8.02 | 7.94 | 7.85 | -0.09 |
| LC G200E | 8.02 | 7.94 | 7.85 | -0.09 |
| LC R202D | 8.02 | 7.94 | 7.85 | -0.09 |
| LC R202E | 8.02 | 7.94 | 7.85 | -0.09 |
| LC S203D | 8.02 | 7.94 | 7.85 | -0.09 |
| LC S203E | 8.02 | 7.94 | 7.85 | -0.09 |
| LC P204D | 8.02 | 7.94 | 7.85 | -0.09 |
| LC P204E | 8.02 | 7.94 | 7.85 | -0.09 |
| LC V205D | 8.02 | 7.94 | 7.85 | -0.09 |
| LC V205E | 8.02 | 7.94 | 7.85 | -0.09 |
| LC T206D | 8.02 | 7.94 | 7.85 | -0.09 |
| LC T206E | 8.02 | 7.94 | 7.85 | -0.09 |
| LC K207D | 8.02 | 7.85 | 7.61 | -0.21 |
| LC K207E | 8.02 | 7.85 | 7.61 | -0.21 |
| LC S208D | 8.02 | 7.94 | 7.85 | -0.09 |
| LC S208E | 8.02 | 7.94 | 7.85 | -0.09 |
| LC N210D | 8.02 | 7.94 | 7.85 | -0.09 |
| LC N210E | 8.02 | 7.94 | 7.85 | -0.09 |
| LC R211D | 8.02 | 7.85 | 7.61 | -0.21 |
| LC R211E | 8.02 | 7.85 | 7.61 | -0.21 |
| LC G212D | 8.02 | 7.94 | 7.85 | -0.09 |
| LC G212E | 8.02 | 7.94 | 7.85 | -0.09 |
| LC C214D | 8.02 | 7.95 | 7.86 | -0.08 |
| LC C214E | 8.02 | 7.95 | 7.86 | -0.08 |

Figure 49A

| Variant | Basic to Neutral | | | |
| --- | --- | --- | --- | --- |
| | IgG1 / IgG1 | pI / IgG1 | pI / pI | delta pI |
| LC K126A | 8.02 | 7.94 | 7.85 | -0.09 |
| LC K126F | 8.02 | 7.94 | 7.85 | -0.09 |
| LC K126G | 8.02 | 7.94 | 7.85 | -0.09 |
| LC K126H | 8.02 | 7.94 | 7.85 | -0.09 |
| LC K126I | 8.02 | 7.94 | 7.85 | -0.09 |
| LC K126L | 8.02 | 7.94 | 7.85 | -0.09 |
| LC K126M | 8.02 | 7.94 | 7.85 | -0.09 |
| LC K126N | 8.02 | 7.94 | 7.85 | -0.09 |
| LC K126P | 8.02 | 7.94 | 7.85 | -0.09 |
| LC K126Q | 8.02 | 7.94 | 7.85 | -0.09 |
| LC K126S | 8.02 | 7.94 | 7.85 | -0.09 |
| LC K126T | 8.02 | 7.94 | 7.85 | -0.09 |
| LC K126V | 8.02 | 7.94 | 7.85 | -0.09 |
| LC K126W | 8.02 | 7.94 | 7.85 | -0.09 |
| LC K126Y | 8.02 | 7.94 | 7.85 | -0.09 |
| LC R142A | 8.02 | 7.94 | 7.85 | -0.09 |
| LC R142F | 8.02 | 7.94 | 7.85 | -0.09 |
| LC R142G | 8.02 | 7.94 | 7.85 | -0.09 |
| LC R142H | 8.02 | 7.94 | 7.85 | -0.09 |
| LC R142I | 8.02 | 7.94 | 7.85 | -0.09 |
| LC R142L | 8.02 | 7.94 | 7.85 | -0.09 |
| LC R142M | 8.02 | 7.94 | 7.85 | -0.09 |
| LC R142N | 8.02 | 7.94 | 7.85 | -0.09 |
| LC R142P | 8.02 | 7.94 | 7.85 | -0.09 |
| LC R142Q | 8.02 | 7.94 | 7.85 | -0.09 |
| LC R142S | 8.02 | 7.94 | 7.85 | -0.09 |
| LC R142T | 8.02 | 7.94 | 7.85 | -0.09 |
| LC R142V | 8.02 | 7.94 | 7.85 | -0.09 |
| LC R142W | 8.02 | 7.94 | 7.85 | -0.09 |
| LC R142Y | 8.02 | 7.94 | 7.84 | -0.09 |
| LC K145A | 8.02 | 7.94 | 7.85 | -0.09 |
| LC K145F | 8.02 | 7.94 | 7.85 | -0.09 |
| LC K145G | 8.02 | 7.94 | 7.85 | -0.09 |
| LC K145H | 8.02 | 7.94 | 7.85 | -0.09 |
| LC K145I | 8.02 | 7.94 | 7.85 | -0.09 |
| LC K145L | 8.02 | 7.94 | 7.85 | -0.09 |
| LC K145M | 8.02 | 7.94 | 7.85 | -0.09 |
| LC K145N | 8.02 | 7.94 | 7.85 | -0.09 |
| LC K145P | 8.02 | 7.94 | 7.85 | -0.09 |
| LC K145Q | 8.02 | 7.94 | 7.85 | -0.09 |
| LC K145S | 8.02 | 7.94 | 7.85 | -0.09 |
| LC K145T | 8.02 | 7.94 | 7.85 | -0.09 |
| LC K145V | 8.02 | 7.94 | 7.85 | -0.09 |
| LC K145W | 8.02 | 7.94 | 7.85 | -0.09 |
| LC K145Y | 8.02 | 7.94 | 7.85 | -0.09 |
| LC K149A | 8.02 | 7.94 | 7.85 | -0.09 |
| LC K149F | 8.02 | 7.94 | 7.85 | -0.09 |
| LC K149G | 8.02 | 7.94 | 7.85 | -0.09 |

Figure 49B

| Basic to Neutral | | | | |
|---|---|---|---|---|
| Variant | IgG1 / IgG1 | pI / IgG1 | pI / pI | delta pI |
| LC K149H | 8.02 | 7.94 | 7.85 | -0.09 |
| LC K149I | 8.02 | 7.94 | 7.85 | -0.09 |
| LC K149L | 8.02 | 7.94 | 7.85 | -0.09 |
| LC K149M | 8.02 | 7.94 | 7.85 | -0.09 |
| LC K149N | 8.02 | 7.94 | 7.85 | -0.09 |
| LC K149P | 8.02 | 7.94 | 7.85 | -0.09 |
| LC K149Q | 8.02 | 7.94 | 7.85 | -0.09 |
| LC K149S | 8.02 | 7.94 | 7.85 | -0.09 |
| LC K149T | 8.02 | 7.94 | 7.85 | -0.09 |
| LC K149V | 8.02 | 7.94 | 7.85 | -0.09 |
| LC K149W | 8.02 | 7.94 | 7.85 | -0.09 |
| LC K149Y | 8.02 | 7.94 | 7.85 | -0.09 |
| LC K169A | 8.02 | 7.94 | 7.85 | -0.09 |
| LC K169F | 8.02 | 7.94 | 7.85 | -0.09 |
| LC K169G | 8.02 | 7.94 | 7.85 | -0.09 |
| LC K169H | 8.02 | 7.94 | 7.85 | -0.09 |
| LC K169I | 8.02 | 7.94 | 7.85 | -0.09 |
| LC K169L | 8.02 | 7.94 | 7.85 | -0.09 |
| LC K169M | 8.02 | 7.94 | 7.85 | -0.09 |
| LC K169N | 8.02 | 7.94 | 7.85 | -0.09 |
| LC K169P | 8.02 | 7.94 | 7.85 | -0.09 |
| LC K169Q | 8.02 | 7.94 | 7.85 | -0.09 |
| LC K169S | 8.02 | 7.94 | 7.85 | -0.09 |
| LC K169T | 8.02 | 7.94 | 7.85 | -0.09 |
| LC K169V | 8.02 | 7.94 | 7.85 | -0.09 |
| LC K169W | 8.02 | 7.94 | 7.85 | -0.09 |
| LC K169Y | 8.02 | 7.94 | 7.85 | -0.09 |
| LC K183A | 8.02 | 7.94 | 7.85 | -0.09 |
| LC K183F | 8.02 | 7.94 | 7.85 | -0.09 |
| LC K183G | 8.02 | 7.94 | 7.85 | -0.09 |
| LC K183H | 8.02 | 7.94 | 7.85 | -0.09 |
| LC K183I | 8.02 | 7.94 | 7.85 | -0.09 |
| LC K183L | 8.02 | 7.94 | 7.85 | -0.09 |
| LC K183M | 8.02 | 7.94 | 7.85 | -0.09 |
| LC K183N | 8.02 | 7.94 | 7.85 | -0.09 |
| LC K183P | 8.02 | 7.94 | 7.85 | -0.09 |
| LC K183Q | 8.02 | 7.94 | 7.85 | -0.09 |
| LC K183S | 8.02 | 7.94 | 7.85 | -0.09 |
| LC K183T | 8.02 | 7.94 | 7.85 | -0.09 |
| LC K183V | 8.02 | 7.94 | 7.85 | -0.09 |
| LC K183W | 8.02 | 7.94 | 7.85 | -0.09 |
| LC K183Y | 8.02 | 7.94 | 7.85 | -0.09 |
| LC K188A | 8.02 | 7.94 | 7.85 | -0.09 |
| LC K188F | 8.02 | 7.94 | 7.85 | -0.09 |
| LC K188G | 8.02 | 7.94 | 7.85 | -0.09 |
| LC K188H | 8.02 | 7.94 | 7.85 | -0.09 |
| LC K188I | 8.02 | 7.94 | 7.85 | -0.09 |
| LC K188L | 8.02 | 7.94 | 7.85 | -0.09 |
| LC K188M | 8.02 | 7.94 | 7.85 | -0.09 |
| LC K188N | 8.02 | 7.94 | 7.85 | -0.09 |

Figure 49C

| Variant | Basic to Neutral | | | |
|---|---|---|---|---|
| | IgG1 / IgG1 | pI / IgG1 | pI / pI | delta pI |
| LC K188P | 8.02 | 7.94 | 7.85 | -0.09 |
| LC K188Q | 8.02 | 7.94 | 7.85 | -0.09 |
| LC K188S | 8.02 | 7.94 | 7.85 | -0.09 |
| LC K188T | 8.02 | 7.94 | 7.85 | -0.09 |
| LC K188V | 8.02 | 7.94 | 7.85 | -0.09 |
| LC K188W | 8.02 | 7.94 | 7.85 | -0.09 |
| LC K188Y | 8.02 | 7.94 | 7.85 | -0.09 |
| LC K190A | 8.02 | 7.94 | 7.85 | -0.09 |
| LC K190F | 8.02 | 7.94 | 7.85 | -0.09 |
| LC K190G | 8.02 | 7.94 | 7.85 | -0.09 |
| LC K190H | 8.02 | 7.94 | 7.85 | -0.09 |
| LC K190I | 8.02 | 7.94 | 7.85 | -0.09 |
| LC K190L | 8.02 | 7.94 | 7.85 | -0.09 |
| LC K190M | 8.02 | 7.94 | 7.85 | -0.09 |
| LC K190N | 8.02 | 7.94 | 7.85 | -0.09 |
| LC K190P | 8.02 | 7.94 | 7.85 | -0.09 |
| LC K190Q | 8.02 | 7.94 | 7.85 | -0.09 |
| LC K190S | 8.02 | 7.94 | 7.85 | -0.09 |
| LC K190T | 8.02 | 7.94 | 7.85 | -0.09 |
| LC K190V | 8.02 | 7.94 | 7.85 | -0.09 |
| LC K190W | 8.02 | 7.94 | 7.85 | -0.09 |
| LC K190Y | 8.02 | 7.94 | 7.85 | -0.09 |
| LC R202A | 8.02 | 8.02 | 8.02 | 0.00 |
| LC R202F | 8.02 | 8.02 | 8.02 | 0.00 |
| LC R202G | 8.02 | 8.02 | 8.02 | 0.00 |
| LC R202H | 8.02 | 8.02 | 8.02 | 0.00 |
| LC R202I | 8.02 | 8.02 | 8.02 | 0.00 |
| LC R202L | 8.02 | 8.02 | 8.02 | 0.00 |
| LC R202M | 8.02 | 8.02 | 8.02 | 0.00 |
| LC R202N | 8.02 | 8.02 | 8.02 | 0.00 |
| LC R202P | 8.02 | 8.02 | 8.02 | 0.00 |
| LC R202Q | 8.02 | 8.02 | 8.02 | 0.00 |
| LC R202S | 8.02 | 8.02 | 8.02 | 0.00 |
| LC R202T | 8.02 | 8.02 | 8.02 | 0.00 |
| LC R202V | 8.02 | 8.02 | 8.02 | 0.00 |
| LC R202W | 8.02 | 8.02 | 8.02 | 0.00 |
| LC R202Y | 8.02 | 8.02 | 8.02 | 0.00 |
| LC K207A | 8.02 | 7.94 | 7.85 | -0.09 |
| LC K207F | 8.02 | 7.94 | 7.85 | -0.09 |
| LC K207G | 8.02 | 7.94 | 7.85 | -0.09 |
| LC K207H | 8.02 | 7.94 | 7.85 | -0.09 |
| LC K207I | 8.02 | 7.94 | 7.85 | -0.09 |
| LC K207L | 8.02 | 7.94 | 7.85 | -0.09 |
| LC K207M | 8.02 | 7.94 | 7.85 | -0.09 |
| LC K207N | 8.02 | 7.94 | 7.85 | -0.09 |
| LC K207P | 8.02 | 7.94 | 7.85 | -0.09 |
| LC K207Q | 8.02 | 7.94 | 7.85 | -0.09 |
| LC K207S | 8.02 | 7.94 | 7.85 | -0.09 |
| LC K207T | 8.02 | 7.94 | 7.85 | -0.09 |
| LC K207V | 8.02 | 7.94 | 7.85 | -0.09 |

Figure 49D

| Variant | Basic to Neutral | | | |
| --- | --- | --- | --- | --- |
| | IgG1 / IgG1 | pI / IgG1 | pI / pI | delta pI |
| LC K207W | 8.02 | 7.94 | 7.85 | -0.09 |
| LC K207Y | 8.02 | 7.94 | 7.85 | -0.09 |
| LC R211A | 8.02 | 7.94 | 7.85 | -0.09 |
| LC R211F | 8.02 | 7.94 | 7.85 | -0.09 |
| LC R211G | 8.02 | 7.94 | 7.85 | -0.09 |
| LC R211H | 8.02 | 7.94 | 7.85 | -0.09 |
| LC R211I | 8.02 | 7.94 | 7.85 | -0.09 |
| LC R211L | 8.02 | 7.94 | 7.85 | -0.09 |
| LC R211M | 8.02 | 7.94 | 7.85 | -0.09 |
| LC R211N | 8.02 | 7.94 | 7.85 | -0.09 |
| LC R211P | 8.02 | 7.94 | 7.85 | -0.09 |
| LC R211Q | 8.02 | 7.94 | 7.85 | -0.09 |
| LC R211S | 8.02 | 7.94 | 7.85 | -0.09 |
| LC R211T | 8.02 | 7.94 | 7.85 | -0.09 |
| LC R211V | 8.02 | 7.94 | 7.85 | -0.09 |
| LC R211W | 8.02 | 7.94 | 7.85 | -0.09 |
| LC R211Y | 8.02 | 7.94 | 7.84 | -0.09 |

Figure 50A

| Variant | Neutral or Acidic to Basic | | | |
|---|---|---|---|---|
| | IgG1 / IgG1 | pI / IgG1 | pI / pI | delta pI |
| LC T109K | 8.02 | 8.10 | 8.16 | 0.07 |
| LC T109R | 8.02 | 8.10 | 8.16 | 0.07 |
| LC V110K | 8.02 | 8.10 | 8.16 | 0.07 |
| LC V110R | 8.02 | 8.10 | 8.16 | 0.07 |
| LC A112K | 8.02 | 8.10 | 8.16 | 0.07 |
| LC A112R | 8.02 | 8.10 | 8.16 | 0.07 |
| LC S114K | 8.02 | 8.10 | 8.16 | 0.07 |
| LC S114R | 8.02 | 8.10 | 8.16 | 0.07 |
| LC P119K | 8.02 | 8.10 | 8.16 | 0.07 |
| LC P119R | 8.02 | 8.10 | 8.16 | 0.07 |
| LC D122K | 8.02 | 8.16 | 8.27 | 0.13 |
| LC D122R | 8.02 | 8.16 | 8.28 | 0.13 |
| LC E123K | 8.02 | 8.16 | 8.27 | 0.13 |
| LC E123R | 8.02 | 8.16 | 8.28 | 0.13 |
| LC S127K | 8.02 | 8.10 | 8.16 | 0.07 |
| LC S127R | 8.02 | 8.10 | 8.16 | 0.07 |
| LC G128K | 8.02 | 8.10 | 8.16 | 0.07 |
| LC G128R | 8.02 | 8.10 | 8.16 | 0.07 |
| LC T129K | 8.02 | 8.10 | 8.16 | 0.07 |
| LC T129R | 8.02 | 8.10 | 8.16 | 0.07 |
| LC N138K | 8.02 | 8.10 | 8.16 | 0.07 |
| LC N138R | 8.02 | 8.10 | 8.16 | 0.07 |
| LC E143K | 8.02 | 8.16 | 8.27 | 0.13 |
| LC E143R | 8.02 | 8.16 | 8.28 | 0.13 |
| LC Q147K | 8.02 | 8.10 | 8.16 | 0.07 |
| LC Q147R | 8.02 | 8.10 | 8.16 | 0.07 |
| LC D151K | 8.02 | 8.16 | 8.27 | 0.13 |
| LC D151R | 8.02 | 8.16 | 8.28 | 0.13 |
| LC N152K | 8.02 | 8.10 | 8.16 | 0.07 |
| LC N152R | 8.02 | 8.10 | 8.16 | 0.07 |
| LC A153K | 8.02 | 8.10 | 8.16 | 0.07 |
| LC A153R | 8.02 | 8.10 | 8.16 | 0.07 |
| LC L154K | 8.02 | 8.10 | 8.16 | 0.07 |
| LC L154R | 8.02 | 8.10 | 8.16 | 0.07 |
| LC S156K | 8.02 | 8.10 | 8.16 | 0.07 |
| LC S156R | 8.02 | 8.10 | 8.16 | 0.07 |
| LC G157K | 8.02 | 8.10 | 8.16 | 0.07 |
| LC G157R | 8.02 | 8.10 | 8.16 | 0.07 |
| LC N158K | 8.02 | 8.10 | 8.16 | 0.07 |
| LC N158R | 8.02 | 8.10 | 8.16 | 0.07 |
| LC S159K | 8.02 | 8.10 | 8.16 | 0.07 |
| LC S159R | 8.02 | 8.10 | 8.16 | 0.07 |
| LC Q160K | 8.02 | 8.10 | 8.16 | 0.07 |
| LC Q160R | 8.02 | 8.10 | 8.16 | 0.07 |
| LC E161K | 8.02 | 8.16 | 8.27 | 0.13 |
| LC E161R | 8.02 | 8.16 | 8.28 | 0.13 |
| LC E165K | 8.02 | 8.16 | 8.27 | 0.13 |
| LC E165R | 8.02 | 8.16 | 8.28 | 0.13 |

Figure 50B

| Variant | Neutral or Acidic to Basic | | | |
|---|---|---|---|---|
| | IgG1 / IgG1 | pI / IgG1 | pI / pI | delta pI |
| LC D167K | 8.02 | 8.16 | 8.27 | 0.13 |
| LC D167R | 8.02 | 8.16 | 8.28 | 0.13 |
| LC S168K | 8.02 | 8.10 | 8.16 | 0.07 |
| LC S168R | 8.02 | 8.10 | 8.16 | 0.07 |
| LC D170K | 8.02 | 8.16 | 8.27 | 0.13 |
| LC D170R | 8.02 | 8.16 | 8.28 | 0.13 |
| LC T180K | 8.02 | 8.10 | 8.16 | 0.07 |
| LC T180R | 8.02 | 8.10 | 8.16 | 0.07 |
| LC L181K | 8.02 | 8.10 | 8.16 | 0.07 |
| LC L181R | 8.02 | 8.10 | 8.16 | 0.07 |
| LC S182K | 8.02 | 8.10 | 8.16 | 0.07 |
| LC S182R | 8.02 | 8.10 | 8.16 | 0.07 |
| LC A184K | 8.02 | 8.10 | 8.16 | 0.07 |
| LC A184R | 8.02 | 8.10 | 8.16 | 0.07 |
| LC D185K | 8.02 | 8.16 | 8.27 | 0.13 |
| LC D185R | 8.02 | 8.16 | 8.28 | 0.13 |
| LC E187K | 8.02 | 8.16 | 8.27 | 0.13 |
| LC E187R | 8.02 | 8.16 | 8.28 | 0.13 |
| LC H189K | 8.02 | 8.09 | 8.16 | 0.07 |
| LC H189R | 8.02 | 8.10 | 8.16 | 0.07 |
| LC V191K | 8.02 | 8.10 | 8.16 | 0.07 |
| LC V191R | 8.02 | 8.10 | 8.16 | 0.07 |
| LC T197K | 8.02 | 8.10 | 8.16 | 0.07 |
| LC T197R | 8.02 | 8.10 | 8.16 | 0.07 |
| LC Q199K | 8.02 | 8.10 | 8.16 | 0.07 |
| LC Q199R | 8.02 | 8.10 | 8.16 | 0.07 |
| LC G200K | 8.02 | 8.10 | 8.16 | 0.07 |
| LC G200R | 8.02 | 8.10 | 8.16 | 0.07 |
| LC S203K | 8.02 | 8.10 | 8.16 | 0.07 |
| LC S203R | 8.02 | 8.10 | 8.16 | 0.07 |
| LC P204K | 8.02 | 8.10 | 8.16 | 0.07 |
| LC P204R | 8.02 | 8.10 | 8.16 | 0.07 |
| LC V205K | 8.02 | 8.10 | 8.16 | 0.07 |
| LC V205R | 8.02 | 8.10 | 8.16 | 0.07 |
| LC T206K | 8.02 | 8.10 | 8.16 | 0.07 |
| LC T206R | 8.02 | 8.10 | 8.16 | 0.07 |
| LC S208K | 8.02 | 8.10 | 8.16 | 0.07 |
| LC S208R | 8.02 | 8.10 | 8.16 | 0.07 |
| LC N210K | 8.02 | 8.10 | 8.16 | 0.07 |
| LC N210R | 8.02 | 8.10 | 8.16 | 0.07 |
| LC G212K | 8.02 | 8.10 | 8.16 | 0.07 |
| LC G212R | 8.02 | 8.10 | 8.16 | 0.07 |
| LC E213K | 8.02 | 8.16 | 8.27 | 0.13 |
| LC E213R | 8.02 | 8.16 | 8.28 | 0.13 |
| LC C214K | 8.02 | 8.10 | 8.18 | 0.08 |
| LC C214R | 8.02 | 8.10 | 8.18 | 0.08 |

Figure 51A

| Variant | Acidic to Neutral | | | |
|---|---|---|---|---|
| | IgG1 / IgG1 | pI / IgG1 | pI / pI | delta pI |
| LC D122A | 8.02 | 8.10 | 8.16 | 0.07 |
| LC D122F | 8.02 | 8.10 | 8.16 | 0.07 |
| LC D122G | 8.02 | 8.10 | 8.16 | 0.07 |
| LC D122H | 8.02 | 8.10 | 8.16 | 0.07 |
| LC D122I | 8.02 | 8.10 | 8.16 | 0.07 |
| LC D122L | 8.02 | 8.10 | 8.16 | 0.07 |
| LC D122M | 8.02 | 8.10 | 8.16 | 0.07 |
| LC D122N | 8.02 | 8.10 | 8.16 | 0.07 |
| LC D122P | 8.02 | 8.10 | 8.16 | 0.07 |
| LC D122Q | 8.02 | 8.10 | 8.16 | 0.07 |
| LC D122S | 8.02 | 8.10 | 8.16 | 0.07 |
| LC D122T | 8.02 | 8.10 | 8.16 | 0.07 |
| LC D122V | 8.02 | 8.10 | 8.16 | 0.07 |
| LC D122W | 8.02 | 8.10 | 8.16 | 0.07 |
| LC D122Y | 8.02 | 8.10 | 8.16 | 0.07 |
| LC E123A | 8.02 | 8.10 | 8.16 | 0.07 |
| LC E123F | 8.02 | 8.10 | 8.16 | 0.07 |
| LC E123G | 8.02 | 8.10 | 8.16 | 0.07 |
| LC E123H | 8.02 | 8.10 | 8.16 | 0.07 |
| LC E123I | 8.02 | 8.10 | 8.16 | 0.07 |
| LC E123L | 8.02 | 8.10 | 8.16 | 0.07 |
| LC E123M | 8.02 | 8.10 | 8.16 | 0.07 |
| LC E123N | 8.02 | 8.10 | 8.16 | 0.07 |
| LC E123P | 8.02 | 8.10 | 8.16 | 0.07 |
| LC E123Q | 8.02 | 8.10 | 8.16 | 0.07 |
| LC E123S | 8.02 | 8.10 | 8.16 | 0.07 |
| LC E123T | 8.02 | 8.10 | 8.16 | 0.07 |
| LC E123V | 8.02 | 8.10 | 8.16 | 0.07 |
| LC E123W | 8.02 | 8.10 | 8.16 | 0.07 |
| LC E123Y | 8.02 | 8.10 | 8.16 | 0.07 |
| LC E143A | 8.02 | 8.10 | 8.16 | 0.07 |
| LC E143F | 8.02 | 8.10 | 8.16 | 0.07 |
| LC E143G | 8.02 | 8.10 | 8.16 | 0.07 |
| LC E143H | 8.02 | 8.10 | 8.16 | 0.07 |
| LC E143I | 8.02 | 8.10 | 8.16 | 0.07 |
| LC E143L | 8.02 | 8.10 | 8.16 | 0.07 |
| LC E143M | 8.02 | 8.10 | 8.16 | 0.07 |
| LC E143N | 8.02 | 8.10 | 8.16 | 0.07 |
| LC E143P | 8.02 | 8.10 | 8.16 | 0.07 |
| LC E143Q | 8.02 | 8.10 | 8.16 | 0.07 |
| LC E143S | 8.02 | 8.10 | 8.16 | 0.07 |
| LC E143T | 8.02 | 8.10 | 8.16 | 0.07 |
| LC E143V | 8.02 | 8.10 | 8.16 | 0.07 |
| LC E143W | 8.02 | 8.10 | 8.16 | 0.07 |
| LC E143Y | 8.02 | 8.10 | 8.16 | 0.07 |
| LC D151A | 8.02 | 8.10 | 8.16 | 0.07 |
| LC D151F | 8.02 | 8.10 | 8.16 | 0.07 |
| LC D151G | 8.02 | 8.10 | 8.16 | 0.07 |

Figure 51B

| Variant | Acidic to Neutral | | | |
|---|---|---|---|---|
| | IgG1 / IgG1 | pI / IgG1 | pI / pI | delta pI |
| LC D151H | 8.02 | 8.10 | 8.16 | 0.07 |
| LC D151I | 8.02 | 8.10 | 8.16 | 0.07 |
| LC D151L | 8.02 | 8.10 | 8.16 | 0.07 |
| LC D151M | 8.02 | 8.10 | 8.16 | 0.07 |
| LC D151N | 8.02 | 8.10 | 8.16 | 0.07 |
| LC D151P | 8.02 | 8.10 | 8.16 | 0.07 |
| LC D151Q | 8.02 | 8.10 | 8.16 | 0.07 |
| LC D151S | 8.02 | 8.10 | 8.16 | 0.07 |
| LC D151T | 8.02 | 8.10 | 8.16 | 0.07 |
| LC D151V | 8.02 | 8.10 | 8.16 | 0.07 |
| LC D151W | 8.02 | 8.10 | 8.16 | 0.07 |
| LC D151Y | 8.02 | 8.10 | 8.16 | 0.07 |
| LC E161A | 8.02 | 8.10 | 8.16 | 0.07 |
| LC E161F | 8.02 | 8.10 | 8.16 | 0.07 |
| LC E161G | 8.02 | 8.10 | 8.16 | 0.07 |
| LC E161H | 8.02 | 8.10 | 8.16 | 0.07 |
| LC E161I | 8.02 | 8.10 | 8.16 | 0.07 |
| LC E161L | 8.02 | 8.10 | 8.16 | 0.07 |
| LC E161M | 8.02 | 8.10 | 8.16 | 0.07 |
| LC E161N | 8.02 | 8.10 | 8.16 | 0.07 |
| LC E161P | 8.02 | 8.10 | 8.16 | 0.07 |
| LC E161Q | 8.02 | 8.10 | 8.16 | 0.07 |
| LC E161S | 8.02 | 8.10 | 8.16 | 0.07 |
| LC E161T | 8.02 | 8.10 | 8.16 | 0.07 |
| LC E161V | 8.02 | 8.10 | 8.16 | 0.07 |
| LC E161W | 8.02 | 8.10 | 8.16 | 0.07 |
| LC E161Y | 8.02 | 8.10 | 8.16 | 0.07 |
| LC E165A | 8.02 | 8.10 | 8.16 | 0.07 |
| LC E165F | 8.02 | 8.10 | 8.16 | 0.07 |
| LC E165G | 8.02 | 8.10 | 8.16 | 0.07 |
| LC E165H | 8.02 | 8.10 | 8.16 | 0.07 |
| LC E165I | 8.02 | 8.10 | 8.16 | 0.07 |
| LC E165L | 8.02 | 8.10 | 8.16 | 0.07 |
| LC E165M | 8.02 | 8.10 | 8.16 | 0.07 |
| LC E165N | 8.02 | 8.10 | 8.16 | 0.07 |
| LC E165P | 8.02 | 8.10 | 8.16 | 0.07 |
| LC E165Q | 8.02 | 8.10 | 8.16 | 0.07 |
| LC E165S | 8.02 | 8.10 | 8.16 | 0.07 |
| LC E165T | 8.02 | 8.10 | 8.16 | 0.07 |
| LC E165V | 8.02 | 8.10 | 8.16 | 0.07 |
| LC E165W | 8.02 | 8.10 | 8.16 | 0.07 |
| LC E165Y | 8.02 | 8.10 | 8.16 | 0.07 |
| LC D167A | 8.02 | 8.10 | 8.16 | 0.07 |
| LC D167F | 8.02 | 8.10 | 8.16 | 0.07 |
| LC D167G | 8.02 | 8.10 | 8.16 | 0.07 |
| LC D167H | 8.02 | 8.10 | 8.16 | 0.07 |
| LC D167I | 8.02 | 8.10 | 8.16 | 0.07 |
| LC D167L | 8.02 | 8.10 | 8.16 | 0.07 |
| LC D167M | 8.02 | 8.10 | 8.16 | 0.07 |
| LC D167N | 8.02 | 8.10 | 8.16 | 0.07 |

Figure 51C

| Variant | Acidic to Neutral | | | |
| --- | --- | --- | --- | --- |
| | IgG1 / IgG1 | pI / IgG1 | pI / pI | delta pI |
| LC D167P | 8.02 | 8.10 | 8.16 | 0.07 |
| LC D167Q | 8.02 | 8.10 | 8.16 | 0.07 |
| LC D167S | 8.02 | 8.10 | 8.16 | 0.07 |
| LC D167T | 8.02 | 8.10 | 8.16 | 0.07 |
| LC D167V | 8.02 | 8.10 | 8.16 | 0.07 |
| LC D167W | 8.02 | 8.10 | 8.16 | 0.07 |
| LC D167Y | 8.02 | 8.10 | 8.16 | 0.07 |
| LC D170A | 8.02 | 8.10 | 8.16 | 0.07 |
| LC D170F | 8.02 | 8.10 | 8.16 | 0.07 |
| LC D170G | 8.02 | 8.10 | 8.16 | 0.07 |
| LC D170H | 8.02 | 8.10 | 8.16 | 0.07 |
| LC D170I | 8.02 | 8.10 | 8.16 | 0.07 |
| LC D170L | 8.02 | 8.10 | 8.16 | 0.07 |
| LC D170M | 8.02 | 8.10 | 8.16 | 0.07 |
| LC D170N | 8.02 | 8.10 | 8.16 | 0.07 |
| LC D170P | 8.02 | 8.10 | 8.16 | 0.07 |
| LC D170Q | 8.02 | 8.10 | 8.16 | 0.07 |
| LC D170S | 8.02 | 8.10 | 8.16 | 0.07 |
| LC D170T | 8.02 | 8.10 | 8.16 | 0.07 |
| LC D170V | 8.02 | 8.10 | 8.16 | 0.07 |
| LC D170W | 8.02 | 8.10 | 8.16 | 0.07 |
| LC D170Y | 8.02 | 8.10 | 8.16 | 0.07 |
| LC D185A | 8.02 | 8.10 | 8.16 | 0.07 |
| LC D185F | 8.02 | 8.10 | 8.16 | 0.07 |
| LC D185G | 8.02 | 8.10 | 8.16 | 0.07 |
| LC D185H | 8.02 | 8.10 | 8.16 | 0.07 |
| LC D185I | 8.02 | 8.10 | 8.16 | 0.07 |
| LC D185L | 8.02 | 8.10 | 8.16 | 0.07 |
| LC D185M | 8.02 | 8.10 | 8.16 | 0.07 |
| LC D185N | 8.02 | 8.10 | 8.16 | 0.07 |
| LC D185P | 8.02 | 8.10 | 8.16 | 0.07 |
| LC D185Q | 8.02 | 8.10 | 8.16 | 0.07 |
| LC D185S | 8.02 | 8.10 | 8.16 | 0.07 |
| LC D185T | 8.02 | 8.10 | 8.16 | 0.07 |
| LC D185V | 8.02 | 8.10 | 8.16 | 0.07 |
| LC D185W | 8.02 | 8.10 | 8.16 | 0.07 |
| LC D185Y | 8.02 | 8.10 | 8.16 | 0.07 |
| LC E187A | 8.02 | 8.10 | 8.16 | 0.07 |
| LC E187F | 8.02 | 8.10 | 8.16 | 0.07 |
| LC E187G | 8.02 | 8.10 | 8.16 | 0.07 |
| LC E187H | 8.02 | 8.10 | 8.16 | 0.07 |
| LC E187I | 8.02 | 8.10 | 8.16 | 0.07 |
| LC E187L | 8.02 | 8.10 | 8.16 | 0.07 |
| LC E187M | 8.02 | 8.10 | 8.16 | 0.07 |
| LC E187N | 8.02 | 8.10 | 8.16 | 0.07 |
| LC E187P | 8.02 | 8.10 | 8.16 | 0.07 |
| LC E187Q | 8.02 | 8.10 | 8.16 | 0.07 |
| LC E187S | 8.02 | 8.10 | 8.16 | 0.07 |
| LC E187T | 8.02 | 8.10 | 8.16 | 0.07 |
| LC E187V | 8.02 | 8.10 | 8.16 | 0.07 |

Figure 51D

| Variant | Acidic to Neutral | | | |
|---|---|---|---|---|
| | IgG1 / IgG1 | pI / IgG1 | pI / pI | delta pI |
| LC E187W | 8.02 | 8.10 | 8.16 | 0.07 |
| LC E187Y | 8.02 | 8.10 | 8.16 | 0.07 |
| LC E213A | 8.02 | 8.10 | 8.16 | 0.07 |
| LC E213F | 8.02 | 8.10 | 8.16 | 0.07 |
| LC E213G | 8.02 | 8.10 | 8.16 | 0.07 |
| LC E213H | 8.02 | 8.10 | 8.16 | 0.07 |
| LC E213I | 8.02 | 8.10 | 8.16 | 0.07 |
| LC E213L | 8.02 | 8.10 | 8.16 | 0.07 |
| LC E213M | 8.02 | 8.10 | 8.16 | 0.07 |
| LC E213N | 8.02 | 8.10 | 8.16 | 0.07 |
| LC E213P | 8.02 | 8.10 | 8.16 | 0.07 |
| LC E213Q | 8.02 | 8.10 | 8.16 | 0.07 |
| LC E213S | 8.02 | 8.10 | 8.16 | 0.07 |
| LC E213T | 8.02 | 8.10 | 8.16 | 0.07 |
| LC E213V | 8.02 | 8.10 | 8.16 | 0.07 |
| LC E213W | 8.02 | 8.10 | 8.16 | 0.07 |
| LC E213Y | 8.02 | 8.10 | 8.16 | 0.07 |

Figure 52A

|          | 118 | 119 | 120 | 121 | 122 | 123 | 124 | 125 | 126 | 127 | 128 | 129 | 130 | 131 | 132 | 133 | 134 | 135 | 136 | 137 |
|----------|-----|-----|-----|-----|-----|-----|-----|-----|-----|-----|-----|-----|-----|-----|-----|-----|-----|-----|-----|-----|
| IgG1     | A | S | T | K | G | P | S | V | F | P | L | A | P | S | S | K | S | T | S | G |
| IgG2     | A | S | T | K | G | P | S | V | F | P | L | A | P | C | S | R | S | T | S | E |
| IgG3     | A | S | T | K | G | P | S | V | F | P | L | A | P | C | S | R | S | T | S | G |
| IgG4     | A | S | T | K | G | P | S | V | F | P | L | A | P | C | S | R | S | T | S | E |
| ISO(-)   | A | S | T | K | G | P | S | V | F | P | L | A | P | S | S | K | S | T | S | G |
| ISO(+RR) | A | S | T | K | G | P | S | V | F | P | L | A | P | S | S | K | S | T | S | G |
| ISO(+)   | A | S | T | K | G | P | S | V | F | P | L | A | P | S | S | K | S | T | S | G |

|          | 138 | 139 | 140 | 141 | 142 | 143 | 144 | 145 | 146 | 147 | 148 | 149 | 150 | 151 | 152 | 153 | 154 | 155 | 156 | 157 |
|----------|-----|-----|-----|-----|-----|-----|-----|-----|-----|-----|-----|-----|-----|-----|-----|-----|-----|-----|-----|-----|
| IgG1     | G | T | A | A | L | G | C | L | V | K | D | Y | F | P | E | P | V | T | V | S |
| IgG2     | S | T | A | A | L | G | C | L | V | K | D | Y | F | P | E | P | V | T | V | S |
| IgG3     | G | T | A | A | L | G | C | L | V | K | D | Y | F | P | E | P | V | T | V | S |
| IgG4     | S | T | A | A | L | G | C | L | V | K | D | Y | F | P | E | P | V | T | V | S |
| ISO(-)   | G | T | A | A | L | G | C | L | V | K | D | Y | F | P | E | P | V | T | V | S |
| ISO(+RR) | G | T | A | A | L | G | C | L | V | K | D | Y | F | P | E | P | V | T | V | S |
| ISO(+)   | G | T | A | A | L | G | C | L | V | K | D | Y | F | P | E | P | V | T | V | S |

|          | 158 | 159 | 160 | 161 | 162 | 163 | 164 | 165 | 166 | 167 | 168 | 169 | 170 | 171 | 172 | 173 | 174 | 175 | 176 | 177 |
|----------|-----|-----|-----|-----|-----|-----|-----|-----|-----|-----|-----|-----|-----|-----|-----|-----|-----|-----|-----|-----|
| IgG1     | W | N | S | G | A | L | T | S | G | V | H | T | F | P | A | V | L | Q | S | S |
| IgG2     | W | N | S | G | A | L | T | S | G | V | H | T | F | P | A | V | L | Q | S | S |
| IgG3     | W | N | S | G | A | L | T | S | G | V | H | T | F | P | A | V | L | Q | S | S |
| IgG4     | W | N | S | G | A | L | T | S | G | V | H | T | F | P | A | V | L | Q | S | S |
| ISO(-)   | W | N | S | G | A | L | T | S | G | V | H | T | F | P | A | V | L | Q | S | S |
| ISO(+RR) | W | N | S | G | A | L | T | S | G | V | H | T | F | P | A | V | L | Q | S | S |
| ISO(+)   | W | N | S | G | A | L | T | S | G | V | H | T | F | P | A | V | L | Q | S | S |

|          | 178 | 179 | 180 | 181 | 182 | 183 | 184 | 185 | 186 | 187 | 188 | 189 | 190 | 191 | 192 | 193 | 194 | 195 | 196 | 197 |
|----------|-----|-----|-----|-----|-----|-----|-----|-----|-----|-----|-----|-----|-----|-----|-----|-----|-----|-----|-----|-----|
| IgG1     | G | L | Y | S | L | S | S | V | V | T | V | P | S | S | S | L | G | T | Q | T |
| IgG2     | G | L | Y | S | L | S | S | V | V | T | V | P | S | S | N | F | G | T | Q | T |
| IgG3     | G | L | Y | S | L | S | S | V | V | T | V | P | S | S | S | L | G | T | Q | T |
| IgG4     | G | L | Y | S | L | S | S | V | V | T | V | P | S | S | S | L | G | T | K | T |
| ISO(-)   | G | L | Y | S | L | S | S | V | V | T | V | P | S | S | S | L | G | T | Q | T |
| ISO(+RR) | G | L | Y | S | L | S | S | V | V | T | V | P | S | S | S | L | G | T | K | T |
| ISO(+)   | G | L | Y | S | L | S | S | V | V | T | V | P | S | S | S | L | G | T | K | T |

|          | 198 | 199 | 200 | 201 | 202 | 203 | 204 | 205 | 206 | 207 | 208 | 209 | 210 | 211 | 212 | 213 | 214 | 215 | 216 | 217 |
|----------|-----|-----|-----|-----|-----|-----|-----|-----|-----|-----|-----|-----|-----|-----|-----|-----|-----|-----|-----|-----|
| IgG1     | Y | I | C | N | V | N | H | K | P | S | N | T | K | V | D | K | K | V | E | P |
| IgG2     | Y | T | C | N | V | D | H | K | P | S | N | T | K | V | D | K | T | V | E | R |
| IgG3     | Y | T | C | N | V | N | H | K | P | S | N | T | K | V | D | K | R | V | E | L |
| IgG4     | Y | T | C | N | V | D | H | K | P | S | N | T | K | V | D | K | R | V | E | S |
| ISO(-)   | Y | T | C | N | V | D | H | K | P | S | N | T | K | V | D | K | K | V | E | P |
| ISO(+RR) | Y | T | C | N | V | N | H | K | P | S | N | T | K | V | D | K | K | V | E | R |
| ISO(+)   | Y | T | C | N | V | N | H | K | P | S | N | T | K | V | D | K | K | V | E | P |

Figure 52B

|         | 218 | 219 | 220 | ... | ... | 221 | 222 | 223 | 224 | 225 | ... | 226 | 227 | 228 | 229 | 230 | 231 | 232 | 233 | 234 |
|---------|-----|-----|-----|-----|-----|-----|-----|-----|-----|-----|-----|-----|-----|-----|-----|-----|-----|-----|-----|-----|
| IgG1    | K | S | C |   |   | D | K | T | H | T |   | C | P | P | C | P | A | P | E | L |
| IgG2    | K | C | C |   |   |   | V |   | E |   |   | C | P | P | C | P | A | P | P | V |
| IgG3    | K | T | P | L | G | D | T | T | H | T | ... | C | P | R | C | P | A | P | E | L |
| IgG4    | K | Y | G |   |   |   |   |   | P | P |   | C | P | S | C | P | A | P | E | F |
| ISO(-)  | K | S | C |   |   | D | K | T | H | T |   | C | P | P | C | P | A | P | E | L |
| ISO(+RR)| K | S | C |   |   | D | K | T | H | T |   | C | P | R | C | P | A | P | E | L |
| ISO(+)  | K | S | C |   |   | D | K | T | H | T |   | C | P | P | C | P | A | P | E | L |

|         | 235 | 236 | 237 | 238 | 239 | 240 | 241 | 242 | 243 | 244 | 245 | 246 | 247 | 248 | 249 | 250 | 251 | 252 | 253 | 254 |
|---------|-----|-----|-----|-----|-----|-----|-----|-----|-----|-----|-----|-----|-----|-----|-----|-----|-----|-----|-----|-----|
| IgG1    | L | G | G | P | S | V | F | L | F | P | P | K | P | K | D | T | L | M | I | S |
| IgG2    | A |   | G | P | S | V | F | L | F | P | P | K | P | K | D | T | L | M | I | S |
| IgG3    | L | G | G | P | S | V | F | L | F | P | P | K | P | K | D | T | L | M | I | S |
| IgG4    | L | G | G | P | S | V | F | L | F | P | P | K | P | K | D | T | L | M | I | S |
| ISO(-)  | L | G | G | P | S | V | F | L | F | P | P | K | P | K | D | T | L | M | I | S |
| ISO(+RR)| L | G | G | P | S | V | F | L | F | P | P | K | P | K | D | T | L | M | I | S |
| ISO(+)  | L | G | G | P | S | V | F | L | F | P | P | K | P | K | D | T | L | M | I | S |

|         | 255 | 256 | 257 | 258 | 259 | 260 | 261 | 262 | 263 | 264 | 265 | 266 | 267 | 268 | 269 | 270 | 271 | 272 | 273 | 274 |
|---------|-----|-----|-----|-----|-----|-----|-----|-----|-----|-----|-----|-----|-----|-----|-----|-----|-----|-----|-----|-----|
| IgG1    | R | T | P | E | V | T | C | V | V | V | D | V | S | H | E | D | P | E | V | K |
| IgG2    | R | T | P | E | V | T | C | V | V | V | D | V | S | H | E | D | P | E | V | Q |
| IgG3    | R | T | P | E | V | T | C | V | V | V | D | V | S | H | E | D | P | E | V | Q |
| IgG4    | R | T | P | E | V | T | C | V | V | V | D | V | S | Q | E | D | P | E | V | Q |
| ISO(-)  | R | T | P | E | V | T | C | V | V | V | D | V | S | H | E | D | P | E | V | Q |
| ISO(+RR)| R | T | P | E | V | T | C | V | V | V | D | V | S | H | E | D | P | E | V | K |
| ISO(+)  | R | T | P | E | V | T | C | V | V | V | D | V | S | H | E | D | P | E | V | K |

|         | 275 | 276 | 277 | 278 | 279 | 280 | 281 | 282 | 283 | 284 | 285 | 286 | 287 | 288 | 289 | 290 | 291 | 292 | 293 | 294 |
|---------|-----|-----|-----|-----|-----|-----|-----|-----|-----|-----|-----|-----|-----|-----|-----|-----|-----|-----|-----|-----|
| IgG1    | F | N | W | Y | V | D | G | V | E | V | H | N | A | K | T | K | P | R | E | E |
| IgG2    | F | N | W | Y | V | D | G | V | E | V | H | N | A | K | T | K | P | R | E | E |
| IgG3    | F | K | W | Y | V | D | G | V | E | V | H | N | A | K | T | K | P | R | E | E |
| IgG4    | F | N | W | Y | V | D | G | V | E | V | H | N | A | K | T | K | P | R | E | E |
| ISO(-)  | F | N | W | Y | V | D | G | V | E | V | H | N | A | K | T | K | P | R | E | E |
| ISO(+RR)| F | K | W | Y | V | D | G | V | E | V | H | N | A | K | T | K | P | R | E | E |
| ISO(+)  | F | K | W | Y | V | D | G | V | E | V | H | N | A | K | T | K | P | R | E | E |

|         | 295 | 296 | 297 | 298 | 299 | 300 | 301 | 302 | 303 | 304 | 305 | 306 | 307 | 308 | 309 | 310 | 311 | 312 | 313 | 314 |
|---------|-----|-----|-----|-----|-----|-----|-----|-----|-----|-----|-----|-----|-----|-----|-----|-----|-----|-----|-----|-----|
| IgG1    | Q | Y | N | S | T | Y | R | V | V | S | V | L | T | V | L | H | Q | D | W | L |
| IgG2    | Q | F | N | S | T | F | R | V | V | S | V | L | T | V | V | H | Q | D | W | L |
| IgG3    | Q | Y | N | S | T | F | R | V | V | S | V | L | T | V | L | H | Q | D | W | L |
| IgG4    | Q | F | N | S | T | Y | R | V | V | S | V | L | T | V | L | H | Q | D | W | L |
| ISO(-)  | Q | Y | N | S | T | Y | R | V | V | S | V | L | T | V | L | H | Q | D | W | L |
| ISO(+RR)| Q | Y | N | S | T | Y | R | V | V | S | V | L | T | V | L | H | Q | D | W | L |
| ISO(+)  | Q | Y | N | S | T | Y | R | V | V | S | V | L | T | V | L | H | Q | D | W | L |

Figure 52C

|         | 315 | 316 | 317 | 318 | 319 | 320 | 321 | 322 | 323 | 324 | 325 | 326 | 327 | 328 | 329 | 330 | 331 | 332 | 333 | 334 |
|---------|-----|-----|-----|-----|-----|-----|-----|-----|-----|-----|-----|-----|-----|-----|-----|-----|-----|-----|-----|-----|
| IgG1    | N | G | K | E | Y | K | C | K | V | S | N | K | A | L | P | A | P | I | E | K |
| IgG2    | N | G | K | E | Y | K | C | K | V | S | N | K | G | L | P | A | P | I | E | K |
| IgG3    | N | G | K | E | Y | K | C | K | V | S | N | K | A | L | P | A | P | I | E | K |
| IgG4    | N | G | K | E | Y | K | C | K | V | S | N | K | G | L | P | S | S | I | E | K |
| ISO(-)  | N | G | K | E | Y | K | C | K | V | S | N | K | A | L | P | A | P | I | E | K |
| ISO(+RR)| N | G | K | E | Y | K | C | K | V | S | N | K | A | L | P | A | P | I | E | K |
| ISO(+)  | N | G | K | E | Y | K | C | K | V | S | N | K | A | L | P | A | P | I | E | K |

|         | 335 | 336 | 337 | 338 | 339 | 340 | 341 | 342 | 343 | 344 | 345 | 346 | 347 | 348 | 349 | 350 | 351 | 352 | 353 | 354 |
|---------|-----|-----|-----|-----|-----|-----|-----|-----|-----|-----|-----|-----|-----|-----|-----|-----|-----|-----|-----|-----|
| IgG1    | T | I | S | K | A | K | G | Q | P | R | E | P | Q | V | Y | T | L | P | P | S |
| IgG2    | T | I | S | K | T | K | G | Q | P | R | E | P | Q | V | Y | T | L | P | P | S |
| IgG3    | T | I | S | K | T | K | G | Q | P | R | E | P | Q | V | Y | T | L | P | P | S |
| IgG4    | T | I | S | K | A | K | G | Q | P | R | E | P | Q | V | Y | T | L | P | P | S |
| ISO(-)  | T | I | S | K | A | K | G | Q | P | R | E | P | Q | V | Y | T | L | P | P | S |
| ISO(+RR)| T | I | S | K | A | K | G | Q | P | R | E | P | Q | V | Y | T | L | P | P | S |
| ISO(+)  | T | I | S | K | A | K | G | Q | P | R | E | P | Q | V | Y | T | L | P | P | S |

|         | 355 | 356 | 357 | 358 | 359 | 360 | 361 | 362 | 363 | 364 | 365 | 366 | 367 | 368 | 369 | 370 | 371 | 372 | 373 | 374 |
|---------|-----|-----|-----|-----|-----|-----|-----|-----|-----|-----|-----|-----|-----|-----|-----|-----|-----|-----|-----|-----|
| IgG1    | R | E | E | M | T | K | N | Q | V | S | L | T | C | L | V | K | G | F | Y | P |
| IgG2    | R | E | E | M | T | K | N | Q | V | S | L | T | C | L | V | K | G | F | Y | P |
| IgG3    | R | E | E | M | T | K | N | Q | V | S | L | T | C | L | V | K | G | F | Y | P |
| IgG4    | Q | E | E | M | T | K | N | Q | V | S | L | T | C | L | V | K | G | F | Y | P |
| ISO(-)  | Q | E | E | M | T | K | N | Q | V | S | L | T | C | L | V | K | G | F | Y | P |
| ISO(+RR)| R | E | E | M | T | K | N | Q | V | S | L | T | C | L | V | K | G | F | Y | P |
| ISO(+)  | R | E | E | M | T | K | N | Q | V | S | L | T | C | L | V | K | G | F | Y | P |

|         | 375 | 376 | 377 | 378 | 379 | 380 | 381 | 382 | 383 | 384 | 385 | 386 | 387 | 388 | 389 | 390 | 391 | 392 | 393 | 394 |
|---------|-----|-----|-----|-----|-----|-----|-----|-----|-----|-----|-----|-----|-----|-----|-----|-----|-----|-----|-----|-----|
| IgG1    | S | D | I | A | V | E | W | E | S | N | G | Q | P | E | N | N | Y | K | T | T |
| IgG2    | S | D | I | A | V | E | W | E | S | N | G | Q | P | E | N | N | Y | K | T | T |
| IgG3    | S | D | I | A | V | E | W | E | S | S | G | Q | P | E | N | N | Y | N | T | T |
| IgG4    | S | D | I | A | V | E | W | E | S | N | G | Q | P | E | N | N | Y | K | T | T |
| ISO(-)  | S | D | I | A | V | E | W | E | S | S | G | Q | P | E | N | N | Y | N | T | T |
| ISO(+RR)| S | D | I | A | V | E | W | E | S | N | G | Q | P | E | N | N | Y | K | T | T |
| ISO(+)  | S | D | I | A | V | E | W | E | S | N | G | Q | P | E | N | N | Y | K | T | T |

|         | 395 | 396 | 397 | 398 | 399 | 400 | 401 | 402 | 403 | 404 | 405 | 406 | 407 | 408 | 409 | 410 | 411 | 412 | 413 | 414 |
|---------|-----|-----|-----|-----|-----|-----|-----|-----|-----|-----|-----|-----|-----|-----|-----|-----|-----|-----|-----|-----|
| IgG1    | P | P | V | L | D | S | D | G | S | F | F | L | Y | S | K | L | T | V | D | K |
| IgG2    | P | P | M | L | D | S | D | G | S | F | F | L | Y | S | K | L | T | V | D | K |
| IgG3    | P | P | M | L | D | S | D | G | S | F | F | L | Y | S | K | L | T | V | D | K |
| IgG4    | P | P | V | L | D | S | D | G | S | F | F | L | Y | S | R | L | T | V | D | K |
| ISO(-)  | P | P | M | L | D | S | D | G | S | F | F | L | Y | S | K | L | T | V | D | K |
| ISO(+RR)| P | P | V | L | D | S | D | G | S | F | F | L | Y | S | K | L | T | V | D | K |
| ISO(+)  | P | P | V | L | D | S | D | G | S | F | F | L | Y | S | K | L | T | V | D | K |

Figure 52D

|        | 415 | 416 | 417 | 418 | 419 | 420 | 421 | 422 | 423 | 424 | 425 | 426 | 427 | 428 | 429 | 430 | 431 | 432 | 433 | 434 |
|--------|-----|-----|-----|-----|-----|-----|-----|-----|-----|-----|-----|-----|-----|-----|-----|-----|-----|-----|-----|-----|
| IgG1   | S | R | W | Q | Q | G | N | V | F | S | C | S | V | M | H | E | A | L | H | N |
| IgG2   | S | R | W | Q | Q | G | N | V | F | S | C | S | V | M | H | E | A | L | H | N |
| IgG3   | S | R | W | Q | Q | G | N | I | F | S | C | S | V | M | H | E | A | L | H | N |
| IgG4   | S | R | W | Q | E | G | N | V | F | S | C | S | V | M | H | E | A | L | H | N |
| ISO(-) | S | R | W | Q | E | G | N | V | F | S | C | S | V | M | H | E | A | L | H | N |
| ISO(+RR) | S | R | W | Q | Q | G | N | V | F | S | C | S | V | M | H | E | A | L | H | N |
| ISO(+) | S | R | W | Q | Q | G | N | V | F | S | C | S | V | M | H | E | A | L | H | N |

|        | 435 | 436 | 437 | 438 | 439 | 440 | 441 | 442 | 443 | 444 | 445 | 446 | 447 |
|--------|-----|-----|-----|-----|-----|-----|-----|-----|-----|-----|-----|-----|-----|
| IgG1   | H | Y | T | Q | K | S | L | S | L | S | P | G | K |
| IgG2   | H | Y | T | Q | K | S | L | S | L | S | P | G | K |
| IgG3   | R | F | T | Q | K | S | L | S | L | S | P | G | K |
| IgG4   | H | Y | T | Q | K | S | L | S | L | S | L | G | K |
| ISO(-) | H | Y | T | Q | K | S | L | S | L | S | P | G |   |
| ISO(+RR) | H | Y | T | Q | K | S | L | S | L | S | P | G | K |
| ISO(+) | H | Y | T | Q | K | S | L | S | L | S | P | G | K |

IgG1 = SEQ ID NO: 2  
IgG2 = SEQ ID NO: 3  
IgG3 = SEQ ID NO: 4  
IgG4 = SEQ ID NO: 5  
ISO(-) = SEQ ID NO: 74  
ISO(+RR) = SEQ ID NO: 76  
ISO(+) = SEQ ID NO: 75

Figure 53A

ISO(-) (SEQ ID NO: 74)

ASTKGPSVFPLAPSSKSTSGGTAALGCLVKDYFPEPVTVSWNSGALTSGVHTFPAVLQS
SGLYSLSSVVTVPSSSLGTQTYTCNVDHKPSNTKVDKKVEPKSCDKTHTCPPCPAPELL
GGPSVFLFPPKPKDTLMISRTPEVTCVVVDVSHEDPEVQFNWYVDGVEVHNAKTKPREE
QYNSTYRVVSVLTVLHQDWLNGKEYKCKVSNKALPAPIEKTISKAKGQPREPQVYTLPPS
QEEMTKNQVSLTCLVKGFYPSDIAVEWESSGQPENNYNTTPPMLDSDGSFFLYSKLTVD
KSRWQEGNVFSCSVMHEALHNHYTQKSLSLSPG

ISO(+)(SEQ ID NO: 75)

ASTKGPSVFPLAPSSKSTSGGTAALGCLVKDYFPEPVTVSWNSGALTSGVHTFPAVLQS
SGLYSLSSVVTVPSSSLGTKTYTCNVNHKPSNTKVDKKVEPKSCDKTHTCPPCPAPELL
GGPSVFLFPPKPKDTLMISRTPEVTCVVVDVSHEDPEVKFKWYVDGVEVHNAKTKPREE
QYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVD
KSRWQQGNVFSCSVMHEALHNHYTQKSLSLSPGK

ISO(+RR) (SEQ ID NO: 76)

ASTKGPSVFPLAPSSKSTSGGTAALGCLVKDYFPEPVTVSWNSGALTSGVHTFPAVLQS
SGLYSLSSVVTVPSSSLGTKTYTCNVNHKPSNTKVDKKVERKSCDKTHTCPRCPAPELL
GGPSVFLFPPKPKDTLMISRTPEVTCVVVDVSHEDPEVKFKWYVDGVEVHNAKTKPREE
QYNSTYRVVSVLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSFFLYSKLTVD
KSRWQQGNVFSCSVMHEALHNHYTQKSLSLSPGK

Anti-VEGF ISO(-) Heavy Chain (SEQ ID NO: 77)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTQTYTCNVDHKPSNTKVDKKVEPKSCDKTHTCP
PCPAPELLGGPSVFLFPPKPKDTLMISRTPEVTCVVVDVSHEDPEVQFNWYVDGVEVHN
AKTKPREEQYNSTYRVVSVLTVLHQDWLNGKEYKCKVSNKALPAPIEKTISKAKGQPRE
PQVYTLPPSQEEMTKNQVSLTCLVKGFYPSDIAVEWESSGQPENNYNTTPPMLDSDGS
FFLYSKLTVDKSRWQEGNVFSCSVMHEALHNHYTQKSLSLSPG

Anti-VEGF ISO(+) Heavy Chain (SEQ ID NO: 78)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTKTYTCNVNHKPSNTKVDKKVEPKSCDKTHTCP
PCPAPELLGGPSVFLFPPKPKDTLMISRTPEVTCVVVDVSHEDPEVKFKWYVDGVEVHN
AKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

Figure 53B

Anti-VEGF_ISO(+RR) Heavy Chain (SEQ ID NO: 79)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTKTYTCNVNHKPSNTKVDKKVERKSCDKTHTCP
RCPAPELLGGPSVFLFPPKPKDTLMISRTPEVTCVVVDVSHEDPEVKFKWYVDGVEVHN
AKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

Figure 54

Heavy Chain 1 of XENP10783 Anti-VEGF_ISO(-) x IgG1(WT) (SEQ ID NO: 80)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTQTYTCNVDHKPSNTKVDKKVEPKSCDKTHTCP
PCPAPELLGGPSVFLFPPKPKDTLMISRTPEVTCVVVDVSHEDPEVQFNWYVDGVEVHN
AKTKPREEQYNSTYRVVSVLTVLHQDWLNGKEYKCKVSNKALPAPIEKTISKAKGQPRE
PQVYTLPPSQEEMTKNQVSLTCLVKGFYPSDIAVEWESSGQPENNYNTTPPMLDSDGS
FFLYSKLTVDKSRWQEGNVFSCSVMHEALHNHYTQKSLSLSPG

Heavy Chain 2 of XENP10783 Anti-VEGF_ISO(-) x IgG1(WT) (SEQ ID NO: 81)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK

Light Chain of XENP10783 Anti-VEGF_ISO(-) x IgG1(WT) (SEQ ID NO: 82)

DIQMTQSPSSLSASVGDRVTITCSASQDISNYLNWYQQKPGKAPKVLIYFTSSLHSGVPS
RFSGSGSGTDFTLTISSLQPEDFATYYCQQYSTVPWTFGQGTKVEIKRTVAAPSVFIFPP
SDEQLKSGTASVVCLLNNFYPREAKVQWKVDNALQSGNSQESVTEQDSKDSTYSLSST
LTLSKADYEKHKVYACEVTHQGLSSPVTKSFNRGEC

ISO(-)/ISO(-) Homodimer     pI = 6.6
ISO(-)/IgG1(WT) Heterodimer  pI = 7.3
ISO(WT)/ISO(WT) Homodimer    pI = 8.0

Figure 55

Heavy Chain 1 of XENP10784 Anti-VEGF_ISO(+RR) x IgG1(WT) (SEQ ID NO: 83)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTKTYTCNVNHKPSNTKVDKKVERKSCDKTHTCP
RCPAPELLGGPSVFLFPPKPKDTLMISRTPEVTCVVVDVSHEDPEVKFKWYVDGVEVHN
AKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

Heavy Chain 2 of XENP10784 Anti-VEGF_ISO(+RR) x IgG1(WT) (SEQ ID NO:84)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGSFF
LYSKLTVDKSRWQQGNVFSCSVMHEALHNHYTQKSLSLSPGK

Light Chain of XENP10784 Anti-VEGF_ISO(+RR) x IgG1(WT) (SEQ ID NO: 85)

DIQMTQSPSSLSASVGDRVTITCSASQDISNYLNWYQQKPGKAPKVLIYFTSSLHSGVPS
RFSGSGSGTDFTLTISSLQPEDFATYYCQQYSTVPWTFGQGTKVEIKRTVAAPSVFIFPP
SDEQLKSGTASVVCLLNNFYPREAKVQWKVDNALQSGNSQESVTEQDSKDSTYSLSST
LTLSKADYEKHKVYACEVTHQGLSSPVTKSFNRGEC

IgG1(WT)/IgG1(WT) Homodimer pI = 8.0

ISO(+RR)/IgG1(WT) Heterodimer pI = 8.3

ISO(+RR)/ISO(+RR) Homodimer pI = 8.5

Figure 56

Heavy Chain 1 of XENP10896 Anti-VEGF_ISO(-) x ISO(+RR) (SEQ ID NO: 86)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTQTYTCNVDHKPSNTKVDKKVEPKSCDKTHTCP
PCPAPELLGGPSVFLFPPKPKDTLMISRTPEVTCVVVDVSHEDPEVQFNWYVDGVEVHN
AKTKPREEQYNSTYRVVSVLTVLHQDWLNGKEYKCKVSNKALPAPIEKTISKAKGQPRE
PQVYTLPPSQEEMTKNQVSLTCLVKGFYPSDIAVEWESSGQPENNYNTTPPMLDSDGS
FFLYSKLTVDKSRWQEGNVFSCSVMHEALHNHYTQKSLSLSPG

Heavy Chain 2 of XENP10896 Anti-VEGF_ISO(-) x ISO(+RR) (SEQ ID NO: 87)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTKTYTCNVNHKPSNTKVDKKVERKSCDKTHTCP
RCPAPELLGGPSVFLFPPKPKDTLMISRTPEVTCVVVDVSHEDPEVKFKWYVDGVEVHN
AKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

Light Chain of XENP10896 Anti-VEGF_ISO(-) x ISO(+RR) (SEQ ID NO: 88)

DIQMTQSPSSLSASVGDRVTITCSASQDISNYLNWYQQKPGKAPKVLIYFTSSLHSGVPS
RFSGSGSGTDFTLTISSLQPEDFATYYCQQYSTVPWTFGQGTKVEIKRTVAAPSVFIFPP
SDEQLKSGTASVVCLLNNFYPREAKVQWKVDNALQSGNSQESVTEQDSKDSTYSLSST
LTLSKADYEKHKVYACEVTHQGLSSPVTKSFNRGEC

ISO(-)/ISO(-)        Homodimer pI = 6.6

ISO(-)/ISO(+RR)      Heterodimer pI = 7.9

ISO(+RR)/ISO(+RR)    Homodimer pI = 8.5

Figure 57

Heavy Chain 1 of XENP10901 Anti-VEGF_ISO(-) x ISO(+)(SEQ ID NO: 89)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTQTYTCNVDHKPSNTKVDKKVEPKSCDKTHTCP
PCPAPELLGGPSVFLFPPKPKDTLMISRTPEVTCVVVDVSHEDPEVQFNWYVDGVEVHN
AKTKPREEQYNSTYRVVSVLTVLHQDWLNGKEYKCKVSNKALPAPIEKTISKAKGQPRE
PQVYTLPPSQEEMTKNQVSLTCLVKGFYPSDIAVEWESSGQPENNYNTTPPMLDSDGS
FFLYSKLTVDKSRWQEGNVFSCSVMHEALHNHYTQKSLSLSPG

Heavy Chain 2 of XENP10901 Anti-VEGF_ISO(-) x ISO(+)(SEQ ID NO: 90)

EVQLVESGGGLVQPGGSLRLSCAASGYTFTNYGMNWVRQAPGKGLEWVGWINTYTGE
PTYAADFKRRFTFSLDTSKSTAYLQMNSLRAEDTAVYYCAKYPHYYGSSHWYFDVWGQ
GTLVTVSSASTKGPSVFPLAPSSKSTSGGTAALGCLVKDYFPEPVTVSWNSGALTSGVH
TFPAVLQSSGLYSLSSVVTVPSSSLGTKTYTCNVNHKPSNTKVDKKVEPKSCDKTHTCP
PCPAPELLGGPSVFLFPPKPKDTLMISRTPEVTCVVVDVSHEDPEVKFKWYVDGVEVHN
AKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

Light Chain of XENP10901 Anti-VEGF_ISO(-) x ISO(+)(SEQ ID NO:91)

DIQMTQSPSSLSASVGDRVTITCSASQDISNYLNWYQQKPGKAPKVLIYFTSSLHSGVPS
RFSGSGSGTDFTLTISSLQPEDFATYYCQQYSTVPWTFGQGTKVEIKRTVAAPSVFIFPP
SDEQLKSGTASVVCLLNNFYPREAKVQWKVDNALQSGNSQESVTEQDSKDSTYSLSST
LTLSKADYEKHKVYACEVTHQGLSSPVTKSFNRGEC

ISO(-)/ISO(-) Homodimer pI = 6.6

ISO(-)/ISO(+)      Heterodimer pI = 7.6

ISO(+)/ISO(+)      Homodimer pI = 8.3

Figure 58A

| Variant | # of sub(s) | pI / pI | pI / WT | WT/ WT | avg delta pI |
|---|---|---|---|---|---|
| G137E/N203D/K274Q/R355Q/K392N/Q419E/K447_ | 7 | 6.43 | 7.14 | 8.02 | -0.79 |
| G137E/N203D/K274Q/R355Q/K392N/Q419E | 6 | 6.58 | 7.30 | 8.02 | -0.72 |
| G137E/N203D/K274Q/R355Q/K392N/K447_ | 6 | 6.58 | 7.30 | 8.02 | -0.72 |
| G137E/N203D/K274Q/R355Q/Q419E/K447_ | 6 | 6.58 | 7.30 | 8.02 | -0.72 |
| G137E/N203D/K274Q/K392N/Q419E/K447_ | 6 | 6.58 | 7.30 | 8.02 | -0.72 |
| G137E/N203D/R355Q/K392N/Q419E/K447_ | 6 | 6.58 | 7.30 | 8.02 | -0.72 |
| G137E/K274Q/R355Q/K392N/Q419E/K447_ | 6 | 6.58 | 7.30 | 8.02 | -0.72 |
| N203D/K274Q/R355Q/K392N/Q419E/K447_ | 6 | 6.58 | 7.30 | 8.02 | -0.72 |
| G137E/N203D/K274Q/R355Q/K392N | 5 | 6.76 | 7.46 | 8.02 | -0.63 |
| G137E/N203D/K274Q/R355Q/Q419E | 5 | 6.76 | 7.46 | 8.02 | -0.63 |
| G137E/N203D/K274Q/R355Q/K447_ | 5 | 6.76 | 7.46 | 8.02 | -0.63 |
| G137E/N203D/K274Q/K392N/Q419E | 5 | 6.76 | 7.46 | 8.02 | -0.63 |
| G137E/N203D/K274Q/K392N/K447_ | 5 | 6.76 | 7.46 | 8.02 | -0.63 |
| G137E/N203D/K274Q/Q419E/K447_ | 5 | 6.76 | 7.46 | 8.02 | -0.63 |
| G137E/N203D/R355Q/K392N/Q419E | 5 | 6.76 | 7.46 | 8.02 | -0.63 |
| G137E/N203D/R355Q/K392N/K447_ | 5 | 6.76 | 7.46 | 8.02 | -0.63 |
| G137E/N203D/R355Q/Q419E/K447_ | 5 | 6.76 | 7.46 | 8.02 | -0.63 |
| G137E/N203D/K392N/Q419E/K447_ | 5 | 6.76 | 7.46 | 8.02 | -0.63 |
| G137E/K274Q/R355Q/K392N/Q419E | 5 | 6.76 | 7.46 | 8.02 | -0.63 |
| G137E/K274Q/R355Q/K392N/K447_ | 5 | 6.76 | 7.46 | 8.02 | -0.63 |
| G137E/K274Q/R355Q/Q419E/K447_ | 5 | 6.76 | 7.46 | 8.02 | -0.63 |
| G137E/K274Q/K392N/Q419E/K447_ | 5 | 6.76 | 7.46 | 8.02 | -0.63 |
| G137E/R355Q/K392N/Q419E/K447_ | 5 | 6.76 | 7.46 | 8.02 | -0.63 |
| N203D/K274Q/R355Q/K392N/Q419E | 5 | 6.76 | 7.46 | 8.02 | -0.63 |
| N203D/K274Q/R355Q/K392N/K447_ | 5 | 6.76 | 7.46 | 8.02 | -0.63 |
| N203D/K274Q/R355Q/Q419E/K447_ | 5 | 6.76 | 7.46 | 8.02 | -0.63 |
| N203D/K274Q/K392N/Q419E/K447_ | 5 | 6.76 | 7.46 | 8.02 | -0.63 |
| N203D/R355Q/K392N/Q419E/K447_ | 5 | 6.76 | 7.46 | 8.02 | -0.63 |
| K274Q/R355Q/K392N/Q419E/K447_ | 5 | 6.76 | 7.46 | 8.02 | -0.63 |
| G137E/N203D/K274Q/R355Q | 4 | 7.00 | 7.61 | 8.02 | -0.51 |
| G137E/N203D/K274Q/K392N | 4 | 7.00 | 7.61 | 8.02 | -0.51 |
| G137E/N203D/K274Q/Q419E | 4 | 7.00 | 7.61 | 8.02 | -0.51 |
| G137E/N203D/K274Q/K447_ | 4 | 7.00 | 7.61 | 8.02 | -0.51 |
| G137E/N203D/R355Q/K392N | 4 | 7.00 | 7.61 | 8.02 | -0.51 |
| G137E/N203D/R355Q/Q419E | 4 | 7.00 | 7.61 | 8.02 | -0.51 |
| G137E/N203D/R355Q/K447_ | 4 | 7.00 | 7.61 | 8.02 | -0.51 |
| G137E/N203D/K392N/Q419E | 4 | 7.00 | 7.61 | 8.02 | -0.51 |
| G137E/N203D/K392N/K447_ | 4 | 7.00 | 7.61 | 8.02 | -0.51 |
| G137E/N203D/Q419E/K447_ | 4 | 7.00 | 7.61 | 8.02 | -0.51 |
| G137E/K274Q/R355Q/K392N | 4 | 7.00 | 7.61 | 8.02 | -0.51 |
| G137E/K274Q/R355Q/Q419E | 4 | 7.00 | 7.61 | 8.02 | -0.51 |
| G137E/K274Q/R355Q/K447_ | 4 | 7.00 | 7.61 | 8.02 | -0.51 |
| G137E/K274Q/K392N/Q419E | 4 | 7.00 | 7.61 | 8.02 | -0.51 |
| G137E/K274Q/K392N/K447_ | 4 | 7.00 | 7.61 | 8.02 | -0.51 |
| G137E/K274Q/Q419E/K447_ | 4 | 7.00 | 7.61 | 8.02 | -0.51 |
| G137E/R355Q/K392N/Q419E | 4 | 7.00 | 7.61 | 8.02 | -0.51 |
| G137E/R355Q/K392N/K447_ | 4 | 7.00 | 7.61 | 8.02 | -0.51 |

Figure 58B

| Variant | # of sub(s) | pI / pI | pI / WT | WT/ WT | avg delta pI |
|---|---|---|---|---|---|
| G137E/R355Q/Q419E/K447_ | 4 | 7.00 | 7.61 | 8.02 | -0.51 |
| G137E/K392N/Q419E/K447_ | 4 | 7.00 | 7.61 | 8.02 | -0.51 |
| N203D/K274Q/R355Q/K392N | 4 | 7.00 | 7.61 | 8.02 | -0.51 |
| N203D/K274Q/R355Q/Q419E | 4 | 7.00 | 7.61 | 8.02 | -0.51 |
| N203D/K274Q/R355Q/K447_ | 4 | 7.00 | 7.61 | 8.02 | -0.51 |
| N203D/K274Q/K392N/Q419E | 4 | 7.00 | 7.61 | 8.02 | -0.51 |
| N203D/K274Q/K392N/K447_ | 4 | 7.00 | 7.61 | 8.02 | -0.51 |
| N203D/K274Q/Q419E/K447_ | 4 | 7.00 | 7.61 | 8.02 | -0.51 |
| N203D/R355Q/K392N/Q419E | 4 | 7.00 | 7.61 | 8.02 | -0.51 |
| N203D/R355Q/K392N/K447_ | 4 | 7.00 | 7.61 | 8.02 | -0.51 |
| N203D/R355Q/Q419E/K447_ | 4 | 7.00 | 7.61 | 8.02 | -0.51 |
| N203D/K392N/Q419E/K447_ | 4 | 7.00 | 7.61 | 8.02 | -0.51 |
| K274Q/R355Q/K392N/Q419E | 4 | 7.00 | 7.61 | 8.02 | -0.51 |
| K274Q/R355Q/K392N/K447_ | 4 | 7.00 | 7.61 | 8.02 | -0.51 |
| K274Q/R355Q/Q419E/K447_ | 4 | 7.00 | 7.61 | 8.02 | -0.51 |
| K274Q/K392N/Q419E/K447_ | 4 | 7.00 | 7.61 | 8.02 | -0.51 |
| R355Q/K392N/Q419E/K447_ | 4 | 7.00 | 7.61 | 8.02 | -0.51 |
| G137E/N203D/K274Q | 3 | 7.30 | 7.74 | 8.02 | -0.36 |
| G137E/N203D/R355Q | 3 | 7.30 | 7.74 | 8.02 | -0.36 |
| G137E/N203D/K392N | 3 | 7.30 | 7.74 | 8.02 | -0.36 |
| G137E/N203D/Q419E | 3 | 7.30 | 7.74 | 8.02 | -0.36 |
| G137E/N203D/K447_ | 3 | 7.30 | 7.74 | 8.02 | -0.36 |
| G137E/K274Q/R355Q | 3 | 7.30 | 7.74 | 8.02 | -0.36 |
| G137E/K274Q/K392N | 3 | 7.30 | 7.74 | 8.02 | -0.36 |
| G137E/K274Q/Q419E | 3 | 7.30 | 7.74 | 8.02 | -0.36 |
| G137E/K274Q/K447_ | 3 | 7.30 | 7.74 | 8.02 | -0.36 |
| G137E/R355Q/K392N | 3 | 7.30 | 7.74 | 8.02 | -0.36 |
| G137E/R355Q/Q419E | 3 | 7.30 | 7.74 | 8.02 | -0.36 |
| G137E/R355Q/K447_ | 3 | 7.30 | 7.74 | 8.02 | -0.36 |
| G137E/K392N/Q419E | 3 | 7.30 | 7.74 | 8.02 | -0.36 |
| G137E/K392N/K447_ | 3 | 7.30 | 7.74 | 8.02 | -0.36 |
| G137E/Q419E/K447_ | 3 | 7.30 | 7.74 | 8.02 | -0.36 |
| N203D/K274Q/R355Q | 3 | 7.30 | 7.74 | 8.02 | -0.36 |
| N203D/K274Q/K392N | 3 | 7.30 | 7.74 | 8.02 | -0.36 |
| N203D/K274Q/Q419E | 3 | 7.30 | 7.74 | 8.02 | -0.36 |
| N203D/K274Q/K447_ | 3 | 7.30 | 7.74 | 8.02 | -0.36 |
| N203D/R355Q/K392N | 3 | 7.30 | 7.74 | 8.02 | -0.36 |
| N203D/R355Q/Q419E | 3 | 7.30 | 7.74 | 8.02 | -0.36 |
| N203D/R355Q/K447_ | 3 | 7.30 | 7.74 | 8.02 | -0.36 |
| N203D/K392N/Q419E | 3 | 7.30 | 7.74 | 8.02 | -0.36 |
| N203D/K392N/K447_ | 3 | 7.30 | 7.74 | 8.02 | -0.36 |
| N203D/Q419E/K447_ | 3 | 7.30 | 7.74 | 8.02 | -0.36 |
| K274Q/R355Q/K392N | 3 | 7.30 | 7.74 | 8.02 | -0.36 |
| K274Q/R355Q/Q419E | 3 | 7.30 | 7.74 | 8.02 | -0.36 |
| K274Q/R355Q/K447_ | 3 | 7.30 | 7.74 | 8.02 | -0.36 |
| K274Q/K392N/Q419E | 3 | 7.30 | 7.74 | 8.02 | -0.36 |
| K274Q/K392N/K447_ | 3 | 7.30 | 7.74 | 8.02 | -0.36 |
| K274Q/Q419E/K447_ | 3 | 7.30 | 7.74 | 8.02 | -0.36 |
| R355Q/K392N/Q419E | 3 | 7.30 | 7.74 | 8.02 | -0.36 |
| R355Q/K392N/K447_ | 3 | 7.30 | 7.74 | 8.02 | -0.36 |

Figure 58C

| Variant | # of sub(s) | pI / pI | pI / WT | WT/ WT | avg delta pI |
|---|---|---|---|---|---|
| R355Q/Q419E/K447_ | 3 | 7.30 | 7.74 | 8.02 | -0.36 |
| K392N/Q419E/K447_ | 3 | 7.30 | 7.74 | 8.02 | -0.36 |
| G137E/N203D | 2 | 7.61 | 7.85 | 8.02 | -0.21 |
| G137E/K274Q | 2 | 7.61 | 7.85 | 8.02 | -0.21 |
| G137E/R355Q | 2 | 7.61 | 7.85 | 8.02 | -0.21 |
| G137E/K392N | 2 | 7.61 | 7.85 | 8.02 | -0.21 |
| G137E/Q419E | 2 | 7.61 | 7.85 | 8.02 | -0.21 |
| G137E/K447_ | 2 | 7.61 | 7.85 | 8.02 | -0.21 |
| N203D/K274Q | 2 | 7.61 | 7.85 | 8.02 | -0.21 |
| N203D/R355Q | 2 | 7.61 | 7.85 | 8.02 | -0.21 |
| N203D/K392N | 2 | 7.61 | 7.85 | 8.02 | -0.21 |
| N203D/Q419E | 2 | 7.61 | 7.85 | 8.02 | -0.21 |
| N203D/K447_ | 2 | 7.61 | 7.85 | 8.02 | -0.21 |
| K274Q/R355Q | 2 | 7.61 | 7.85 | 8.02 | -0.21 |
| K274Q/K392N | 2 | 7.61 | 7.85 | 8.02 | -0.21 |
| K274Q/Q419E | 2 | 7.61 | 7.85 | 8.02 | -0.21 |
| K274Q/K447_ | 2 | 7.61 | 7.85 | 8.02 | -0.21 |
| R355Q/K392N | 2 | 7.61 | 7.85 | 8.02 | -0.21 |
| R355Q/Q419E | 2 | 7.61 | 7.85 | 8.02 | -0.21 |
| R355Q/K447_ | 2 | 7.61 | 7.85 | 8.02 | -0.21 |
| K392N/Q419E | 2 | 7.61 | 7.85 | 8.02 | -0.21 |
| K392N/K447_ | 2 | 7.61 | 7.85 | 8.02 | -0.21 |
| Q419E/K447_ | 2 | 7.61 | 7.85 | 8.02 | -0.21 |
| G137E | 1 | 7.85 | 7.94 | 8.02 | -0.09 |
| N203D | 1 | 7.85 | 7.94 | 8.02 | -0.09 |
| K274Q | 1 | 7.85 | 7.94 | 8.02 | -0.09 |
| R355Q | 1 | 7.85 | 7.94 | 8.02 | -0.09 |
| K392N | 1 | 7.85 | 7.94 | 8.02 | -0.09 |
| Q419E | 1 | 7.85 | 7.94 | 8.02 | -0.09 |
| K447_ | 1 | 7.85 | 7.94 | 8.02 | -0.09 |

Figure 59

| Variant | # of sub(s) | pI / pI | pI / WT | WT/ WT | avg delta pI |
| --- | --- | --- | --- | --- | --- |
| Q196K/P217R/P228R/N276K/H435R | 5 | 8.53 | 8.32 | 8.02 | 0.25 |
| Q196K/P217R/P228R/N276K | 4 | 8.45 | 8.27 | 8.02 | 0.22 |
| Q196K/P217R/P228R/H435R | 4 | 8.46 | 8.28 | 8.02 | 0.22 |
| Q196K/P217R/N276K/H435R | 4 | 8.45 | 8.27 | 8.02 | 0.22 |
| Q196K/P228R/N276K/H435R | 4 | 8.45 | 8.27 | 8.02 | 0.22 |
| P217R/P228R/N276K/H435R | 4 | 8.46 | 8.28 | 8.02 | 0.22 |
| Q196K/P217R/P228R | 3 | 8.37 | 8.22 | 8.02 | 0.17 |
| Q196K/P217R/N276K | 3 | 8.37 | 8.22 | 8.02 | 0.17 |
| Q196K/P217R/H435R | 3 | 8.37 | 8.22 | 8.02 | 0.17 |
| Q196K/P228R/N276K | 3 | 8.37 | 8.22 | 8.02 | 0.17 |
| Q196K/P228R/H435R | 3 | 8.37 | 8.22 | 8.02 | 0.17 |
| Q196K/N276K/H435R | 3 | 8.37 | 8.22 | 8.02 | 0.17 |
| P217R/P228R/N276K | 3 | 8.37 | 8.22 | 8.02 | 0.17 |
| P217R/P228R/H435R | 3 | 8.37 | 8.22 | 8.02 | 0.18 |
| P217R/N276K/H435R | 3 | 8.37 | 8.22 | 8.02 | 0.17 |
| P228R/N276K/H435R | 3 | 8.37 | 8.22 | 8.02 | 0.17 |
| Q196K/P217R | 2 | 8.27 | 8.16 | 8.02 | 0.13 |
| Q196K/P228R | 2 | 8.27 | 8.16 | 8.02 | 0.13 |
| Q196K/N276K | 2 | 8.27 | 8.16 | 8.02 | 0.13 |
| Q196K/H435R | 2 | 8.27 | 8.16 | 8.02 | 0.13 |
| P217R/P228R | 2 | 8.28 | 8.16 | 8.02 | 0.13 |
| P217R/N276K | 2 | 8.27 | 8.16 | 8.02 | 0.13 |
| P217R/H435R | 2 | 8.28 | 8.16 | 8.02 | 0.13 |
| P228R/N276K | 2 | 8.27 | 8.16 | 8.02 | 0.13 |
| P228R/H435R | 2 | 8.28 | 8.16 | 8.02 | 0.13 |
| N276K/H435R | 2 | 8.27 | 8.16 | 8.02 | 0.13 |
| Q196K | 1 | 8.16 | 8.10 | 8.02 | 0.07 |
| P217R | 1 | 8.16 | 8.10 | 8.02 | 0.07 |
| P228R | 1 | 8.16 | 8.10 | 8.02 | 0.07 |
| N276K | 1 | 8.16 | 8.10 | 8.02 | 0.07 |
| H435R | 1 | 8.16 | 8.10 | 8.02 | 0.07 |

Figure 60
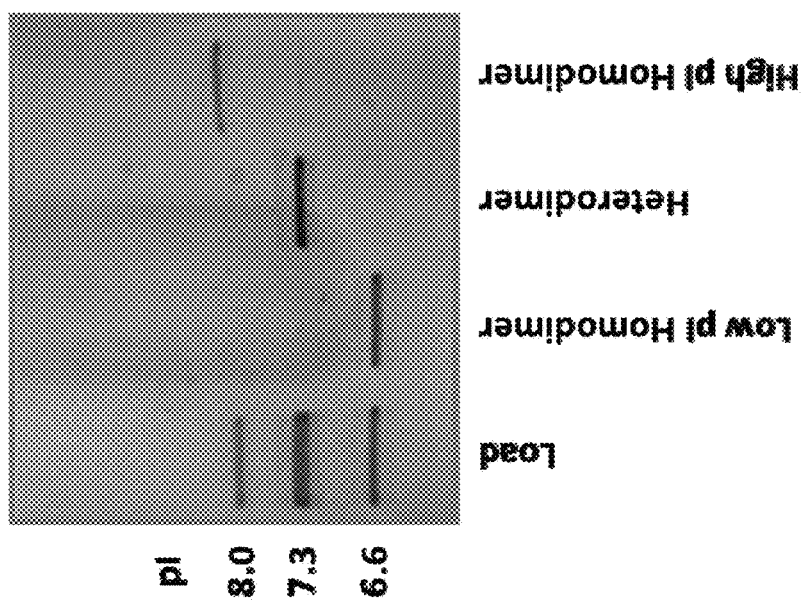
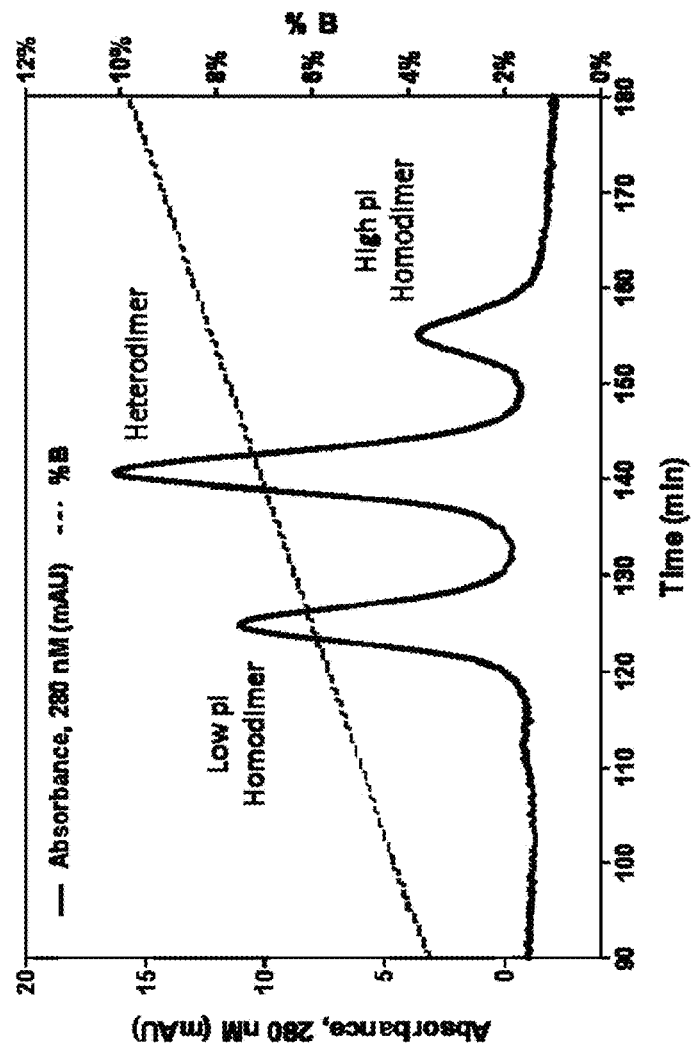

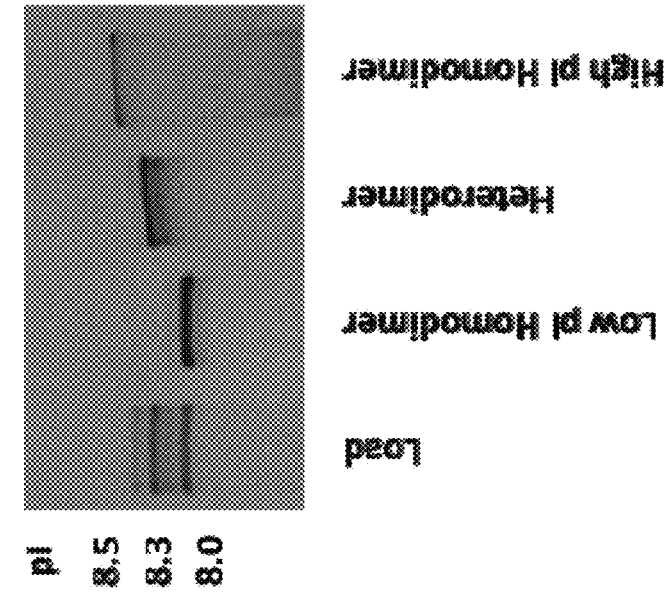
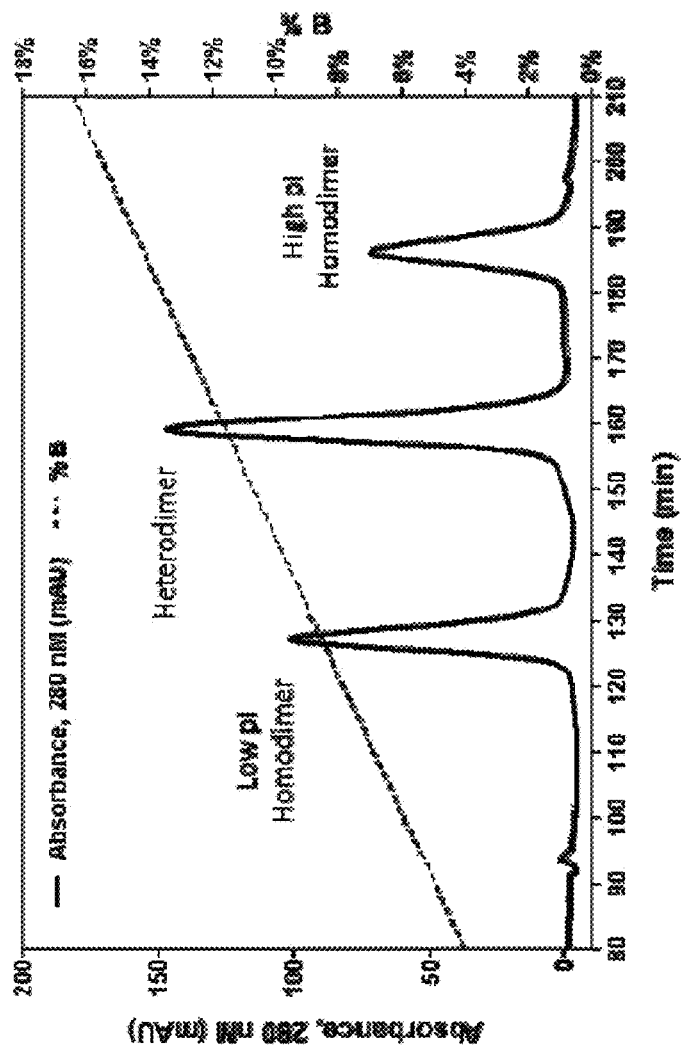
Figure 61

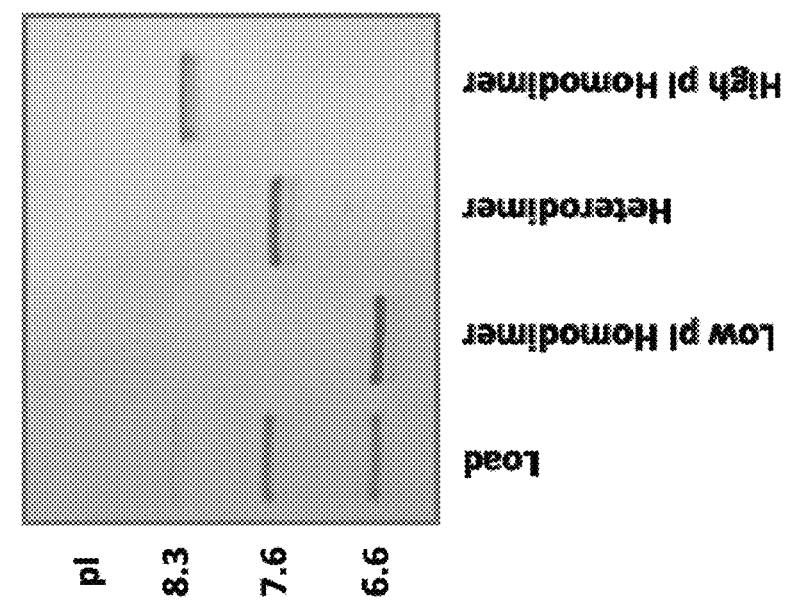
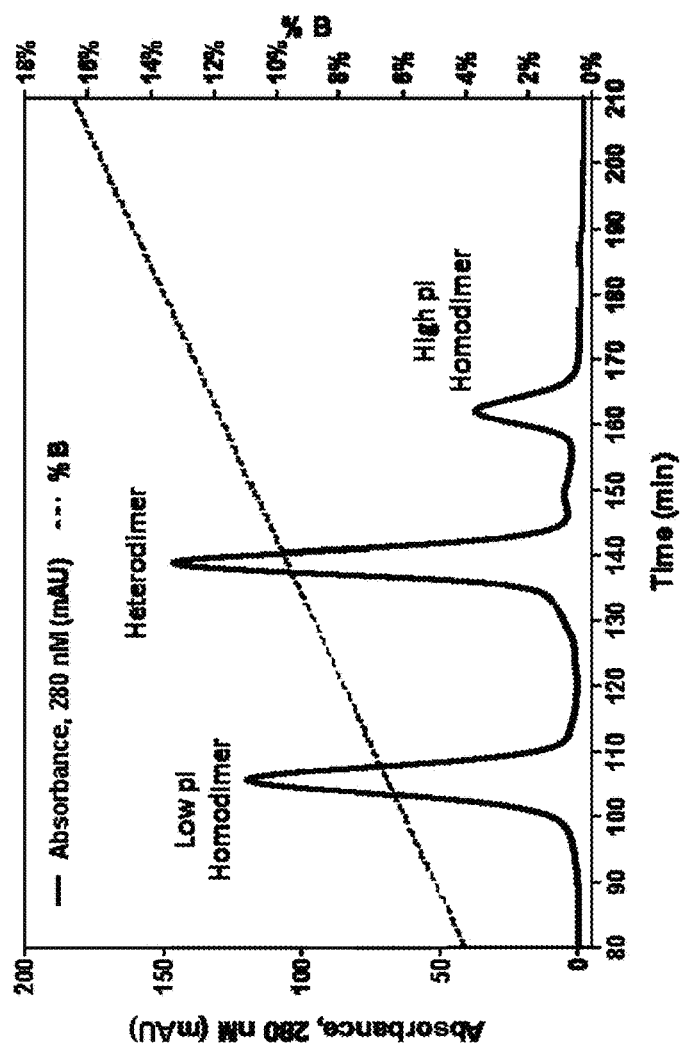
Figure 63
Purification of XENP10901: anti-VEGF ISO(-) x ISO(+) mAb

Figure 64

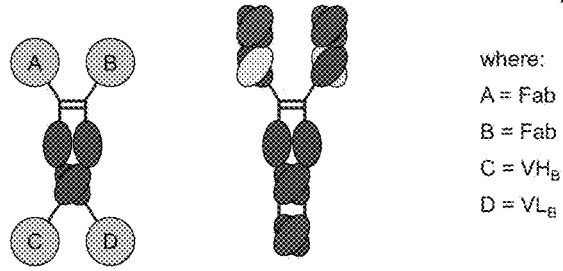

where:
A = Fab
B = Fab
C = VH_B
D = VL_B

Heavy Chain 1 of anti-CD19 x anti-CD3 mAb-Fv [HC ISO(-) (VH)]   SEQ ID NO: 92

EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPSSKSTSGGTAALGCLVKDYFPEPVTVSWNSGALTSGVHTFPAVLQSSGLYSLSSVVTV
PSSSLGTQTYTCNVDHKPSNTKVDKKVEPKSCDKTHTCPPCPAPELLGGPSVFLFPPKPKDTLMI
SRTPEVTCVVVDVSHEDPEVQFNWYVDGVEVHNAKTKPREEQYNSTYRVVSVLTVLHQDWLNG
KEYKCKVSNKALPAPIEKTISKAKGQPREPQVYTLPPSQEEMTKNQVSLTCLVKGFYPSDIAVEW
ESSGQPENNYNTTPPMLDSDGSFFLYSKLTVDKSRWQEGNVFSCSVMHEALHNHYTQKSLSLS
PGSSDKTHTSPPSPSGQVQLVQSGAEVKKPGASVKVSCKASGYTFTRYTMHWVRQAPGQGLE
WMGYINPSRGYTNYNQKFQGRVTMTTDKSTSTAYMELSSLRSEDTAVYYCARYYDDHYSLDYW
GQGTTVTVSS

Heavy Chain 2 of anti-CD19 x anti-CD3 mAb-Fv [HC ISO(+RR) (VL)]   SEQ ID NO: 93

EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPSSKSTSGGTAALGCLVKDYFPEPVTVSWNSGALTSGVHTFPAVLQSSGLYSLSSVVTV
PSSSLGTKTYTCNVNHKPSNTKVDKKVERKSCDKTHTCPRCPAPELLGGPSVFLFPPKPKDTLMI
SRTPEVTCVVVDVSHEDPEVKFKWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLS
PGKSSDKTHTSPPSPSGQIVLTQSPATLSLSPGERATLSCRASSSVSYMNWYQQKPGQSPRRLI
YDTSKLASGVPARFRGSGSGTDYTLTISSLEPEDFAVYYCQQWSSNPFTFGSGTKLEIK

Light Chain of anti-CD19 x anti-CD3 mAb-Fv   SEQ ID NO: 94

DIVMTQSPATLSLSPGERATLSCRSSKSLQNVNGNTYLYWFQQKPGQSPQLLIYRMSNLNSGVP
DRFSGSGSGTEFTLTISSLEPEDFAVYYCMQHLEYPITFGAGTKLEIKRTVAAPSVFIFPPSDEQLK
SGTASVVCLLNNFYPREAKVQWKVDNALQSGNSQESVTEQDSKDSTYSLSSTLTLSKADYEKHK
VYACEVTHQGLSSPVTKSFNRGEC

ISO(-)/ISO(-) Homodimer        pI = 7.31
ISO(-)/ISO(+RR) Heterodimer    pI = 8.22
ISO(+RR)/ISO(+RR) Homodimer    pI = 8.59

Figure 65

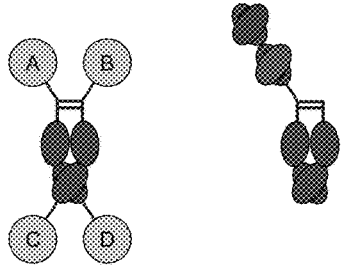

where:
A = (scFv)$_2$ (e.g., VH$_A$-(Gly$_4$Ser)$_3$-VL$_A$-(Gly$_4$Ser)-VH$_B$-(Gly$_4$Ser)$_3$-VL$_B$)
B = n.a.
C = n.a.
D = n.a.

Heavy Chain 1 of anti-CD19 x anti-CD3 scFv$_2$-Fc [HC ISO(-)]  SEQ ID NO: 95

EPKSSDKTHTCPPCPAPELLGGPSVFLFPPKPKDTLMISRTPEVTCVVVDVSHEDPEVQFNWYV
DGVEVHNAKTKPREEQYNSTYRVVSVLTVLHQDWLNGKEYKCKVSNKALPAPIEKTISKAKGQP
REPQVYTLPPSQEEMTKNQVSLTCLVKGFYPSDIAVEWESSGQPENNYNTTPPMLDSDGSFFLY
SKLTVDKSRWQEGNVFSCSVMHEALHNHYTQKSLSLSPG

Heavy Chain 2 of anti-CD19 x anti-CD3 scFv$_2$-Fc [HC ISO(+RR) (scFv2)]  SEQ ID NO: 96

EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSGGGGSG
GGGSGGGGSDIVMTQSPATLSLSPGERATLSCRSSKSLQNVNGNTYLYWFQQKPGQSPQLLIY
RMSNLNSGVPDRFSGSGSGTEFTLTISSLEPEDFAVYYCMQHLEYPITFGAGTKLEIKSGGGGSQ
VQLVQSGAEVKKPGASVKVSCKASGYTFTRYTMHWVRQAPGQGLEWMGYINPSRGYTNYNQK
FQGRVTMTTDKSTSTAYMELSSLRSEDTAVYYCARYYDDHYSLDYWGQGTTVTVSSGGGGSG
GGGSGGGGSQIVLTQSPATLSLSPGERATLSCRASSSVSYMNWYQQKPGQSPRRLIYDTSKLAS
GVPARFRGSGSGTDYTLTISSLEPEDFAVYYCQQWSSNPFTFGSGTKLEIKERKSSDKTHTCPRC
PAPELLGGPSVFLFPPKPKDTLMISRTPEVTCVVVDVSHEDPEVKFKWYVDGVEVHNAKTKPREE
QYNSTYRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQGNVF
SCSVMHEALHNHYTQKSLSLSPGK

ISO(-)/ISO(-) Homodimer    pI = 5.83

ISO(-)/ISO(+RR) Heterodimer    pI = 8.06

ISO(+RR)/ISO(+RR) Homodimer    pI = 8.66

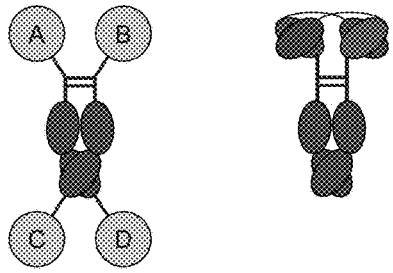

Figure 66 where:
A = VL$_A$-(Gly$_4$Ser)$_3$-VH$_B$
B = VL$_B$-(Gly$_4$Ser)$_3$-VH$_A$
C = n.a.
D = n.a.

<u>Heavy Chain 1 of anti-CD19 x anti-CD3 DART-Fc [HC ISO(-) (anti-CD19 VL/anti-CD3 VH)]</u>

DIVMTQSPATLSLSPGERATLSCRSSKSLQNVNGNTYLYWFQQKPGQSPQLLIYRMSNLNSGVP
DRFSGSGSGTEFTLTISSLEPEDFAVYYCMQHLEYPITFGAGTKLEIKGGGGSGGGGSGGGGSQ
VQLVQSGAEVKKPGASVKVSCKASGYTFTRYTMHWVRQAPGQGLEWMGYINPSRGYTNYNQK
FQGRVTMTTDKSTSTAYMELSSLRSEDTAVYYCARYYDDHYSLDYWGQGTTVTVSSEPKSSDK
THTCPPCPAPELLGGPSVFLFPPKPKDTLMISRTPEVTCVVVDVSHEDPEVQFNWYVDGVEVHN
AKTKPREEQYNSTYRVVSVLTVLHQDWLNGKEYKCKVSNKALPAPIEKTISKAKGQPREPQVYTL
PPSQEEMTKNQVSLTCLVKGFYPSDIAVEWESSGQPENNYNTTPPMLDSDGSFFLYSKLTVDKS
RWQEGNVFSCSVMHEALHNHYTQKSLSLSPG SEQ ID NO: 97

<u>Heavy Chain 2 of anti-CD19 x anti-CD3 DART-Fc [HC ISO(+RR) (anti-CD3 VL/anti-CD19 VH)]</u>

QIVLTQSPATLSLSPGERATLSCRASSSVSYMNWYQQKPGQSPRRLIYDTSKLASGVPARFRGS
GSGTDYTLTISSLEPEDFAVYYCQQWSSNPFTFGSGTKLEIKGGGGSGGGGSGGGGSEVQLVE
SGGGLVKPGGSLKLSCAASGYTFTSYVMHWVRQAPGKGLEWIGYINPYNDGTKYNEKFQGRVTI
SSDKSISTAYMELSSLRSEDTAMYYCARGTYYYGTRVFDYWGQGTLVTVSSERKSSDKTHTCPR
CPAPELLGGPSVFLFPPKPKDTLMISRTPEVTCVVVDVSHEDPEVKFKWYVDGVEVHNAKTKPR
EEQYNSTYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQG
NVFSCSVMHEALHNHYTQKSLSLSPGK SEQ ID NO: 98

ISO(-)/ISO(-) Homodimer    pI = 6.42

ISO(-)/ISO(+RR) Heterodimer    pI = 8.06

ISO(+RR)/ISO(+RR) Homodimer    pI = 8.71

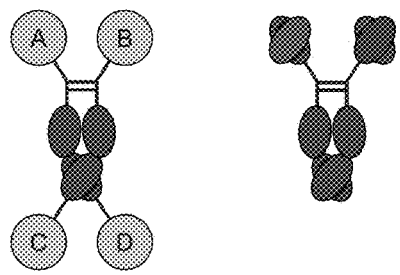

Figure 67 where:

A = scFv (e.g., VH$_A$-(Gly$_4$Ser)$_3$-VL$_A$)

B = scFv (e.g., VH$_B$-(Gly$_4$Ser)$_3$-VL$_B$)

C = n.a.

D = n.a.

Heavy Chain 1 of anti-CD19 x anti-CD3 scFv-Fc [HC ISO(-) (anti-CD19 scFv)]

EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSGGGGSG
GGGSGGGGSDIVMTQSPATLSLSPGERATLSCRSSKSLQNVNGNTYLYWFQQKPGQSPQLLIY
RMSNLNSGVPDRFSGSGSGTEFTLTISSLEPEDFAVYYCMQHLEYPITFGAGTKLEIKEPKSSDKT
HTCPPCPAPELLGGPSVFLFPPKPKDTLMISRTPEVTCVVVDVSHEDPEVQFNWYVDGVEVHNA
KTKPREEQYNSTYRVVSVLTVLHQDWLNGKEYKCKVSNKALPAPIEKTISKAKGQPREPQVYTLP
PSQEEMTKNQVSLTCLVKGFYPSDIAVEWESSGQPENNYNTTPPMLDSDGSFFLYSKLTVDKSR
WQEGNVFSCSVMHEALHNHYTQKSLSLSPG SEQ ID NO: 99

Heavy Chain 2 of anti-CD19 x anti-CD3 scFv-Fc [HC ISO(+RR) (anti-CD3 scFv)]

QVQLVQSGAEVKKPGASVKVSCKASGYTFTRYTMHWVRQAPGQGLEWMGYINPSRGYTNYNQ
KFQGRVTMTTDKSTSTAYMELSSLRSEDTAVYYCARYYDDHYSLDYWGQGTTVTVSSGGGGSG
GGGSGGGGSQIVLTQSPATLSLSPGERATLSCRASSSVSYMNWYQQKPGQSPRRLIYDTSKLAS
GVPARFRGSGSGTDYTLTISSLEPEDFAVYYCQQWSSNPFTFGSGTKLEIKERKSSDKTHTCPRC
PAPELLGGPSVFLFPPKPKDTLMISRTPEVTCVVVDVSHEDPEVKFKWYVDGVEVHNAKTKPREE
QYNSTYRVVSVLTVLHQDWLNGKEYKCKVSNKALPAPIEKTISKAKGQPREPQVYTLPPSREEMT
KNQVSLTCLVKGFYPSDIAVEWESNGQPENNYKTTPPVLDSDGSFFLYSKLTVDKSRWQQGNVF
SCSVMHEALHNHYTQKSLSLSPGK SEQ ID NO: 100

ISO(-)/ISO(-) Homodimer    pI = 6.05
ISO(-)/ISO(+RR) Heterodimer    pI = 8.06
ISO(+RR)/ISO(+RR) Homodimer    pI = 8.86

Figure 68

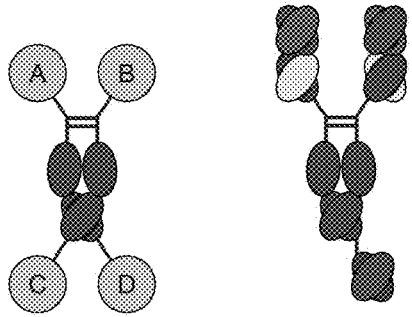

where:
A = Fab
B = Fab
C = n.a.
D = scFv (e.g., $VH_B$-$(Gly_4Ser)_3$-$VL_B$)

Heavy Chain 1 of anti-CD19 x anti-CD3 mAb-scFv [HC ISO(-)]
EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPSSKSTSGGTAALGCLVKDYFPEPVTVSWNSGALTSGVHTFPAVLQSSGLYSLSSVVTV
PSSSLGTQTYTCNVDHKPSNTKVDKKVEPKSCDKTHTCPPCPAPELLGGPSVFLPPKPKDTLMI
SRTPEVTCVVVDVSHEDPEVQFNWYVDGVEVHNAKTKPREEQYNSTYRVVSVLTVLHQDWLNG
KEYKCKVSNKALPAPIEKTISKAKGQPREPQVYTLPPSQEEMTKNQVSLTCLVKGFYPSDIAVEW
ESSGQPENNYNTTPPMLDSDGSFFLYSKLTVDKSRWQEGNVFSCSVMHEALHNHYTQKSLSLS
PG SEQ ID NO: 101

Heavy Chain 2 of anti-CD19 x anti-CD3 mAb-scFv [HC ISO(+RR) (scFv)]
EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPSSKSTSGGTAALGCLVKDYFPEPVTVSWNSGALTSGVHTFPAVLQSSGLYSLSSVVTV
PSSSLGTKTYTCNVNHKPSNTKVDKKVERKSCDKTHTCPRCPAPELLGGPSVFLPPKPKDTLMI
SRTPEVTCVVVDVSHEDPEVKFKWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLS
PGKGGGGSGGGGSQVQLVQSGAEVKKPGASVKVSCKASGYTFTRYTMHWVRQAPGQGLEWM
GYINPSRGYTNYNQKFQGRVTMTTDKSTSTAYMELSSLRSEDTAVYYCARYYDDHYSLDYWGQ
GTTVTVSSGGGGSGGGGSGGGGSQIVLTQSPATLSLSPGERATLSCRASSSVSYMNWYQQKP
GQSPRRLIYDTSKLASGVPARFRGSGSGTDYTLTISSLEPEDFAVYYCQQWSSNPFTFGSGTKLE
IK SEQ ID NO: 102

Light Chain of anti-CD19 x anti-CD3 mAb-scFv
DIVMTQSPATLSLSPGERATLSCRSSKSLQNVNGNTYLYWFQQKPGQSPQLLIYRMSNLNSGVP
DRFSGSGSGTEFTLTISSLEPEDFAVYYCMQHLEYPITFGAGTKLEIKRTVAAPSVFIFPPSDEQLK
SGTASVVCLLNNFYPREAKVQWKVDNALQSGNSQESVTEQDSKDSTYSLSSTLTLSKADYEKHK
VYACEVTHQGLSSPVTKSFNRGEC SEQ ID NO: 103

ISO(-)/ISO(-) Homodimer     pI = 6.55
ISO(-)/ISO(+RR) Heterodimer  pI = 8.22
ISO(+RR)/ISO(+RR) Homodimer  pI = 8.68

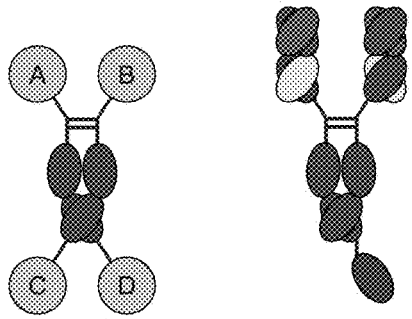

Figure 69 where:
A = Fab
B = Fab
C = n.a.
D = dAb (e.g., VH$_B$ or VL$_B$)

Heavy Chain 1 of anti-CD19 x anti-CD3 mAb-dAb [HC ISO(-)]

EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPSSKSTSGGTAALGCLVKDYFPEPVTVSWNSGALTSGVHTFPAVLQSSGLYSLSSVVTV
PSSSLGTQTYTCNVDHKPSNTKVDKKVEPKSCDKTHTCPPCPAPELLGGPSVFLFPPKPKDTLMI
SRTPEVTCVVVDVSHEDPEVQFNWYVDGVEVHNAKTKPREEQYNSTYRVVSVLTVLHQDWLNG
KEYKCKVSNKALPAPIEKTISKAKGQPREPQVYTLPPSQEEMTKNQVSLTCLVKGFYPSDIAVEW
ESSGQPENNYNTTPPMLDSDGSFFLYSKLTVDKSRWQEGNVFSCSVMHEALHNHYTQKSLSLS
PG  SEQ ID NO: 104

Heavy Chain 2 of anti-CD19 x anti-CD3 mAb-dAb [ISO(+RR) (scFv)]

EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPSSKSTSGGTAALGCLVKDYFPEPVTVSWNSGALTSGVHTFPAVLQSSGLYSLSSVVTV
PSSSLGTKTYTCNVNHKPSNTKVDKKVERKSCDKTHTCPRCPAPELLGGPSVFLFPPKPKDTLMI
SRTPEVTCVVVDVSHEDPEVKFKWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLS
PGKGGGGSGGGGSQVQLVQSGAEVKKPGASVKVSCKASGYTFTRYTMHWVRQAPGQGLEWM
GYINPSRGYTNYNQKFQGRVTMTTDKSTSTAYMELSSLRSEDTAVYYCARYYDDHYSLDYWGQ
GTTVTVSS  SEQ ID NO: 105

Light Chain of anti-CD19 x anti-CD3 mAb-dAb
DIVMTQSPATLSLSPGERATLSCRSSKSLQNVNGNTYLYWFQQKPGQSPQLLIYRMSNLNSGVP
DRFSGSGSGTEFTLTISSLEPEDFAVYYCMQHLEYPITFGAGTKLEIKRTVAAPSVFIFPPSDEQLK
SGTASVVCLLNNFYPREAKVQWKVDNALQSGNSQESVTEQDSKDSTYSLSSTLTLSKADYEKHK
VYACEVTHQGLSSPVTKSFNRGEC  SEQ ID NO: 106
ISO(-)/ISO(-) Homodimer      pI ≈ 6.55
ISO(-)/ISO(+RR) Heterodimer  pI ≈ 8.06
ISO(+RR)/ISO(+RR) Homodimer  pI ≈ 8.58

Figure 70

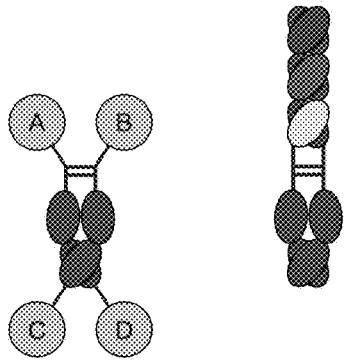

where:
A = VL$_A$-VL$_B$-CL
B = VH$_A$-VH$_B$-CH1
C = n.a.
D = n.a.

Heavy Chain 1 of anti-CD19 x anti-CD3 Fv-Fab-Fc [HC ISO(-) (VL-VL-CL)]

DIVMTQSPATLSLSPGERATLSCRSSKSLQNVNGNTYLYWFQQKPGQSPQLLIYRMSNLNSGVP
DRFSGSGSGTEFTLTISSLEPEDFAVYYCMQHLEYPITFGAGTKLEIKTVAAPSVFIFPPQIVLTQSP
ATLSLSPGERATLSCRASSSVSYMNWYQQKPGQSPRRLIYDTSKLASGVPARFRGSGSGTDYTL
TISSLEPEDFAVYYCQQWSSNPFTFGSGTKLEIKRTVAAPSVFIFPPSDEQLKSGTASVVCLLNNF
YPREAKVQWKVDNALQSGNSQESVTEQDSKDSTYSLSSTLTLSKADYEKHKVYACEVTHQGLSS
PVTKSFNRGECDKTHTCPPCPAPELLGGPSVFLFPPKPKDTLMISRTPEVTCVVVDVSHEDPEVQ
FNWYVDGVEVHNAKTKPREEQYNSTYRVVSVLTVLHQDWLNGKEYKCKVSNKALPAPIEKTISK
AKGQPREPQVYTLPPSQEEMTKNQVSLTCLVKGFYPSDIAVEWESSGQPENNYNTTPPMLDSD
GSFFLYSKLTVDKSRWQEGNVFSCSVMHEALHNHYTQKSLSLSPG SEQ ID NO: 107

Heavy Chain 2 of anti-CD19 x anti-CD3 Fv-Fab-Fc [HC ISO(+RR) (VH-VH-CH1)]

EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPQVQLVQSGAEVKKPGASVKVSCKASGYTFTRYTMHWVRQAPGQGLEWMGYINPSR
GYTNYNQKFQGRVTMTTDKSTSTAYMELSSLRSEDTAVYYCARYYDDHYSLDYWGQGTTVTVS
SASTKGPSVFPLAPSSKSTSGGTAALGCLVKDYFPEPVTVSWNSGALTSGVHTFPAVLQSSGLY
SLSSVVTVPSSSLGTKTYTCNVNHKPSNTKVDKKVERKSSDKTHTCPRCPAPELLGGPSVFLFPP
KPKDTLMISRTPEVTCVVVDVSHEDPEVKFKWYVDGVEVHNAKTKPREEQYNSTYRVVSVLTVL
HQDWLNGKEYKCKVSNKALPAPIEKTISKAKGQPREPQVYTLPPSREEMTKNQVSLTCLVKGFYP
SDIAVEWESNGQPENNYKTTPPVLDSDGSFFLYSKLTVDKSRWQQGNVFSCSVMHEALHNHYT
QKSLSLSPGK SEQ ID NO: 108

ISO(-)/ISO(-) Homodimer        pl = 6.27
ISO(-)/ISO(+RR) Heterodimer    pl = 8.37
ISO(+RR)/ISO(+RR) Homodimer    pl = 8.95

Figure 71

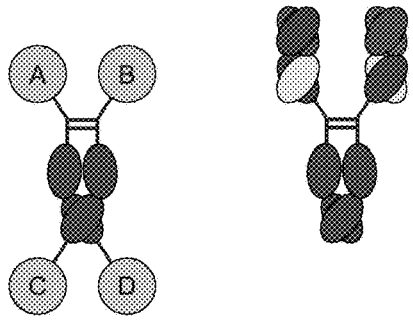

where:
A = Fab_A (with LC_A)
B = Fab_B (with LC_A)
C = n.a.
D = n.a.

Heavy Chain 1 of anti-CD19 x anti-CD3 common light chain mAb [HC ISO(-) (anti-CD19 Fab with anti-CD3 LC)]

EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPSSKSTSGGTAALGCLVKDYFPEPVTVSWNSGALTSGVHTFPAVLQSSGLYSLSSVVTV
PSSSLGTQTYTCNVDHKPSNTKVDKKVEPKSCDKTHTCPPCPAPELLGGPSVFLFPPKPKDTLMI
SRTPEVTCVVVDVSHEDPEVQFNWYVDGVEVHNAKTKPREEQYNSTYRVVSVLTVLHQDWLNG
KEYKCKVSNKALPAPIEKTISKAKGQPREPQVYTLPPSQEEMTKNQVSLTCLVKGFYPSDIAVEW
ESSGQPENNYNTTPPMLDSDGSFFLYSKLTVDKSRWQEGNVFSCSVMHEALHNHYTQKSLSLS
PG    SEQ ID NO: 109

Heavy Chain 2 of anti-CD19 x anti-CD3 common light chain mAb ISO(+RR) [(anti-CD3 Fab with anti-CD3 LC)]

QVQLVQSGAEVKKPGASVKVSCKASGYTFTRYTMHWVRQAPGQGLEWMGYINPSRGYTNYNQ
KFQGRVTMTTDKSTSTAYMELSSLRSEDTAVYYCARYYDDHYSLDYWGQGTTVTVSSASTKGP
SVFPLAPSSKSTSGGTAALGCLVKDYFPEPVTVSWNSGALTSGVHTFPAVLQSSGLYSLSSVVTV
PSSSLGTKTYTCNVNHKPSNTKVDKKVERKSCDKTHTCPRCPAPELLGGPSVFLFPPKPKDTLMI
SRTPEVTCVVVDVSHEDPEVKFKWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLS
PGK    SEQ ID NO: 110

Light Chain of anti-CD19 x anti-CD3 common light chain mAb

QIVLTQSPATLSLSPGERATLSCRASSSVSYMNWYQQKPGQSPRRLIYDTSKLASGVPARFRGS
GSGTDYTLTISSLEPEDFAVYYCQQWSSNPFTFGSGTKLEIKRTVAAPSVFIFPPSDEQLKSGTAS
VVCLLNNFYPREAKVQWKVDNALQSGNSQESVTEQDSKDSTYSLSSTLTLSKADYEKHKVYACE
VTHQGLSSPVTKSFNRGEC    SEQ ID NO: 111

ISO(-)/ISO(-) Homodimer      pI = 7.60
ISO(-)/ISO(+RR) Heterodimer  pI = 8.46
ISO(+RR)/ISO(+RR) Homodimer  pI = 8.95

Figure 72

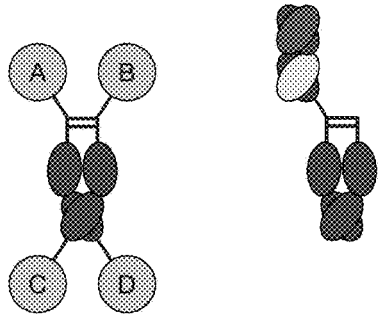

where:
A = Fab
B = n.a.
C = n.a.
D = n.a.

Heavy Chain 1 of anti-CD3 one-arm mAb [HC ISO(-)]

EPKSSDKTHTCPPCPAPELLGGPSVFLFPPKPKDTLMISRTPEVTCVVVDVSHEDPEVQFNWYV
DGVEVHNAKTKPREEQYNSTYRVVSVLTVLHQDWLNGKEYKCKVSNKALPAPIEKTISKAKGQP
REPQVYTLPPSQEEMTKNQVSLTCLVKGFYPSDIAVEWESSGQPENNYNTTPPMLDSDGSFFLY
SKLTVDKSRWQEGNVFSCSVMHEALHNHYTQKSLSLSPG SEQ ID NO: 112

Heavy Chain 2 of anti-CD3 one-arm mAb [HC ISO(+RR) (anti-CD3 Fab)]

QVQLVQSGAEVKKPGASVKVSCKASGYTFTRYTMHWVRQAPGQGLEWMGYINPSRGYTNYNQ
KFQGRVTMTTDKSTSTAYMELSSLRSEDTAVYYCARYYDDHYSLDYWGQGTTVTVSSASTKGP
SVFPLAPSSKSTSGGTAALGCLVKDYFPEPVTVSWNSGALTSGVHTFPAVLQSSGLYSLSSVVTV
PSSSLGTKTYTCNVNHKPSNTKVDKKVERKSCDKTHTCPRCPAPELLGGPSVFLFPPKPKDTLMI
SRTPEVTCVVVDVSHEDPEVKFKWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLS
PGK SEQ ID NO: 113

Light Chain of anti-CD3 one-arm mAb

QIVLTQSPATLSLSPGERATLSCRASSSVSYMNWYQQKPGQSPRRLIYDTSKLASGVPARFRGS
GSGTDYTLTISSLEPEDFAVYYCQQWSSNPFTFGSGTKLEIKRTVAAPSVFIFPPSDEQLKSGTAS
VVCLLNNFYPREAKVQWKVDNALQSGNSQESVTEQDSKDSTYSLSSTLTLSKADYEKHKVYACE
VTHQGLSSPVTKSFNRGEC SEQ ID NO: 114

ISO(-)/ISO(-) Homodimer     pI = 6.37
ISO(-)/ISO(+RR) Heterodimer  pI = 8.35
ISO(+RR)/ISO(+RR) Homodimer  pI = 8.82

Figure 73

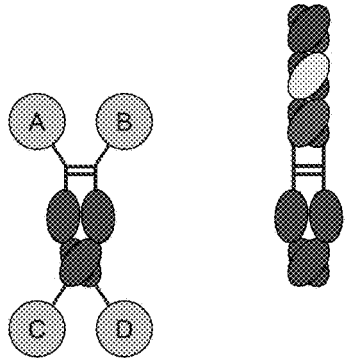

where:
A = VH$_A$-CH1-VH$_B$
B = VL$_A$-CL-VL$_B$
C = n.a.
D = n.a.

Heavy Chain 1 of anti-CD19 x anti-CD3 Fab-Fv-Fc [HC ISO(-) (VL-CL-VL)]

DIVMTQSPATLSLSPGERATLSCRSSKSLQNVNGNTYLYWFQQKPGQSPQLLIYRMSNLNSGVP
DRFSGSGSGTEFTLTISSLEPEDFAVYYCMQHLEYPITFGAGTKLEIKRTVAAPSVFIFPPSDEQLK
SGTASVVCLLNNFYPREAKVQWKVDNALQSGNSQESVTEQDSKDSTYSLSSTLTLSKADYEKHK
VYACEVTHQGLSSPVTKSFNRGECTVAAPSVFIFPPQIVLTQSPATLSLSPGERATLSCRASSSVS
YMNWYQQKPGQSPRRLIYDTSKLASGVPARFRGSGSGTDYTLTISSLEPEDFAVYYCQQWSSN
PFTFGSGTKLEIKEPKSSDKTHTCPPCPAPELLGGPSVFLFPPKPKDTLMISRTPEVTCVVVDVSH
EDPEVQFNWYVDGVEVHNAKTKPREEQYNSTYRVVSVLTVLHQDWLNGKEYKCKVSNKALPAPI
EKTISKAKGQPREPQVYTLPPSQEEMTKNQVSLTCLVKGFYPSDIAVEWESSGQPENNYNTTPP
MLDSDGSFFLYSKLTVDKSRWQEGNVFSCSVMHEALHNHYTQKSLSLSPG SEQ ID NO: 115

Heavy Chain 2 of anti-CD19 x anti-CD3 Fab-Fv-Fc [HC ISO(+RR) (VH-CH1-VH)]

EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPSSKSTSGGTAALGCLVKDYFPEPVTVSWNSGALTSGVHTFPAVLQSSGLYSLSSVVTV
PSSSLGTKTYTCNVNHKPSNTKVDKKVERKSCASTKGPSVFPLAPQVQLVQSGAEVKKPGASVK
VSCKASGYTFTRYTMHWVRQAPGQGLEWMGYINPSRGYTNYNQKFQGRVTMTTDKSTSTAYM
ELSSLRSEDTAVYYCARYYDDHYSLDYWGQGTTVTVSSERKSSDKTHTCPRCPAPELLGGPSVF
LFPPKPKDTLMISRTPEVTCVVVDVSHEDPEVKFKWYVDGVEVHNAKTKPREEQYNSTYRVVSV
LTVLHQDWLNGKEYKCKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQGNVFSCSVMHEALH
NHYTQKSLSLSPGK SEQ ID NO: 116

ISO(-)/ISO(-) Homodimer pI = 6.27
ISO(-)/ISO(+RR) Heterodimer pI = 8.41
ISO(+RR)/ISO(+RR) Homodimer pI = 8.97

Figure 74

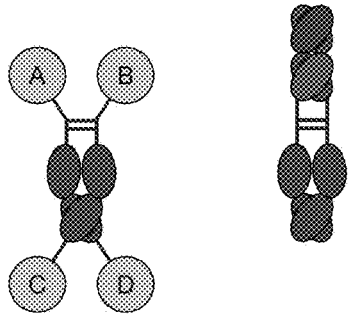

where:
A = VH$_A$-VH$_B$
B = VL$_A$-VL$_B$
C = n.a.
D = n.a.

Heavy Chain 1 of anti-CD19 x anti-CD3 Fv-Fv-Fc [HC ISO(-) (VL-VL)]

DIVMTQSPATLSLSPGERATLSCRSSKSLQNVNGNTYLYWFQQKPGQSPQLLIYRMSNLNSGVP
DRFSGSGSGTEFTLTISSLEPEDFAVYYCMQHLEYPITFGAGTKLEIKTVAAPSVFIFPPQIVLTQSP
ATLSLSPGERATLSCRASSSVSYMNWYQQKPGQSPRRLIYDTSKLASGVPARFRGSGSGTDYTL
TISSLEPEDFAVYYCQQWSSNPFTFGSGTKLEIKEPKSSDKTHTCPPCPAPELLGGPSVFLFPPKP
KDTLMISRTPEVTCVVVDVSHEDPEVQFNWYVDGVEVHNAKTKPREEQYNSTYRVVSVLTVLHQ
DWLNGKEYKCKVSNKALPAPIEKTISKAKGQPREPQVYTLPPSQEEMTKNQVSLTCLVKGFYPSD
IAVEWESSGQPENNYNTTPPMLDSDGSFFLYSKLTVDKSRWQEGNVFSCSVMHEALHNHYTQK
SLSLSPG SEQ ID NO: 117

Heavy Chain 2 of anti-CD19 x anti-CD3 Fv-Fv-Fc [HC ISO(+RR) (VH-VH)]

EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPQVQLVQSGAEVKKPGASVKVSCKASGYTFTRYTMHWVRQAPGQGLEWMGYINPSR
GYTNYNQKFQGRVTMTTDKSTSTAYMELSSLRSEDTAVYYCARYYDDHYSLDYWGQGTTVTVS
SERKSSDKTHTCPRCPAPELLGGPSVFLFPPKPKDTLMISRTPEVTCVVVDVSHEDPEVKFKWYV
DGVEVHNAKTKPREEQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKTTPPVLDSDGSFFLY
SKLTVDKSRWQQGNVFSCSVMHEALHNHYTQKSLSLSPGK SEQ ID NO: 118

ISO(-)/ISO(-) Homodimer pI ≈ 6.31
ISO(-)/ISO(+RR) Heterodimer pI ≈ 8.16
ISO(+RR)/ISO(+RR) Homodimer pI ≈ 8.75

Figure 75

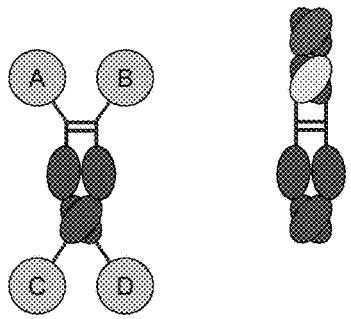

where:
A = VH-CH1
B = VL-CL
C = n.a.
D = n.a.

Heavy Chain 1 of anti-CD3 monovalent mAb [HC ISO(-) (VL-CL)]

QIVLTQSPATLSLSPGERATLSCRASSSVSYMNWYQQKPGQSPRRLIYDTSKLASGVPARFRGS
GSGTDYTLTISSLEPEDFAVYYCQQWSSNPFTFGSGTKLEIKRTVAAPSVFIFPPSDEQLKSGTAS
VVCLLNNFYPREAKVQWKVDNALQSGNSQESVTEQDSKDSTYSLSSTLTLSKADYEKHKVYACE
VTHQGLSSPVTKSFNRGECDKTHTCPPCPAPELLGGPSVFLFPPKPKDTLMISRTPEVTCVVVDV
SHEDPEVQFNWYVDGVEVHNAKTKPREEQYNSTYRVVSVLTVLHQDWLNGKEYKCKVSNKALP
APIEKTISKAKGQPREPQVYTLPPSQEEMTKNQVSLTCLVKGFYPSDIAVEWESSGQPENNYNTT
PPMLDSDGSFFLYSKLTVDKSRWQEGNVFSCSVMHEALHNHYTQKSLSLSPG SEQ ID NO: 119

Heavy Chain 2 of anti-CD3 monovalent mAb [HC ISO(+RR) (VH-CH1)]

QVQLVQSGAEVKKPGASVKVSCKASGYTFTRYTMHWVRQAPGQGLEWMGYINPSRGYTNYNQ
KFQGRVTMTTDKSTSTAYMELSSLRSEDTAVYYCARYYDDHYSLDYWGQGTTVTVSSASTKGP
SVFPLAPSSKSTSGGTAALGCLVKDYFPEPVTVSWNSGALTSGVHTFPAVLQSSGLYSLSSVVTV
PSSSLGTKTYTCNVNHKPSNTKVDKKVERKSCDKTHTCPRCPAPELLGGPSVFLFPPKPKDTLMI
SRTPEVTCVVVDVSHEDPEVKFKWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLS
PGK SEQ ID NO: 120

ISO(-)/ISO(-) Homodimer      pI = 6.37
ISO(-)/ISO(+RR) Heterodimer  pI = 8.39
ISO(+RR)/ISO(+RR) Homodimer  pI = 8.95

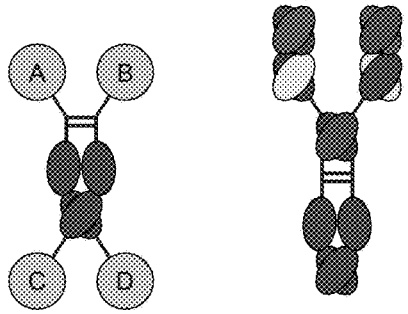

Figure 76 where:
A = Fab-VH$_B$
B = Fab-VL$_B$
C = n.a.
D = n.a.

Heavy Chain 1 of anti-CD19 x anti-CD3 central mAb-Fv [HC ISO(-) (Fab-VH)]  SEQ ID NO: 121
EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPSSKSTSGGTAALGCLVKDYFPEPVTVSWNSGALTSGVHTFPAVLQSSGLYSLSSVVTV
PSSSLGTQTYTCNVDHKPSNTKVDKKVEPKSCASTKGPSVFPLAPQVQLVQSGAEVKKPGASVK
VSCKASGYTFTRYTMHWVRQAPGQGLEWMGYINPSRGYTNYNQKFQGRVTMTTDKSTSTAYM
ELSSLRSEDTAVYYCARYYDDHYSLDYWGQGTTVTVSSEPKSSDKTHTCPPCPAPELLGGPSVF
LFPPKPKDTLMISRTPEVTCVVVDVSHEDPEVQFNWYVDGVEVHNAKTKPREEQYNSTYRVVSV
LTVLHQDWLNGKEYKCKVSNKALPAPIEKTISKAKGQPREPQVYTLPPSQEEMTKNQVSLTCLVK
GFYPSDIAVEWESSGQPENNYNTTPPMLDSDGSFFLYSKLTVDKSRWQEGNVFSCSVMHEALH
NHYTQKSLSLSPG Heavy Chain 2 of anti-CD19 x anti-CD3 central mAb-Fv [HC ISO(+RR) (Fab-VL)]  SEQ ID NO: 122
EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPSSKSTSGGTAALGCLVKDYFPEPVTVSWNSGALTSGVHTFPAVLQSSGLYSLSSVVTV
PSSSLGTKTYTCNVNHKPSNTKVDKKVEPKSCTVAAPSVFIFPPQIVLTQSPATLSLSPGERATLS
CRASSSVSYMNWYQQKPGQSPRRLIYDTSKLASGVPARFRGSGSGTDYTLTISSLEPEDFAVYY
CQQWSSNPFTFGSGTKLEIKERKSSDKTHTCPRCPAPELLGGPSVFLFPPKPKDTLMISRTPEVT
CVVVDVSHEDPEVKFKWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK Light Chain of anti-CD19 x anti-CD3 central mAb-Fv  SEQ ID NO: 123
DIVMTQSPATLSLSPGERATLSCRSSKSLQNVNGNTYLYWFQQKPGQSPQLLIYRMSNLNSGVP
DRFSGSGSGTEFTLTISSLEPEDFAVYYCMQHLEYPITFGAGTKLEIKRTVAAPSVFIFPPSDEQLK
SGTASVVCLLNNFYPREAKVQWKVDNALQSGNSQESVTEQDSKDSTYSLSSTLTLSKADYEKHK
VYACEVTHQGLSSPVTKSFNRGEC ISO(-)/ISO(-) Homodimer      pI = 7.58
ISO(-)/ISO(+RR) Heterodimer  pI = 8.26
ISO(+RR)/ISO(+RR) Homodimer  pI = 8.59

Figure 77

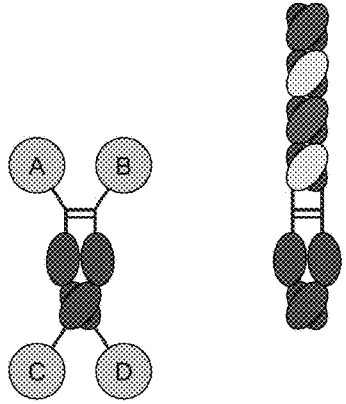

where:
A = VL$_A$-CL-VL$_B$-CL
B = VH$_A$-CH1-VH$_B$-CH1
C = n.a.
D = n.a.

Heavy Chain 1 of anti-CD19 x anti-CD3 Fab-Fab-Fc [HC ISO(-) (VL-CL-VL-CL)]
DIVMTQSPATLSLSPGERATLSCRSSKSLQNVNGNTYLYWFQQKPGQSPQLLIYRMSNLNSGVP
DRFSGSGSGTEFTLTISSLEPEDFAVYYCMQHLEYPITFGAGTKLEIKRTVAAPSVFIFPPSDEQLK
SGTASVVCLLNNFYPREAKVQWKVDNALQSGNSQESVTEQDSKDSTYSLSSTLTLSKADYEKHK
VYACEVTHQGLSSPVTKSFNRGECTVAAPSVFIFPPQIVLTQSPATLSLSPGERATLSCRASSSVS
YMNWYQQKPGQSPRRLIYDTSKLASGVPARFRGSGSGTDYTLTISSLEPEDFAVYYCQQWSSN
PFTFGSGTKLEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGECDKTHTCPPC
PAPELLGGPSVFLFPPKPKDTLMISRTPEVTCVVVDVSHEDPEVQFNWYVDGVEVHNAKTKPRE
EQYNSTYRVVSVLTVLHQDWLNGKEYKCKVSNKALPAPIEKTISKAKGQPREPQVYTLPPSQEEM
TKNQVSLTCLVKGFYPSDIAVEWESSGQPENNYNTTPPMLDSDGSFFLYSKLTVDKSRWQEGNV
FSCSVMHEALHNHYTQKSLSLSPG SEQ ID NO: 124

Heavy Chain 2 of anti-CD19 x anti-CD3 Fab-Fab-Fc [HC ISO(+RR) (VH-CH1-VH-CH1)]
EVQLVESGGGLVKPGGSLKLSCAASGYTFTSYVMHWVRQAPGKGLEWIGYINPYNDGTKYNEK
FQGRVTISSDKSISTAYMELSSLRSEDTAMYYCARGTYYYGTRVFDYWGQGTLVTVSSASTKGP
SVFPLAPSSKSTSGGTAALGCLVKDYFPEPVTVSWNSGALTSGVHTFPAVLQSSGLYSLSSVVTV
PSSSLGTKTYTCNVNHKPSNTKVDKKVERKSCASTKGPSVFPLAPQVQLVQSGAEVKKPGASVK
VSCKASGYTFTRYTMHWVRQAPGQGLEWMGYINPSRGYTNYNQKFQGRVTMTTDKSTSTAYM
ELSSLRSEDTAVYYCARYYDDHYSLDYWGQGTTVTVSSASTKGPSVFPLAPSSKSTSGGTAALG
CLVKDYFPEPVTVSWNSGALTSGVHTFPAVLQSSGLYSLSSVVTVPSSSLGTKTYTCNVNHKPS
NTKVDKKVERKSCDKTHTCPRCPAPELLGGPSVFLFPPKPKDTLMISRTPEVTCVVVDVSHEDPE
VKFKWYVDGVEVHNAKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK SEQ ID NO: 125

ISO(-)/ISO(-) Homodimer pI = 6.24
ISO(-)/ISO(+RR) Heterodimer pI = 8.50
ISO(+RR)/ISO(+RR) Homodimer pI = 9.07

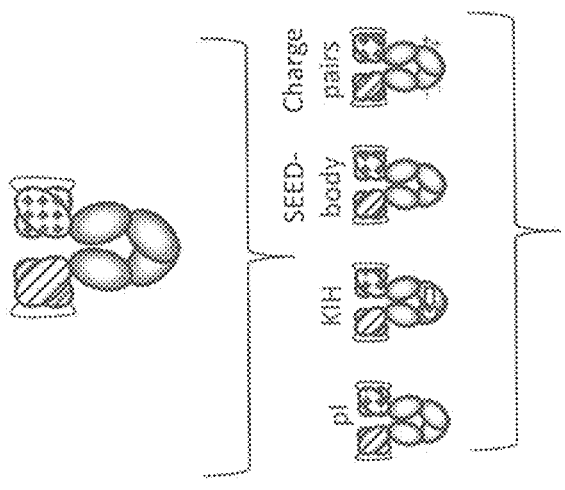

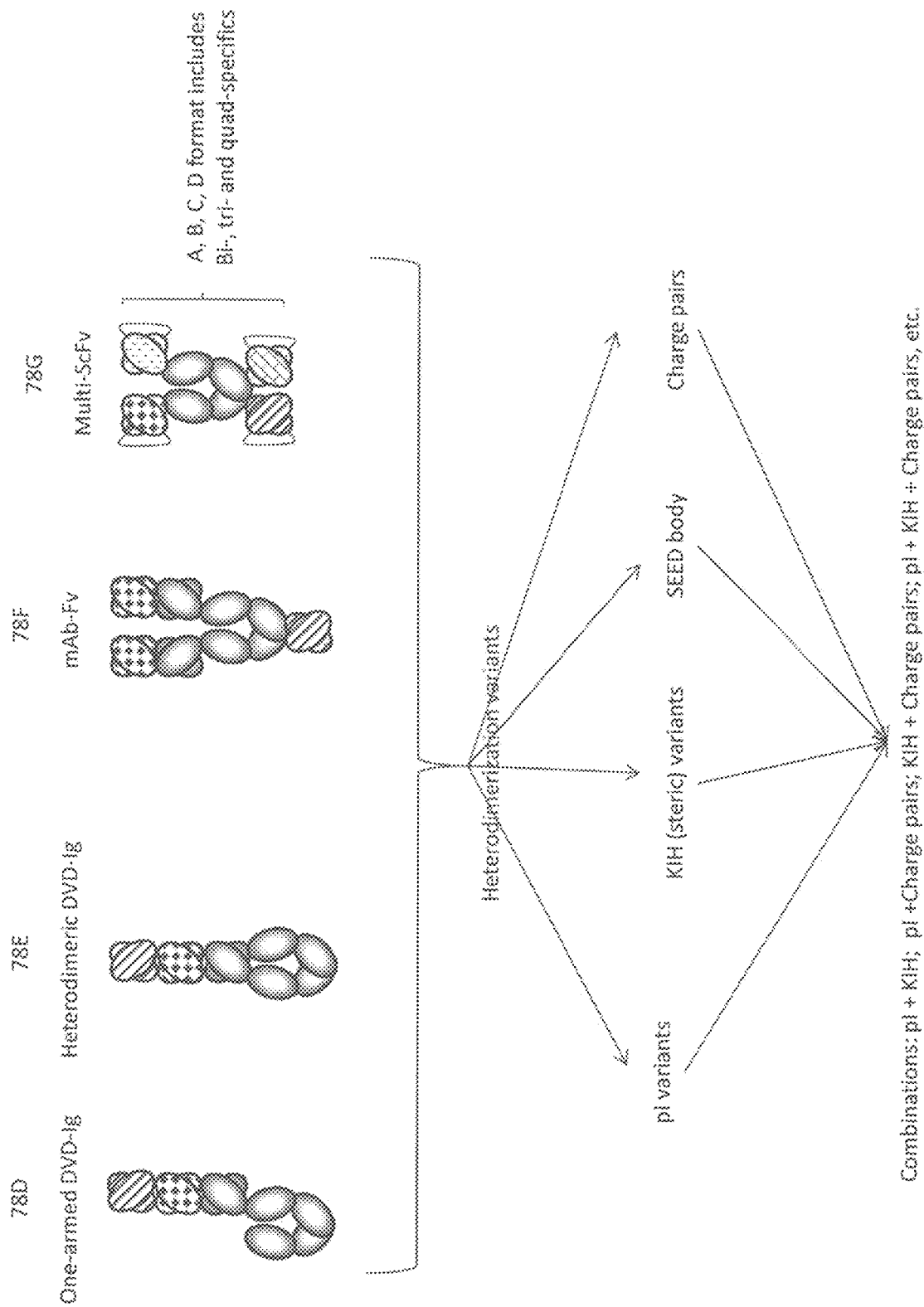

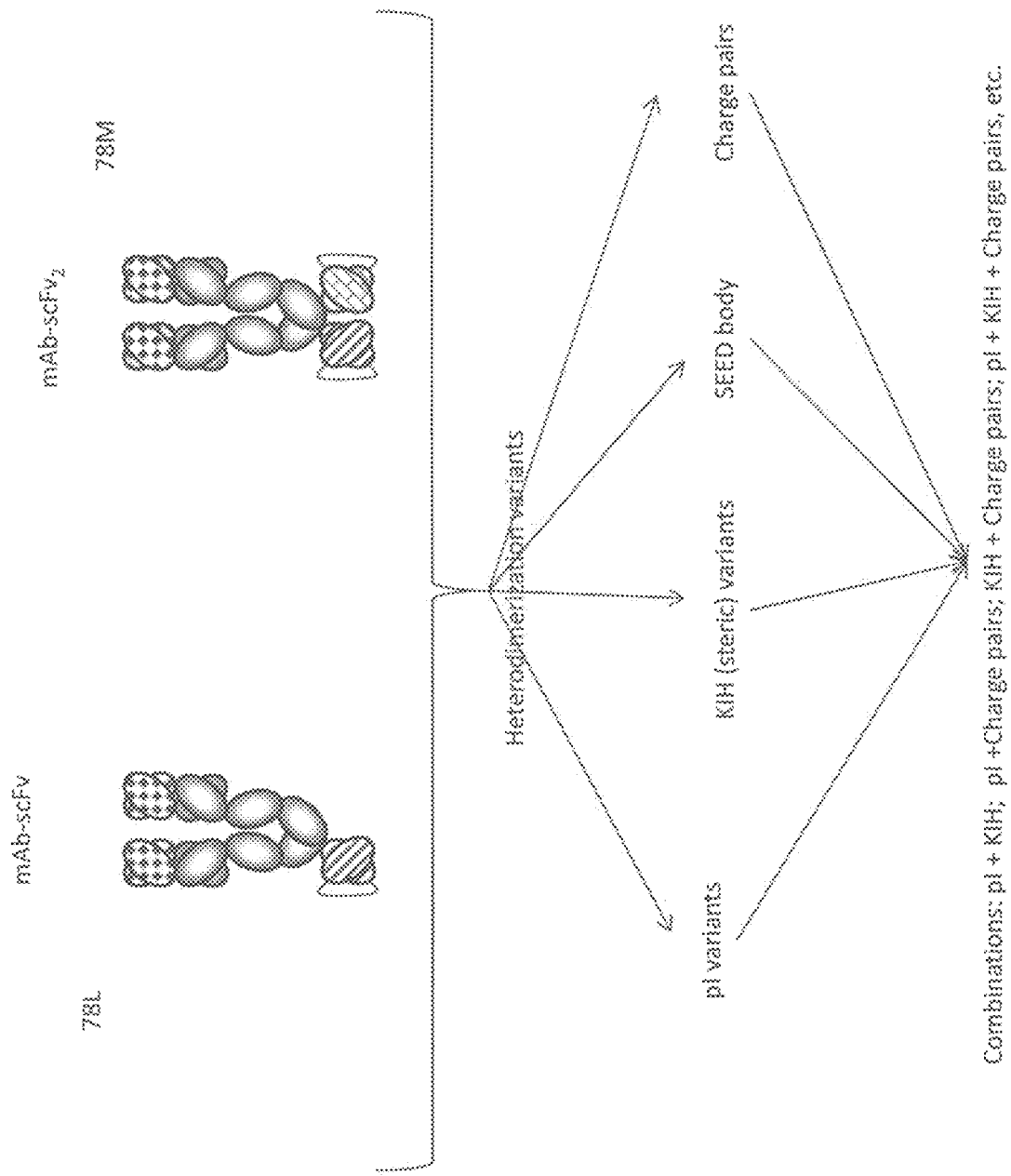

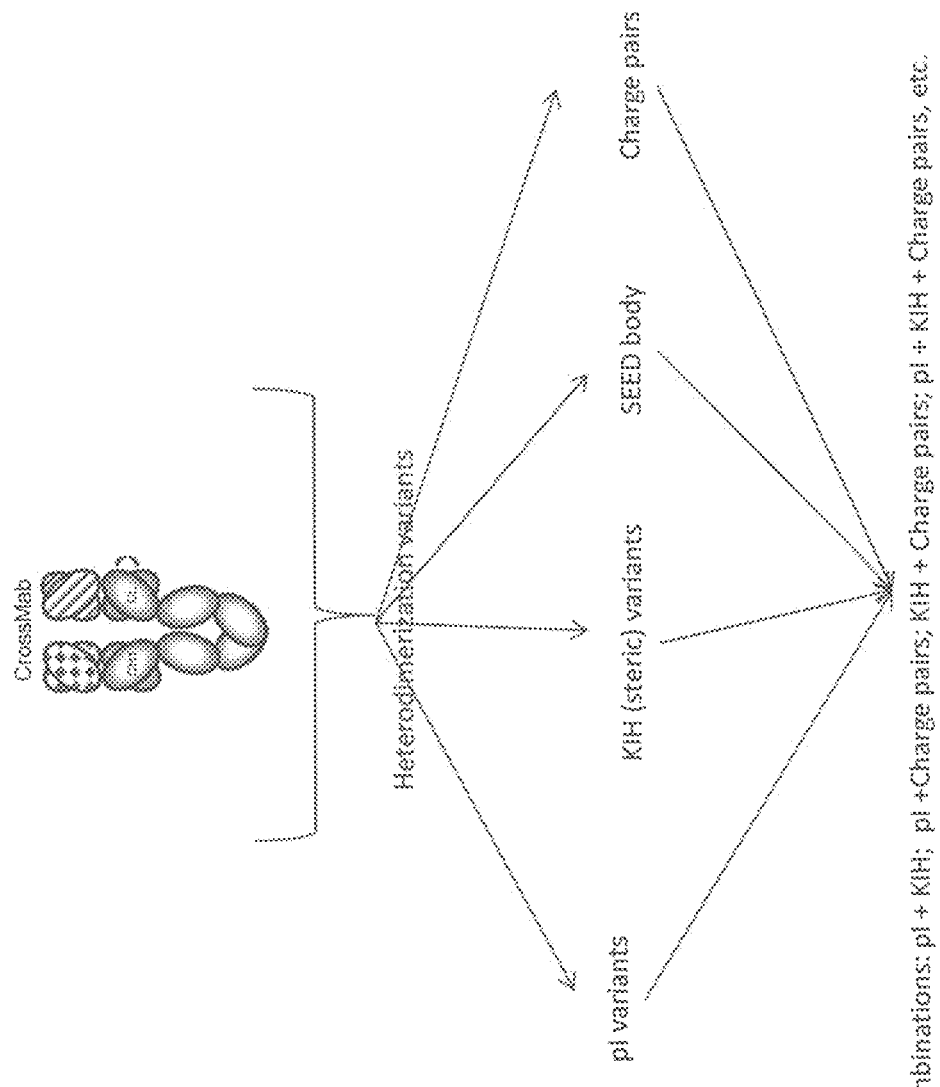

Figure 79A

Preferred steric variants that favor Fc heterodimerization.

| Monomer 1 | Monomer 2 |
|---|---|
| F405A | T394F |
| S364D | Y349K |
| S364E | L368K |
| S364E | Y349K |
| S364F | K370G |
| S364H | Y349K |
| S364H | Y349T |
| S364Y | K370G |
| T411K | K370E |
| V397S/F405A | T394F |
| K370R/T411K | K370E/T411E |
| L351E/S364D | Y349K/L351K |
| L351E/S364E | Y349K/L351K |
| L351E/T366D | L351K/T366K |
| P395T/V397S/F405A | T394F |
| S364D/K370G | S364Y/K370R |
| S364D/T394F | Y349K/F405A |
| S364E/F405A | Y349K/T394F |
| S364E/F405S | Y349K/T394Y |
| S364E/T411E | Y349K/D401K |
| S364H/D401K | Y349T/T411E |
| S364H/F405A | Y349T/T394F |
| S364H/T394F | Y349T/F405A |
| Y349C/S364E | Y349K/S354C |
| L351E/S364D/F405A | Y349K/L351K/T394F |
| L351K/S364H/D401K | Y349T/L351E/T411E |
| S364E/T411E/F405A | Y349K/T394F/D401K |
| S364H/D401K/F405A | Y349T/T394F/T411E |
| S364H/F405A/T411E | Y349T/T394F/D401K |
| Y349T | S364H |
| T394F | F405A |
| Y349T/T394F | S364H/F405A |
| K370E | T411K |
| K370E/T411D | T411K |
| K370E/T411E | K370R/T411K |
| L368E/K409E | L368K |
| Y349T/T411E | S364H/D401K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |

Figure 79B

Specifically preferred steric variants that favor Fc heterodimerization.

| Variant 1 | Variant 2 |
|---|---|
| F405A | T394F |
| S364D | Y349K |
| S364E | Y349K |
| S364H | Y349T |
| L351K | L351E |
| D401K | T411E |
| S364D/T394F | Y349K/F405A |
| S364E/F405A | Y349K/T394F |
| S364H/D401K | Y349T/T411E |
| S364H/F405A | Y349T/T394F |
| S364H/T394F | Y349T/F405A |
| L351K/S364H/D401K | Y349T/L351E/T411E |
| S364H/D401K/F405A | Y349T/T394F/T411E |
| S364H/F405A/T411E | Y349T/T394F/D401K |
| Y349T | S364H |
| T394F | F405A |
| Y349T/T394F | S364H/F405A |
| K370E | T411K |
| K370E/T411D | T411K |
| K370E/T411E | K370R/T411K |
| L368E/K409E | L368K |
| Y349T/T411E | S364H/D401K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |

Figure 80A

PREFERRED HETERODIMERIZATION VARIANTS

| Fc monomer 1 substitutions | Fc monomer 2 substitutions |
|---|---|
| Y407T | T366Y |
| F405A | T394W |
| T366Y/F405A | T394W/Y407T |
| Y407A | T366W |
| T366S/L368A/Y407V | T366W |
| T366S/L368A/Y407V/Y349C | T366W/S354C |
| K392D/K409D | E356K/D399K |
| K370D/K392D/K409D | E356K/E357K/D399K |
| Y349T | S364H |
| T394F | F405A |
| Y349T/T394F | S364H/F405A |
| K370E | T411K |
| K370E/T411D | T411K |
| K370E/T411E | K370R/T411K |
| L368E/K409E | L368K |
| Y349T/T411E | S364H/D401K |
| Y349T/T394F/S354C | S364H/F405A/Y349C |
| T411E | D401K |
| T411E | D401R/T411R |
| Q347E/K360E | Q347R |
| L368E | S364K |
| I199T/N203D/K247Q/R355Q/N384S/K392N/V397M/Q419E/K447_ (deletion of K447) | Q196K/I199T/P217R/P228R/N276K |
| I199T/N203D/K247Q/R355Q/N384S/K392N/V397M/Q419E/K447 | Q196K/I199T/N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| Y349T | S364H |
| T394F | F405A |
| Y349T/T394F | S364H/F405A |
| K370E | T411K |
| K370E/T411D | T411K |
| K370E/T411E | K370R/T411K |
| L368E/K409E | L368K |
| Y349T/T411E | S364H/D401K |
| Y349T/T394F/S354C | S364H/F405A/Y349C |
| T411E | D401K |
| T411E | D401R/T411R |

Figure 80B

| | |
|---|---|
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |

Figure 81A

HETERODIMERIZATION VARIANTS

| | IgG1 | IgG2 | IgG3 | IgG4 | Variants |
|---|---|---|---|---|---|
| 196 | Q | Q | Q | K | K |
| 199 | I | T | T | T | T |
| 203 | N | D | N | D | D |
| 217 | P | R | L | S | R |
| 220 | C | C | P | G | E,R (IgG2) |
| 221 | D | | LGD | | E,R (IgG1) |
| 222 | K | V | T | | E,R (IgG2) |
| 223 | T | | T | | D,E,R,K |
| 225 | T | | T | P | D,E,R,K |
| 228 | P | P | RCPEPK SCDTPP PCPRCP EPKSCD TPPPCP RCPEPK SCDTPP PCPR | S | D,E,R,K |
| 247 | P | P | P | P | Q |
| 276 | N | N | K | N | K |
| 340 | K | K | K | K | E,Q |
| 345 | E | E | E | E | K |
| | Q | Q | Q | Q | E,K,R |
| 349 | Y | Y | Y | Y | A,C,D,E,I,K,S,T,W |
| 350 | T | T | T | T | I |
| 351 | L | L | L | L | E,K,V,Y |
| 354 | S | S | S | S | C |
| 355 | R | R | R | Q | E,Q |
| 356 | D | E | E | E | K,L,R |
| 357 | E | E | E | E | K,R,Q,T |
| | K | K | K | K | D,E |
| 362 | Q | Q | Q | Q | E,K |
| | S | S | S | S | C,D,E,F,G,H,K,R,T,Y |
| 366 | T | T | T | T | A,D,I,K,L,M,S,V,W,Y |
| | L | L | L | L | A,D,E,K,S all but C,P |
| 370 | K | K | K | K | C,D,E,G,R,S,T,V all but C,P |
| 371 | G | G | G | G | D |
| 384 | N | N | S | N | S |
| 390 | N | N | N | N | D,E,K,R |
| 392 | K | K | N | K | C,D,E,F,L,M,N |
| 394 | T | T | T | T | F,S,V,W,Y |

Figure 81B

| | IgG1 | IgG2 | IgG3 | IgG4 | Variants |
|---|---|---|---|---|---|
| 395 | P | P | P | P | T,V |
| 396 | P | P | P | P | T,V |
| 397 | V | M | M | V | M,S,T |
| 399 | D | D | D | D | all but C,P<br>C,K,R |
| 400 | S | S | S | S | A,D,E,K,R |
| 401 | D | D | D | D | K,N,R |
| 405 | F | F | F | F | L, all but C,P<br>A,F,L,M,S,T,V |
| 407 | Y | Y | Y | Y | T,V<br>all but C,P<br>A,L,M,V |
| 409 | K | K | K | R | R<br>,all but C,P<br>D,E,F,K,L,M,V,W |
|  | T | T | T | T | D,E,K,L,N,R,S |
| 419 | Q | Q | Q | E | E |
| 439 | K | K | K | K | D,E |

Figure 82

| Fc monomer 1 substitutions | Fc monomer 2 substitutions |
|---|---|
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| N203D/K247Q/R355Q/N384S/K392N/V397M/Q419E/K447_ | Q196K/P217R/P228R/N276K |
| N203D/K247Q/R355Q/N384S/K392N/V397M/Q419E/K447_ | Q196K/N276K |
| N203D/K247Q/R355Q/N384S/K392N/Q419E/K447_ | Q196K/P217R/P228R/N276K |
| N203D/K247Q/R355Q/N384S/K392N/Q419E/K447_ | Q196K/N276K |

Figure 83

COMBINATIONS OF VARIANTS INTO HETERODIMERIZATION FORMATS

| Heterodimerization format | FcRn variants Monomer 1 and/or Monomer 2 | Fc variants Monomer 1 and/or Monomer 2 | pI variants | Steric variants (including charge pairs) | Combinations (See Legend E) |
|---|---|---|---|---|---|
| Dual scFv-Fv (Fig 76A) | See Legend A | See Legend B | See Legend C | See Legend D | 1), 2), 3), 4), 5), 6), 7), 8), 9) and 10) |
| Bispecific IgG (Fig 78B) | See Legend A | See Legend B | See Legend C | See Legend D | 1), 2), 3), 4), 5), 6), 7), 8), 9) and 10) |
| Common Light Chain (Fig 78C) | See Legend A | See Legend B | See Legend C | See Legend D | 1), 2), 3), 4), 5), 6), 7), 8), 9) and 10) |
| One-armed DVD-Ig (Fig 78D) | See Legend A | See Legend B | See Legend C | See Legend D | 1), 2), 3), 4), 5), 6), 7), 8), 9) and 10) |
| Heterodimeric DVD-Ig (Fig 78E) | See Legend A | See Legend B | See Legend C | See Legend D | 1), 2), 3), 4), 5), 6), 7), 8), 9) and 10) |
| mAb-Fv (Fig 78F) | See Legend A | See Legend B | See Legend C | See Legend D | 1), 2), 3), 4), 5), 6), 7), 8), 9) and 10) |
| Multi-ScFv (Fig 78G) | See Legend A | See Legend B | See Legend C | See Legend D | 1), 2), 3), 4), 5), 6), 7), 8), 9) and 10) |
| Heterodimeric Fab-Fc (Fig 76H) | See Legend A | See Legend B | See Legend C | See Legend D | 1), 2), 3), 4), 5), 6), 7), 8), 9) and 10) |
| One-armed Fab-Fc (Fig 78I) | See Legend A | See Legend B | See Legend C | See Legend D | 1), 2), 3), 4), 5), 6), 7), 8), 9) and 10) |
| One-armed scFv-Fc (Fig 78J) | See Legend A | See Legend B | See Legend C | See Legend D | 1), 2), 3), 4), 5), 6), 7), 8), 9) and 10) |
| scFv-CH3 (Fig 78K) | See Legend A | See Legend B | See Legend C | See Legend D | 1), 2), 3), 4), 5), 6), 7), 8), 9) and 10) |
| mAb-scFv (Fig 78L) | See Legend A | See Legend B | See Legend C | See Legend D | 1), 2), 3), 4), 5), 6), 7), 8), 9) and 10) |
| mAb-scFv2 (Fig 78M) | See Legend A | See Legend B | See Legend C | See Legend D | 1), 2), 3), 4), 5), 6), 7), 8), 9) and 10) |
| CrossMab (Fig 78N) | See Legend A | See Legend B | See Legend C | See Legend D | 1), 2), 3), 4), 5), 6), 7), 8), 9) and 10) |
| IgG Antibody (Fig 78O) | See Legend A | See Legend B | See Legend C | See Legend D | 1), 2), 3), 4), 5), 6), 7), 8), 9) and 10) |
| mAb-Fv (Fig 78P) | See Legend A | See Legend B | See Legend C | See Legend D | 1), 2), 3), 4), 5), 6), 7), 8), 9) and 10) |
| mAb-Fab (Fig 78Q) | See Legend A | See Legend B | See Legend C | See Legend D | 1), 2), 3), 4), 5), 6), 7), 8), 9) and 10) |
| Fab-Fv (Fig 78R) | See Legend A | See Legend B | See Legend C | See Legend D | 1), 2), 3), 4), 5), 6), 7), 8), 9) and 10) |
| Fab-Fab (Fig 78S) | See Legend A | See Legend B | See Legend C | See Legend D | 1), 2), 3), 4), 5), 6), 7), 8), 9) and 10) |

HETERODIMERIC PROTEINS

CROSS-REFERENCE TO RELATED APPLICATIONS

This application is a continuation of U.S. patent application Ser. No. 15/444,026, filed Feb. 27, 2017 which is a continuation of U.S. patent application Ser. No. 14/200,821, filed Mar. 7, 2014 which claims the benefit of U.S. Provisional Application No. 61/794,695, filed Mar. 15, 2013, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 25, 2019, is named 067461_5167_US02_ST25.txt and is 431,032 bytes in size.

INCORPORATION OF RELATED APPLICATIONS

The following applications are incorporated by reference in their entirety, U.S. Ser. Nos. 61/302,707, 61/732,813, 61/598,686, 61/441,552, 13/648,951, 12/875,015; 61/311,472; 61/450,457; 61/545,498; 61/239,316; 13/568,028; 61/515,745; 61/785,241; 61/785,265; 61/752,349; 61/764,954; 61/780,310; 61/780,334; 13/194,904; 61/368,969; 61/391,509; 61/391,515; 61/439,263; 61/593,846; 61/368,962.

BACKGROUND OF THE INVENTION

Antibody-based therapeutics have been used successfully to treat a variety of diseases, including cancer and autoimmune/inflammatory disorders. Yet improvements to this class of drugs are still needed, particularly with respect to enhancing their clinical efficacy. One avenue being explored is the engineering of additional and novel antigen binding sites into antibody-based drugs such that a single immunoglobulin molecule co-engages two different antigens. Such non-native or alternate antibody formats that engage two different antigens are often referred to as bispecifics. Because the considerable diversity of the antibody variable region (Fv) makes it possible to produce an Fv that recognizes virtually any molecule, the typical approach to bispecific generation is the introduction of new variable regions into the antibody.

A number of alternate antibody formats have been explored for bispecific targeting (Chames & Baty, 2009, mAbs 1[6]:1-9; Holliger & Hudson, 2005, Nature Biotechnology 23[9]:1126-1136; Kontermann, mAbs 4(2):182 (2012), all of which are expressly incorporated herein by reference). Initially, bispecific antibodies were made by fusing two cell lines that each produced a single monoclonal antibody (Milstein et al., 1983, Nature 305:537-540). Although the resulting hybrid hybridoma or quadroma did produce bispecific antibodies, they were only a minor population, and extensive purification was required to isolate the desired antibody. An engineering solution to this was the use of antibody fragments to make bispecifics. Because such fragments lack the complex quaternary structure of a full length antibody, variable light and heavy chains can be linked in single genetic constructs. Antibody fragments of many different forms have been generated, including diabodies, single chain diabodies, tandem scFv's, and Fab$_2$ bispecifics (Chames & Baty, 2009, mAbs 1[6]:1-9; Holliger & Hudson, 2005, Nature Biotechnology 23[9]:1126-1136; expressly incorporated herein by reference). While these formats can be expressed at high levels in bacteria and may have favorable penetration benefits due to their small size, they clear rapidly in vivo and can present manufacturing obstacles related to their production and stability. A principal cause of these drawbacks is that antibody fragments typically lack the constant region of the antibody with its associated functional properties, including larger size, high stability, and binding to various Fc receptors and ligands that maintain long half-life in serum (i.e. the neonatal Fc receptor FcRn) or serve as binding sites for purification (i.e. protein A and protein G).

More recent work has attempted to address the shortcomings of fragment-based bispecifics by engineering dual binding into full length antibody-like formats (Wu et al., 2007, Nature Biotechnology 25[11]:1290-1297; U.S. Ser. No. 12/477,711; Michaelson et al., 2009, mAbs 1[2]:128-141; PCT/US2008/074693; Zuo et al., 2000, Protein Engineering 13[5]:361-367; U.S. Pat. No. 9,865,198; Shen et al., 2006, J Biol Chem 281[16]:10706-10714; Lu et al., 2005, J Biol Chem 280[20]:19665-19672; PCT/US2005/025472; expressly incorporated herein by reference). These formats overcome some of the obstacles of the antibody fragment bispecifics, principally because they contain an Fc region. One significant drawback of these formats is that, because they build new antigen binding sites on top of the homodimeric constant chains, binding to the new antigen is always bivalent.

For many antigens that are attractive as co-targets in a therapeutic bispecific format, the desired binding is monovalent rather than bivalent. For many immune receptors, cellular activation is accomplished by cross-linking of a monovalent binding interaction. The mechanism of cross-linking is typically mediated by antibody/antigen immune complexes, or via effector cell to target cell engagement. For example, the low affinity Fc gamma receptors (FcγRs) such as FcγRIIa, FcγRIIb, and FcγRIIIa bind monovalently to the antibody Fc region. Monovalent binding does not activate cells expressing these FcγRs; however, upon immune complexation or cell-to-cell contact, receptors are cross-linked and clustered on the cell surface, leading to activation. For receptors responsible for mediating cellular killing, for example FcγRIIIa on natural killer (NK) cells, receptor cross-linking and cellular activation occurs when the effector cell engages the target cell in a highly avid format (Bowles & Weiner, 2005, J Immunol Methods 304:88-99, expressly incorporated by reference). Similarly, on B cells the inhibitory receptor FcγRIIb downregulates B cell activation only when it engages into an immune complex with the cell surface B-cell receptor (BCR), a mechanism that is mediated by immune complexation of soluble IgG's with the same antigen that is recognized by the BCR (Heyman 2003, Immunol Lett 88[2]:157-161; Smith and Clatworthy, 2010, Nature Reviews Immunology 10:328-343; expressly incorporated by reference). As another example, CD3 activation of T-cells occurs only when its associated T-cell receptor (TCR) engages antigen-loaded MHC on antigen presenting cells in a highly avid cell-to-cell synapse (Kuhns et al., 2006, Immunity 24:133-139). Indeed nonspecific bivalent cross-linking of CD3 using an anti-CD3 antibody elicits a cytokine storm and toxicity (Perruche et al., 2009, J Immunol 183 [2]:953-61; Chatenoud & Bluestone, 2007, Nature Reviews Immunology 7:622-632; expressly incorporated by reference). Thus for practical clinical use, the preferred mode of CD3 co-engagement for redirected killing of targets cells is monovalent binding that results in activation only upon engagement with the co-engaged target.

Thus while bispecifics generated from antibody fragments suffer biophysical and pharmacokinetic hurdles, a drawback of those built with full length antibody-like formats is that they engage co-target antigens multivalently in the absence of the primary target antigen, leading to nonspecific activation and potentially toxicity. The present invention solves this problem by introducing a novel set of bispecific formats that enable the multivalent co-engagement of distinct target antigens.

BRIEF SUMMARY OF THE INVENTION

The present invention describes novel immunoglobulin compositions that co-engage at least two antigens, e.g. a first and second antigen, or, as outlined herein, three or four antigens can be bound, in some of the scaffold formats described herein. First and second antigens of the invention are herein referred to as antigen-1 and antigen-2 respectively (or antigen-3 and antigen-4, if applicable. As outlined herein, a number of different formats can be used, with some scaffolds relying combinations of monovalent and bivalent bindings.

In preferred embodiments of the invention, the antigen binding regions of the immunoglobulin are antibody variable regions. In these embodiments, binding to antigens is mediated by variable regions, also referred to as Fv regions, each comprising a VH domain and a VL domain. The Fv region that binds antigen-1 is referred to as Fv-1, while the Fv region that binds antigen-2 is referred to as Fv-2, etc. However, as outlined herein, ligands can also be used in the "Fc fusion" constructs outlined herein.

The present invention describes methods for generating the novel compositions of the invention. The present invention describes purification methods for the immungloublins herein, particularly methods for separating heterodimeric and homodimeric protein species. Also described are methods of testing the immunoglobulins herein, including in vitro and in vivo experiments.

The present invention provides isolated nucleic acids encoding the novel immunoglobulin compositions described herein. The present invention provides vectors comprising said nucleic acids, optionally, operably linked to control sequences. The present invention provides host cells containing the vectors, and methods for producing and optionally recovering the immunoglobulin compositions.

The present invention provides compositions comprising immunoglobulin polypeptides described herein, and a physiologically or pharmaceutically acceptable carrier or diluent.

The present invention contemplates therapeutic and diagnostic uses for the immunoglobulin polypeptides disclosed herein.

Thus, in one aspect, the present invention provides compositions comprising a heterodimer protein comprising a a first monomer comprising a first variant heavy chain constant region and a first fusion partner; and a second monomer comprising: a second variant heavy chain constant region and a second fusion partner. In some cases the heterodimeric proteins are constructed such that the isoelectric points (pIs) of the first and second variant heavy chain constant regions are at least 0.5 logs apart. In additional cases, the Fc region of the first and second constant regions comprise a set of amino acid substitutions from FIG. 79. In additional cases, the Fc region of said first and second constant regions comprise a set of amino acid substitutions from FIG. 80. In further cases, the Fc region of the first and second constant regions comprise a set of amino acid substitutions from FIG. 82.

In further aspects, the heterodimeric protein compositions of the invention has a structure selected from the group consisting of the structures in FIGS. 78A-78N and 78P-78S.

In an addition aspect, any of the heterodimeric proteins, particularly heterodimeric antibodies, has a first monomer comprising at these the pI substitutions ISO(−): I199T/N203D/K274Q/R355Q/N384S/K392N/V397M/Q419E/DEL44 and monomer 2 comprises pI substitutions ISO(+RR): Q196K/I199T/P217R/P228R/N276K.

In further aspects, the heterdimeric proteins of the invention can have a third fusion partner. In some aspects, the heterdimeric proteins of the invention can have a fourth fusion partner.

In further aspects, the fusion partners are independently selected from the group consisting of an immunoglobulin component, a peptide, a cytokine, a chemokine, an immune receptor and a blood factor. The immunoglobulin component can be selected from the group consisting of Fab, VH, VL, scFv, scFv2, dAb. In some cases, two, three or four of the fusion partners are immunoglobulin components, in particular, scFv and Fab components find particular use as fusion partners. In some cases, the fusion partner cytokine is selected from the group consisting of IL-2, IL-10, IL-12 and GM-CSF. In some cases, the fusion partner chemokine is selected from the group consisting of RANTES, CXCL9, CXCL10 and CXCL12. In some cases, the fusion partner immune receptor is selected from the group consisting of CTLA-4, TNFRI, TNFRII, a TNFSF protein, and TNFRSF. In some cases, the fusion partner blood factor is selected from the group consisting of Factor VII, Factor VIII and Factor IX. Any and all of these fusion partners may be independently and optionally combined with any other.

In an additional aspect, at least one Fc domain of one monomer heavy chain comprises an amino acid variant selected from the group consisting of 236A, 239D, 239E, 332E, 332D, 239D/332E, 267D, 267E, 328F, 267E/328F, 236A/332E, 239D/332E/330Y, 239D, 332E/330L, 236R, 328R, 236R/328R, 243L, 298A and 299T. In these cases, the heterodimeric protein can have altered binding to FcγR receptors, particularly increased binding to FcγRIIb and/or FcγRIIIa. IN some cases both monomers comprise the Fc variants.

In a further aspect, at least one Fc domain of one monomer heavy chain comprises an amino acid variant selected from the group consisting of 434A, 434S, 428L, 308F, 259I, 428L/434S, 259I/308F, 436I/428L, 436I or V/434S, 436V/428L, 252Y, 252Y/254T/256E and 259I/308F/428L. In these cases, the heterodimeric protein can have altered binding to FcRn receptors, particularly increased binding. In some cases both monomers comprise the Fc variants.

BRIEF DESCRIPTION OF THE DRAWINGS

FIG. 1. Amino acid sequences of wild-type constant regions used in the invention.

FIG. 2A-2C. Engineering of heavy chain CH1 domains. List of CH1 residues for the four IgG isotypes, fraction exposed, and examples of substitutions that can be made to lower pI. Numbering is according to the EU index.

FIG. 3A-3C. Engineering of light chain CK domains. List of CK residues, fraction exposed, and substitutions that can be made to lower pI. Numbering is according to the EU index.

FIG. 4. Amino acid sequences of pI engineered constant regions IgG1-CH1-pI(6) and CK-pI(6).

FIG. 5. Amino acid sequences of wild-type anti-VEGF VH and VL variable regions used in the invention.

FIG. 6. Amino acid sequences of the heavy and light chains of pI engineered anti-VEGF antibody XENP9493 IgG1-CH1-pI(6)-CK-pI(6) used in the invention.

FIG. 17A-17D. Amino acid sequence alignment of the IgG subclasses. Residues with a bounded box illustrate isotypic differences between the IgG's. Residues which contribute to a higher pI (K, R, and H) or lower pI (D and E) are highlighted in bold. Designed substitutions that either lower the pI, or extend an epitope are shown in gray.

FIG. 18. Amino acid sequence of the CK and Cλ light constant chains. Residues which contribute to a higher pI (K, R, and H) or lower pI (D and E) are highlighted in bold. Preferred positions that can be modified to lower the pI are shown in gray.

FIG. 19A-19B. Amino acid sequences of pI-engineered variant heavy chains.

FIG. 20. Amino acid sequences of pI-engineered variant light chains.

FIG. 23. Correlation between half-life and isoelectric point (pI) of native bevacizumab antibodies, pI-engineered variant versions with reduced pI, and native and pI-engineered versions that incorporate Fc modifications that improve binding to human FcRn.

FIG. 24A-24C. Amino acid sequence alignment of novel isotype IgG-pI-Iso3 with the IgG subclasses. Blue indicates a match between pI-iso3 and residues in the four native IgG's IgG1, IgG2, IgG3, and IgG4. Residues with a bounded box illustrate IgG isotypic differences that have been incorporated into IgG-pI-Iso3 that reduce pI.

FIG. 27. Amino acid illustration of the CK-pI(4) variant. Red indicates lysine to glutamic acid charge substitutions relative to the native CK light constant chain.

FIG. 28A-28D. Amino acid sequences of pI-engineered heavy and light constant chains.

FIG. 29. Analysis of basic residues in the antibody Fc region showing fraction exposed and the calculated energy for substitution to Glu normalized against the energy of the WT residue. Basic residues with a high fraction exposed and a favorable delta E for substitution to Glu are targets for charge swap mutations to lower pI.

FIG. 36. Literature pIs of the 20 amino acids. It should be noted that the listed pIs are calculated as free amino acids; the actual pI of any side chain in the context of a protein is different, and thus this list is used to show pI trends and not absolute numbers for the purposes of the invention.

Figure 37A:
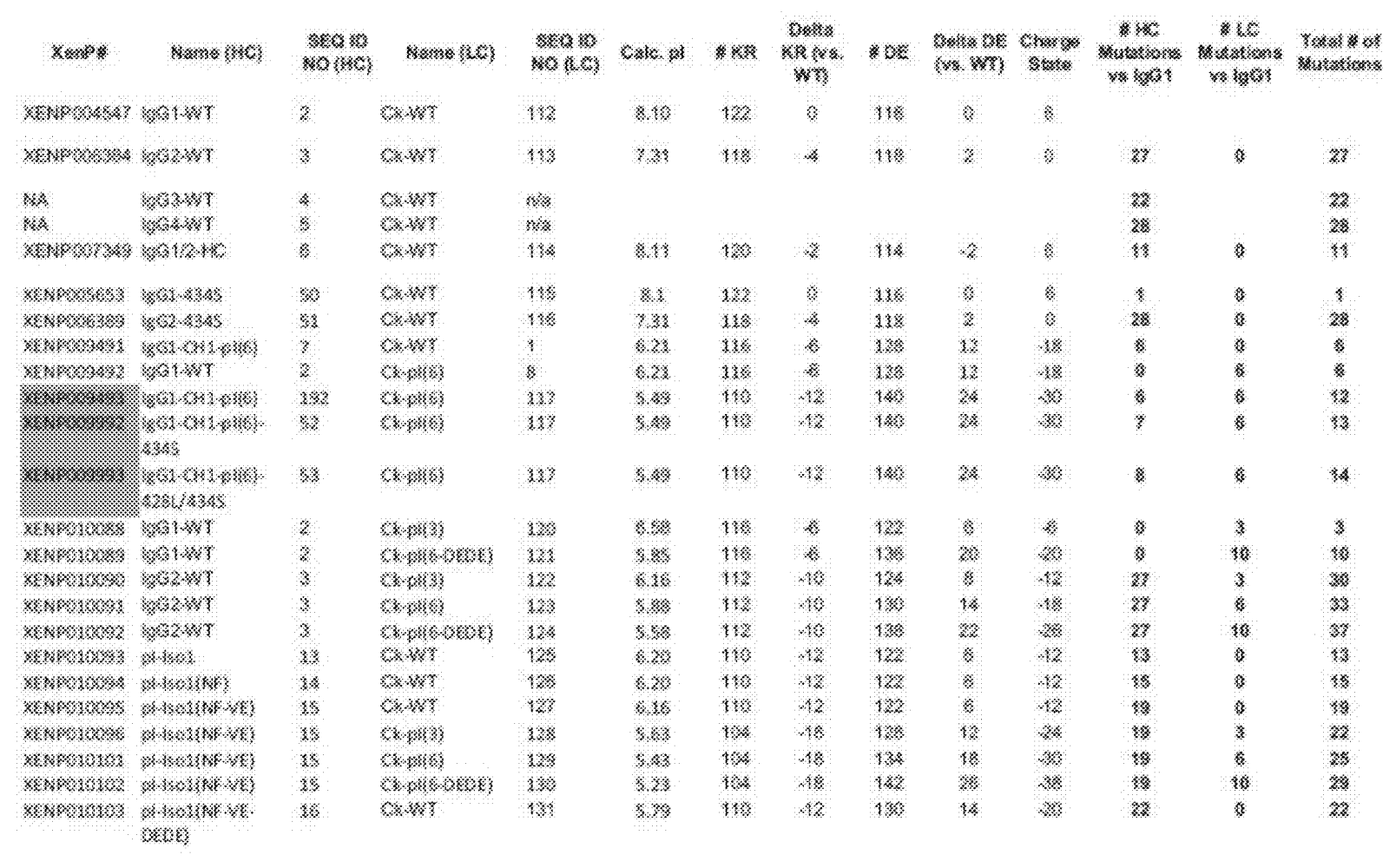
Figure 37B:
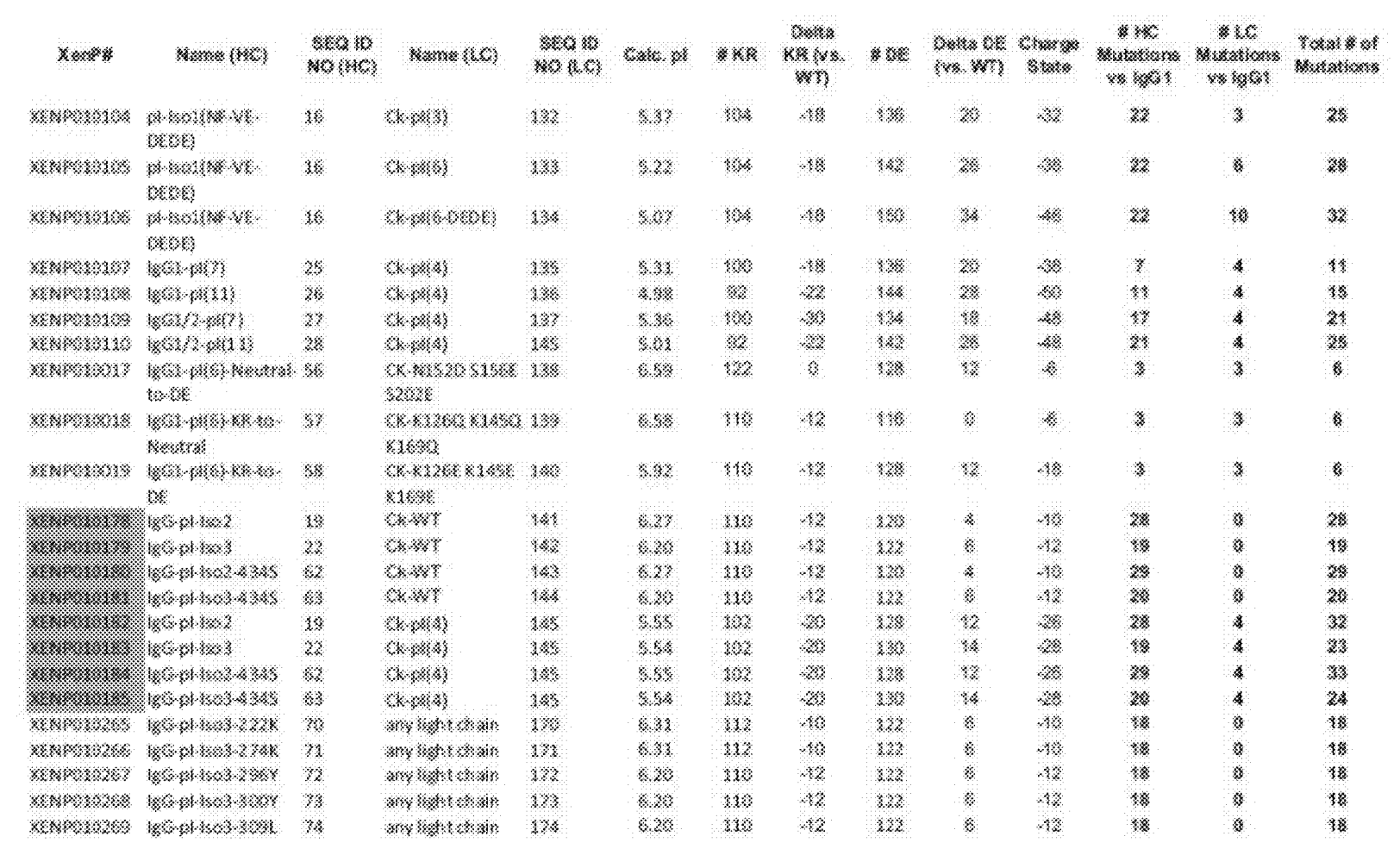
Figure 37C:
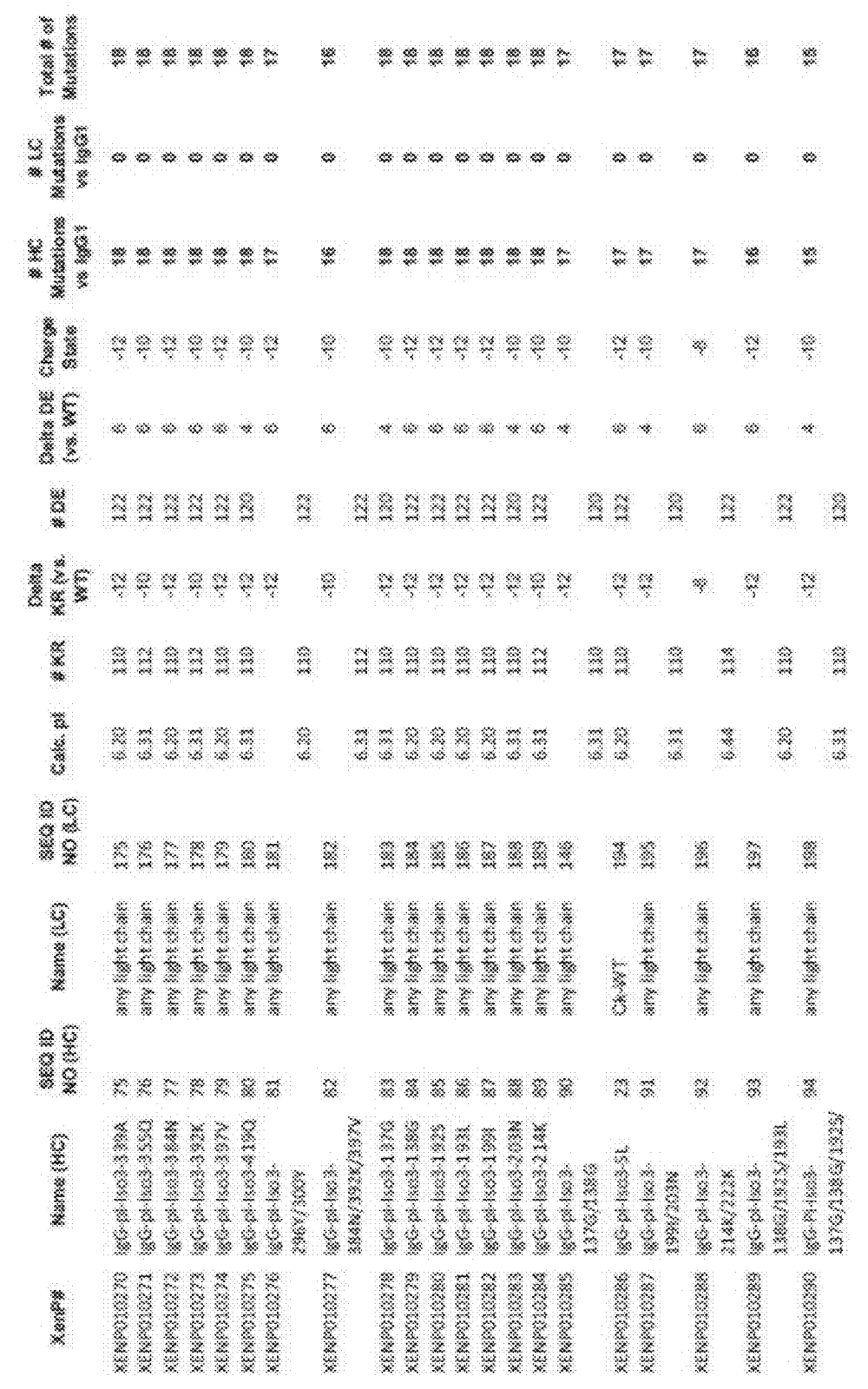
Figure 37D:
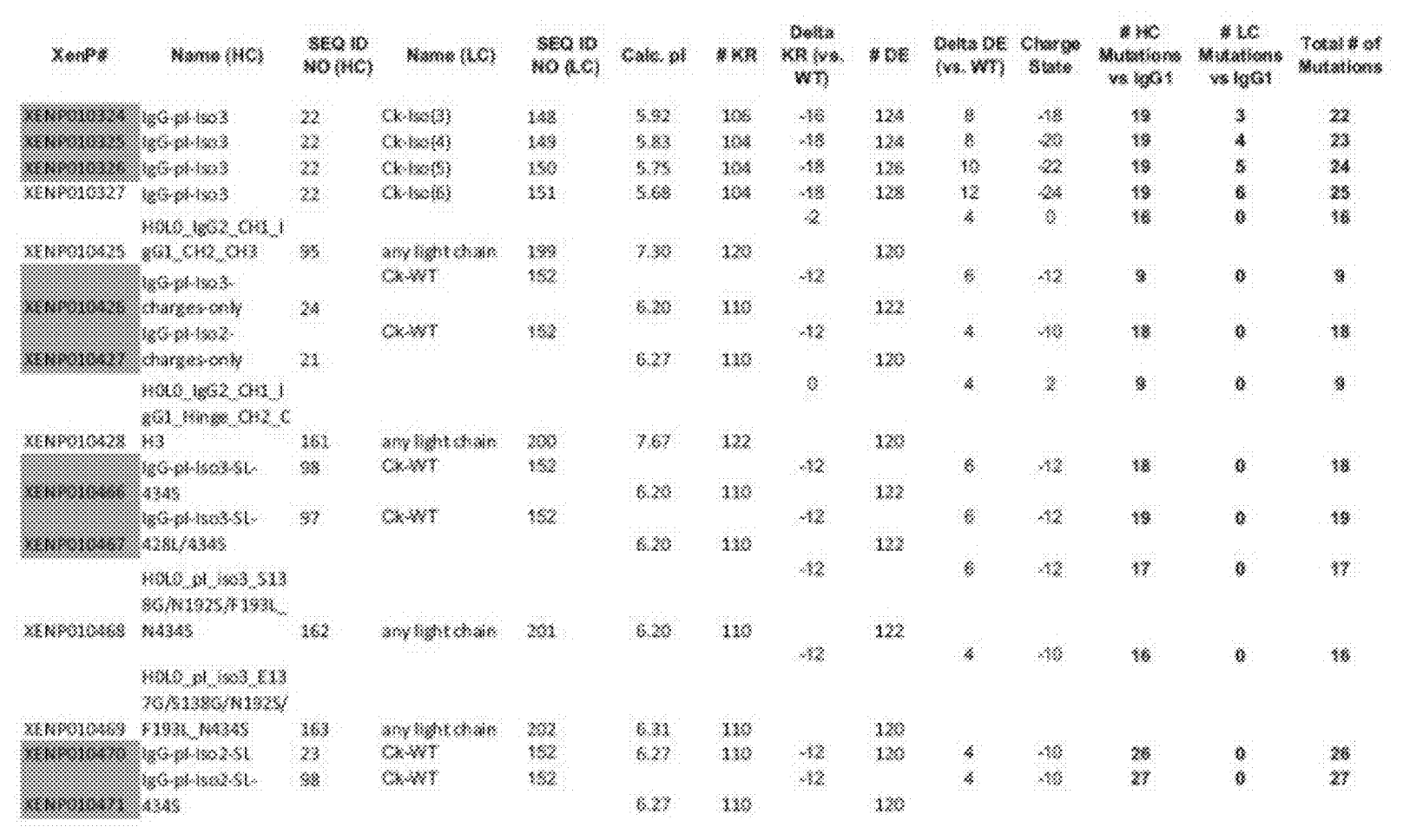
Figure 37E:
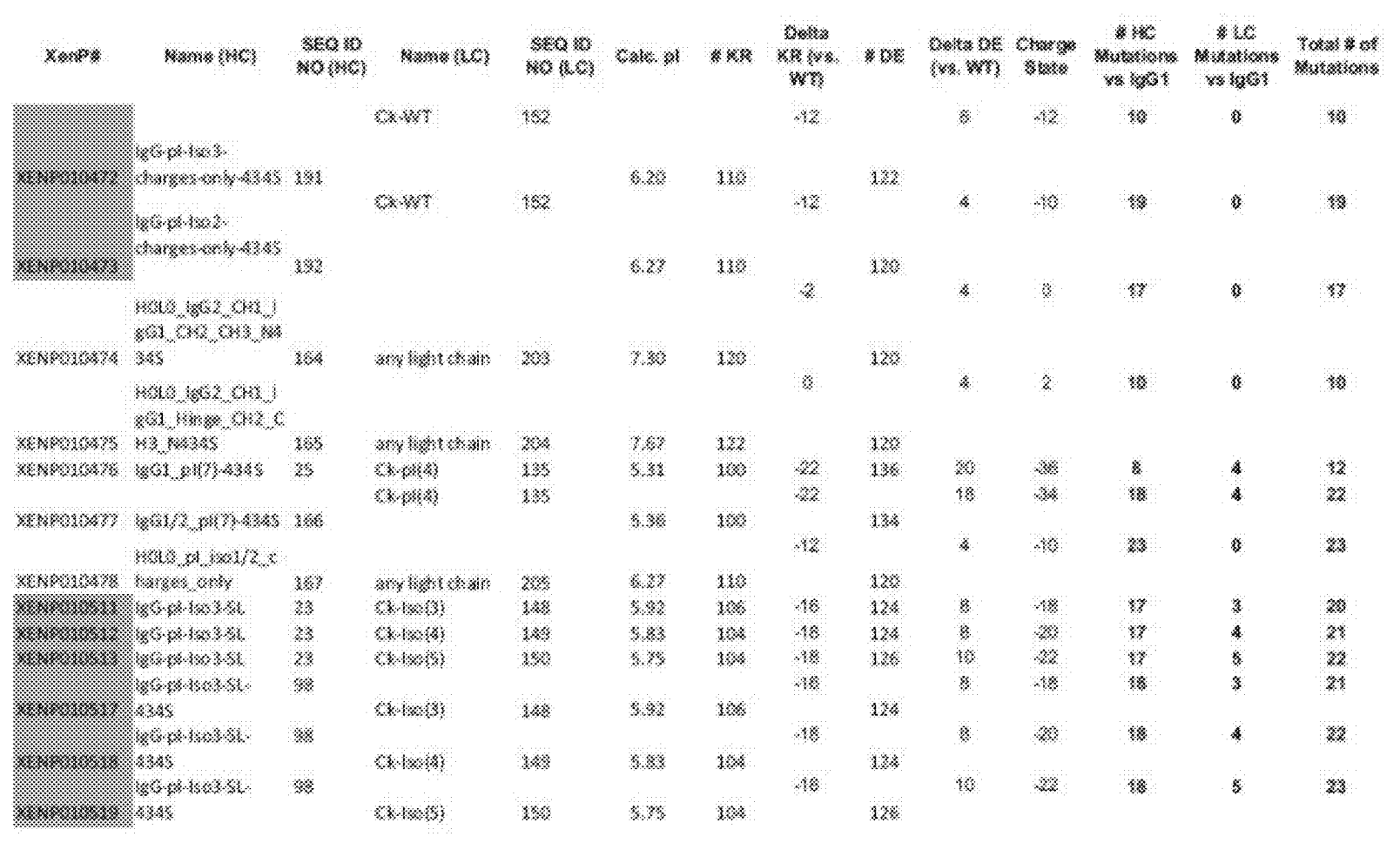
Figure 37F:
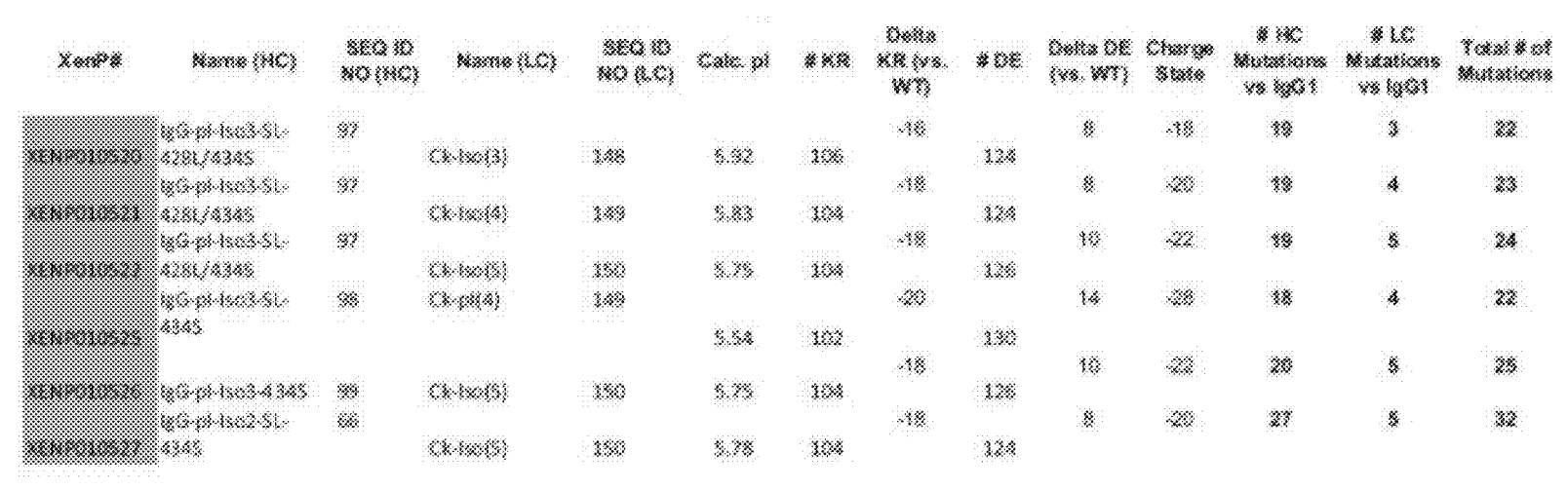

FIG. 37A-37F. Data table of exemplary pI-engineered variants listing:

| | |
|---|---|
| XenP# | the internal reference number |
| Name (HC) | heavy chain sequence designation |
| SEQ ID NO (HC) | corresponding SEQ ID NO of the heavy chain sequence |
| Name (LC) | light chain sequence designation |
| SEQ ID NO (LC) | corresponding SEQ ID NO of the light chain sequence |
| Calc. pI | calculated pI value for the entire antibody sequence, including heavy and light chain Fv + constant domains, with the Fv of bevacizumab and the constant domains as defined in the table |
| #KR | number of Lys or Arg residues in IgG1 with the Fv of bevacizumab and the constant domains as defined in the table |
| Delta KR (vs. WT) | change in the number of Lys or Arg residues relative to IgG1 wild-type sequence of bevacizumab |
| #DE | number of Asp or Glu residues in IgG1 with the Fv of bevacizumab and the constant domains as defined in the table |
| Delta DE (vs. WT) | change in the number of Asp or Glu acid residues relative to IgG1 wild-type sequence of bevacizumab |
| Charge state | derived from the total number of Lys and Arg minus the total number of Asp and Glu residues, assuming a pH of 7 |
| # HC Mutations vs IgG1 | number of mutations in the heavy chain constant domain as compared to IgG1 |
| # LC Mutations vs IgG1 | number of mutations in the light chain constant domain as compared to IgG1 |
| Total # of Mutations | total number of mutations in the heavy chain and light chain constant domains as compared to IgG1 |

It should be noted that FIG. 20 has SEQ ID NO:s that are associated with the sequence listing filed in U.S. Ser. No. 13/648,951, and are hereby expressly incorporated by reference.

Figure 38:
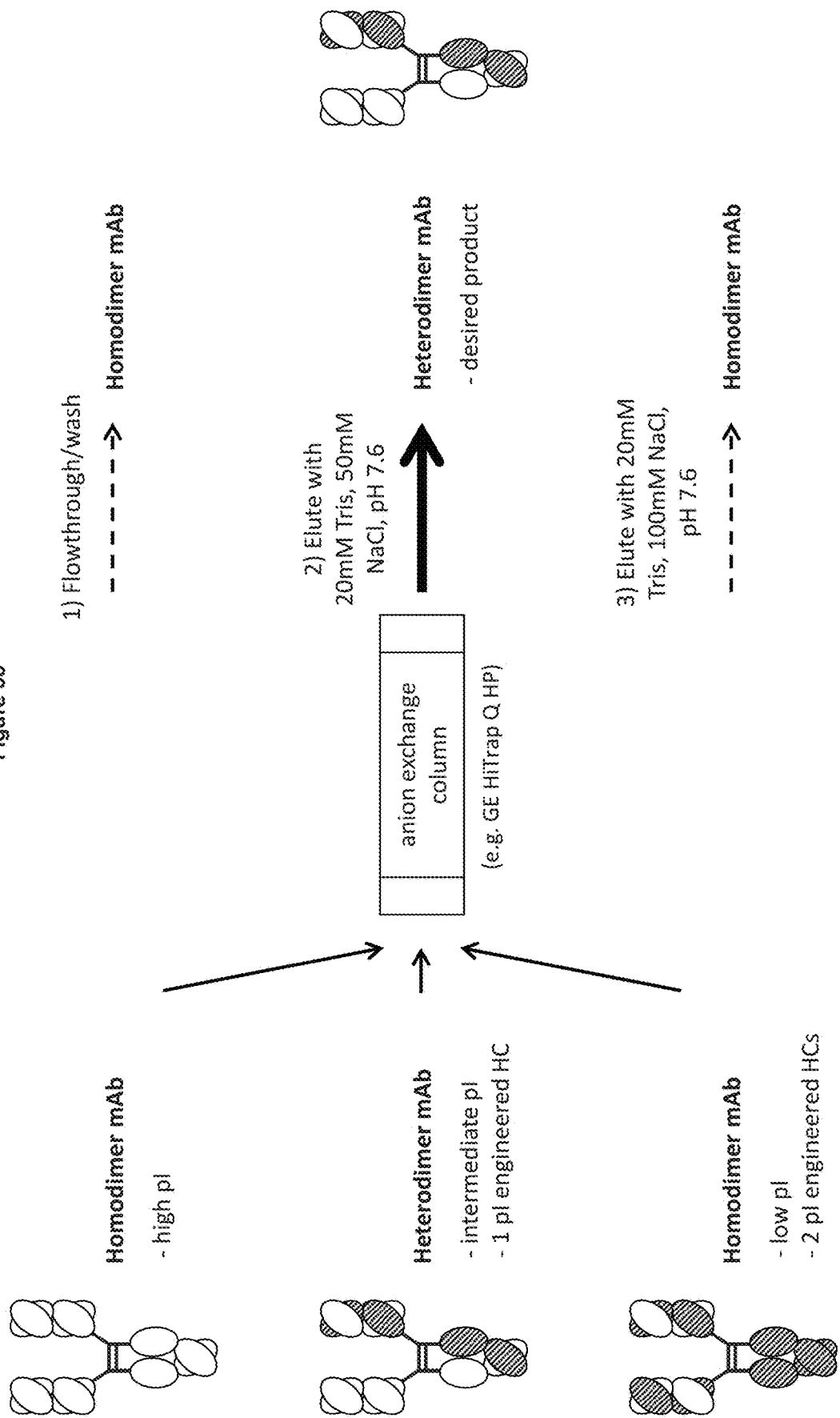

FIG. 38. Outline of method of purifying a desired heterodimeric antibody species from a mixture of contaminating homodimer species by engineering to modify isoelectric points of individual chains. As will be appreciated by those in the art, while the schematic is shown for a "standard" bispecific antibody format, the method is the same for other multispecific heterodimers relying on pI variants for purification; see for example FIG. 39A-39E. Sequences of pI engineered variants, including heterodimeric and bispecific constructs.

FIG. 40. IEF gel showing purification of the heterodimer species of the pI engineered variant XENP10653 from the homodimer species by anion exchange chromatography. As can be seen from lane 3, the desired heterodimer is obtained in high purity.

Figure 41:
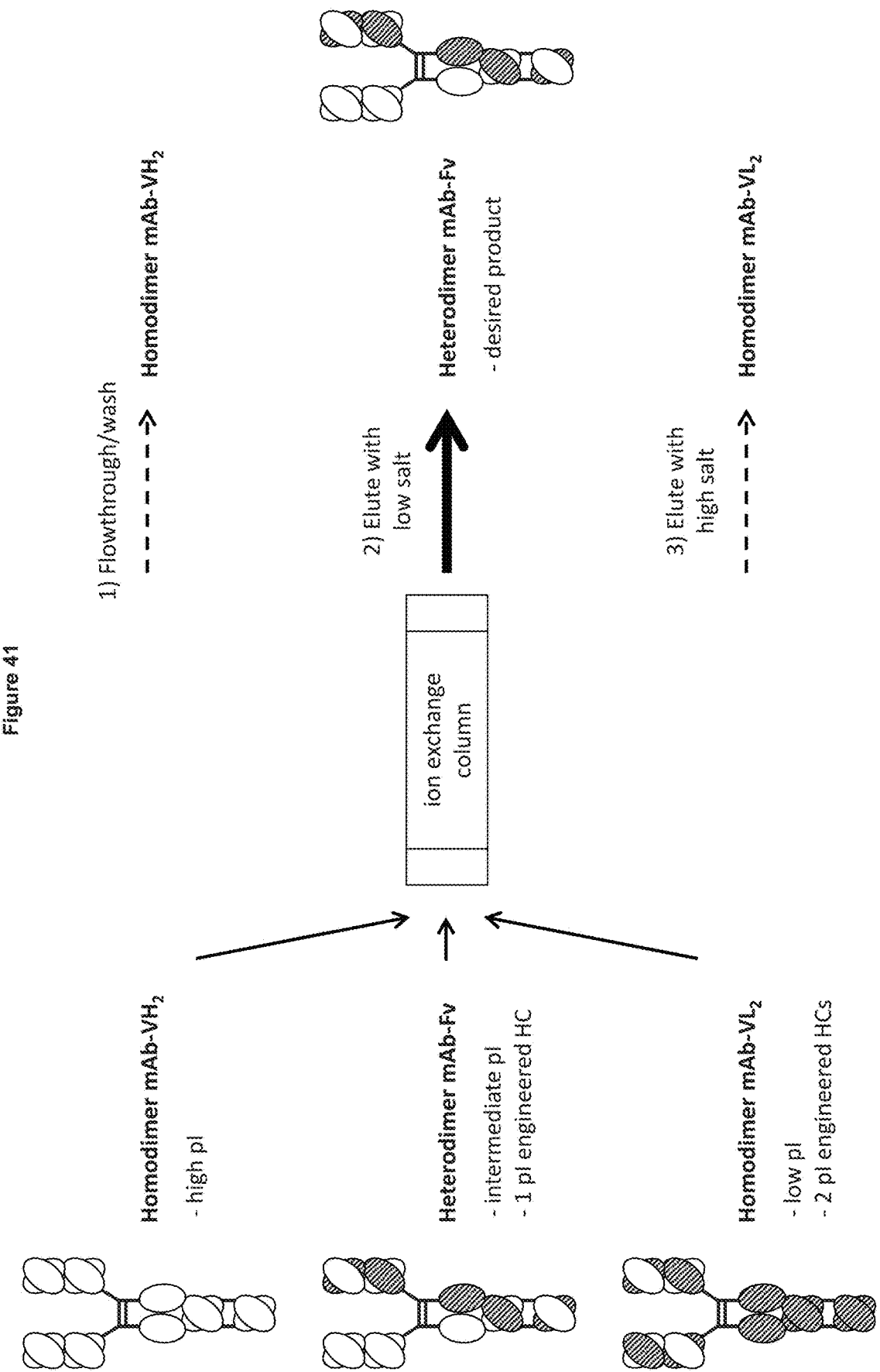

FIG. 41. Outline of method of purifying a desired heterodimeric bispecific Mab-Fv from a mixture of contaminating homodimer species by engineering to modify isoelectric points of individual chains.

Figure 42:
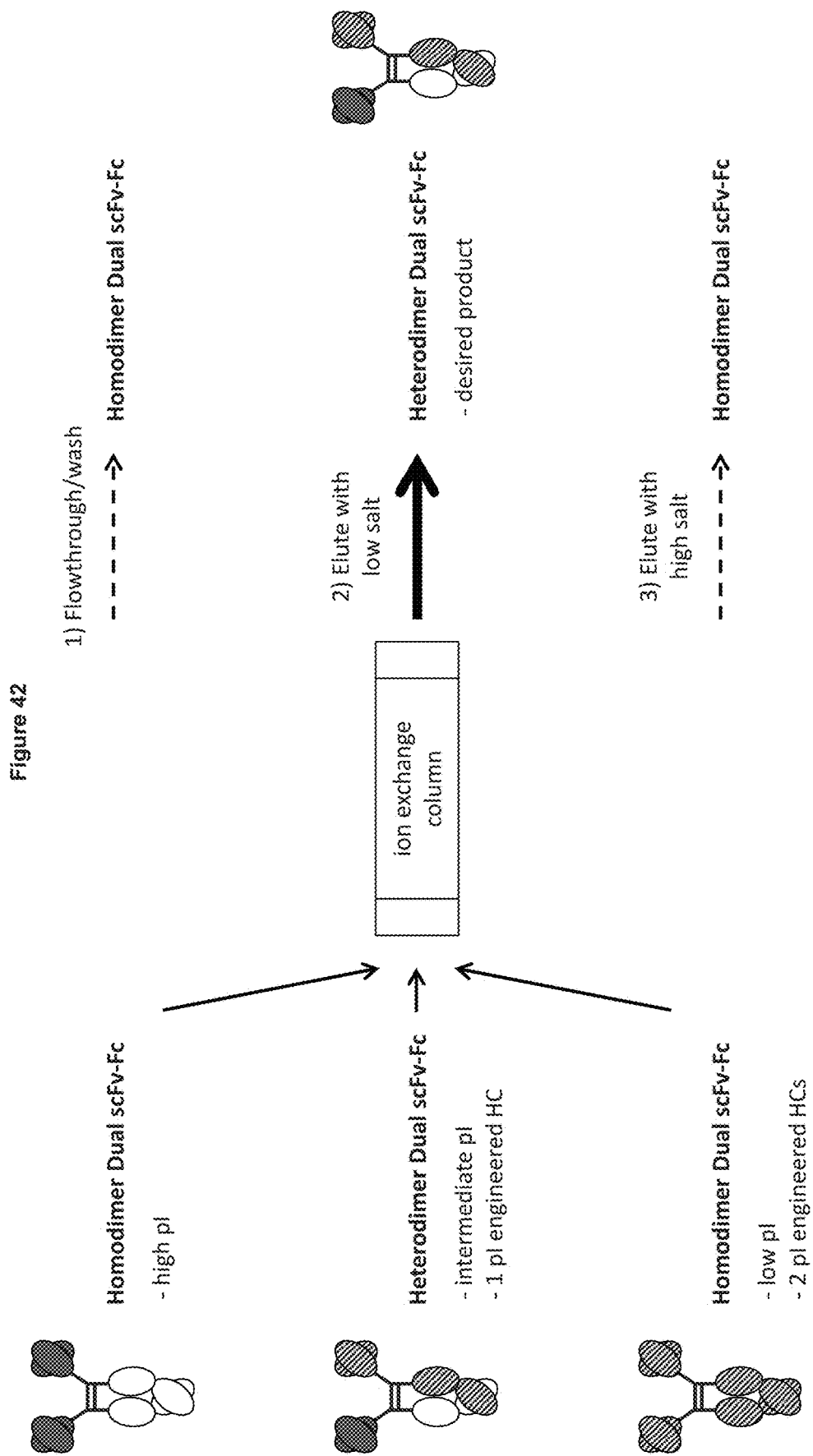

FIG. 42. Outline of method of purifying a desired heterodimeric bispecific scFv-Fc from a mixture of contaminating homodimer species by engineering to modify isoelectric points of individual chains.

FIG. 43A-43E. List of heavy chain and light chain residues for human IgG1 and percent exposed surface area. Numbering is according to the EU index.

FIG. 44A-44G. Examples of acidic substitutions that can be made in the heavy chain to facilitate easy purification of a heterodimeric species. Calculated pI in the context of bevacizumab are listed for zero-substitution homodimer (IgG1/IgG1), one-substitution pI-engineered heterodimer (pI/IgG1), and two-substitution pI-engineered homodimer (pI/pI). The average difference in pI of the heterodimer from the homodimers (delta pI) is also listed.

FIG. 45A-45I. Examples of basic to neutral substitutions that can be made in the heavy chain to faciliate easy purification of a heterodimeric species. Calculated pI in the context of bevacizumab are listed for zero-substitution homodimer (IgG1/IgG1), one-substitution pI-engineered heterodimer (pI/IgG1), and two-substitution pI-engineered homodimer (pI/pI). The average difference in pI of the heterodimer from the homodimers (delta pI) is also listed.

FIG. 46A-46G. Examples of basic substitutions that can be made in the heavy chain to facilitate easy purification of a heterodimeric species. Calculated pI in the context of bevacizumab are listed for zero-substitution homodimer (IgG1/IgG1), one-substitution pI-engineered heterodimer (pI/IgG1), and two-substitution pI-engineered homodimer (pI/pI). The average difference in pI of the heterodimer from the homodimers (delta pI) is also listed.

FIG. 47A-47H. Examples of acidic to neutral substitutions that can be made in the heavy chain to facilitate easy purification of a heterodimeric species. Calculated pI in the context of bevacizumab are listed for zero-substitution homodimer (IgG1/IgG1), one-substitution pI-engineered heterodimer (pI/IgG1), and two-substitution pI-engineered homodimer (pI/pI). The average difference in pI of the heterodimer from the homodimers (delta pI) is also listed.

FIG. 48A-48B. Examples of acidic substitutions that can be made in the light chain to facilitate easy purification of a heterodimeric species. Calculated pI in the context of bevacizumab are listed for zero-substitution homodimer (IgG1/IgG1), one-substitution pI-engineered heterodimer (pI/IgG1), and two-substitution pI-engineered homodimer (pI/pI). The average difference in pI of the heterodimer from the homodimers (delta pI) is also listed.

FIG. 49A-49D. Examples of basic to neutral substitutions that can be made in the light chain to faciliate easy purification of a heterodimeric species. Calculated pI in the context of bevacizumab are listed for zero-substitution homodimer (IgG1/IgG1), one-substitution pI-engineered heterodimer (pI/IgG1), and two-substitution pI-engineered homodimer (pI/pI). The average difference in pI of the heterodimer from the homodimers (delta pI) is also listed.

FIG. 50A-50B. Examples of basic substitutions that can be made in the light chain to faciliate easy purification of a heterodimeric species. Calculated pI in the context of bevacizumab are listed for zero-substitution homodimer (IgG1/IgG1), one-substitution pI-engineered heterodimer (pI/IgG1), and two-substitution pI-engineered homodimer (pI/pI). The average difference in pI of the heterodimer from the homodimers (delta pI) is also listed.

FIG. 51A-51D. Examples of acidic to neutral substitutions that can be made in the light chain to facilitate easy purification of a heterodimeric species. Calculated pI in the context of bevacizumab are listed for zero-substitution homodimer (IgG1/IgG1), one-substitution pI-engineered heterodimer (pI/IgG1), and two-substitution pI-engineered homodimer (pI/pI). The average difference in pI of the heterodimer from the homodimers (delta pI) is also listed.

FIG. 52A-52D. Sequence alignment of IgG1, IgG2, IgG3, IgG4, ISO(-), ISO(+RR), and ISO(+). For IgG1-4, differences from the IgG1 sequence are highlighted in grey. For isotypic pI variants, differences from IgG1 are shown in black with white text.

FIG. 53A-53-B. Sequences of IOS(-), ISO(+), ISO(+RR), Anti-VEGF ISO(-), Anti-VEGF ISO(+), and Anti-VEGF ISO(+RR).

FIG. 54. Sequence of XENP10783, Anti-VEGF ISO(-)×IgG1(WT). Also listed are the three expected species and their respective pI after transfection and protein A purification.

FIG. 55. Sequence of XENP10784, Anti-VEGF ISO(+RR)×IgG1(WT). Also listed are the three expected species and their respective pI after transfection and protein A purification.

FIG. 56. Sequence of XENP10896, Anti-VEGF ISO(-)×ISO(+RR). Also listed are the three expected species and their respective pI after transfection and protein A purification.

FIG. 57. Sequence of XENP10901, Anti-VEGF ISO(-)×ISO(+). Also listed are the three expected species and their respective pI after transfection and protein A purification.

FIG. 58A-58C. List of all possible reduced pI variants created from isotypic substitutions of IgG1-4. Shown are the pI values for the three expected species as well as the average delta pI between the heterodimer and the two homodimer species present when the variant heavy chain is transfected with IgG1-WT heavy chain.

FIG. 59. List of all possible increased pI variants created from isotypic substitutions of IgG1-4. Shown are the pI values for the three expected species as well as the average delta pI between the heterodimer and the two homodimer species present when the variant heavy chain is transfected with IgG1-WT heavy chain.

FIG. 60. Chromatogram and IEF gel demonstrating purification of the heterodimer species present when Anti-VEGF ISO(-), IgG1-WT, and Anti-VEGF WT light chain are transfected together. Purification is performed on a HiTrap SP HP cation exchange column using 50 mM MES @ pH 6.0 and eluted with a linear NaCl gradient (0-130 mM).

FIG. 61. Chromatogram and IEF gel demonstrating purification of the heterodimer species present when Anti-VEGF ISO(+RR), IgG1-WT, and Anti-VEGF WT light chain are transfected together. Purification is performed on a HiTrap SP HP cation exchange column using 50 mM MES @ pH 6.0 and eluted with a linear NaCl gradient (0-180 mM).

Figure 62:
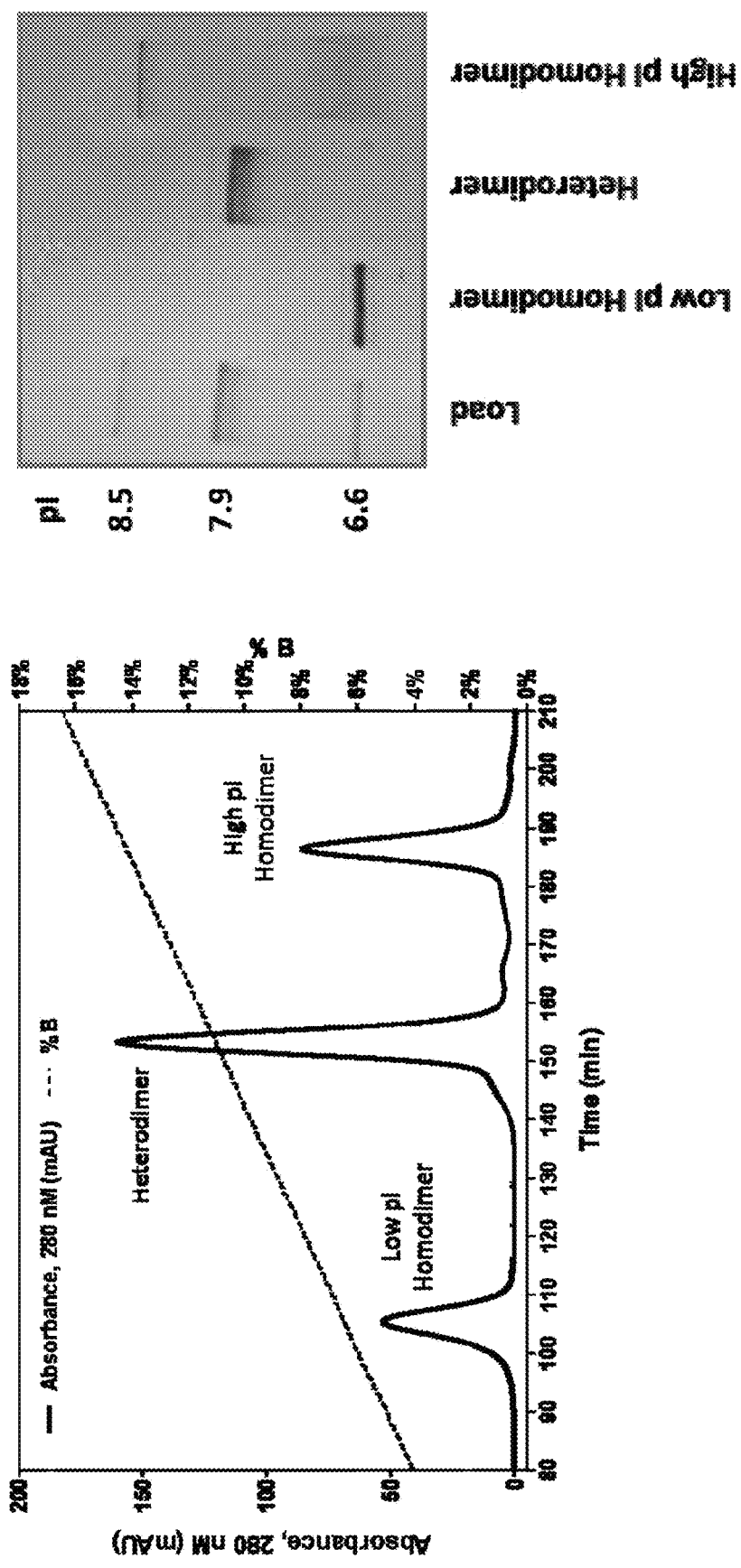

FIG. 62. Chromatogram and IEF gel demonstrating purification of the heterodimer species present when Anti-VEGF ISO(−), ISO(+RR), and Anti-VEGF WT light chain are transfected together. Purification is performed on a HiTrap SP HP cation exchange column using 50 mM MES @ pH 6.0 and eluted with a linear NaCl gradient (0-180 mM).

FIG. 63. Chromatogram and IEF gel demonstrating purification of the heterodimer species present when Anti-VEGF ISO(−), ISO(+), and Anti-VEGF WT light chain are transfected together. Purification is performed on a HiTrap SP HP cation exchange column using 50 mM MES @ pH 6.0 and eluted with a linear NaCl gradient (0-180 mM).

FIG. 64. Structure and sequences of a pI-engineered variant, specifically an anti-CD19× anti-CD3 mAb-Fv. The calculated pI of heterodimeric and homodimeric species is listed.

FIG. 65. Structure and sequences of a pI-engineered variant, specifically an anti-CD19× anti-CD3 scFv2-Fc. The calculated pI of heterodimeric and homodimeric species is listed.

FIG. 66. Structure and sequences of a pI-engineered variant, specifically an anti-CD19× anti-CD3 DART-Fc. The calculated pI of heterodimeric and homodimeric species is listed.

FIG. 67. Structure and sequences of a pI-engineered variant, specifically an anti-CD19× anti-CD3 scFv-Fc. The calculated pI of heterodimeric and homodimeric species is listed.

FIG. 68. Structure and sequences of a pI-engineered variant, specifically an anti-CD19× anti-CD3 mAb-scFv. The calculated pI of heterodimeric and homodimeric species is listed.

FIG. 69. Structure and sequences of a pI-engineered variant, specifically an anti-CD19× anti-CD3 mAb-dAb. The calculated pI of heterodimeric and homodimeric species is listed.

FIG. 70. Structure and sequences of a pI-engineered variant, specifically an anti-CD19× anti-CD3 Fv-Fab-Fc. The calculated pI of heterodimeric and homodimeric species is listed.

FIG. 71. Structure and sequences of a pI-engineered variant, specifically an anti-CD19× anti-CD3 common light chain mAb. The calculated pI of heterodimeric and homodimeric species is listed.

FIG. 72. Structure and sequences of a pI-engineered variant, specifically an anti-CD3 one-arm mAb. The calculated pI of heterodimeric and homodimeric species is listed.

FIG. 73. Structure and sequences of a pI-engineered variant, specifically an anti-CD19× anti-CD3 Fab-Fv-Fc. The calculated pI of heterodimeric and homodimeric species is listed.

FIG. 74. Structure and sequences of a pI-engineered variant, specifically an anti-CD19× anti-CD3 Fv-Fv-Fc. The calculated pI of heterodimeric and homodimeric species is listed.

FIG. 75. Structure and sequences of a pI-engineered variant, specifically an anti-CD3 monovalent mAb. The calculated pI of heterodimeric and homodimeric species is listed.

FIG. 76. Structure and sequences of a pI-engineered variant, specifically an anti-CD19× anti-CD3 central mAb-Fv. The calculated pI of heterodimeric and homodimeric species is listed.

FIG. 77. Structure and sequences of a pI-engineered variant, specifically an anti-CD19× anti-CD3 Fab-Fab-Fc. The calculated pI of heterodimeric and homodimeric species is listed.

Figure 78B:
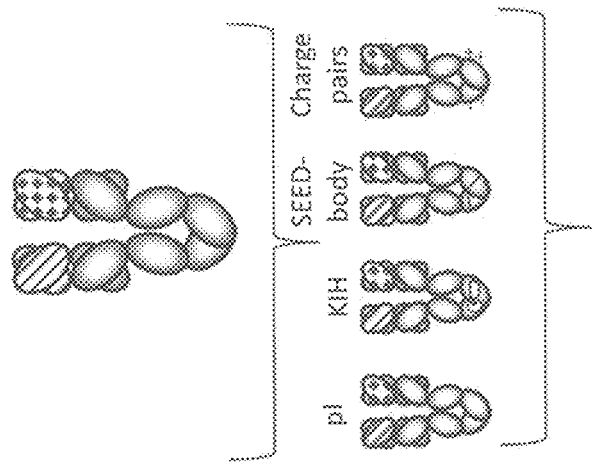
Figure 78C:
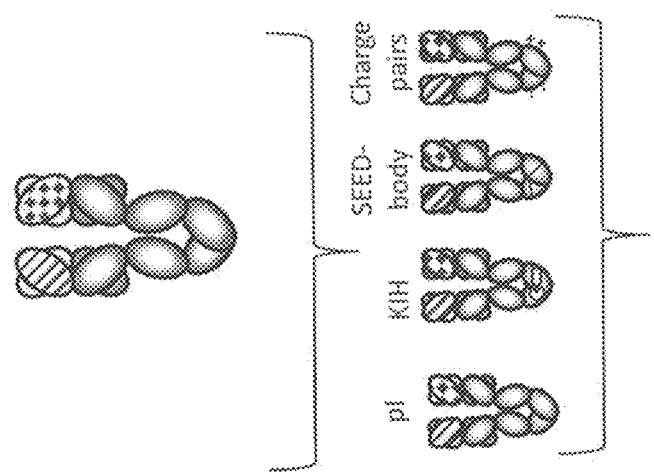
Figures 78H, 78I, 78J, 78K:
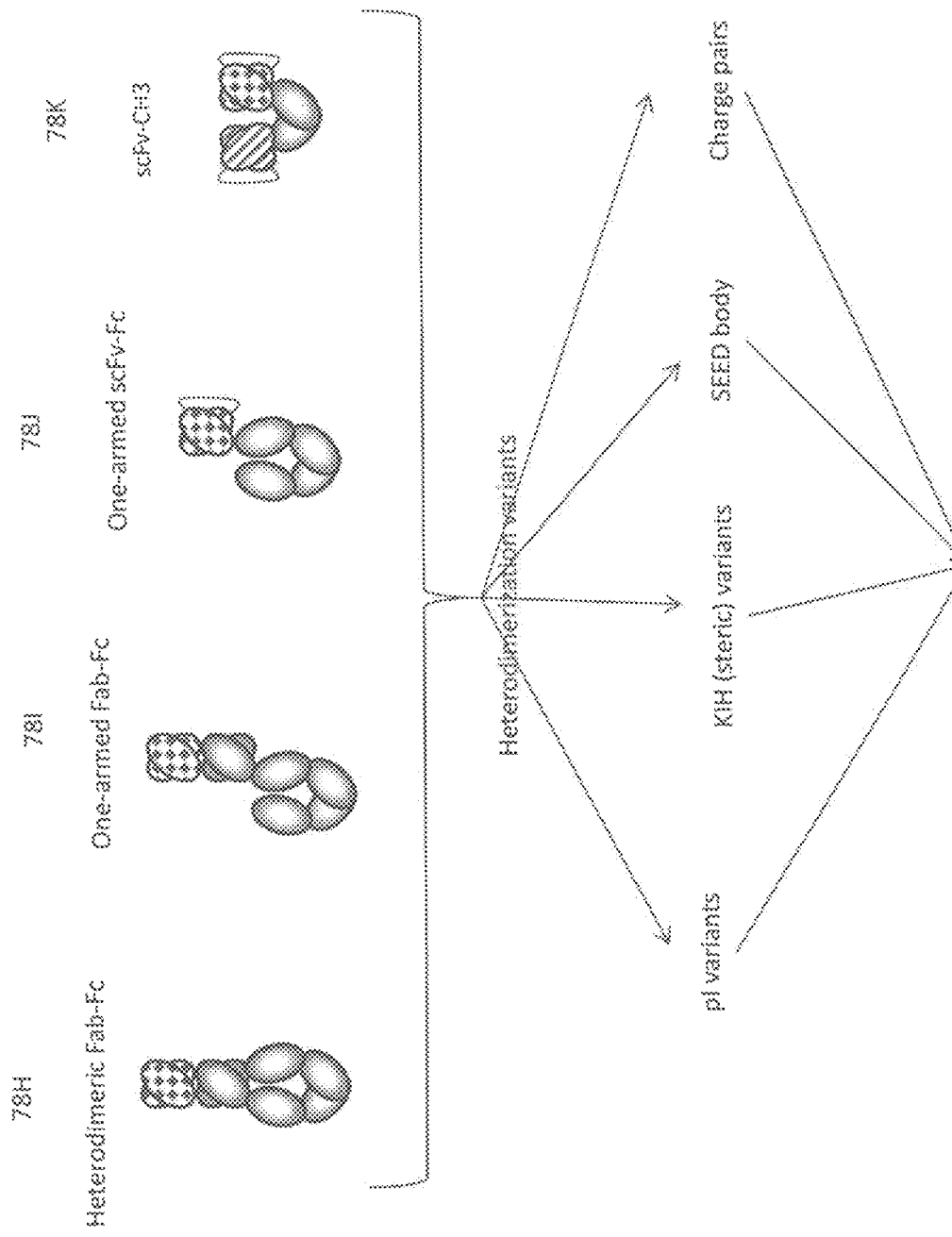

FIGS. 78A-78N depict a variety of heterodimerization formats. As a preliminary matter, the structures of FIG. 78 all show a fusion partner of a variable region (including scFvs). However, as described herein for fusion proteins, other binding ligands can take the place of these variable regions. FIG. 78A shows a dual scFv-Fc format, that, as for all heterodimerization formats herein can include heterodimerization variants such as pI variants, knobs in holes (KIH, also referred to herein as steric variants), charge pairs (a subset of steric variants), and SEED body ("strand-exchange engineered domain"; see Klein et al., mAbs 4:6 653-663 (2012) and Davis et al, Protein Eng Des Sel 2010 23:195-202) which rely on the fact that the CH3 domains of human IgG and IgA do not bind to each other. As for all the heterodimeric structures herein, these heterodimerization variants can be combined, optionally and independently and in any combination. What is important is that the "strandedness" of the monomer pairs remains intact although variants listed as "monomer 1" variants in the steric list can be crossed with "monomer 2" variants in the pI list. That is, any set can be combined with any other, regardless of which "monomer" list to which they are associated. FIG. 78B depicts a bispecific IgG, again with the option of a variety of heterodimerization variants. FIG. 78C depicts the bispecific IgG but with the use of common light chains. FIG. 78D depicts the "one armed" version of DVD-Ig which utilizes two different variable heavy and variable light domains. FIG. 78E is similar, except that rather than an "empty arm", the variable heavy and light chains are on opposite heavy chains. FIG. 78F is generally refered as "mAb-Fv". FIG. 78G depicts a multi-scFv format; as will be appreciated by those in the art, similar to the "A, B, C, D" formats depicted in FIG. 64-77, there may be any number of associated scFvs (or, for that matter, any other binding ligands or functionalities). Thus, FIG. 78G could have 1, 2, 3 or 4 scFvs (e.g. for bispecifics, the scFv could be "cis" or "trans", or both on one "end" of the molecule). FIG. 78H depicts a heterodimeric FabFc with the Fab being formed by two different heavy chains one containing heavy chain Fab sequences and the other containing light chain Fab sequences. FIG. 78I depicts the "one armed Fab-Fc", where one heavy chain comprises the Fab. FIG. 78J depicts a "one armed scFv-Fc", wherein one heavy chain Fc comprises an scFv and the other heavy chain is "empty". FIG. 78K shows a scFv-CH3, wherein only heavy chain CH3 regions are used, each with their own scFv. FIG. 78L depicts a mAb-scFv, wherein one end of the molecule engages an antigen bivalently with a monovalent engagement using an scFv on one of the heavy chains. FIG. 78M depicts the same structure except that both heavy chains comprise an additional scFv, which can either bind the same antigen or different antigens. FIG. 78N shows the "CrossMab" structure, where the problem of multiplex formation due to two different light chains is addressed by switching sequences in the Fab portion.

FIGS. 79A and 79B show novel steric variants. As will be understood by those in the art, the first column of each table represents "corresponding" monomer pairs: that is, monomer 1 has 405A and the corresponding steric variant is 394F.

FIG. 80A-80B depicts heterodimerization variants that find particular use in the present invention.

FIG. 81A-81B depicts heterodimerization variants of use in the present invention.

FIG. 82 depicts novel pI heterodimerization variants.

FIG. 83 depicts a matrix of possible combinations of heterodimerization formats, heterodimerization variants (separated into pI variants and steric variants (which includes charge pair variants), Fc variants, FcRn variants and combinations. Legend A are suitable FcRn variants: 434A, 434S, 428L, 308F, 259I, 428L/434S, 259I/308F, 436I/428L, 436I or V/434S, 436V/428L, 252Y, 252Y/254T/256E and 259I/308F/428L. That is, the dual scFv-Fc format of FIG. 78A can have any of these FcRn variants. For clarity, as each heavy chain is different, FcRn variants (as well as the Fc variants) can reside on one or both monomers. Legend B are suitable Fc variants: 236A, 239D, 239E, 332E, 332D, 239D/332E, 267D, 267E, 328F, 267E/328F, 236A/332E, 239D/332E/330Y, 239D, 332E/330L, 236R, 328R, 236R/328R, 236N/267E, 243L, 298A and 299T. (Note, additional suitable Fc variants are found in FIG. 41 of US 2006/0024298, the figure and legend of which are hereby incorporated by reference in their entirety). Legend C are suitable pI variants, and these, for brevity are imported from FIG. 82, again with the understanding that there is a "strandedness" to pI variants. Legend D are suitable steric variants (including charge pair variants); again, for brevity are imported from FIG. 80, again with the understanding that there is a "strandedness" to steric variants. Legend E reflects the following possible combinations, again, with each variant being independently and optionally combined from the appropriate source Legend: 1) pI variants plus FcRn variants; 2) pI variants plus Fc variants; 3) pI variants plus FcRn variants plus Fc variants; 4) steric variants plus FcRn variants; 5) steric variants plus Fc variants; 6) steric variants plus FcRn variants plus Fc variants; 7) pI variants plus steric variants plus FcRn variants; 8) pI variants plus steric variants plus Fc variants; 9) pI variants plus steric variants plus FcRn variants plus Fc variants; and 10) pI variants plus steric variants.

FIGS. 1-76 of U.S. Ser. No. 61/593,846 and the associated legends and discussion in the specification are hereby incorporated by reference.

FIGS. 2 and 17 of U.S. Ser. No. 61/778,157, inclusive of all the sequences including the optimized CD3 sequences are expressly incorporated herein by reference.

DETAILED DESCRIPTION OF THE INVENTION

I. Overview

The present invention is directed to novel constructs to provide bispecific antibodies (or, as discussed below, trispecific or tetraspecific antibodies can also be made). An ongoing problem in antibody technologies is the desire for "bispecific" (and/or multispecific) antibodies that bind to two (or more) different antigens simultaneously, in general thus allowing the different antigens to be brought into proximity and resulting in new functionalities and new therapies. In general, these antibodies are made by including genes for each heavy and light chain into the host cells. This generally results in the formation of the desired heterodimer (A-B), as well as the two homodimers (A-A and B-B). However, a major obstacle in the formation of multispecific antibodies is the difficulty in purifying the heterodimeric antibodies away from the homodimeric antibodies and/or biasing the formation of the heterodimer over the formation of the homodimers.

The present invention is generally directed to the creation of heterodimeric proteins including antibodies, that can co-engage antigens in several ways, relying on amino acid variants in the constant regions that are different on each chain to promote heterodimeric formation and/or allow for ease of purification of heterodimers over the homodimers.

There are a number of mechanisms that can be used to generate the heterodimers of the present invention. In addition, as will be appreciated by those in the art, these mechanisms can be combined to ensure high heterodimerization. Thus, amino acid variants that lead to the production of heterodimers are referred to as "heterodimerization variants". As discussed below, heterodimerization variants can include steric variants (e.g. the "knobs and holes" variants described below and the "charge pairs" variants described below) as well as "pI variants", which allows purification of homodimers away from heterodimers.

One mechanism is generally referred to in the art as "knobs and holes", referring to amino acid engineering that creates steric influences to favor heterodimeric formation and disfavor homodimeric formation, as described in U.S. Ser. No. 61/596,846 and U.S. Ser. No. 12/875,0015, Ridgway et al., Protein Engineering 9(7):617 (1996); Atwell et al., J. Mol. Biol. 1997 270:26; U.S. Pat. No. 8,216,805, US 2012/0149876, all of which are hereby incorporated by reference in their entirety. The Figures identify a number of "monomer A—monomer B" pairs that rely on "knobs and holes". In addition, as described in Merchant et al., Nature Biotech. 16:677 (1998), these "knobs and hole" mutations can be combined with disulfide bonds to skew formation to heterodimerization.

An additional mechanism that finds use in the generation of heterodimers is sometimes referred to as "electrostatic steering" or "charge pairs" as described in Gunasekaran et al., J. Biol. Chem. 285(25):19637 (2010), hereby incorporated by reference in its entirety. This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". These include, but are not limited to, D221E/P228E/L368E paired with D221R/P228R/K409R (e.g. these are "monomer corresponding sets) and C220E/P228E/368E paired with C220R/E224R/P228R/K409R.

In the present invention, in some embodiments, pI variants are used to alter the pI of one or both of the monomers and thus allowing the isoelectric purification of A-A, A-B and B-B dimeric proteins.

In the present invention that utilizes pI as a separation mechanism to allow the purification of heterodimeric proteins, amino acid variants can be introduced into one or both of the monomer polypeptides; that is, the pI of one of the monomers (referred to herein for simplicity as "monomer A") can be engineered away from monomer B, or both monomer A and B change be changed, with the pI of monomer A increasing and the pI of monomer B decreasing. As is outlined more fully below, the pI changes of either or both monomers can be done by removing or adding a charged residue (e.g. a neutral amino acid is replaced by a positively or negatively charged amino acid residue, e.g. glycine to glutamic acid), changing a charged residue from positive or negative to the opposite charge (aspartic acid to lysine) or changing a charged residue to a neutral residue (e.g. loss of a charge; lysine to serine).

Accordingly, in this embodiment of the present invention provides for creating a sufficient change in pI in at least one of the monomers such that heterodimers can be separated from homodimers. As will be appreciated by those in the art, and as discussed further below, this can be done by using a "wild type" heavy chain constant region and a variant region that has been engineered to either increase or decrease it's pI (wt A−+B or wt A− −B), or by increasing one region and decreasing the other region (A+−B− or A− B+).

Thus, in general, a component of some embodiments of the present invention are amino acid variants in the constant regions of antibodies that are directed to altering the isoelectric point (pI) of at least one, if not both, of the monomers of a dimeric protein to form "pI heterodimers" (when the protein is an antibody, these are referred to as "pI antibodies") by incorporating amino acid substitutions ("pI variants" or "pI substitutions") into one or both of the monomers. As shown herein, the separation of the heterodimers from the two homodimers can be accomplished if the pIs of the two monomers differ by as little as 0.1 pH unit, with 0.2, 0.3, 0.4 and 0.5 or greater all finding use in the present invention.

Furthermore, as will be appreciated by those in the art and outlined herein, in some cases, heterodimers can be separated from homodimers on the basis of size.

By using the constant region of the heavy chain, a more modular approach to designing and purifying multispecific proteins, including antibodies, is provided. In addition, in some embodiments, the possibility of immunogenicity resulting from the pI variants is significantly reduced by importing pI variants from different IgG isotypes such that pI is changed without introducing significant immunogenicity. Thus, an additional problem to be solved is the elucidation of low pI constant domains with high human sequence content, e.g. the minimization or avoidance of non-human residues at any particular position.

A side benefit that can occur with this pI engineering is also the extension of serum half-life and increased FcRn binding. That is, as described in U.S. Ser. No. 13/194,904 (incorporated by reference in its entirety), lowering the pI of antibody constant domains (including those found in antibodies and Fc fusions) can lead to longer serum retention in vivo. These pI variants for increased serum half life also facilitate pI changes for purification.

In addition, it should be noted that the pI variants of the heterodimerization variants give an additional benefit for the analytics and quality control process of bispecific antibodies, as, particularly in the case of CD3 antibodies, the ability to either eliminate, minimize and distinguish when homodimers are present is significant. Similarly, the ability to reliably test the reproducibility of the heterodimeric protein production is important.

In addition to all or part of a variant heavy constant domain, one or both of the monomers may contain one or two fusion partners, such that the heterodimers form multivalent proteins. As is generally depicted the Figures, the fusion partners are depicted as A, B, C and D, with all combinations possible. In general, A, B, C and D are selected such that the heterodimer is at least bispecific or bivalent in its ability to interact with additional proteins.

As will be appreciated by those in the art and discussed more fully below, the heterodimeric fusion proteins of the present invention can take on a wide variety of configurations, as are generally depicted in the FIG. 78. Some figures depict "single ended" configurations, where there is one type of specificity on one "arm" of the molecule and a different specificity on the other "arm". Other figures depict "dual ended" configurations, where there is at least one type of specificity at the "top" of the molecule and one or more different specificities at the "bottom" of the molecule. Furthermore as is shown, these two configurations can be combined, where there can be triple or quadruple specificities based on the particular combination. Thus, the present invention provides "multispecific" binding proteins, including multispecific antibodies.

In addition, as further described below, additional amino acid substitutions can be engineered into the Fc region of the proteins of the invention, to alter a variety of additional functionalities such as altered FcγR binding (e.g. ADCC, for example), altered FcRn binding (to alter half-life of the antibody in the serum), etc.

Definitions

In order that the application may be more completely understood, several definitions are set forth below. Such definitions are meant to encompass grammatical equivalents.

By "ablation" herein is meant a decrease or removal of activity. Thus for example, "ablating FcγR binding" means the Fc region amino acid variant has less than 50% starting binding as compared to an Fc region not containing the specific variant, with less than 70-80-90-95-98% loss of activity being preferred, and in general, with the activity being below the level of detectable binding in a Biacore assay. Of particular use in the ablation of FcγR binding is the double variant 236R/328R, and 236R and 328R separately as well.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233- or E233# designates a deletion of glutamic acid at position 233. Additionally, EDA233- or EDA233# designates a deletion of the sequence GluAspAla that begins at position 233.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4, although human sequences with variants can also serve as "parent polypeptides". The protein variant sequence herein will preferably possess at least about 80% identity with a parent protein sequence, and most preferably at least about 90% identity, more preferably at least about 95-98-99% identity. Variant protein can refer to the variant protein itself, compositions comprising the protein variant, or the DNA sequence that encodes it. Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The Fc variants of the present invention are defined according to the amino acid modifications that compose them. Thus, for example, N434S or 434S is an Fc variant with the substitution serine at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, 428L/434S is the same Fc variant as M428L/N434S, and so on. For all positions discussed in the present invention that relate to antibodies, unless otherwise noted, amino acid position numbering is according to the EU index. The EU index or EU index as in Kabat or EU numbering scheme refers to the numbering of the EU antibody (Edelman et al., 1969, Proc Natl Acad Sci USA 63:78-85, hereby entirely incorporated by reference.) The modification can be an addition, deletion, or substitution. Substitutions can include naturally occurring amino acids and, in some cases, synthetic amino acids. Examples include U.S. Pat. No. 6,586,207; WO 98/48032; WO 03/073238; US2004-0214988A1; WO 05/35727A2; WO 05/74524A2; J. W. Chin et al., (2002), Journal of the American Chemical Society 124:9026-9027; J. W. Chin, & P. G. Schultz, (2002), ChemBioChem 11:1135-1137; J. W. Chin, et al., (2002), PICAS United States of America 99:11020-11024; and, L. Wang, & P. G. Schultz, (2002), Chem. 1-10, all entirely incorporated by reference.

As used herein, "protein" herein is meant at least two covalently attached amino acids, which includes proteins, polypeptides, oligopeptides and peptides. The peptidyl group may comprise naturally occurring amino acids and peptide bonds, or synthetic peptidomimetic structures, i.e. "analogs", such as peptoids (see Simon et al., PNAS USA 89(20):9367 (1992), entirely incorporated by reference). The amino acids may either be naturally occurring or synthetic (e.g. not an amino acid that is coded for by DNA); as will be appreciated by those in the art. For example, homophenylalanine, citrulline, ornithine and noreleucine are considered synthetic amino acids for the purposes of the invention, and both D- and L-(R or S) configured amino acids may be utilized. The variants of the present invention may comprise modifications that include the use of synthetic amino acids incorporated using, for example, the technologies developed by Schultz and colleagues, including but not limited to methods described by Cropp & Shultz, 2004, Trends Genet. 20(12):625-30, Anderson et al., 2004, Proc Natl Acad Sci USA 101 (2):7566-71, Zhang et al., 2003, 303(5656):371-3, and Chin et al., 2003, Science 301(5635): 964-7, all entirely incorporated by reference. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Asparagine 297 (also referred to as Asn297 or N297) is a residue at position 297 in the human antibody IgG1.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein. By "Fv" or "Fv fragment" or "Fv region" as used herein is meant a polypeptide that comprises the VL and VH domains of a single antibody.

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the IgGs comprise a serine at position 434, the substitution 434S in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "IgG Fc ligand" as used herein is meant a molecule, preferably a polypeptide, from any organism that binds to the Fc region of an IgG antibody to form an Fc/Fc ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcqammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. A variety of FcRn variants used to increase binding to the FcRn receptor, and in some cases, to increase serum half-life, are shown in the Figure Legend of FIG. 83.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "Fc fusion protein" or "immunoadhesin" herein is meant a protein comprising an Fc region, generally linked (optionally through a linker moiety, as described herein) to a different protein, such as a binding moiety to a target protein, as described herein).

By "position" as used herein is meant a location in the sequence of a protein. Positions may be numbered sequentially, or according to an established format, for example the EU index for antibody numbering.

By "target antigen" as used herein is meant the molecule that is bound specifically by the variable region of a given antibody. A target antigen may be a protein, carbohydrate, lipid, or other chemical compound. A wide number of suitable target antigens are described below.

By "strandedness" in the context of the monomers of the heterodimeric proteins of the invention herein is meant that, similar to the two strands of DNA that "match", heterodimerization variants are incorporated into each monomer so as to preserve the ability to "match" to form heterodimers. For example, if some pI variants are engineered into monomer A (e.g. making the pI higher) then steric variants that are "charge pairs" that can be utilized as well do not interfere with the pI variants, e.g. the charge variants that make a pI higher are put on the same "strand" or "monomer" to preserve both functionalities.

By "target cell" as used herein is meant a cell that expresses a target antigen.

By "variable region" as used herein is meant the region of an immunoglobulin that comprises one or more Ig domains substantially encoded by any of the V.kappa., V.lamda., and/or VH genes that make up the kappa, lambda, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

Heterodimeric Proteins

The present invention is directed to the generation of multispecific, particularly bispecific binding proteins, and in particular, multispecific antibodies.

Antibodies

The present invention relates to the generation of heterodimeric antibodies, generally therapeutic antibodies, through the use of "heterodimerization amino acid variants". As is discussed below, the term "antibody" is used generally. Antibodies that find use in the present invention can take on a number of formats as described herein, including traditional antibodies as well as antibody derivatives, fragments and mimetics, described below. In general, the term "antibody" includes any polypeptide that includes at least one constant domain, including, but not limited to, CH1, CH2, CH3 and CL.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to the IgG class, which has several subclasses, including, but not limited to IgG1, IgG2, IgG3, and IgG4. Thus, "isotype" as used herein is meant any of the subclasses of immunoglobulins defined by the chemical and antigenic characteristics of their constant regions. It should be understood that therapeutic antibodies can also comprise hybrids of isotypes and/or subclasses. For example, as shown herein, the present invention covers heterodimers that can contain one or both chains that are IgG1/G2 hybrids (see SEQ ID NO:6, for example).

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

Throughout the present specification, the Kabat numbering system is generally used when referring to a residue in the variable domain (approximately, residues 1-107 of the light chain variable region and residues 1-113 of the heavy chain variable region) (e.g, Kabat et al., supra (1991)).

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning."

In some embodiments, the antibodies are full length. By "full length antibody" herein is meant the structure that constitutes the natural biological form of an antibody, including variable and constant regions, including one or more modifications as outlined herein.

Alternatively, the antibodies can be a variety of structures, including, but not limited to, antibody fragments, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

Antibody Fragments

In one embodiment, the antibody is an antibody fragment. Of particular interest are antibodies that comprise Fc regions, Fc fusions, and the constant region of the heavy chain (CH1-hinge-CH2-CH3), again also including constant heavy region fusions.

Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), (viii) bispecific single chain Fv (WO 03/11161, hereby incorporated by reference) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448, all entirely incorporated by reference). The antibody fragments may be modified. For example, the molecules may be stabilized by the incorporation of disulphide bridges linking the VH and VL domains (Reiter et al., 1996, Nature Biotech. 14:1239-1245, entirely incorporated by reference).

Chimeric and Humanized Antibodies

In some embodiments, the scaffold components can be a mixture from different species. As such, if the protein is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321: 522-525, Verhoeyen et al., 1988, Science 239:1534-1536, all entirely incorporated by reference. "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213, all entirely incorporated by reference). The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654, entirely incorporated by reference. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all entirely incorporated by reference). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

In one embodiment, the antibody is a minibody. Minibodies are minimized antibody-like proteins comprising a scFv joined to a CH3 domain. Hu et al., 1996, Cancer Res. 56:3055-3061, entirely incorporated by reference. In some cases, the scFv can be joined to the Fc region, and may include some or the entire hinge region.

Fc Fusion Heterodimeric Proteins

In addition to heterodimeric antibody constructs, the invention further provides Fc fusion heterodimeric proteins. That is, rather than have the Fc domain of an antibody joined to an antibody variable region, the Fc domain can be joined to other moieties, particularly binding moieties such as ligands. By "Fc fusion" as used herein is meant a protein wherein one or more polypeptides is operably linked to an Fc region. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200, both entirely incorporated by reference). An Fc fusion combines the Fc region of an immunoglobulin with a fusion partner, which in general can be any protein or small molecule. Virtually any protein or small molecule may be linked to Fc to generate an Fc fusion. Protein fusion partners may include, but are not limited to, the variable region of any antibody, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, which is implicated in disease. Thus, the IgG variants can be linked to one or more fusion partners.

Thus, while many embodiments herein depict antibody components such as variable heavy and light chains or scFvs, other binding moeities can be fused to Fc regions to form heterodimeric proteins. For example, as discussed in Kontermann, supra, any number of dual targeting strategies can be done. For example (assuming only two binding moieties per heterodimer, e.g generally one per monomer), both monomers can bind and/or neutralize two ligands or two receptors, or bind and activate two ligands or two receptors. Similarly, one monomer may bind a receptor and the other a ligand (again, independently activating or neutralizing the binding partner). Further, each monomer may bind to same receptor or ligand in different locations (e.g. different epitopes). See FIG. 1 of Kontermann, expressly incorporated by reference. Suitable receptors and ligands are outlined below in the "Target" section.

Heterodimerization Variants

Accordingly, the present invention provides heterodimeric proteins based on the use of monomers containing variant heavy chain constant regions as a first domain. By "monomer" herein is meant one half of the heterodimeric protein. It should be noted that antibodies are actually tetrameric (two heavy chains and two light chains). In the context of the present invention, as applicable, one pair of heavy-light chains is considered a "monomer". In the case where an Fv region is one fusion partner (e.g. heavy and light chain) and a non-antibody protein is another fusion partner, each "half" is considered a monomer. Essentially, each monomer comprises sufficient heavy chain constant region to allow heterodimerization engineering, whether that be all the constant region, e.g. Ch1-hinge-CH2-CH3, the Fc region (CH2-CH3).

The variant heavy chain constant regions can comprise all or part of the heavy chain constant region, including the full length construct, CH1-hinge-CH2-CH3, or portions thereof, including for example CH2-CH3. In addition, the heavy chain region of each monomer can be the same backbone (CH1-hinge-CH2-CH3 or CH2-CH3) or different. N- and C-terminal truncations and additions are also included within the definition; for example, some pI variants include the addition of charged amino acids to the C-terminus of the heavy chain domain.

Furthermore, in addition to the pI substitutions outlined herein, the heavy chain regions may also contain additional amino acid substitutions, including changes for altering Fc binding as discussed below.

In addition, some monomers can utilize linkers between the variant heavy chain constant region and the fusion partner. Traditional peptide linkers can be used, including flexible linkers of glycine and serine. In some cases, the linkers for use as components of the monomer are different from those defined below for the ADC constructs, and are in many embodiments not cleavable linkers (such as those susceptible to proteases), although cleavable linkers may find use in some embodiments.

The heterodimerization variants include a number of different types of variants, including, but not limited to, steric variants, pI variants, and other variants (e.g. charge variants), that can be optionally and independently combined with any other variants. In these embodiments, it is important to match "monomer A" with "monomer B"; that is, if a heterodimeric protein relies on both steric variants and pI variants, these need to be correctly matched to each monomer: e.g. the set of steric variants that work (1 set on monomer A, 1 set on monomer B) is combined with pI variant sets (1 set on monomer A, 1 set on monomer B), such that the variants on each monomer are designed to achieve the desired function.

Steric Variants

In some embodiments, the formation of heterodimers can be facilitated by the addition of steric variants. That is, by changing amino acids in each heavy chain, different heavy chains are more likely to associate to form the heterodimeric structure than to form homodimers with the same Fc amino acid sequences. Suitable steric variants are shown in the Figures, particularly FIGS. 79, 80 and 81.

One mechanism is generally referred to in the art as "knobs and holes", referring to amino acid engineering that creates steric influences to favor heterodimeric formation and disfavor homodimeric formation can also optionally be used; this is sometimes referred to as "knobs and holes", as described in U.S. Ser. No. 61/596,846, Ridgway et al., Protein Engineering 9(7):617 (1996); Atwell et al., J. Mol. Biol. 1997 270:26; U.S. Pat. No. 8,216,805, all of which are hereby incorporated by reference in their entirety. FIG. 4, further described below, identifies a number of "monomer A-monomer B" pairs that rely on "knobs and holes". In addition, as described in Merchant et al., Nature Biotech. 16:677 (1998), these "knobs and hole" mutations can be combined with disulfide bonds to skew formation to heterodimerization. Some of these variants are shown in FIGS. 79A, 79B, 80 and 81.

An additional mechanism that finds use in the generation of heterodimers is sometimes referred to as "electrostatic steering" as described in Gunasekaran et al., J. Biol. Chem. 285(25):19637 (2010), hereby incorporated by reference in its entirety. This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". These include, but are not limited to, D221E/P228E/L368E paired with D221R/P228R/K409R (e.g. these are "monomer corresponding sets) and C220E/P228E/368E paired with C220R/E224R/P228R/K409R.

Additional monomer A and monomer B variants that can be combined with other variants, optionally and independently in any amount, such as pI variants outlined herein or other steric variants that are shown in FIG. 37 of US 2012/0149876, the figure and legend of which are incorporated expressly by reference herein.

In some embodiments, the steric variants outlined herein can be optionally and independently incorporated with any pI variant (or other variants such as Fc variants, FcRn variants, etc.) into one or both monomers.

pI Variants for Heterodimers

In general, as will be appreciated by those in the art, there are two general categories of pI variants: those that increase the pI of the protein (basic changes) and those that decrease the pI of the protein (acidic changes). As described herein, all combinations of these variants can be done: one monomer may be wild type, or a variant that does not display a significantly different pI from wild-type, and the other can be either more basic or more acidic. Alternatively, each monomer is changed, one to more basic and one to more acidic.

Preferred combinations of pI variants are shown in FIG. 82.

Heavy Chain Acidic pI Changes

Accordingly, when one monomer comprising a variant heavy chain constant domain is to be made more positive (e.g. lower the pI), one or more of the following substitutions can be made: S119E, K133E, K133Q, T164E, K205E, K205Q, N208D, K210E, K210Q, K274E, K320E, K322E, K326E, K334E, R355E, K392E, a deletion of K447, adding peptide DEDE at the c-terminus, G137E, N203D, K274Q, R355Q, K392N and Q419E. As outlined herein and shown in the figures, these changes are shown relative to IgG1, but all isotypes can be altered this way, as well as isotype hybrids.

In the case where the heavy chain constant domain is from IgG2-4, R133E and R133Q can also be used.

Basic pI Changes

Accordingly, when one monomer comprising a variant heavy chain constant domain is to be made more negative (e.g. increase the pI), one or more of the following substitutions can be made: Q196K, P217R, P228R, N276K and H435R. As outlined herein and shown in the figures, these changes are shown relative to IgG1, but all isotypes can be altered this way, as well as isotype hybrids.

Antibody Heterodimers Light Chain Variants

In the case of antibody based heterodimers, e.g. where at least one of the monomers comprises a light chain in addition to the heavy chain domain, pI variants can also be made in the light chain. Amino acid substitutions for lowering the pI of the light chain include, but are not limited to, K126E, K126Q, K145E, K145Q, N152D, S156E, K169E, S202E, K207E and adding peptide DEDE at the c-terminus of the light chain. Changes in this category based on the constant lambda light chain include one or more substitutions at R108Q, Q124E, K126Q, N138D, K145T and Q199E. In addition, increasing the pI of the light chains can also be done.

Isotypic Variants

In addition, many embodiments of the invention rely on the "importation" of pI amino acids at particular positions from one IgG isotype into another, thus reducing or eliminating the possibility of unwanted immunogenicity being introduced into the variants. That is, IgG1 is a common isotype for therapeutic antibodies for a variety of reasons, including high effector function. However, the heavy constant region of IgG1 has a higher pI than that of IgG2 (8.10 versus 7.31). By introducing IgG2 residues at particular positions into the IgG1 backbone, the pI of the resulting monomer is lowered (or increased) and additionally exhibits longer serum half-life. For example, IgG1 has a glycine (pI 5.97) at position 137, and IgG2 has a glutamic acid (pI 3.22); importing the glutamic acid will affect the pI of the resulting protein. As is described below, a number of amino acid substitutions are generally required to significant affect the pI of the variant antibody. However, it should be noted as discussed below that even changes in IgG2 molecules allow for increased serum half-life.

In other embodiments, non-isotypic amino acid changes are made, either to reduce the overall charge state of the resulting protein (e.g. by changing a higher pI amino acid to a lower pI amino acid), or to allow accommodations in structure for stability, etc. as is more further described below.

In addition, by pI engineering both the heavy and light constant domains, significant changes in each monomer of the heterodimer can be seen. As discussed herein, having the pIs of the two monomers differ by at least 0.5 can allow separation.

Calculating pI

The pI of each monomer can depend on the pI of the variant heavy chain constant domain and the pI of the total monomer, including the variant heavy chain constant domain and the fusion partner. Thus, in some embodiments, the change in pI is calculated on the basis of the variant heavy chain constant domain, using the chart in the Figures. Alternatively, the pI of each monomer can be compared.

pI Variants that Also Confer Better FcRn In Vitro Binding

In the case where the pI variant decreases the pI of the monomer, they can have the added benefit of improving serum retention in vivo.

Although still under examination, Fc regions are believed to have longer half-lives in vivo, because binding to FcRn at pH 6 in an endosome sequesters the Fc (Ghetie and Ward, 1997 Immunol Today. 18(12): 592-598, entirely incorporated by reference). The endosomal compartment then recycles the Fc to the cell surface. Once the compartment opens to the extracellular space, the higher pH, ~7.4, induces the release of Fc back into the blood. In mice, Dall'Acqua et al. showed that Fc mutants with increased FcRn binding at pH 6 and pH 7.4 actually had reduced serum concentrations and the same half life as wild-type Fc (Dall' Acqua et al. 2002, J. Immunol. 169:5171-5180, entirely incorporated by reference). The increased affinity of Fc for FcRn at pH 7.4 is thought to forbid the release of the Fc back into the blood. Therefore, the Fc mutations that will increase Fc's half-life in vivo will ideally increase FcRn binding at the lower pH while still allowing release of Fc at higher pH. The amino acid histidine changes its charge state in the pH range of 6.0 to 7.4. Therefore, it is not surprising to find His residues at important positions in the Fc/FcRn complex.

Recently it has been suggested that antibodies with variable regions that have lower isoelectric points may also have longer serum half-lives (Igawa et al., 2010 PEDS. 23(5): 385-392, entirely incorporated by reference). However, the mechanism of this is still poorly understood. Moreover, variable regions differ from antibody to antibody. Constant region variants with reduced pI and extended half-life would provide a more modular approach to improving the pharmacokinetic properties of antibodies, as described herein.

Combination of Heterodimeric Variants

As will be appreciated by those in the art, all of the recited heterodimerization variants can be optionally and independently combined in any way, as long as they retain their "strandedness" or "monomer partition". In addition, all of these variants can be combined into any of the hterodimerization formats. See FIG. 83.

In the case of pI variants, while embodiments finding particular use are shown in the Figures, other combinations can be generated, following the basic rule of altering the pI difference between two monomers to facilitate purification.

Suitable Multispecific Formats

As will be appreciated by those in the art, there are a wide variety of possible multispecific formats that find use in the present invention, see for example Kontermann, mAbs 4(2): 182-197 (2012), hereby incorporated by reference in its entirety and particularly Tables 1 and 2 and FIGS. 1 and 2, with specific reference to the constructs of Kontermann that contain an Fc region. See also Klein et al., Of use in the present invention are heterodimers that contain constant heavy chain and/or constant light chain regions, and in particular, Fc domains. That is, some variants discussed herein are within the vhCH1, although many of the variants are within the Fc domain (hinge-CH2-CH3).

As will be appreciated by those in the art and discussed more fully below, the heterodimeric fusion proteins of the present invention can take on a wide variety of configurations, as are generally depicted in the Figures. Some figures depict "single ended" configurations, where there is one type of specificity on one "arm" of the molecule and a different specificity on the other "arm". Other figures depict "dual ended" configurations, where there is at least one type of specificity at the "top" of the molecule and one or more different specificities at the "bottom" of the molecule. Furthermore as is shown, these two configurations can be combined, where there can be triple or quadruple specificities based on the particular combination. Thus, the present invention provides "multispecific" binding proteins, including multispecific antibodies.

In some embodiments, the heterodimers resemble traditional antibodies although they are bispecific and have two different variable regions; see FIG. 78. As outlined herein, the constant regions comprise heterodimerization variants, such as steric variants ("knobs in holes", sometimes referred to in the art as "kih" variants) or pI variants, etc. In some cases, to reduce the complexity with regard to the light chains, some of these formats variable regions that share a common light chain (e.g. two separate heavy chains with a light chain that will assemble with both but confers two different specificities.

In some embodiments, the heterodimers are bispecific in a format generally referred to in the art as "CrossMab". In this embodiment, in addition to using the heterodimeric variants described herein, one heavy chain monomer and one light chain monomer are also engineered such that the heavy chain monomer comprises a constant light region in place of the vhCH1 domain, and the light chain contains the vhCH1 region with the variable light region. This ensures that the correct light chains will pair with the correct heavy chains. See FIG. 78N and Schaefer et al., PNAS 108(27) 11187-11192 (hereby incorporated by reference in its entirety.

In some embodiments, sometimes referred to in the art as IgG-scFab, one of the heavy chains has a scFab on it, such that one antigen is engaged bivalently and the other monovalently (e.g. two binding regions on one "end" and a single binding region on the other "end"). (See FIG. 78).

In some embodiments, sometimes referred to as mAb-Fv, each heavy chain of the heterodimer has an additional variable region on the terminus. One monomer has the variable heavy domain and the other monomer has a variable light domain (See FIG. 78E). See for example PCT US2010/047741, hereby incorporated by reference. In this embodiment, in general, there are two different types of antibody analogs that allow for co-engagement mechanisms, one that utilizes three antigen binding domains (e.g. one antigen is bound bivalently and the other is bound monovalently, although as is further described below, there can also be three different antigens that are bound or a single antigen), and one that relies on two antigen binding domains (e.g. each antigen is bound monovalently).

Additional Modifications

In addition to the modifications outlined above, other modifications can be made. For example, the molecules may be stabilized by the incorporation of disulphide bridges linking the VH and VL domains (Reiter et al., 1996, Nature Biotech. 14:1239-1245, entirely incorporated by reference). In addition, there are a variety of covalent modifications of antibodies that can be made as outlined below.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with a-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

In addition, modifications at cysteines are particularly useful in antibody-drug conjugate (ADC) applications, further described below. In some embodiments, the constant region of the antibodies can be engineered to contain one or more cysteines that are particularly "thiol reactive", so as to allow more specific and controlled placement of the drug moiety. See for example U.S. Pat. No. 7,521,541, incorporated by reference in its entirety herein.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods, in addition to methods described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cynomolgusogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, Proteins: Structure and Molecular Properties, W. H. Freeman & Co., San Francisco, pp. 79-86 [1983], entirely incorporated by reference), acetylation of the N-terminal amine, and amidation of any C-terminal carboxyl group.

In addition, as will be appreciated by those in the art, labels (including fluorescent, enzymatic, magnetic, radioactive, etc. can all be added to the antibodies (as well as the other compositions of the invention).

Glycosylation

Another type of covalent modification is alterations in glycosylation. In another embodiment, the antibodies disclosed herein can be modified to include one or more engineered glycoforms. By "engineered glycoform" as used herein is meant a carbohydrate composition that is covalently attached to the antibody, wherein said carbohydrate composition differs chemically from that of a parent antibody. Engineered glycoforms may be useful for a variety of purposes, including but not limited to enhancing or reducing effector function. A preferred form of engineered glycoform is afucosylation, which has been shown to be correlated to an increase in ADCC function, presumably through tighter binding to the FcγRIIIa receptor. In this context, "afucosylation" means that the majority of the antibody produced in the host cells is substantially devoid of fucose, e.g. 90-95-98% of the generated antibodies do not have appreciable fucose as a component of the carbohydrate moiety of the antibody (generally attached at N297 in the Fc region). Defined functionally, afucosylated antibodies generally exhibit at least a 50% or higher affinity to the FcγRIIIa receptor.

Engineered glycoforms may be generated by a variety of methods known in the art (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1, all entirely incorporated by reference; (Potelligent® technology [Biowa, Inc., Princeton, N.J.]; GlycoMAb® glycosylation engineering technology [Glycart Biotechnology AG, Zurich, Switzerland]). Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells, by regulating enzymes involved in the glycosylation pathway (for example FUT8 [α1,6-fucosyltranserase] and/or β1-4-N-acetylglucosaminyltransferase III [GnTIII]), or by modifying carbohydrate(s) after the IgG has been expressed. For example, the "sugar engineered antibody" or "SEA technology" of Seattle Genetics functions by adding modified saccharides that inhibit fucosylation during production; see for example 20090317869, hereby incorporated by reference in its entirety. Engineered glycoform typically refers to the different carbohydrate or oligosaccharide; thus an antibody can include an engineered glycoform.

Alternatively, engineered glycoform may refer to the IgG variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, 1981, CRC Crit. Rev. Biochem., pp. 259-306, both entirely incorporated by reference.

Removal of carbohydrate moieties present on the starting antibody (e.g. post-translationally) may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

Other Fc Modifications

In addition to heterodimerization variants, other amino acid modifications (particularly amino acid substitutions) find use to alter additional properties of the heterodimer.

FcγR Variants

In one embodiment, the heterodimers of the invention can include amino acid modifications to alter binding to one or more of the FcγR receptors. Substitutions that result in increased binding as well as decreased binding can be useful. For example, it is known that increased binding to FcγRIIIa generally results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell). Similarly, decreased binding to FcγRIIb (an inhibitory receptor) can be beneficial as well in some circumstances. Amino acid substitutions that find use in the present invention include those listed in U.S. Ser. No. 11/124,620 (particularly FIG. 41, specifically incorporated herein), Ser. Nos. 11/174,287, 11/396,495, 11/538,406, all of which are expressly incorporated herein by reference in their entirety and specifically for the variants disclosed therein.

Particular variants that find use include, but are not limited to, 236A, 239D, 239E, 332E, 332D, 239D/332E, 267D, 267E, 328F, 267E/328F, 236A/332E, 239D/332E/330Y, 239D, 332E/330L, 236R, 328R, 236R/328R, 243L, 298A and 299T. Additional uitable Fc variants are found in FIG. 41 of US 2006/0024298, the figure and legend of which are hereby incorporated by reference in their entirety.

FcRn Modifications

Figure 9A:
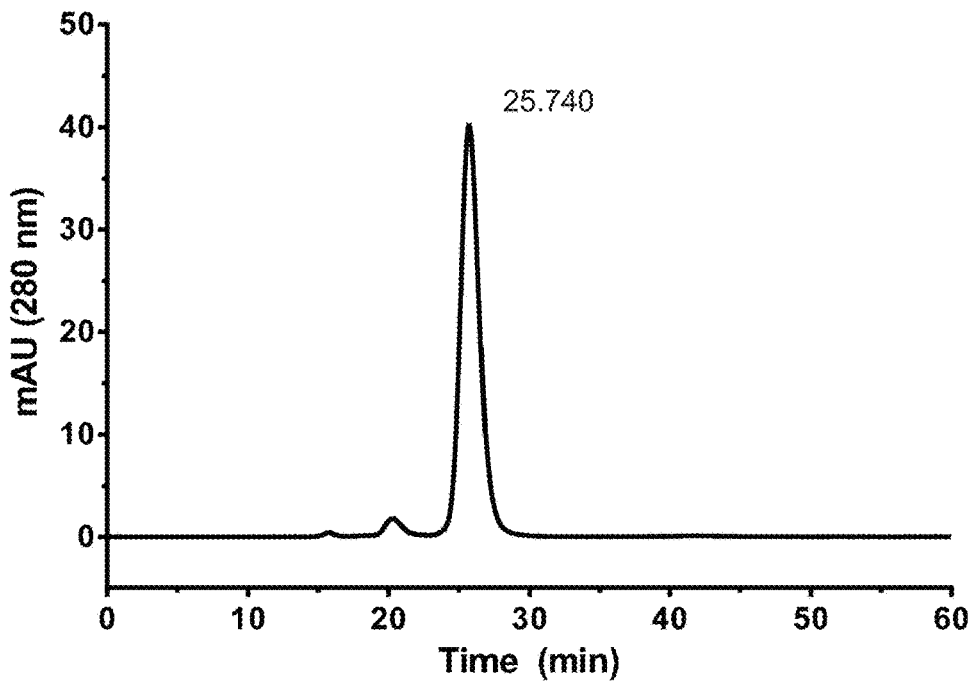
FIG. 9A-9C. Analysis of pI engineered anti-VEGF variants on SEC showing high purity.
Figure 9B:
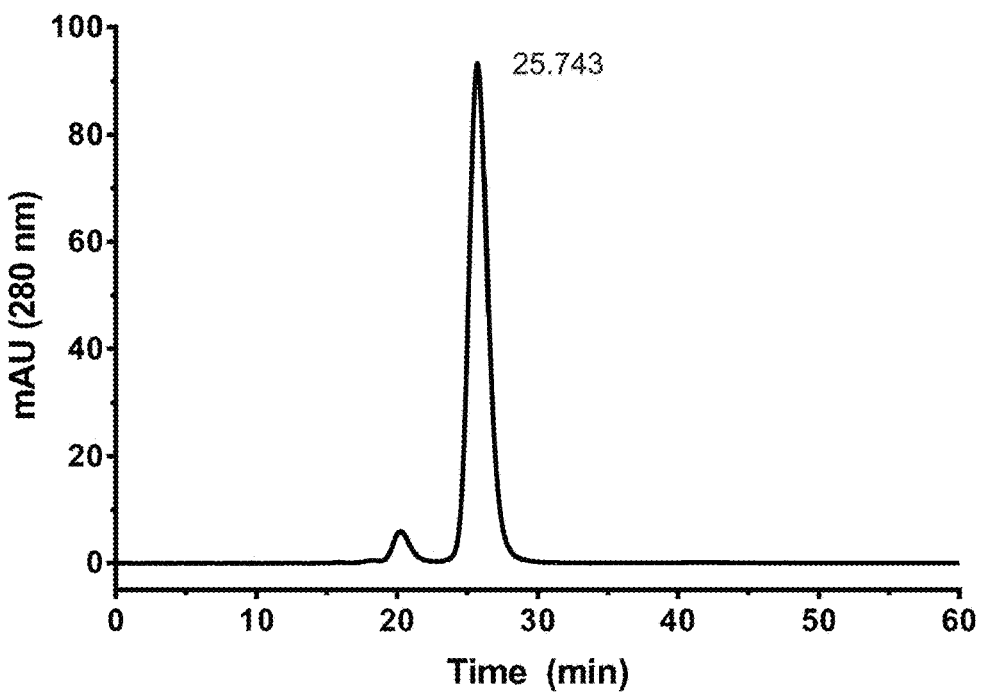
Figure 9C:
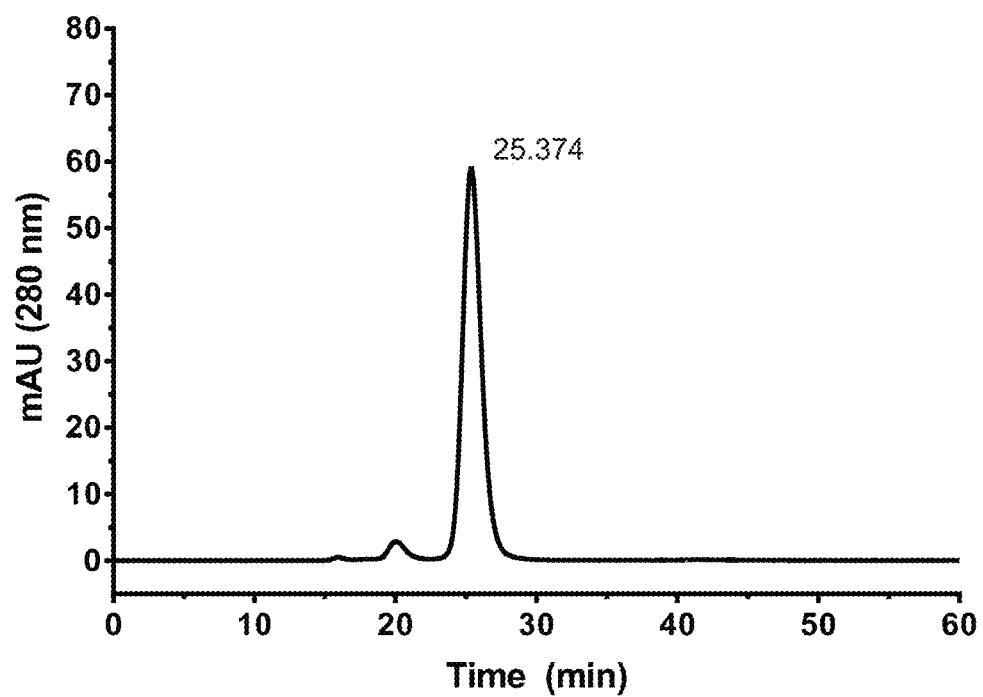
Figure 10:
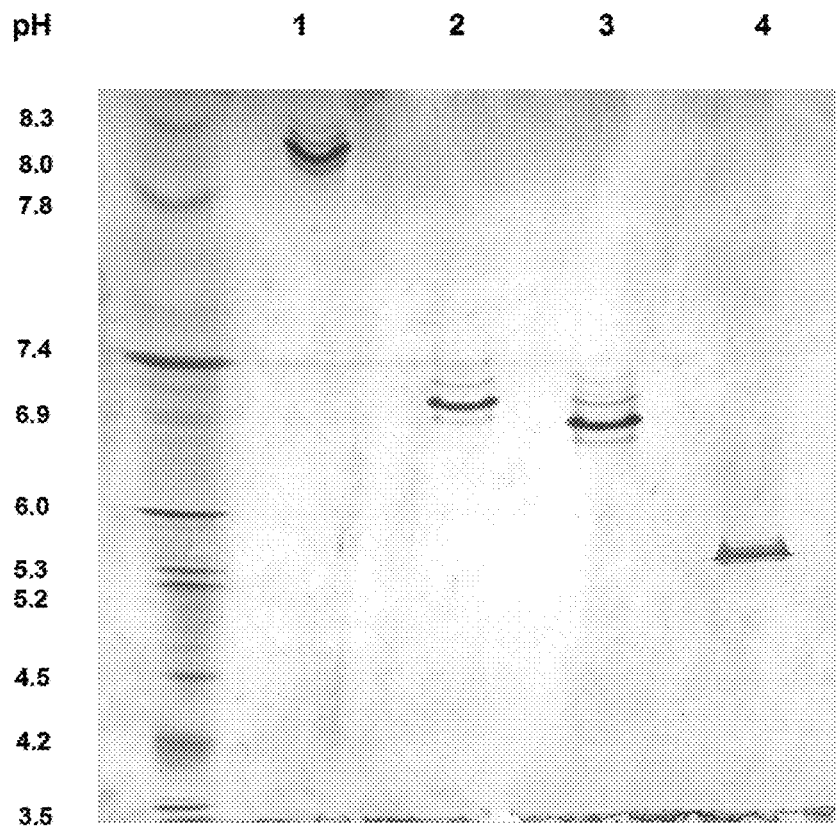
FIG. 10. Analysis of pI engineered anti-VEGF variants on an IEF gel showing variants have altered pI.

In addition, there are additional Fc substitutions that find use in increased binding to the FcRn receptor and/or increased serum half life, as specifically disclosed in U.S. Ser. No. 12/341,769, hereby incorporated by reference in its entirety (particularly FIGS. 9 and 10), including, but not limited to, 434A, 434S, 428L, 308F, 259I, 428L/434S, 259I/308F, 436I/428L, 436I or V/434S, 436V/428L, 252Y, 252Y/254T/256E and 259I/308F/428L.

Binding Moieties/Targets

The heterodimeric proteins (for example the heterodimeric immunoglobulins) of the invention may target virtually any antigens. As noted above, there are a wide variety of suitable heterodimeric antibody formats, with some preferably co-engage two target antigens, although in some cases, three or four antigens can be engaged.

Particular suitable applications of the immunoglobulins herein are co-target pairs for which it is beneficial or critical to engage a target antigen monovalently. Such antigens may be, for example, immune receptors that are activated upon immune complexation. Cellular activation of many immune receptors occurs only by cross-linking, achieved typically by antibody/antigen immune complexes, or via effector cell to target cell engagement. For some immune receptors, for example the CD3 signaling receptor on T cells, activation only upon engagement with co-engaged target is critical, as nonspecific cross-linking in a clinical setting can elicit a cytokine storm and toxicity. Therapeutically, by engaging such antigens monovalently rather than multivalently, using the immunoglobulins herein, such activation occurs only in response to cross-linking only in the microenvironment of the primary target antigen. The ability to target two different antigens with different valencies is a novel and useful aspect of the present invention. Examples of target antigens for which it may be therapeutically beneficial or necessary to co-engage monovalently include but are not limited to immune activating receptors such as CD3, FcγRs, toll-like receptors (TLRs) such as TLR4 and TLR9, cytokine, chemokine, cytokine receptors, and chemokine receptors.

Virtually any antigen may be targeted by the immunoglobulins herein, including but not limited to proteins, subunits, domains, motifs, and/or epitopes belonging to the following list of target antigens, which includes both soluble factors such as cytokines and membrane-bound factors, including transmembrane receptors: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAMS, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp 120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, MET-ALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mucl), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, 5100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEMS, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors. To form the bispecific or trispecific antibodies of the invention, antibodies to any combination of these antigens can be made; that is, each of these antigens can be optionally and independently included or excluded from a multispecific antibody according to the present invention.

Exemplary antigens that may be targeted specifically by the immunoglobulins of the invention include but are not limited to: CD20, CD19, Her2, EGFR, EpCAM, CD3, FcγRIIIa (CD16), FcγRIIa (CD32a), FcγRIIb (CD32b), FcγRI (CD64), Toll-like receptors (TLRs) such as TLR4 and TLR9, cytokines such as IL-2, IL-5, IL-13, IL-12, IL-23, and TNFα, cytokine receptors such as IL-2R, chemokines, chemokine receptors, growth factors such as VEGF and HGF, and the like. To form the bispecific or trispecific antibodies of the invention, antibodies to any combination of these antigens can be made; that is, each of these antigens can be optionally and independently included or excluded from a multispecific antibody according to the present invention.

The choice of suitable target antigens and co-targets depends on the desired therapeutic application. Some targets that have proven especially amenable to antibody therapy are those with signaling functions. Other therapeutic antibodies exert their effects by blocking signaling of the receptor by inhibiting the binding between a receptor and its cognate ligand. Another mechanism of action of therapeutic antibodies is to cause receptor down regulation. Other antibodies do not work by signaling through their target antigen. The choice of co-targets will depend on the detailed biology underlying the pathology of the indication that is being treated.

Monoclonal antibody therapy has emerged as an important therapeutic modality for cancer (Weiner et al., 2010, Nature Reviews Immunology 10:317-327; Reichert et al., 2005, Nature Biotechnology 23[9]:1073-1078; herein expressly incorporated by reference). For anti-cancer treatment it may be desirable to target one antigen (antigen-1) whose expression is restricted to the cancerous cells while co-targeting a second antigen (antigen-2) that mediates some immunological killing activity. For other treatments it may be beneficial to co-target two antigens, for example two angiogenic factors or two growth factors, that are each known to play some role in proliferation of the tumor. Exemplary co-targets for oncology include but are not limited to HGF and VEGF, IGF-1R and VEGF, Her2 and VEGF, CD19 and CD3, CD20 and CD3, Her2 and CD3, CD19 and FcγRIIIa, CD20 and FcγRIIIa, Her2 and FcγRIIIa. An immunoglobulin of the invention may be capable of binding VEGF and phosphatidylserine; VEGF and ErbB3; VEGF and PLGF; VEGF and ROBO4; VEGF and BSG2; VEGF and CDCP1; VEGF and ANPEP; VEGF and c-MET; HER-2 and ERB3; HER-2 and BSG2; HER-2 and CDCP1; HER-2 and ANPEP; EGFR and CD64; EGFR and BSG2; EGFR and CDCP1; EGFR and ANPEP; IGF1R and PDGFR; IGF1R and VEGF; IGF1R and CD20; CD20 and CD74; CD20 and CD30; CD20 and DR4; CD20 and VEGFR2; CD20 and CD52; CD20 and CD4; HGF and c-MET; HGF and NRP1; HGF and phosphatidylserine; ErbB3 and IGF1R; ErbB3 and IGF1,2; c-Met and Her-2; c-Met and NRP1; c-Met and IGF1R; IGF1,2 and PDGFR; IGF1,2 and CD20; IGF1,2 and IGF1R; IGF2 and EGFR; IGF2 and HER2; IGF2 and CD20; IGF2 and VEGF; IGF2 and IGF1R; IGF1 and IGF2; PDGFRa and VEGFR2; PDGFRa and PLGF; PDGFRa and VEGF; PDGFRa and c-Met; PDGFRa and EGFR; PDGFRb and VEGFR2; PDGFRb and c-Met; PDGFRb and EGFR; RON and c-Met; RON and MTSP1; RON and MSP; RON and CDCP1; VGFR1 and PLGF; VGFR1 and RON; VGFR1 and EGFR; VEGFR2 and PLGF; VEGFR2 and NRP1; VEGFR2 and RON; VEGFR2 and DLL4; VEGFR2 and EGFR; VEGFR2 and ROBO4; VEGFR2 and CD55; LPA and S1P; EPHB2 and RON; CTLA4 and VEGF; CD3 and EPCAM; CD40 and IL6; CD40 and IGF; CD40 and CD56; CD40 and CD70; CD40 and VEGFR1; CD40 and DR5; CD40 and DR4; CD40 and APRIL; CD40 and BCMA; CD40 and RANKL; CD28 and MAPG; CD80 and CD40; CD80 and CD30; CD80 and CD33; CD80 and CD74; CD80 and CD2; CD80 and CD3; CD80 and CD19; CD80 and CD4; CD80 and CD52; CD80 and VEGF; CD80 and DR5; CD80 and VEGFR2; CD22 and CD20; CD22 and CD80; CD22 and CD40; CD22 and CD23; CD22 and CD33; CD22 and CD74; CD22 and CD19; CD22 and DR5; CD22 and DR4; CD22 and VEGF; CD22 and CD52; CD30 and CD20; CD30 and CD22; CD30 and CD23; CD30 and CD40; CD30 and VEGF; CD30 and CD74; CD30 and CD19; CD30 and DR5; CD30 and DR4; CD30 and VEGFR2; CD30 and CD52; CD30 and CD4; CD138 and RANKL; CD33 and FTL3; CD33 and VEGF; CD33 and VEGFR2; CD33 and CD44; CD33 and DR4; CD33 and DR5; DR4 and CD137; DR4 and IGF1,2; DR4 and IGF1R; DR4 and DR5; DR5 and CD40; DR5 and CD137; DR5 and CD20; DR5 and EGFR; DR5 and IGF1,2; DR5 and IGFR, DR5 and HER-2, and EGFR and DLL4. Other target combinations include one or more members of the EGF/erb-2/erb-3 family.

Other targets (one or more) involved in oncological diseases that the immunoglobulins herein may bind include, but are not limited to those selected from the group consisting of: CD52, CD20, CD19, CD3, CD4, CD8, BMP6, IL12A, IL1A, IL1B, 1L2, IL24, INHA, TNF, TNFSF10, BMP6, EGF, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, GRP, IGF1, IGF2, IL12A, IL1A, IL1B, 1L2, INHA, TGFA, TGFB1, TGFB2, TGFB3, VEGF, CDK2, FGF10, FGF18, FGF2, FGF4, FGF7, IGF1R, IL2, BCL2, CD164, CDKN1A, CDKN1B, CDKN1C, CDKN2A, CDKN2B, CDKN2C, CDKN3, GNRH1, IGFBP6, IL1A, IL1B, ODZ1, PAWR, PLG, TGFB1I1, AR, BRCA1, CDK3, CDK4, CDK5, CDK6, CDK7, CDK9, E2F1, EGFR, ENO1, ERBB2, ESR1, ESR2, IGFBP3, IGFBP6, IL2, INSL4, MYC, NOX5, NR6A1, PAP, PCNA, PRKCQ, PRKD1, PRL, TP53, FGF22, FGF23, FGF9, IGFBP3, IL2, INHA, KLK6, TP53, CHGB, GNRH1, IGF1, IGF2, INHA, INSL3, INSL4, PRL, KLK6, SHBG, NR1D1, NR1H3, NR1I3, NR2F6, NR4A3, ESR1, ESR2, NR0B1, NR0B2, NR1D2, NR1H2, NR1H4, NR1I2, NR2C1, NR2C2, NR2E1, NR2E3, NR2F1, NR2F2, NR3C1, NR3C2, NR4A1, NR4A2, NR5A1, NR5A2, NR6 μl, PGR, BARB, FGF1, FGF2, FGF6, KLK3, KRT1, APOC1, BRCA1, CHGA, CHGB, CLU, COL1A1, COL6A1, EGF, ERBB2, ERK8, FGF1, FGF10, FGF11, FGF13, FGF14, FGF16, FGF17, FGF18, FGF2, FGF20, FGF21, FGF22, FGF23, FGF3, FGF4, FGF5, FGF6, FGF7, FGF8, FGF9, GNRH1, IGF1, IGF2, IGFBP3, IGFBP6, IL12A, IL1A, IL1B, 1L2, IL24, INHA, INSL3, INSL4, KLK10, KLK12, KLK13, KLK14, KLK15, KLK3, KLK4, KLK5, KLK6, KLK9, MMP2, MMP9, MSMB, NTN4, ODZ1, PAP, PLAU, PRL, PSAP, SERPINA3, SHBG, TGFA, TIMP3, CD44, CDH1, CDH10, CDH19, CDH20, CDH7, CDH9, CDH1, CDH10, CDH13, CDH18, CDH19, CDH20, CDH7, CDH8, CDH9, ROBO2, CD44, ILK, ITGA1, APC, CD164, COL6A1, MTSS1, PAP, TGFB1I1, AGR2, AIG1, AKAP1, AKAP2, CANT1, CAV1, CDH12, CLDN3, CLN3, CYB5, CYCL DAB21P, DES, DNCL1, ELAC2, ENO2, ENO3, FASN, FLJ12584, FLJ25530, GAGEB1, GAGEC1, GGT1, GSTP1, HIP1, HUMCYT2A, IL29, K6HF, KAI1, KRT2A, MIB1, PART1, PATE, PCA3, PIAS2, PIK3CG, PPID, PR1, PSCA, SLC2A2, SLC33 μl, SLC43 μl, STEAP, STEAP2, TPM1, TPM2, TRPC6, ANGPT1, ANGPT2, ANPEP, ECGF1, EREG, FGF1, FGF2, FIGF, FLT1, JAG1, KDR, LAMA5, NRP1, NRP2, PGF, PLXDC1, STAB 1, VEGF, VEGFC, ANGPTL3, BAI1, COL4A3, IL8, LAMA5, NRP1, NRP2, STAB 1, ANGPTL4, PECAM1, PF4, PROK2, SERPINF1, TNFAIP2, CCL11, CCL2, CXCL1, CXCL10, CXCL3, CXCL5, CXCL6, CXCL9, IFNA1, IFNB1, IFNG, IL1B, IL6, MDK, EDG1, EFNA1, EFNA3, EFNB2, EGF, EPHB4, FGFR3, HGF, IGF1, ITGB3, PDGFA, TEK, TGFA, TGFB1, TGFB2, TGFBR1, CCL2, CDH5, COL1A1, EDG1, ENG, ITGAV, ITGB3, THBS1, THBS2, BAD, BAG1, BCL2, CCNA1, CCNA2, CCND1, CCNE1, CCNE2, CDH1

(E-cadherin), CDKN1B (p27Kip1), CDKN2A (p161NK4a), COL6A1, CTNNB1 (b-catenin), CTSB (cathepsin B), ERBB2 (Her-2), ESR1, ESR2, F3 (TF), FOSL1 (FRA-1), GATA3, GSN (Gelsolin), IGFBP2, IL2RA, IL6, IL6R, IL6ST (glycoprotein 130), ITGA6 (a6 integrin), JUN, KLK5, KRT19, MAP2K7 (c-Jun), MKI67 (Ki-67), NGFB (GF), NGFR, NME1 (M23A), PGR, PLAU (uPA), PTEN, SERPINB5 (maspin), SERPINE1 (PAI-1), TGFA, THBS1 (thrombospondin-1), TIE (Tie-1), TNFRSF6 (Fas), TNFSF6 (FasL), TOP2A (topoisomerase IIa), TP53, AZGP1 (zinc-a-glycoprotein), BPAG1 (plectin), CDKN1A (p21Wap1/Cip1), CLDN7 (claudin-7), CLU (clusterin), ERBB2 (Her-2), FGF1, FLRT1 (fibronectin), GABRP (GABAa), GNAS1, ID2, ITGA6 (a6 integrin), ITGB4 (b 4 integrin), KLF5 (GC Box BP), KRT19 (Keratin 19), KRTHB6 (hair-specific type II keratin), MACMARCKS, MT3 (metallothionectin-III), MUC1 (mucin), PTGS2 (COX-2), RAC2 (p21Rac2), S100A2, SCGB1D2 (lipophilin B), SCGB2A1 (mammaglobin 2), SCGB2A2 (mammaglobin 1), SPRR1B (Spr1), THBS1, THBS2, THBS4, and TNFAIP2 (B94), RON, c-Met, CD64, DLL4, PLGF, CTLA4, phophatidylserine, ROBO4, CD80, CD22, CD40, CD23, CD28, CD80, CD55, CD38, CD70, CD74, CD30, CD138, CD56, CD33, CD2, CD137, DR4, DR5, RANKL, VEGFR2, PDGFR, VEGFR1, MTSP1, MSP, EPHB2, EPHA1, EPHA2, EpCAM, PGE2, NKG2D, LPA, SIP, APRIL, BCMA, MAPG, FLT3, PDGFR alpha, PDGFR beta, ROR1, PSMA, PSCA, SCD1, and CD59. To form the bispecific or trispecific antibodies of the invention, antibodies to any combination of these antigens can be made; that is, each of these antigens can be optionally and independently included or excluded from a multispecific antibody according to the present invention.

Monoclonal antibody therapy has become an important therapeutic modality for treating autoimmune and inflammatory disorders (Chan & Carter, 2010, Nature Reviews Immunology 10:301-316; Reichert et al., 2005, Nature Biotechnology 23[9]:1073-1078; herein expressly incorporated by reference). Many proteins have been implicated in general autoimmune and inflammatory responses, and thus may be targeted by the immunogloublins of the invention. Autoimmune and inflammatory targets include but are not limited to C5, CCL1 (1-309), CCL11 (eotaxin), CCL13 (mcp-4), CCL15 (MIP-1d), CCL16 (HCC-4), CCL17 (TARC), CCL18 (PARC), CCL19, CCL2 (mcp-1), CCL20 (MIP-3a), CCL21 (MIP-2), CCL23 (MPIF-1), CCL24 (MPIF-2/eotaxin-2), CCL25 (TECK), CCL26, CCL3 (MIP-1a), CCL4 (MIP-1b), CCL5 (RANTES), CCL7 (mcp-3), CCL8 (mcp-2), CXCL1, CXCL10 (IP-10), CXCL11 (1-TAC/IP-9), CXCL12 (SDF1), CXCL13, CXCL14, CXCL2, CXCL3, CXCL5 (ENA-78/LIX), CXCL6 (GCP-2), CXCL9, IL13, IL8, CCL13 (mcp-4), CCR1, CCR2, CCR3, CCR4, CCR5, CCR6, CCR7, CCR8, CCR9, CX3CR1, IL8RA, XCR1 (CCXCR1), IFNA2, IL10, IL13, IL17C, IL1A, IL1B, IL1F10, IL1F5, IL1F6, IL1F7, IL1F8, IL1F9, IL22, IL5, IL8, IL9, LTA, LTB, MIF, SCYE1 (endothelial Monocyte-activating cytokine), SPP1, TNF, TNFSF5, IFNA2, IL10RA, IL10RB, IL13, IL13RA1, IL5RA, IL9, IL9R, ABCF1, BCL6, C3, C4A, CEBPB, CRP, ICEBERG, IL1R1, IL1RN, IL8RB, LTB4R, TOLLIP, FADD, IRAK1, IRAK2, MYD88, NCK2, TNFAIP3, TRADD, TRAF1, TRAF2, TRAF3, TRAF4, TRAF5, TRAF6, ACVR1, ACVR1B, ACVR2, ACVR2B, ACVRL1, CD28, CD3E, CD3G, CD3Z, CD69, CD80, CD86, CNR1, CTLA4, CYSLTR1, FCER1A, FCER2, FCGR3A, GPR44, HAVCR2, OPRD1, P2RX7, TLR2, TLR3, TLR4, TLR5, TLR6, TLR7, TLR8, TLR9, TLR10, BLR1, CCL1, CCL2, CCL3, CCL4, CCL5, CCL7, CCL8, CCL11, CCL13, CCL15, CCL16, CCL17, CCL18, CCL19, CCL20, CCL21, CCL22, CCL23, CCL24, CCL25, CCR1, CCR2, CCR3, CCR4, CCR5, CCR6, CCR7, CCR8, CCR9, CX3CL1, CX3CR1, CXCL1, CXCL2, CXCL3, CXCL5, CXCL6, CXCL10, CXCL11, CXCL12, CXCL13, CXCR4, GPR2, SCYE1, SDF2, XCL1, XCL2, XCR1, AMH, AMHR2, BMPR1A, BMPR1B, BMPR2, C19orf10 (IL27w), CER1, CSF1, CSF2, CSF3, DKFZp451J0118, FGF2, GFI1, IFNA1, IFNB1, IFNG, IGF1, IL1A, IL1B, IL1R1, IL1R2, IL2, IL2RA, IL2RB, IL2RG, IL3, IL4, IL4R, IL5, IL5RA, IL6, IL6R, IL6ST, IL7, IL8, IL8RA, IL8RB, IL9, IL9R, IL10, IL10RA, IL10RB, IL11, IL12RA, IL12A, IL12B, IL12RB1, IL12RB2, IL13, IL13RA1, IL13RA2, IL15, IL15RA, IL16, IL17, IL17R, IL18, IL18R1, IL19, IL20, KITLG, LEP, LTA, LTB, LTB4R, LTB4R2, LTBR, MIF, NPPB, PDGFB, TBX21, TDGF1, TGFA, TGFB1, TGFB1I1, TGFB2, TGFB3, TGFB1, TGFBR1, TGFBR2, TGFBR3, TH1L, TNF, TNFRSF1A, TNFRSF1B, TNFRSF7, TNFRSF8, TNFRSF9, TNFRSF11A, TNFRSF21, TNFSF4, TNFSF5, TNFSF6, TNFSF11, VEGF, ZFPM2, and RNF110 (ZNF144). To form the bispecific or trispecific antibodies of the invention, antibodies to any combination of these antigens can be made; that is, each of these antigens can be optionally and independently included or excluded from a multispecific antibody according to the present invention.

Exemplary co-targets for autoimmune and inflammatory disorders include but are not limited to IL-1 and TNFalpha, IL-6 and TNFalpha, IL-6 and IL-1, IgE and IL-13, IL-1 and IL-13, IL-4 and IL-13, IL-5 and IL-13, IL-9 and IL-13, CD19 and FcγRIIb, and CD79 and FcγRIIb.

Immunglobulins of the invention with specificity for the following pairs of targets to treat inflammatory disease are contemplated: TNF and IL-17A; TNF and RANKL; TNF and VEGF; TNF and SOST; TNF and DKK; TNF and alphaVbeta3; TNF and NGF; TNF and IL-23p19; TNF and IL-6; TNF and SOST; TNF and IL-6R; TNF and CD-20; IgE and IL-13; IL-13 and IL23p19; IgE and IL-4; IgE and IL-9; IgE and IL-9; IgE and IL-13; IL-13 and IL-9; IL-13 and IL-4; IL-13 and IL-9; IL-13 and IL-9; IL-13 and IL-4; IL-13 and IL-23p19; IL-13 and IL-9; IL-6R and VEGF; IL-6R and IL-17A; IL-6R and RANKL; IL-17A and IL-1beta; IL-1beta and RANKL; IL-1beta and VEGF; RANKL and CD-20; IL-1alpha and IL-1beta; IL-1alpha and IL-1beta.

Pairs of targets that the immunoglobulins described herein can bind and be useful to treat asthma may be determined. In an embodiment, such targets include, but are not limited to, IL-13 and IL-1beta, since IL-1beta is also implicated in inflammatory response in asthma; IL-13 and cytokines and chemokines that are involved in inflammation, such as IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; and IL-13 and ADAMS. The immunoglobulins herein may have specify for one or more targets involved in asthma selected from the group consisting of CSF1 (MCSF), CSF2 (GM-CSF), CSF3 (GCSF), FGF2, IFNA1, IFNB1, IFNG, histamine and histamine receptors, IL1A, IL1B, IL2, IL3, IL4, IL5, IL6, IL7, IL8, IL9, IL10, IL11, IL12A, IL12B, IL13, IL14, IL15, IL16, IL17, IL18, IL19, KITLG, PDGFB, IL2RA, IL4R, IL5RA, IL8RA, IL8RB, IL12RB1, IL12RB2, IL13RA1, IL13RA2, IL18R1, TSLP, CCLi, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCLi, CCR2, CCR3, CCR4, CCR5, CCR6, CCR7, CCR8, CX3CR1, GPR2, XCR1, FOS, GATA3, JAK1, JAK3, STAT6, TBX21, TGFB1, TNF, TNFSF6, YY1, CYS- LTR1, FCER1A, FCER2, LTB4R, TB4R2, LTBR, and Chitinase. To form the bispecific or trispecific antibodies of the invention, antibodies to any combination of these antigens can be made; that is, each of these antigens can be optionally and independently included or excluded from a multispecific antibody according to the present invention.

Pairs of targets involved in rheumatoid arthritis (RA) may be co-targeted by the invention, including but not limited to TNF and IL-18; TNF and IL-12; TNF and IL-23; TNF and IL-1beta; TNF and MIF; TNF and IL-17; and TNF and IL-15.

Antigens that may be targeted in order to treat systemic lupus erythematosus (SLE) by the immunoglobulins herein include but are not limited to CD-20, CD-22, CD-19, CD28, CD4, CD80, HLA-DRA, IL10, IL2, IL4, TNFRSF5, TNFRSF6, TNFSF5, TNFSF6, BLR1, HDAC4, HDAC5, HDAC7A, HDAC9, ICOSL, IGBP1, MS4A1, RGSI, SLA2, CD81, IFNB1, IL10, TNFRSF5, TNFRSF7, TNFSF5, AICDA, BLNK, GALNAC4S-6ST, HDAC4, HDAC5, HDAC7A, HDAC9, IL10, IL11, IL4, INHA, INHBA, KLF6, TNFRSF7, CD28, CD38, CD69, CD80, CD83, CD86, DPP4, FCER2, IL2RA, TNFRSF8, TNFSF7, CD24, CD37, CD40, CD72, CD74, CD79A, CD79B, CR2, ILIR2, ITGA2, ITGA3, MS4A1, ST6GALI, CDIC, CHSTIO, HLA-A, HLA-DRA, and NT5E; CTLA4, B7.1, B7.2, BlyS, BAFF, C5, IL-4, IL-6, IL-10, IFN-α, and TNF-α. To form the bispecific or trispecific antibodies of the invention, antibodies to any combination of these antigens can be made; that is, each of these antigens can be optionally and independently included or excluded from a multispecific antibody according to the present invention.

The immunoglobulins herein may target antigens for the treatment of multiple sclerosis (MS), including but not limited to IL-12, TWEAK, IL-23, CXCL13, CD40, CD40L, IL-18, VEGF, VLA-4, TNF, CD45RB, CD200, IFNgamma, GM-CSF, FGF, C5, CD52, and CCR2. An embodiment includes co-engagement of anti-IL-12 and TWEAK for the treatment of MS.

One aspect of the invention pertains to immunoglobulins capable of binding one or more targets involved in sepsis, in an embodiment two targets, selected from the group consisting TNF, IL-1, MIF, IL-6, IL-8, IL-18, IL-12, IL-23, FasL, LPS, Toll-like receptors, TLR-4, tissue factor, MIP-2, ADORA2A, CASP1, CASP4, IL-10, IL-1B, NFκB1, PROC, TNFRSFIA, CSF3, CCR3, ILIRN, MIF, NFκB1, PTAFR, TLR2, TLR4, GPR44, HMOX1, midkine, IRAK1, NFκB2, SERPINA1, SERPINE1, and TREM1. To form the bispecific or trispecific antibodies of the invention, antibodies to any combination of these antigens can be made; that is, each of these antigens can be optionally and independently included or excluded from a multispecific antibody according to the present invention.

In some cases, immunoglobulins herein may be directed against antigens for the treatment of infectious diseases.

Antibodies for Engineering

In some embodiments, the heterodimeric engineering and multispecific engineering described herein is done with portions of therapeutic antibodies. A number of antibodies that are approved for use, in clinical trials, or in development may benefit from the pI variants of the present invention. These antibodies are herein referred to as "clinical products and candidates". Thus in a preferred embodiment, the heterodimerization variants may find use in a range of clinical products and candidates. For example the heterodimerization variants of the present invention may find use in an antibody that has components, e.g. the variable domains, the CDRs, etc., of clinical antibodies including, but not limited to, rituximab (Rituxan®, IDEC/Genentech/Roche) (see for example U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT/US2003/040426, entitled "Immunoglobulin Variants and Uses Thereof"). A number of antibodies that target members of the family of epidermal growth factor receptors, including EGFR (ErbB-1), Her2/neu (ErbB-2), Her3 (ErbB-3), Her4 (ErbB-4), may benefit from pI engineered constant region(s) of the invention. For example the pI engineered constant region(s) of the invention may find use in an antibody that is substantially similar to trastuzumab (Herceptin®, Genentech) (see for example U.S. Pat. No. 5,677,171), a humanized anti-Her2/neu antibody approved to treat breast cancer; pertuzumab (rhuMab-2C4, Omnitarg™), currently being developed by Genentech; an anti-Her2 antibody described in U.S. Pat. No. 4,753,894; cetuximab (Erbitux®, Imclone) (U.S. Pat. No. 4,943,533; PCT WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Ser. No. 10/172, 317), currently being developed by Genmab; 425, EMD55900, EMD62000, and EMD72000 (Merck KGaA) (U.S. Pat. No. 5,558,864; Murthy et al. 1987, Arch Biochem Biophys. 252(2):549-60; Rodeck et al., 1987, J Cell Biochem. 35(4):315-20; Kettleborough et al., 1991, Protein Eng. 4(7):773-83); ICR62 (Institute of Cancer Research) (PCT WO 95/20045; Modjtahedi et al., 1993, J. Cell Biophys. 1993, 22(1-3):129-46; Modjtahedi et al., 1993, Br J Cancer. 1993, 67(2):247-53; Modjtahedi et al, 1996, Br J Cancer, 73(2):228-35; Modjtahedi et al, 2003, Int J Cancer, 105(2):273-80); TheraCIM hR3 (YM Biosciences, Canada and Centro de Immunologia Molecular, Cuba (U.S. Pat. Nos. 5,891,996; 6,506,883; Mateo et al, 1997, Immunotechnology, 3(1):71-81); mAb-806 (Ludwig Institue for Cancer Research, Memorial Sloan-Kettering) (Jungbluth et al. 2003, Proc Natl Acad Sci USA. 100(2):639-44); KSB-102 (KS Biomedix); MR1-1 (IVAX, National Cancer Institute) (PCT WO 0162931A2); and SC100 (Seamen) (PCT WO 01/88138). In another preferred embodiment, the pI engineered constant region(s) of the present invention may find use in alemtuzumab (Campath®, Millenium), a humanized monoclonal antibody currently approved for treatment of B-cell chronic lymphocytic leukemia. The pI engineered constant region(s) of the present invention may find use in a variety of antibodies that are substantially similar to other clinical products and candidates, including but not limited to muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amevive®), an anti-LFA-3 Fc fusion developed by Biogen), abciximab (ReoPro®), developed by Centocor/Lilly, basiliximab (Simulect®), developed by Novartis, palivizumab (Synagis®), developed by MedImmune, infliximab (Remicade®), an anti-TNFalpha antibody developed by Centocor, adalimumab (Humira®), an anti-TNFalpha antibody developed by Abbott, Humicade™, an anti-TNFalpha antibody developed by Celltech, etanercept (Enbrel®), an anti-TNFalpha Fc fusion developed by Immunex/Amgen, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 In development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren® (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-β2 antibody being developed by Cambridge Antibody Technology, J695, an anti-IL-12 antibody being developed by Cambridge Antibody Technology and Abbott, CAT-192, an anti-TGFβ1 antibody being developed by Cambridge Antibody Technology and Genzyme, CAT-213, an anti-Eotaxin1 antibody being developed by Cambridge Antibody Technology, LymphoStat-B™ an anti-Blys antibody being developed by Cambridge Antibody Technology and Human Genome Sciences Inc., TRAIL-R1mAb, an anti-TRAIL-R1 antibody being developed by Cambridge Antibody Technology and Human Genome Sciences, Inc., Avastin™ (bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair™ (Omalizumab), an anti-IgE antibody being developed by Genentech, Raptiva™ (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide™ (labetuzumab), an anti-carcinoembryonic antigen (CEA) antibody being developed by Immunomedics, LymphoCide™ (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem™ (IDM-1), and anti-Her2 antibody being developed by Medarex and Immuno-Designed Molecules, HuMax™-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAF™, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, and MLN01, an anti-Beta2 integrin antibody being developed by Xoma, an pI-ADC antibody being developed by Seattle Genetics, all of the above-cited references in this paragraph are expressly incorporated herein by reference.

The antibodies of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about 10-4 M, at least about 10-5 M, at least about 10-6 M, at least about 10-7 M, at least about 10-8 M, at least about 10-9 M, alternatively at least about 10-10 M, at least about 10-11 M, at least about 10-12 M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

Methods for Making Heterodimers

As will be appreciated by those in the art, general techniques are used to make and then purify the heterodimers as discussed herein and shown in the examples below.

As will be appreciated by those in the art, standard protocols are used to make the multispecific binding proteins of the invention. General methods for antibody molecular biology, expression, purification, and screening are described in Antibody Engineering, edited by Kontermann & Dubel, Springer, Heidelberg, 2001; and Hayhurst & Georgiou, 2001, Curr Opin Chem Biol 5:683-689; Maynard & Georgiou, 2000, Annu Rev Biomed Eng 2:339-76.

In one embodiment disclosed herein, nucleic acids are created that encode the multispecific binding proteins, and that may then be cloned into host cells, expressed and assayed, if desired. Thus, nucleic acids, and particularly DNA, may be made that encode each protein sequence. These practices are carried out using well-known procedures. For example, a variety of methods that may find use in generating multispecific binding proteins, similar to the production of antibodies, are disclosed herein are described in Molecular Cloning—A Laboratory Manual, 3rd Ed. (Maniatis, Cold Spring Harbor Laboratory Press, New York, 2001), and Current Protocols in Molecular Biology (John Wiley & Sons), both incorporated entirely by reference. There are a variety of techniques that may be used to efficiently generate DNA encoding multispecific binding proteins disclosed herein. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in for generating nucleic acids that encode multispecific binding proteins.

The multispecific binding proteins disclosed herein may be produced by culturing a host cell transformed with nucleic acid, e.g., an expression vector, containing nucleic acid encoding the multispecific binding proteins, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, yeast, and plant cells. For example, a variety of cell lines that may find use in generating multispecific binding proteins disclosed herein are described in the ATCC® cell line catalog, available from the American Type Culture Collection.

In one embodiment, the multispecific binding proteins are expressed in mammalian expression systems, including systems in which the expression constructs are introduced into the mammalian cells using virus such as retrovirus or adenovirus. Any mammalian cells may be used, e.g., human, mouse, rat, hamster, and primate cells. Suitable cells also include known research cells, including but not limited to Jurkat T cells, NIH3T3, CHO, BHK, COS, HEK293, PER C.6, HeLa, Sp2/0, NSO cells and variants thereof. In an alternateembodiment, library proteins are expressed in bacterial cells. Bacterial expression systems are well known in the art, and include Escherichia coli (E. coli), Bacillus subtilis, Streptococcus cremoris, and Streptococcus lividans. In alternate embodiments, antibodies are produced in insect cells (e.g. Sf21/Sf9, Trichoplusia ni Bti-Tn5b1-4) or yeast cells (e.g. S. cerevisiae, Pichia, etc). In an alternate embodiment, antibodies are expressed in vitro using cell free translation systems. In vitro translation systems derived from both prokaryotic (e.g. E. coli) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the antibodies may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode multispecific binding proteins disclosed herein may be incorporated into an expression vector in order to express the protein. A variety of expression vectors may be utilized for protein expression. Expression vectors may comprise self-replicating extrachromosomal vectors or vectors which integrate into a host genome. Expression vectors are constructed to be compatible with the host cell type. Thus expression vectors which find use in generating antibodies disclosed herein include but are not limited to those which enable protein expression in mammalian cells, bacteria, insect cells, yeast, and in in vitro systems. As is known in the art, a variety of expression vectors are available, commercially or otherwise, that may find use for expressing antibodies disclosed herein.

The disclosed multispecific binding proteins can be encoded by multiple nucleic acid molecules. For example, the heavy and light chains of an antibody can be introduced into a host cell independently. Though present on separate nucleic acids, their expression yields a single polypeptide.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

In one embodiment, multispecific binding proteins are purified or isolated after expression. Proteins may be isolated or purified in a variety of ways known to those skilled in the art. Purification may be particularly useful in the invention for separating heterodimeric heavy chain species from homodimeric heavy chain species, as described herein. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, isoelectric focusing, immunological, precipitation, dialysis, and chromatofocusing techniques. Ultrafiltration and diafiltration techniques, in conjunction with protein concentration, are also useful. fusion is employed, Ni+2 affinity chromatography if a His-tag is employed, or immobilized anti-flag antibody if a flag-tag is used. For general guidance in suitable purification techniques, see, e.g. incorporated entirely by reference Protein Purification: Principles and Practice, 3rd Ed., Scopes, Springer-Verlag, NY, 1994, incorporated entirely by reference. The degree of purification necessary will vary depending on the screen or use of the antibodies. In some instances no purification is needed.

Antibody-Drug Conjugates

In some embodiments, the multispecific antibodies of the invention are conjugated with drugs to form antibody-drug conjugates (ADCs). In general, ADCs are used in oncology applications, where the use of antibody-drug conjugates for the local delivery of cytotoxic or cytostatic agents allows for the targeted delivery of the drug moiety to tumors, which can allow higher efficacy, lower toxicity, etc. An overview of this technology is provided in Ducry et al., Bioconjugate Chem., 21:5-13 (2010), Carter et al., Cancer J. 14(3):154 (2008) and Senter, Current Opin. Chem. Biol. 13:235-244 (2009), all of which are hereby incorporated by reference in their entirety.

Thus the invention provides multispecific antibodies conjugated to drugs. Generally, conjugation is done by covalent attachment to the antibody, as further described below, and generally relies on a linker, often a peptide linkage (which, as described below, may be designed to be sensitive to cleavage by proteases at the target site or not). In addition, as described above, linkage of the linker-drug unit (LU-D) can be done by attachment to cysteines within the antibody. As will be appreciated by those in the art, the number of drug moieties per antibody can change, depending on the conditions of the reaction, and can vary from 1:1 to 10:1 drug: antibody. As will be appreciated by those in the art, the actual number is an average.

Thus the invention provides multispecific antibodies conjugated to drugs. As described below, the drug of the ADC can be any number of agents, including but not limited to cytotoxic agents such as chemotherapeutic agents, growth inhibitory agents, toxins (for example, an enzymatically active toxin of bacterial, fungal, plant, or animal origin, or fragments thereof), or a radioactive isotope (that is, a radioconjugate) are provided. In other embodiments, the invention further provides methods of using the ADCs.

Drugs for use in the present invention include cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the *vinca* drugs, the mitomycins, the bleomycins, the cytotoxic nucleosides, the pteridine family of drugs, diynenes, the podophyllotoxins, dolastatins, maytansinoids, differentiation inducers, and taxols.

Members of these classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxanes including taxol, taxotere retinoic acid, butyric acid, N8-acetyl spermidine, camptothecin, calicheamicin, esperamicin, ene-diynes, duocarmycin A, duocarmycin SA, calicheamicin, camptothecin, maytansinoids (including DM1), monomethylauristatin E (MMAE), monomethylauristatin F (MMAF), and maytansinoids (DM4) and their analogues.

Toxins may be used as antibody-toxin conjugates and include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). Toxins may exert their cytotoxic and cytostatic effects by mechanisms including tubulin binding, DNA binding, or topoisomerase inhibition.

Conjugates of a multispecific antibody and one or more small molecule toxins, such as a maytansinoids, dolastatins, auristatins, a trichothecene, calicheamicin, and CC1065, and the derivatives of these toxins that have toxin activity, are contemplated.

Maytansinoids

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. As described below, drugs may be modified by the incorporation of a functionally active group such as a thiol or amine group for conjugation to the antibody.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/–C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/–dechloro (U.S. Pat. No. 4,294,757) (prepared by acylation using acyl chlorides) and those having modifications at other positions Exemplary maytansinoid drug moieties also include those having modifications such as: C-9-SH (U.S. Pat. No. 4,424,219) (prepared by the reaction of maytansinol with H2S or P2S5); C-14-alkoxymethyl(demethoxy/CH2OR) (U.S. Pat. No. 4,331,598); C-14-hydroxymethyl or acyloxymethyl (CH2OH or CH2OAc) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

Of particular use are DM1 (disclosed in U.S. Pat. No. 5,208,020, incorporated by reference) and DM4 (disclosed in U.S. Pat. No. 7,276,497, incorporated by reference). See also a number of additional maytansinoid derivatives and methods in U.S. Pat. No. 5,416,064, WO/01/24763, 7,303, 749, 7,601,354, U.S. Ser. No. 12/631,508, WO02/098883, U.S. Pat. Nos. 6,441,163, 7,368,565, WO02/16368 and WO04/1033272, all of which are expressly incorporated by reference in their entirety.

ADCs containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×10⁵ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Auristatins and Dolastatins

In some embodiments, the ADC comprises a multispecific antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004 and described in United States Patent Publication No. 2005/0238648, the disclosure of which is expressly incorporated by reference in its entirety.

An exemplary auristatin embodiment is MMAE (see U.S. Pat. No. 6,884,869 expressly incorporated by reference in its entirety).

Another exemplary auristatin embodiment is MMAF (see US 2005/0238649, 5,767,237 and 6,124,431, expressly incorporated by reference in their entirety).

Additional exemplary embodiments comprising MMAE or MMAF and various linker components (described further herein) have the following structures and abbreviations (wherein Ab means antibody and p is 1 to about 8):

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

Calicheamicin

In other embodiments, the ADC comprises an antibody of the invention conjugated to one or more calicheamicin molecules. For example, Mylotarg is the first commercial ADC drug and utilizes calicheamicin yl as the payload (see U.S. Pat. No. 4,970,198, incorporated by reference in its entirety). Additional calicheamicin derivatives are described in U.S. Pat. Nos. 5,264,586, 5,384,412, 5,550,246, 5,739,116, 5,773,001, 5,767,285 and 5,877,296, all expressly incorporated by reference. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, γ1I, α2I, α2I, N-acetyl-γ1I, PSAG and θI1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Duocarmycins

CC-1065 (see 4,169,888, incorporated by reference) and duocarmycins are members of a family of antitumor antibiotics utilized in ADCs. These antibiotics appear to work through sequence-selectively alkylating DNA at the N3 of adenine in the minor groove, which initiates a cascade of events that result in apoptosis.

Important members of the duocarmycins include duocarmycin A (U.S. Pat. No. 4,923,990, incorporated by reference) and duocarmycin SA (U.S. Pat. No. 5,101,038, incorporated by reference), and a large number of analogues as described in U.S. Pat. Nos. 7,517,903, 7,691,962, 5,101,038; 5,641,780; 5,187,186; 5,070,092; 5,070,092; 5,641,780; 5,101,038; 5,084,468, 5,475,092, 5,585,499, 5,846,545, WO2007/089149, W02009/017394A1, 5,703,080, 6,989, 452, 7,087,600, 7,129,261, 7,498,302, and 7,507,420, all of which are expressly incorporated by reference.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present invention further contemplates an ADC formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as Tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate Iodine-123. "Monoclonal Antibodies in Immunoscintigraphy" (Chatal, CRC Press 1989) describes other methods in detail.

For compositions comprising a plurality of antibodies, the drug loading is represented by p, the average number of drug molecules per Antibody. Drug loading may range from 1 to 20 drugs (D) per Antibody. The average number of drugs per antibody in preparation of conjugation reactions may be characterized by conventional means such as mass spectroscopy, ELISA assay, and HPLC. The quantitative distribution of Antibody-Drug-Conjugates in terms of p may also be determined.

In some instances, separation, purification, and characterization of homogeneous Antibody-Drug-conjugates where p is a certain value from Antibody-Drug-Conjugates with other drug loadings may be achieved by means such as reverse phase HPLC or electrophoresis. In exemplary embodiments, p is 2, 3, 4, 5, 6, 7, or 8 or a fraction thereof.

The generation of Antibody-drug conjugate compounds can be accomplished by any technique known to the skilled artisan. Briefly, the Antibody-drug conjugate compounds can include a multispecific antibody as the Antibody unit, a drug, and optionally a linker that joins the drug and the binding agent.

A number of different reactions are available for covalent attachment of drugs and/or linkers to binding agents. This is can be accomplished by reaction of the amino acid residues of the binding agent, for example, antibody molecule, including the amine groups of lysine, the free carboxylic acid groups of glutamic and aspartic acid, the sulfhydryl groups of cysteine and the various moieties of the aromatic amino acids. A commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule.

Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan and within the scope of the present invention.

In some embodiments, an intermediate, which is the precursor of the linker, is reacted with the drug under appropriate conditions. In other embodiments, reactive groups are used on the drug and/or the intermediate. The product of the reaction between the drug and the intermediate, or the derivatized drug, is subsequently reacted with an multispecific antibody of the invention under appropriate conditions.

It will be understood that chemical modifications may also be made to the desired compound in order to make reactions of that compound more convenient for purposes of preparing conjugates of the invention. For example a functional group e.g. amine, hydroxyl, or sulfhydryl, may be appended to the drug at a position which has minimal or an acceptable effect on the activity or other properties of the drug Linker Units Typically, the antibody-drug conjugate compounds comprise a Linker unit between the drug unit and the antibody unit. In some embodiments, the linker is cleavable under intracellular or extracellular conditions, such that cleavage of the linker releases the drug unit from the antibody in the appropriate environment. For example, solid tumors that secrete certain proteases may serve as the target of the cleavable linker; in other embodiments, it is the intracellular proteases that are utilized. In yet other embodiments, the linker unit is not cleavable and the drug is released, for example, by antibody degradation in lysosomes.

In some embodiments, the linker is cleavable by a cleaving agent that is present in the intracellular environment (for example, within a lysosome or endosome or caveolea). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long or more.

Cleaving agents can include, without limitation, cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Peptidyl linkers that are cleavable by enzymes that are present in CD38-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO: 144)). Other examples of such linkers are described, e.g., in U.S. Pat. No. 6,214,345, incorporated herein by reference in its entirety and for all purposes.

In some embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker).

In other embodiments, the cleavable linker is pH-sensitive, that is, sensitive to hydrolysis at certain pH values. Typically, the pH-sensitive linker hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) may be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (for example, a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In other embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. (See U.S. Publication No. 2005/0238649 incorporated by reference herein in its entirety and for all purposes).

In many embodiments, the linker is self-immolative. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved. See for example, WO 2007059404A2, WO06110476A2, WO05112919A2, WO2010/062171, WO09/017394, WO07/089149, WO 07/018431, WO04/043493 and WO02/083180, which are directed to drug-cleavable substrate conjugates where the drug and cleavable substrate are optionally linked through a self-immolative linker and which are all expressly incorporated by reference.

Often the linker is not substantially sensitive to the extracellular environment. As used herein, "not substantially sensitive to the extracellular environment," in the context of a linker, means that no more than about 20%, 15%, 10%, 5%, 3%, or no more than about 1% of the linkers, in a sample of antibody-drug conjugate compound, are cleaved when the antibody-drug conjugate compound presents in an extracellular environment (for example, in plasma).

Whether a linker is not substantially sensitive to the extracellular environment can be determined, for example, by incubating with plasma the antibody-drug conjugate compound for a predetermined time period (for example, 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (that is, in the milieu of the linker-therapeutic agent moiety of the antibody-drug conjugate compound as described herein). In yet other embodiments, the linker promotes cellular internalization when conjugated to both the auristatin compound and the multispecific antibodies of the invention.

A variety of exemplary linkers that can be used with the present compositions and methods are described in WO 2004-010957, U.S. Publication No. 2006/0074008, U.S. Publication No. 20050238649, and U.S. Publication No. 2006/0024317 (each of which is incorporated by reference herein in its entirety and for all purposes).

Drug Loading

Drug loading is represented by p and is the average number of Drug moieties per antibody in a molecule. Drug loading ("p") may be 1, 2, 3, 4, 5, 6, 7, 8, 9, 10, 11, 12, 13, 14, 15, 16, 17, 18, 19, 20 or more moieties (D) per antibody, although frequently the average number is a fraction or a decimal. Generally, drug loading of from 1 to 4 is frequently useful, and from 1 to 2 is also useful. ADCs of the invention include collections of antibodies conjugated with a range of drug moieties, from 1 to 20. The average number of drug moieties per antibody in preparations of ADC from conjugation reactions may be characterized by conventional means such as mass spectroscopy and, ELISA assay.

The quantitative distribution of ADC in terms of p may also be determined. In some instances, separation, purification, and characterization of homogeneous ADC where p is a certain value from ADC with other drug loadings may be achieved by means such as electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the invention ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antibody may be less than 8, and may be about 2 to about 5. See US 2005-0238649 A1 (herein incorporated by reference in its entirety).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments (such as thioMab or thioFab prepared as disclosed herein and in WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography.

In some embodiments, a homogeneous ADC with a single loading value may be isolated from the conjugation mixture by electrophoresis or chromatography.

Methods of Determining Cytotoxic Effect of ADCs

Methods of determining whether a Drug or Antibody-Drug conjugate exerts a cytostatic and/or cytotoxic effect on a cell are known. Generally, the cytotoxic or cytostatic activity of an Antibody Drug conjugate can be measured by: exposing mammalian cells expressing a target protein of the Antibody Drug conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug conjugate.

For determining whether an Antibody Drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of 3H-thymidine during the final 8 hours of the 72-hour period. The incorporation of 3H-thymidine into cells of the culture is measured in the presence and absence of the Antibody Drug conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an Antibody Drug conjugate is useful in the treatment of cancers.

Cell viability can be measured by determining in a cell the uptake of a dye such as neutral red, trypan blue, or ALAMAR™ blue (see, e.g., Page et al., 1993, Intl. J. Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, J. Natl. Cancer Inst. 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55-63).

Apoptosis can be quantitated by measuring, for example, DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, Cancer Research 55:3110-16).

In vivo, the effect of a therapeutic composition of the multispecific antibody of the invention can be evaluated in a suitable animal model. For example, xenogenic cancer models can be used, wherein cancer explants or passaged xenograft tissues are introduced into immune compromised animals, such as nude or SCID mice (Klein et al., 1997, Nature Medicine 3: 402-408). Efficacy can be measured using assays that measure inhibition of tumor formation, tumor regression or metastasis, and the like.

Therapeutic Uses of Heterodimers

The multispecific proteins, particularly the multispecific antibodies of the present invention find use in a variety of therapeutic uses. As discussed in FIG. 1 of Kontermann, supra, incorporated herein by reference, there are a number of dual targeting strategies for cancer, inflammation, etc.

Pharmaceutical Formulations, Administration and Dosing

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

Antibody Compositions for In Vivo Administration

Formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to provide antibodies with other specifcities. Alternatively, or in addition, the composition may comprise a cytotoxic agent, cytokine, growth inhibitory agent and/or small molecule antagonist. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration should be sterile, or nearly so. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Administrative Modalities

The antibodies and chemotherapeutic agents of the invention are administered to a subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

Treatment Modalities

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

Thus for B cell tumors, the subject may experience a decrease in the so-called B symptoms, i.e., night sweats, fever, weight loss, and/or urticaria. For pre-malignant conditions, therapy with an multispecific therapeutic agent may block and/or prolong the time before development of a related malignant condition, for example, development of multiple myeloma in subjects suffering from monoclonal gammopathy of undetermined significance (MGUS).

An improvement in the disease may be characterized as a complete response. By "complete response" is intended an absence of clinically detectable disease with normalization of any previously abnormal radiographic studies, bone marrow, and cerebrospinal fluid (CSF) or abnormal monoclonal protein in the case of myeloma.

Such a response may persist for at least 4 to 8 weeks, or sometimes 6 to 8 weeks, following treatment according to the methods of the invention. Alternatively, an improvement in the disease may be categorized as being a partial response. By "partial response" is intended at least about a 50% decrease in all measurable tumor burden (i.e., the number of malignant cells present in the subject, or the measured bulk of tumor masses or the quantity of abnormal monoclonal protein) in the absence of new lesions, which may persist for 4 to 8 weeks, or 6 to 8 weeks.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the multispecific antibodies used in the present invention depend on the disease or condition to be treated and may be determined by the persons skilled in the art.

An exemplary, non-limiting range for a therapeutically effective amount of an multispecific antibody used in the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg. In another embodiment, he antibody is administered in a dose of 1 mg/kg or more, such as a dose of from 1 to 20 mg/kg, e.g. a dose of from 5 to 20 mg/kg, e.g. a dose of 8 mg/kg.

A medical professional having ordinary skill in the art may readily determine and prescribe the effective amount of the pharmaceutical composition required. For example, a physician or a veterinarian could start doses of the medicament employed in the pharmaceutical composition at levels lower than that required in order to achieve the desired therapeutic effect and gradually increase the dosage until the desired effect is achieved.

In one embodiment, the multispecific antibody is administered by infusion in a weekly dosage of from 10 to 500 mg/kg such as of from 200 to 400 mg/kg Such administration may be repeated, e.g., 1 to 8 times, such as 3 to 5 times. The administration may be performed by continuous infusion over a period of from 2 to 24 hours, such as of from 2 to 12 hours.

In one embodiment, the multispecific antibody is administered by slow continuous infusion over a long period, such as more than 24 hours, if required to reduce side effects including toxicity.

In one embodiment the multispecific antibody is administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the multispecific antibody.

In a further embodiment, the multispecific antibody is administered once weekly for 2 to 12 weeks, such as for 3 to 10 weeks, such as for 4 to 8 weeks.

In one embodiment, the multispecific antibody is administered by maintenance therapy, such as, e.g., once a week for a period of 6 months or more.

In one embodiment, the multispecific antibody is administered by a regimen including one infusion of an multispecific antibody followed by an infusion of an multispecific antibody conjugated to a radioisotope. The regimen may be repeated, e.g., 7 to 9 days later.

As non-limiting examples, treatment according to the present invention may be provided as a daily dosage of an antibody in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

In some embodiments the multispecific antibody molecule thereof is used in combination with one or more additional therapeutic agents, e.g. a chemotherapeutic agent. Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

In some embodiments, the antibodies of the invention can be used prior to, concurrent with, or after treatment with Velcade® (bortezomib).

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

EXAMPLES

Examples are provided below to illustrate the present invention. These examples are not meant to constrain the present invention to any particular application or theory of operation. For all constant region positions discussed in the present invention, numbering is according to the EU index as in Kabat (Kabat et al., 1991, Sequences of Proteins of Immunological Interest, 5th Ed., United States Public Health Service, National Institutes of Health, Bethesda, entirely incorporated by reference). Those skilled in the art of antibodies will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

Example 1. Design of Non-Native Charge Substitutions to Reduce pI

Antibody constant chains were modified with lower pI by engineering substitutions in the constant domains. Reduced pI can be engineered by making substitutions of basic amino acids (K or R) to acidic amino acids (D or E), which result in the largest decrease in pI. Mutations of basic amino acids to neutral amino acids and neutral amino acids to acidic amino acids will also result in a decrease in pI. A list of amino acid pK values can be found in Table 1 of Bjellqvist et al., 1994, Electrophoresis 15:529-539.

We chose to explore substitutions in the antibody CH1 (Cγ1) and CL (Ckappa or CK) regions (sequences are shown in FIG. 1) because, unlike the Fc region, they do not interact with native ligands that impact the antibody's pharmacological properties. In deciding which positions to mutate, the surrounding environment and number of contacts the WT amino acid makes with its neighbors was taken into account such as to minimize the impact of a substitution or set of substitutions on structure and/or function. The solvent accessibility or fraction exposed of each CH1 and CK position was calculated using relevant crystal structures of antibody Fab domains. The results are shown in FIGS. 2 and 3 for the Cγ1 and CK respectively. Design was guided further by examining the CH1 and CL domains for positions that are isotypic between the immunoglobulin isotypes (IgG1, IgG2, IgG3, and IgG4). Because such variations occur naturally, such position are expected to be amenable to substitution. Based on this analysis, a number of substitutions were identified that reduce pI but are predicted to have minimal impact on the biophysical properties of the domains.

Example 2. Anti-VEGF Antibodies with Engineered CH1 and CK Regions Having Lower pI Amino acid modifications were engineered in the CH1 and CK domains of an IgG1 antibody to lower the pI of the antibody. Based on the above analysis, chosen substitutions for the heavy chain CH1 were 119E, 133E, 164E, 205E, 208D, and 210E, and substitutions for the light chain Cκ substitutions were 126E, 145E, 152D, 156E, 169E, and 202E. These variant constant chains are referred to as IgG1-CH1-pI(6) and CK-pI(6) respectively, and their amino acid sequences are provided in FIG. 4.

Figure 7:
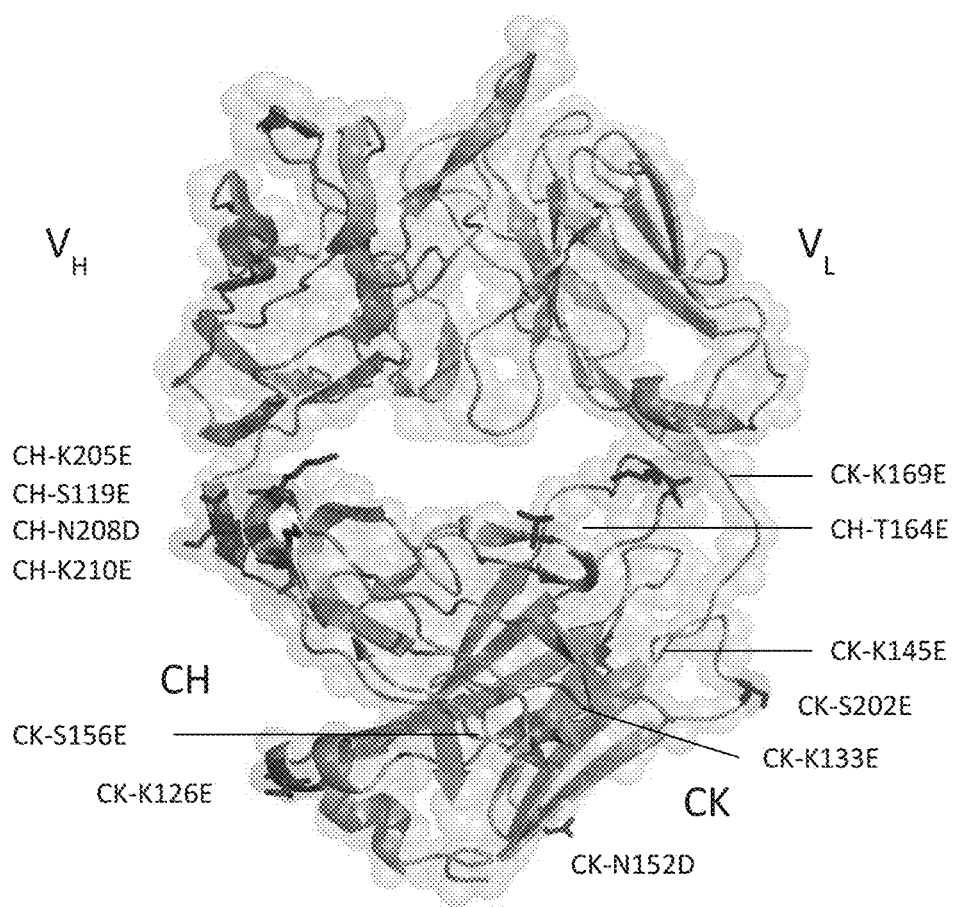
FIG. 7. Structure of an antibody Fab domain showing the locations of pI lowering mutations in XENP9493 IgG1-CH1-pI(6)-CK-pI(6).

CH1 and CK variants were engineered in the context of an antibody targeting vascular endothelial factor (VEGF). The heavy and light chain variable regions (VH and VL) are those of a humanized version of the antibody A4.6.1, also referred to as bevacizumab (Avastin®), which is approved for the treatment of a variety of cancers. These variable region sequences are provided in FIG. 5. The anti-VEGF antibody variant containing the low pI substitutions is referred to as XENP9493 Bevacizumab-IgG1-CH1-pI(6)-CK-pI(6), and the amino acid sequences of the heavy and light chains of this antibody are provided in FIG. 6. A structural model of the Fab domain showing the 6 substitutions of CH1-pI(6) and the 6 substitutions of CK-pI(6) is shown in FIG. 7. The calculated pI of WT anti-VEGF (bevacizumab) is 8.14. The calculated pI of the engineered anti-VEGF CH1 variant is 6.33 and that of the anti-VEGF CK variant is 6.22. When the heavy chain and light chain pI engineered anti-VEGF variants are co-transfected, the full-length anti-VEGF mAb has a calculated pI of 5.51.

Genes encoding the heavy and light chains of the anti-VEGF antibodies were constructed in the mammalian expression vector pTT5. The human IgG1 constant chain gene was obtained from IMAGE clones and subcloned into the pTT5 vector. VH and VL genes encoding the anti-VEGF antibodies were synthesized commercially (Blue Heron Biotechnologies, Bothell Wash.), and subcloned into the vectors encoding the appropriate CL and IgG1 constant chains. Amino acid modifications were constructed using site-directed mutagenesis using the QuikChange® site-directed mutagenesis methods (Stratagene, La Jolla Calif.). All DNA was sequenced to confirm the fidelity of the sequences.

Plasmids containing heavy chain gene (VH-Cγ1-Cγ2-Cγ3) were co-transfected with plasmid containing light chain gene (VL-Cκ) into 293E cells using llipofectamine (Invitrogen, Carlsbad Calif.) and grown in FreeStyle 293 media (Invitrogen, Carlsbad Calif.). After 5 days of growth, the antibodies were purified from the culture supernatant by protein A affinity using the MabSelect resin (GE Healthcare). Antibody concentrations were determined by bicinchoninic acid (BCA) assay (Pierce).

Figure 8:
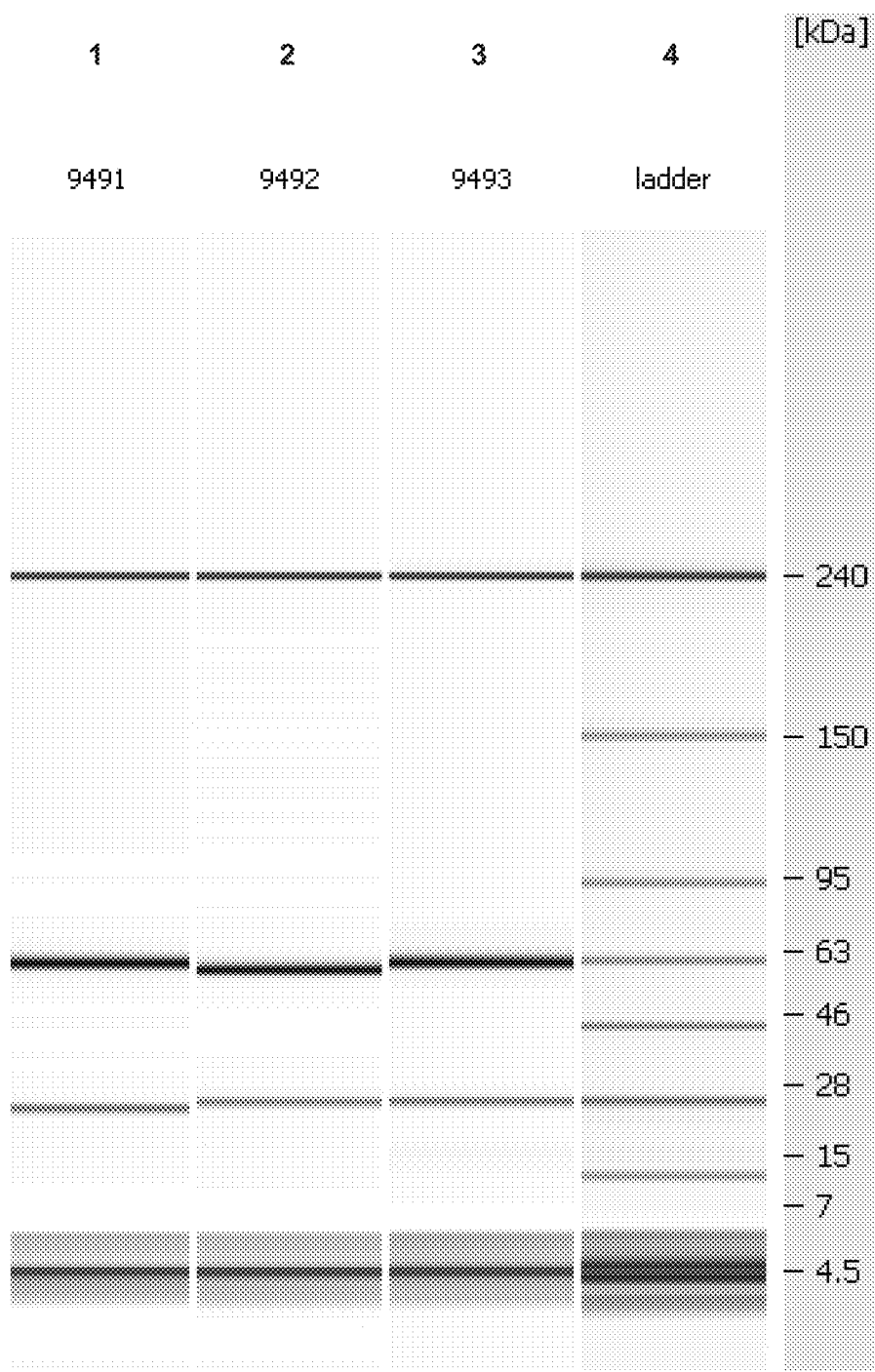
FIG. 8. Analysis of pI engineered anti-VEGF variants on an Agilent Bioanalyzer showing high purity.
Figure 11A:
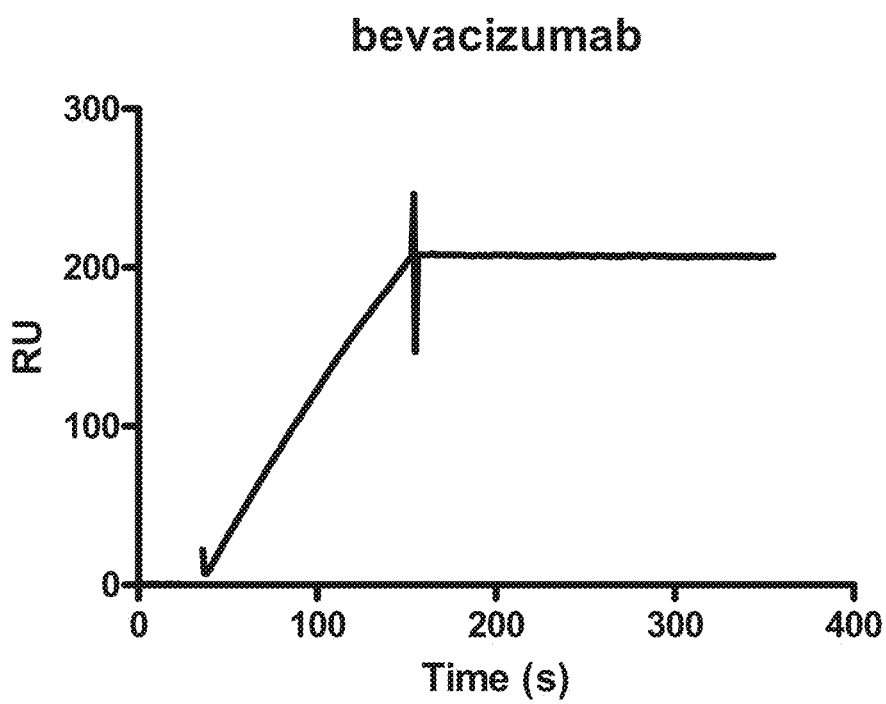
FIG. 11A-11B. Binding analysis (Biacore) of bevacizumab and pI engineered anti-VEGF binding to VEGF.
Figure 11B:
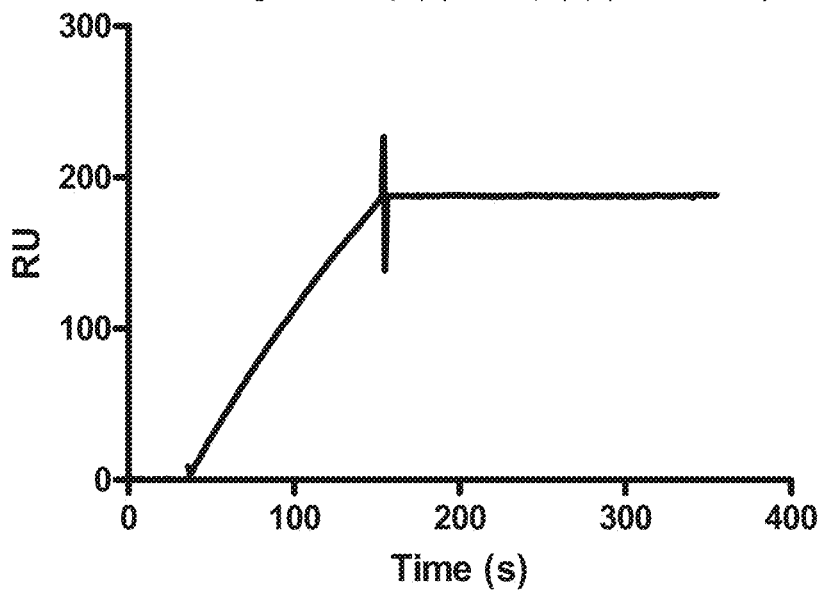
Figure 12:
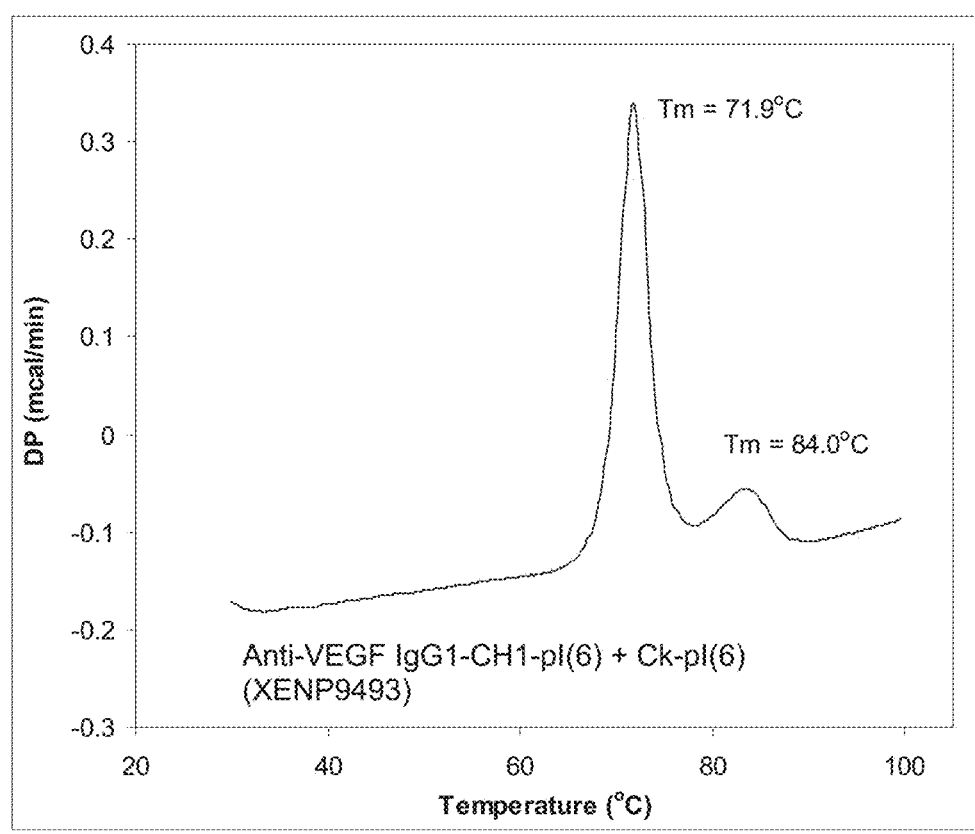
FIG. 12. DSC analysis of CH1 and CK pI engineered anti-VEGF showing high thermostability.

The pI engineered anti-VEGF mAbs were characterized by SDS PAGE on an Agilent Bioanalyzer (FIG. 8), by size exclusion chromatography (SEC) (FIG. 9), isoelectric focusing (IEF) gel electrophoresis (FIG. 10), binding to antigen VEGF by Biacore (FIG. 11), and differential scanning calorimetry (DSC) (FIG. 12). All mAbs showed high purity on SDS-PAGE and SEC. IEF gels indicated that each variant had the designed isoelectric point. VEGF binding analysis on Biacore showed that pI engineered anti-VEGF bound to VEGF with similar affinity as bevacizumab, indicating that the designed substitutions did not perturb the function of the mAb. DSC showed that the anti-VEGF variant with both CH1 and CL engineered substitutions had high thermostability with a Tm of 71.9° C.

Pharmacokinetic experiments were performed in B6 mice that are homozygous knock-outs for murine FcRn and heterozygous knock-ins of human FcRn (mFcRn−/−, hFcRn+) (Petkova et al., 2006, Int Immunol 18(12):1759-69, entirely incorporated by reference), herein referred to as hFcRn or hFcRn+ mice. Samples tested included the parent IgG1/2 constant region, the pI-engineered variant with a pI of 5.51, referred to as IgG1_CH-CL_pI_eng, and an Fc variant version of IgG1/2 containing the substitution N434S, which improves affinity to human FcRn.

A single, intravenous tail vein injection of anti-VEGF antibody (2 mg/kg) was given to groups of 4-7 female mice randomized by body weight (20-30 g range). Blood (~50 ul) was drawn from the orbital plexus at each time point, processed to serum, and stored at −80° C. until analysis. Antibody concentrations were determined using an ELISA assay. Serum concentration of antibody was measured using a recombinant VEGF (VEGF-165, PeproTech, Rocky Hill, N.J.) as capture reagent, and detection was carried out with biotinylated anti-human kappa antibody and europium-labeled streptavidin. The time resolved fluorescence signal was collected. PK parameters were determined for individual mice with a non-compartmental model using WinNonLin (Pharsight Inc, Mountain View Calif.). Nominal times and dose were used with uniform weighing of points.

Figure 13:
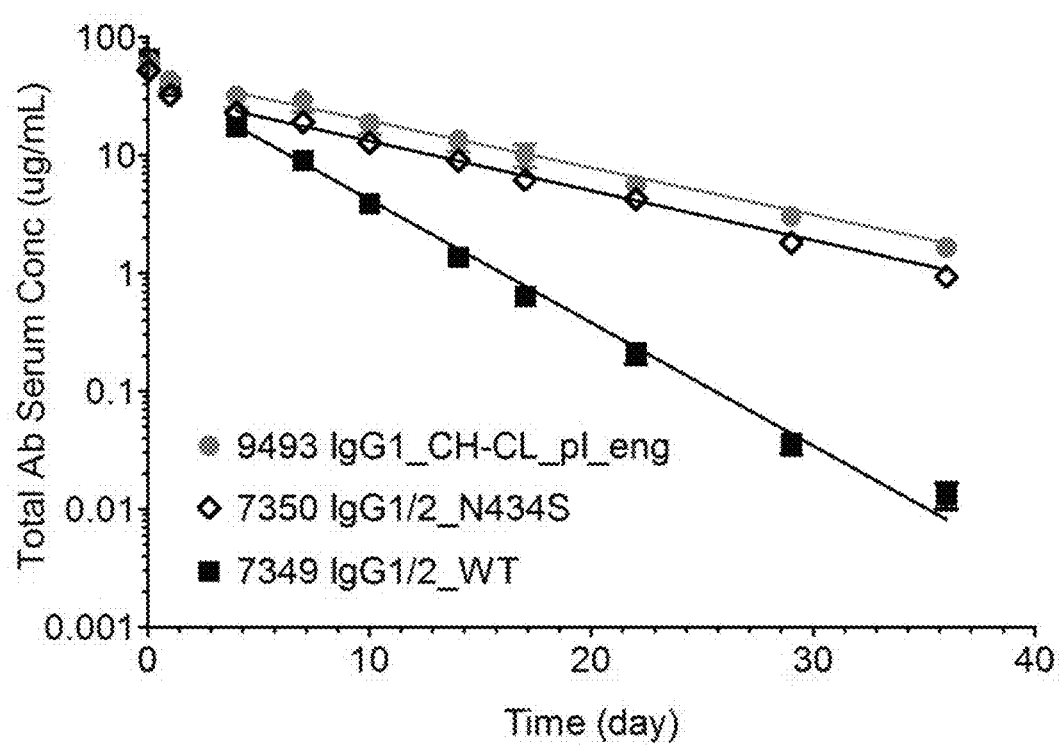
FIG. 13. PK of bevacizumab variants in huFcRn mice. The 9493 variant with pI-engineered CH1 and CK domains extends half-life in vivo.

Results are shown in FIG. 13. Fitted half-life (t½) values, which represents the beta phase that characterizes elimination of antibody from serum, are shown in Table 1. The pI-engineered variant, containing substitutions in CH1 and CL that reduce the pI, extended half-life to 7.4 days, an improvement of approximately 2.6-fold relative to IgG1/2. The pI-engineered variant had a comparable half-life to the Fc variant version N434S. Combinations of antibody variants are contemplated that reduce pI and improve affinity for FcRn for extending the half-lives of antibodies and Fc fusions.

TABLE 1

PK results of pI-engineered variant

| Group | Variant | n | Individual mice t½ (days) | | | | Average t½ (days) | St. Dev. (days) |
|---|---|---|---|---|---|---|---|---|
| | | | n1 | n2 | n3 | n4 | | |
| 7349 | IgG1/2_WT | 4 | 2.9 | 2.5 | 3.2 | 2.8 | 2.9 | 0.3 |
| 7350 | IgG1/2_N434S | 4 | 6.3 | 7.7 | 7.3 | 6.5 | 7.0 | 0.7 |
| 9493 | IgG1_CH-CL_pI_eng | 3 | 7.4 | 8.4 | 6.4 | | 7.4 | 1.0 |

Example 3. PK Analysis of IgG Constant Regions

Figure 14:
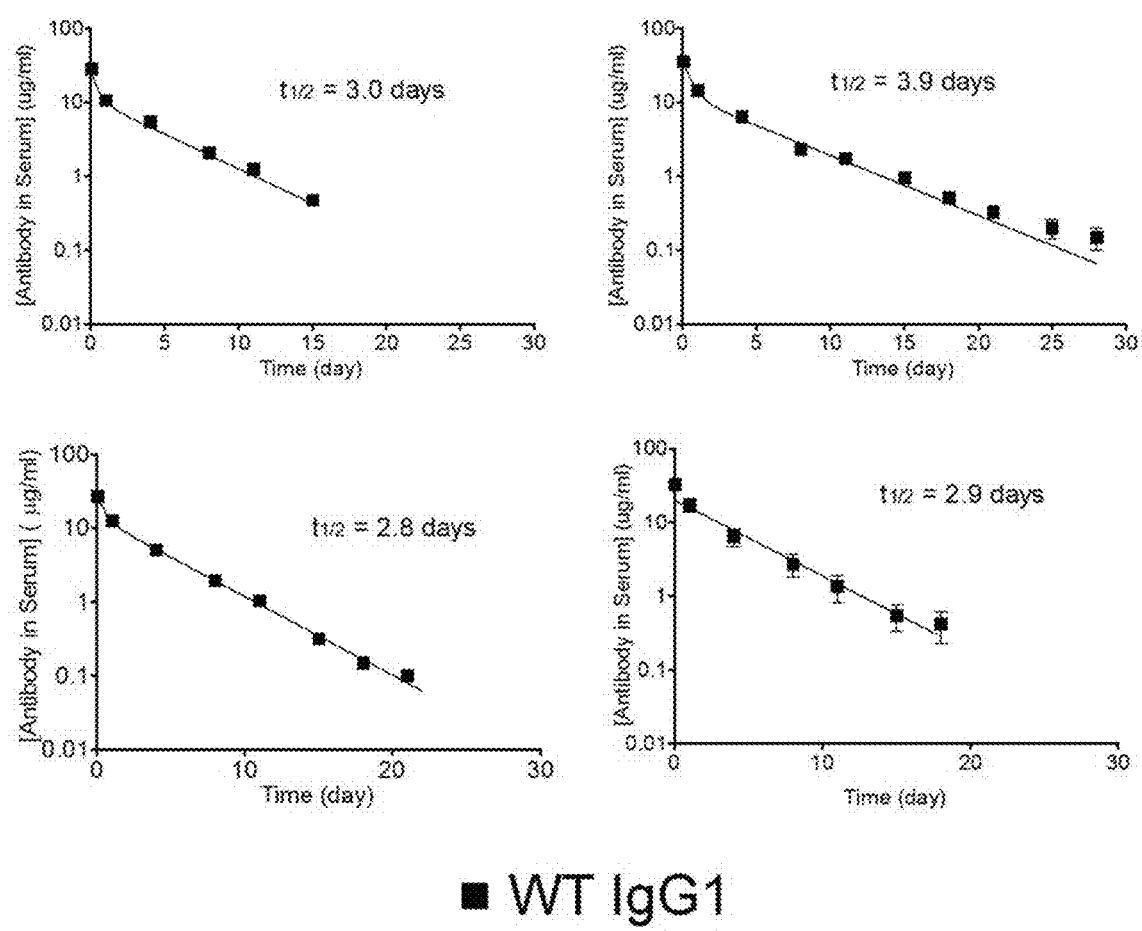
FIG. 14. PK of a native IgG1 version of bevacizumab in four separate in vivo studies in huFcRn mice. The average IgG1 half-life was 3.2 days.
Figure 15:
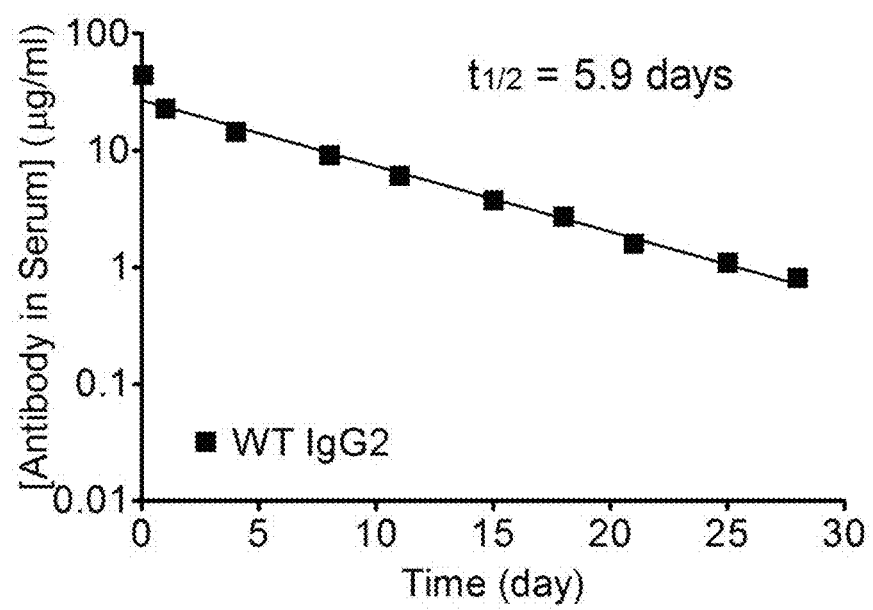
FIG. 15. PK of a native IgG2 version of bevacizumab in huFcRn mice.

PK studies of IgG1 and IgG2 isotype versions of bevacizumab were carried out in the huFcRn mice as described above. The IgG1 results from four separate PK studies are shown in FIG. 14. The half-lives from the four studies were 3.0, 3.9, 2.8, and 2.9 days, resulting in an average half-life of 3.2 days. The PK results from the IgG2 study are shown in FIG. 15. The half-life of IgG2 was 5.9 days.

Figure 16:
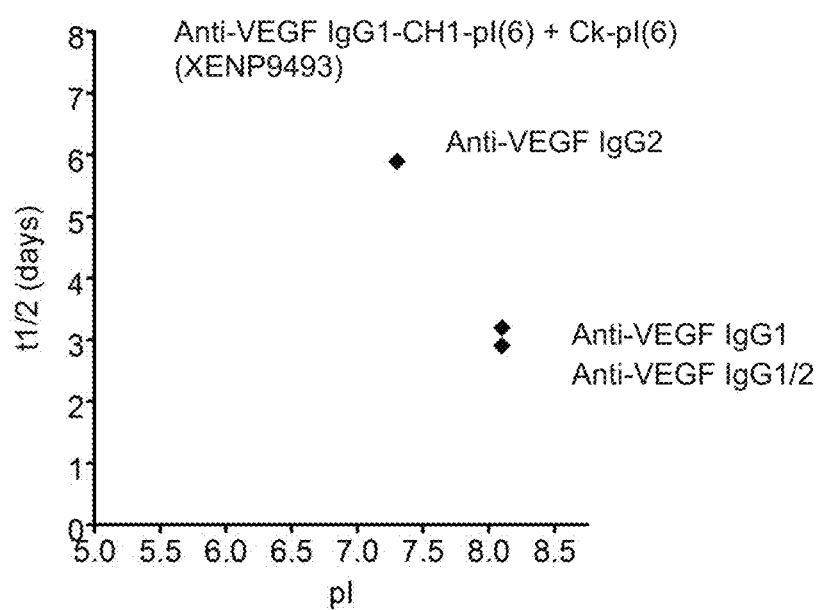
FIG. 16. Correlation between half-life and isoelectric point (pI) of antibody variants with different constant chains.

The PK results from the IgG1 and IgG2 were analyzed with the results from the IgG1/2 and pI-engineered versions of bevacizumab. Table 2 shows the half-lives of the antibodies along with their calculated pI. These data are plotted in FIG. 16.

TABLE 2

PK results of antibodies with identical Fv (bevacizumab) but constant regions with different pI's

| XENP | IgG | pI | Average t ½ (days) |
|---|---|---|---|
| 4547 | IgG1 | 8.1 | 3.2 |
| 7349 | IgG1/2 | 8.1 | 2.9 |
| 6384 | IgG2 | 7.3 | 5.9 |
| 9493 | IgG1_CH-CL_pI_eng [aka IgG1-pI(12)] | 5.6 | 7.4 |

A correlation was observed between half-life and the pI of the antibodies. These data further suggest that engineering of antibody constant chains, including heavy and light chain constant regions, for reduced isoelectric point is potentially a novel generalizable approach to extending the serum half-lives of antibodies and Fc fusions.

Example 4. Engineering Approaches to Constant Region pI Engineering

Reduction in the pI of a protein or antibody can be carried out using a variety of approaches. At the most basic level, residues with high pKa's (lysine, arginine, and to some extent histidine) are replaced with neutral or negative residues, and/or neutral residues are replaced with low pKa residues (aspartic acid and glutamic acid). The particular replacements may depend on a variety of factors, including location in the structure, role in function, and immunogenicity.

Because immunogenicity is a concern, efforts can be made to minimize the risk that a substitution that lowers the pI will elicit immunogenicity. One way to minimize risk is to minimize the mutational load of the variants, i.e. to reduce the pI with the fewest number of mutations. Charge swapping mutations, where a K, R, or H is replaced with a D or E, have the greatest impact on reducing pI, and so these substitutions are preferred. Another approach to minimizing the risk of immunogenicity while reducing pI is to utilize substitutions from homologous human proteins. Thus for antibody constant chains, the isotypic differences between the IgG subclasses (IgG1, IgG2, IgG3, and IgG4) provide low-risk substitutions. Because immune recognition occurs at a local sequence level, i.e. MHC II and T-cell receptors recognize epitopes typically 9 residues in length, pI-altering substitutions may be accompanied by isotypic substitutions proximal in sequence. In this way, epitopes can be extended to match a natural isotype. Such substitutions would thus make up epitopes that are present in other human IgG isotypes, and thus would be expected to be tolerized.

FIG. 17 shows an amino acid sequence alignment of the IgG subclasses. Residues with a bounded box illustrate isotypic differences between the IgG's. Residues which contribute to a higher pI (K, R, and H) or lower pI (D and E) are highlighted in bold. Designed substitutions that either lower the pI, or extend an epitope to match a natural isotype are shown in gray.

FIG. 18 shows the amino acid sequence of the Cκ and Cλ light constant chains. Homology between Cκ and Cλ is not as high as between the IgG subclasses. Nonetheless the alignment may be used to guide substitutions. Residues which contribute to a higher pI (K, R, and H) or lower pI (D and E) are highlighted in bold. Gray indicates lysine, arginines, and histidines that may be substituted, preferably with aspartic or glutatmic acids, to lower the isoelectric point.

Another approach to engineering lower pI into proteins and antibodies is to fuse negatively charged residues to the N- or C-termini. Thus for example, peptides consisting principally of aspartic acids and glutamic acid may be fused to the N-terminus or C-terminus to the antibody heavy chain, light chain or both. Because the N-termini are structurally close to the antigen binding site, the C-termini are preferred.

Based on the described engineering approaches, a number of variants were designed to reduce the isoelectric point of both the antibody heavy chain and light chain. The heavy chain variants comprise various combinations of isotypic substitutions, as well as C-terminal negatively charged peptides. Relative to a native IgG1, the variants comprise one or more isotypic substitutions from the group consisting of G137E, G138S, S192N, L193F, I199T, N203D, K214T, K222T, substitution of 221-225 DKTHT to VE, H268Q, K274Q, R355Q, N384S, K392N, V397M, Q419E, and a deletion of K447 (referred to as K447#), wherein numbering is according to the EU index. The light chain variants comprise various combinations of non-isotypic substitutions and C-terminal negatively charged peptides. Cκ variants comprise one or more substitutions from the group consisting of K126E, K145E, N152D, S156E, K169E, and S202E, wherein numbering is according to the EU index.

Sequences of the variant heavy chains are provided in FIG. 19, and sequences of the variant light chains are provided in FIG. 20. Table 3 lists the variants constructed, along with the calculated pI's of the heavy constant chain, light constant chain, as well as the pI of the full length monoclonal antibody (mAb) containing the variable region (Fv) of the anti-VEGF antibody Bevacizumab.

Example 5. Determination of Charge-Dependency of pI Engineering and Potential Combination with Fc Variants that Enhance Binding to FcRn A series of new pI-engineered variants were generated to test two aspects of the relationship between low pI and extended half-life. First, the parameter of charge was investigated by making a controlled set of variants based on the 9493 IgG1-pI(12) variant. These variants, 10017, 10018, and 10019, are described in Table 4, along with their pI and the differences in positively and negatively charged residues relative to bevacizumab IgG1 WT.

TABLE 4

Engineered constructs exploring charge and Fc variants

| XENP | HC Identity | HC Substitutions | LC Substitutions | pI | Charge State | # KR | # DE |
|---|---|---|---|---|---|---|---|
| 4547 | IgG1-WT | | | 8.1 | (+6) | 0 | 0 |
| 9493 | IgG1-pI(12) | CH1-pI(6) | Ck-pI(6) | 5.6 | (−30) | (−12) | (+24) |
| 9992 | IgG1-pI(12) | CH1-pI(6) + N434S | Ck-pI(6) | 5.6 | (−30) | (−12) | (+24) |
| 9993 | IgG1-pI(12) | CH1-pI(6) + M428L/N434S | Ck-pI(6) | 5.6 | (−30) | (−12) | (+24) |
| 10017 | IgG1-pI(6)-Neutral-to-DE | S119E T164E N208D | N152D S156E S202E | 6.6 | (−6) | 0 | (+12) |
| 10018 | IgG1-pI(6)-KR-to-Neutral | K133Q K205Q K210Q | K126Q K145Q K169Q | 6.6 | (−6) | (−12) | 0 |
| 10019 | IgG1-pI(6)-KR-to-DE | K133E K205E K210E | K126E K145E K169E | 5.9 | (−18) | (−12) | (+12) |

CH1-pI(6) = S119E K133E T164E K205E N208D K210E
Ck-pI(6) = K126E K145E N152D S156E K169E S202E
pI calculated with Fv = Bevacizumab

TABLE 3 pI-engineered antibody constant chain variants

| Heavy Chain Identity | pI | Light Chain Identity | pI | Fv Iden-tity[a] | VH pI | VL pI | mAb[b] pI |
|---|---|---|---|---|---|---|---|
| IgG1-WT | 8.46 | Ck-WT | 6.1 | Bev | 6.99 | 6.75 | 8.10 |
| IgG1-WT | 8.46 | Ck-pI(3) | 4.6 | Bev | 6.99 | 6.75 | 6.58 |
| IgG1-WT | 8.46 | Ck-pI(6) | 4.4 | Bev | 6.99 | 6.75 | 6.21 |
| IgG1-WT | 8.46 | Ck-pI(6-DEDE) | 4.3 | Bev | 6.99 | 6.75 | 5.85 |
| IgG2-WT | 7.66 | Ck-WT | 6.1 | Bev | 6.99 | 6.75 | 7.31 |
| IgG2-WT | 7.66 | Ck-pI(3) | 4.6 | Bev | 6.99 | 6.75 | 6.16 |
| IgG2-WT | 7.66 | Ck-pI(6) | 4.4 | Bev | 6.99 | 6.75 | 5.88 |
| IgG2-WT | 7.66 | Ck-pI(6-DEDE) | 4.3 | Bev | 6.99 | 6.75 | 5.58 |
| pI-iso1 | 5.93 | Ck-WT | 6.1 | Bev | 6.99 | 6.75 | 6.16 |
| pI-iso1(NF) | 5.93 | Ck-WT | 6.1 | Bev | 6.99 | 6.75 | 6.16 |
| pI-iso1(NF-VE) | 5.85 | Ck-WT | 6.1 | Bev | 6.99 | 6.75 | 6.11 |
| pI-iso1(NF-VE) | 5.85 | Ck-pI(3) | 4.6 | Bev | 6.99 | 6.75 | 5.58 |
| pI-iso1(NF-VE) | 5.85 | Ck-pI(6) | 4.4 | Bev | 6.99 | 6.75 | 5.38 |
| pI-iso1(NF-VE) | 5.85 | Ck-pI(6-DEDE) | 4.3 | Bev | 6.99 | 6.75 | 5.18 |
| pI-iso1(NF-VE-DEDE) | 5.36 | Ck-WT | 6.1 | Bev | 6.99 | 6.75 | 5.74 |
| pI-iso1(NF-VE-DEDE) | 5.36 | Ck-pI(3) | 4.6 | Bev | 6.99 | 6.75 | 5.32 |
| pI-iso1(NF-VE-DEDE) | 5.36 | Ck-pI(6) | 4.4 | Bev | 6.99 | 6.75 | 5.18 |
| pI-iso1(NF-VE-DEDE) | 5.36 | Ck-pI(6-DEDE) | 4.3 | Bev | 6.99 | 6.75 | 5.03 |

[a] Bev = the variable region of the anti-VEGF antibody Bevacizumab
[b] mAb pI = the pI of the full length monoclonal antibody containing the Fv of Bevacizumab The experimental rationale here is as follows. If all the mechanism for improved half-life is based on removal of positive charge, 10018 and 10019 should be as good as 9493 while 10017 would not be extended. If the mechanism is based on an increase in negative charge, 10018 will not be extended, while 10017 and 10019 will have equivalent half-life that is extended relative to IgG1 but shorter than 9493. If overall pI (or charge state) is the basis, the result will be 9493>10019>10017=10018.

In addition to the charge-controlled variant set, the 9493 IgG1-pI(12) variant was combined with substitutions that improve binding to FcRn at pH 6.0 in order to test whether the two mechanisms of half-life improvement, charge state and FcRn, are compatible. These variants, 9992 IgG1-pI (12)-N434S and 9993 IgG1-pI(12)-M428L/N434S, are listed in Table 4.

Figure 21:
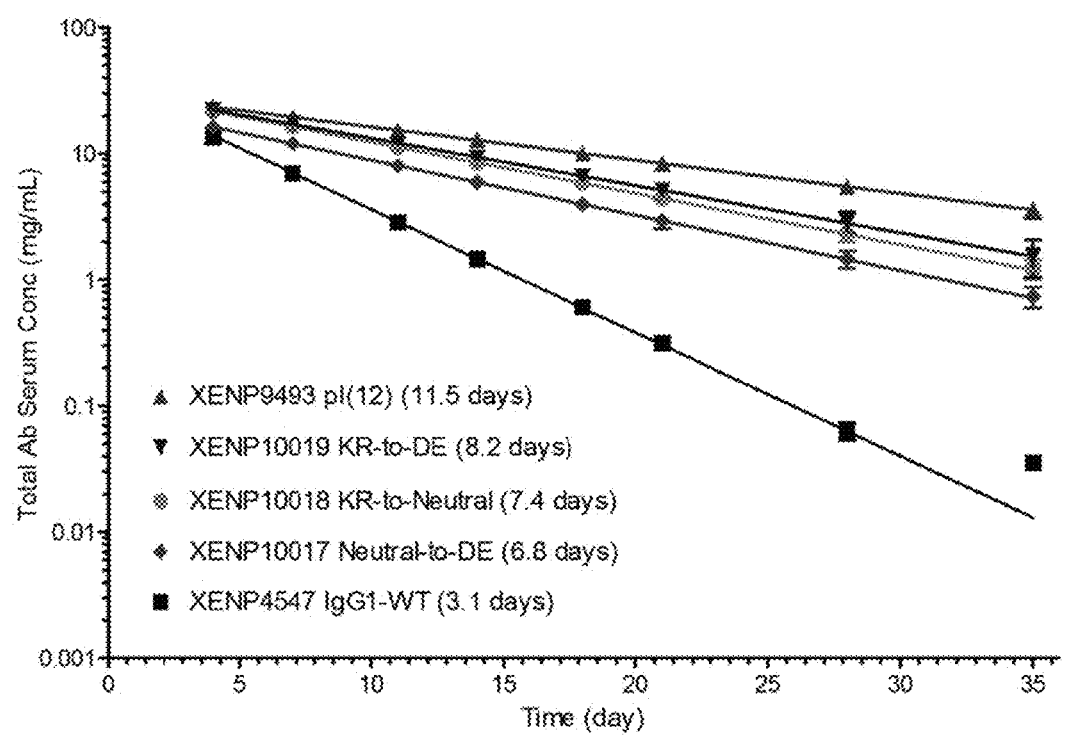
FIG. 21. PK results of pI-engineered variant bevacizumab antibodies in huFcRn mice.
Figure 22:
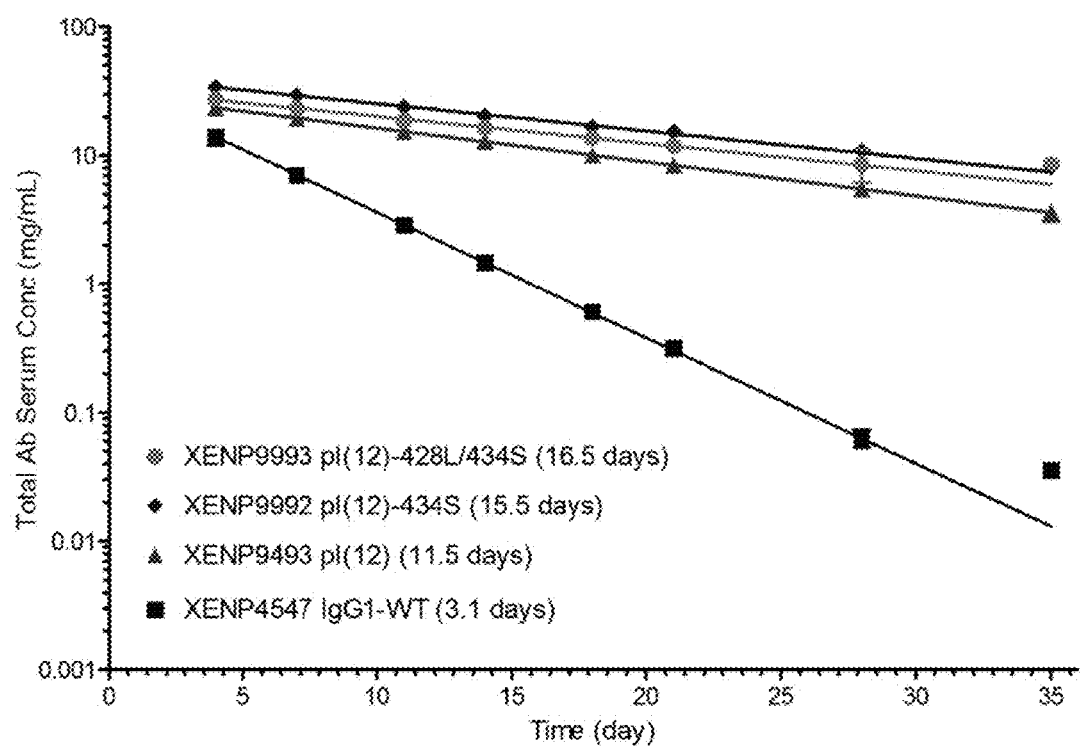
FIG. 22. PK results of variants that combine pI-engineered modifications with Fc modifications that enhance binding to FcRn.

Antibody variants were constructed with the variable region of bevacizumab using molecular biology techniques as described above. Antibodies were expressed, purified, and characterized as described above. PK studies of the variant and control antibodies were carried out in the huFcRn mice as described above. The group mean averages of the serum concentrations are plotted in FIGS. 21 and 22, along with the half-lives obtained from the fits of the data.

The results indicate that both reducing positive charge and increasing negative charge contribute to improved half-life. In addition, the results indicate that engineered lower pI and increased binding to FcRn can be used in combination to obtain even greater enhancements in half-life. A plot of the half-life vs. pI relationship is provided in FIG. 23 for variant and native IgG's of identical Fv (bevacizumab) that have been tested in the huFcRn mice. The graph illustrates again the inverse relationship between half-life and pI, as well as the combinability of variants engineered for lower pI and Fc variants that improve binding to FcRn.

Example 6. New pI-Engineered Constructs

As described above, efforts can be made to minimize the risk that substitutions that lower pI will elicit immunogenicity by utilizing the isotypic differences between the IgG subclasses (IgG1, IgG2, IgG3, and IgG4). A new set of novel isotypes was designed based on this principal. Again, because immune recognition occurs at a local sequence level, i.e. MHC II and T-cell receptors recognize epitopes typically 9 residues in length, pI-altering substitutions were accompanied by isotypic substitutions proximal in sequence. In this way, epitopes were extended to match a natural isotype. Such substitutions would thus make up epitopes that are present in other human IgG isotypes, and thus would be expected to be tolerized.

Figure 25:
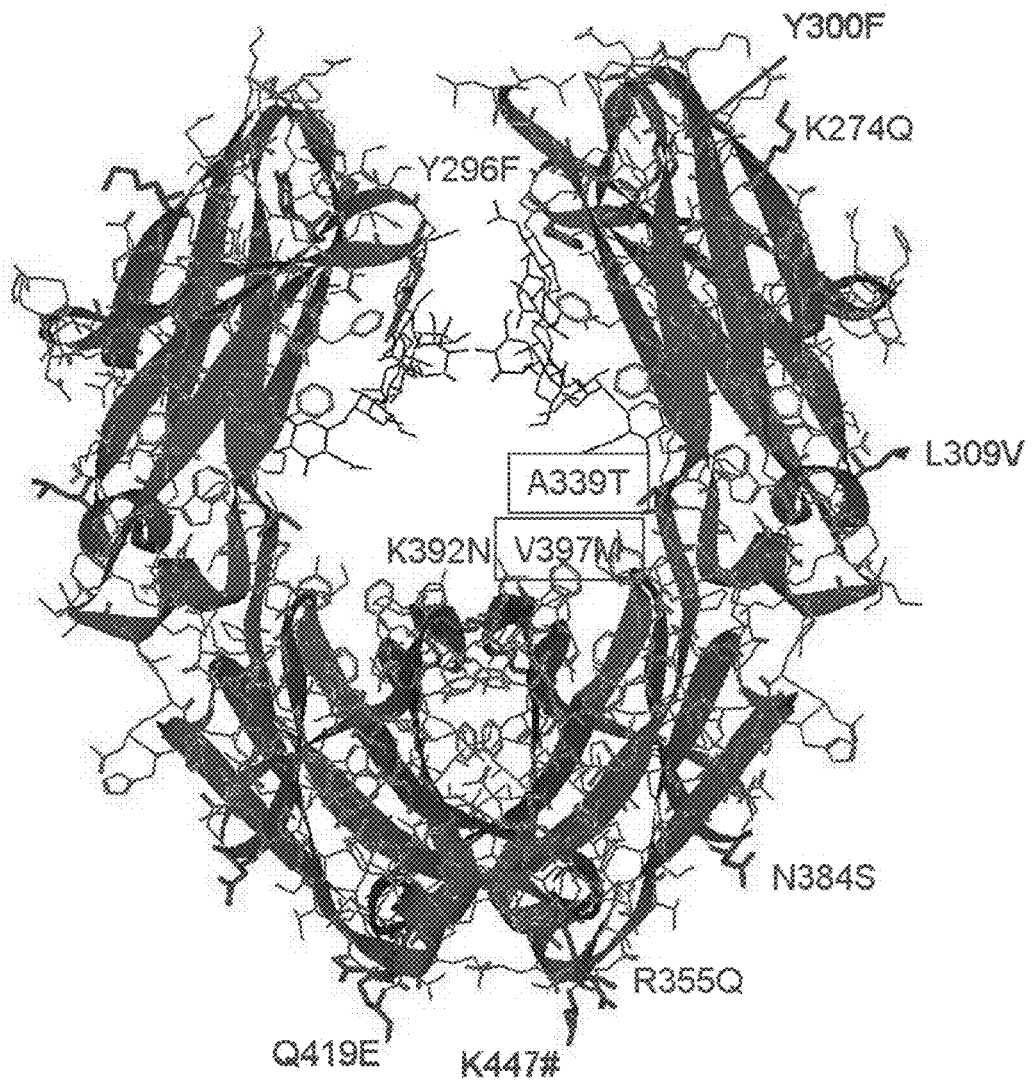
FIG. 25. Differences between IgG1 and IgG-pI-Iso3 in the hinge and Fc region.
Figure 26:
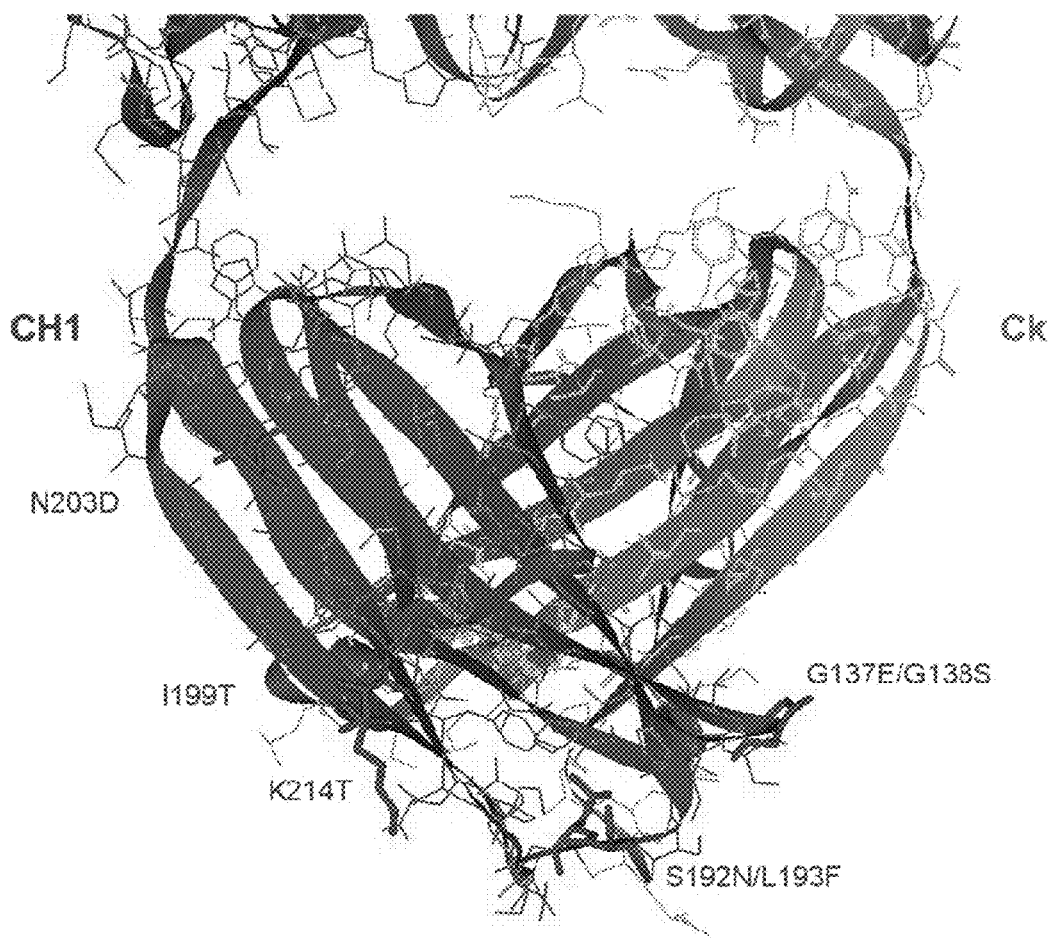
FIG. 26. Differences between IgG1 and IgG-pI-Iso3 in the CH1 region.

The designed low-pI isotypes, referred to as IgG-pI-Iso2, IgG-pI-Iso2-SL, IgG-pI-Iso2-charges-only, IgG-pI-Iso3, IgG-pI-Iso3-SL, and IgG-pI-Iso3-charges-only are described in Table 5, along with their pI and effector function properties. FIG. 24 provides a sequence alignment of IgG-pI-Iso3 with the native IgG isotypes, and depicts residue identities and residues that reduce pI relative to one or more of the native IgG isotypes. FIGS. 25 and 26 illustrate the structural differences between IgG1 and IgG-pI-Iso3. IgG-pI-Iso2, IgG-pI-Iso2-SL, and IgG-pI-Iso2-charges-only were designed to have low (weak) effector function, as determined by IgG2-like residues in the hinge (233P, 234V, 235A) and CH2 domain (327G). IgG-pI-Iso3, IgG-pI-Iso3-SL, and IgG-pI-Iso3-charges-only were designed to have high (strong) effector function, as determined by IgG1-like residues in the hinge (233E, 234L, 235L, 236G) and CH2 domain (327A). Isotypic low pI variants with the "SL" designation indicate that these variants differ from IgG-pI-Iso2 and IgG-pI-Iso3 by having 192S and 193L. Serine and leucine at these positions were found to be more compatible than 192N/193F due to differences in neighboring residues that are present in IgG1 and IgG2. Low pI isotype variants designated as "charges only" contain charge affecting isotypic substitutions, but do not contain the neighboring non-charge altering substitutions. The novel isotypes can be combined with a native light chain constant region (Ckappa or Clambda), or a variant version engineered with substitutions to further reduce the pI. An example of a pI-engineered light constant chain is a new variant referred to as CK-pI(4), described schematically in FIG. 27. In addition, the novel isotypes can be engineered with Fc variants that improve affinity to FcRn, thereby further enabling extended half-life. Such Fc variants may include, for example 434S or 428L/434S as described in Table 5, or other Fc variants as described herein. Amino acid sequences of IgG-pI-Iso2, IgG-pI-Iso2-SL, IgG-pI-Iso2-charges-only, IgG-pI-Iso3, IgG-pI-Iso3-SL, IgG-pI-Iso3-charges-only and CK-pI(4) are provided in FIG. 28.

TABLE 5

Novel IgG isotypes with low pI

| XENP | Heavy | Light | Fc variant | pI | Effector Function |
|---|---|---|---|---|---|
| 10178 | IgG-pI-Iso2 | WT | | 6.3 | Low |
| 10470 | IgG-pI-Iso2-SL | WT | | 6.3 | Low |
| 10180 | IgG-pI-Iso2 | WT | 434S | 6.3 | Low |
| 10471 | IgG-pI-Iso2-SL | WT | 434S | 6.3 | Low |
| 10182 | IgG-pI-Iso2 | CK-pI(4) | | 5.6 | Low |
| 10184 | IgG-pI-Iso2 | CK-pI(4) | 434S | 5.6 | Low |
| 10427 | IgG-pI-Iso2-charges-only | WT | | 6.3 | Low |
| 10473 | IgG-pI-Iso2-charges-only | WT | 434S | 6.3 | Low |
| 10179 | IgG-pI-Iso3 | WT | | 6.2 | High |
| 10286 | IgG-pI-Iso3-SL | WT | | 6.2 | High |
| 10181 | IgG-pI-Iso3 | WT | 434S | 6.2 | High |
| 10466 | IgG-pI-Iso3-SL | WT | 434S | 6.2 | High |
| 10467 | IgG-pI-Iso3-SL | WT | 428L/434S | 6.2 | High |
| 10183 | IgG-pI-Iso3 | CK-pI(4) | | 5.5 | High |
| 10185 | IgG-pI-Iso3 | CK-pI(4) | 434S | 5.5 | High |
| 10525 | IgG-pI-Iso3-SL | CK-pI(4) | 434S | 5.5 | High |
| 10426 | IgG-pI-Iso3-charges-only | WT | | 6.2 | High |
| 10472 | IgG-pI-Iso3-charges-only | WT | 434S | 6.2 | High |

SL = 192S/193L
CK-pI(4) = K126E/K145E/K169E/K207E
pI calculated with Fv = Bevacizumab The novel engineered isotypes can be combined with other Fc variants to generate antibodies or Fc fusions with extended half-life and other improved properties. For example, IgG-pI-Iso2-SL and/or IgG-pI-Iso3-SL may incorporate variants 239D, 332E, 267E, and/or 328F that modulate binding to FcγRs to provide enhanced effector function or immunomodulatory properties (as well as other variants listed in Legend B of FIG. 83. The novel isotypes may be combined with other Fc variants that improve binding to FcRn, including for example 428L, 428L/434S, T250Q/M428L, M252Y/S254T/T256E, and N434A/T307Q, (and others listed in Legend A of FIG. 83) thereby potentially further extending in vivo half-life. Exemplary heavy chains are described in Table 6. Such variants may be expressed with a light chain that has a native constant light chain (CK or CX), or one that also incorporates constant light chain modifications that reduce pI, including for example any of the engineered constant light chains described herein, including for example CK-pI(4).

TABLE 6

Engineered combinations of pI isotype variants with other variants.

| Heavy | Fc |
|---|---|
| IgG-pI-Iso3-SL | 332E |
| IgG-pI-Iso3-SL | 239D/332E |
| IgG-pI-Iso3-SL | 332E/434S |
| IgG-pI-Iso3-SL | 239D/332E/434S |
| IgG-pI-Iso2-SL | 267E/328F |
| IgG-pI-Iso2-SL | 434S/267E/328F |
| IgG-pI-Iso2-SL | 267E/328F |
| IgG-pI-Iso3-SL | 434S/267E/328F |
| IgG-pI-Iso2-SL | 428L/434S |
| IgG-pI-Iso3-SL | 428L/434S |
| IgG-pI-Iso2-SL | 428L |
| IgG-pI-Iso3-SL | 428L |
| IgG-pI-Iso2-SL | 250Q/428L |
| IgG-pI-Iso3-SL | 250Q/428L |
| IgG-pI-Iso2-SL | 252Y/254T/256E |
| IgG-pI-Iso3-SL | 252Y/254T/256E |
| IgG-pI-Iso2-SL | 434A/307Q |
| IgG-pI-Iso3-SL | 434A/307Q |

Figure 30:
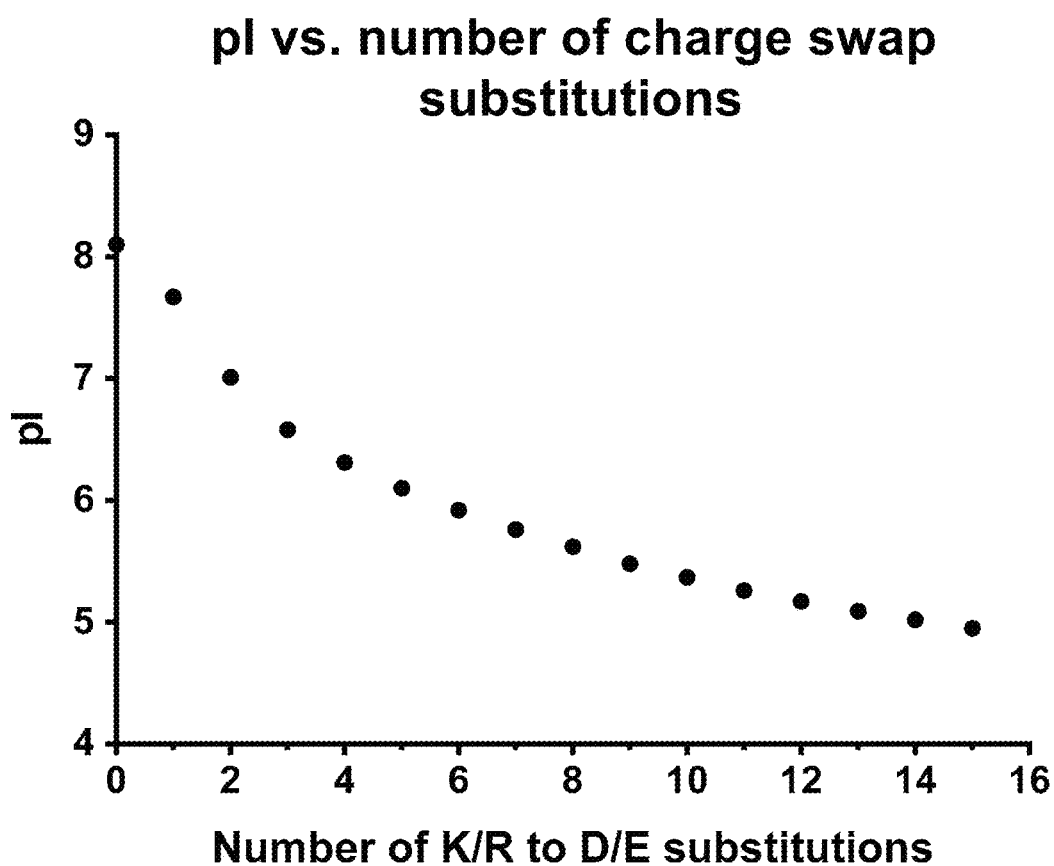
FIG. 30. Plot showing the effect of charge swap mutations on antibody pI. As the pI gets lower the change in pI per charge swap decreases.

In order to reduce pI even further, additional variant heavy constant chains with reduced pI were designed to minimize mutational load by introducing charge swapping mutations, i.e. where K and R were replaced with D or E, as described above. To aid in the design of these variants, fraction exposed as well as the energy change upon substitution to Glu were calculated for each K and R residue in the Fc region (FIG. 29). These new variants are referred to as pI(7) and pI(11). pI(7) incorporated amino acid modifications K133E, K205E, K210E, K274E, R355E, K392E, and a deletion of the Lys at 447, and pI(11) incorporated amino acid modifications K133E, K205E, K210E, K274E, K320E, K322E, K326E, K334E, R355E, K392E, and a deletion of the Lys at 447 These modifications were introduced into heavy constant chains to result in antibodies with strong effector function, IgG1-pI(7) and IgG1-pI(11), and weak effector function IgG1/2-pI(7) and IgG1/2-pI(11). As can be seen in FIG. 30, as mAb pI gets lower, it requires a greater number of charge swap substitutions to decrease pI further. These pI-engineered variants are described in Table 7, and amino acid sequences are provided in FIG. 28.

TABLE 7

Engineered charge swaps

| XENP | Heavy | Fc variant | Light | pI |
|---|---|---|---|---|
| 10107 | IgG1-pI(7) | | CK-pI(4) | 5.3 |
| 10108 | IgG1-pI(11) | | CK-pI(4) | 5.0 |
| 10109 | IgG1/2-pI(7) | | CK-pI(4) | 5.4 |
| 10110 | IgG1/2-pI(11) | | CK-pI(4) | 5.0 |
| 10476 | IgG1/2-pI(7) | 434S | CK-pI(4) | 5.4 |

Figure 31:
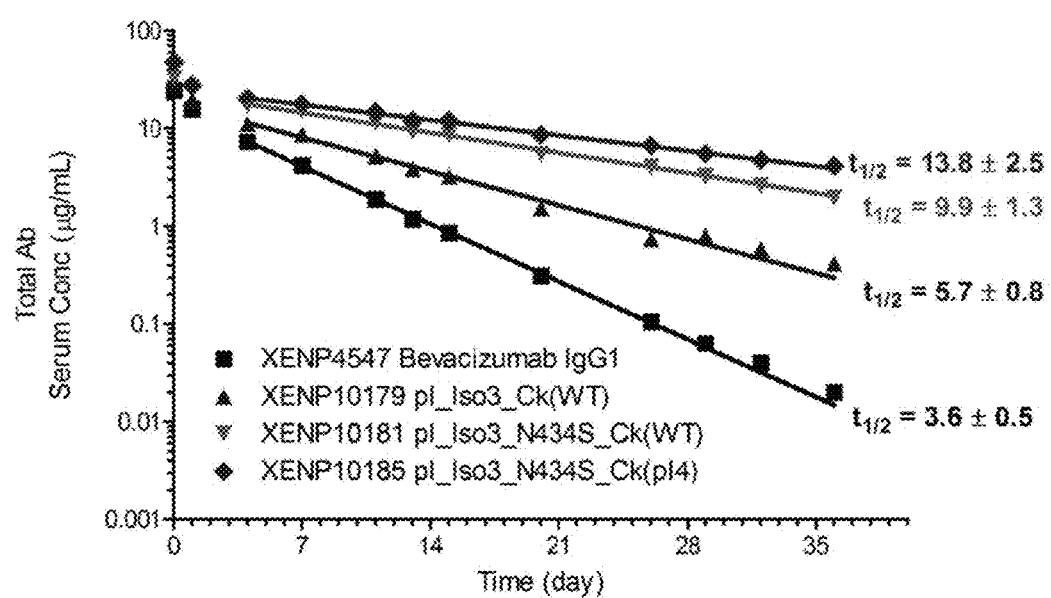
FIG. 31. PK results of pI-engineered isotypic variant bevacizumab antibodies (IgG-pI-Iso3) and combinations with substitution N434S in huFcRn mice.
Figure 32:
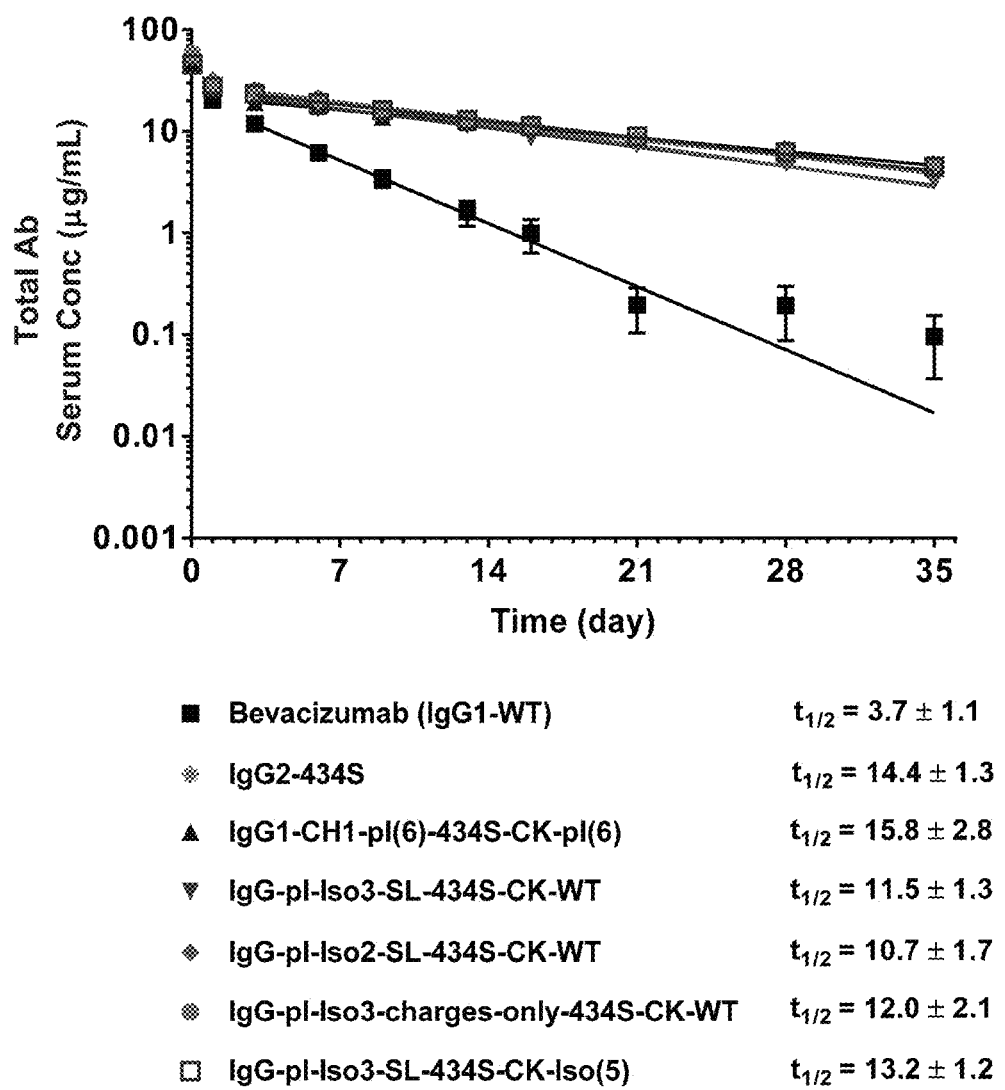
FIG. 32. PK results of pI-engineered isotypic variant bevacizumab antibodies and combinations with substitution N434S in huFcRn mice.
Figure 33:
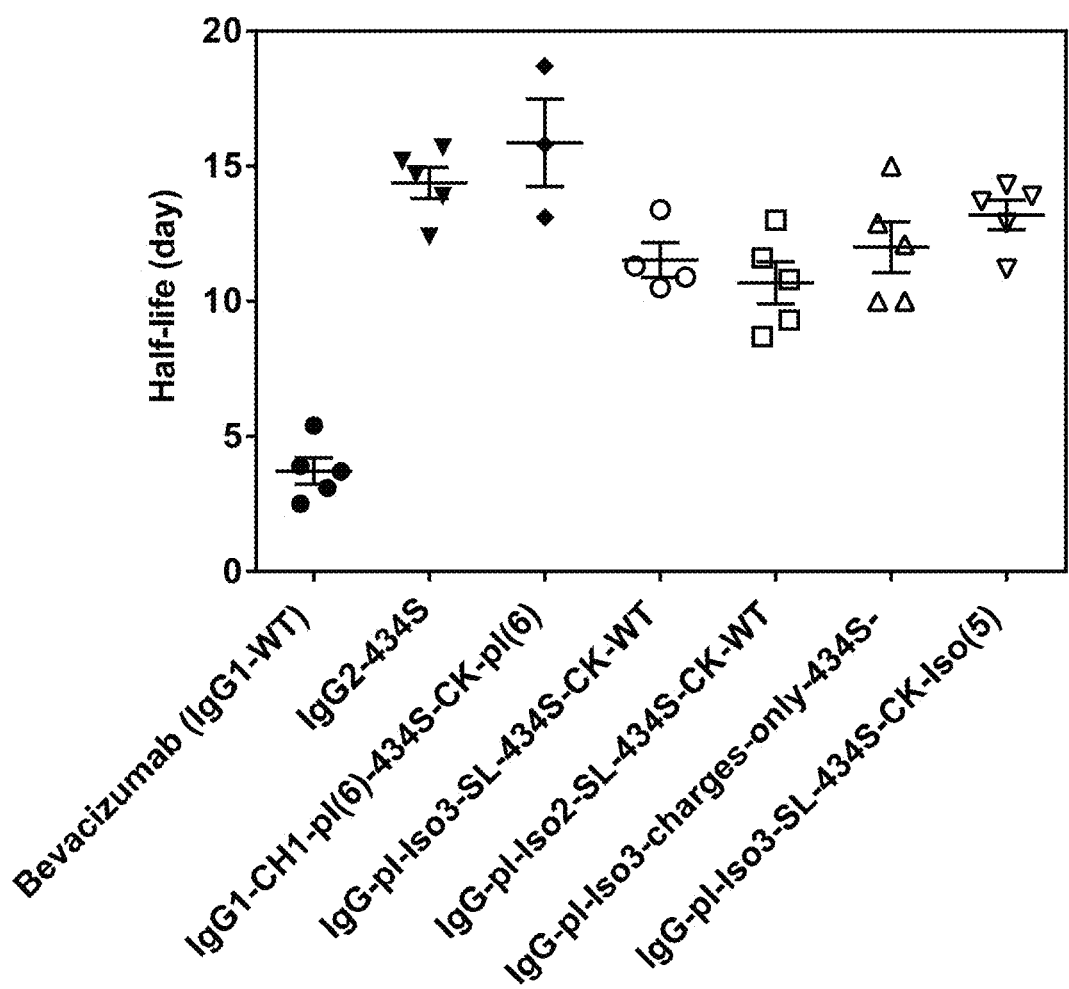
FIG. 33. Scatter plot of PK results of pI-engineered isotypic variant bevacizumab antibodies and combinations with substitution N434S in huFcRn mice. Each point represents a single mouse from the study. It should be noted that the 428L substitution can also be added to each of these pI antibodies.
Figure 34:
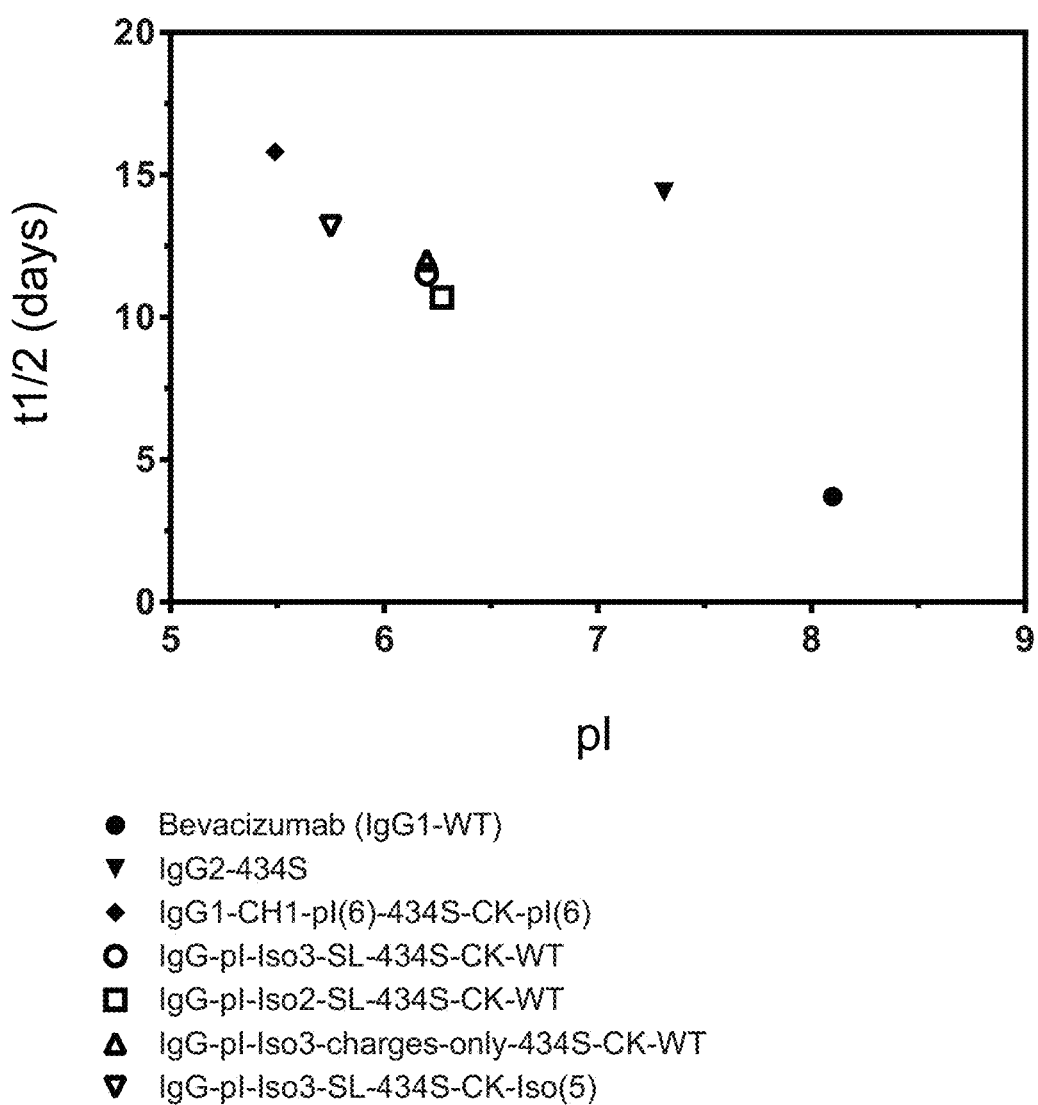
FIG. 34. Plot showing correlation between pI engineered variant pI and half-life (t½).

IgG1-pI(7) = K133E/K205E/K210E/K274E/R355E/K392E/K447#
IgG1-pI(11) = K133E/K205E/K210E/K274E/K320E/K322E/K326E/K334E/R355E/K392E/K447#
IgG1/2-pI(7) = K133E/K205E/K210E/Q274E/R355E/K392E/K447#
IgG1/2-pI(11) = K133E/K205E/K210E/Q274E/K320E/K322E/K326E/K334E/R355E/K392E/K447#
CK-pI(4) = K126E/K145E/K169E/K207E
pI calculated with Fv = Bevacizumab Antibody variants were constructed with the variable region of bevacizumab using molecular biology techniques as described above. Antibodies were expressed, purified, and characterized as described above. PK studies of the variant and control antibodies were carried out in the huFcRn mice as described above. The group mean averages of the serum concentrations are plotted in FIG. 31 and FIG. 32, along with the half-lives obtained from the fits of the data. Half-lives for individual mice are plotted in FIG. 33. The data clearly demonstrate the additivity of low pI from isotypic pI variants as well as enhanced FcRn binding from the N434S substitution as shown by a plot of half-life vs. pI as shown in FIG. 34.

Example 7. Isotypic Light Chain Constant Region Variants

Figure 35:
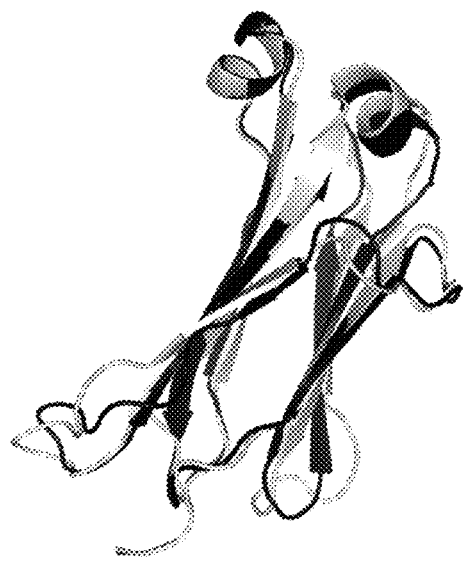
FIG. 35. Structural alignment of CK and C-lambda domains.

Homology between CK and CX is not as high as between the IgG subclasses (as shown in FIG. 18), however the sequence and structural homology that exists may still be used to guide substitutions to create an isotypic low-pI light chain constant region. In FIG. 18, positions with residues contributing to a higher pI (K, R, and H) or lower pI (D and E) are highlighted in bold. Gray indicates lysine, arginines, and histidines that may be substituted, preferably with aspartic or glutatmic acids, to lower the isoelectric point. A structural alignment of CK and CX was constructed (FIG. 35) and used along with the sequence alignment as a guide to make several CK/CX isotypic variants. These pI-engineered variants are described in Table 8, and amino acid sequences are provided in FIG. 28.

TABLE 8

Engineered low-pI variants containing isotypic light chain constant regions

| XENP | Heavy | Light | Fc variant | pI | Effector Function |
|---|---|---|---|---|---|
| 10324 | IgG-pI-Iso3 | CK-Iso(3) | | 5.9 | High |
| 10325 | IgG-pI-Iso3 | CK-Iso(4) | | 5.8 | High |
| 10326 | IgG-pI-Iso3 | CK-Iso(5) | | 5.8 | High |
| 10327 | IgG-pI-Iso3 | CK-Iso(6) | | 5.7 | High |
| 10511 | IgG-pI-Iso3-SL | CK-Iso(3) | | 5.9 | High |
| 10512 | IgG-pI-Iso3-SL | CK-Iso(4) | | 5.8 | High |
| 10513 | IgG-pI-Iso3-SL | CK-Iso(5) | | 5.8 | High |
| 10517 | IgG-pI-Iso3-SL | CK-Iso(3) | 434S | 5.9 | High |
| 10518 | IgG-pI-Iso3-SL | CK-Iso(4) | 434S | 5.8 | High |
| 10519 | IgG-pI-Iso3-SL | CK-Iso(5) | 434S | 5.8 | High |
| 10520 | IgG-pI-Iso3-SL | CK-Iso(3) | 428L/434S | 5.9 | High |
| 10521 | IgG-pI-Iso3-SL | CK-Iso(4) | 428L/434S | 5.8 | High |
| 10522 | IgG-pI-Iso3-SL | CK-Iso(5) | 428L/434S | 5.8 | High |
| 10526 | IgG-pI-Iso3 | CK-Iso(5) | 434S | 5.8 | High |
| 10527 | IgG-pI-Iso2-SL | CK-Iso(5) | 434S | 5.8 | Low |

Antibody variants were constructed with the variable region of bevacizumab using molecular biology techniques as described above. Antibodies were expressed, purified, and characterized as described above. PK studies of the variant and control antibodies were carried out in the huFcRn mice as described above. The group mean averages of the serum concentrations as well as the half-lives obtained from fits of the data for one of these variants (XENP10519-IgG-pI-Iso3-SL-434S-CK-Iso(5)) are plotted in FIG. 32 and the half-lives for individual mice in FIG. 33. This variant is also included in the correlation plot shown in FIG. 34. The benefit of lower pI due to the CK-Iso(5) light chain is clearly shown.

Example 8. Purifying Mixtures of Antibody Variants with Modified Isolectric Points Substitutions that modify the antibody isoelectric point may be introduced into one or more chains of an antibody variant to facilitate analysis and purification. For instance, heterodimeric antibodies such as those disclosed in US2011/0054151A1 can be purified by modifying the isoelectric point of one chain, so that the multiple species present after expression and Protein A purification can be purified by methods that separate proteins based on differences in charge, such as ion exchange chromatography. An overview of the process using two different heavy chains—one unmodified IgG1, and one with modified isoelectric point, is shown in FIG. 38.

As an example, the heavy chain of bevacizumab was modified by introducing substitutions to lower its isoelectric point such that the difference in charges between the three species produced when WT-IgG1-HC, low-pI-HC, and WT-LC are transfected in 293E cells is large enough to facilitate purification by anion exchange chromatography. Clones were created as described above, and transfection and initial purification by Protein A chromatography is also as described above. Sequences of the three chains are listed in FIG. 39 as "Heavy chain 1 of XENP10653", "Heavy chain 2 of XENP10653", and "Light chain of XENP10653". After Protein A purification, three species with nearly identical molecular weights, but different charges are obtained. These are the WT-IgG1-HC/WT-IgG1-HC homodimer (pI=8.12), WT-IgG1-HC/low-pI-HC heterodimer (pI=6.89), and low-pI-HC/low-pI-HC homodimer (pI=6.20). The mixture was loaded onto a GE HiTrap Q HP column in 20 mM Tris, pH 7.6 and eluted with a step-wise gradient of NaCl consisting of 50 mM, 100 mM, and finally 200 mM NaCl in the same Tris buffer. Elution was monitored by A280, and each fraction analyzed on Invitrogen pH 3-10 IEF gels with Novex running buffer and these results are shown in FIG. 40. WT-IgG1-HC/WT-IgG1-HC homodimer does not bind to the anion exchange column at pH 7.6 and is thus present in the flowthrough and wash (lanes 1-2). The desired heterodimer elutes with 50 mM NaCl (lane 3), while the low-pI-HC/low-pI-HC homodimer binds tightest to the column and elutes at 100 (lane 4) and 200 mM (lane 5) NaCl. Thus the desired heterodimer variant, which is difficult to purify by other means because of its similar molecular weight to the other two species, is easily purified by the introduction of low pI substitutions into one chain. This method of purifying antibodies by engineering the isoelectric point of each chain can be applied to methods of purifying various bispecific antibody constructs as outlined in FIG. 41 and FIG. 42. The method is particularly useful when the desired species in the mixture has similar molecular weight and other properties such that normal purification techniques are not capable of separating the desired species in high yield. Specific heterodimeric and/or bispecific constructs and sequences with isoelectric points engineered for easy purification are shown in Tables 9 and 10, and FIG. 39, respectively.

TABLE 9

Heterodimeric and/or bispecific constructs with isoelectric points engineered for easy purification and list of isoelectric points.

| | Calculated pI | | |
|---|---|---|---|
| Protein | Low pI Homodimer | Heterodimer | High pI Homodimer |
| XENP10653 | 6.20 | 6.87 | 8.02 |
| Anti-HER2 × anti-CD16 mAb-Fv | 6.07 | 7.31 | 8.47 |
| Anti-CD19 × anti-CD16 mAb-Fv | 5.84 | 6.63 | 8.21 |
| Anti-CD19 × anti-CD32b mAb-Fv | 6.23 | 6.74 | 7.80 |
| Anti-CD40 × anti-CD32b mAb-Fv | 6.54 | 7.46 | 8.22 |
| Anti-HER2 × anti-CD3 mAb-Fv | 7.58 | 8.21 | 8.52 |
| Anti-HER2 × anti-CD3 scFv-Fc | 7.31 | 8.31 | 8.69 |

TABLE 10

Heterodimeric and/or bispecific constructs with isoelectric points engineered for easy purification and list of charge state at pH 7.4.

| | Calculated charge state at pH 7.4 | | |
|---|---|---|---|
| Protein | Low pI Homodimer | Heterodimer | High pI Homodimer |
| XENP10653 | −12.57 | −3.59 | +5.40 |
| Anti-HER2 × anti-CD16 mAb-Fv | −16.67 | −0.65 | +15.37 |
| Anti-CD19 × anti-CD16 mAb-Fv | −22.68 | −6.66 | +9.36 |
| Anti-CD19 × anti-CD32b mAb-Fv | −14.53 | −5.59 | +3.35 |
| Anti-CD40 × anti-CD32b mAb-Fv | −8.51 | +0.43 | +9.37 |
| Anti-HER2 × anti-CD3 mAb-Fv | +1.25 | +9.32 | +17.40 |
| Anti-HER2 × anti-CD3 scFv-Fc | −0.34 | +6.68 | +13.71 |

Example 9. Design of Non-Native Charge Substitutions to Alter PI

The pI of antibody constant chains were altered by engineering substitutions in the constant domains. Reduced pI can be engineered by making substitutions of basic amino acids (K or R) to acidic amino acids (D or E), which result in the largest decrease in pI. Mutations of basic amino acids to neutral amino acids and neutral amino acids to acidic amino acids will also result in a decrease in pI. Conversely, increased pI can be engineered by making substitutions of acidic amino acids (D or E) to basic amino acids (K or R), which result in the largest increase in pI. Mutations of acidic amino acids to neutral amino acids and neutral amino acids to basic amino acids will also result in a increase in pI. A list of amino acid pK values can be found in Table 1 of Bjellqvist et al., 1994, Electrophoresis 15:529-539.

In deciding which positions to mutate, the surrounding environment and number of contacts the WT amino acid makes with its neighbors was taken into account such as to minimize the impact of a substitution or set of substitutions on structure and/or function. The solvent accessibility or fraction exposed of each constant region position was calculated using relevant crystal structures. The results are shown in FIG. 43. Based on this analysis, a number of substitutions were identified that reduce or increase pI but are predicted to have minimal impact on the biophysical properties of the domains. Proof of concept results in the context of bevacizumab are shown in FIGS. 44-47 (heavy chain) and FIGS. 48-51 (light chain).

Calculation of protein pI was performed as follows. First, a count was taken of the number of D, E, C, H, K, R, and Y amino acids as well as the number of N- and C-termini present in the protein. Then, the pI was calculated by identifying the pH for which the protein has an overall charge of zero. This was done by calculating the net charge of the protein at a number of test pH values. Test pH values were set in an iterative manner, stepping up from a low pH of 0 to a high pH of 14 by increments of 0.001 until the charge of the protein reached or surpassed zero. Net charge of a protein at a given pH was calculated by the following formula:

$$q_{protein}(\text{pH}) = \sum_{i=H,K,R,Ntermini} \frac{N_i}{1 + 10^{pH-pK_i}} - \sum_{i=D,E,C,Y,Ctermini} \frac{N_i}{1 + 10^{pK_i-pH}}$$

where $q_{protein}(pH)$ is the net charge on the protein at the given pH, is the number of amino acid i (or N- or C-termini) present in the protein, and is the pK of amino acid i (or N- or C-termini).

Example 10. Isotypic Constant Region Variants

As described above, efforts can be made to minimize the risk that substitutions that increase or decrease pI will elicit immunogenicity by utilizing the isotypic differences between the IgG subclasses (IgG1, IgG2, IgG3, and IgG4). A new set of novel isotypes was designed based on this principal. If possible, pI-altering substitutions were accompanied by isotypic substitutions proximal in sequence. In this way, epitopes were extended to match a natural isotype. Such substitutions would thus make up epitopes that are present in other human IgG isotypes, and thus would be expected to be tolerized. These new variants are called ISO(−), ISO(+), and ISO(+RR). ISO(−) has reduced pI while ISO(+) and ISO(+RR) have increased pI. A sequence alignment showing the isotypic variation in IgG1-4 as well as the sequences of the new isotypic pI variants are shown in FIG. 52. The sequences of these new variants are also shown in FIG. 53-57. All possible combinations of pI lowering isotypic mutations from IgG1, IgG2, IgG3, and IgG4 are shown in FIG. 58. All possible combinations of pI increasing isotypic mutations are shown in FIG. 59.

Example 11. Purifying Mixtures of Antibody Variants with Modified Isolectric Points As mentioned previously, substitutions that modify the antibody isoelectric point may be introduced into one or more chains of an antibody variant to facilitate analysis and purification. This is especially useful when a preparation of antibody contains a mixture of very similar species as in the case of heterodimeric and/or bispecific constructs that produce a mixture of hetero- and homodimers. In order to demonstrate purification of a nearly identical antibody heterodimer species from the corresponding homodimers, we constructed our isotypic pI variants in the context of the antibody bevacizumab. Variants were constructed by transfecting two different heavy chain DNAs (ISO(−), ISO(+), ISO(+RR), or IgG1(WT)) with the bevacizumab light chain. Variants were first purified by Protein A, and then loaded onto a GE Healthcare HiTrap SP HP cation exchange column in 50 mM MES (pH 6.0) and eluted with an NaCl gradient. Following elution, fractions from each peak were loaded onto a Lonza IsoGel IEF plate (pH range 7-11) for analysis. Data are shown in FIGS. 60-63. As can be seen from the data, separation of the middle pI heterodimer is achieved in each case, with separation improved when the heterodimer has a larger difference in pI from the homodimers.

Example 12. Design of Mixtures of Immunoglobulin Variants with Modified Isoelectric Points This method of purifying antibodies by engineering the isoelectric point of each chain can be applied to methods of purifying various bispecific antibody constructs. The method is particularly useful when the desired species in the mixture has similar molecular weight and other properties such that normal purification techniques are not capable of separating the desired species in high yield. Specific heterodimeric and/or bispecific constructs and sequences with isoelectric points engineered for easy purification are shown in FIGS. 64-77.

What is claimed is:

1. A composition comprising a heterodimeric protein comprising a heterodimeric Fc domain, said heterodimeric Fc domain comprising:
    a) a first monomer comprising a first variant Fc domain comprising amino acid substitutions S239D, 332E, L368E, K370S; and
    b) a second monomer comprising a second variant Fc domain comprising amino acid substitutions S239D, 332E, and S364K wherein numbering is according to the EU index as in Kabat and wherein said first variant Fc domain and said second variant Fc domain are variant human IgG Fc domains.

2. A composition according to claim 1 wherein said first monomer further comprises a first fusion partner and said second monomer further comprises a second fusion partner.

3. A composition according to claim 2, wherein said first monomer comprises a third fusion partner.

4. A composition according to claim 3, wherein said second monomer comprises a fourth fusion partner.

5. A composition according to claim 2, wherein said fusion partners are independently selected from the group consisting of an immunoglobulin component, a peptide, a cytokine, a chemokine, an immune receptor and a blood factor.

6. A composition according to claim 5, wherein said immunoglobulin component is selected from the group consisting of Fab, VH, VL, scFv, scFv2, and dAb.

7. A composition according to claim 5, wherein both fusion partners are immunoglobulin components.

8. A nucleic acid composition comprising:
    a) a first nucleic acid nucleic acid encoding a first monomer according to claim 1; and
    b) a second nucleic acid encoding a second monomer according to claim 1.

9. A host cell comprising the nucleic acid composition of claim 8.

10. A method of making a composition according to claim 1 comprising culturing a host cell according to claim 1 under conditions whereby said composition is produced.

* * * * *

SEQUENCE LISTING

```
<160> NUMBER OF SEQ ID NOS: 144

<210> SEQ ID NO 1
<211> LENGTH: 107
<212> TYPE: PRT
<213> ORGANISM: Artificial Sequence
<220> FEATURE:
<223> OTHER INFORMATION: Kappa constant light chain (CK)

<400> SEQUENCE: 1

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 2
```

<211> LENGTH: 330
<212> TYPE: PRT
<213> ORGANISM: Artificial Sequence
<220> FEATURE:
<223> OTHER INFORMATION: IgG1 constant heavy chain (CH1-hinge-CH2-CH3)

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 326
<212> TYPE: PRT
<213> ORGANISM: Artificial Sequence
<220> FEATURE:
<223> OTHER INFORMATION: IgG2 constant heavy chain (CH1-hinge-CH2-CH3)

<400> SEQUENCE: 3

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 4
<211> LENGTH: 377
<212> TYPE: PRT
<213> ORGANISM: Artificial Sequence
<220> FEATURE:
<223> OTHER INFORMATION: IgG3 constant heavy chain (CH1-hinge-CH2-CH3)

<400> SEQUENCE: 4

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
```

```
                20                  25                  30
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
            130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
            210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 5
<211> LENGTH: 327
<212> TYPE: PRT
<213> ORGANISM: Artificial Sequence
<220> FEATURE:
<223> OTHER INFORMATION: IgG4 constant heavy chain (CH1-hinge-CH2-CH3)

<400> SEQUENCE: 5

Ala Ser Thr Lys Gly Pro Ser Val Phe Pro Leu Ala Pro Cys Ser Arg
```

```
                1               5                    10                   15
            Ser Thr Ser Glu Ser Thr Ala Ala Leu Gly Cys Leu Val Lys Asp Tyr
                            20                  25                  30

Phe Pro Glu Pro Val Thr Val Ser Trp Asn Ser Gly Ala Leu Thr Ser
                            35                  40                  45

Gly Val His Thr Phe Pro Ala Val Leu Gln Ser Ser Gly Leu Tyr Ser
                            50                  55                  60

Leu Ser Ser Val Val Thr Val Pro Ser Ser Leu Gly Thr Lys Thr
            65                  70                  75                  80

Tyr Thr Cys Asn Val Asp His Lys Pro Ser Asn Thr Lys Val Asp Lys
                                85                  90                  95

Arg Val Glu Ser Lys Tyr Gly Pro Pro Cys Pro Ser Cys Pro Ala Pro
                            100                 105                 110

Glu Phe Leu Gly Gly Pro Ser Val Phe Leu Phe Pro Pro Lys Pro Lys
                            115                 120                 125

Asp Thr Leu Met Ile Ser Arg Thr Pro Glu Val Thr Cys Val Val Val
                            130                 135                 140

Asp Val Ser Gln Glu Asp Pro Glu Val Gln Phe Asn Trp Tyr Val Asp
            145                 150                 155                 160

Gly Val Glu Val His Asn Ala Lys Thr Lys Pro Arg Glu Glu Gln Phe
                                165                 170                 175

Asn Ser Thr Tyr Arg Val Val Ser Val Leu Thr Val Leu His Gln Asp
                            180                 185                 190

Trp Leu Asn Gly Lys Glu Tyr Lys Cys Lys Val Ser Asn Lys Gly Leu
                            195                 200                 205

Pro Ser Ser Ile Glu Lys Thr Ile Ser Lys Ala Lys Gly Gln Pro Arg
                            210                 215                 220

Glu Pro Gln Val Tyr Thr Leu Pro Pro Ser Gln Glu Glu Met Thr Lys
            225                 230                 235                 240

Asn Gln Val Ser Leu Thr Cys Leu Val Lys Gly Phe Tyr Pro Ser Asp
                            245                 250                 255

Ile Ala Val Glu Trp Glu Ser Asn Gly Gln Pro Glu Asn Asn Tyr Lys
                            260                 265                 270

Thr Thr Pro Pro Val Leu Asp Ser Asp Gly Ser Phe Phe Leu Tyr Ser
                            275                 280                 285

Arg Leu Thr Val Asp Lys Ser Arg Trp Gln Glu Gly Asn Val Phe Ser
                            290                 295                 300

Cys Ser Val Met His Glu Ala Leu His Asn His Tyr Thr Gln Lys Ser
            305                 310                 315                 320

Leu Ser Leu Ser Leu Gly Lys
                            325

<210> SEQ ID NO 6
<211> LENGTH: 329
<212> TYPE: PRT
<213> ORGANISM: Artificial Sequence
<220> FEATURE:
<223> OTHER INFORMATION: IgG1/2 constant heavy chain (CH1-hinge-CH2-CH3)

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
```

```
                35                  40                  45
Gly Val His Thr Phe Pro Ala Val Leu Gln Ser Ser Gly Leu Tyr Ser
             50                  55                  60
Leu Ser Ser Val Val Thr Val Pro Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
                100                 105                 110
Pro Ala Pro Pro Val Ala Gly Pro Ser Val Phe Leu Phe Pro Pro Lys
            115                 120                 125
Pro Lys Asp Thr Leu Met Ile Ser Arg Thr Pro Glu Val Thr Cys Val
130                 135                 140
Val Val Asp Val Ser His Glu Asp Pro Glu Val Gln Phe Asn Trp Tyr
145                 150                 155                 160
Val Asp Gly Val Glu Val His Asn Ala Lys Thr Lys Pro Arg Glu Glu
                165                 170                 175
Gln Phe Asn Ser Thr Phe Arg Val Val Ser Val Leu Thr Val Val His
            180                 185                 190
Gln Asp Trp Leu Asn Gly Lys Glu Tyr Lys Cys Lys Val Ser Asn Lys
        195                 200                 205
Gly Leu Pro Ala Pro Ile Glu Lys Thr Ile Ser Lys Thr Lys Gly Gln
    210                 215                 220
Pro Arg Glu Pro Gln Val Tyr Thr Leu Pro Pro Ser Arg Glu Glu Met
225                 230                 235                 240
Thr Lys Asn Gln Val Ser Leu Thr Cys Leu Val Lys Gly Phe Tyr Pro
                245                 250                 255
Ser Asp Ile Ala Val Glu Trp Glu Ser Asn Gly Gln Pro Glu Asn Asn
            260                 265                 270
Tyr Lys Thr Thr Pro Pro Met Leu Asp Ser Asp Gly Ser Phe Phe Leu
        275                 280                 285
Tyr Ser Lys Leu Thr Val Asp Lys Ser Arg Trp Gln Gln Gly Asn Val
    290                 295                 300
Phe Ser Cys Ser Val Met His Glu Ala Leu His Asn His Tyr Thr Gln
305                 310                 315                 320
Lys Ser Leu Ser Leu Ser Pro Gly Lys
                325

<210> SEQ ID NO 7
<211> LENGTH: 330
<212> TYPE: PRT
<213> ORGANISM: Artificial Sequence
<220> FEATURE:
<223> OTHER INFORMATION: IgG1-CH1-pI(6)

<400> SEQUENCE: 7

Ala Glu Thr Lys Gly Pro Ser Val Phe Pro Leu Ala Pro Ser Ser Glu
 1               5                  10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Glu Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
```

```
              65                  70                  75                  80
Tyr Ile Cys Asn Val Asn His Glu Pro Ser Asp Thr Glu Val Asp Lys
                    85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 8
<211> LENGTH: 107
<212> TYPE: PRT
<213> ORGANISM: Artificial Sequence
<220> FEATURE:
<223> OTHER INFORMATION: CK-pI(6)

<400> SEQUENCE: 8

Arg Thr Val Ala Ala Pro Ser Val Phe Ile Phe Pro Pro Ser Asp Glu
1               5                   10                  15
Gln Leu Glu Ser Gly Thr Ala Ser Val Val Cys Leu Leu Asn Asn Phe
                20                  25                  30
Tyr Pro Arg Glu Ala Glu Val Gln Trp Lys Val Asp Asp Ala Leu Gln
            35                  40                  45
Glu Gly Asn Ser Gln Glu Ser Val Thr Glu Gln Asp Ser Glu Asp Ser
        50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Glu Ser
                85                  90                  95
Pro Val Thr Lys Ser Phe Asn Arg Gly Glu Cys
```

<210> SEQ ID NO 9
<211> LENGTH: 123
<212> TYPE: PRT
<213> ORGANISM: Artificial Sequence
<220> FEATURE:
<223> OTHER INFORMATION: Anti-VEGF VH

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

<210> SEQ ID NO 10
<211> LENGTH: 107
<212> TYPE: PRT
<213> ORGANISM: Artificial Sequence
<220> FEATURE:
<223> OTHER INFORMATION: Anti-VEGF VL

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 11
<211> LENGTH: 453
<212> TYPE: PRT
<213> ORGANISM: Artificial Sequence
<220> FEATURE:
<223> OTHER INFORMATION: Heavy chain of XENP9493_Bevacizumab-IgG1-CH1-
      pI(6)-CK-pI(6)

<400> SEQUENCE: 11

```
Glu Val Gln Leu Val Glu Ser Gly Gly Gly Leu Val Gln Pro Gly Gly
```

-continued

```
1               5                   10                  15
Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Glu Thr Lys Gly
            115                 120                 125

Pro Ser Val Phe Pro Leu Ala Pro Ser Ser Glu Ser Thr Ser Gly Gly
            130                 135                 140

Thr Ala Leu Gly Cys Leu Val Lys Asp Tyr Phe Pro Glu Pro Val
145                 150                 155                 160

Thr Val Ser Trp Asn Ser Gly Ala Leu Glu Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Glu Pro Ser Asp Thr Glu Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

Val Met His Glu Ala Leu His Asn His Tyr Thr Gln Lys Ser Leu Ser
            435                 440                 445

Leu Ser Pro Gly Lys
        450

<210> SEQ ID NO 12
<211> LENGTH: 214
<212> TYPE: PRT
<213> ORGANISM: Artificial Sequence
<220> FEATURE:
<223> OTHER INFORMATION: Light chain of XENP9493_Bevacizumab-IgG1-CH1-
      pI(6)-CK-pI(6)

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Glu Ser Gly
        115                 120                 125

Thr Ala Ser Val Val Cys Leu Leu Asn Asn Phe Tyr Pro Arg Glu Ala
    130                 135                 140

Glu Val Gln Trp Lys Val Asp Asp Ala Leu Gln Glu Gly Asn Ser Gln
145                 150                 155                 160

Glu Ser Val Thr Glu Gln Asp Ser Glu Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Glu Ser Pro Val Thr Lys Ser
        195                 200                 205

Phe Asn Arg Gly Glu Cys
        210

<210> SEQ ID NO 13
<211> LENGTH: 329
<212> TYPE: PRT
<213> ORGANISM: Artificial Sequence
<220> FEATURE:
<223> OTHER INFORMATION: pI-iso1

<400> SEQUENCE: 13

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Pro Lys Ser Cys Asp Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
            275                 280                 285

Leu Tyr Ser Lys Leu Thr Val Asp Lys Ser Arg Trp Gln Glu Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 14
<211> LENGTH: 329
<212> TYPE: PRT
<213> ORGANISM: Artificial Sequence
<220> FEATURE:
<223> OTHER INFORMATION: pI-iso1(NF)

<400> SEQUENCE: 14

Ala Ser Thr Lys Gly Pro Ser Val Phe Pro Leu Ala Pro Ser Ser Lys
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80
```

Tyr Thr Cys Asn Val Asp His Lys Pro Ser Asn Thr Lys Val Asp Lys
            85                  90                  95

Thr Val Glu Pro Lys Ser Cys Asp Thr Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Ser Ser Gly Gln Pro Glu Asn
            260                 265                 270

Asn Tyr Asn Thr Thr Pro Pro Met Leu Asp Ser Asp Gly Ser Phe Phe
            275                 280                 285

Leu Tyr Ser Lys Leu Thr Val Asp Lys Ser Arg Trp Gln Glu Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 15
<211> LENGTH: 326
<212> TYPE: PRT
<213> ORGANISM: Artificial Sequence
<220> FEATURE:
<223> OTHER INFORMATION: pI-iso1(NF-VE)

<400> SEQUENCE: 15

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Pro Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Ser Gly Gln Pro Glu Asn Asn Tyr Asn
            260                 265                 270

Thr Thr Pro Pro Met Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly
                325

<210> SEQ ID NO 16
<211> LENGTH: 330
<212> TYPE: PRT
<213> ORGANISM: Artificial Sequence
<220> FEATURE:
<223> OTHER INFORMATION: pI-iso1(NF-VE-DEDE)

<400> SEQUENCE: 16

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Pro Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Ala Leu
    195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Ser Gly Gln Pro Glu Asn Asn Tyr Asn
        260                 265                 270

Thr Thr Pro Pro Met Leu Asp Ser Asp Gly Ser Phe Phe Leu Tyr Ser
    275                 280                 285

Lys Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Asp Glu Asp Glu
            325                 330

<210> SEQ ID NO 17
<211> LENGTH: 107
<212> TYPE: PRT
<213> ORGANISM: Artificial Sequence
<220> FEATURE:
<223> OTHER INFORMATION: CK-pI(3)

<400> SEQUENCE: 17

Arg Thr Val Ala Ala Pro Ser Val Phe Ile Phe Pro Pro Ser Asp Glu
1               5                   10                  15

Gln Leu Glu Ser Gly Thr Ala Ser Val Val Cys Leu Leu Asn Asn Phe
            20                  25                  30

Tyr Pro Arg Glu Ala Glu Val Gln Trp Lys Val Asp Asn Ala Leu Gln
        35                  40                  45

Ser Gly Asn Ser Gln Glu Ser Val Thr Glu Gln Asp Ser Glu Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
        100                 105

<210> SEQ ID NO 18
<211> LENGTH: 111
<212> TYPE: PRT
<213> ORGANISM: Artificial Sequence
<220> FEATURE:
<223> OTHER INFORMATION: CK-pI(6-DEDE)

<400> SEQUENCE: 18

Arg Thr Val Ala Ala Pro Ser Val Phe Ile Phe Pro Pro Ser Asp Glu
1               5                   10                  15
```

```
Gln Leu Glu Ser Gly Thr Ala Ser Val Cys Leu Leu Asn Asn Phe
             20                  25                  30

Tyr Pro Arg Glu Ala Glu Val Gln Trp Lys Val Asp Asp Ala Leu Gln
             35                  40                  45

Glu Gly Asn Ser Gln Glu Ser Val Thr Glu Gln Asp Ser Glu Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Glu Ser
                 85                  90                  95

Pro Val Thr Lys Ser Phe Asn Arg Gly Glu Cys Asp Glu Asp Glu
            100                 105                 110
```

<210> SEQ ID NO 19
<211> LENGTH: 325
<212> TYPE: PRT
<213> ORGANISM: Artificial Sequence
<220> FEATURE:
<223> OTHER INFORMATION: IgG-pI-Iso2

<400> SEQUENCE: 19

```
Ala Ser Thr Lys Gly Pro Ser Val Phe Pro Leu Ala Pro Ser Ser Lys
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Ser Gly Gln Pro Glu Asn Asn Tyr Asn Thr
            260                 265                 270
```

```
Thr Pro Pro Met Leu Asp Ser Asp Gly Ser Phe Phe Leu Tyr Ser Lys
            275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 20
<211> LENGTH: 325
<212> TYPE: PRT
<213> ORGANISM: Artificial Sequence
<220> FEATURE:
<223> OTHER INFORMATION: IgG-pI-Iso2-SL

<400> SEQUENCE: 20

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Ser Gly Gln Pro Glu Asn Asn Tyr Asn Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300
```

Ser Val Met His Glu Ala Leu His Asn His Tyr Thr Gln Lys Ser Leu
305                 310                 315                 320

Ser Leu Ser Pro Gly
                325

<210> SEQ ID NO 21
<211> LENGTH: 325
<212> TYPE: PRT
<213> ORGANISM: Artificial Sequence
<220> FEATURE:
<223> OTHER INFORMATION: IgG-pI-Iso2-charges-only

<400> SEQUENCE: 21

Ala Ser Thr Lys Gly Pro Ser Val Phe Pro Leu Ala Pro Ser Ser Lys
1               5                   10                  15

Ser Thr Ser Glu Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asp His Lys Pro Ser Asn Thr Lys Val Asp Lys
                85                  90                  95

Thr Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Asn Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 22
<211> LENGTH: 329
<212> TYPE: PRT
<213> ORGANISM: Artificial Sequence
<220> FEATURE:
<223> OTHER INFORMATION: IgG-pI-Iso3

<400> SEQUENCE: 22

```
Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Pro Lys Ser Cys Asp Thr Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 23
<211> LENGTH: 329
<212> TYPE: PRT
<213> ORGANISM: Artificial Sequence
<220> FEATURE:
<223> OTHER INFORMATION: IgG-pI-Iso3-SL

<400> SEQUENCE: 23

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Pro Lys Ser Cys Asp Thr Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Glu Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 24
<211> LENGTH: 329
<212> TYPE: PRT
<213> ORGANISM: Artificial Sequence
<220> FEATURE:
<223> OTHER INFORMATION: IgG-pI-Iso3-charges-only

<400> SEQUENCE: 24

Ala Ser Thr Lys Gly Pro Ser Val Phe Pro Leu Ala Pro Ser Ser Lys

```
                1               5                   10                  15
            Ser Thr Ser Glu Gly Thr Ala Ala Leu Gly Cys Leu Val Lys Asp Tyr
                            20                  25                  30

Phe Pro Glu Pro Val Thr Val Ser Trp Asn Ser Gly Ala Leu Thr Ser
                            35                  40                  45

Gly Val His Thr Phe Pro Ala Val Leu Gln Ser Ser Gly Leu Tyr Ser
                            50                  55                  60

Leu Ser Ser Val Val Thr Val Pro Ser Ser Leu Gly Thr Gln Thr
            65                  70                  75                  80

Tyr Ile Cys Asn Val Asp His Lys Pro Ser Asn Thr Lys Val Asp Lys
                            85                  90                  95

Thr Val Glu Pro Lys Ser Cys Asp Thr Thr His Thr Cys Pro Pro Cys
                            100                 105                 110

Pro Ala Pro Glu Leu Leu Gly Gly Pro Ser Val Phe Leu Phe Pro Pro
                            115                 120                 125

Lys Pro Lys Asp Thr Leu Met Ile Ser Arg Thr Pro Glu Val Thr Cys
                            130                 135                 140

Val Val Val Asp Val Ser His Glu Asp Pro Glu Val Gln Phe Asn Trp
            145                 150                 155                 160

Tyr Val Asp Gly Val Glu Val His Asn Ala Lys Thr Lys Pro Arg Glu
                            165                 170                 175

Glu Gln Tyr Asn Ser Thr Tyr Arg Val Val Ser Val Leu Thr Val Leu
                            180                 185                 190

His Gln Asp Trp Leu Asn Gly Lys Glu Tyr Lys Cys Lys Val Ser Asn
                            195                 200                 205

Lys Ala Leu Pro Ala Pro Ile Glu Lys Thr Ile Ser Lys Ala Lys Gly
                            210                 215                 220

Gln Pro Arg Glu Pro Gln Val Tyr Thr Leu Pro Pro Ser Gln Glu Glu
            225                 230                 235                 240

Met Thr Lys Asn Gln Val Ser Leu Thr Cys Leu Val Lys Gly Phe Tyr
                            245                 250                 255

Pro Ser Asp Ile Ala Val Glu Trp Glu Ser Asn Gly Gln Pro Glu Asn
                            260                 265                 270

Asn Tyr Asn Thr Thr Pro Pro Val Leu Asp Ser Asp Gly Ser Phe Phe
                            275                 280                 285

Leu Tyr Ser Lys Leu Thr Val Asp Lys Ser Arg Trp Gln Glu Gly Asn
                            290                 295                 300

Val Phe Ser Cys Ser Val Met His Glu Ala Leu His Asn His Tyr Thr
            305                 310                 315                 320

Gln Lys Ser Leu Ser Leu Ser Pro Gly
                            325

<210> SEQ ID NO 25
<211> LENGTH: 329
<212> TYPE: PRT
<213> ORGANISM: Artificial Sequence
<220> FEATURE:
<223> OTHER INFORMATION: IgG1-pI(7)

<400> SEQUENCE: 25

Ala Ser Thr Lys Gly Pro Ser Val Phe Pro Leu Ala Pro Ser Ser Glu
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
```

```
            35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Glu Pro Ser Asn Thr Glu Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Glu Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Glu Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Glu Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 26
<211> LENGTH: 329
<212> TYPE: PRT
<213> ORGANISM: Artificial Sequence
<220> FEATURE:
<223> OTHER INFORMATION: IgG1-pI(11)

<400> SEQUENCE: 26

Ala Ser Thr Lys Gly Pro Ser Val Phe Pro Leu Ala Pro Ser Ser Glu
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Glu Pro Ser Asn Thr Glu Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Glu Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Glu Cys Glu Val Ser Asn
        195                 200                 205

Glu Ala Leu Pro Ala Pro Ile Glu Glu Thr Ile Ser Lys Ala Lys Gly
    210                 215                 220

Gln Pro Arg Glu Pro Gln Val Tyr Thr Leu Pro Pro Ser Glu Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Glu Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 27
<211> LENGTH: 328
<212> TYPE: PRT
<213> ORGANISM: Artificial Sequence
<220> FEATURE:
<223> OTHER INFORMATION: IgG1/2-pI(7)

<400> SEQUENCE: 27

Ala Ser Thr Lys Gly Pro Ser Val Phe Pro Leu Ala Pro Ser Ser Glu
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Glu Pro Ser Asn Thr Glu Val Asp Lys
                85                  90                  95

Lys Val Glu Pro Lys Ser Cys Asp Lys Thr His Thr Cys Pro Pro Cys
```

-continued

```
                100                 105                 110
Pro Ala Pro Pro Val Ala Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Glu Phe Asn Trp Tyr
145                 150                 155                 160

Val Asp Gly Val Glu Val His Asn Ala Lys Thr Lys Pro Arg Glu Glu
            165                 170                 175

Gln Phe Asn Ser Thr Phe Arg Val Val Ser Val Leu Thr Val Val His
        180                 185                 190

Gln Asp Trp Leu Asn Gly Lys Glu Tyr Lys Cys Lys Val Ser Asn Lys
    195                 200                 205

Gly Leu Pro Ala Pro Ile Glu Lys Thr Ile Ser Lys Thr Lys Gly Gln
210                 215                 220

Pro Arg Glu Pro Gln Val Tyr Thr Leu Pro Pro Ser Glu Glu Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
        260                 265                 270

Tyr Glu Thr Thr Pro Pro Met Leu Asp Ser Asp Gly Ser Phe Phe Leu
    275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 28
<211> LENGTH: 328
<212> TYPE: PRT
<213> ORGANISM: Artificial Sequence
<220> FEATURE:
<223> OTHER INFORMATION: IgG1/2-pI(11)

<400> SEQUENCE: 28

Ala Ser Thr Lys Gly Pro Ser Val Phe Pro Leu Ala Pro Ser Ser Glu
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Glu Pro Ser Asn Thr Glu Val Asp Lys
            85                  90                  95

Lys Val Glu Pro Lys Ser Cys Asp Lys Thr His Thr Cys Pro Pro Cys
        100                 105                 110

Pro Ala Pro Pro Val Ala Gly Pro Ser Val Phe Leu Phe Pro Pro Lys
    115                 120                 125

Pro Lys Asp Thr Leu Met Ile Ser Arg Thr Pro Glu Val Thr Cys Val
```

```
                130                 135                 140
Val Val Asp Val Ser His Glu Asp Pro Glu Val Glu Phe Asn Trp Tyr
145                 150                 155                 160

Val Asp Gly Val Glu Val His Asn Ala Lys Thr Lys Pro Arg Glu Glu
            165                 170                 175

Gln Phe Asn Ser Thr Phe Arg Val Val Ser Val Leu Thr Val Val His
        180                 185                 190

Gln Asp Trp Leu Asn Gly Lys Glu Tyr Glu Cys Glu Val Ser Asn Glu
            195                 200                 205

Gly Leu Pro Ala Pro Ile Glu Glu Thr Ile Ser Lys Thr Lys Gly Gln
        210                 215                 220

Pro Arg Glu Pro Gln Val Tyr Thr Leu Pro Pro Ser Glu Glu Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
        260                 265                 270

Tyr Glu Thr Thr Pro Pro Met Leu Asp Ser Asp Gly Ser Phe Phe Leu
    275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 29
<211> LENGTH: 107
<212> TYPE: PRT
<213> ORGANISM: Artificial Sequence
<220> FEATURE:
<223> OTHER INFORMATION: CK-pI(4)

<400> SEQUENCE: 29

Arg Thr Val Ala Ala Pro Ser Val Phe Ile Phe Pro Pro Ser Asp Glu
1               5                   10                  15

Gln Leu Glu Ser Gly Thr Ala Ser Val Val Cys Leu Leu Asn Asn Phe
            20                  25                  30

Tyr Pro Arg Glu Ala Glu Val Gln Trp Lys Val Asp Asn Ala Leu Gln
        35                  40                  45

Ser Gly Asn Ser Gln Glu Ser Val Thr Glu Gln Asp Ser Glu Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Glu Ser Phe Asn Arg Gly Glu Cys
            100                 105

<210> SEQ ID NO 30
<211> LENGTH: 107
<212> TYPE: PRT
<213> ORGANISM: Artificial Sequence
<220> FEATURE:
<223> OTHER INFORMATION: CK-Iso(3)

<400> SEQUENCE: 30
```

Gln Thr Val Ala Ala Pro Ser Val Phe Ile Phe Pro Pro Ser Asp Glu
1               5                   10                  15

Gln Leu Gln Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Glu Gly Leu Ser Ser
                85                  90                  95

Pro Val Thr Lys Ser Phe Asn Arg Gly Glu Cys
                100                 105

<210> SEQ ID NO 31
<211> LENGTH: 107
<212> TYPE: PRT
<213> ORGANISM: Artificial Sequence
<220> FEATURE:
<223> OTHER INFORMATION: CK-Iso(4)

<400> SEQUENCE: 31

Gln Thr Val Ala Ala Pro Ser Val Phe Ile Phe Pro Pro Ser Asp Glu
1               5                   10                  15

Gln Leu Gln Ser Gly Thr Ala Ser Val Val Cys Leu Leu Asn Asn Phe
            20                  25                  30

Tyr Pro Arg Glu Ala Thr Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Glu Gly Leu Ser Ser
                85                  90                  95

Pro Val Thr Lys Ser Phe Asn Arg Gly Glu Cys
                100                 105

<210> SEQ ID NO 32
<211> LENGTH: 107
<212> TYPE: PRT
<213> ORGANISM: Artificial Sequence
<220> FEATURE:
<223> OTHER INFORMATION: CK-Iso(5)

<400> SEQUENCE: 32

Gln Thr Val Ala Ala Pro Ser Val Phe Ile Phe Pro Pro Ser Asp Glu
1               5                   10                  15

Glu Leu Gln Ser Gly Thr Ala Ser Val Val Cys Leu Leu Asn Asn Phe
            20                  25                  30

Tyr Pro Arg Glu Ala Thr Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Glu Gly Leu Ser Ser
                85                  90                  95

```
Pro Val Thr Lys Ser Phe Asn Arg Gly Glu Cys
            100                 105
```

<210> SEQ ID NO 33
<211> LENGTH: 107
<212> TYPE: PRT
<213> ORGANISM: Artificial Sequence
<220> FEATURE:
<223> OTHER INFORMATION: CK-Iso(6)

<400> SEQUENCE: 33

```
Gln Thr Val Ala Ala Pro Ser Val Phe Ile Phe Pro Pro Ser Asp Glu
1               5                   10                  15

Glu Leu Gln Ser Gly Thr Ala Ser Val Val Cys Leu Leu Asn Asp Phe
            20                  25                  30

Tyr Pro Arg Glu Ala Thr Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Glu Gly Leu Ser Ser
                85                  90                  95

Pro Val Thr Lys Ser Phe Asn Arg Gly Glu Cys
            100                 105
```

<210> SEQ ID NO 34
<211> LENGTH: 453
<212> TYPE: PRT
<213> ORGANISM: Artificial Sequence
<220> FEATURE:
<223> OTHER INFORMATION: Heavy Chain 1

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
                180               185                 190
Thr Val Pro Ser Ser Leu Gly Thr Gln Thr Tyr Ile Cys Asn Val
            195                 200                 205
Asn His Lys Pro Ser Asn Thr Lys Val Asp Lys Val Glu Pro Lys
            210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
        290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
            355                 360                 365
Val Ser Leu Thr Cys Leu Val Lys Gly Phe Tyr Pro Ser Asp Ile Ala
        370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
            435                 440                 445
Leu Ser Pro Gly Lys
        450

<210> SEQ ID NO 35
<211> LENGTH: 452
<212> TYPE: PRT
<213> ORGANISM: Artificial Sequence
<220> FEATURE:
<223> OTHER INFORMATION: Heavy Chain 2

<400> SEQUENCE: 35

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn Tyr
            20                  25                  30
Gly Met Asn Trp Val Arg Gln Ala Pro Gly Lys Gly Leu Glu Trp Val
        35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
```

```
                        85                  90                  95
Ala Lys Tyr Pro His Tyr Gly Ser Ser His Trp Tyr Phe Asp Val
                100                 105                 110
Trp Gly Gln Gly Thr Leu Val Thr Val Ser Ser Ala Ser Thr Lys Gly
                115                 120                 125
Pro Ser Val Phe Pro Leu Ala Pro Ser Ser Lys Ser Thr Ser Gly Gly
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Glu Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Leu Gly Thr Gln Thr Tyr Ile Cys Asn Val
            195                 200                 205
Asn His Lys Pro Ser Asp Thr Glu Val Asp Lys Lys Val Glu Pro Lys
        210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Gln Phe Asn Trp Tyr Val Asp Gly Val
            275                 280                 285
Glu Val His Asn Ala Lys Thr Lys Pro Arg Glu Glu Gln Tyr Asn Ser
        290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Gln Glu Glu Met Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Ser Gly Gln Pro Glu Asn Asn Tyr Asn Thr Thr
385                 390                 395                 400
Pro Pro Met Leu Asp Ser Asp Gly Ser Phe Phe Leu Tyr Ser Lys Leu
                405                 410                 415
Thr Val Asp Lys Ser Arg Trp Gln Glu Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly
    450

<210> SEQ ID NO 36
<211> LENGTH: 214
<212> TYPE: PRT
<213> ORGANISM: Artificial Sequence
<220> FEATURE:
<223> OTHER INFORMATION: Light Chain
```

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 37
<211> LENGTH: 599
<212> TYPE: PRT
<213> ORGANISM: Artificial Sequence
<220> FEATURE:
<223> OTHER INFORMATION: Heavy Chain 1 of anti-HER2 x anti-CD16 mAb-Fv

<400> SEQUENCE: 37

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
```

-continued

```
            130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
                340                 345                 350

Thr Leu Pro Pro Ser Arg Glu Met Thr Lys Asn Gln Val His Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys Ser Ser Asp Lys Thr His Thr Ser Pro Pro Ser Pro Gly Gly
        450                 455                 460

Gly Gly Ser Gly Gly Gly Gly Ser Gly Gly Gly Gly Ser Gly Gly Gly
465                 470                 475                 480

Gly Gln Val Thr Leu Lys Glu Ser Gly Pro Gly Ile Leu Gln Pro Ser
                485                 490                 495

Gln Thr Leu Ser Leu Thr Cys Ser Phe Ser Gly Phe Ser Leu Arg Thr
            500                 505                 510

Ser Gly Met Gly Val Gly Trp Ile Arg Gln Pro Ser Gly Lys Gly Leu
            515                 520                 525

Glu Trp Leu Ala His Ile Trp Trp Asp Asp Asp Lys Arg Tyr Asn Pro
        530                 535                 540

Ala Leu Lys Ser Arg Leu Thr Ile Ser Lys Asp Thr Ser Ser Asn Gln
545                 550                 555                 560
```

-continued

```
Val Phe Leu Lys Ile Ala Ser Val Asp Thr Ala Asp Thr Ala Thr Tyr
                565                 570                 575

Tyr Cys Ala Gln Ile Asn Pro Ala Trp Phe Ala Tyr Trp Gly Gln Gly
                580                 585                 590

Thr Leu Val Thr Val Ser Ala
        595

<210> SEQ ID NO 38
<211> LENGTH: 592
<212> TYPE: PRT
<213> ORGANISM: Artificial Sequence
<220> FEATURE:
<223> OTHER INFORMATION: Heavy Chain 2 of anti-HER2 x anti-CD16 mAb-Fv

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Glu Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asp Thr Glu Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

Glu Tyr Lys Cys Lys Val Ser Asn Lys Ala Leu Pro Ala Pro Ile Glu
              325                 330                 335

Lys Thr Ile Ser Lys Ala Lys Gly Gln Pro Arg Glu Pro Gln Val Thr
          340                 345                 350

Thr Leu Pro Pro Cys Gln Glu Glu Met Thr Lys Asn Gln Val Ser Leu
      355                 360                 365

Thr Cys Leu Val Lys Gly Phe Tyr Pro Ser Asp Ile Ala Val Glu Trp
  370                 375                 380

Glu Ser Ser Gly Gln Pro Glu Asn Asn Tyr Asn Thr Phe Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Ser Asp Lys Thr His Thr Ser Pro Pro Ser Pro Gly Gly
    450                 455                 460

Gly Gly Ser Gly Gly Gly Ser Gly Gly Gly Ser Gly Gly Gly
465                 470                 475                 480

Gly Asp Ile Val Leu Thr Gln Ser Pro Ala Ser Leu Ala Val Ser Leu
                485                 490                 495

Gly Gln Arg Ala Thr Ile Ser Cys Lys Ala Ser Gln Ser Val Asp Phe
            500                 505                 510

Asp Gly Asp Ser Phe Met Asn Trp Tyr Gln Gln Lys Pro Gly Gln Pro
        515                 520                 525

Pro Lys Leu Leu Ile Tyr Thr Thr Ser Asn Leu Glu Ser Gly Ile Pro
    530                 535                 540

Ala Arg Phe Ser Ala Ser Gly Ser Gly Thr Asp Phe Thr Leu Asn Ile
545                 550                 555                 560

His Pro Val Glu Glu Glu Asp Thr Ala Thr Tyr Tyr Cys Gln Gln Ser
                565                 570                 575

Asn Glu Asp Pro Tyr Thr Phe Gly Gly Gly Thr Lys Leu Glu Leu Lys
            580                 585                 590

<210> SEQ ID NO 39
<211> LENGTH: 214
<212> TYPE: PRT
<213> ORGANISM: Artificial Sequence
<220> FEATURE:
<223> OTHER INFORMATION: Light Chain of anti-HER2 x anti-CD16 mAb-Fv

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 40
<211> LENGTH: 600
<212> TYPE: PRT
<213> ORGANISM: Artificial Sequence
<220> FEATURE:
<223> OTHER INFORMATION: Heavy Chain 1 of anti-CD19 x anti-CD16 mAb-Fv

<400> SEQUENCE: 40

Glu Val Gln Leu Val Glu Ser Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Tyr Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Glu Glu Met Thr Lys Asn Gln Val His
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Ala Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Ser Ser Asp Lys Thr His Thr Ser Pro Pro Ser Pro Gly
            450                 455                 460

Gly Gly Gly Ser Gly Gly Gly Ser Gly Gly Gly Ser Gly Gly
465                 470                 475                 480

Gly Gly Gln Val Thr Leu Lys Glu Ser Gly Pro Gly Ile Leu Gln Pro
                485                 490                 495

Ser Gln Thr Leu Ser Leu Thr Cys Ser Phe Ser Gly Phe Ser Leu Arg
            500                 505                 510

Thr Ser Gly Met Gly Val Gly Trp Ile Arg Gln Pro Ser Gly Lys Gly
            515                 520                 525

Leu Glu Trp Leu Ala His Ile Trp Trp Asp Asp Asp Lys Arg Tyr Asn
            530                 535                 540

Pro Ala Leu Lys Ser Arg Leu Thr Ile Ser Lys Asp Thr Ser Ser Asn
545                 550                 555                 560

Gln Val Phe Leu Lys Ile Ala Ser Val Asp Thr Ala Asp Thr Ala Thr
                565                 570                 575

Tyr Tyr Cys Ala Gln Ile Asn Pro Ala Trp Phe Ala Tyr Trp Gly Gln
            580                 585                 590

Gly Thr Leu Val Thr Val Ser Ala
            595                 600

<210> SEQ ID NO 41
<211> LENGTH: 593
<212> TYPE: PRT
<213> ORGANISM: Artificial Sequence
<220> FEATURE:
<223> OTHER INFORMATION: Heavy Chain 2 of anti-CD19 x anti-CD16 mAb-Fv

<400> SEQUENCE: 41

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Thr Arg Val Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Glu Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asp Thr Glu Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Thr Thr Leu Pro Pro Cys Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Ser Gly Gln Pro Glu Asn Asn Tyr Asn Thr Phe Pro Pro
385                 390                 395                 400

Met Leu Asp Ser Asp Gly Ser Phe Phe Leu Tyr Ser Lys Leu Thr Val
                405                 410                 415
```

```
Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Ser Ser Asp Lys Thr His Thr Ser Pro Pro Ser Pro Gly
            450                 455                 460

Gly Gly Gly Ser Gly Gly Gly Ser Gly Gly Gly Ser Gly Gly
465                 470                 475                 480

Gly Gly Asp Ile Val Leu Thr Gln Ser Pro Ala Ser Leu Ala Val Ser
            485                 490                 495

Leu Gly Gln Arg Ala Thr Ile Ser Cys Lys Ala Ser Gln Ser Val Asp
            500                 505                 510

Phe Asp Gly Asp Ser Phe Met Asn Trp Tyr Gln Gln Lys Pro Gly Gln
            515                 520                 525

Pro Pro Lys Leu Leu Ile Tyr Thr Thr Ser Asn Leu Glu Ser Gly Ile
            530                 535                 540

Pro Ala Arg Phe Ser Ala Ser Gly Ser Gly Thr Asp Phe Thr Leu Asn
545                 550                 555                 560

Ile His Pro Val Glu Glu Glu Asp Thr Ala Thr Tyr Tyr Cys Gln Gln
            565                 570                 575

Ser Asn Glu Asp Pro Tyr Thr Phe Gly Gly Gly Thr Lys Leu Glu Leu
            580                 585                 590

Lys

<210> SEQ ID NO 42
<211> LENGTH: 219
<212> TYPE: PRT
<213> ORGANISM: Artificial Sequence
<220> FEATURE:
<223> OTHER INFORMATION: Light Chain of anti-CD19 x anti-CD16 mAb-Fv

<400> SEQUENCE: 42

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Asn Ser Gly Val Pro
            50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
            85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
```

```
              180                 185                 190
Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 43
<211> LENGTH: 600
<212> TYPE: PRT
<213> ORGANISM: Artificial Sequence
<220> FEATURE:
<223> OTHER INFORMATION: Heavy Chain 1 of anti-CD19 x anti-CD32b mAb-Fv

<400> SEQUENCE: 43

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
                325                 330                 335
Glu Lys Thr Ile Ser Lys Ala Lys Gly Gln Pro Arg Glu Pro Gln Val
            340                 345                 350
Cys Thr Leu Pro Pro Ser Arg Glu Glu Met Thr Lys Asn Gln Val His
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Ala Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys Ser Ser Asp Lys Thr His Thr Ser Pro Pro Ser Pro Gly
    450                 455                 460
Gly Gly Gly Ser Gly Gly Gly Gly Ser Gly Gly Gly Gly Ser Gly Gly
465                 470                 475                 480
Gly Gly Glu Val Gln Leu Val Glu Ser Gly Gly Gly Leu Val Ser Pro
                485                 490                 495
Gly Gly Ser Leu Lys Leu Ser Cys Val Ala Ser Gly Phe Ala Phe Ser
            500                 505                 510
Ser Tyr Asp Met Ser Trp Val Arg Gln Thr Pro Glu Lys Arg Leu Glu
        515                 520                 525
Trp Val Ala Lys Ile Asn Ser Ala Gly Gly Arg Thr Asn Tyr Pro Asp
    530                 535                 540
Thr Val Lys Gly Arg Phe Thr Ile Ser Arg Asp Asn Ala Glu Asn Thr
545                 550                 555                 560
Leu Tyr Leu Gln Met Ser Ser Leu Lys Ser Glu Asp Thr Ala Met Tyr
                565                 570                 575
Tyr Cys Ala Gly His Ser Tyr Asp Tyr Pro Phe Thr Tyr Trp Gly Gln
            580                 585                 590
Gly Thr Leu Val Thr Val Ser Ala
        595                 600

<210> SEQ ID NO 44
<211> LENGTH: 589
<212> TYPE: PRT
<213> ORGANISM: Artificial Sequence
<220> FEATURE:
<223> OTHER INFORMATION: Heavy Chain 2 of anti-CD19 x anti-CD32b mAb-Fv

<400> SEQUENCE: 44

Glu Val Gln Leu Val Glu Ser Gly Gly Gly Leu Val Lys Pro Gly Gly
1               5                   10                  15
Ser Leu Lys Leu Ser Cys Ala Ala Ser Gly Tyr Thr Phe Thr Ser Tyr
            20                  25                  30
Val Met His Trp Val Arg Gln Ala Pro Gly Lys Gly Leu Glu Trp Ile
        35                  40                  45
Gly Tyr Ile Asn Pro Tyr Asn Asp Gly Thr Lys Tyr Asn Glu Lys Phe
    50                  55                  60
Gln Gly Arg Val Thr Ile Ser Ser Asp Lys Ser Ile Ser Thr Ala Tyr
65                  70                  75                  80
Met Glu Leu Ser Ser Leu Arg Ser Glu Asp Thr Ala Met Tyr Tyr Cys
```

-continued

```
                85                  90                  95
Ala Arg Gly Thr Tyr Tyr Tyr Gly Thr Arg Val Phe Asp Tyr Trp Gly
                    100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Glu Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asp Thr Glu Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Thr Thr Leu Pro Pro Cys Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Ser Gly Gln Pro Glu Asn Asn Tyr Asn Thr Phe Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Ser Ser Asp Lys Thr His Thr Ser Pro Pro Ser Pro Gly
    450                 455                 460

Gly Gly Gly Ser Gly Gly Gly Ser Gly Gly Gly Gly Ser Gly Gly Gly
465                 470                 475                 480

Gly Gly Asp Val Val Leu Thr Gln Ser Pro Ala Thr Leu Ser Val Thr
                485                 490                 495

Pro Gly Asp Ser Val Ser Leu Ser Cys Arg Ala Ser Gln Gly Ile Ser
            500                 505                 510
```

Asn Asn Leu His Trp Tyr Gln Gln Lys Ser His Glu Ser Pro Arg Leu
            515                 520                 525

Leu Ile Lys Tyr Ala Ser Gln Ser Ile Ser Gly Ile Pro Ser Arg Phe
        530                 535                 540

Ser Gly Ser Gly Ser Gly Thr Asp Phe Thr Leu Ser Ile Asn Ser Val
545                 550                 555                 560

Glu Thr Glu Asp Phe Gly Met Tyr Phe Cys Gln Gln Ser Asp Ser Trp
                565                 570                 575

Pro His Thr Phe Gly Gly Gly Thr Lys Leu Glu Ile Lys
            580                 585

<210> SEQ ID NO 45
<211> LENGTH: 219
<212> TYPE: PRT
<213> ORGANISM: Artificial Sequence
<220> FEATURE:
<223> OTHER INFORMATION: Light Chain of anti-CD19 x anti-CD32b mAb-Fv

<400> SEQUENCE: 45

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 46
<211> LENGTH: 592
<212> TYPE: PRT
<213> ORGANISM: Artificial Sequence
<220> FEATURE:
<223> OTHER INFORMATION: Heavy Chain 1 of anti-CD40 x anti-CD32b mAb-Fv

<400> SEQUENCE: 46

Gln Val Lys Leu Glu Glu Ser Gly Pro Gly Leu Val Ala Pro Ser Gln

-continued

```
1               5                   10                  15
Ser Leu Ser Ile Thr Cys Thr Val Ser Gly Phe Ser Leu Ser Arg Tyr
                20                  25                  30

Ser Val Tyr Trp Val Arg Gln Pro Gly Lys Gly Leu Glu Trp Leu
        35                  40                  45

Gly Met Met Trp Gly Gly Ser Thr Asp Tyr Asn Ser Ala Leu Lys
    50                  55                  60

Ser Arg Leu Ser Ile Ser Lys Asp Thr Ser Lys Ser Gln Val Phe Leu
65                  70                  75                  80

Lys Met Asn Ser Leu Gln Thr Asp Asp Thr Ala Met Tyr Tyr Cys Val
                85                  90                  95

Arg Thr Asp Gly Asp Tyr Trp Gly Gln Gly Thr Ser Val Thr Val Ser
                100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
                180                 185                 190

Thr Tyr Ile Cys Asn Val Asn His Lys Pro Ser Asn Thr Lys Val Asp
            195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Cys Thr Leu Pro Pro Ser Arg Glu
            340                 345                 350

Glu Met Thr Lys Asn Gln Val His Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Ala Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430
```

-continued

```
Thr Gln Lys Ser Leu Ser Leu Ser Pro Gly Lys Ser Ser Asp Lys Thr
        435                 440                 445
His Thr Ser Pro Pro Ser Pro Gly Gly Gly Ser Gly Gly Gly Gly
    450                 455                 460
Ser Gly Gly Gly Ser Gly Gly Gly Gly Glu Val Gln Leu Val Glu
465                 470                 475                 480
Ser Gly Gly Gly Leu Val Ser Pro Gly Gly Ser Leu Lys Leu Ser Cys
                485                 490                 495
Val Ala Ser Gly Phe Ala Phe Ser Ser Tyr Asp Met Ser Trp Val Arg
                500                 505                 510
Gln Thr Pro Glu Lys Arg Leu Glu Trp Val Ala Lys Ile Asn Ser Ala
                515                 520                 525
Gly Gly Arg Thr Asn Tyr Pro Asp Thr Val Lys Gly Arg Phe Thr Ile
            530                 535                 540
Ser Arg Asp Asn Ala Glu Asn Thr Leu Tyr Leu Gln Met Ser Ser Leu
545                 550                 555                 560
Lys Ser Glu Asp Thr Ala Met Tyr Tyr Cys Ala Gly His Ser Tyr Asp
                565                 570                 575
Tyr Pro Phe Thr Tyr Trp Gly Gln Gly Thr Leu Val Thr Val Ser Ala
                580                 585                 590

<210> SEQ ID NO 47
<211> LENGTH: 581
<212> TYPE: PRT
<213> ORGANISM: Artificial Sequence
<220> FEATURE:
<223> OTHER INFORMATION: Heavy Chain 2 of anti-CD40 x anti-CD32b mAb-Fv

<400> SEQUENCE: 47

Gln Val Lys Leu Glu Glu Ser Gly Pro Gly Leu Val Ala Pro Ser Gln
1               5                   10                  15
Ser Leu Ser Ile Thr Cys Thr Val Ser Gly Phe Ser Leu Ser Arg Tyr
            20                  25                  30
Ser Val Tyr Trp Val Arg Gln Pro Pro Gly Lys Gly Leu Glu Trp Leu
        35                  40                  45
Gly Met Met Trp Gly Gly Gly Ser Thr Asp Tyr Asn Ser Ala Leu Lys
    50                  55                  60
Ser Arg Leu Ser Ile Ser Lys Asp Thr Ser Lys Ser Gln Val Phe Leu
65                  70                  75                  80
Lys Met Asn Ser Leu Gln Thr Asp Asp Thr Ala Met Tyr Tyr Cys Val
                85                  90                  95
Arg Thr Asp Gly Asp Tyr Trp Gly Gln Gly Thr Ser Val Thr Val Ser
            100                 105                 110
Ser Ala Ser Thr Lys Gly Pro Ser Val Phe Pro Leu Ala Pro Ser Ser
        115                 120                 125
Lys Ser Thr Ser Gly Gly Thr Ala Ala Leu Gly Cys Leu Val Lys Asp
    130                 135                 140
Tyr Phe Pro Glu Pro Val Thr Val Ser Trp Asn Ser Gly Ala Leu Glu
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Gln
            180                 185                 190
Thr Tyr Ile Cys Asn Val Asn His Lys Pro Ser Asp Thr Glu Val Asp
        195                 200                 205
```

Lys Lys Val Glu Pro Lys Ser Cys Asp Lys Thr His Thr Cys Pro Pro
            210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Thr Thr Leu Pro Pro Cys Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Ser Gly Gln Pro Glu
370                 375                 380

Asn Asn Tyr Asn Thr Phe Pro Pro Met Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys Ser Ser Asp Lys Thr
        435                 440                 445

His Thr Ser Pro Pro Ser Pro Gly Gly Gly Ser Gly Gly Gly
450                 455                 460

Ser Gly Gly Gly Ser Gly Gly Gly Asp Val Val Leu Thr Gln
465                 470                 475                 480

Ser Pro Ala Thr Leu Ser Val Thr Pro Gly Asp Ser Val Ser Leu Ser
                485                 490                 495

Cys Arg Ala Ser Gln Gly Ile Ser Asn Asn Leu His Trp Tyr Gln Gln
            500                 505                 510

Lys Ser His Glu Ser Pro Arg Leu Leu Ile Lys Tyr Ala Ser Gln Ser
        515                 520                 525

Ile Ser Gly Ile Pro Ser Arg Phe Ser Gly Ser Gly Ser Gly Thr Asp
530                 535                 540

Phe Thr Leu Ser Ile Asn Ser Val Glu Thr Glu Asp Phe Gly Met Tyr
545                 550                 555                 560

Phe Cys Gln Gln Ser Asp Ser Trp Pro His Thr Phe Gly Gly Gly Thr
                565                 570                 575

Lys Leu Glu Ile Lys
            580

<210> SEQ ID NO 48
<211> LENGTH: 219
<212> TYPE: PRT
<213> ORGANISM: Artificial Sequence
<220> FEATURE:

<223> OTHER INFORMATION: Light Chain of anti-CD40 x anti-CD32b mAb-Fv

<400> SEQUENCE: 48

```
Glu Leu Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val Asn Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 49
<211> LENGTH: 600
<212> TYPE: PRT
<213> ORGANISM: Artificial Sequence
<220> FEATURE:
<223> OTHER INFORMATION: Heavy Chain 1 of anti-HER2 x anti-CD3 mAb-Fv

<400> SEQUENCE: 49

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Glu Glu Met Thr Lys Asn Gln Val His Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Ser Asp Lys Thr His Thr Ser Pro Pro Ser Pro Gly Gly
    450                 455                 460

Gly Gly Ser Gly Gly Gly Ser Gly Gly Gly Ser Gly Gly Gly
465                 470                 475                 480

Gly Gln Val Gln Leu Val Gln Ser Gly Ala Glu Val Lys Lys Pro Gly
                485                 490                 495

Ala Ser Val Lys Val Ser Cys Lys Ala Ser Gly Tyr Thr Phe Thr Arg
            500                 505                 510

Tyr Thr Met His Trp Val Arg Gln Ala Pro Gly Gln Gly Leu Glu Trp
        515                 520                 525

Met Gly Tyr Ile Asn Pro Ser Arg Gly Tyr Thr Asn Tyr Asn Gln Lys
    530                 535                 540
```

```
Phe Gln Gly Arg Val Thr Met Thr Thr Asp Lys Ser Thr Ser Thr Ala
545                 550                 555                 560

Tyr Met Glu Leu Ser Ser Leu Arg Ser Glu Asp Thr Ala Val Tyr Tyr
                565                 570                 575

Cys Ala Arg Tyr Tyr Asp Asp His Tyr Ser Leu Asp Tyr Trp Gly Gln
            580                 585                 590

Gly Thr Thr Val Thr Val Ser Ser
            595                 600

<210> SEQ ID NO 50
<211> LENGTH: 330
<212> TYPE: PRT
<213> ORGANISM: Artificial Sequence
<220> FEATURE:
<223> OTHER INFORMATION: IgG1-434S

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Ser His Tyr Thr
305                 310                 315                 320

Gln Lys Ser Leu Ser Leu Ser Pro Gly Lys
                325                 330

<210> SEQ ID NO 51
<211> LENGTH: 326
<212> TYPE: PRT
<213> ORGANISM: Artificial Sequence
<220> FEATURE:
<223> OTHER INFORMATION: IgG2-434S

<400> SEQUENCE: 51

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Ser His Tyr Thr Gln Lys Ser Leu
305                 310                 315                 320

Ser Leu Ser Pro Gly Lys
                325
```

<210> SEQ ID NO 52
<211> LENGTH: 330
<212> TYPE: PRT
<213> ORGANISM: Artificial Sequence
<220> FEATURE:
<223> OTHER INFORMATION: IgG1-CH1-pI(6)-434S

<400> SEQUENCE: 52

```
Ala Glu Thr Lys Gly Pro Ser Val Phe Pro Leu Ala Pro Ser Ser Glu
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Glu Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Glu Pro Ser Asp Thr Glu Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Ser His Tyr Thr
305                 310                 315                 320

Gln Lys Ser Leu Ser Leu Ser Pro Gly Lys
                325                 330
```

<210> SEQ ID NO 53
<211> LENGTH: 330
<212> TYPE: PRT
<213> ORGANISM: Artificial Sequence
<220> FEATURE:

<223> OTHER INFORMATION: IgG1-CH1-pI(6)-428L/434S

<400> SEQUENCE: 53

```
Ala Glu Thr Lys Gly Pro Ser Val Phe Pro Leu Ala Pro Ser Ser Glu
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Glu Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Glu Pro Ser Asp Thr Glu Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
                325                 330
```

<210> SEQ ID NO 54
<211> LENGTH: 107
<212> TYPE: PRT
<213> ORGANISM: Artificial Sequence
<220> FEATURE:
<223> OTHER INFORMATION: CK-pI(3)

<400> SEQUENCE: 54

```
Arg Thr Val Ala Ala Pro Ser Val Phe Ile Phe Pro Pro Ser Asp Glu
1               5                   10                  15
```

Gln Leu Glu Ser Gly Thr Ala Ser Val Val Cys Leu Leu Asn Asn Phe
              20                  25                  30

Tyr Pro Arg Glu Ala Glu Val Gln Trp Lys Val Asp Asn Ala Leu Gln
              35                  40                  45

Ser Gly Asn Ser Gln Glu Ser Val Thr Glu Gln Asp Ser Glu Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 55
<211> LENGTH: 330
<212> TYPE: PRT
<213> ORGANISM: Artificial Sequence
<220> FEATURE:
<223> OTHER INFORMATION: IgG1-pI(6)-Neutral-to-DE

<400> SEQUENCE: 55

Ala Glu Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
              20                  25                  30

Phe Pro Glu Pro Val Thr Val Ser Trp Asn Ser Gly Ala Leu Glu Ser
              35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asp Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 56
<211> LENGTH: 330
<212> TYPE: PRT
<213> ORGANISM: Artificial Sequence
<220> FEATURE:
<223> OTHER INFORMATION: IgG1-pI(6)-KR-to-Neutral

<400> SEQUENCE: 56

Ala Ser Thr Lys Gly Pro Ser Val Phe Pro Leu Ala Pro Ser Ser Gln
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Gln Pro Ser Asn Thr Gln Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 57
<211> LENGTH: 330
<212> TYPE: PRT
<213> ORGANISM: Artificial Sequence
<220> FEATURE:
<223> OTHER INFORMATION: IgG1-pI(6)-KR-to-DE

<400> SEQUENCE: 57

Ala Ser Thr Lys Gly Pro Ser Val Phe Pro Leu Ala Pro Ser Ser Glu
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Glu Pro Ser Asn Thr Glu Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

-continued

```
<210> SEQ ID NO 58
<211> LENGTH: 107
<212> TYPE: PRT
<213> ORGANISM: Artificial Sequence
<220> FEATURE:
<223> OTHER INFORMATION: CK-N152D S156E S202E

<400> SEQUENCE: 58
```

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asp Ala Leu Gln
        35                  40                  45

Glu Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Glu Ser
                85                  90                  95

Pro Val Thr Lys Ser Phe Asn Arg Gly Glu Cys
            100                 105

```
<210> SEQ ID NO 59
<211> LENGTH: 107
<212> TYPE: PRT
<213> ORGANISM: Artificial Sequence
<220> FEATURE:
<223> OTHER INFORMATION: CK-K126Q K145Q K169Q

<400> SEQUENCE: 59
```

Arg Thr Val Ala Ala Pro Ser Val Phe Ile Phe Pro Pro Ser Asp Glu
1               5                   10                  15

Gln Leu Gln Ser Gly Thr Ala Ser Val Val Cys Leu Leu Asn Asn Phe
            20                  25                  30

Tyr Pro Arg Glu Ala Gln Val Gln Trp Lys Val Asp Asn Ala Leu Gln
        35                  40                  45

Ser Gly Asn Ser Gln Glu Ser Val Thr Glu Gln Asp Ser Gln Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

```
<210> SEQ ID NO 60
<211> LENGTH: 107
<212> TYPE: PRT
<213> ORGANISM: Artificial Sequence
<220> FEATURE:
<223> OTHER INFORMATION: CK-K126E K145E K169E

<400> SEQUENCE: 60
```

Arg Thr Val Ala Ala Pro Ser Val Phe Ile Phe Pro Pro Ser Asp Glu
1               5                   10                  15

Gln Leu Glu Ser Gly Thr Ala Ser Val Val Cys Leu Leu Asn Asn Phe
            20                  25                  30

-continued

Tyr Pro Arg Glu Ala Glu Val Gln Trp Lys Val Asp Asn Ala Leu Gln
             35                  40                  45

Ser Gly Asn Ser Gln Glu Ser Val Thr Glu Gln Asp Ser Glu Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 61
<211> LENGTH: 325
<212> TYPE: PRT
<213> ORGANISM: Artificial Sequence
<220> FEATURE:
<223> OTHER INFORMATION: IgG-pI-Iso2-434S

<400> SEQUENCE: 61

Ala Ser Thr Lys Gly Pro Ser Val Phe Pro Leu Ala Pro Ser Ser Lys
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Ser Gly Gln Pro Glu Asn Asn Tyr Asn Thr
            260                 265                 270

Thr Pro Pro Met Leu Asp Ser Asp Gly Ser Phe Phe Leu Tyr Ser Lys
        275                 280                 285

```
Leu Thr Val Asp Lys Ser Arg Trp Gln Glu Gly Asn Val Phe Ser Cys
            290                 295                 300
Ser Val Met His Glu Ala Leu His Ser His Tyr Thr Gln Lys Ser Leu
305                 310                 315                 320
Ser Leu Ser Pro Gly
            325

<210> SEQ ID NO 62
<211> LENGTH: 329
<212> TYPE: PRT
<213> ORGANISM: Artificial Sequence
<220> FEATURE:
<223> OTHER INFORMATION: IgG-pI-Iso3-434S

<400> SEQUENCE: 62

Ala Ser Thr Lys Gly Pro Ser Val Phe Pro Leu Ala Pro Ser Ser Lys
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Pro Lys Ser Cys Asp Thr Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Gln Phe Asn Trp
145                 150                 155                 160
Tyr Val Asp Gly Val Glu Val His Asn Ala Lys Thr Lys Pro Arg Glu
                165                 170                 175
Glu Gln Phe Asn Ser Thr Phe Arg Val Val Ser Val Leu Thr Val Val
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Thr Lys Gly
    210                 215                 220
Gln Pro Arg Glu Pro Gln Val Tyr Thr Leu Pro Pro Ser Gln Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Ser Gly Gln Pro Glu Asn
            260                 265                 270
Asn Tyr Asn Thr Thr Pro Pro Met Leu Asp Ser Asp Gly Ser Phe Phe
            275                 280                 285
Leu Tyr Ser Lys Leu Thr Val Asp Lys Ser Arg Trp Gln Glu Gly Asn
    290                 295                 300
Val Phe Ser Cys Ser Val Met His Glu Ala Leu His Ser His Tyr Thr
305                 310                 315                 320
```

Gln Lys Ser Leu Ser Leu Ser Pro Gly
                325

<210> SEQ ID NO 63
<211> LENGTH: 329
<212> TYPE: PRT
<213> ORGANISM: Artificial Sequence
<220> FEATURE:
<223> OTHER INFORMATION: IgG-pI-Iso3-SL-434S

<400> SEQUENCE: 63

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Pro Lys Ser Cys Asp Thr Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Glu Gly Asn
    290                 295                 300

Val Phe Ser Cys Ser Val Met His Glu Ala Leu His Ser His Tyr Thr
305                 310                 315                 320

Gln Lys Ser Leu Ser Leu Ser Pro Gly
                325

<210> SEQ ID NO 64
<211> LENGTH: 329

```
<212> TYPE: PRT
<213> ORGANISM: Artificial Sequence
<220> FEATURE:
<223> OTHER INFORMATION: IgG-pI-Iso3-SL-428L/434S

<400> SEQUENCE: 64

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Pro Lys Ser Cys Asp Thr Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Glu Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly
                325

<210> SEQ ID NO 65
<211> LENGTH: 325
<212> TYPE: PRT
<213> ORGANISM: Artificial Sequence
<220> FEATURE:
<223> OTHER INFORMATION: IgG-pI-Iso2-SL-434S

<400> SEQUENCE: 65
```

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Ser Gly Gln Pro Glu Asn Asn Tyr Asn Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Ser His Tyr Thr Gln Lys Ser Leu
305                 310                 315                 320

Ser Leu Ser Pro Gly
            325

<210> SEQ ID NO 66
<211> LENGTH: 329
<212> TYPE: PRT
<213> ORGANISM: Artificial Sequence
<220> FEATURE:
<223> OTHER INFORMATION: IgG-pI-Iso3-charges-only-434S

<400> SEQUENCE: 66

Ala Ser Thr Lys Gly Pro Ser Val Phe Pro Leu Ala Pro Ser Ser Lys
1               5                   10                  15

Ser Thr Ser Glu Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asp His Lys Pro Ser Asn Thr Lys Val Asp Lys
                85                  90                  95

Thr Val Glu Pro Lys Ser Cys Asp Thr Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Asn Thr Thr Pro Pro Val Leu Asp Ser Asp Gly Ser Phe Phe
            275                 280                 285

Leu Tyr Ser Lys Leu Thr Val Asp Lys Ser Arg Trp Gln Glu Gly Asn
            290                 295                 300

Val Phe Ser Cys Ser Val Met His Glu Ala Leu His Ser His Tyr Thr
305                 310                 315                 320

Gln Lys Ser Leu Ser Leu Ser Pro Gly
                325

<210> SEQ ID NO 67
<211> LENGTH: 325
<212> TYPE: PRT
<213> ORGANISM: Artificial Sequence
<220> FEATURE:
<223> OTHER INFORMATION: IgG-pI-Iso2-charges-only-434S

<400> SEQUENCE: 67

Ala Ser Thr Lys Gly Pro Ser Val Phe Pro Leu Ala Pro Ser Ser Lys
1               5                   10                  15

Ser Thr Ser Glu Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

-continued

Leu Ser Ser Val Val Thr Val Pro Ser Ser Leu Gly Thr Gln Thr
65                  70                  75                  80

Tyr Ile Cys Asn Val Asp His Lys Pro Ser Asn Thr Lys Val Asp Lys
                85                  90                  95

Thr Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Asn Thr
            260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Glu Gly Asn Val Phe Ser Cys
290                 295                 300

Ser Val Met His Glu Ala Leu His Ser His Tyr Thr Gln Lys Ser Leu
305                 310                 315                 320

Ser Leu Ser Pro Gly
            325

<210> SEQ ID NO 68
<211> LENGTH: 329
<212> TYPE: PRT
<213> ORGANISM: Artificial Sequence
<220> FEATURE:
<223> OTHER INFORMATION: IgG1-pI(7)-434S

<400> SEQUENCE: 68

Ala Ser Thr Lys Gly Pro Ser Val Phe Pro Leu Ala Pro Ser Ser Glu
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Glu Pro Ser Asn Thr Glu Val Asp Lys
                85                  90                  95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Glu Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Glu Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Glu Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Ser His Tyr Thr
305                 310                 315                 320

Gln Lys Ser Leu Ser Leu Ser Pro Gly
                325

<210> SEQ ID NO 69
<211> LENGTH: 328
<212> TYPE: PRT
<213> ORGANISM: Artificial Sequence
<220> FEATURE:
<223> OTHER INFORMATION: IgG1/2_pI(7)-434S

<400> SEQUENCE: 69

Ala Ser Thr Lys Gly Pro Ser Val Phe Pro Leu Ala Pro Ser Ser Glu
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Glu Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125
```

```
Pro Lys Asp Thr Leu Met Ile Ser Arg Thr Pro Glu Val Thr Cys Val
    130                 135                 140

Val Val Asp Val Ser His Glu Asp Pro Glu Val Glu Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Glu Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Glu Thr Thr Pro Pro Met Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Ser His Tyr Thr Gln
305                 310                 315                 320

Lys Ser Leu Ser Leu Ser Pro Gly
                325

<210> SEQ ID NO 70
<211> LENGTH: 587
<212> TYPE: PRT
<213> ORGANISM: Artificial Sequence
<220> FEATURE:
<223> OTHER INFORMATION: Heavy Chain 2 of anti-HER2 x anti-CD3 mAb-Fv

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

-continued

```
Trp Asn Ser Gly Ala Leu Glu Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asp Thr Glu Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Thr
            340                 345                 350

Thr Leu Pro Pro Cys Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Ser Gly Gln Pro Glu Asn Asn Tyr Thr Phe Pro Pro Met
385                 390                 395                 400

Leu Asp Ser Asp Gly Ser Phe Phe Leu Tyr Ser Lys Leu Thr Val Asp
            405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Ser Asp Lys Thr His Thr Ser Pro Pro Ser Pro Gly Gly
    450                 455                 460

Gly Gly Ser Gly Gly Gly Gly Ser Gly Gly Gly Gly Ser Gly Gly Gly
465                 470                 475                 480

Gly Gln Ile Val Leu Thr Gln Ser Pro Ala Thr Leu Ser Leu Ser Pro
            485                 490                 495

Gly Glu Arg Ala Thr Leu Ser Cys Arg Ala Ser Ser Ser Val Ser Tyr
        500                 505                 510

Met Asn Trp Tyr Gln Gln Lys Pro Gly Gln Ser Pro Arg Arg Leu Ile
        515                 520                 525

Tyr Asp Thr Ser Lys Leu Ala Ser Gly Val Pro Ala Arg Phe Arg Gly
        530                 535                 540

Ser Gly Ser Gly Thr Asp Tyr Thr Leu Thr Ile Ser Ser Leu Glu Pro
545                 550                 555                 560

Glu Asp Phe Ala Val Tyr Tyr Cys Gln Gln Trp Ser Ser Asn Pro Phe
            565                 570                 575
```

```
Thr Phe Gly Ser Gly Thr Lys Leu Glu Ile Lys
            580                 585
```

<210> SEQ ID NO 71
<211> LENGTH: 214
<212> TYPE: PRT
<213> ORGANISM: Artificial Sequence
<220> FEATURE:
<223> OTHER INFORMATION: Light Chain of anti-HER2 x anti-CD3 mAb-Fv

<400> SEQUENCE: 71

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 72
<211> LENGTH: 474
<212> TYPE: PRT
<213> ORGANISM: Artificial Sequence
<220> FEATURE:
<223> OTHER INFORMATION: Heavy Chain 1 of anti-HER2 x anti-CD3 scFv-Fc

<400> SEQUENCE: 72

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly
            115                 120                 125

Ser Gly Gly Gly Ser Gln Ile Val Leu Thr Gln Ser Pro Ala Thr
130                 135                 140

Leu Ser Leu Ser Pro Gly Glu Arg Ala Thr Leu Ser Cys Arg Ala Ser
145                 150                 155                 160

Ser Ser Val Ser Tyr Met Asn Trp Tyr Gln Gln Lys Pro Gly Gln Ser
                165                 170                 175

Pro Arg Arg Leu Ile Tyr Asp Thr Ser Lys Leu Ala Ser Gly Val Pro
            180                 185                 190

Ala Arg Phe Arg Gly Ser Gly Ser Gly Thr Asp Tyr Thr Leu Thr Ile
            195                 200                 205

Ser Ser Leu Glu Pro Glu Asp Phe Ala Val Tyr Tyr Cys Gln Gln Trp
210                 215                 220

Ser Ser Asn Pro Phe Thr Phe Gly Ser Gly Thr Lys Leu Glu Ile Lys
225                 230                 235                 240

Arg Thr Glu Pro Lys Ser Ser Asp Lys Thr His Thr Cys Pro Pro Cys
            245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Cys Thr Leu Pro Pro Ser Arg Glu Glu
            370                 375                 380

Met Thr Lys Asn Gln Val His Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Ala
            420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
450                 455                 460

Gln Lys Ser Leu Ser Leu Ser Pro Gly Lys
465                 470

<210> SEQ ID NO 73
<211> LENGTH: 476

<212> TYPE: PRT
<213> ORGANISM: Artificial Sequence
<220> FEATURE:
<223> OTHER INFORMATION: Heavy Chain 2 of anti-HER2 x anti-CD3 scFv-Fc

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Asp Ile Gln Met Thr Gln Ser Pro Ser
130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys Arg Thr Glu Pro Lys Ser Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Gln Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Thr Thr Leu Pro Pro Cys Gln
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Ser Gly Gln Pro
            405                 410                 415

Glu Asn Asn Tyr Asn Thr Phe Pro Pro Met Leu Asp Ser Asp Gly Ser
            420                 425                 430

Phe Phe Leu Tyr Ser Lys Leu Thr Val Asp Lys Ser Arg Trp Gln Glu
        435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly Lys
465                 470                 475

<210> SEQ ID NO 74
<211> LENGTH: 329
<212> TYPE: PRT
<213> ORGANISM: Artificial Sequence
<220> FEATURE:
<223> OTHER INFORMATION: ISO(-)

<400> SEQUENCE: 74

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

```
Asn Tyr Asn Thr Thr Pro Pro Met Leu Asp Ser Asp Gly Ser Phe Phe
            275                 280                 285

Leu Tyr Ser Lys Leu Thr Val Asp Lys Ser Arg Trp Gln Glu Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325
```

<210> SEQ ID NO 75
<211> LENGTH: 330
<212> TYPE: PRT
<213> ORGANISM: Artificial Sequence
<220> FEATURE:
<223> OTHER INFORMATION: ISO(+)

<400> SEQUENCE: 75

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Lys Thr
65                  70                  75                  80

Tyr Thr Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300
```

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 76
<211> LENGTH: 330
<212> TYPE: PRT
<213> ORGANISM: Artificial Sequence
<220> FEATURE:
<223> OTHER INFORMATION: ISO(+RR)

<400> SEQUENCE: 76

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asn His Lys Pro Ser Asn Thr Lys Val Asp Lys
                85                  90                  95

Lys Val Glu Arg Lys Ser Cys Asp Lys Thr His Thr Cys Pro Arg Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

-continued

<210> SEQ ID NO 77
<211> LENGTH: 452
<212> TYPE: PRT
<213> ORGANISM: Artificial Sequence
<220> FEATURE:
<223> OTHER INFORMATION: Anti-VEGF_ISO(-) Heavy Chain

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asp His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

```
Val Ser Leu Thr Cys Leu Val Lys Gly Phe Tyr Pro Ser Asp Ile Ala
    370             375                 380

Val Glu Trp Glu Ser Ser Gly Gln Pro Glu Asn Asn Tyr Asn Thr Thr
385             390                 395                 400

Pro Pro Met Leu Asp Ser Asp Gly Ser Phe Phe Leu Tyr Ser Lys Leu
            405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
    450

<210> SEQ ID NO 78
<211> LENGTH: 453
<212> TYPE: PRT
<213> ORGANISM: Artificial Sequence
<220> FEATURE:
<223> OTHER INFORMATION: Anti-VEGF_ISO(+) Heavy Chain

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

```
Ser His Glu Asp Pro Glu Val Lys Phe Lys Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 79
<211> LENGTH: 453
<212> TYPE: PRT
<213> ORGANISM: Artificial Sequence
<220> FEATURE:
<223> OTHER INFORMATION: Anti-VEGF_ISO(+RR) Heavy Chain

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asn His Lys Pro Ser Asn Thr Lys Val Asp Lys Lys Val Glu Arg Lys
    210                 215                 220

Ser Cys Asp Lys Thr His Thr Cys Pro Arg Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Lys Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 80
<211> LENGTH: 452
<212> TYPE: PRT
<213> ORGANISM: Artificial Sequence
<220> FEATURE:
<223> OTHER INFORMATION: Heavy Chain 1 of XENP10783 Anti-VEGF_ISO(-) x
      IgG1(WT)

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Tyr Ala Ala Asp Phe
    50                  55                  60

Lys Arg Arg Phe Thr Phe Ser Leu Asp Thr Ser Lys Ser Thr Ala Tyr
65                  70                  75                  80
```

```
Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asp His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Ser Gly Gln Pro Glu Asn Asn Tyr Asn Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 81
<211> LENGTH: 453
<212> TYPE: PRT
<213> ORGANISM: Artificial Sequence
<220> FEATURE:
```

<223> OTHER INFORMATION: Heavy Chain 2 of XENP10783 Anti-VEGF_ISO(-) x IgG1(WT)

<400> SEQUENCE: 81

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 82
<211> LENGTH: 214
<212> TYPE: PRT
<213> ORGANISM: Artificial Sequence
<220> FEATURE:
<223> OTHER INFORMATION: Light Chain of XENP10783 Anti-VEGF_ISO(-) x
      IgG1(WT)

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 83
<211> LENGTH: 453
<212> TYPE: PRT
<213> ORGANISM: Artificial Sequence
<220> FEATURE:
<223> OTHER INFORMATION: Heavy Chain 1 of XENP10784 Anti-VEGF_ISO(+RR) x
      IgG1(WT)

<400> SEQUENCE: 83

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Tyr Thr Phe Thr Asn Tyr
         20                  25                  30

Gly Met Asn Trp Val Arg Gln Ala Pro Gly Lys Gly Leu Glu Trp Val
         35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asn His Lys Pro Ser Asn Thr Lys Val Asp Lys Val Glu Arg Lys
            210                 215                 220

Ser Cys Asp Lys Thr His Thr Cys Pro Arg Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Lys Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

Val Met His Glu Ala Leu His Asn His Tyr Thr Gln Lys Ser Leu Ser
                435                 440                 445

Leu Ser Pro Gly Lys
    450

<210> SEQ ID NO 84
<211> LENGTH: 453
<212> TYPE: PRT
<213> ORGANISM: Artificial Sequence
<220> FEATURE:
<223> OTHER INFORMATION: Heavy Chain 2 of XENP10784 Anti-VEGF_ISO(+RR) x
      IgG1(WT)

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

```
Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 85
<211> LENGTH: 214
<212> TYPE: PRT
<213> ORGANISM: Artificial Sequence
<220> FEATURE:
<223> OTHER INFORMATION: Light Chain of XENP10784 Anti-VEGF_ISO(+RR) x
      IgG1(WT)

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 86
<211> LENGTH: 452
<212> TYPE: PRT
<213> ORGANISM: Artificial Sequence
<220> FEATURE:
<223> OTHER INFORMATION: Heavy Chain 1 of XENP10896 Anti-VEGF_ISO(-) x
      ISO(+RR)

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asp His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365
```

```
Val Ser Leu Thr Cys Leu Val Lys Gly Phe Tyr Pro Ser Asp Ile Ala
        370                 375                 380

Val Glu Trp Glu Ser Ser Gly Gln Pro Glu Asn Asn Tyr Asn Thr Thr
385                 390                 395                 400

Pro Pro Met Leu Asp Ser Asp Gly Ser Phe Phe Leu Tyr Ser Lys Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450
```

<210> SEQ ID NO 87
<211> LENGTH: 453
<212> TYPE: PRT
<213> ORGANISM: Artificial Sequence
<220> FEATURE:
<223> OTHER INFORMATION: Heavy Chain 2 of XENP10896 Anti-VEGF_ISO(-) x
      ISO(+RR)

<400> SEQUENCE: 87

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asn His Lys Pro Ser Asn Thr Lys Val Asp Lys Lys Val Glu Arg Lys
    210                 215                 220

Ser Cys Asp Lys Thr His Thr Cys Pro Arg Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

Ser His Glu Asp Pro Glu Val Lys Phe Lys Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 88
<211> LENGTH: 214
<212> TYPE: PRT
<213> ORGANISM: Artificial Sequence
<220> FEATURE:
<223> OTHER INFORMATION: Light Chain of XENP10896 Anti-VEGF_ISO(-) x
      ISO(+RR)

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser

```
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 89
<211> LENGTH: 452
<212> TYPE: PRT
<213> ORGANISM: Artificial Sequence
<220> FEATURE:
<223> OTHER INFORMATION: Heavy Chain 1 of XENP10901 Anti-VEGF_ISO(-) x
      ISO(+)

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asp His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Gln Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

-continued

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Ser Gly Gln Pro Glu Asn Asn Tyr Asn Thr Thr
385                 390                 395                 400

Pro Pro Met Leu Asp Ser Asp Gly Ser Phe Phe Leu Tyr Ser Lys Leu
            405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
    450
```

<210> SEQ ID NO 90
<211> LENGTH: 453
<212> TYPE: PRT
<213> ORGANISM: Artificial Sequence
<220> FEATURE:
<223> OTHER INFORMATION: Heavy Chain 2 of XENP10901 Anti-VEGF_ISO(-) x
      ISO(+)

<400> SEQUENCE: 90

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205
```

Asn His Lys Pro Ser Asn Thr Lys Val Asp Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Lys Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 91
<211> LENGTH: 214
<212> TYPE: PRT
<213> ORGANISM: Artificial Sequence
<220> FEATURE:
<223> OTHER INFORMATION: Light Chain of XENP10901 Anti-VEGF_ISO(-) x
      ISO(+)

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala

```
            100                 105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 92
<211> LENGTH: 589
<212> TYPE: PRT
<213> ORGANISM: Artificial Sequence
<220> FEATURE:
<223> OTHER INFORMATION: Heavy Chain 1 of anti-CD19 x anti-CD3 mAb-Fv
      [HC ISO(-) (VH)]

<400> SEQUENCE: 92

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Thr Arg Val Phe Asp Tyr Trp Gly Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Ser Gly Gln Pro Glu Asn Asn Tyr Asn Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Ser Ser Asp Lys Thr His Thr Ser Pro Pro Ser Pro Ser Gly
    450                 455                 460

Glu Val Gln Leu Val Glu Ser Gly Gly Gly Leu Val Gln Pro Gly Gly
465                 470                 475                 480

Ser Leu Arg Leu Ser Cys Ala Ala Ser Gly Phe Thr Phe Asn Thr Tyr
                485                 490                 495

Ala Met Asn Trp Val Arg Gln Ala Pro Gly Lys Gly Leu Glu Trp Val
            500                 505                 510

Gly Arg Ile Arg Ser Lys Tyr Asn Asn Tyr Ala Thr Tyr Tyr Ala Asp
        515                 520                 525

Ser Val Lys Gly Arg Phe Thr Ile Ser Arg Asp Asp Ser Lys Asn Thr
    530                 535                 540

Leu Tyr Leu Gln Met Asn Ser Leu Arg Ala Glu Asp Thr Ala Val Tyr
545                 550                 555                 560

Tyr Cys Val Arg His Gly Asn Phe Gly Asn Ser Tyr Val Ser Trp Phe
                565                 570                 575

Ala Tyr Trp Gly Gln Gly Thr Leu Val Thr Val Ser Ser
            580                 585

<210> SEQ ID NO 93
<211> LENGTH: 574
<212> TYPE: PRT
<213> ORGANISM: Artificial Sequence
<220> FEATURE:
<223> OTHER INFORMATION: Heavy Chain 2 of anti-CD19 x anti-CD3 mAb-Fv
      [HC ISO(+RR) (VL)]

<400> SEQUENCE: 93

Glu Val Gln Leu Val Glu Ser Gly Gly Gly Leu Val Lys Pro Gly Gly
1               5                   10                  15
```

```
Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asn His
        195                 200                 205

Lys Pro Ser Asn Thr Lys Val Asp Lys Lys Val Glu Arg Lys Ser Cys
    210                 215                 220

Asp Lys Thr His Thr Cys Pro Arg Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Lys Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

```
His Glu Ala Leu His Asn His Tyr Thr Gln Lys Ser Leu Ser Leu Ser
            435                 440                 445

Pro Gly Lys Ser Ser Asp Lys Thr His Thr Ser Pro Pro Ser Pro Ser
450                 455                 460

Gly Gln Ala Val Val Thr Gln Glu Pro Ser Leu Thr Val Ser Pro Gly
465                 470                 475                 480

Gly Thr Val Thr Leu Thr Cys Gly Ser Ser Thr Gly Ala Val Thr Thr
                485                 490                 495

Ser Asn Tyr Ala Asn Trp Val Gln Gln Lys Pro Gly Gln Ala Pro Arg
                500                 505                 510

Gly Leu Ile Gly Gly Thr Asn Lys Arg Ala Pro Gly Val Pro Ala Arg
            515                 520                 525

Phe Ser Gly Ser Leu Leu Gly Gly Lys Ala Ala Leu Thr Leu Ser Gly
        530                 535                 540

Ala Gln Pro Glu Asp Glu Ala Glu Tyr Tyr Cys Ala Leu Trp Tyr Ser
545                 550                 555                 560

Asn Leu Trp Val Phe Gly Gly Gly Thr Lys Leu Thr Val Leu
                565                 570
```

<210> SEQ ID NO 94
<211> LENGTH: 219
<212> TYPE: PRT
<213> ORGANISM: Artificial Sequence
<220> FEATURE:
<223> OTHER INFORMATION: Light Chain of anti-CD19 x anti-CD3 mAb-Fv

<400> SEQUENCE: 94

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 95
<211> LENGTH: 231
<212> TYPE: PRT
<213> ORGANISM: Artificial Sequence
<220> FEATURE:
<223> OTHER INFORMATION: Heavy Chain 1 of anti-CD19 x anti-CD3 scFv2-Fc
      [HC ISO(-)]

<400> SEQUENCE: 95

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Gln Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Glu Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230

<210> SEQ ID NO 96
<211> LENGTH: 735
<212> TYPE: PRT
<213> ORGANISM: Artificial Sequence
<220> FEATURE:
<223> OTHER INFORMATION: Heavy Chain 2 of anti-CD19 x anti-CD3 scFv2-Fc
      [HC ISO(+RR) (scFv2)]

<400> SEQUENCE: 96

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

```
Gln Gly Arg Val Thr Ile Ser Ser Asp Lys Ser Ile Ser Thr Ala Tyr
 65                  70                  75                  80

Met Glu Leu Ser Ser Leu Arg Ser Glu Asp Thr Ala Met Tyr Tyr Cys
                 85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Val Met Thr Gln Ser Pro
130                 135                 140

Ala Thr Leu Ser Leu Ser Pro Gly Glu Arg Ala Thr Leu Ser Cys Arg
145                 150                 155                 160

Ser Ser Lys Ser Leu Gln Asn Val Asn Gly Asn Thr Tyr Leu Tyr Trp
            165                 170                 175

Phe Gln Gln Lys Pro Gly Gln Ser Pro Gln Leu Leu Ile Tyr Arg Met
            180                 185                 190

Ser Asn Leu Asn Ser Gly Val Pro Asp Arg Phe Ser Gly Ser Gly Ser
            195                 200                 205

Gly Thr Glu Phe Thr Leu Thr Ile Ser Ser Leu Glu Pro Glu Asp Phe
210                 215                 220

Ala Val Tyr Tyr Cys Met Gln His Leu Glu Tyr Pro Ile Thr Phe Gly
225                 230                 235                 240

Ala Gly Thr Lys Leu Glu Ile Lys Ser Gly Gly Gly Gly Ser Glu Val
            245                 250                 255

Gln Leu Val Glu Ser Gly Gly Gly Leu Val Gln Pro Gly Gly Ser Leu
            260                 265                 270

Arg Leu Ser Cys Ala Ala Ser Gly Phe Thr Phe Asn Thr Tyr Ala Met
            275                 280                 285

Asn Trp Val Arg Gln Ala Pro Gly Lys Gly Leu Glu Trp Val Gly Arg
            290                 295                 300

Ile Arg Ser Lys Tyr Asn Asn Tyr Ala Thr Tyr Tyr Ala Asp Ser Val
305                 310                 315                 320

Lys Gly Arg Phe Thr Ile Ser Arg Asp Asp Ser Lys Asn Thr Leu Tyr
            325                 330                 335

Leu Gln Met Asn Ser Leu Arg Ala Glu Asp Thr Ala Val Tyr Tyr Cys
            340                 345                 350

Val Arg His Gly Asn Phe Gly Asn Ser Tyr Val Ser Trp Phe Ala Tyr
            355                 360                 365

Trp Gly Gln Gly Thr Leu Val Thr Val Ser Ser Gly Gly Gly Gly Ser
            370                 375                 380

Gly Gly Gly Gly Ser Gly Gly Gly Ser Gln Ala Val Val Thr Gln
385                 390                 395                 400

Glu Pro Ser Leu Thr Val Ser Pro Gly Gly Thr Val Thr Leu Thr Cys
                405                 410                 415

Gly Ser Ser Thr Gly Ala Val Thr Thr Ser Asn Tyr Ala Asn Trp Val
            420                 425                 430

Gln Gln Lys Pro Gly Gln Ala Pro Arg Gly Leu Ile Gly Gly Thr Asn
            435                 440                 445

Lys Arg Ala Pro Gly Val Pro Ala Arg Phe Ser Gly Ser Leu Leu Gly
            450                 455                 460

Gly Lys Ala Ala Leu Thr Leu Ser Gly Ala Gln Pro Glu Asp Glu Ala
465                 470                 475                 480

Glu Tyr Tyr Cys Ala Leu Trp Tyr Ser Asn Leu Trp Val Phe Gly Gly
```

485                 490                 495
Gly Thr Lys Leu Thr Val Leu Glu Arg Lys Ser Ser Asp Lys Thr His
                500                 505                 510

Thr Cys Pro Arg Cys Pro Ala Pro Glu Leu Leu Gly Gly Pro Ser Val
                515                 520                 525

Phe Leu Phe Pro Pro Lys Pro Lys Asp Thr Leu Met Ile Ser Arg Thr
            530                 535                 540

Pro Glu Val Thr Cys Val Val Asp Val Ser His Glu Asp Pro Glu
545                 550                 555                 560

Val Lys Phe Lys Trp Tyr Val Asp Gly Val Glu Val His Asn Ala Lys
                565                 570                 575

Thr Lys Pro Arg Glu Glu Gln Tyr Asn Ser Thr Tyr Arg Val Val Ser
                580                 585                 590

Val Leu Thr Val Leu His Gln Asp Trp Leu Asn Gly Lys Glu Tyr Lys
                595                 600                 605

Cys Lys Val Ser Asn Lys Ala Leu Pro Ala Pro Ile Glu Lys Thr Ile
                610                 615                 620

Ser Lys Ala Lys Gly Gln Pro Arg Glu Pro Gln Val Tyr Thr Leu Pro
625                 630                 635                 640

Pro Ser Arg Glu Glu Met Thr Lys Asn Gln Val Ser Leu Thr Cys Leu
                645                 650                 655

Val Lys Gly Phe Tyr Pro Ser Asp Ile Ala Val Glu Trp Glu Ser Asn
                660                 665                 670

Gly Gln Pro Glu Asn Asn Tyr Lys Thr Thr Pro Pro Val Leu Asp Ser
                675                 680                 685

Asp Gly Ser Phe Phe Leu Tyr Ser Lys Leu Thr Val Asp Lys Ser Arg
            690                 695                 700

Trp Gln Gln Gly Asn Val Phe Ser Cys Ser Val Met His Glu Ala Leu
705                 710                 715                 720

His Asn His Tyr Thr Gln Lys Ser Leu Ser Leu Ser Pro Gly Lys
                725                 730                 735

<210> SEQ ID NO 97
<211> LENGTH: 483
<212> TYPE: PRT
<213> ORGANISM: Artificial Sequence
<220> FEATURE:
<223> OTHER INFORMATION: Heavy Chain 1 of anti-CD19 x anti-CD3 DART-Fc
      [HC ISO(-) (anti-CD19 VL/anti-CD3 VH)]

<400> SEQUENCE: 97

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
                20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Asn Ser Gly Val Pro
        50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
                100                 105                 110

Gly Gly Gly Ser Gly Gly Gly Ser Gly Gly Gly Ser Glu
            115                 120             125

Val Gln Leu Val Glu Ser Gly Gly Leu Val Gln Pro Gly Gly Ser
    130                 135                 140

Leu Arg Leu Ser Cys Ala Ala Ser Gly Phe Thr Phe Asn Thr Tyr Ala
145                 150                 155                 160

Met Asn Trp Val Arg Gln Ala Pro Gly Lys Gly Leu Glu Trp Val Gly
                165                 170                 175

Arg Ile Arg Ser Lys Tyr Asn Asn Tyr Ala Thr Tyr Tyr Ala Asp Ser
            180                 185                 190

Val Lys Gly Arg Phe Thr Ile Ser Arg Asp Asp Ser Lys Asn Thr Leu
        195                 200                 205

Tyr Leu Gln Met Asn Ser Leu Arg Ala Glu Asp Thr Ala Val Tyr Tyr
    210                 215                 220

Cys Val Arg His Gly Asn Phe Gly Asn Ser Tyr Val Ser Trp Phe Ala
225                 230                 235                 240

Tyr Trp Gly Gln Gly Thr Leu Val Thr Val Ser Ser Glu Pro Lys Ser
                245                 250                 255

Ser Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Gln Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Ser Gly Gln Pro Glu Asn Asn Tyr Asn Thr Thr Pro
            420                 425                 430

Pro Met Leu Asp Ser Asp Gly Ser Phe Phe Leu Tyr Ser Lys Leu Thr
        435                 440                 445

Val Asp Lys Ser Arg Trp Gln Glu Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly

<210> SEQ ID NO 98
<211> LENGTH: 477
<212> TYPE: PRT
<213> ORGANISM: Artificial Sequence
<220> FEATURE:
<223> OTHER INFORMATION: Heavy Chain 2 of anti-CD19 x anti-CD3 DART-Fc
      [HC ISO(+RR) (anti-CD3 VL/anti-CD19 VH)]

<400> SEQUENCE: 98

| | | | | | | | | | | | | | | |
|---|---|---|---|---|---|---|---|---|---|---|---|---|---|---|
| Gln | Ala | Val | Val | Thr | Gln | Glu | Pro | Ser | Leu | Thr | Val | Ser | Pro | Gly | Gly |
| 1 | | | | 5 | | | | | 10 | | | | | 15 | |
| Thr | Val | Thr | Leu | Thr | Cys | Gly | Ser | Ser | Thr | Gly | Ala | Val | Thr | Thr | Ser |
| | | | 20 | | | | | 25 | | | | | 30 | | |
| Asn | Tyr | Ala | Asn | Trp | Val | Gln | Gln | Lys | Pro | Gly | Gln | Ala | Pro | Arg | Gly |
| | | 35 | | | | | 40 | | | | | 45 | | | |
| Leu | Ile | Gly | Gly | Thr | Asn | Lys | Arg | Ala | Pro | Gly | Val | Pro | Ala | Arg | Phe |
| 50 | | | | | 55 | | | | | 60 | | | | | |
| Ser | Gly | Ser | Leu | Leu | Gly | Gly | Lys | Ala | Ala | Leu | Thr | Leu | Ser | Gly | Ala |
| 65 | | | | 70 | | | | | 75 | | | | | 80 | |
| Gln | Pro | Glu | Asp | Glu | Ala | Glu | Tyr | Tyr | Cys | Ala | Leu | Trp | Tyr | Ser | Asn |
| | | | | 85 | | | | | 90 | | | | | 95 | |
| Leu | Trp | Val | Phe | Gly | Gly | Gly | Thr | Lys | Leu | Thr | Val | Leu | Gly | Gly | Gly |
| | | | | 100 | | | | | 105 | | | | | 110 | |
| Gly | Ser | Gly | Gly | Gly | Gly | Ser | Gly | Gly | Gly | Gly | Ser | Glu | Val | Gln | Leu |
| | | | 115 | | | | | 120 | | | | | 125 | | |
| Val | Glu | Ser | Gly | Gly | Gly | Leu | Val | Lys | Pro | Gly | Gly | Ser | Leu | Lys | Leu |
| | 130 | | | | | 135 | | | | | 140 | | | | |
| Ser | Cys | Ala | Ala | Ser | Gly | Tyr | Thr | Phe | Thr | Ser | Tyr | Val | Met | His | Trp |
| 145 | | | | | 150 | | | | | 155 | | | | | 160 |
| Val | Arg | Gln | Ala | Pro | Gly | Lys | Gly | Leu | Glu | Trp | Ile | Gly | Tyr | Ile | Asn |
| | | | | 165 | | | | | 170 | | | | | 175 | |
| Pro | Tyr | Asn | Asp | Gly | Thr | Lys | Tyr | Asn | Glu | Lys | Phe | Gln | Gly | Arg | Val |
| | | | 180 | | | | | 185 | | | | | 190 | | |
| Thr | Ile | Ser | Ser | Asp | Lys | Ser | Ile | Ser | Thr | Ala | Tyr | Met | Glu | Leu | Ser |
| | | 195 | | | | | 200 | | | | | 205 | | | |
| Ser | Leu | Arg | Ser | Glu | Asp | Thr | Ala | Met | Tyr | Tyr | Cys | Ala | Arg | Gly | Thr |
| | 210 | | | | | 215 | | | | | 220 | | | | |
| Tyr | Tyr | Tyr | Gly | Thr | Arg | Val | Phe | Asp | Tyr | Trp | Gly | Gln | Gly | Thr | Leu |
| 225 | | | | | 230 | | | | | 235 | | | | | 240 |
| Val | Thr | Val | Ser | Ser | Glu | Arg | Lys | Ser | Ser | Asp | Lys | Thr | His | Thr | Cys |
| | | | | 245 | | | | | 250 | | | | | 255 | |
| Pro | Arg | Cys | Pro | Ala | Pro | Glu | Leu | Leu | Gly | Gly | Pro | Ser | Val | Phe | Leu |
| | | | 260 | | | | | 265 | | | | | 270 | | |
| Phe | Pro | Pro | Lys | Pro | Lys | Asp | Thr | Leu | Met | Ile | Ser | Arg | Thr | Pro | Glu |
| | | 275 | | | | | 280 | | | | | 285 | | | |
| Val | Thr | Cys | Val | Val | Val | Asp | Val | Ser | His | Glu | Asp | Pro | Glu | Val | Lys |
| | 290 | | | | | 295 | | | | | 300 | | | | |
| Phe | Lys | Trp | Tyr | Val | Asp | Gly | Val | Glu | Val | His | Asn | Ala | Lys | Thr | Lys |
| 305 | | | | | 310 | | | | | 315 | | | | | 320 |
| Pro | Arg | Glu | Glu | Gln | Tyr | Asn | Ser | Thr | Tyr | Arg | Val | Val | Ser | Val | Leu |
| | | | | 325 | | | | | 330 | | | | | 335 | |
| Thr | Val | Leu | His | Gln | Asp | Trp | Leu | Asn | Gly | Lys | Glu | Tyr | Lys | Cys | Lys |
| | | | 340 | | | | | 345 | | | | | 350 | | |
| Val | Ser | Asn | Lys | Ala | Leu | Pro | Ala | Pro | Ile | Glu | Lys | Thr | Ile | Ser | Lys |
| | | 355 | | | | | 360 | | | | | 365 | | | |
| Ala | Lys | Gly | Gln | Pro | Arg | Glu | Pro | Gln | Val | Tyr | Thr | Leu | Pro | Pro | Ser |
| | 370 | | | | | 375 | | | | | 380 | | | | |
| Arg | Glu | Glu | Met | Thr | Lys | Asn | Gln | Val | Ser | Leu | Thr | Cys | Leu | Val | Lys |
| 385 | | | | | 390 | | | | | 395 | | | | | 400 |
| Gly | Phe | Tyr | Pro | Ser | Asp | Ile | Ala | Val | Glu | Trp | Glu | Ser | Asn | Gly | Gln |

```
                        405                 410                 415
Pro Glu Asn Asn Tyr Lys Thr Thr Pro Pro Val Leu Asp Ser Asp Gly
                420                 425                 430

Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
        450                 455                 460

His Tyr Thr Gln Lys Ser Leu Ser Leu Ser Pro Gly Lys
465                 470                 475

<210> SEQ ID NO 99
<211> LENGTH: 479
<212> TYPE: PRT
<213> ORGANISM: Artificial Sequence
<220> FEATURE:
<223> OTHER INFORMATION: Heavy Chain 1 of anti-CD19 x anti-CD3 scFv-Fc
      [HC ISO(-) (anti-CD19 scFv)]

<400> SEQUENCE: 99

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Val Met Thr Gln Ser Pro
    130                 135                 140

Ala Thr Leu Ser Leu Ser Pro Gly Glu Arg Ala Thr Leu Ser Cys Arg
145                 150                 155                 160

Ser Ser Lys Ser Leu Gln Asn Val Asn Gly Asn Thr Tyr Leu Tyr Trp
                165                 170                 175

Phe Gln Gln Lys Pro Gly Gln Ser Pro Gln Leu Leu Ile Tyr Arg Met
            180                 185                 190

Ser Asn Leu Asn Ser Gly Val Pro Asp Arg Phe Ser Gly Ser Gly Ser
        195                 200                 205

Gly Thr Glu Phe Thr Leu Thr Ile Ser Ser Leu Glu Pro Glu Asp Phe
    210                 215                 220

Ala Val Tyr Tyr Cys Met Gln His Leu Glu Tyr Pro Ile Thr Phe Gly
225                 230                 235                 240

Ala Gly Thr Lys Leu Glu Ile Lys Glu Pro Lys Ser Ser Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285
```

Thr Pro Glu Val Thr Cys Val Val Asp Val Ser His Glu Asp Pro
290                 295                 300

Glu Val Gln Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
370                 375                 380

Pro Pro Ser Gln Glu Glu Met Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Ser Gly Gln Pro Glu Asn Asn Tyr Asn Thr Thr Pro Pro Met Leu Asp
            420                 425                 430

Ser Asp Gly Ser Phe Phe Leu Tyr Ser Lys Leu Thr Val Asp Lys Ser
        435                 440                 445

Arg Trp Gln Glu Gly Asn Val Phe Ser Cys Ser Val Met His Glu Ala
450                 455                 460

Leu His Asn His Tyr Thr Gln Lys Ser Leu Ser Leu Ser Pro Gly
465                 470                 475

<210> SEQ ID NO 100
<211> LENGTH: 481
<212> TYPE: PRT
<213> ORGANISM: Artificial Sequence
<220> FEATURE:
<223> OTHER INFORMATION: Heavy Chain 2 of anti-CD19 x anti-CD3 scFv-Fc
      [HC ISO(+RR) (anti-CD3 scFv)]

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ala Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Thr Ser Asn Tyr Ala Asn
                165                 170                 175

-continued

Trp Val Gln Gln Lys Pro Gly Gln Ala Pro Arg Gly Leu Ile Gly Gly
            180                 185                 190

Thr Asn Lys Arg Ala Pro Gly Val Pro Ala Arg Phe Ser Gly Ser Leu
        195                 200                 205

Leu Gly Gly Lys Ala Ala Leu Thr Leu Ser Gly Ala Gln Pro Glu Asp
210                 215                 220

Glu Ala Glu Tyr Tyr Cys Ala Leu Trp Tyr Ser Asn Leu Trp Val Phe
225                 230                 235                 240

Gly Gly Gly Thr Lys Leu Thr Val Leu Glu Arg Lys Ser Ser Asp Lys
                245                 250                 255

Thr His Thr Cys Pro Arg Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Asp Val Ser His Glu Asp
290                 295                 300

Pro Glu Val Lys Phe Lys Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
370                 375                 380

Leu Pro Pro Ser Arg Glu Glu Met Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys

<210> SEQ ID NO 101
<211> LENGTH: 450
<212> TYPE: PRT
<213> ORGANISM: Artificial Sequence
<220> FEATURE:
<223> OTHER INFORMATION: Heavy Chain 1 of anti-CD19 x anti-CD3 mAb-scFv
      [HC ISO(-)]

<400> SEQUENCE: 101

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

-continued

```
Gly Tyr Ile Asn Pro Tyr Asn Asp Gly Thr Lys Tyr Asn Glu Lys Phe
     50                  55                  60

Gln Gly Arg Val Thr Ile Ser Ser Asp Lys Ser Ile Ser Thr Ala Tyr
 65                  70                  75                  80

Met Glu Leu Ser Ser Leu Arg Ser Glu Asp Thr Ala Met Tyr Tyr Cys
                 85                  90                  95

Ala Arg Gly Thr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Leu Gly Thr Gln Thr Tyr Thr Cys Asn Val Asp His
            195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Ser Gly Gln Pro Glu Asn Asn Tyr Asn Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450
```

<210> SEQ ID NO 102
<211> LENGTH: 710
<212> TYPE: PRT
<213> ORGANISM: Artificial Sequence
<220> FEATURE:
<223> OTHER INFORMATION: Heavy Chain 2 of anti-CD19 x anti-CD3 mAb-scFv
[HC ISO(+RR) (scFv)]

<400> SEQUENCE: 102

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asn His
        195                 200                 205

Lys Pro Ser Asn Thr Lys Val Asp Lys Lys Val Glu Arg Lys Ser Cys
    210                 215                 220

Asp Lys Thr His Thr Cys Pro Arg Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Lys Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Gly Gly Gly Ser Gly Gly Gly Ser Glu Val Gln
    450                 455                 460

Leu Val Glu Ser Gly Gly Gly Leu Val Gln Pro Gly Ser Leu Arg
465                 470                 475                 480

Leu Ser Cys Ala Ala Ser Gly Phe Thr Phe Asn Thr Tyr Ala Met Asn
            485                 490                 495

Trp Val Arg Gln Ala Pro Gly Lys Gly Leu Glu Trp Val Gly Arg Ile
            500                 505                 510

Arg Ser Lys Tyr Asn Asn Tyr Ala Thr Tyr Tyr Ala Asp Ser Val Lys
            515                 520                 525

Gly Arg Phe Thr Ile Ser Arg Asp Asp Ser Lys Asn Thr Leu Tyr Leu
            530                 535                 540

Gln Met Asn Ser Leu Arg Ala Glu Asp Thr Ala Val Tyr Tyr Cys Val
545                 550                 555                 560

Arg His Gly Asn Phe Gly Asn Ser Tyr Val Ser Trp Phe Ala Tyr Trp
            565                 570                 575

Gly Gln Gly Thr Leu Val Thr Val Ser Ser Gly Gly Gly Gly Ser Gly
            580                 585                 590

Gly Gly Gly Ser Gly Gly Gly Gly Ser Gln Ala Val Val Thr Gln Glu
            595                 600                 605

Pro Ser Leu Thr Val Ser Pro Gly Gly Thr Val Thr Leu Thr Cys Gly
    610                 615                 620

Ser Ser Thr Gly Ala Val Thr Thr Ser Asn Tyr Ala Asn Trp Val Gln
625                 630                 635                 640

Gln Lys Pro Gly Gln Ala Pro Arg Gly Leu Ile Gly Gly Thr Asn Lys
            645                 650                 655

Arg Ala Pro Gly Val Pro Ala Arg Phe Ser Gly Ser Leu Leu Gly Gly
            660                 665                 670

Lys Ala Ala Leu Thr Leu Ser Gly Ala Gln Pro Glu Asp Glu Ala Glu
            675                 680                 685

Tyr Tyr Cys Ala Leu Trp Tyr Ser Asn Leu Trp Val Phe Gly Gly Gly
            690                 695                 700

Thr Lys Leu Thr Val Leu
705                 710

<210> SEQ ID NO 103
<211> LENGTH: 219
<212> TYPE: PRT
<213> ORGANISM: Artificial Sequence
<220> FEATURE:
<223> OTHER INFORMATION: Light Chain of anti-CD19 x anti-CD3 mAb-scFv

<400> SEQUENCE: 103

Asp Ile Val Met Thr Gln Ser Pro Ala Thr Leu Ser Leu Ser Pro Gly
1               5                   10                  15
```

```
Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 104
<211> LENGTH: 450
<212> TYPE: PRT
<213> ORGANISM: Artificial Sequence
<220> FEATURE:
<223> OTHER INFORMATION: Heavy Chain 1 of anti-CD19 x anti-CD3 mAb-dAb
      [HC ISO(-)]

<400> SEQUENCE: 104

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
```

-continued

```
145                 150                 155                 160
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Leu Gly Thr Gln Thr Tyr Thr Cys Asn Val Asp His
                195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Gln Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Gln Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Ser Gly Gln Pro Glu Asn Asn Tyr Asn Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Glu Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 105
<211> LENGTH: 586
<212> TYPE: PRT
<213> ORGANISM: Artificial Sequence
<220> FEATURE:
<223> OTHER INFORMATION: Heavy Chain 2 of anti-CD19 x anti-CD3 mAb-dAb
      [ISO(+RR) (scFv)]

<400> SEQUENCE: 105

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
                20                  25                  30

Val Met His Trp Val Arg Gln Ala Pro Gly Lys Gly Leu Glu Trp Ile
                35                  40                  45
```

-continued

```
Gly Tyr Ile Asn Pro Tyr Asn Asp Gly Thr Lys Tyr Asn Glu Lys Phe
     50                  55                  60

Gln Gly Arg Val Thr Ile Ser Ser Asp Lys Ser Ile Ser Thr Ala Tyr
 65                  70                  75                  80

Met Glu Leu Ser Ser Leu Arg Ser Glu Asp Thr Ala Met Tyr Tyr Cys
                 85                  90                  95

Ala Arg Gly Thr Tyr Tyr Gly Thr Arg Val Phe Asp Tyr Trp Gly
            100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asn His
                195                 200                 205

Lys Pro Ser Asn Thr Lys Val Asp Lys Lys Val Glu Arg Lys Ser Cys
210                 215                 220

Asp Lys Thr His Thr Cys Pro Arg Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Lys Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Gly Gly Gly Gly Ser Gly Gly Gly Gly Ser Glu Val Gln
450                 455                 460

Leu Val Glu Ser Gly Gly Gly Leu Val Gln Pro Gly Gly Ser Leu Arg
```

465                 470                 475                 480
Leu Ser Cys Ala Ala Ser Gly Phe Thr Phe Asn Thr Tyr Ala Met Asn
                    485                 490                 495

Trp Val Arg Gln Ala Pro Gly Lys Gly Leu Glu Trp Val Gly Arg Ile
                    500                 505                 510

Arg Ser Lys Tyr Asn Asn Tyr Ala Thr Tyr Tyr Ala Asp Ser Val Lys
                    515                 520                 525

Gly Arg Phe Thr Ile Ser Arg Asp Asp Ser Lys Asn Thr Leu Tyr Leu
                    530                 535                 540

Gln Met Asn Ser Leu Arg Ala Glu Asp Thr Ala Val Tyr Tyr Cys Val
545                 550                 555                 560

Arg His Gly Asn Phe Gly Asn Ser Tyr Val Ser Trp Phe Ala Tyr Trp
                    565                 570                 575

Gly Gln Gly Thr Leu Val Thr Val Ser Ser
                    580                 585

<210> SEQ ID NO 106
<211> LENGTH: 219
<212> TYPE: PRT
<213> ORGANISM: Artificial Sequence
<220> FEATURE:
<223> OTHER INFORMATION: Light Chain of anti-CD19 x anti-CD3 mAb-dAb

<400> SEQUENCE: 106

Asp Ile Val Met Thr Gln Ser Pro Ala Thr Leu Ser Leu Ser Pro Gly
1                   5                   10                  15

Glu Arg Ala Thr Leu Ser Cys Arg Ser Ser Lys Ser Leu Gln Asn Val
                    20                  25                  30

Asn Gly Asn Thr Tyr Leu Tyr Trp Phe Gln Gln Lys Pro Gly Gln Ser
                    35                  40                  45

Pro Gln Leu Leu Ile Tyr Arg Met Ser Asn Leu Asn Ser Gly Val Pro
            50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                    85                  90                  95

Leu Glu Tyr Pro Ile Thr Phe Gly Ala Gly Thr Lys Leu Glu Ile Lys
                    100                 105                 110

Arg Thr Val Ala Ala Pro Ser Val Phe Ile Phe Pro Pro Ser Asp Glu
                    115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                    165                 170                 175

Thr Tyr Ser Leu Ser Ser Thr Leu Thr Leu Ser Lys Ala Asp Tyr Glu
                    180                 185                 190

Lys His Lys Val Tyr Ala Cys Glu Val Thr His Gln Gly Leu Ser Ser
                    195                 200                 205

Pro Val Thr Lys Ser Phe Asn Arg Gly Glu Cys
            210                 215

<210> SEQ ID NO 107
<211> LENGTH: 566
<212> TYPE: PRT

<213> ORGANISM: Artificial Sequence
<220> FEATURE:
<223> OTHER INFORMATION: Heavy Chain 1 of anti-CD19 x anti-CD3 Fv-Fab-Fc
[HC ISO(-) (VL-VL-CL)]

<400> SEQUENCE: 107

```
Asp Ile Val Met Thr Gln Ser Pro Ala Thr Leu Ser Leu Ser Pro Gly
1               5                  10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Thr Val Ala Ala Pro Ser Val Phe Ile Phe Pro Pro Gln Ala Val Val
        115                 120                 125

Thr Gln Glu Pro Ser Leu Thr Val Ser Pro Gly Gly Thr Val Thr Leu
    130                 135                 140

Thr Cys Gly Ser Ser Thr Gly Ala Val Thr Thr Ser Asn Tyr Ala Asn
145                 150                 155                 160

Trp Val Gln Gln Lys Pro Gly Gln Ala Pro Arg Gly Leu Ile Gly Gly
                165                 170                 175

Thr Asn Lys Arg Ala Pro Gly Val Pro Ala Arg Phe Ser Gly Ser Leu
            180                 185                 190

Leu Gly Gly Lys Ala Ala Leu Thr Leu Ser Gly Ala Gln Pro Glu Asp
        195                 200                 205

Glu Ala Glu Tyr Tyr Cys Ala Leu Trp Tyr Ser Asn Leu Trp Val Phe
    210                 215                 220

Gly Gly Gly Thr Lys Leu Thr Val Leu Arg Thr Val Ala Ala Pro Ser
225                 230                 235                 240

Val Phe Ile Phe Pro Pro Ser Asp Glu Gln Leu Lys Ser Gly Thr Ala
                245                 250                 255

Ser Val Val Cys Leu Leu Asn Asn Phe Tyr Pro Arg Glu Ala Lys Val
            260                 265                 270

Gln Trp Lys Val Asp Asn Ala Leu Gln Ser Gly Asn Ser Gln Glu Ser
        275                 280                 285

Val Thr Glu Gln Asp Ser Lys Asp Ser Thr Tyr Ser Leu Ser Ser Thr
    290                 295                 300

Leu Thr Leu Ser Lys Ala Asp Tyr Glu Lys His Lys Val Tyr Ala Cys
305                 310                 315                 320

Glu Val Thr His Gln Gly Leu Ser Ser Pro Val Thr Lys Ser Phe Asn
                325                 330                 335

Arg Gly Glu Cys Asp Lys Thr His Thr Cys Pro Pro Cys Pro Ala Pro
            340                 345                 350

Glu Leu Leu Gly Gly Pro Ser Val Phe Leu Phe Pro Pro Lys Pro Lys
        355                 360                 365

Asp Thr Leu Met Ile Ser Arg Thr Pro Glu Val Thr Cys Val Val Val
    370                 375                 380
```

```
Asp Val Ser His Glu Asp Pro Glu Val Gln Phe Asn Trp Tyr Val Asp
385                 390                 395                 400

Gly Val Glu Val His Asn Ala Lys Thr Lys Pro Arg Glu Glu Gln Tyr
            405                 410                 415

Asn Ser Thr Tyr Arg Val Val Ser Val Leu Thr Val Leu His Gln Asp
            420                 425                 430

Trp Leu Asn Gly Lys Glu Tyr Lys Cys Lys Val Ser Asn Lys Ala Leu
            435                 440                 445

Pro Ala Pro Ile Glu Lys Thr Ile Ser Lys Ala Lys Gly Gln Pro Arg
450                 455                 460

Glu Pro Gln Val Tyr Thr Leu Pro Pro Ser Gln Glu Glu Met Thr Lys
465                 470                 475                 480

Asn Gln Val Ser Leu Thr Cys Leu Val Lys Gly Phe Tyr Pro Ser Asp
            485                 490                 495

Ile Ala Val Glu Trp Glu Ser Ser Gly Gln Pro Glu Asn Asn Tyr Asn
            500                 505                 510

Thr Thr Pro Pro Met Leu Asp Ser Asp Gly Ser Phe Phe Leu Tyr Ser
            515                 520                 525

Lys Leu Thr Val Asp Lys Ser Arg Trp Gln Glu Gly Asn Val Phe Ser
530                 535                 540

Cys Ser Val Met His Glu Ala Leu His Asn His Tyr Thr Gln Lys Ser
545                 550                 555                 560

Leu Ser Leu Ser Pro Gly
                565

<210> SEQ ID NO 108
<211> LENGTH: 589
<212> TYPE: PRT
<213> ORGANISM: Artificial Sequence
<220> FEATURE:
<223> OTHER INFORMATION: Heavy Chain 2 of anti-CD19 x anti-CD3 Fv-Fab-Fc
      [HC ISO(+RR) (VH-VH-CH1)]

<400> SEQUENCE: 108

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Tyr Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Thr Phe Asn Thr Tyr Ala Met Asn Trp Val Arg Gln Ala Pro Gly
                165                 170                 175
```

```
Lys Gly Leu Glu Trp Val Gly Arg Ile Arg Ser Lys Tyr Asn Asn Tyr
            180                 185                 190

Ala Thr Tyr Tyr Ala Asp Ser Val Lys Gly Arg Phe Thr Ile Ser Arg
        195                 200                 205

Asp Asp Ser Lys Asn Thr Leu Tyr Leu Gln Met Asn Ser Leu Arg Ala
    210                 215                 220

Glu Asp Thr Ala Val Tyr Tyr Cys Val Arg His Gly Asn Phe Gly Asn
225                 230                 235                 240

Ser Tyr Val Ser Trp Phe Ala Tyr Trp Gly Gln Gly Thr Leu Val Thr
                245                 250                 255

Val Ser Ser Ala Ser Thr Lys Gly Pro Ser Val Phe Pro Leu Ala Pro
            260                 265                 270

Ser Ser Lys Ser Thr Ser Gly Gly Thr Ala Ala Leu Gly Cys Leu Val
        275                 280                 285

Lys Asp Tyr Phe Pro Glu Pro Val Thr Val Ser Trp Asn Ser Gly Ala
    290                 295                 300

Leu Thr Ser Gly Val His Thr Phe Pro Ala Val Leu Gln Ser Ser Gly
305                 310                 315                 320

Leu Tyr Ser Leu Ser Ser Val Val Thr Val Pro Ser Ser Ser Leu Gly
                325                 330                 335

Thr Lys Thr Tyr Thr Cys Asn Val Asn His Lys Pro Ser Asn Thr Lys
            340                 345                 350

Val Asp Lys Lys Val Glu Arg Lys Ser Ser Asp Lys Thr His Thr Cys
        355                 360                 365

Pro Arg Cys Pro Ala Pro Glu Leu Leu Gly Gly Pro Ser Val Phe Leu
    370                 375                 380

Phe Pro Pro Lys Pro Lys Asp Thr Leu Met Ile Ser Arg Thr Pro Glu
385                 390                 395                 400

Val Thr Cys Val Val Val Asp Val Ser His Glu Asp Pro Glu Val Lys
                405                 410                 415

Phe Lys Trp Tyr Val Asp Gly Val Glu Val His Asn Ala Lys Thr Lys
            420                 425                 430

Pro Arg Glu Glu Gln Tyr Asn Ser Thr Tyr Arg Val Val Ser Val Leu
        435                 440                 445

Thr Val Leu His Gln Asp Trp Leu Asn Gly Lys Glu Tyr Lys Cys Lys
    450                 455                 460

Val Ser Asn Lys Ala Leu Pro Ala Pro Ile Glu Lys Thr Ile Ser Lys
465                 470                 475                 480

Ala Lys Gly Gln Pro Arg Glu Pro Gln Val Tyr Thr Leu Pro Pro Ser
                485                 490                 495

Arg Glu Glu Met Thr Lys Asn Gln Val Ser Leu Thr Cys Leu Val Lys
            500                 505                 510

Gly Phe Tyr Pro Ser Asp Ile Ala Val Glu Trp Glu Ser Asn Gly Gln
        515                 520                 525

Pro Glu Asn Asn Tyr Lys Thr Thr Pro Pro Val Leu Asp Ser Asp Gly
    530                 535                 540

Ser Phe Phe Leu Tyr Ser Lys Leu Thr Val Asp Lys Ser Arg Trp Gln
545                 550                 555                 560

Gln Gly Asn Val Phe Ser Cys Ser Val Met His Glu Ala Leu His Asn
                565                 570                 575

His Tyr Thr Gln Lys Ser Leu Ser Leu Ser Pro Gly Lys
            580                 585
```

-continued

<210> SEQ ID NO 109
<211> LENGTH: 450
<212> TYPE: PRT
<213> ORGANISM: Artificial Sequence
<220> FEATURE:
<223> OTHER INFORMATION: Heavy Chain 1 of anti-CD19 x anti-CD3 common
      light chain mAb [HC ISO(-) (anti-CD19 Fab with anti-CD19
      VH-CH1/anti-CD3 LC)]

<400> SEQUENCE: 109

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
```

```
                355                 360                 365
Leu Thr Cys Leu Val Lys Gly Phe Tyr Pro Ser Asp Ile Ala Val Glu
            370                 375                 380
Trp Glu Ser Ser Gly Gln Pro Glu Asn Asn Tyr Asn Thr Thr Pro Pro
385                 390                 395                 400
Met Leu Asp Ser Asp Gly Ser Phe Phe Leu Tyr Ser Lys Leu Thr Val
            405                 410                 415
Asp Lys Ser Arg Trp Gln Glu Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly
    450

<210> SEQ ID NO 110
<211> LENGTH: 455
<212> TYPE: PRT
<213> ORGANISM: Artificial Sequence
<220> FEATURE:
<223> OTHER INFORMATION: Heavy Chain 2 of anti-CD19 x anti-CD3 common
      light chain mAb ISO(+RR) [(anti-CD3 Fab with anti-CD3
      VH-CH1/anti-CD3 LC)]

<400> SEQUENCE: 110

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asn Thr Tyr
            20                  25                  30
Ala Met Asn Trp Val Arg Gln Ala Pro Gly Lys Gly Leu Glu Trp Val
        35                  40                  45
Gly Arg Ile Arg Ser Lys Tyr Asn Asn Tyr Ala Thr Tyr Tyr Ala Asp
    50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Val Arg His Gly Asn Phe Gly Asn Ser Tyr Val Ser Trp Phe
            100                 105                 110
Ala Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
    130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
        195                 200                 205
Asn Val Asn His Lys Pro Ser Asn Thr Lys Val Asp Lys Lys Val Glu
    210                 215                 220
Arg Lys Ser Cys Asp Lys Thr His Thr Cys Pro Arg Cys Pro Ala Pro
225                 230                 235                 240
Glu Leu Leu Gly Gly Pro Ser Val Phe Leu Phe Pro Pro Lys Pro Lys
                245                 250                 255
```

Asp Thr Leu Met Ile Ser Arg Thr Pro Glu Val Thr Cys Val Val Val
            260                 265                 270

Asp Val Ser His Glu Asp Pro Glu Val Lys Phe Lys Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 111
<211> LENGTH: 216
<212> TYPE: PRT
<213> ORGANISM: Artificial Sequence
<220> FEATURE:
<223> OTHER INFORMATION: Light Chain of anti-CD19 x anti-CD3 common
      light chain mAb

<400> SEQUENCE: 111

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn

```
145                 150                 155                 160
Ser Gln Glu Ser Val Thr Glu Gln Asp Ser Lys Asp Ser Thr Tyr Ser
                    165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys
    210                 215
```

<210> SEQ ID NO 112
<211> LENGTH: 231
<212> TYPE: PRT
<213> ORGANISM: Artificial Sequence
<220> FEATURE:
<223> OTHER INFORMATION: Heavy Chain 1 of anti-CD3 one-arm mAb
      [HC ISO(-)]

<400> SEQUENCE: 112

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Gln Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Gln Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Glu Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230
```

<210> SEQ ID NO 113
<211> LENGTH: 455
<212> TYPE: PRT
<213> ORGANISM: Artificial Sequence
<220> FEATURE:
<223> OTHER INFORMATION: Heavy Chain 2 of anti-CD3 one-arm mAb
      [HC ISO(+RR) (anti-CD3 Fab)]

<400> SEQUENCE: 113

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asn His Lys Pro Ser Asn Thr Lys Val Asp Lys Lys Val Glu
    210                 215                 220

Arg Lys Ser Cys Asp Lys Thr His Thr Cys Pro Arg Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Lys Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415
```

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
            450             455

<210> SEQ ID NO 114
<211> LENGTH: 216
<212> TYPE: PRT
<213> ORGANISM: Artificial Sequence
<220> FEATURE:
<223> OTHER INFORMATION: Light Chain of anti-CD3 one-arm mAb

<400> SEQUENCE: 114

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 115
<211> LENGTH: 571
<212> TYPE: PRT
<213> ORGANISM: Artificial Sequence
<220> FEATURE:
<223> OTHER INFORMATION: Heavy Chain 1 of anti-CD19 x anti-CD3 Fab-Fv-Fc
      [HC ISO(-) (VL-CL-VL)]

<400> SEQUENCE: 115

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

-continued

```
Asn Gly Asn Thr Tyr Leu Tyr Trp Phe Gln Gln Lys Pro Gly Gln Ser
             35                  40                  45

Pro Gln Leu Leu Ile Tyr Arg Met Ser Asn Leu Asn Ser Gly Val Pro
         50                  55                  60

Asp Arg Phe Ser Gly Ser Gly Ser Gly Thr Glu Phe Thr Leu Thr Ile
 65                  70                  75                  80

Ser Ser Leu Glu Pro Glu Asp Phe Ala Val Tyr Tyr Cys Met Gln His
                 85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Thr Val Ala Ala Pro
    210                 215                 220

Ser Val Phe Ile Phe Pro Pro Gln Ala Val Thr Gln Glu Pro Ser
225                 230                 235                 240

Leu Thr Val Ser Pro Gly Gly Thr Val Thr Leu Thr Cys Gly Ser Ser
                245                 250                 255

Thr Gly Ala Val Thr Thr Ser Asn Tyr Ala Asn Trp Val Gln Gln Lys
            260                 265                 270

Pro Gly Gln Ala Pro Arg Gly Leu Ile Gly Gly Thr Asn Lys Arg Ala
        275                 280                 285

Pro Gly Val Pro Ala Arg Phe Ser Gly Ser Leu Leu Gly Gly Lys Ala
    290                 295                 300

Ala Leu Thr Leu Ser Gly Ala Gln Pro Glu Asp Glu Ala Glu Tyr Tyr
305                 310                 315                 320

Cys Ala Leu Trp Tyr Ser Asn Leu Trp Val Phe Gly Gly Gly Thr Lys
                325                 330                 335

Leu Thr Val Leu Glu Pro Lys Ser Ser Asp Lys Thr His Thr Cys Pro
            340                 345                 350

Pro Cys Pro Ala Pro Glu Leu Leu Gly Gly Pro Ser Val Phe Leu Phe
        355                 360                 365

Pro Pro Lys Pro Lys Asp Thr Leu Met Ile Ser Arg Thr Pro Glu Val
    370                 375                 380

Thr Cys Val Val Val Asp Val Ser His Glu Asp Pro Glu Val Gln Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
```

```
                450             455             460
Lys Gly Gln Pro Arg Glu Pro Gln Val Tyr Thr Leu Pro Pro Ser Gln
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Gly Gln Pro
            500                 505                 510

Glu Asn Asn Tyr Asn Thr Thr Pro Pro Met Leu Asp Ser Asp Gly Ser
            515                 520                 525

Phe Phe Leu Tyr Ser Lys Leu Thr Val Asp Lys Ser Arg Trp Gln Glu
        530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 116
<211> LENGTH: 594
<212> TYPE: PRT
<213> ORGANISM: Artificial Sequence
<220> FEATURE:
<223> OTHER INFORMATION: Heavy Chain 2 of anti-CD19 x anti-CD3 Fab-Fv-Fc
      [HC ISO(+RR) (VH-CH1-VH)]

<400> SEQUENCE: 116

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asn His
        195                 200                 205

Lys Pro Ser Asn Thr Lys Val Asp Lys Lys Val Glu Arg Lys Ser Cys
    210                 215                 220

Ala Ser Thr Lys Gly Pro Ser Val Phe Pro Leu Ala Pro Glu Val Gln
225                 230                 235                 240
```

Leu Val Glu Ser Gly Gly Gly Leu Val Gln Pro Gly Gly Ser Leu Arg
            245                 250                 255

Leu Ser Cys Ala Ala Ser Gly Phe Thr Phe Asn Thr Tyr Ala Met Asn
        260                 265                 270

Trp Val Arg Gln Ala Pro Gly Lys Gly Leu Glu Trp Val Gly Arg Ile
        275                 280                 285

Arg Ser Lys Tyr Asn Asn Tyr Ala Thr Tyr Tyr Ala Asp Ser Val Lys
    290                 295                 300

Gly Arg Phe Thr Ile Ser Arg Asp Asp Ser Lys Asn Thr Leu Tyr Leu
305                 310                 315                 320

Gln Met Asn Ser Leu Arg Ala Glu Asp Thr Ala Val Tyr Tyr Cys Val
                325                 330                 335

Arg His Gly Asn Phe Gly Asn Ser Tyr Val Ser Trp Phe Ala Tyr Trp
            340                 345                 350

Gly Gln Gly Thr Leu Val Thr Val Ser Ser Glu Arg Lys Ser Ser Asp
        355                 360                 365

Lys Thr His Thr Cys Pro Arg Cys Pro Ala Pro Glu Leu Leu Gly Gly
    370                 375                 380

Pro Ser Val Phe Leu Phe Pro Pro Lys Pro Lys Asp Thr Leu Met Ile
385                 390                 395                 400

Ser Arg Thr Pro Glu Val Thr Cys Val Val Val Asp Val Ser His Glu
                405                 410                 415

Asp Pro Glu Val Lys Phe Lys Trp Tyr Val Asp Gly Val Glu Val His
            420                 425                 430

Asn Ala Lys Thr Lys Pro Arg Glu Glu Gln Tyr Asn Ser Thr Tyr Arg
        435                 440                 445

Val Val Ser Val Leu Thr Val Leu His Gln Asp Trp Leu Asn Gly Lys
    450                 455                 460

Glu Tyr Lys Cys Lys Val Ser Asn Lys Ala Leu Pro Ala Pro Ile Glu
465                 470                 475                 480

Lys Thr Ile Ser Lys Ala Lys Gly Gln Pro Arg Glu Pro Gln Val Tyr
                485                 490                 495

Thr Leu Pro Pro Ser Arg Glu Glu Met Thr Lys Asn Gln Val Ser Leu
            500                 505                 510

Thr Cys Leu Val Lys Gly Phe Tyr Pro Ser Asp Ile Ala Val Glu Trp
        515                 520                 525

Glu Ser Asn Gly Gln Pro Glu Asn Asn Tyr Lys Thr Thr Pro Pro Val
    530                 535                 540

Leu Asp Ser Asp Gly Ser Phe Phe Leu Tyr Ser Lys Leu Thr Val Asp
545                 550                 555                 560

Lys Ser Arg Trp Gln Gln Gly Asn Val Phe Ser Cys Ser Val Met His
                565                 570                 575

Glu Ala Leu His Asn His Tyr Thr Gln Lys Ser Leu Ser Leu Ser Pro
            580                 585                 590

Gly Lys

<210> SEQ ID NO 117
<211> LENGTH: 464
<212> TYPE: PRT
<213> ORGANISM: Artificial Sequence
<220> FEATURE:
<223> OTHER INFORMATION: Heavy Chain 1 of anti-CD19 x anti-CD3 Fv-Fv-Fc
      [HC ISO(-) (VL-VL)]

<400> SEQUENCE: 117

-continued

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Thr Val Ala Ala Pro Ser Val Phe Ile Phe Pro Pro Gln Ala Val Val
        115                 120                 125

Thr Gln Glu Pro Ser Leu Thr Val Ser Pro Gly Gly Thr Val Thr Leu
    130                 135                 140

Thr Cys Gly Ser Ser Thr Gly Ala Val Thr Thr Ser Asn Tyr Ala Asn
145                 150                 155                 160

Trp Val Gln Gln Lys Pro Gly Gln Ala Pro Arg Gly Leu Ile Gly Gly
                165                 170                 175

Thr Asn Lys Arg Ala Pro Gly Val Pro Ala Arg Phe Ser Gly Ser Leu
            180                 185                 190

Leu Gly Gly Lys Ala Ala Leu Thr Leu Ser Gly Ala Gln Pro Glu Asp
        195                 200                 205

Glu Ala Glu Tyr Tyr Cys Ala Leu Trp Tyr Ser Asn Leu Trp Val Phe
    210                 215                 220

Gly Gly Gly Thr Lys Leu Thr Val Leu Glu Pro Lys Ser Ser Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Ser Gly Gln Pro Glu Asn Asn Tyr Asn Thr Thr Pro Pro Met Leu
                405                 410                 415

Asp Ser Asp Gly Ser Phe Phe Leu Tyr Ser Lys Leu Thr Val Asp Lys
```

```
                        420                 425                 430
Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Pro Gly
            450                 455                 460

<210> SEQ ID NO 118
<211> LENGTH: 491
<212> TYPE: PRT
<213> ORGANISM: Artificial Sequence
<220> FEATURE:
<223> OTHER INFORMATION: Heavy Chain 2 of anti-CD19 x anti-CD3 Fv-Fv-Fc
      [HC ISO(+RR) (VH-VH)]

<400> SEQUENCE: 118

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Thr Phe Asn Thr Tyr Ala Met Asn Trp Val Arg Gln Ala Pro Gly
                165                 170                 175

Lys Gly Leu Glu Trp Val Gly Arg Ile Arg Ser Lys Tyr Asn Asn Tyr
            180                 185                 190

Ala Thr Tyr Tyr Ala Asp Ser Val Lys Gly Arg Phe Thr Ile Ser Arg
        195                 200                 205

Asp Asp Ser Lys Asn Thr Leu Tyr Leu Gln Met Asn Ser Leu Arg Ala
    210                 215                 220

Glu Asp Thr Ala Val Tyr Tyr Cys Val Arg His Gly Asn Phe Gly Asn
225                 230                 235                 240

Ser Tyr Val Ser Trp Phe Ala Tyr Trp Gly Gln Gly Thr Leu Val Thr
                245                 250                 255

Val Ser Ser Glu Arg Lys Ser Ser Asp Lys Thr His Thr Cys Pro Arg
            260                 265                 270

Cys Pro Ala Pro Glu Leu Leu Gly Gly Pro Ser Val Phe Leu Phe Pro
        275                 280                 285

Pro Lys Pro Lys Asp Thr Leu Met Ile Ser Arg Thr Pro Glu Val Thr
    290                 295                 300

Cys Val Val Val Asp Val Ser His Glu Asp Pro Glu Val Lys Phe Lys
305                 310                 315                 320
```

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Ala Leu Pro Ala Pro Ile Glu Lys Thr Ile Ser Lys Ala Lys
370                 375                 380

Gly Gln Pro Arg Glu Pro Gln Val Tyr Thr Leu Pro Pro Ser Arg Glu
385                 390                 395                 400

Glu Met Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
            420                 425                 430

Asn Asn Tyr Lys Thr Thr Pro Pro Val Leu Asp Ser Asp Gly Ser Phe
        435                 440                 445

Phe Leu Tyr Ser Lys Leu Thr Val Asp Lys Ser Arg Trp Gln Gln Gly
450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Lys
                485                 490

<210> SEQ ID NO 119
<211> LENGTH: 442
<212> TYPE: PRT
<213> ORGANISM: Artificial Sequence
<220> FEATURE:
<223> OTHER INFORMATION: Heavy Chain 1 of anti-CD3 monovalent mAb
      [HC ISO(-) (VL-CL)]

<400> SEQUENCE: 119

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

```
Val Tyr Ala Cys Glu Val Thr His Gln Gly Leu Ser Ser Pro Val Thr
            195                 200                 205

Lys Ser Phe Asn Arg Gly Glu Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Ser Gly Gln Pro Glu
            370                 375                 380

Asn Asn Tyr Asn Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly
            435                 440

<210> SEQ ID NO 120
<211> LENGTH: 455
<212> TYPE: PRT
<213> ORGANISM: Artificial Sequence
<220> FEATURE:
<223> OTHER INFORMATION: Heavy Chain 2 of anti-CD3 monovalent mAb
      [HC ISO(+RR) (VH-CH1)]

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Val Arg His Gly Asn Phe Gly Asn Ser Tyr Val Ser Trp Phe
```

```
            100                 105                 110
Ala Tyr Trp Gly Gln Gly Thr Leu Val Thr Val Ser Ser Ala Ser Thr
            115                 120                 125
Lys Gly Pro Ser Val Phe Pro Leu Ala Pro Ser Ser Lys Ser Thr Ser
            130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                    165                 170                 175
Thr Phe Pro Ala Val Leu Gln Ser Ser Gly Leu Tyr Ser Leu Ser Ser
                180                 185                 190
Val Val Thr Val Pro Ser Ser Ser Leu Gly Thr Lys Thr Tyr Thr Cys
            195                 200                 205
Asn Val Asn His Lys Pro Ser Asn Thr Lys Val Asp Lys Lys Val Glu
            210                 215                 220
Arg Lys Ser Cys Asp Lys Thr His Thr Cys Pro Arg Cys Pro Ala Pro
225                 230                 235                 240
Glu Leu Leu Gly Gly Pro Ser Val Phe Leu Phe Pro Pro Lys Pro Lys
                245                 250                 255
Asp Thr Leu Met Ile Ser Arg Thr Pro Glu Val Thr Cys Val Val Val
                260                 265                 270
Asp Val Ser His Glu Asp Pro Glu Val Lys Phe Lys Trp Tyr Val Asp
                275                 280                 285
Gly Val Glu Val His Asn Ala Lys Thr Lys Pro Arg Glu Glu Gln Tyr
            290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
                340                 345                 350
Glu Pro Gln Val Tyr Thr Leu Pro Pro Ser Arg Glu Glu Met Thr Lys
            355                 360                 365
Asn Gln Val Ser Leu Thr Cys Leu Val Lys Gly Phe Tyr Pro Ser Asp
            370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
                420                 425                 430
Cys Ser Val Met His Glu Ala Leu His Asn His Tyr Thr Gln Lys Ser
            435                 440                 445
Leu Ser Leu Ser Pro Gly Lys
450                 455

<210> SEQ ID NO 121
<211> LENGTH: 593
<212> TYPE: PRT
<213> ORGANISM: Artificial Sequence
<220> FEATURE:
<223> OTHER INFORMATION: Heavy Chain 1 of anti-CD19 x anti-CD3 central
      Fv [HC ISO(-) (Fab-VH)]

<400> SEQUENCE: 121
```

-continued

```
Glu Val Gln Leu Val Glu Ser Gly Gly Leu Val Lys Pro Gly Gly
 1               5                  10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
 65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Lys Val Glu Pro Lys Ser Cys
    210                 215                 220

Ala Ser Thr Lys Gly Pro Ser Val Phe Pro Leu Ala Pro Glu Val Gln
225                 230                 235                 240

Leu Val Glu Ser Gly Gly Gly Leu Val Gln Pro Gly Gly Ser Leu Arg
                245                 250                 255

Leu Ser Cys Ala Ala Ser Gly Phe Thr Phe Asn Thr Tyr Ala Met Asn
            260                 265                 270

Trp Val Arg Gln Ala Pro Gly Lys Gly Leu Glu Trp Val Gly Arg Ile
        275                 280                 285

Arg Ser Lys Tyr Asn Asn Tyr Ala Thr Tyr Tyr Ala Asp Ser Val Lys
    290                 295                 300

Gly Arg Phe Thr Ile Ser Arg Asp Asp Ser Lys Asn Thr Leu Tyr Leu
305                 310                 315                 320

Gln Met Asn Ser Leu Arg Ala Glu Asp Thr Ala Val Tyr Tyr Cys Val
                325                 330                 335

Arg His Gly Asn Phe Gly Asn Ser Tyr Val Ser Trp Phe Ala Tyr Trp
            340                 345                 350

Gly Gln Gly Thr Leu Val Thr Val Ser Ser Pro Lys Ser Ser Asp
        355                 360                 365

Lys Thr His Thr Cys Pro Pro Cys Pro Ala Pro Glu Leu Leu Gly Gly
    370                 375                 380

Pro Ser Val Phe Leu Phe Pro Pro Lys Pro Lys Asp Thr Leu Met Ile
385                 390                 395                 400

Ser Arg Thr Pro Glu Val Thr Cys Val Val Val Asp Val Ser His Glu
                405                 410                 415

Asp Pro Glu Val Gln Phe Asn Trp Tyr Val Asp Gly Val Glu Val His
```

```
                    420                 425                 430
Asn Ala Lys Thr Lys Pro Arg Glu Glu Gln Tyr Asn Ser Thr Tyr Arg
            435                 440                 445

Val Val Ser Val Leu Thr Val Leu His Gln Asp Trp Leu Asn Gly Lys
        450                 455                 460

Glu Tyr Lys Cys Lys Val Ser Asn Lys Ala Leu Pro Ala Pro Ile Glu
465                 470                 475                 480

Lys Thr Ile Ser Lys Ala Lys Gly Gln Pro Arg Glu Pro Gln Val Tyr
                485                 490                 495

Thr Leu Pro Pro Ser Gln Glu Glu Met Thr Lys Asn Gln Val Ser Leu
            500                 505                 510

Thr Cys Leu Val Lys Gly Phe Tyr Pro Ser Asp Ile Ala Val Glu Trp
        515                 520                 525

Glu Ser Ser Gly Gln Pro Glu Asn Asn Tyr Asn Thr Thr Pro Pro Met
530                 535                 540

Leu Asp Ser Asp Gly Ser Phe Phe Leu Tyr Ser Lys Leu Thr Val Asp
545                 550                 555                 560

Lys Ser Arg Trp Gln Glu Gly Asn Val Phe Ser Cys Ser Val Met His
                565                 570                 575

Glu Ala Leu His Asn His Tyr Thr Gln Lys Ser Leu Ser Leu Ser Pro
            580                 585                 590

Gly

<210> SEQ ID NO 122
<211> LENGTH: 577
<212> TYPE: PRT
<213> ORGANISM: Artificial Sequence
<220> FEATURE:
<223> OTHER INFORMATION: Heavy Chain 2 of anti-CD19 x anti-CD3 central
      Fv [HC ISO(+RR) (Fab-VL)]

<400> SEQUENCE: 122

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
```

```
                180             185             190
Pro Ser Ser Ser Leu Gly Thr Lys Thr Tyr Thr Cys Asn Val Asn His
            195             200             205
Lys Pro Ser Asn Thr Lys Val Asp Lys Val Glu Pro Lys Ser Cys
    210             215             220
Thr Val Ala Ala Pro Ser Val Phe Ile Phe Pro Pro Gln Ala Val Val
225             230             235             240
Thr Gln Glu Pro Ser Leu Thr Val Ser Pro Gly Gly Thr Val Thr Leu
                245             250             255
Thr Cys Gly Ser Ser Thr Gly Ala Val Thr Thr Ser Asn Tyr Ala Asn
            260             265             270
Trp Val Gln Gln Lys Pro Gly Gln Ala Pro Arg Gly Leu Ile Gly Gly
    275             280             285
Thr Asn Lys Arg Ala Pro Gly Val Pro Ala Arg Phe Ser Gly Ser Leu
    290             295             300
Leu Gly Gly Lys Ala Ala Leu Thr Leu Ser Gly Ala Gln Pro Glu Asp
305             310             315             320
Glu Ala Glu Tyr Tyr Cys Ala Leu Trp Tyr Ser Asn Leu Trp Val Phe
                325             330             335
Gly Gly Gly Thr Lys Leu Thr Val Leu Glu Arg Lys Ser Ser Asp Lys
            340             345             350
Thr His Thr Cys Pro Arg Cys Pro Ala Pro Glu Leu Leu Gly Gly Pro
            355             360             365
Ser Val Phe Leu Phe Pro Pro Lys Pro Lys Asp Thr Leu Met Ile Ser
370             375             380
Arg Thr Pro Glu Val Thr Cys Val Val Val Asp Val Ser His Glu Asp
385             390             395             400
Pro Glu Val Lys Phe Lys Trp Tyr Val Asp Gly Val Glu Val His Asn
                405             410             415
Ala Lys Thr Lys Pro Arg Glu Glu Gln Tyr Asn Ser Thr Tyr Arg Val
            420             425             430
Val Ser Val Leu Thr Val Leu His Gln Asp Trp Leu Asn Gly Lys Glu
            435             440             445
Tyr Lys Cys Lys Val Ser Asn Lys Ala Leu Pro Ala Pro Ile Glu Lys
    450             455             460
Thr Ile Ser Lys Ala Lys Gly Gln Pro Arg Glu Pro Gln Val Tyr Thr
465             470             475             480
Leu Pro Pro Ser Arg Glu Glu Met Thr Lys Asn Gln Val Ser Leu Thr
                485             490             495
Cys Leu Val Lys Gly Phe Tyr Pro Ser Asp Ile Ala Val Glu Trp Glu
            500             505             510
Ser Asn Gly Gln Pro Glu Asn Asn Tyr Lys Thr Thr Pro Pro Val Leu
            515             520             525
Asp Ser Asp Gly Ser Phe Phe Leu Tyr Ser Lys Leu Thr Val Asp Lys
530             535             540
Ser Arg Trp Gln Gln Gly Asn Val Phe Ser Cys Ser Val Met His Glu
545             550             555             560
Ala Leu His Asn His Tyr Thr Gln Lys Ser Leu Ser Leu Ser Pro Gly
                565             570             575
Lys

<210> SEQ ID NO 123
<211> LENGTH: 219
```

```
<212> TYPE: PRT
<213> ORGANISM: Artificial Sequence
<220> FEATURE:
<223> OTHER INFORMATION: Light Chain of anti-CD19 x anti-CD3 central Fv

<400> SEQUENCE: 123

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 124
<211> LENGTH: 673
<212> TYPE: PRT
<213> ORGANISM: Artificial Sequence
<220> FEATURE:
<223> OTHER INFORMATION: Heavy Chain 1 of anti-CD19 x anti-CD3
      Fab-Fab-Fc [HC ISO(-) (VL-CL-VL-CL)]

<400> SEQUENCE: 124

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
```

```
                100             105                 110
Arg Thr Val Ala Ala Pro Ser Val Phe Ile Phe Pro Pro Ser Asp Glu
            115                 120                 125
Gln Leu Lys Ser Gly Thr Ala Ser Val Val Cys Leu Leu Asn Asn Phe
            130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
                195                 200                 205
Pro Val Thr Lys Ser Phe Asn Arg Gly Glu Cys Thr Val Ala Ala Pro
            210                 215                 220
Ser Val Phe Ile Phe Pro Pro Gln Ala Val Thr Gln Glu Pro Ser
225                 230                 235                 240
Leu Thr Val Ser Pro Gly Gly Thr Val Thr Leu Thr Cys Gly Ser Ser
                245                 250                 255
Thr Gly Ala Val Thr Thr Ser Asn Tyr Ala Asn Trp Val Gln Gln Lys
                260                 265                 270
Pro Gly Gln Ala Pro Arg Gly Leu Ile Gly Gly Thr Asn Lys Arg Ala
            275                 280                 285
Pro Gly Val Pro Ala Arg Phe Ser Gly Ser Leu Leu Gly Gly Lys Ala
            290                 295                 300
Ala Leu Thr Leu Ser Gly Ala Gln Pro Glu Asp Glu Ala Glu Tyr Tyr
305                 310                 315                 320
Cys Ala Leu Trp Tyr Ser Asn Leu Trp Val Phe Gly Gly Thr Lys
                325                 330                 335
Leu Thr Val Leu Arg Thr Val Ala Ala Pro Ser Val Phe Ile Phe Pro
                340                 345                 350
Pro Ser Asp Glu Gln Leu Lys Ser Gly Thr Ala Ser Val Val Cys Leu
                355                 360                 365
Leu Asn Asn Phe Tyr Pro Arg Glu Ala Lys Val Gln Trp Lys Val Asp
            370                 375                 380
Asn Ala Leu Gln Ser Gly Asn Ser Gln Glu Ser Val Thr Glu Gln Asp
385                 390                 395                 400
Ser Lys Asp Ser Thr Tyr Ser Leu Ser Ser Thr Leu Thr Leu Ser Lys
                405                 410                 415
Ala Asp Tyr Glu Lys His Lys Val Tyr Ala Cys Glu Val Thr His Gln
                420                 425                 430
Gly Leu Ser Ser Pro Val Thr Lys Ser Phe Asn Arg Gly Glu Cys Asp
            435                 440                 445
Lys Thr His Thr Cys Pro Pro Cys Pro Ala Pro Glu Leu Leu Gly Gly
            450                 455                 460
Pro Ser Val Phe Leu Phe Pro Pro Lys Pro Lys Asp Thr Leu Met Ile
465                 470                 475                 480
Ser Arg Thr Pro Glu Val Thr Cys Val Val Val Asp Val Ser His Glu
                485                 490                 495
Asp Pro Glu Val Gln Phe Asn Trp Tyr Val Asp Gly Val Glu Val His
                500                 505                 510
Asn Ala Lys Thr Lys Pro Arg Glu Glu Gln Tyr Asn Ser Thr Tyr Arg
                515                 520                 525
```

```
Val Val Ser Val Leu Thr Val Leu His Gln Asp Trp Leu Asn Gly Lys
    530                 535                 540

Glu Tyr Lys Cys Lys Val Ser Asn Lys Ala Leu Pro Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Ser Gln Glu Glu Met Thr Lys Asn Gln Val Ser Leu
            580                 585                 590

Thr Cys Leu Val Lys Gly Phe Tyr Pro Ser Asp Ile Ala Val Glu Trp
        595                 600                 605

Glu Ser Ser Gly Gln Pro Glu Asn Asn Tyr Asn Thr Thr Pro Pro Met
    610                 615                 620

Leu Asp Ser Asp Gly Ser Phe Phe Leu Tyr Ser Lys Leu Thr Val Asp
625                 630                 635                 640

Lys Ser Arg Trp Gln Glu Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly

<210> SEQ ID NO 125
<211> LENGTH: 692
<212> TYPE: PRT
<213> ORGANISM: Artificial Sequence
<220> FEATURE:
<223> OTHER INFORMATION: Heavy Chain 2 of anti-CD19 x anti-CD3
      Fab-Fab-Fc [HC ISO(+RR) (VH-CH1-VH-CH1)]

<400> SEQUENCE: 125

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Thr Arg Val Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asn His
        195                 200                 205
```

```
Lys Pro Ser Asn Thr Lys Val Asp Lys Val Glu Arg Lys Ser Cys
    210                 215                 220
Ala Ser Thr Lys Gly Pro Ser Val Phe Pro Leu Ala Pro Glu Val Gln
225                 230                 235                 240
Leu Val Glu Ser Gly Gly Gly Leu Val Gln Pro Gly Gly Ser Leu Arg
                245                 250                 255
Leu Ser Cys Ala Ala Ser Gly Phe Thr Phe Asn Thr Tyr Ala Met Asn
            260                 265                 270
Trp Val Arg Gln Ala Pro Gly Lys Gly Leu Glu Trp Val Gly Arg Ile
        275                 280                 285
Arg Ser Lys Tyr Asn Asn Tyr Ala Thr Tyr Tyr Ala Asp Ser Val Lys
    290                 295                 300
Gly Arg Phe Thr Ile Ser Arg Asp Asp Ser Lys Asn Thr Leu Tyr Leu
305                 310                 315                 320
Gln Met Asn Ser Leu Arg Ala Glu Asp Thr Ala Val Tyr Tyr Cys Val
                325                 330                 335
Arg His Gly Asn Phe Gly Asn Ser Tyr Val Ser Trp Phe Ala Tyr Trp
            340                 345                 350
Gly Gln Gly Thr Leu Val Thr Val Ser Ser Ala Ser Thr Lys Gly Pro
        355                 360                 365
Ser Val Phe Pro Leu Ala Pro Ser Ser Lys Ser Thr Ser Gly Gly Thr
    370                 375                 380
Ala Ala Leu Gly Cys Leu Val Lys Asp Tyr Phe Pro Glu Pro Val Thr
385                 390                 395                 400
Val Ser Trp Asn Ser Gly Ala Leu Thr Ser Gly Val His Thr Phe Pro
                405                 410                 415
Ala Val Leu Gln Ser Ser Gly Leu Tyr Ser Leu Ser Ser Val Val Thr
            420                 425                 430
Val Pro Ser Ser Ser Leu Gly Thr Lys Thr Tyr Thr Cys Asn Val Asn
        435                 440                 445
His Lys Pro Ser Asn Thr Lys Val Asp Lys Lys Val Glu Arg Lys Ser
    450                 455                 460
Cys Asp Lys Thr His Thr Cys Pro Arg Cys Pro Ala Pro Glu Leu Leu
465                 470                 475                 480
Gly Gly Pro Ser Val Phe Leu Phe Pro Pro Lys Pro Lys Asp Thr Leu
                485                 490                 495
Met Ile Ser Arg Thr Pro Glu Val Thr Cys Val Val Val Asp Val Ser
            500                 505                 510
His Glu Asp Pro Glu Val Lys Phe Lys Trp Tyr Val Asp Gly Val Glu
        515                 520                 525
Val His Asn Ala Lys Thr Lys Pro Arg Glu Glu Gln Tyr Asn Ser Thr
    530                 535                 540
Tyr Arg Val Val Ser Val Leu Thr Val Leu His Gln Asp Trp Leu Asn
545                 550                 555                 560
Gly Lys Glu Tyr Lys Cys Lys Val Ser Asn Lys Ala Leu Pro Ala Pro
                565                 570                 575
Ile Glu Lys Thr Ile Ser Lys Ala Lys Gly Gln Pro Arg Glu Pro Gln
            580                 585                 590
Val Tyr Thr Leu Pro Pro Ser Arg Glu Glu Met Thr Lys Asn Gln Val
        595                 600                 605
Ser Leu Thr Cys Leu Val Lys Gly Phe Tyr Pro Ser Asp Ile Ala Val
    610                 615                 620
```

```
Glu Trp Glu Ser Asn Gly Gln Pro Glu Asn Asn Tyr Lys Thr Thr Pro
625                 630                 635                 640

Pro Val Leu Asp Ser Asp Gly Ser Phe Phe Leu Tyr Ser Lys Leu Thr
                645                 650                 655

Val Asp Lys Ser Arg Trp Gln Gln Gly Asn Val Phe Ser Cys Ser Val
            660                 665                 670

Met His Glu Ala Leu His Asn His Tyr Thr Gln Lys Ser Leu Ser Leu
        675                 680                 685

Ser Pro Gly Lys
    690

<210> SEQ ID NO 126
<211> LENGTH: 104
<212> TYPE: PRT
<213> ORGANISM: Artificial Sequence
<220> FEATURE:
<223> OTHER INFORMATION: IgG1 (Figure 2A-2C)

<400> SEQUENCE: 126

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Arg Val Glu Pro Lys Ser Cys
            100

<210> SEQ ID NO 127
<211> LENGTH: 103
<212> TYPE: PRT
<213> ORGANISM: Artificial Sequence
<220> FEATURE:
<223> OTHER INFORMATION: IgG2 (Figure 2A-2C)

<400> SEQUENCE: 127

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys
            100

<210> SEQ ID NO 128
```

```
<211> LENGTH: 103
<212> TYPE: PRT
<213> ORGANISM: Artificial Sequence
<220> FEATURE:
<223> OTHER INFORMATION: IgG3 (Figure 2A-2C)

<400> SEQUENCE: 128

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro
            100

<210> SEQ ID NO 129
<211> LENGTH: 103
<212> TYPE: PRT
<213> ORGANISM: Artificial Sequence
<220> FEATURE:
<223> OTHER INFORMATION: IgG4 (Figure 2A-2C)

<400> SEQUENCE: 129

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly
            100

<210> SEQ ID NO 130
<211> LENGTH: 107
<212> TYPE: PRT
<213> ORGANISM: Artificial Sequence
<220> FEATURE:
<223> OTHER INFORMATION: Ckappa (Figure 3A-3B)

<400> SEQUENCE: 130

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45
```

-continued

```
Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 131
<211> LENGTH: 107
<212> TYPE: PRT
<213> ORGANISM: Artificial Sequence
<220> FEATURE:
<223> OTHER INFORMATION: Amino acid sequence of the CK and C  light
      constant chains

<400> SEQUENCE: 131

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 132
<211> LENGTH: 104
<212> TYPE: PRT
<213> ORGANISM: Artificial Sequence
<220> FEATURE:
<223> OTHER INFORMATION: Amino acid sequence of the CK and C  light
      constant chains

<400> SEQUENCE: 132

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
             20                  25                  30

Tyr Pro Gly Ala Val Thr Val Ala Trp Lys Ala Asp Ser Ser Pro Val
         35                  40                  45

Lys Ala Gly Val Glu Thr Thr Thr Pro Ser Lys Gln Ser Asn Asn Lys
 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys
            100

<210> SEQ ID NO 133
<211> LENGTH: 16
```

```
<212> TYPE: PRT
<213> ORGANISM: Artificial Sequence
<220> FEATURE:
<223> OTHER INFORMATION: IgG1 (Figure 25)

<400> SEQUENCE: 133

Asp Lys Thr His Thr Cys Pro Pro Cys Pro Ala Pro Glu Leu Leu Gly
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: pI_Iso3 (Figure 25)

<400> SEQUENCE: 134

Asp Thr Thr His Thr Cys Pro Pro Cys Pro Ala Pro Glu Leu Leu Gly
1               5                   10                  15

<210> SEQ ID NO 135
<211> LENGTH: 107
<212> TYPE: PRT
<213> ORGANISM: Artificial Sequence
<220> FEATURE:
<223> OTHER INFORMATION: Amino acid illustration of the CK-pI(4) variant

<400> SEQUENCE: 135

Arg Thr Val Ala Ala Pro Ser Val Phe Ile Phe Pro Pro Ser Asp Glu
1               5                   10                  15

Gln Leu Glu Ser Gly Thr Ala Ser Val Val Cys Leu Leu Asn Asn Phe
            20                  25                  30

Tyr Pro Arg Glu Ala Glu Val Gln Trp Lys Val Asp Asn Ala Leu Gln
        35                  40                  45

Ser Gly Asn Ser Gln Glu Ser Val Thr Glu Gln Asp Ser Glu Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Glu Ser Phe Asn Arg Gly Glu Cys
            100                 105

<210> SEQ ID NO 136
<211> LENGTH: 330
<212> TYPE: PRT
<213> ORGANISM: Artificial Sequence
<220> FEATURE:
<223> OTHER INFORMATION: Chain H

<400> SEQUENCE: 136

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 137
<211> LENGTH: 107
<212> TYPE: PRT
<213> ORGANISM: Artificial Sequence
<220> FEATURE:
<223> OTHER INFORMATION: Chain L

<400> SEQUENCE: 137

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Arg Ser
                85                  90                  95

Pro Val Thr Lys Ser Phe Asn Arg Gly Glu Cys
            100                 105

<210> SEQ ID NO 138
<211> LENGTH: 330
<212> TYPE: PRT
<213> ORGANISM: Artificial Sequence
<220> FEATURE:
<223> OTHER INFORMATION: IgG1-WT

<400> SEQUENCE: 138

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 139
<211> LENGTH: 326
<212> TYPE: PRT
<213> ORGANISM: Artificial Sequence
<220> FEATURE:

<223> OTHER INFORMATION: IgG2-WT

<400> SEQUENCE: 139

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 140
<211> LENGTH: 123
<212> TYPE: PRT
<213> ORGANISM: Artificial Sequence
<220> FEATURE:
<223> OTHER INFORMATION: Bevacizumab VH

<400> SEQUENCE: 140

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Tyr Thr Phe Thr Asn Tyr
        20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
            115                 120

<210> SEQ ID NO 141
<211> LENGTH: 107
<212> TYPE: PRT
<213> ORGANISM: Artificial Sequence
<220> FEATURE:
<223> OTHER INFORMATION: CK-WT

<400> SEQUENCE: 141

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 142
<211> LENGTH: 107
<212> TYPE: PRT
<213> ORGANISM: Artificial Sequence
<220> FEATURE:
<223> OTHER INFORMATION: CK-pI(6)

<400> SEQUENCE: 142

Arg Thr Val Ala Ala Pro Ser Val Phe Ile Phe Pro Pro Ser Asp Glu
1               5                   10                  15

Gln Leu Glu Ser Gly Thr Ala Ser Val Val Cys Leu Leu Asn Asn Phe
            20                  25                  30

Tyr Pro Arg Glu Ala Glu Val Gln Trp Lys Val Asp Asp Ala Leu Gln
        35                  40                  45

Glu Gly Asn Ser Gln Glu Ser Val Thr Glu Gln Asp Ser Glu Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Glu Ser
```

```
                    85                  90                  95
Pro Val Thr Lys Ser Phe Asn Arg Gly Glu Cys
                100                 105

<210> SEQ ID NO 143
<211> LENGTH: 107
<212> TYPE: PRT
<213> ORGANISM: Artificial Sequence
<220> FEATURE:
<223> OTHER INFORMATION: Bevacizumab VL

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
                100                 105

<210> SEQ ID NO 144
<211> LENGTH: 4
<212> TYPE: PRT
<213> ORGANISM: Artificial Sequence
<220> FEATURE:
<223> OTHER INFORMATION: sequence linker

<400> SEQUENCE: 144

Gly Phe Leu Gly
1
```